(12) United States Patent
Jin et al.

(10) Patent No.: US 12,103,924 B2
(45) Date of Patent: Oct. 1, 2024

(54) MITOGEN-ACTIVATED PROTEIN KINASE KINASE (MEK) DEGRADATION COMPOUNDS AND METHODS OF USE

(71) Applicant: Icahn School of Medicine at Mount Sinai, New York, NY (US)

(72) Inventors: Jian Jin, New York, NY (US); Jing Liu, New York, NY (US); Jianping Hu, New York, NY (US); Jieli Wei, Kunming (CN); Hyerin Yim, New York, NY (US); Md Kabir, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 124 days.

(21) Appl. No.: 17/336,059

(22) Filed: Jun. 1, 2021

(65) Prior Publication Data

US 2021/0395244 A1  Dec. 23, 2021

Related U.S. Application Data

(60) Provisional application No. 63/120,467, filed on Dec. 2, 2020, provisional application No. 63/118,367, filed on Nov. 25, 2020, provisional application No. 63/033,133, filed on Jun. 1, 2020.

(51) Int. Cl.
*C07D 417/12* (2006.01)
*A61K 9/00* (2006.01)
*A61P 35/00* (2006.01)

(52) U.S. Cl.
CPC .......... *C07D 417/12* (2013.01); *A61K 9/0019* (2013.01); *A61P 35/00* (2018.01)

(58) Field of Classification Search
CPC ...... C07D 417/12; A61P 35/00; A61K 9/0019
See application file for complete search history.

(56) References Cited

U.S. PATENT DOCUMENTS

| | | | |
|---|---|---|---|
| 5,691,147 A | 10/1997 | Draetta et al. | |
| 8,377,937 B2 | 2/2013 | Bencsik et al. | |
| 8,648,096 B2 | 2/2014 | Muller et al. | |
| 9,809,603 B1 | 11/2017 | Jacques | |
| 9,822,094 B2 | 11/2017 | Man et al. | |
| 2002/0098161 A1 | 7/2002 | Uhrich | |
| 2004/0063773 A1 | 4/2004 | Tang et al. | |
| 2011/0172107 A1 | 7/2011 | Katz et al. | |
| 2011/0196150 A1 | 8/2011 | Man et al. | |
| 2014/0031325 A1 | 1/2014 | Bartlett et al. | |
| 2014/0356322 A1 | 12/2014 | Crews et al. | |
| 2015/0119435 A1 | 4/2015 | Crews et al. | |
| 2015/0274738 A1 | 10/2015 | Gray et al. | |
| 2015/0291562 A1 | 10/2015 | Crew et al. | |
| 2016/0045504 A1 | 2/2016 | Grembecka et al. | |
| 2017/0008904 A1 | 1/2017 | Crew et al. | |
| 2017/0114098 A1 | 4/2017 | Aivado et al. | |
| 2017/0121321 A1* | 5/2017 | Crews | A61K 47/55 |
| 2017/0224685 A1 | 8/2017 | Duncan et al. | |
| 2017/0283807 A1 | 10/2017 | Mounir et al. | |
| 2018/0072741 A1 | 3/2018 | Vechorkin et al. | |
| 2018/0086767 A1 | 3/2018 | Fesik et al. | |
| 2018/0134684 A1 | 5/2018 | Bradner et al. | |
| 2018/0186800 A1 | 7/2018 | Yamamoto et al. | |
| 2019/0092768 A1 | 3/2019 | Gray et al. | |
| 2019/0255041 A1 | 8/2019 | Jin et al. | |
| 2019/0336503 A1 | 11/2019 | Jin et al. | |
| 2019/0367525 A1 | 12/2019 | Ioannidis et al. | |
| 2020/0338070 A1 | 10/2020 | Jin et al. | |
| 2020/0399266 A1 | 12/2020 | Jin et al. | |
| 2021/0261538 A1 | 8/2021 | Jin et al. | |
| 2021/0283261 A1 | 9/2021 | Jin et al. | |
| 2021/0355140 A1 | 11/2021 | Shunatona et al. | |
| 2022/0054488 A1 | 2/2022 | Jin et al. | |
| 2023/0022524 A1 | 1/2023 | Jin et al. | |
| 2023/0070613 A1 | 3/2023 | Jin et al. | |
| 2023/0167106 A1 | 6/2023 | Jin et al. | |
| 2023/0391765 A1 | 12/2023 | Jin et al. | |

FOREIGN PATENT DOCUMENTS

| | | |
|---|---|---|
| CN | 102822165 | 12/2012 |
| CN | 103189067 | 7/2013 |
| CN | 104736569 | 6/2015 |
| CN | 105085620 | 11/2015 |
| CN | 105175284 | 12/2015 |
| CN | 108137507 | 6/2018 |

(Continued)

OTHER PUBLICATIONS

Jieli Wei, Jianping Hu, Li Wang, Ling Xie, Margaret S. Jin, Xian Chen, Jing Liu, and Jian Jin. Discovery of a First-in-Class Mitogen-Activated Protein Kinase Kinase 1/2 Degrader. Journal of Medicinal Chemistry 2019 62 (23), 10897-10911. DOI: 10.1021/acs.jmedchem.9b01528. (Year: 2019).*
J. Popow, et al. Highly Selective PTK2 Proteolysis Targeting Chimeras to Probe Focal Adhesion Kinase Scaffolding Functions. Journal of Medicinal Chemistry 2019 62 (5), 2508-2520 DOI: 10.1021/acs.jmedchem.8b01826 (Year: 2019).*
G. Xue et al. (Protein degradation through covalent inhibitor-based PROTACs. Chem. Commun. 2020 VL 56, IS 10 DO:10.1039/C9CC08238G. "Xue"). (Year: 2020).*
J. Wei, et al. Discovery of a First-in-Class Mitogen-Activated Protein Kinase Kinase 1/2 Degrader. Journal of Medicinal Chemistry 2019, 62 (23), 10897-10911. DOI: 10.1021/acs.jmedchem.9b01528. (Year: 2019).*
C. Herrera-Montavez et al. (MEK 1/2 Targeting PROTACs Promote the Collateral Degradation of CRAF in KRAS Mutant Cells, bioRxiv preprint doi: https://doi.org/10.1101/2023.06.15.545136. (Year: 2023).*
EP Extended European Search Report in European Appln. No. 19821826.5, dated May 3, 2022, 10 pages.

(Continued)

*Primary Examiner* — Bahar Craigo
*Assistant Examiner* — Manahil Mirghani Ali Abdalhameed
(74) *Attorney, Agent, or Firm* — Fish & Richardson P.C.

(57) ABSTRACT

This disclosure relates to heterobifunctional compounds (e.g., bi-functional small molecule compounds), compositions comprising one or more of the heterobifunctional compounds, and to methods of use the heterobifunctional compounds for the treatment of certain disease in a subject in need thereof. The disclosure also relates to methods for identifying such heterobifunctional compounds.

3 Claims, 11 Drawing Sheets

(56) References Cited

FOREIGN PATENT DOCUMENTS

| | | |
|---|---|---|
| CN | 109071552 | 12/2018 |
| CN | 109790143 | 5/2019 |
| CN | 112778303 | 5/2021 |
| JP | 2007-512364 | 5/2007 |
| JP | 2008-525526 | 7/2008 |
| JP | 2009-542721 | 12/2009 |
| JP | 2009-542723 | 12/2009 |
| JP | 2010-532386 | 10/2010 |
| JP | 2010-532387 | 10/2010 |
| JP | 2015-508414 | 3/2015 |
| JP | 2016-540811 | 12/2016 |
| JP | 2017-513862 | 6/2017 |
| JP | 2018-502097 | 1/2018 |
| JP | 2018-526430 | 9/2018 |
| JP | 2019-514883 | 5/2020 |
| MX | 2018000471 | 4/2018 |
| MX | 2018000360 | 6/2018 |
| WO | WO 2008/109104 | 9/2008 |
| WO | WO 2014/100719 | 6/2014 |
| WO | WO 2015/101293 | 7/2015 |
| WO | WO 2015/104677 | 7/2015 |
| WO | WO 2015/192123 | 12/2015 |
| WO | WO 2016/073956 | 5/2016 |
| WO | WO 2016/105518 | 6/2016 |
| WO | WO 2016/106518 | 7/2016 |
| WO | WO 2016/115480 | 7/2016 |
| WO | WO 2016/149668 | 9/2016 |
| WO | WO 2016/168992 | 10/2016 |
| WO | WO 2016/174130 | 11/2016 |
| WO | WO 2016/197032 | 12/2016 |
| WO | WO 2016/208595 | 12/2016 |
| WO | WO 2017/011371 | 1/2017 |
| WO | WO 2017/011590 | 1/2017 |
| WO | WO 2017/024317 | 2/2017 |
| WO | WO 2017/024319 | 2/2017 |
| WO | WO 2017/079267 | 5/2017 |
| WO | WO 2017/147700 | 9/2017 |
| WO | WO 2017/147701 | 9/2017 |
| WO | WO 2017/185031 | 10/2017 |
| WO | WO 2017/197051 | 11/2017 |
| WO | WO 2017/197055 | 11/2017 |
| WO | WO 2018/049200 | 3/2018 |
| WO | WO 2018/098280 | 5/2018 |
| WO | WO 2018/106870 | 6/2018 |
| WO | WO 2018/117177 | 6/2018 |
| WO | WO-2018119441 A1 * 6/2018 ........... A61K 31/427 |
| WO | WO 2019/084030 | 5/2019 |
| WO | WO 2019/222380 | 11/2019 |
| WO | WO 2019/246570 | 12/2019 |
| WO | WO 2020/252043 | 12/2020 |
| WO | WO 2021/021904 | 2/2021 |
| WO | WO 2021/057872 | 4/2021 |
| WO | WO 2023/006063 | 2/2023 |

OTHER PUBLICATIONS

Fisher et al., "Targeted protein degradation and the enzymology of degraders," Current Opinion in Chemical Biology, 2018, 44:47-55.
AU Office Action in Australian Appln. No. 2022201488, dated Feb. 14, 2023, 6 pages.
CN Office Action in Chinese Appln. No. 201980030599.4, dated Jan. 5, 2023, 13 pages (with English Translation).
EP Extended European Search Report in European Appln. No. 20802303.6, dated Dec. 23, 2022, 6 pages.
EP Office Action in European Appln. No. 17863645.2, dated Nov. 11, 2022, 6 pages.
Fioravanti et al., "Six years (2012-2018) of researches on catalytic EZH2 inhibitors: The boom of the 2-pyridone compounds," Manuscript, The Chemical Record, 2018, 18(12):1818-1832.
Kumar et al., "EZH2 Inhibitor GSK126 for Cancer Treatment: Metabolism, drug transporter and rat pharmacokinetic studies," Medical Research Archives, 2015, Issue 3, 31 pages.

PCT Invitation to Pay Additional Fees in International Appln. No. PCT/US2022/050929, dated Feb. 6, 2023, 3 pages.
Stazi et al., "EZH2 inhibitors: a patent review (2014-2016)," Expert Opinion on Therapeutic Patents, 2017, 27(7):797-813.
CN Office Action in Chinese Appln. No. 201780085879.6, dated Jun. 27, 2022, 15 pages (with English Translation).
JP Office Action in Japanese Appln. No. 2019-522841, dated Jul. 12, 2022, 8 pages (with English Translation).
CN Office Action in Chinese Appln. No. 201780081246.8, dated Mar. 4, 2023, 16 pages (with English Translation).
PCT International Search Report and Written Opinion in International Appln. No. PCT/US2022/050929, dated Apr. 7, 2023, 13 pages.
U.S. Appl. No. 16/345,591, filed Apr. 26, 2019, Jian Jin.
U.S. Appl. No. 16/926,418, filed Jul. 10, 2020, Jian Jin.
U.S. Appl. No. 17/978,696, filed Nov. 1, 2022, Jian Jin.
U.S. Appl. No. 16/467,888, filed Jun. 7, 2019, Jian Jin.
U.S. Appl. No. 17/453,619, filed Nov. 4, 2021, Jian Jin.
U.S. Appl. No. 16/769,326, filed Jun. 3, 2020, Jian Jin.
U.S. Appl. No. 16/970,305, filed Aug. 14, 2020, Jian Jin.
U.S. Appl. No. 16/977,654, filed Sep. 2, 2020, Jian Jin.
U.S. Appl. No. 17/938,502, filed Oct. 6, 2022, Jian Jin.
U.S. Appl. No. 17/256,516, filed Dec. 28, 2020, Jian Jin.
U.S. Appl. No. 17/254,345, filed Dec. 21, 2020, Jian Jin.
U.S. Appl. No. 17/604,636, filed Oct. 18, 2021, Jian Jin.
EP Office Action in European Appln. No. 17877800.7, dated May 24, 2022, 6 pages.
PCT International Search Report and Written Opinion in International Appln. No. PCT/US2022/013225, dated Jun. 6, 2022, 24 pages.
Ishoey et al., "Translation Termination Factor GSPT1 Is a Phenotypically Relevant Off-Target of Heterobifunctional Phthalimide Degraders," ACS Chemical Biology, Jan. 22, 2018, 13(3):553-560.
Office Action in Chinese Appln. No. 202080049386.9, mailed on Feb. 2, 2024, 23 pages (with Machine translation).
Abramovich et al., "Hox regulation of normal and leukemic hematopoietic stem cells," Curr. Opin. Hematol., May 2005, 12(3):210-216.
Addie et al., "Discovery of 4-Amino-N-[(1S)-1-(4-chlorophenyl)-3-hydroxypropyl]-1-(7H-pyrrolo[2,3-d]pyrimidin-4-yl)piperidine-4-carboxamide (AZD5363), an Orally Bioavailable, Potent Inhibitor of Akt Kinases," J. Med. Chem., Mar. 2013, 56(5):2059-2073.
Aguilar et al., "Discovery of 4-((3'R,4'S,5'R)-6"-Chloro-4'-(3-chloro-2-fluorophenyl)l'-ethyl-2"-oxodispiro[cyclohexane-1,2'-pyrrolidine-3',3"-indoline]-5'-carboxamido)bicyclo[2.2.2]octane-1-carboxylic Acid (AA-115/APG-115): A Potent and Orally Active Murine Double Minute 2 (MDM2) Inhibitor in Clinical Development," Journal of Medicinal Chemistry, Mar. 2017, 60(7):2819-2839.
Alinari et al., "Selective inhibition of protein arginine methyltransferase 5 blocks initiation and maintenance of B-cell transformation," Blood, Apr. 2015, 125(16):2530-2543.
Alzabin et al., "Hematopoietic progenitor kinase 1 is a critical component of prostaglandin E2-mediated suppression of the antitumor immune response," Cancer Immunol. Immunother., 2010, 59:419-429.
Alzabin et al., "Hematopoietic Progenitor Kinase 1 Is a Negative Regulator of Dendritic Cell Activation," J Immunol, 2009, 182:6187-6194.
Anders et al., "Differential expression analysis for sequence count data," Genome Biol., 2010 11:R106.
Armstrong et al., "MLL translocations specify a distinct gene expression profile that distinguishes a unique leukemia," Nat Genet., Jan. 2002, 30:41-47.
Artinger et al., "An MLL-dependent network sustains hematopoiesis," Proc. Natl. Acad. Sci. USA, Jul. 2013, 110(29):12000-12005.
Asiaban et al., "Cell-Based Ligand Discovery for the ENL YEATS Domain," ACS Chem. Biol., Apr. 2020, 15(4):895-903.
AU Notice of Allowance in Australian Appln. No. 2017348322, dated Dec. 14, 2021, 3 pages.
AU Office Action in Australian Appln. No. 2017348322, dated Dec. 10, 2020, 7 pages.
AU Office Action in Australian Appln. No. 2017348322, dated Sep. 27, 2021, 2 pages.

(56) References Cited

OTHER PUBLICATIONS

Ayton et al., "Molecular mechanisms of leukemogenesis mediated by MLL fusion proteins," Oncogene, Oct. 2001, 20:5695-5707.
Bachman et al., "EZH2 Expression Is Associated With High Proliferation Rate and Aggressive Tumor Subgroups in Cutaneous Melanoma and Cancers of the Endometrium, Prostate, and Breast," J. Clin. Oncol., 2006, 24(2):268-273.
Bai et al., "Targeted degradation of BET proteins in triple-negative breast cancer," Cancer Res., May 1, 2017, 77(9):2476-2487.
Basiorka et al. "Lenalidomide Stabilizes the Erythropoietin Receptor by Inhibiting the E3 Ubiquitin Ligase RNF41," Cancer Res., Apr. 2016, 76:3531-3540.
Bennett et al., "The Role of Nuclear Receptor-Binding SET Domain Family Histone Lysine Methyltransferases in Cancer," Cold Spring Harb. Perspect. Med., Jun. 2017, 7(6):a026708.
Berge et al., "Pharmaceutical Salts," Journal of Pharmaceutical Science, 1997, 66:1-19.
Bilsland et al., "Behavioral and neurochemical alterations in mice deficient in anaplastic lymphoma kinase suggest therapeutic potential for psychiatric indications," Neuropsychopharmacology, 2008, 33:685-700.
Biondi et al., "Biological and therapeutic aspects of infant leukemia.," Blood, Jul. 2000, 96:24-33.
Biswas et al., "Function of leukemogenic mixed lineage leukemia 1 (MLL) fusion proteins through distinct partner protein complexes," Proc. Natl. Acad. Sci. USA, Sep. 2011, 108(38):15751-15756.
Bitoun et al., "The mixed-lineage leukemia fusion partner 10 AF4 stimulates RNA polymerase II transcriptional elongation and mediates coordinated chromatin remodeling," Human Molecular Genetics, Jan. 2007, 16:92-106.
Blake et al., "Discovery and preclinical pharmacology of a selective ATP-competitive Akt inhibitor (GDC-0068) for the treatment of human tumors," J. Med. Chem., Sep. 2012, 55(18):8110-8127.
Bolshan et al., "Synthesis, optimization, and evaluation of novel small molecules as antagonists of WDR5-MLL interaction," ACS Medicinal Chemistry Letters, Mar. 2013, 4(3):353-357.
Bondeson et al., "Catalytic in vivo protein knockdown by small-molecule PROTACs," Nature Chemical Biology, 2015, 11(8):611-617.
Bondeson et al., "Lessons in PROTAC design from selective degradation with a promiscuous warhead," Cell Chem. Biol., Jan. 2018, 25:78-87e5.
Bottcher et al., "Fragment-based discovery of a chemical probe for the PWWP1 domain of NSD3," Nat. Chem. Biol., Aug. 2019, 15:822-829.
Bourdi et al., "Safety Assessment of Metarrestin in Dogs: A Clinical Candidate Targeting a Subnuclear Structure Unique to Metastatic Cancer Cell," Regul. Toxicol. Pharmacol., Aug. 2020, 116:104716.
Bracken et al., "EZH2 is downstream of the pRB-E2F pathway, essential for proliferation and amplified in cancer," EMBO J., 2003, 22(20)5323-5335.
Bradley et al., "EZH2 Inhibitor Efficacy in Non-Hodgkin's Lymphoma Does Not Require Suppression of H3K27 Monomethylation," Chem. Biol., 2014, 21(11):1463-1475.
Brand et al., "Homolog-selective degradation as a strategy to probe the function of CDK6 in AML," Cell Chem. Biol., Feb. 2019, 26(2):300-306e9.
Brauer et al., "Building a better understanding of the intracellular tyrosine kinase PTK6-BRK by BRK," Biochim. Biophys. Acta., Aug. 2010, 1806:66-73.
Braun et al., "Coordinated Splicing of Regulatory Detained Introns within Oncogenic Transcripts Creates an Exploitable Vulnerability in Malignant Glioma," Cancer Cell, Oct. 2017, 32(4):411-426.
Broom et al., "Polycomb repressive complex 2 structure with inhibitor reveals a mechanism of activation and drug resistance," Nat. Commun., Apr. 28, 2016, 7:11384, 12 pages.
Browne et al., "Regulation of peptide-chain elongation in mammalian cells," Eur. J. Biochem., Nov. 2002, 269:5360-5368.
Buckley et al., "HaloPROTACS: use of small molecule PROTACs to induce degradation of HaloTag fusion proteins," ACS Chemical Biology, Aug. 2015, 10(8):1831-1837.
Buckley et al., "Small-molecule control of intracellular protein levels through modulation of the ubiquitin proteasome system," Angew Chem. Int. Ed. Engl., 2014, 53(9):2312-2330.
Buckley et al., "Small-molecule inhibitors of the interaction between the E3 ligase VHL and HIF1α," Angew Chem Int. Ed. Engl., 2012, 51(46):11463-11467.
Buckley et al., "Targeting the von Hippel-Lindau E3 ubiquitin ligase using small molecules to disrupt the VHL/HIF-1α interaction," Journal of the American Chemical Society, 2012, 134(10):4465-4468.
Burkhart et al., "Cellular mechanisms of tumour suppression by the retinoblastoma gene," Nature Reviews Cancer, 2008, 8(9):671-682.
Burnet, "The concept of immunological surveillance, " Progress Exp. Tumor Res., 1970, 13:1-27.
Burslem et al., "Small-molecule modulation of protein homeostasis," Chem. Rev., Aug. 2017, 117(17):11269-11301.
Burslem et al., "The advantages of targeted protein degradation over inhibition: An RTK case study," Cell Chem. Biol., Jan. 2018, 25:67-77e3.
Cai et al., "Subunit composition and substrate specificity of a MOF-containing histone acetyltransferase distinct from the male-specific lethal (MSL) complex," The Journal of Biological Chemistry, Feb. 2010, 285(7):4268-4272.
Cai et al., "ZFX Mediates Non-canonical Oncogenic Functions of the Androgen Receptor Splice Variant 7 in Castrate-Resistant Prostate Cancer," 2018, Mol. Cell 72, 341-354 e346.
Campbell et al., "EPZ011989, A Potent, Orally-Available EZH2 Inhibitor with Robust in Vivo Activity," ACS Med. Chem. Lett., 2015, 6(5):491-495.
Cao et al., "Regulation and functional role of eEF1A2 in pancreatic carcinoma," Biochem. Biophys. Res. Commun., 2009, 380(1):11-16.
Cao et al., "Role of Histone H3 Lysine 27 Methylation in Polycomb-Group Silencing," Science, 2002, 298(5595):1039-1043.
Cao et al., "Targeting MLL1 H3K4 methyltransferase activity in mixed-lineage leukemia," Molecular Cell, Jan. 2014, 53(2):247-261.
Cappuzzo et al., "Erlotinib as maintenance treatment in advanced non-small-cell lung cancer: a multicentre, randomised, placebo-controlled phase 3 study," Lancet Oncol., Jun. 2010, 11:521-529.
Cardenas et al., "Enantioselective Synthesis of Pyrrolopyrimidine Scaffolds through Cation-Directed Nucleophilic Aromatic Substitution," Org. Lett., Mar. 2018, 20:2037-2041.
Carugo et al., "In vivo functional platform targeting patient-derived xenografts identifies WDR5-Myc association as a critical determinant of pancreatic cancer," Cell Reports, Jun. 2016, 16(1):133-147.
Castro et al., "Breast tumor kinase and extracellular signal-regulated kinase 5 mediate Met receptor signaling to cell migration in breast cancer cells," Breast Cancer Research, 2010, 12:R60, 15 pages.
Chamberlain et al., "Structure of the human Cereblon-DDB1-lenalidomide complex reveals basis for responsiveness to thalidomide analogs," Nat. Struct. Mol. Biol., 2014, 21(9):803-809.
Chang et al., "EZH2 promotes expansion of breast tumor initiating cells through activation of RAF1-β-catenin signaling, " Cancer Cell, 2011, 19(1):86-100.
Chan-Penebre et al., "A selective inhibitor of PRMT5 with in vivo and in vitro potency in MCL models," Nature Chemical Biology, Apr. 2015, 11:432-437.
Chau et al., "An Anatomical Site and Genetic-Base Prognostic Model for Patients With Nuclear Protein in Testis (NUT) Midline Carcinoma: Analysis of 124 Patients," JNCI Cancer Spectr 4, 2020, pkz094 2020.
Chawade et al., "Normalyzer: a tool for rapid evaluation of normalization methods for omics data sets," J. Proteome. Res., 2014, 13:3114-31202014.
Chen et al., "Design, synthesis, and initial evaluation of affinity-based small molecular probe for detection of WDR5," Bioorganic Chemistry, Feb. 2018, 76:380-385.
Chen et al., "Gene expression profiling of WDR5 regulated genes in bladder cancer," Genomics Data, Sep. 2015, 5:27-29.

(56) References Cited

OTHER PUBLICATIONS

Chen et al., "PTK6 promotes hepatocellular carcinoma cell proliferation and invasion," Am. J. Transl. Res., Oct. 2016, (10):4354-4361.
Chen et al., "Upregulated WDR5 promotes proliferation, self-renewal and chemoresistance in bladder cancer via mediating H3K4 trimethylation," Scientific Reports, Feb. 2015, 5: 12 pages.
Chi et al., "Covalent histone modifications—miswritten, misinterpreted and mis-erased in human cancers," Nat. Rev. Cancer, 2010, 10:457-469.
Choi et al., "EML4-ALK mutations in lung cancer that confer resistance to ALK inhibitors," N. Engl. J. Med., Oct. 2010, 363(18):1734-1739.
Choi et al., "Identification of novel isoforms of the EML4-ALK transforming gene in non-small cell lung cancer," Cancer Res., Jul. 2008, 68(13):4971-4976.
Christott et al., "Discovery of a Selective Inhibitor for the YEATS Domains of ENL/AF9.," SLAS Discov., 2019, 24:133-141.
Chung et al., "Cbx8 acts non-canonically with Wdr5 to promote mammary tumorigenesis," Cell Reports, Jul. 2016, 16(2):472-486.
Clinicaltrials.gov [online], "Metarrestin (ML-246) in Subjects with Metastatic Solid Tumors," Jan. 10, 2020, retrieved on Mar. 16, 2022, retrieved from URL<https://clinicaltrials.gov/ct2/show/NCT04222413>, 12 pages.
CN Office Action in Chinese Appln. No. 201780081246.8, dated Dec. 2, 2021, 18 pages (with English Translation).
CN Office Action in Chinese Appln. No. 201780081246.8, dated Jun. 4, 2021, 19 pages (with English Translation).
CN Office Action in Chinese Appln. No. 201780085879.6, dated Jan. 5, 2022, 18 pages (with English Translation).
Corthay, "Does the immune system naturally protect against cancer?" Front. Immunol., May 2014, 5(197):1-8.
Cromm et al., "Addressing kinase-independent functions of Fak via PROTAC-mediated degradation," J. Am. Chem. Soc., Nov. 2018, 140(49):17019-17026.
Cromm et al., "Targeted protein degradation: from chemical biology to drug discovery," Cell Chem. Biol., Sep. 2017, 24(9):1181-1190.
Czermin et al., "*Drosophila* enhancer of Zeste/ESC complexes have a histone H3 methyltransferase activity that marks chromosomal Polycomb sites," Cell, 2002, 111(2):185-196.
Dai et al., "WDR5 expression is prognostic of breast cancer outcome," PLoS One, Sep. 2015, 10: 15 pages.
Davies et al., "Monoacidic Inhibitors of the Kelch-like ECH-Associated Protein 1: Nuclear Factor Erythroid 2-Related Factor 2 (KEAP1 :NRF2) Protein-Protein Interaction with High Cell Potency Identified by Fragment-Based Discovery," Journal of Medicinal Chemistry, Apr. 2016, 59(8):3991-4006.
Dawson et al., "Inhibition of BET recruitment to chromatin as an effective treatment for MLL-fusion leukaemia," Nature, 2011, 478:529-15 533.
Deng et al., "Protein arginine methyltransferase 5 functions as an epigenetic activator of the androgen receptor to promote prostate cancer cell growth," Oncogene, 2017, 36:1223-1231.
Derry et al., "Altered localization and activity of the intracellular tyrosine kinase BRK/Sik in prostate tumor cells," Oncogene, Jul. 2003, 22:4212-4220.
Deshpande et al., "Chromatin modifications as therapeutic targets in MLL-rearranged leukemia," Trends Immunol., Nov. 2012, 33(11):563-570.
Dias et al., "Structural analysis of the KANSL1/WDR5/KANSL2 complex reveals that WDR5 is required for efficient assembly and chromatin targeting of the NSL complex," Genes & Development, May 2014, 28(9):929-942.
Douglass, Jr. et al., "A comprehensive mathematical model for three-body binding equilibria," J. Am. Chem. Soc., Apr. 2013, 135(16):6092-6099.
Du et al., "FOXC1, a target of polycomb, inhibits metastasis of breast cancer cells," Breast Cancer Res. Treat., 2012, 131(1):65-73.

Duanmin et al., "eEF1A2 protein expression correlates with lymph node metastasis and decreased survival in pancreatic ductal adenocarcinoma," Hepatogastroenterology, Jun. 2013, 60(124):870-875.
Dumble et al., "Discovery of novel AKT inhibitors with enhanced anti-tumor effects in combination with the MEK inhibitor," PloS One, Jun. 2014, 9(6), 11 pages.
EA Office Action in Eurasian Appln. No. 201991071, dated Jun. 10, 2020, 4 pages (with English translation).
Ee et al., "An embryonic stem cell-specific NuRD complex functions through interaction with WDR5," Stem Cell Reports, Jun. 2017, 8(6): 9 pages.
EP Extended European Search Report in European Appln. No. 17863645.2, dated Aug. 6, 2020, 10 pages.
EP Extended European Search Report in European Appln. No. 17877800.7, dated Feb. 19, 2021, 9 pages.
EP Extended European Search Report in European Appln. No. 19757825.5, dated Jan. 26, 2022, 14 pages.
EP Extended European Search Report in European Appln. No. 19763958.6, dated Dec. 8, 2021, 12 pages.
EP Extended European Search Report in European Appln. No. 19830269.7, dated Mar. 7, 2022, 6 pages.
EP Office Action in European Appln. No. 17863645.2, dated Apr. 6, 2021, 7 pages.
EP Office Action in European Appln. No. 17863645.2, dated Mar. 11, 2022, 5 pages.
EP Office Action in European Appln. No. 19821826.5, dated Jan. 13, 2022, 4 pages.
EP Partial Supplementary Search Report in European Appln. No. 19757825.5, dated Oct. 18, 2021, 16 pages.
Erb et al. (2017). Transcription control by the ENL YEATS domain in acute leukaemia. Nature 543, 270-274.
Fabian et al., "A small molecule-kinase interaction map for clinical kinase inhibitors," Nat. Biotechnol., Mar. 2005, 23(3):329-336.
Fan et al., "A Kinase Inhibitor Targeted to mTORC1 Drives Regression in Glioblastoma," Cancer Cell, Mar. 2017, 31(3):424-435.
Fan et al., "BAHCC1 binds H3K27me3 via a conserved BAH module to mediate gene silencing and oncogenesis," Nature genetics, 2020, 52:1384-1396.
fda.gov [online], "Data Standards Manual (Monographs)," Feb. 27, 2018, retrieved on Feb. 7, 2022, retrieved from URL <https://www.fda.gov/drugs/electronic-regulatory-submission-and-review/data-standards-manual-monographs>, 1 page.
fda.gov [online], "Development & Approval Process | Drugs," Oct. 28, 2019, retrieved on Feb. 4, 2022, retrieved from URL <https://www.fda.gov/drugs/development-approval-process-drugs>, 4 pages.
Fei et al., "PROTAC and its Application in the Treatment of Cancer," Chemistry of Life, Aug. 2014, 34(4):549-554 (with English abstract).
Ferguson et al., "Kinase inhibitors: the road ahead," Nat. Rev. Drug Discov., May 2018, 17:353-377.
Ferrando et al., "Gene expression signatures in MLL-rearranged T-lineage and B-precursor acute leukemias: dominance of HOX dysregulation," Blood, Jul. 2003, 102(1):262-268.
Finn et al., "The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study," The Lancet Oncology, 2015, 16(1):25-35.
Fischer et al., "Structure of the DDB1-CRBN E3 ubiquitin ligase in complex with thalidomide," Nature, Aug. 2014, 512(7512):49-53.
Frankowski et al., "Metarrestin, a perinucleolar compartment inhibitor, effectively suppresses metastasis," Science Translational Medicine, May 2018, 10(441), 13 pages.
Frost et al., "Potent and selective chemical probe of hypoxic signalling downstream of HIF-α hydroxylation via VHL inhibition," Nat. Commun., Nov. 2016, 7:13312, 12 pages.
Fujii et al., "Enhancer of Zeste Homologue 2 (EZH2) Down-regulates RUNX3 by Increasing Histone H3 Methylation," J. Biol. Chem., 2008, 283(25):17324-17332.

(56) References Cited

OTHER PUBLICATIONS

Fujii et al., "MEKERK pathway regulates EZH2 overexpression in association with aggressive breast cancer subtypes," Oncogene, 2011, 30(39):4118-4128.
Gadd et al., "A Children's Oncology Group and TARGET initiative exploring the genetic landscape of Wilms tumor," Nat. Genet., Oct. 2017, 49:1487-1494.
Galdeano et al., "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities," J. Med. Chem., 2014, 57(20):8657-8663.
Gao et al., "ZLD1122, a novel EZH2 and EZH1 small molecular inhibitor, blocks H3K27 methylation and diffuse large B cell lymphoma cell growth," RSC Adv., 2016, 6:28512-28521.
Garapaty-Rao et al., "Identification of EZH2 and EZH1 small molecule inhibitors with selective impact on diffuse large B cell lymphoma cell growth," Chem. Biol., 2013, 20(11):1329-1339.
Garnar-Wortzel et al., "Chemical Inhibition of ENL/AF9 YEATS Domains in Acute Leukemia," ACS Central Science, Apr. 2021, 7(5):815-830.
Ge et al., "WDR5 high expression and its effect on tumorigenesis in leukemia," Oncotarget, Jun. 2016, 7(25):37740-37754.
Gehling et al., "Discovery, design, and synthesis of indole-based EZH2 inhibitors," Bioorg. Med. Chem. Lett., 2015, 25(17):3644-3649.
Genscript.com [online], "Gen Script Make Research Easy," available on or before Mar. 3, 2015, retrieved on Mar. 17, 2022, retrieved from URL<https://www.genscript.com/gRNAdatabase.html>.
Getlik et al., "Structure-based optimization of a small molecule antagonist of the interaction between WD repeat-containing protein 5 (WDR5) and mixed-lineage leukemia 1 (MLL1)," Journal of Medicinal Chemistry, Mar. 2016, 59(6):2478-2496.
Gillis et al., "Biochemical and biological characterization of lymphocyte regulatory molecules; V. Identification of an interleukin 2-producing human leukemia T cell line," The Journal of experimental medicine, Dec. 1980,152:1709-1719.
Github.com [online], "PreprocessCore," Oct. 26, 2021, retrieved on Mar. 17, 2022, retrieved from URL<Gihttps://github.com/bmbolstad/preprocessCore>, 1 pages.
Github.com [online], "ProteiNorm," Jul. 27, 2020, retrieved on Mar. 17, 2022, retrieved from URL <https://github.com/ByrumLab/proteiNorm>, 3 page.
Gluz et al., "Triplenegative breast cancer—current status and future directions," Ann. Oncol., 2009, 20(12):1913-1927.
Godin-Heymann et al., "The T790M 'gatekeeper' mutation in EGFR mediates resistance to low concentrations of an irreversible EGFR inhibitor," Mol. Cancer Ther., Apr. 2008, 7(4):874-879.
Gonzalez et al., "Downregulation of EZH2 decreases growth of estrogen receptor-negative invasive breast carcinoma and requires BRCA1," Oncogene, 2009, 28(6):843-853.
Gonzalez et al., "EZH2 expands breast stem cells through activation of NOTCH1 signaling," Proc. Natl. Acad. Sci. USA, 2014, 111(8):3098-3103.
Grabe et al., "C797S Resistance: The undruggable EGFR mutation in non-small cell lung cancer?" ACS Med. Chem. Lett., 2018, 9:779-782.
Grebien et al., "Pharmacological targeting of the Wdr5-MLL interaction in C/EBPα N-terminal leukemia," Nature Chemical Biology, Aug. 2015, 11(8): 11 pages.
Guarnaccia et al., "Moonlighting with WDR5: A cellular multitasker," Journal of Clinical Medicine, Feb. 2018, 7(2): 17 pages.
Gullà et al., "Protein arginine methyltransferase 5 has prognostic relevance and is a druggable target in multiple myeloma," Leukemia, 2018, 32:996-1002.
Haegebarth et al., "Protein tyrosine kinase 6 negatively regulates growth and promotes enterocyte differentiation in the small intestine," Mol. Cell Biol., Jul. 2006, 26:4949-4957.

Hallberg et al., "Mechanistic insight into ALK receptor tyrosine kinase in human cancer biology," Nature Reviews Cancer, Oct. 2013, 13:685-700.
Hamilton et al., "Targeting CDK4/6 in patients with cancer," Cancer Treatment Reviews, 2016, 45:129-138.
Han et al., "Discovery of ARD-69 as a Highly Potent Proteolysis Targeting Chimera (PROTAC) Degrader of Androgen Receptor (AR) for the Treatment of Prostate Cancer," Journal of Medicinal Chemistry, Jan. 2019, 62:941-964.
Harvey et al., "Brk protects breast cancer cells from autophagic cell death induced by loss of anchorage," The American Journal of Pathology, Sep. 2009, 175:1226-1234.
Harvey et al., "Use of RNA interference to validate Brk as a novel therapeutic target in breast cancer: Brk promotes breast carcinoma cell proliferation," Oncogene, Aug. 2003, 22:5006-5010.
He et al., "HIV-1 Tat and Host AFF4 Recruit Two Transcription Elongation Factors into a Bifunctional Complex for Coordinated Activation of HIV-I Transcription," Mol. Cell., May 2010, 38(3):428-438.
He et al., "Human Polymerase-Associated Factor complex (PAFc) connects the Super Elongation Complex (SEC) to RNA polymerase II on chromatin," Proc. Natl. Acad. Sci. USA, Sep. 2011, 108(36):E636-E645.
Heerding et al., "Identification of 4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol (GSK690693), a novel inhibitor of AKT kinase," Journal of Medicinal Chemistry, Sep. 2008, 51(18):5663-5679.
Heidenreich et al., "Structure-Based Approach toward Identification of Inhibitory Fragments for Eleven-Nineteen-Leukemia Protein (ENL)," J. Med. Chem., Nov. 2018, 61(23):10929-10934.
Henning et al., "Degradation of Akt using protein-catalyzed capture agent," Journal of Peptide Science, 2016, 22:196-200.
Herbst et al., "Gefitinib—a novel targeted approach to treating cancer," Nat. Rev. Cancer, Dec. 2004, 4:956-965.
Hernandez et al., "The Kinase Activity of Hematopoietic Progenitor Kinase 1 Is Essential for the Regulation of T Cell Function," Cell reports, Oct. 2018, 25:80-94.
Herrera-Abreu et al., "Early adaptation and acquired resistance to CDK4/6 inhibition in estrogen receptor-positive breast cancer," Cancer Research, 2016, 76(8):2301-2313.
Hess, "MLL: a histone methyltransferase disrupted in leukemia," Trends Mol. Med., Oct. 2004, 10(10):500-507.
Higa et al., "CUL4-DDB 1 ubiquitin ligase interacts with multiple WD40-repeat proteins and regulates histone methylation," Nature Cell Biology, Nov. 2006, 8(11):1277-1283.
Hirai et al., "MK-2206, an allosteric Akt inhibitor, enhances antitumor efficacy by standard chemotherapeutic agents or molecular targeted drugs in vitro and in vivo," Molecular Cancer Therapeutics, Jul. 2010, 9(7):1956-1967.
Hiroyuki et al., "The structure of bestatin," The Journal of Antibiotics, Jan. 1976, 29(1):100-101.
Hirsch et al., "Lung cancer: current therapies and new targeted treatments," Lancet, Jan. 2017, 389:299-311.
Holm et al., "Global H3K27 trimethylation and EZH2 abundance in breast tumor subtypes," Mol. Oncol., 2012, 6(5):494-506.
Hsu et al., "Recognition of histone acetylation by the GAS41 YEATS domain promotes H2A.Z deposition in non-small cell lung cancer," Genes Dev., 2018, 32:58-69.
Hu et al., "Human HPK1, a novel human hematopoietic progenitor kinase that activates the JNK/SAPK kinase cascade," Genes Dev., Sep. 1996, 10:225 1-2264.
Hu et al., "Small Molecule Inhibitors of Protein Arginine Methyltransferases," Expert Opinion Investigational Drugs, 2016, 25:335-358.
Huang et al., "A Chemoproteomic Approach to Query the Degradable Kinome Using a Multi-kinase Degrader," Cell Chemical Biology, Jan. 2018, 25(1):88-99.
Huang et al., "Covalent inhibition of NSD1 histone methyltransferase," Nat. Chem. Biol, 2020, 16:1403-1410.
Huber et al., "Variance stabilization applied to microarray data calibration and to the quantification of differential expression," Bioinformatics, 2002, 18 Suppl 1:S96-104.

(56) References Cited

OTHER PUBLICATIONS

IN Office Action in Indian Appln. No. 201917020814, dated Jun. 23, 2021, 6 pages (with English Translation).
Irie et al., "PTK6 regulates IGF-1-induced anchorage-independent survival," PLoS One, Jul. 2010, 5(7):e11729.
Ito et al., "Identification of a primary target of thalidomide teratogenicity," Science, Mar. 2010, 327(5971):1345-1350.
Ito et al., "PTK6 Inhibition Suppresses Metastases of Triple-Negative Breast Cancer via SNAIL-Dependent E-Cadherin regulation," Cancer Res., Aug. 2016, 76:4406-4417.
Ito et al., "PTK6 regulates growth and survival of endocrine therapy-resistant ER+ breast cancer cells," NPJ Breast Cancer, Nov. 2017, 3:45.
Iwahara et al., "Molecular characterization of ALK, a receptor tyrosine kinase expressed specifically in the nervous system," Oncogene, Jan. 30, 1997, 14:439-449.
Jakobsson et al., "The dual methyltransferase METTL13 targets N terminus and Lys55 of eEF1A and modulates codon-specific translation rates," Nature Communications, Aug. 2018, 15 pages.
Jiang et al., "Development of dual and selective degraders of cyclin-dependent kinases 4 and 6," Angew. Chem. Int. Ed. Engl., May 2019, 58(19):6321-6326.
Jiang et al., "Targeting BRK-Positive Breast Cancers with Small-Molecule Kinase Inhibitors," Cancer Res., Jan. 2017, 77:175-186.
Jiao et al., "Structural basis of histone H3K27 trimethylation by an active polycomb repressive complex 2," Science, 2015, 350(6258):aac4383.
Jin et al., "Targeting methyltransferase PRMT5 eliminates leukemia stem cells in chronic myelogenous leukemia, " The Journal of Clinical Investigation, Oct. 2016, 126:3961-3980.
JP Office Action in Japanese Appln. No. 2019-522841, dated Oct. 5, 2021, 14 pages (with English Translation).
JP Office Action in Japanese Appln. No. 2019-530811, dated Dec. 14, 2021, 4 pages (with English Translation).
Jude et al., "Unique and independent roles for MLL in adult hematopoietic stem cells and progenitors," Cell Stem Cell, Sep. 2007, 1(3):324-337.
Justin et al., "Structural basis of oncogenic histone H3K27M inhibition of human polycomb repressive complex 2," Nat. Commun., 2016, 7:11316.
Kanda et al., "Protein arginine methyltransferase 5 is associated with malignant phenotype and peritoneal metastasis in gastric cancer," International Journal of Oncology, Jun. 2016, 49:1195-1202.
Kanis et al., "A small molecule inhibitor of the perinucleolar compartment, ML246, attenuates growth and spread of ovarian cancer," Gynecol. Oncol. Res. Pract., 2018, 5:7.
Kanis et al., "Metarrestin: A novel compound active against ovarian cancer," Gynecol Oncol., Oct. 2015, 139(1):190.
Kaniskan et al., "Inhibitors of Protein Methyltransferases and Demethylases," Chem. Rev., 2018, 118(3):989-1068.
Kaniskan et al., "Selective inhibitors of protein methyltransferases," Journal of Medicinal Chemistry, 2015, 58:1596-1629.
Karatas et al., "Discovery of a highly potent, cell-permeable macrocyclic peptidomimetic (MM-589) targeting the WD repeat domain 5 protein (WDR5)-mixed lineage leukemia (MLL) protein-protein interaction," Journal of Medicinal Chemistry, Jun. 2017, 60(12):4818-4839.
Khalyfa et al., "Characterization of elongation factor-1A (eEF1A-1) and eEF1A-2/S1 protein expression in normal and wasted mice," Journal of Biological Chemistry, 2001, 276:22915-22922.
Kiefer et al., "HPKI, a hematopoietic protein kinase activating the SAPK/JNK pathway," EMBO J., Dec. 1996, 15(24):7013-7025.
Kim et al., "Targeted disruption of the EZH2-EED complex inhibits EZH2-dependent cancer" Nature Chemical Biology, 2013, 9:643-650.
Kim et al., "Targeting EZH2 in cancer," Nat. Med., 2016, 22(2):128-134.
Kleer et al., "EZH2 is a marker of aggressive breast cancer and promotes neoplastic transformation of breast epithelial cells," PNAS, 2003, 100(20):11606-11611.
Klein et al., "Yaf9 subunit of the NuA4 and SWR1 complexes targets histone H3K27ac through its YEATS domain," Nucleic Acids Res., Jan. 2018, 46:421-430.
Knutson et al., "A selective inhibitor of EZH2 blocks H3K27 methylation and kills mutant lymphoma cells," Nat. Chem. Biol., 8(11):890-896.
Knutson et al., "Durable tumor regression in genetically altered malignant rhabdoid tumors by inhibition of methyltransferase EZH2," Proc. Natl. Acad. Sci. USA., 2013, 110(19):7922-7927.
Kobayashi et al., "EGFR mutation and resistance of non-small-cell lung cancer to gefitinib," N. Engl. J. Med., Feb. 2005, 352(8):786-792.
Koivunen et al., "EML4-ALK fusion gene and efficacy of an ALK kinase inhibitor in lung cancer," Clinical Cancer Research, Jul. 1, 2008, 14(13):4275-4283.
Konze et al., "An Orally Bioavailable Chemical Probe of the Lysine Methyltransferases EZH2 and EZHI," ACS Chem. Biol., 2013, 8(6):1324-1334.
Krause et al., "Tyrosine kinases as targets for cancer therapy," N. Engl. J. Med., Jul. 2005, 353(2):172-187.
Krivtsov et al., "MLL translocations, histone modifications and leukaemia stem-cell development," Nat. Rev. Cancer, Nov. 2007, 7:823-833.
Kryukov et al., "MTAP deletion confers enhanced dependency on the PRMT5 arginine methyltransferase in cancer cells," Science, 2016, 351(6278):1214-1218.
Kuenzi et al., "Polypharmacology-based ceritinib repurposing using integrated functional proteomics," Nat. Chem. Biol., Dec. 2017, 13(12):1222-1231.
Kung et al., "Design and Synthesis of Pyridone-Containing 3,4-Dihydroisoquinoline-1(2H)-ones as a Novel Class of Enhancer of Zeste Homolog 2 (EZH2) Inhibitors," J. Med. Chem., 2016, 59(18):8306-8325.
Kuzmichev et al., "Histone methyltransferase activity associated with a human multiprotein complex containing the Enhancer of Zeste protein," Genes Dev., 2002, 16(22):2893-2905.
Kwak et al., "Anaplastic lymphoma kinase inhibition in non-small-cell lung cancer," New England Journal of Medicine, Oct. 28, 2010, 363(18):1693-1703.
Lai et al., "Induced protein degradation: an emerging drug discovery paradigm," Nat. Rev. Drug Discov., Feb. 2017, 16(2):101-114.
Lai et al., "Modular PROTAC design for the degradation of oncogenic BCR-ABL," Angewandte Chemie International Edition English, Jan. 2016, 55(2):807-810.
Lapierre et al., "Discovery of 3-(3-(4-(1-Aminocyclobutyl)phenyl)-5-phenyl-3H-imidazo[4,5-b]pyridin-2-yl)pyridin-2-amine (ARQ 092): An orally bioavailable, selective, and potent allosteric AKT inhibitor," Journal of Medicinal Chemistry, 2016, 59:6455-6469.
Lebraud et al., "Protein Degradation by In-Cell Self-Assembly of Proteolysis Targeting Chimeras," ACS Central Science, 2016, 2:927-934.
Li et al., "AF9 YEATS domain links histone acetylation to DOTIL-mediated H3K79 methylation," Cell, Oct. 2014, 159(3):558-571.
Li et al., "Discovery of MD-224 as a first-in-class, highly potent, and efficacious proteolysis targeting chimera Murine Double Minute 2 degrader capable of achieving complete and durable tumor regression," J. Med. Chem., 2019, 62(2):448-466.
Li et al., "Discovery of potent and noncovalent reversible EGFR kinase inhibitors of EGFR$^{L858R/T790M/C797S}$," ACS Med. Chem. Lett., Jun. 2019, 10(6):869-873.
Li et al., "High-affinity small molecular blockers of mixed lineage leukemia 1 (MLL1)-WDR5 interaction inhibit MILL1 complex H3K4 methyltransferase activity," European Journal of Medicinal Chemistry, Nov. 2016, 124:480-489.
Li et al., "Molecular Coupling of Histone Crotonylation and Active Transcription by AF9 YEATS Domain," Mol. Cell., Apr. 2016, 62(2):181-193.
Li et al., "RSEM: accurate transcript quantification from RNA-Seq data with or without a reference genome," BMC Bioinformatics, 2011, 12:323.

(56) References Cited

OTHER PUBLICATIONS

Li et al., "Structure-based design and synthesis of small molecular inhibitors disturbing the interaction of MLL1-WDR5," European Journal of Medicinal Chemistry, Aug. 2016, 118:1-8.
Li et al., "Structure-guided development of YEATS domain inhibitors by targeting π-π-π stacking," Nat. Chem. Biol., Dec. 2018, 14:1140-1149.
Li et al., "The OncoPPi network of cancer-focused protein-protein interactions to inform biological insights and therapeutic strategies," Nat. Commun., Feb. 2017, 8:14356.
Li et al., "Understanding histone H3 lysine 36 methylation and its deregulation in disease," Cell. Mol. Life Sci., Aug. 2019, 76(15):2899-2916.
Li et al., "ZMYND11-MBTD1 induces leukemogenesis through hijacking NuA4/TIP60 acetyltransferase complex and a PWWP-mediated chromatin association mechanism," Nat. Commun., 2021, 12(1), 18 pages.
Lim et al., "CDK4/6 inhibitors: promising opportunities beyond breast cancer," Cancer Discovery, 2016, 6(7):697-699.
Lin et al., "AFF4, a component of the ELL/PTEFb elongation complex and a shared subunit of MLL chimeras, can link transcription elongation to leukemia," Mol. Cell., Feb. 2010, 37(3):429-437.
Lin et al., "Clinicopathologic features, patterns of recurrence, and survival among women with triple-negative breast cancer in the National Comprehensive Cancer Network," Cancer, 2012, 118(22):5463-5472.
Lin et al., "Targeting ALK: Precision Medicine Takes on Drug Resistance," Cancer Discovery, Feb. 2017, 7(2):137-155.
Ling et al., "Involvement of hematopoietic progenitor kinase 1 in T cell receptor signaling," The Journal of biological chemistry, Jun. 2001, 276:18908-18914.
Liou et al., "HPK1 is activated by lymphocyte antigen receptors and negatively regulates AP-1," Immunity, Apr. 2000, 12(4):399-408.
Liu et al., "Calcineurin is a common target of cyclophilin-cyclosporin A and FKBP-FK506 complexes," Cell, Aug. 1991, 66(4):807-815.
Liu et al., "Critical role of kinase activity of hematopoietic progenitor kinase 1 in anti-tumor immune surveillance," PloS one, Mar. 2019, 14:e02 12670.
Liu et al., "METTL13 Methylation of eEF1A Increases Translational Output to Promote Tumorigenesis," Cell, Jan. 2019, 176:491-504.e421.
Liu et al., "Widening Synthesis Bottlenecks: Realization of Ultrafast and Continuous-Flow Synthesis of High-Silica Zeolite SSZ-13 for NOx Removal," Angew. Chem., May 4, 2015, 127(19):5775-5779.
Losada et al., "Binding of eEF1A2 to the RNA-dependent protein kinase PKR modulates its activity and promotes tumour cell survival," British Journal of Cancer, Nov. 2018, 119(11):1410-1420.
Lu et al., "Epigenetic Perturbations by Arg882-Mutated DNMT3A Potentiate Aberrant Stem Cell Gene-Expression Program and Acute Leukemia Development," Cancer Cell, 2016, 30:92-107.
Lu et al., "Hijacking the E3 ubiquitin ligase cereblon to efficiently target BRD4," Chemistry & Biology, Jun. 2015, 22(6):755-763.
Lu et al., "Targeting EGFR$^{L858R/T790M}$ and EGFR$^{L858R/T790M/C797S}$ resistance mutations in NSCLC: Current developments in medicinal chemistry," Med. Res. Rev., Jan. 2018, 38(5):1550-1581.
Mahara et al., "HIFI-α activation underlies a functional switch in the paradoxical role of Ezh2/PRC2 in breast cancer," PNAS, 2016, 113(26):E3735-E3744.
Mahmoud et al., "Discovery of 4-anilino α-carbolines as novel Brk inhibitors," Bioorganic & Medicinal Chemistry Letters, Apr. 2014, 24:1948-1951.
Majer et al., "A687V EZH2 is a gain-offunction mutation found in lymphoma patients, " FEBS Lett., 2012, 586(19):3448-3451.
Maniaci et al., "Homo-PROTACs: bivalent small-molecule dimerizers of the VHL E3 ubiquitin ligase to induce self-degradation," Nature Communication, Oct. 2017, 8, 14 pages.
Manning et al., "AKT/PKB signaling: navigating the network," Cell, Apr. 2017, 169(3):381-405.

Marjon et al., "MTAP Deletions in Cancer Create Vulnerability to Targeting of the MAT2A/PRMT5/RIOK1 Axis," Cell Reports, Apr. 2016, 15:574-587.
Marschalek, "MLL Leukemia and Future Treatment Strategies," Arch. Pharm. Chem. Life Sci., Apr. 2015, 348(4):221-228.
Matsushime et al., "Identification and properties of an atypical catalytic subunit (p34$^{PSK-J3}$/cdk4) for mammalian D type Gl cyclins," Cell, 1992, 71(2):323-334.
Mavrakis et al., "Disordered methionine metabolism in MTAP/CDKN2A-deleted cancers leads to dependence on PRMT5," Science, Feb. 2016, 351(6278):1208-1213.
Mcalpine et al., "Abstract 4857: Discovery of PF-06855800, a SAM competitive PRMT5 inhibitor with potent antitumor activity," American Association for Cancer Research Annual Meeting, 2018, 78(13 Supplement), 4 pages.
McCabe et al., "EZH2 inhibition as a therapeutic strategy for lymphoma with EZH2-activating mutations," Nature, 2012, 492(7427):108-112.
McCabe et al., "Mutation of A677 in histone methyltransferase EZH2 in human B-cell lymphoma promotes hypertrimethylation of histone H3 on lysine 27 (H3K27)," Proc. Natl. Acad. Sci. USA, 2012, 109(8):2989-2994.
Meyer et al., "New insights to the MLL recombinome of acute leukemias," Leukemia, Aug. 2009, 23:1490-1499.
Meyer et al., "The MLL recombinome of acute leukemias in 2013," Leukemia, Nov. 2013, 27:2165-2176.
Meyer et al., "The MLL recombinome of acute leukemias," Leukemia, May 2006, 20:777-784.
Meyerson et al., "Identification of $G_1$ kinase activity for cdk6, a novel cyclin D partner," Molecular and Cellular Biology. 1994, 14(3):2077-2086.
Mi et al., "YEATS2 links histone acetylation to tumorigenesis of non-small cell lung cancer," Nat. Commun., Oct. 2017, 8:1088, 14 pages.
Migliori et al., "Symmetric dimethylation of H3R2 is a newly identified histone mark that supports euchromatin maintenance," Nature Structural and Molecular Biology, Feb. 2012, 19(2):136-144.
Miller et al., "COMPASS: a complex of proteins associated with atrithorax-related SET domain protein," Proceedings of the National Academy of Sciences, Nov. 2001, 98(23):12902-12907.
Mitchell et al., "Cloning and characterisation of cDNAs encoding a novel non-receptor tyrosine kinase, brk, expressed in human breast tumours," Oncogene, Aug. 1994, 9:2383-2390.
Mohan et al., "Licensed to elongate: a molecular mechanism for MLL-based leukaemogenesis," Nat. Rev. Cancer, Oct. 2010, 10:721-728.
Mohan et al., "Linking H3K79 trimethylation to Wnt signaling through a novel Dot1-containing complex (DotCom)," Genes Dev., 2010, 24:574-589.
Molander et al., "Efficient hydrolysis of organotrifluoroborates via silica gel and water," Journal of Organic Chemistry, Oct. 2009, 74(19):364-7369.
Morin et al., "Somatic mutations altering EZH2 (Y641) in follicular and diffuse large B-cell lymphomas of germinal-center origin," Nat. Genet., 2010, 42(2):181-185.
Morris et al., "ALK, the chromosome 2 gene locus altered by the t(2;5) in non-Hodgkin's lymphoma, encodes a novel neural receptor tyrosine kinase that is highly related to leukocyte tyrosine kinase (LTK)," Oncogene, Mar. 8, 1997, 14:2175-2188.
Morris et al., "Fusion of a kinase gene, ALK, to a nucleolar protein gene, NPM, in non-Hodgkin's lymphoma," Science, Mar. 4, 1994, 263(5151):1281-1284.
Moustakim et al., "Discovery of an MLLT1/3 YEATS Domain Chemical Probe," Angew. Chem. Int. Ed. Engl., Dec. 2018, 57(50):16302-16307.
Mueller et al., "A role for the MLL fusion partner ENL in transcriptional elongation and chromatin modification," Blood, Dec. 2007, 110(13):4445-4454.
Mueller et al., "Misguided Transcriptional Elongation Causes Mixed Lineage Leukemia," Plos Biol., Nov. 2009, 7(11):e1000249, 15 pages.

(56) References Cited

OTHER PUBLICATIONS

Müller et al., "Histone methyltransferase activity of a *Drosophila* Poly comb group repressor complex," Cell, 2002, 111(2):197-208.
MX Office Action in Mexican Appln. No. MX/a/2019/004950, dated Aug. 6, 2021, 6 pages (with English translation).
MX Office Action in Mexican Appln. No. MX/a/2019/004950, dated Nov. 23, 2021, 8 pages (with English Translation).
Nadeem Abbas et al., "Advances in targeting the epidermal growth factor receptor pathway by synthetic products and its regulation by epigenetic modulators as a therapy for glioblastoma," Cells, Apr. 2019, 8:350, 22 pages.
Neklesa et al., "Small-molecule hydrophobic tagging induced degradation of HaloTag fusion proteins," Nat. Chem. Biol., 2011, 7(8):538-543.
Ni et al., "Structural Insights into Interaction Mechanisms of Alternative Piperazine-urea YEATS Domain Binders in MLLTI," ACS Med. Chem. Lett., Dec. 2019, 10(12):1661-1666.
Nicholson et al., "EGFR and cancer prognosis," Eur. J. Cancer, Sep. 2001, 37(Supp. 4):9-15.
Noble et al., "Protein kinase inhibitors: insights into drug design from structure," Science, Mar. 2004, 303:1800-1805.
Odho et al., "Characterization of a novel WDR5-binding site that recruits RbBP5 through a conserved motif to enhance methylation of histone H3 lysine 4 by mixed lineage leukemia protein-1," Journal of Biological Chemistry, Oct. 2010, 285(43):32967-32976.
Ohoka et al., "In vivo knockdown of pathogenic proteins via specific and nongenetic inhibitor of apoptosis protein (IAP)-dependent protein erasers (SNIPERs)," Journal of Biological Chemistry, Mar. 2017, 292(11):4556-4570.
Okada et al., "hDOT1L links histone methylation to leukemogenesis," Cell, Apr. 2005, 121(2):167-178.
Okuhira et al., "Specific degradation of CRABP-II via cIAPI-mediated ubiquitylation induced by hybrid molecules that crosslink cIAP1 and the target protein," FEBS Lett., Apr. 2011, 585(8):1147-1152.
Olson et al., "Pharmacological perturbation of CDK9 using selective CDK9 inhibition or degradation," Nat. Chem. Biol., Feb. 2018, 14:163-170.
Ono et al., "PTK6 promotes cancer migration and invasion in pancreatic cancer cells dependent on ERK signaling," PLoS One, 2014, 9:e96060.
Ostrander et al., "Brk/PTK6 signaling in normal and cancer cell models," Curr. Opin. Phannacol., 2010, 10:662-669.
Ottis et al., "Proteolysis-targeting chimeras: induced protein degradation as a therapeutic strategy," ACS Chem. Biol., Mar. 2017, 12(4):892-898.
Paez et al., "EGFR mutations in lung cancer: correlation with clinical response to gefitinib therapy," Science, Jun. 2004, 304:1497-500.
Pao et al., "Acquired resistance of lung adenocarcinomas to gefitinib or erlotinib is associated with a second mutation in the EGFR kinase domain," PLoS Med., Feb. 2005, 2(3):e73.
Papazimas et al., "A General Strategy for the Preparation of Thalidomide-Conjugate Linkers," Synlett, Aug. 23, 2017, 28:2881-2885.
Park et al., "Discovery of EGF receptor inhibitors that are selective for the d746-750/T790M/C797S mutant through structure-based de novo design," Angew. Chem. Int. Ed., Jun. 2017, 56(26):7634-7638.
Park et al., "PTK6 inhibition promotes apoptosis of Lapatinib-resistant Her2+ breast cancer cells by inducing Bim," Breast Cancer Res, 2015, 17:86.
Patel et al., "A conserved arginine-containing motif crucial for the assembly and enzymatic activity of the mixed lineage leukemia protein-I core complex," The Journal of Biological Chemistry, Nov. 2008, 283(47):32162-32175.
Patel et al., "Recent updates on third generation EGFR inhibitors and emergence of fourth generation EGFR inhibitors to combat C797S resistance," Eur. J. Med. Chem., Dec. 2017, 142:32-47.
Patel et al., "Structure of WDR5 bound to mixed lineage leukemia protein-I peptide," The Journal of Biological Chemistry, Nov. 2008, 283(47):32158-32161.
PCT International Preliminary Report on Patentability in International Appln No. PCT/US2018/063847, dated Jun. 18, 2020, 8 pages.
PCT International Preliminary Report on Patentability in International Appln. No. PCT/US2019/019123, dated Aug. 27, 2020, 10 pages.
PCT International Preliminary Report on Patentability in International Appln. No. PCT/US2019/038560, dated Dec. 30, 2020, 9 pages.
PCT International Preliminary Report on Patentability in International Appln. No. PCT/US2019/040507, dated Jan. 5, 2021, 7 pages.
PCT International Preliminary Report on Patentability in International Appln. No. PCT/US2020/031527, dated Nov. 2, 2021, 8 pages.
PCT International Search Report and Written Opinion in International Appln. No. PCT/US2017/058718, dated Jan. 28, 2018, 8 pages.
PCT International Search Report and Written Opinion in International Appln. No. PCT/US2017/065027, dated Mar. 6, 2018, 8 pages.
PCT International Search Report and Written Opinion in International Appln. No. PCT/US2018/063847, dated Mar. 27, 2019, 11 pages.
PCT International Search Report and Written Opinion in International Appln. No. PCT/US2019/019123, dated Jun. 20, 2019, 15 pages.
PCT International Search Report and Written Opinion in International Appln. No. PCT/US2019/021014, dated Jun. 27, 2019, 11 pages.
PCT International Search Report and Written Opinion in International Appln. No. PCT/US2019/038560, dated Oct. 10, 2019, 12 pages.
PCT International Search Report and Written Opinion in International Appln. No. PCT/US2019/040507, dated Nov. 12, 2019, 10 pages.
PCT International Search Report and Written Opinion in International Appln. No. PCT/US2020/031527, dated Sep. 14, 2020, 11 pages.
PCT International Search Report and Written Opinion in International Appln. No. PCT/US2021/055574, dated Feb. 25, 2022, 11 pages.
PCT Invitation to Pay Additional Fees in International Appln. No. PCT/US2019/019123, dated Apr. 8, 2019, 3 pages.
PCT Invitation to Pay Additional Fees in International Appln. No. PCT/US2019/021014, dated Apr. 22, 2019, 2 pages.
PCT Invitation to Pay Additional Fees in International Appln. No. PCT/US2019/038560, dated Aug. 14, 2019, 2 pages.
PCT Invitation to Pay Additional Fees in International Appln. No. PCT/US2021/055574, dated Dec. 22, 2021, 2 pages.
Pellegrino et al., "EEF1A2 inactivates p53 by way of PI3K/AKT/mTOR-dependent stabilization of MDM4 in hepatocellular carcinoma," Hepatology, May 2014, 59(5):1886-1899.
Peng et al, "Protein tyrosine kinase 6 promotes ERBB2-induced mammary gland tumorigenesis in the mouse," Cell Death Dis., 2015, 6:e1848.
Perlman et al., "MLLT1 YEATS domain mutations in clinically distinctive Favourable Histology Wilms tumours," Nat. Commun., Dec. 2015, 6:10013, 10 pages.
Peters et al., "Alectinib versus Crizotinib in Untreated ALK Positive Non-Small-Cell Lung Cancer," New England Journal of Medicine, Aug. 31, 2017, 377(9):829-838.
Pettersson et al., "PROteolysis TArgeting Chimeras (PROTACs)—past, present and future," Drug Discov. Today Technol., Apr. 2019, 31:15-27.
Pieters et al., "A treatment protocol for infants younger than 1 year with acute lymphoblastic leukaemia (Interfant-99): an observational study and a multicentre randomised trial," Lancet, Jul. 2007, 370:240-250.

(56) References Cited

OTHER PUBLICATIONS

Prabhu et al., "Adapting AlphaLISA high throughput screen to discover a novel small-molecule inhibitor targeting protein arginine methyltransferase 5 in pancreatic and colorectal cancers," Oncotarget, May 2017, 8(25):39963-39977.
Prêtre et al., "Inhibition of Akt and other AGC kinases: A target for clinical cancer therapy?," Accepted Manuscript, Seminars in Cancer Biology, 2018, 48:70-77.
PubChem-CID-44631912, NIH, National Center for Biotechnology Information, Create Date: Mar. 8, 2010, 30 pages.
Pui et al., "Treating Childhood Acute Lymphoblastic Leukemia without Cranial Irradiation," N. Engl. J. Med., Jun. 2009, 360(26):2730-2741.
Pulford et al., "Detection of anaplastic lymphoma kinase (ALK) and nucleolar protein nucleophosmin (NPM)-ALK proteins in normal and neoplastic cells with the monoclonal antibody ALK1," Blood, Feb. 15, 1997, 89(4):1394-1404.
Qi et al., "Selective inhibition of Ezh2 by a small molecule inhibitor blocks tumor cells proliferation," Proc. Natl. Acad. Sci. USA, 2012, 109(52):21360-21365.
Quentmeier et al., "EZH2 Y641 mutations in follicular lymphoma," Leukemia, 2011, 25(4):726-729.
Raina et al., "PROTACinduced BET protein degradation as a therapy for castration-resistant prostate cancer," Proceedings of the National Academy of Sciences of the United States of America, Jun. 2016, 113(26):7124-7129.
Rao et al., "Hijacked in cancer: the KMT2 (MLL) family of methyltransferases," Nat. Rev. Cancer, Jun. 2015, 15:334-346.
Ren et al., "PHF19 promotes multiple myeloma tumorigenicity through PRC2 activation and broad H3K27me3 domain formation," Blood, 2019, 134:1176-1189.
Ren et al., "Polycomb protein EZH2 regulates tumor invasion via the transcriptional repression of the metastasis suppressor RKIP in breast and prostate cancer," Cancer Res., 2012, 72(12):3091-3104.
Ribas et al., "Cancer immunotherapy using checkpoint blockade," Science (New York, NY), Mar. 2018, 359(6382):1350-1355.
Rikova et al., "Global survey of phosphotyrosine signaling identifies oncogenic kinases in lung cancer," Cell, Dec. 14, 2007, 131(6):1190-1203.
Ritchie et al., "limma powers differential expression analyses for RNA-sequencing and microarray studies," Nucleic Acids Res., 2015, 43(7):e47.
Rodrik-Outmezguine et al., "Overcoming mTOR resistance mutations with a new-generation mTOR inhibitor," Nature, Jun. 2016, 534:272-276.
Roguev et al., "The *Saccharomyces cerevisiae* Set1 complex includes an ash2 homologue and methylates histone 3 lysine," The EMBO journal, Dec. 2001, 20(24):7137-7148.
Rosati et al., "NUP98 is fused to the NSD3 gene in acute myeloid leukemia associated with t(8;11)(p11.2;p15)," Blood, 2002, 99:3857-3860.
Sakamoto et al., "Protacs: chimeric molecules that target proteins to the Skp1-Cullin-F box complex for ubiquitination and degradation," Proc. Natl. Acad. Sci. USA, Jul. 2001, 98(15):8554-8559.
Salami et al., "Waste disposal—An attractive strategy for cancer therapy," Science, Mar. 2017, 355:1163-1167.
Saura et al., "A first-in-human phase I study of the ATP-competitive AKT inhibitor ipatasertib demonstrates robust and safe targeting of AKT in patients with solid tumors," Cancer Discovery, Jan. 2017, 7(1):102-113.
Sauvageau et al., "Poly comb group proteins: multi-faceted regulators of somatic stem cells and cancer," Cell Stem Cell., 2010, 7(3):299-313.
Sawasdikosol et al., "Hematopoietic progenitor kinase 1 (HPK1) regulates prostaglandin $E_2$-induced fos gene transcription," Blood, May 2003, 101(9):3687-3689.
Sawasdikosol et al., "HPK1 as a novel target for cancer immunotherapy," Immunologic Research, Dec. 2012, 54(1-3):262-265.
Sawasdikosol et al., "Prostaglandin $E_2$ activates HPK 1 kinase activity via a PKA-dependent pathway," The Journal of biological chemistry, Nov. 2007, 282(48):34693-34699.
Schapira et al., "Targeted protein degradation: expanding the toolbox," Nat. Rev. Drug Discov., Dec. 2019, 18(12):949-963.
Schmandt et al., "The BRK tyrosine kinase is expressed in high-grade serous carcinoma of the ovary," Cancer Biol. Ther., 2006, 5:1136-1141.
Schneider et al. "Characterization of EBV-genome negative 'null' and 'T' cell lines derived from children with acute lymphoblastic leukemia and leukemic transformed non-Hodgkin lymphoma," International Journal of Cancer, May 1977, 19(5): 621-626.
Schramm et al., "Novel BQCA- and TBPB-derived M1 receptor hybrid ligands: orthosteric carbachol differentially regulates partial agonism," ChemMedChem, Jul. 2019, 14(14):1349-1358.
Senisterra et al., "Small-molecule inhibition of MLL activity by disruption of its interaction with WDR5," Biochemical Journal, Jan. 2013, 449(1):151-159.
Seshacharyulu et al., "Targeting the EGFR signaling pathway in cancer therapy," Expert Opin. Ther. Targets, Jan. 2012, 16:15-31.
Shanle et al., "Association of Taf14 with acetylated histone H3 directs gene transcription and the DNA damage response," Genes Dev., 2015, 29:1795-1800.
Sharma et al., "Epidermal growth factor receptor mutations in lung cancer," Nat. Rev. Cancer, Mar. 2007, 7:169-181.
Shaw et al., "Ceritinib in ALK-rearranged non-small-cell lung cancer," New England Journal of Medicine, Mar. 27, 2014, 370(13):1189-1197.
Shen et al., "Identification of LEM-14 inhibitor of the oncoprotein NSD2," Biochem Biophys. Res. Commun., Jan. 2019, 508(1):102-108.
Shen et al., "NSD3-Short Is an Adaptor Protein that Couples BRD4 to the CHD8 Chromatin Remodeler," Mol. Cell., Dec. 2015, 60(6):847-859.
Shen et al., "Structure-based design of 5-methylpyrimidopyridone derivatives as new wild-type sparing inhibitors of the epidermal growth factor receptor triple mutant ($EGFR^{L858R/T790M/C797S}$)," J. Med. Chem., Jul. 2019, 62:7302-7308.
Sherr et al., "Targeting CDK4 and CDK6: from discovery to therapy," Cancer Discovery, 2016, 6(4):353-367.
Shibata et al., "Development of protein degradation inducers of oncogenic BCR-ABL protein by conjugation of ABL kinase inhibitors and IAP ligands," Cancer Science, Aug. 2017, 108(8):1657-1666.
Shimizu et al., "The protein arginine methyltransferase 5 promotes malignant phenotype of hepatocellular carcinoma cells and is associated with adverse patient outcomes after curative hepatectomy," International Journal of Oncology, Jan. 2017, 50(2):381-386.
Shiota et al., "Hyperphosphorylation of a novel 80 kDa protein-tyrosine kinase similar to Ltk in a human 40 Ki-1 lymphoma cell line, AMS3," Oncogene, Jun. 1994, 9(6):1567-1574.
Shui et al., "Hematopoietic progenitor kinase 1 negatively regulates T-cell receptor signaling and T cell-mediated immune responses," Nature Immunology, Jan. 2007, 8(1):84-91.
Slany, "When epigenetics kills: MLL fusion proteins in leukemia," Hematol. Oncol., Mar. 2005, 23:1-9.
Sneeringer et al., "Coordinated activities of wild-type plus mutant EZH2 drive tumor associated hypertrimethylation of lysine 27 on histone H3 (H3K27) in human B-cell lymphomas," Proc. Natl. Acad. Sci. USA, Dec. 7, 2010, 107(49): 20980-20985.
Soda et al., "Identification of the transforming EML4-ALK fusion gene in non-small-cell lung cancer," Nature, Aug. 2, 2007,448:561-566.
Solomon et al., "First-line crizotinib versus chemotherapy in ALK-positive lung cancer," New England Journal of Medicine, Dec. 4, 2014, 371(23):2167-2177.
Song et al., "Selective inhibition of EZH2 by ZLD1039 blocks H3K27methylation and leads to potent anti-tumor activity in breast cancer," Sci. Rep., 2016, 6:20864.
Song et al., "WDR5 interacts with mixed lineage leukemia (MLL) protein via the histone HJ-binding pocket," The Journal of Biological Chemistry, Dec. 2008, 283(50):35258-35264.

(56) References Cited

OTHER PUBLICATIONS

Soucy et al., "An inhibitor of NEDD8-activating enzyme as a new approach to treat cancer," Nature, Apr. 2009, 458:732-736.
Subramanian et al., "Gene set enrichment analysis: a knowledge-based approach for interpreting genome-wide expression profiles," Proc. Natl. Acad. Sci. USA, Sep. 2005, 102(43):15545-15550.
Suda et al., "The structure of bestatin," The Journal of Antibiotic, Jan. 1976, 29(1):100-101.
Sun et al., "Discovery of AMG 232, a potent, selective, and orally bioavailable MDM2-p53 inhibitor in clinical development," Journal of Medicinal Chemistry, Feb. 2014, 57(4):1454-1472.
Sun et al., "PROTAC-induced BTK degradation as a novel therapy for mutated BTK C481S induced ibrutinib-resistant B-cell malignancies," Cell Research, Jul. 2018, 28(7):779-781.
Sun et al., "Up-regulated WDR5 promotes gastric cancer formation by induced cyclin D1 expression," Journal of Cellular Biochemistry, Apr. 2018, 119(4): 28 pages.
Sun et al., "WDR5 supports an N-Myc transcriptional complex that drives a protumorigenic gene expression signature in neuroblastoma," Cancer Research, Dec. 2015 75(23):5143-5154.
Tahirovic et al., "Discovery of N-alkyl piperazine side chain based CXCR4 antagonists with improved drug-like properties," ACS Med. Chem. Lett., May 2018, 9(5):446-451.
Takeuchi et al., "KIF5B-ALK, a novel fusion oncokinase identified by an immunohistochemistry-based diagnostic system for ALK-positive lung cancer," Clinical Cancer Research, May 1, 2009, 15(9):3143-3149.
Tan et al., "A kinase-independent role for EGF receptor in autophagy initiation," Cell, Jan. 2015, 160(1-2):145-160.
Tan et al., "Next-generation epidermal growth factor receptor tyrosine kinase inhibitors in epidermal growth factor receptor-mutant non-small cell lung cancer," Lung Cancer, Mar. 2016, 93:59-68.
Tan et al., "PBK/AKT-mediated upregulation of WDR5 promotes colorectal cancer metastasis by directly targeting ZNF407," Cell Death and Disease, Mar. 2017, 8(3): 12 pages.
Taniguchi et al., "Silencing of Kruppel-like factor 2 by the histone methyltransferase EZH2 in human cancer," Oncogene, 2012, 31(15):1988-1994.
Tarighat et al., "The dual epigenetic role of PRMT5 in acute myeloid leukemia: gene activation and repression via histone arginine methylation," Leukemia, Nov. 2016, 30:789-799.
Thomas et al., "Interaction with WDR5 promotes target gene recognition and tumorigenesis by MYC," Molecular Cell, May 2015, 58(3):440-452.
Thomas et al., "The MYC-WDR5 nexus and cancer," Cancer Research, Oct. 2015, 75(19):4012-4015.
Thress et al., "Acquired EGFR C797S mutation mediates resistance to AZD9291 in non-small cell lung cancer harboring EGFR T790M," Nat. Med., May 2015, 21:560-562.
Toure et al., "Small-Molecule PROTACS: New Approaches to Protein Degradation," Angewandte Chemie-International Edition, Feb. 2016, 55(6):1966-1973.
Trievel et al., "WDR5, a complexed protein," Nature Structural & Molecular Biology, Jul. 2009, 16(7):678-680.
Turner et al., "Palbociclib in hormone-receptor-positive advanced breast cancer," New England Journal of Medicine, 2015, 373(3):209-219.
Turner-Ivey et al., "Development of mammary hyperplasia, dysplasia, and invasive ductal carcinoma in transgenic mice expressing the 8p11 amplicon oncogene NSD3," Breast Cancer Res. Treat., Jul. 2017, 164(2):349-358.
Varambally et al., "The polycomb group protein EZH2 is involved in progression of prostate cancer," Nature, 2002, 419(6907):624-629.
Varfolomeev et al., "IAP antagonists induce autoubiquitination of c-IAPs, NF-κB activation, and TNFα-dependent apoptosis," Cell, Nov. 2007, 131(4):669-681.
Vassilev et al., "In vivo activation of the p53 pathway by small-molecule antagonists of MDM2," Science, Feb. 2004, 303(5659):844-848.

Verma et al., "Identification of Potent, Selective, Cell-Active Inhibitors of the Histone Lysine Methyltransferase EZH2," ACS Med. Chem. Lett., 2012, 3(12):1091-1096.
Vivanco et al., "A kinase-independent function of AKT promotes cancer cell survival," eLIFE, 2014, 3:e03751.
Vu et al., "Discovery of RG7112: a small-molecule MDM2 inhibitor in clinical development," ACS Medicinal Chemistry Letters, May 2013, 4(5):466-469.
Wakeling, "Use of pure antioestrogens to elucidate the mode of action of oestrogens," Biochemical Pharmacology, May 1995, 49(11):1545-1549.
Wan et al., "ENL links histone acetylation to oncogenic gene expression in acute myeloid leukaemia," Nature, Mar. 2017, 543:265-269.
Wan et al., "Impaired cell fate through gain-of-function mutations in a chromatin reader," Nature, Jan. 2020, 577:121-126.
Wang et al., "EAI045: The fourth-generation EGFR inhibitor overcoming T790M and C797S resistance," Cancer Lett., Jan. 2017, 385:51-54.
Wang et al., "MapSplice: accurate mapping of RNA-seq reads for splice junction discovery," Nucleic Acids Res., 2010, 38:e178.
Wang et al., "NUP98-NSD1 links H3K36 methylation to Hox-A gene activation and leukaemogenesis," Nat. Cell. Biol., Jul. 2007, 9(7):804-812.
Wang et al., "Polycomb genes, miRNA, and their deregulation in B-cell malignancies," Blood, 2015, 125(8):1217-1225.
Wei et al., "Protein arginine methylation of non-histone proteins and its role in diseases," Cell Cycle, 2014, 13(1):32-41.
Weisberg et al., "Smac mimetics: implications for enhancement of targeted therapies in leukemia," Leukemia, Dec. 2010, 24:2100-2109.
Weiss et al., "Anaplastic lymphoma kinase and leukocyte tyrosine kinase: functions and genetic interactions in learning, memory and adult neurogenesis," Pharmacology, Biochemistry and Behavior, Jan. 2012, 100(3):566-574.
Weiss et al., "The role of T3 surface molecules in the activation of human T cells: a two-stimulus requirement for IL 2 production reflects events occurring at a pre-translational level," Journal of Immunology, Aug. 1984, 133(1):123-128.
Wieduwilt et al., "The epidermal growth factor receptor family: biology driving targeted therapeutics," Cell. Mol. Life Sci., May 2008, 65(10):1566-1584.
Winter et al., "Phthalimide conjugation as a strategy for in vivo target protein degradation," Science, May 2015, 348(6241):1376-1381.
Wood et al., "Lack of the t(2;5) or other mutations resulting in expression of anaplastic lymphoma kinase catalytic domain in CD30+ primary cutaneous lymphoproliferative disorders and Hodgkin's disease," Blood, Sep. 1, 1996, 88(5):1765-1770.
Wu et al., "Overexpression of WD repeat domain 5 associates with aggressive clinicopathological features and unfavorable prognosis in head neck squamous cell carcinoma," International Association of Oral Pathologists and the American Academy of Oral Pathology, Apr. 2018, 47(5): 27 pages.
Xie et al., "Pharmacological targeting of the pseudokinase Her3," Nature Chemical Biology, Dec. 2014, 10(12):1006-1012.
Xie et al., "WDR5 positively regulates p53 stability by inhibiting p53 ubiquitination," Biochemical and Biophysical Research Communications, May 2017, 487(2):333-338.
Xu et al., "eEF1A2 promotes cell migration, invasion and metastasis in pancreatic cancer by upregulating MMP-9 expression through Akt activation," Clin. Exp. Metastasis, May 2013, 30(7):933-944.
Xu et al., "Selective inhibition of EZH2 and EZH1 enzymatic activity by a small molecule suppresses MLL-rearranged leukemia," Blood, Jan. 2015, 125:346-357.
Xu et al., "Targeting EZH2 and PRC2 dependence as novel anticancer therapy," Exp. Hematol., 2015, 43(8):698-712.
Yang et al., "Structure-Activity Relationship Studies for Enhancer of Zeste Homologue 2 (EZH2) and Enhancer of Zeste Homologue 1 (EZH1) Inhibitors," J. Med. Chem., 2016, 59(16):7617-7633.

(56) References Cited

OTHER PUBLICATIONS

Yokoyama et al., "A Higher-Order Complex Containing AF4 and ENL Family Proteins with P-TEFb Facilitates Oncogenic and Physiologic MLL-Dependent Transcription," Cancer Cell, Feb. 2010, 17(2):198-212.
You et al., "Discovery of an AKT degrader with prolonged inhibition of downstream signaling," Cell Chemical Biology, 2020, 27(1):66-73.
Yu et al., "Altered Hox Expression and Segmental Identity in Mll-Mutant Mice," Nature, Nov. 1995, 378:505-508.
Yu et al., "Requirement for CDK4 kinase function in breast cancer," Cancer Cell, 2006, 9(1):23-32.
Yu et al., "Targeting AKT1-E17K and the PI3K/AKT pathway with an allosteric AKT inhibitor, ARQ 092," PLOS One, Oct. 2015, 10(10):e0140479.
Yun et al., "The T790M mutation in EGFR kinase causes drug resistance by increasing the affinity for ATP," Proc. Natl. Acad. Sci. USA, Feb. 2008, 105(6):2070-2075.
Zeng et al., "Discovery of novel imidazo[1,2-a]pyrazin-8-amines as Brk/PTK6 inhibitors," Bioorg. Med. Chem. Lett., Oct. 2011, 21(19):5870-5875.
Zengerle et al., "Selective Small Molecule Induced Degradation of the BET Bromodomain Protein BRD4," ACS Chemical Biology, Jun. 2015, 10(8):1770-1777.
Zhang et al., "Proteolysis targeting chimeras (PROTACs) of anaplastic lymphoma linase (ALK)," Eur. J. Med. Chem., May 2018, 151:304-314.
Zhang et al., "Structural Insights into Histone Crotonyl-Lysine Recognition by the AF9 Yeats Domain," Structure, Sep. 2016, 24(9):1606-1612.
Zhao et al., "PROTACs suppression of CDK4/6, crucial kinases for cell cycle regulation in cancer," Chem. Commun. (Camb)., 2019, 55:2704-2707.
Zhao et al., "The language of chromatin modification in human cancers," Nat. Rev. Cancer, Jul. 2021, 21:413-430.
Zheng et al., "PTK6 activation at the membrane regulates epithelial-mesenchymal transition in prostate cancer," Cancer Res., Sep. 2013, 73(17):5426-5437.
Zhou et al., "Discovery of a Small-Molecule Degrader of Bromodomain and Extra-Terminal (BET) Proteins with Picomolar Cellular Potencies and Capable of Achieving Tumor Regression," Journal of Medicinal Chemistry, 2018, 61(2):462-481.
Zuber et al., "RNAi screen identifies Brd4 as a therapeutic target in acute myeloid leukaemia," Nature, 2011, 478:524-528.
Office Action in Chinese Appln. No. 201980054694.8, mailed on Sep. 1, 2023, 21 pages (with Machine translation).
EP Office Action in European Appln. No. 17877800.7, Apr. 13, 2023, 7 pages.
EP Office Action in European Appln. No. 19763958.6, dated May 10, 2023, 4 pages.
EP Office Action in European Appln. No. 19821826.5, dated Apr. 12, 2023, 4 pages.
JP Office Action in Japanese Appln. No. 2020-546159, dated May 9, 2023, 14 pages (with English Translation).
JP Office Action in Japanese Appln. No. 2020-570728, dated Jun. 27, 2023, 11 pages (with English Translation).
JP Office Action in Japanese Appln. No. 2021-500187, dated Jul. 4, 2023, 12 pages (with English Translation).
Office Action in U.S. Appl. No. 16/970,305, mailed on Sep. 8, 2023, 22 pages.
PCT International Preliminary Report on Patentability in International Appln. No. PCT/US2021/055574, dated May 4, 2023, 8 pages.
Wang et al., "Discovery of potent 2-Aryl-6,7-dihydro-5H-pyrrolo[1,2-a] imidazoles as WDR5-WIN-site inhibitors using fragment-based methods and structure-based design," Journal of Medicinal Chemistry, 2018, 61(13):5623-5642.

* cited by examiner

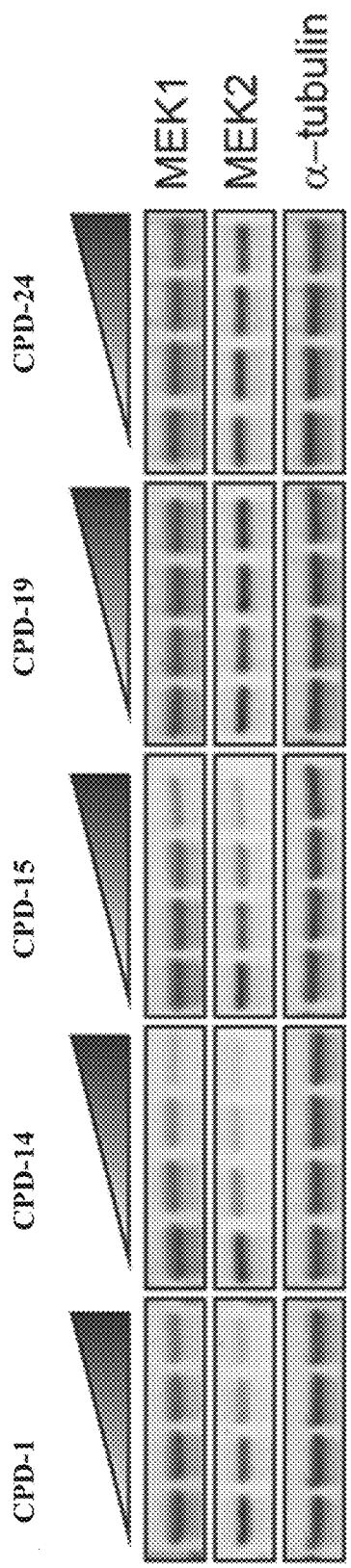
FIG. 1
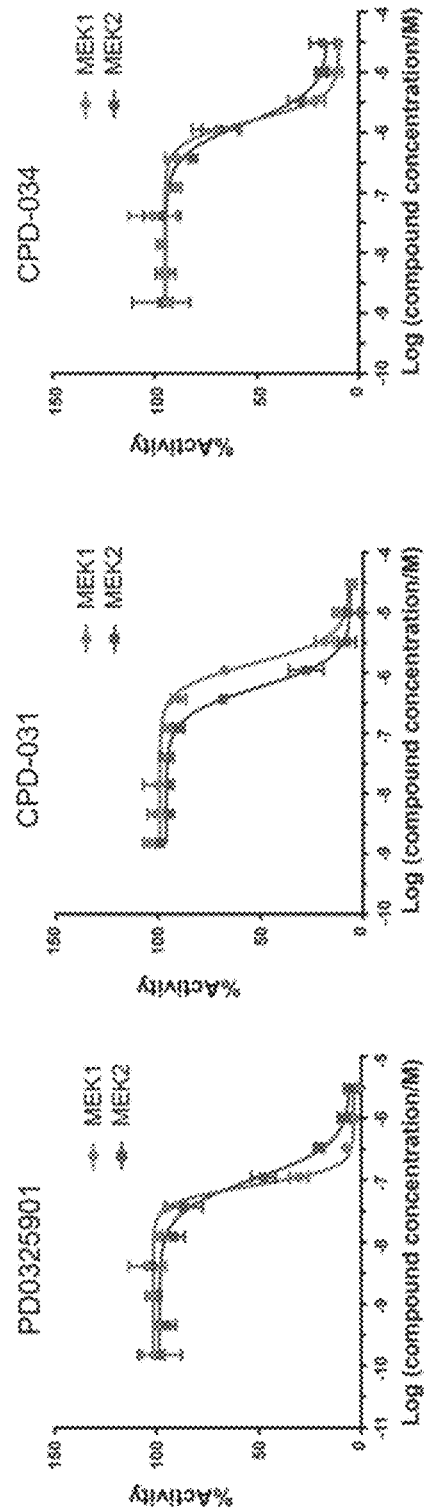
FIG. 2A
FIG. 2B
FIG. 2C

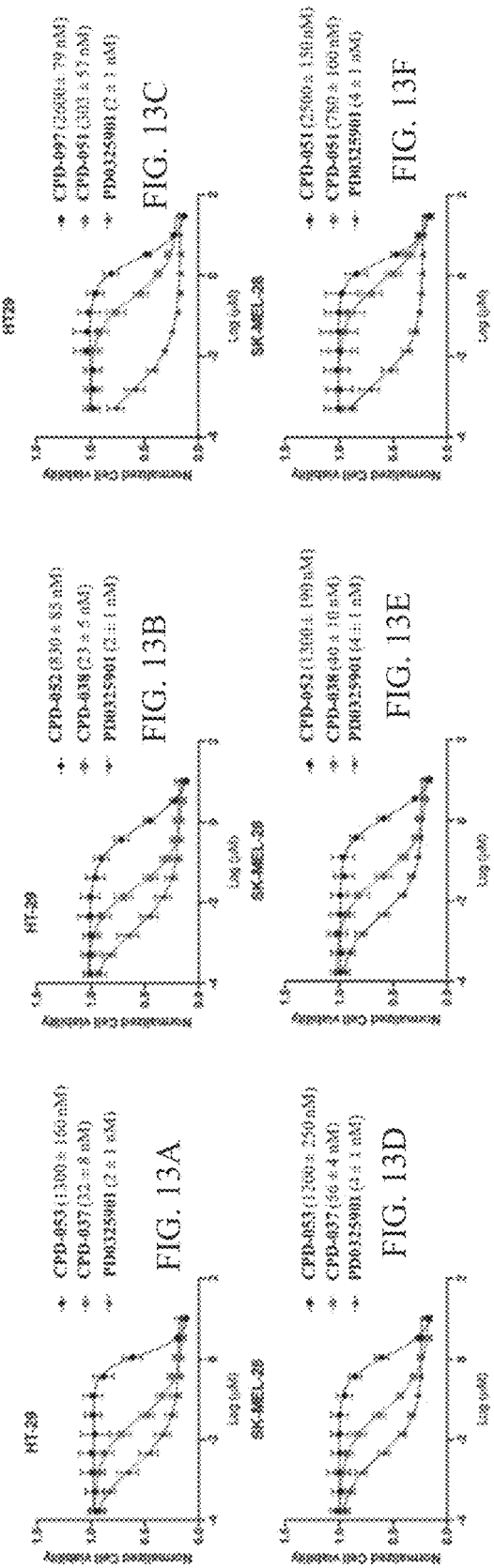
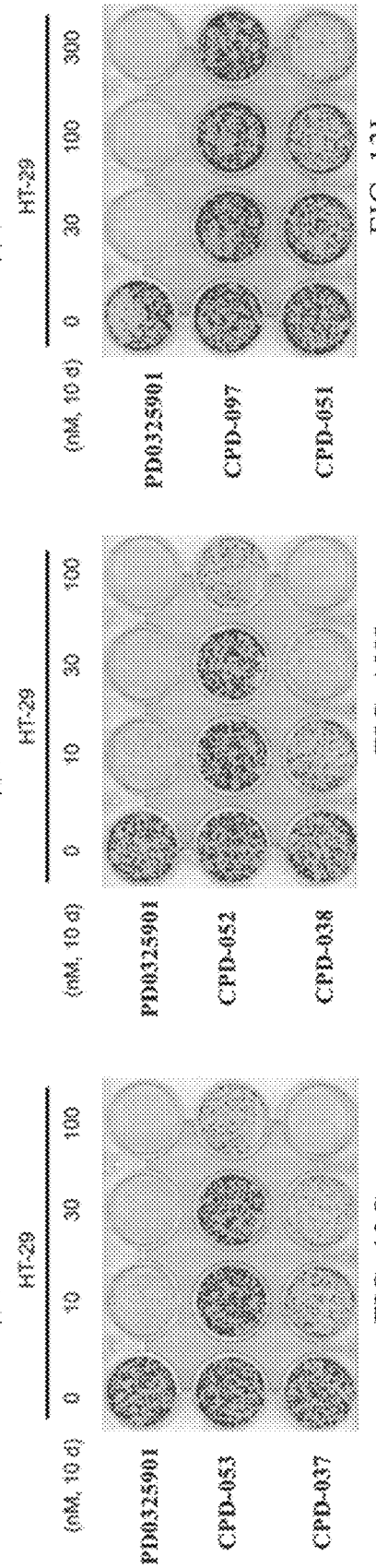
FIG. 13A  FIG. 13B  FIG. 13C
FIG. 13D  FIG. 13E  FIG. 13F
FIG. 13G  FIG. 13H  FIG. 13I

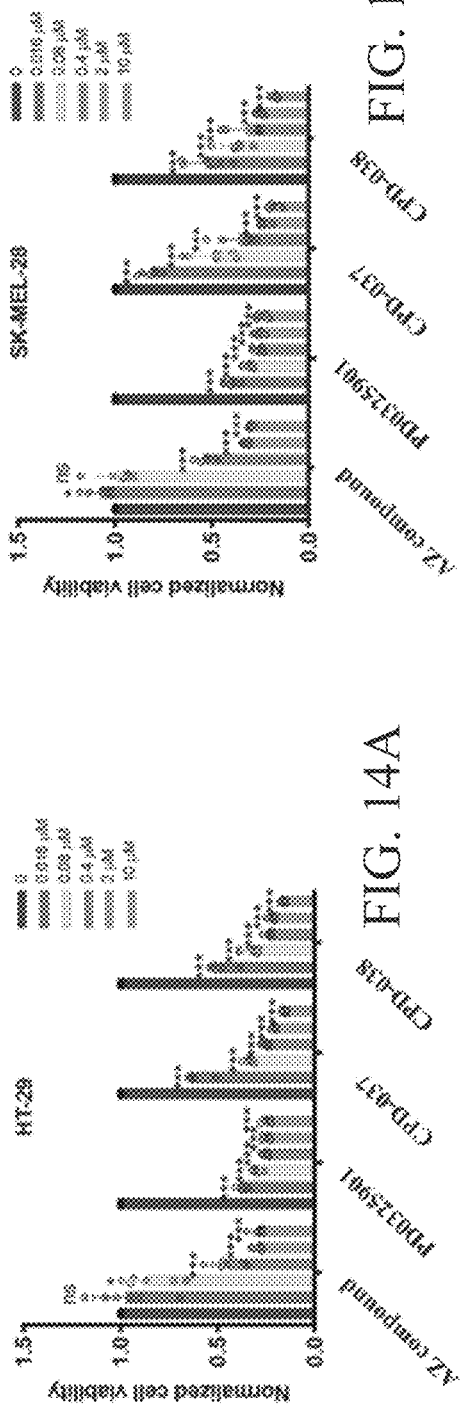
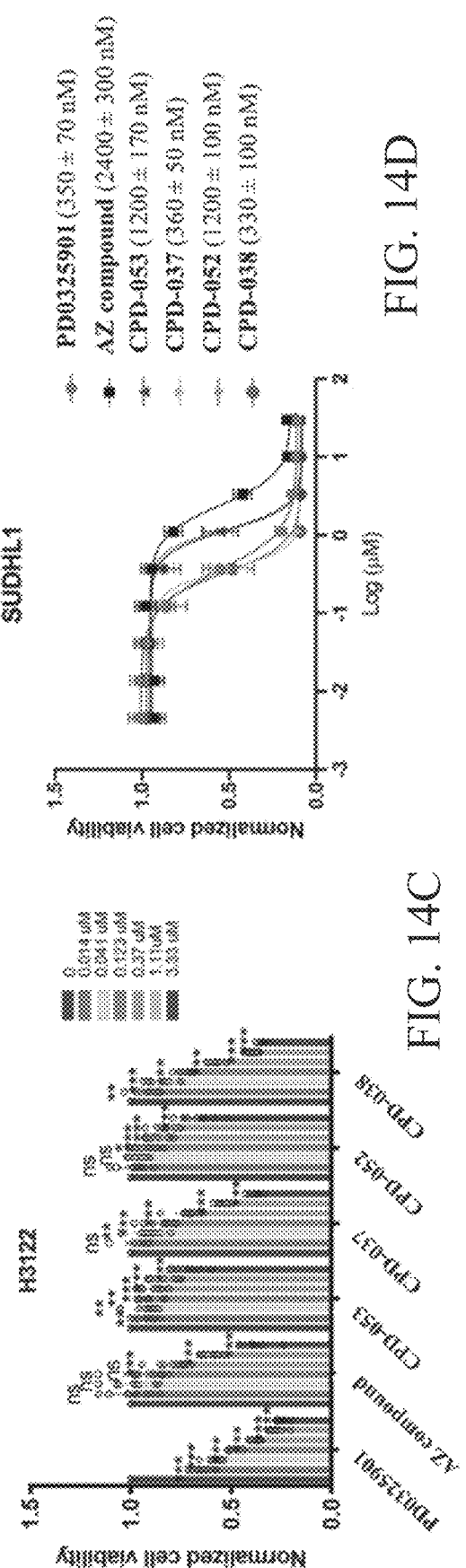
FIG. 14A
FIG. 14B
FIG. 14C
FIG. 14D

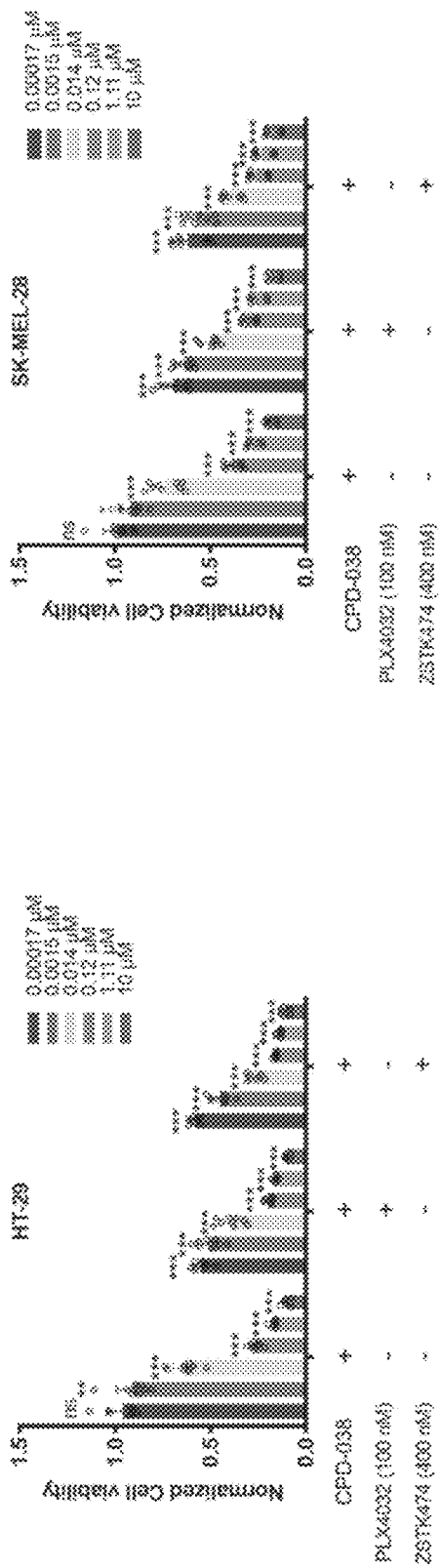
FIG. 15A
FIG. 15B
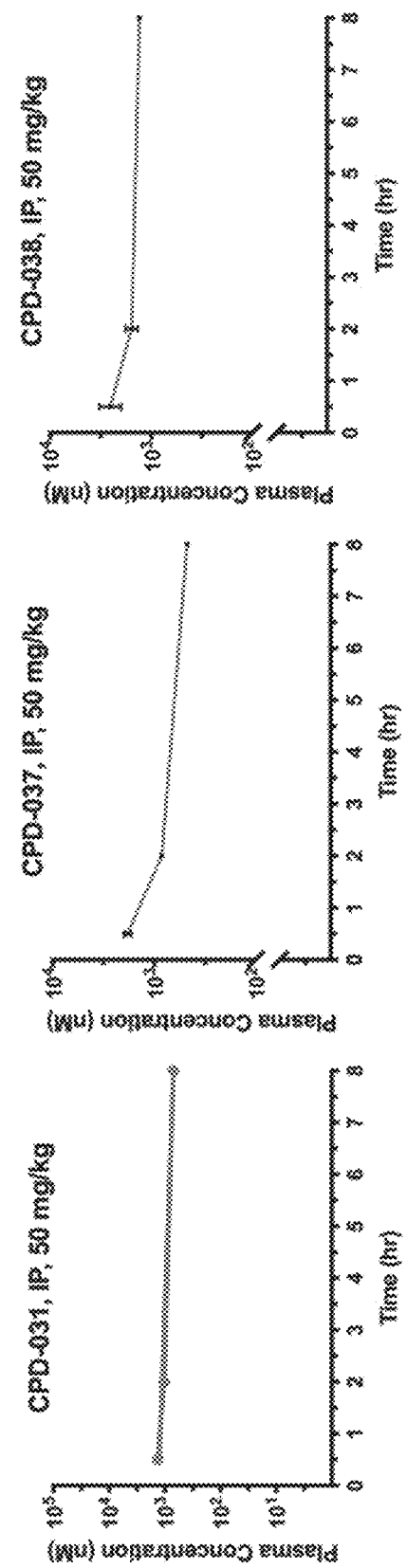
FIG. 16

MITOGEN-ACTIVATED PROTEIN KINASE KINASE (MEK) DEGRADATION COMPOUNDS AND METHODS OF USE

CROSS-REFERENCE TO RELATED APPLICATIONS

This application claims the benefit under 35 U.S.C. § 119(e) of U.S. Patent Application No. 63/120,467, filed Dec. 2, 2020, Application No. 63/118,367, filed Nov. 25, 2020, and Application No. 63/033,133 filed Jun. 1, 2020, which are incorporated herein by reference in their entirety.

BACKGROUND

There is a need in the art for compounds, compositions, and methods of use of the compounds for the treatment of diseases in a subject in need thereof.

SUMMARY

This disclosure relates to heterobifunctional compounds (e.g., bi-functional small molecule compounds), compositions comprising one or more of the heterobifunctional compounds, and to methods of use of the heterobifunctional compounds for the treatment of certain diseases in a subject in need thereof. The disclosure also relates to methods for identifying such heterobifunctional compounds.

According to the first aspect of the present disclosure, a heterobifunctional compound disclosed herein comprises a mitogen-activated protein kinase kinase (MEK) Ligand conjugated to a Degradation Tag through a Linker, which comprises a moiety of FORMULA I:

FORMULA I

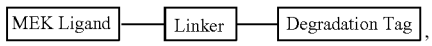

or a pharmaceutically acceptable salt, hydrate, solvate, prodrug, stereoisomer, tautomer, or analog thereof.

In another embodiment, the MEK Ligand moiety in FORMULA I is capable of binding to a MEK protein comprising a MEK mutant, MEK deletion, or a MEK fusion protein.

In another embodiment, the MEK Ligand moiety in FORMULA I is capable of binding to a MEK protein comprising MEK1 and/or MEK 2.

In another embodiment, the MEK Ligand moiety in FORMULA I is a MEK inhibitor or a portion of MEK inhibitor.

In one embodiment, the MEK Ligand moiety in FORMULA I binds to an allosteric site of MEK.

In another embodiment, the MEK Ligand moiety in FORMULA I binds to the ATP-binding site of MEK.

In another embodiment, the MEK Ligand moiety in FORMULA I is selected from the group consisting of PD0316684, PD184352, Cobimetinib, Binimetinib, GDC-0623, G-573, CH5126766, Trametinib, TAK-733, MAP855, E6201, and BI-847325.

In another embodiment, Degradation Tag moiety in FORMULA I is capable of binding to a ubiquitin ligase, or a hydrophobic group, or a tag that leads to misfolding of the MEK proteins.

In another embodiment, Degradation Tag moiety in FORMULA I is capable of binding to an E3 ligase.

In another embodiment, the Degradation Tag moiety in FORMULA I is capable of binding to a VHL E3 ligase, a cereblon E3 ligase, an IAP ligase, a MDM2 ligase, a TRIM24 ligase, a TRIM21 ligase, a KEAP1 ligase, DCAF16 ligase, RNF4 ligase, RNF114 ligase, or AhR ligase.

In another embodiment, Degradation Tag moiety in FORMULA I is capable of binding to a VHL E3 ligase or a cereblon E3 ligase.

In another embodiment, Degradation Tag moiety in FORMULA I is capable of binding to a VHL E3 ligase.

In another embodiment, the Degradation Tag moiety in FORMULA I is selected from the group consisting of VHL-1, pomalidomide, thalidomide, lenalidomide, adamantane, 1-((4,4,5,5,5-pentafluoropentyl)sulfinyl)nonane, nutlin-3a, RG7112, RG7338, AMG232, AA-115, bestatin, MV-1, LCL161, CPD36, GDC-0152, CRBN-1, CRBN-2, CRBN-3, CRBN-4, CRBN-5, CRBN-6, CRBN-7, CRBN-8, CRBN-9, CRBN-10, CRBN-11, CRBN-12, CRBN-13, CRBN-14, CRBN-15, or CRBN-16.

In another embodiment, the heterobifunctional compound disclosed herein comprises a moiety of FORMULA I-1:

FORMULA I-1

or a pharmaceutically acceptable salt, hydrate, solvate, prodrug, stereoisomer, tautomer, or analog thereof, wherein
i) *, $Ar^1$, $Ar^2$, A, and B are defined as hereinafter;
ii) E3 Ligase Binder moiety is of FORMULAE 6A, 6B, and 6C:

FORMULA 6A

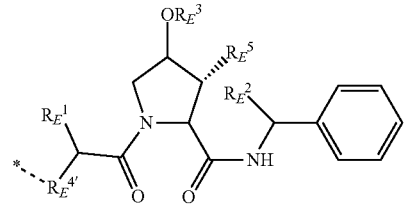

FORMULA 6B

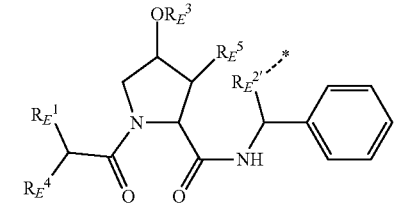

FORMULA 6C

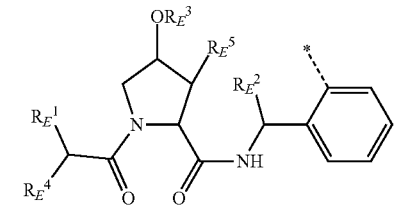

wherein *, $R_E^1$, $R_E^2$, $R_E^{2'}$, $R_E^3$, $R_E^4$, $R_E^{4'}$, $R_E^5$, and $R_E^6$ are defined as hereinafter;

or,

E3 Ligase Binder moiety is of FORMULA 5:

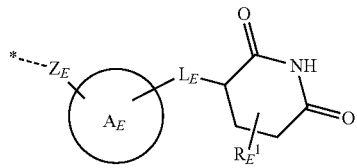

FORMULA 5 wherein *, $R_E^1$, $Z_E$, ring $A_E$, and $L_E$, are defined as hereinafter;

and iii) the Linker moiety is of FORMULA 9:

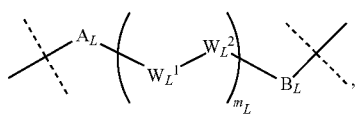

FORMULA 9 wherein $m_L$, $A_L$, $W_L^1$, $W_L^2$ and $B_L$ are defined as hereinafter.

In some embodiments, the compound comprises any one of the compounds in Table 1.

In some embodiments, the heterobifunctional compound is selected from the group consisting of CPD-001 to CPD-097 or a pharmaceutically acceptable salt or analog thereof.

In some embodiments, the heterobifunctional compound is selected from the group consisting of CPD-11, CPD-13, CPD-14, CPD-24, CPD-31, CPD-33, CPD-35, CPD-36, CPD-37, CPD-38, CPD-39, CPD-41, CPD-43, CPD-45, CPD-46, CPD-50, CPD-51 and a pharmaceutically acceptable salt or analog thereof.

In some embodiments, the heterobifunctional compound is selected from the group consisting of CPD-31, CPD-37, CPD-38, and a pharmaceutically acceptable salt or analog thereof.

In one embodiment, the heterobifunctional compound is (2S,4R)-1-((S)-17-(tert-butyl)-1-(3,4-difluoro-2-((2-fluoro-4-iodophenyl)amino)phenyl)-1,15-dioxo-3-oxa-2,7,16-triazaoctadecan-18-oyl)-4-hydroxy-N-(4-(4-methylthiazol-5-yl)benzyl)pyrrolidine-2-carboxamide (CPD-11).

In one embodiment, the heterobifunctional compound is (2S,4R)-1-((S)-19-(tert-butyl)-1-(3,4-difluoro-2-((2-fluoro-4-iodophenyl)amino)phenyl)-1,17-dioxo-3-oxa-2,7,18-triazaicosan-20-oyl)-4-hydroxy-N-(4-(4-methylthiazol-5-yl)benzyl)pyrrolidine-2-carboxamide (CPD-13).

In one embodiment, the heterobifunctional compound is (2S,4R)-1-((S)-20-(tert-butyl)-1-(3,4-difluoro-2-((2-fluoro-4-iodophenyl)amino)phenyl)-1,18-dioxo-3-oxa-2,7,19-triazahenicosan-21-oyl)-4-hydroxy-N-(4-(4-methylthiazol-5-yl)benzyl)pyrrolidine-2-carboxamide (CPD-14).

In one embodiment, the heterobifunctional compound is N-(3-((2-((2-(2,6-dioxopiperidin-3-yl)-1,3-dioxoisoindolin-4-yl)amino)ethyl)amino)propoxy)-3,4-difluoro-2-((2-fluoro-4-iodophenyl)amino)benzamide (CPD-24).

In one embodiment, the heterobifunctional compound is (2S,4R)-1-((S)-20-(tert-butyl)-1-(3,4-difluoro-2-((2-fluoro-4-iodophenyl)amino)phenyl)-1,18-dioxo-3-oxa-2,7,19-triazahenicosan-21-oyl)-4-hydroxy-N—((S)-1-(4-(4-methylthiazol-5-yl)phenyl)ethyl)pyrrolidine-2-carboxamide (CPD-031).

In one embodiment, the heterobifunctional compound is (2S,4R)-1-((S)-21-(tert-butyl)-1-(3,4-difluoro-2-((2-fluoro-4-iodophenyl)amino)phenyl)-1,19-dioxo-3-oxa-2,7,20-triazadocosan-22-oyl)-4-hydroxy-N—((S)-1-(4-(4-methylthiazol-5-yl)phenyl)ethyl)pyrrolidine-2-carboxamide (CPD-33).

In one embodiment, the heterobifunctional compound is (2S,4R)-1-((S)-20-(tert-butyl)-1-(3,4-difluoro-2-((2-fluoro-4-iodophenyl)amino)phenyl)-1,18-dioxo-3-oxa-2,8,19-triazahenicosan-21-oyl)-4-hydroxy-N—((S)-1-(4-(4-methylthiazol-5-yl)phenyl)ethyl)pyrrolidine-2-carboxamide (CPD-35).

In one embodiment, the heterobifunctional compound is (2S,4R)-1-((S)-19-(tert-butyl)-1-(3,4-difluoro-2-((2-fluoro-4-iodophenyl)amino)phenyl)-1,17-dioxo-3-oxa-2,7,18-triazaicosan-20-oyl)-4-hydroxy-N—((S)-1-(4-(4-methylthiazol-5-yl)phenyl)ethyl)pyrrolidine-2-carboxamide (CPD-36).

In one embodiment, the heterobifunctional compound is (2S,4R)-1-((S)-20-(tert-butyl)-1-(3,4-difluoro-2-((2-fluoro-4-iodophenyl)amino)phenyl)-7-methyl-1,18-dioxo-3-oxa-2,7,19-triazahenicosan-21-oyl)-4-hydroxy-N—((S)-1-(4-(4-methylthiazol-5-yl)phenyl)ethyl)pyrrolidine-2-carboxamide (CPD-037).

In one embodiment, the heterobifunctional compound is (2S,4R)-1-((S)-22-(tert-butyl)-1-(3,4-difluoro-2-((2-fluoro-4-iodophenyl)amino)phenyl)-1,20-dioxo-3-oxa-2,8,21-triazatricosan-23-oyl)-4-hydroxy-N—((S)-1-(4-(4-methylthiazol-5-yl)phenyl)ethyl)pyrrolidine-2-carboxamide (CPD-038).

In one embodiment, the heterobifunctional compound is (2S,4R)-1-((S)-21-(tert-butyl)-1-(3,4-difluoro-2-((2-fluoro-4-iodophenyl)amino)phenyl)-1,19-dioxo-3-oxa-2,8,20-triazadocosan-22-oyl)-4-hydroxy-N—((S)-1-(4-(4-methylthiazol-5-yl)phenyl)ethyl)pyrrolidine-2-carboxamide (CPD-39).

In one embodiment, the heterobifunctional compound is N-(3-((3-((2-(2,6-dioxopiperidin-3-yl)-1,3-dioxoisoindolin-5-yl)amino)propyl)amino)propoxy)-3,4-difluoro-2-((2-fluoro-4-iodophenyl)amino)benzamide (CPD-41).

In one embodiment, the heterobifunctional compound is N-(3-((5-((2-(2,6-dioxopiperidin-3-yl)-1,3-dioxoisoindolin-5-yl)amino)pentyl)amino)propoxy)-3,4-difluoro-2-((2-fluoro-4-iodophenyl)amino)benzamide (CPD-43).

In one embodiment, the heterobifunctional compound is N-(3-((7-((2-(2,6-dioxopiperidin-3-yl)-1,3-dioxoisoindolin-5-yl)amino)heptyl)amino)propoxy)-3,4-difluoro-2-((2-fluoro-4-iodophenyl)amino)benzamide (CPD-45).

In one embodiment, the heterobifunctional compound is N-(3-((8-((2-(2,6-dioxopiperidin-3-yl)-1,3-dioxoisoindolin-5-yl)amino)octyl)amino)propoxy)-3,4-difluoro-2-((2-fluoro-4-iodophenyl)amino)benzamide (CPD-46).

In one embodiment, the heterobifunctional compound is N-((1-((2-(2,6-dioxopiperidin-3-yl)-1,3-dioxoisoindolin-5-yl)amino)-3,6,9,12-tetraoxa-15-azaoctadecan-18-yl)oxy)-3,4-difluoro-2-((2-fluoro-4-iodophenyl)amino)benzamide (CPD-50).

In one embodiment, the heterobifunctional compound is N-((1-((2-(2,6-dioxopiperidin-3-yl)-1,3-dioxoisoindolin-5-yl)amino)-3,6,9,12,15-pentaoxa-18-azahenicosan-21-yl)oxy)-3,4-difluoro-2-((2-fluoro-4-iodophenyl)amino)benzamide (CPD-51).

According to the 2nd aspect of the present disclosure, a pharmaceutical composition is provided herein comprising a compound according to the 1st aspect of the present disclosure, and one or more pharmaceutically acceptable carriers.

In one embodiment, the pharmaceutical composition further comprising one or more additional therapeutic agent.

In one embodiment, the additional therapeutic agent is selected from the group consisting of anti-cancer or anti-tumor agents, or the combination thereof.

In one embodiment, the additional therapeutic agent is selected from the group consisting of anti-proliferative agent, immunomodulatory agent, or the combination thereof.

In one embodiment, the additional therapeutic agent is selected from mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, and anti-androgens.

In one embodiment, the additional therapeutic agent is selected from the group consisting of signaling pathway inhibitor, signaling pathway activator, or the combination thereof.

In one embodiment, the additional therapeutic agent is selected from the group consisting of kinase inhibitor, kinase activator, or the combination thereof.

In one embodiment, the additional therapeutic agent a signaling pathway inhibitor, wherein the signaling pathway is selected from the group consisting of RAS/RAF/MEK/ERK pathway, PI3K/AKT/mTOR pathway, EGFR pathway, ALK pathway, BCR-ABL pathway, and the combinations thereof.

In one embodiment, the additional therapeutic agent is an inhibitor of PI3K/AKT/mTOR pathway.

In one embodiment, the additional therapeutic agent is an inhibitor of RAS/RAF/MEK/ERK pathway.

In one embodiment, the additional therapeutic agent is an inhibitor of EGFR pathway.

In one embodiment, the additional therapeutic agent is an inhibitor of ALK pathway.

In one embodiment, the additional therapeutic agent is an inhibitor of BCR-ABL pathway.

In one embodiment, the additional therapeutic agent is a kinase inhibitor.

In one embodiment, the additional therapeutic agent is selected from the group consisting of RAF inhibitor, AKT inhibitor, EGFR inhibitor, ALK inhibitor, BCR-ABL inhibitor, PI3K inhibitor, mTOR inhibitor, mTOR activator, RAS inhibitor, RAF inhibitor, MEK inhibitor, ERK inhibitor, and the combinations thereof.

In one embodiment, the additional therapeutic agent is RAF inhibitor and/or AKT inhibitor.

According to the 3rd aspect of the present disclosure, a method of treating and/or preventing a MEK-mediated disease provided herein comprises administering to a subject in need the heterobifunctional compound or a pharmaceutically acceptable salt or analog thereof.

In one embodiment, the subject in need means a subject with one or more MEK-mediated diseases and/or a subject with elevated MEK function.

In one embodiment, the MEK-mediated disease results from MEK expression, mutation, deletion, or fusion.

In one embodiment, the subject with the MEK-mediated disease has an elevated MEK function relative to a healthy subject without the MEK-mediated disease.

In one embodiment, the subject is mammal, preferably, human.

In one embodiment, the heterobifunctional compound is selected from the group consisting of CPD-001 to CPD-097, or analogs thereof.

In one embodiment, the heterobifunctional compound is administered to the subject orally, parenterally, intradermally, subcutaneously, topically, or rectally.

In one embodiment, the method further comprises administering to the subject an additional therapeutic regimen for treating cancer, hyperproliferative disorder, inflammatory disorders, or autoimmune diseases.

In one embodiment, the additional therapeutic regimen is selected from the group consisting of surgery, chemotherapy, radiation therapy, hormone therapy, targeted therapy, and immunotherapy.

In one embodiment, the MEK-mediated diseases are selected from the group consisting of cancer, hyperproliferative disorder, inflammatory disorders, auto-immune diseases, dermatological disorders, viral infections, dry eye disorders, bone remodeling disorders, organ transplant associated immunological complications, relapsed cancer, or the combination thereof.

In one embodiment, the MEK-mediated cancer is selected from the group consisting of brain cancer, stomach cancer, squamous cell cancer, gastrointestinal tract cancer, liver cancer, biliary passage cancer, breast cancer, ovary cancer, cervix cancer, prostate cancer, testis cancer, penile cancer, genitourinary tract cancer, esophagus cancer, larynx cancer, skin cancer, lung cancer, pancreas cancer, thyroid cancer, gland cancer, bladder cancer, kidney cancer, muscle cancer, bone cancer, head cancer, neck cancer, renal cancer, colorectal cancer, gynecological cancer, cancers of the hematopoietic system, myeloproliferative neoplasms, essential thrombocythemia, polycythemia vera, primary myelofibrosis, chronic neutrophilic leukemia, acute lymphoblastic leukemia, Hodgkin's lymphoma, chronic myelomonocytic leukemia, systemic mast cell disease, hyper eosinophilic syndrome, cutaneous T-cell lymphoma, B-cell lymphoma, and myeloma.

In one embodiment, the MEK-mediated non-cancerous hyperproliferative disorder is selected from benign hyperplasia of the skin (e.g., psoriasis), restenosis, or prostate (e.g., benign prostatic hypertrophy (BPH)).

In one embodiment, the MEK-mediated disorder is selected from benign hyperplasia of the skin (e.g., psoriasis), restenosis, or prostate (e.g., benign prostatic hypertrophy (BPH)).

In one embodiment, the MEK-mediated disorder is selected from pancreatitis or kidney disease (including proliferative glomemlonephritis and diabetes-induced renal disease) In one embodiment, the MEK-mediated disorder is pain.

In one embodiment, the MEK-mediated inflammatory disorders are selected from the group consisting of ankylosing spondylitis, Crohn's disease, inflammatory bowel disease, ulcerative colitis, and ischemia reperfusion injuries.

In one embodiment, the MEK-mediated auto-immune diseases are selected from the group consisting of multiple sclerosis, scleroderma, rheumatoid arthritis, psoriatic arthritis, juvenile idiopathic arthritis, psoriasis, myasthenia gravis, type I diabetes, diabetic retinopathy, systemic lupus erythematosus, IgA nephropathy, autoimmune thyroid disorders, alopecia areata, and bullous pemphigoid.

In one embodiment, the MEK-mediated dermatological disorders are selected from the group consisting of atopic dermatitis, pruritus, alopecia areata, psoriasis, skin rash, skin irritation, skin sensitization, chronic mucocutaneous candidiasis, dermatomyositis, erythema multiforme, palmoplantar pustulosis, vitiligo, polyarteritis nodosa, and STING vasculopathy.

In one embodiment, the MEK-mediated diseases are selected from retinopathy of prematurity, age-related macular degeneration, and hemangioma.

In one embodiment, the MEK-mediated disease is a relapsed cancer.

In one embodiment, the MEK-mediated disease is refractory to one or more previous treatments.

According to the 4th aspect of the present disclosure, a use of the compound according to the $1^{st}$ aspect of the present disclosure, or a pharmaceutically acceptable salt, or analog thereof, or the pharmaceutical composition according to the $2^{nd}$ aspect of the present disclosure in preparing a drug for treating and/or preventing MEK-mediated diseases is provided.

In one embodiment, MEK-mediated diseases are defined as before.

According to the 5th aspect of the present disclosure, a method for identifying a heterobifunctional compound which mediates degradation or reduction of MEK is disclosed. The method comprises:

providing a heterobifunctional test compound comprising an MEK Ligand conjugated to a Degradation Tag through a Linker;

contacting the heterobifunctional test compound with a cell comprising a ubiquitin ligase and MEK;

determining whether MEK level is decreased in the cell; and identifying the heterobifunctional test compound as a heterobifunctional compound which mediates degradation or reduction of MEK.

In one embodiment, the cell is a cancer cell.

In one embodiment, the cancer cell is a MEK-mediated cancer cell.

According to the 6th aspect of the present disclosure, a method of selectively degrading or reducing MEK is provided comprising contacting cells with a compound of the compound according to the $1^{st}$ aspect of the present disclosure, or a pharmaceutically acceptable salt, or analog thereof, or the pharmaceutical composition according to the $2^{nd}$ aspect of the present disclosure.

In one embodiment, the cell is a cancer cell.

In one embodiment, the cancer cell is a MEK-mediated cancer cell (such as HT-29 and SK-MEL-28 cells).

In one embodiment, the method reduces MEK protein levels in the cells.

In one embodiment, the method is an in vitro non-therapeutic method.

According to the $7^{th}$ aspect of the present disclosure, a use of the heterobifunctional compound, or a pharmaceutically acceptable salt, hydrate, solvate, prodrug, stereoisomer, tautomer, or analog thereof, is provided in combination with one or more additional therapeutic agents.

In one embodiment, the heterobifunctional compound is of FORMULA I, or I-1.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1. CPD-001, CPD-014 and CPD-015, but not CPD-19 and CPD-24, reduced MEK1 and MEK2 kinase levels in HT-29 cells.

FIG. 2A-C. PD0325901, CPD-031, and CPD-034 inhibited MEK1 and MEK2 kinase activities.

FIG. 13A-F, 13G-I. CPD-037, CPD-038 and CPD-051 significantly suppressed the growth of HT-29 and SK-MEL-28 cells. CPD-053, CPD-052 and CPD-097 did not significantly suppress the growth of HT-29 and SK-MEL-28 cells.

FIG. 14A-D. CPD-037 and CPD-038 are more potent than AZ compound at the growth inhibition of HT-29, SK-MEL-28, H3122, and SUDHL1 cells.

FIG. 15A-B. Concurrent inhibition of BRAF or PI3K potentiated anti-proliferation potency of CPD-038.

FIG. 16. Plasma concentrations of CPD-031, CPD-037 and CPD-038 in mice following a single intraperitoneal injection.

DETAILED DESCRIPTION

Figure 3A:
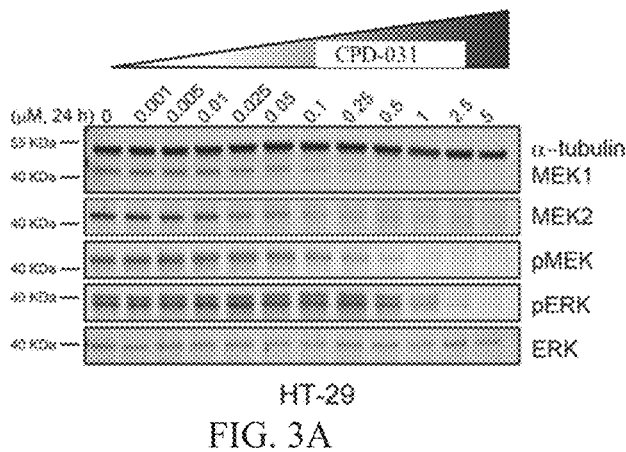
FIG. 3A-B. CPD-031 reduced MEK1 and MEK2 protein levels, and inhibited phosphorylation of MEK and ERK proteins in a concentration-dependent manner in HT-29 and SK-MEL-28 cells.
Figure 3B:
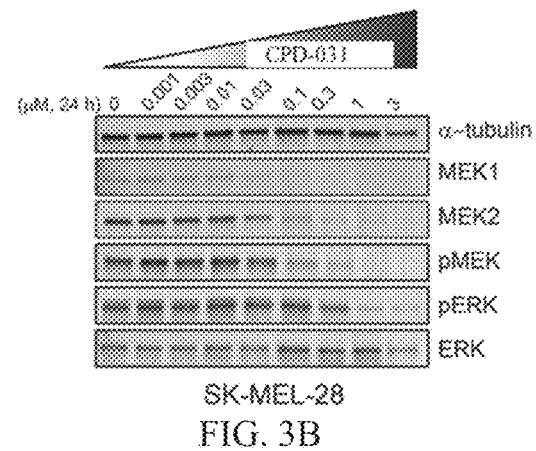
Figure 3C:
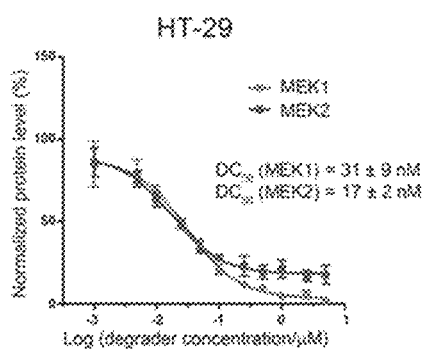
FIG. 3C-D. $DC_{50}$ curves of CPD-031 at the degradation of MEK1 and MEK2 proteins in HT-29 and SK-MEL-28 cells.
Figure 3D:
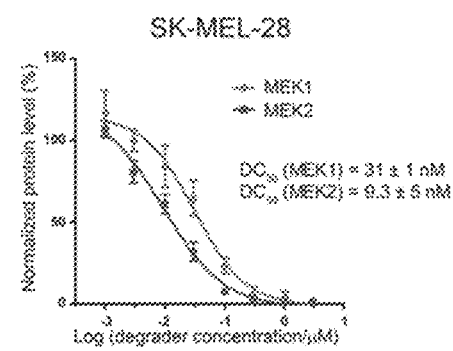

Mitogen-activated protein kinase kinases 1 and 2 (MEK1/2) are critical components of the mitogen-activated protein kinase (MAPK)/extracellular signal-regulated kinase (ERK) signaling transduction pathway, which transmits extracellular signal into the nucleus through a cascade activation of multiple proteins, including Ras, Raf, MEK, and ERK.[1-3] As crucial proteins in the MAPK/ERK signaling, MEK1/2 are phosphorylated and activated by its upstream RAF kinases.[4] Activation of MEK1/2 consequently leads to the phosphorylation of ERK at the threonine and tyrosine residues and activation of the ERK signaling.[5] The MAPK/ERK signaling pathway is associated with a broad array of cellular processes, including cell proliferation, differentiation, cell survival, and apoptosis.[6, 7] Aberrant regulation of this pathway through hyperactivation and mutation has been implicated in a variety of human cancers, such as melanoma, non-small cell lung cancer (NSCLC), colorectal cancer, primary brain tumors, and hepatocellular carcinoma.[1, 8-12]

Pharmacological inhibition of the MAPK/ERK signaling pathway by targeting the catalytic function of Ras, Raf, MEK, and ERK has resulted in multiple FDA approved drugs and many inhibitors in clinic development.[13-20] PD184352 was the first MEK1/2 inhibitor that entered clinical trials.[21] However, development of PD184352 was terminated due to lack of clinical efficacy.[22, 23] Optimization of PD184352 led to another clinical MEK1/2 inhibitor PD0325901 (1) (FIG. 1) with improved potency, solubility and metabolic stability.[24] PD0325901 is a typical non-ATP competitive MEK1/2 inhibitor, which occupies an allosteric binding pocket adjacent to the ATP binding site.[25] Numerous MEK inhibitors have been reported subsequently.[26] Although MEK inhibitors can be used as a single agent to treat diseases, the combination of MEK and BRAF inhibitors has shown delayed drug resistance and prolonged progression-free survival.[27-29] As a result, combination therapies, such as MEK inhibitor trametinib (2) (FIG. 1) with BRAF inhibitor dabrafenib, MEK inhibitor cobimetinib with BRAF inhibitor vemurafenib, and MEK inhibitor binimetinib with BRAF inhibitor encorafenib, have been approved by FDA for treating BRAF mutated melanoma.[30-33] These combination therapies have shown good efficacies for treating melanoma patients. However, acquired drug resistance through reactivation and mutation has been reported.[34, 35] Therefore, new therapeutic strategies to delay or overcome drug resistance are desired.

In addition to the important functions of MEK1/2 in the canonical ERK signaling cascade, MEK1/2 possess other biological roles by phosphorylation of MyoD, HSF1, and β-arrestin 2.[47-49] Furthermore, MEK1/2 have non-catalytic functions, which have been associated with nuclear export of ERK and PPARγ, repression of MyoD transactivation, and regulation of FOXO1 localization.[50-53] Therefore, reduction of MEK1/2 protein levels using PROTACs is expected to diminish both catalytic and non-catalytic functions of the proteins and could have more profound pharmacological effects than inhibition of the kinase activity alone.

Disclosed herein, in some embodiments, are heterobifunctional compounds. In some embodiments, the heterobifunctional compound comprises a chemical structure or formula disclosed herein. The heterobifunctional compound may be or include a MEK degrader. MEK degraders may be characterized by the ability to degrade or reduce cellular protein levels of MEK. Some embodiments relate to a composition that includes the heterobifunctional compound. Some embodiments relate to methods of making the heterobifunctional compound. Some embodiments relate to methods of using the heterobifunctional compound or a pharmaceutical composition of the heterobifunctional compound. For example, the heterobifunctional compound may be used to treat a disorder or a disease. In some cases, the compound is used to treat autoimmune diseases. In some cases, the compound is used to treat inflammatory diseases. In some cases, the compound is used to treat cancers.

This disclosure includes all stereoisomers, geometric isomers, tautomers and isotopes of the structures depicted and compounds named herein. This disclosure also includes compounds described herein, regardless of how they are prepared, e.g., synthetically, through biological process (e.g., metabolism or enzyme conversion), or a combination thereof.

This disclosure includes pharmaceutically acceptable salts of the structures depicted and compounds named herein.

One or more constituent atoms of the compounds presented herein can be replaced or substituted with isotopes of the atoms in natural or non-natural abundance. In some embodiments, the compound does not include any deuterium atoms. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms. In some embodiments, the compound does not include any fluorine atoms. In some embodiments, the compound includes at least one fluorine atom. In some embodiments, the compound includes two or more fluorine atoms. In some embodiments, the compound includes 1-2, 1-3, 1-4, 1-5, or 1-6 fluorine atoms. In some embodiments, all of the hydrogen atoms in a compound can be replaced or substituted by fluorine atoms.

Heterobifunctional Compounds

Disclosed herein, in some embodiments, are compounds. In some embodiments, the compound comprises a MEK-binding moiety disclosed herein. In some embodiments, the compound comprises a MEK allosteric-site-binding moiety disclosed herein. In some embodiments, the compound comprises a MEK ATP-site-binding moiety disclosed herein. In some embodiments, the compound comprises a Degradation Tag disclosed herein. In some embodiments, the compound comprises a VHL-binding moiety. In some embodiments, the compound comprises a CRBN-binding moiety. In some embodiments, the compound comprises a MEK degrader. For example, the compound may result in MEK degradation. The compound may degrade MEK as a result of hijacking VHL ligase function. The compound may degrade MEK as a result of hijacking CRBN ligase function. The compound may bind to or modulate MEK or VHL. The compound may bind to or modulate MEK or CRBN. In some embodiments, the compound comprises a heterobifunctional compound. In some embodiments, the compound comprises a Linker.

According to the first aspect of the present disclosure, a heterobifunctional compound disclosed herein comprises a mitogen-activated protein kinase kinase (MEK) Ligand conjugated to a Degradation Tag through a Linker, which comprises a moiety of FORMULA I:

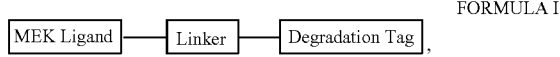

FORMULA I or a pharmaceutically acceptable salt, hydrate, solvate, prodrug, stereoisomer, tautomer, or analog thereof.

In one embodiment, a heterobifunctional compound disclosed herein comprises a moiety of FORMULA I-1

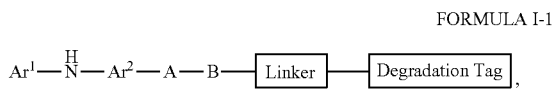

FORMULA I-1 or a pharmaceutically acceptable salt, hydrate, solvate, prodrug, stereoisomer, tautomer, or analog thereof, wherein (i) $Ar^1$ is selected from the group consisting of optionally substituted monocyclic aryl, and optionally substituted monocyclic heteroaryl;

$Ar^2$ is selected from the group consisting of optionally substituted monocyclic or bicyclic aryl, optionally substituted monocyclic or bicyclic pyridinone, and optionally substituted monocyclic or bicyclic heteroaryl;

A is bivalent group selected from the group consisting of $C(O)NR^1$, $S(O)NR^1$, $S(O)_2NR^1$, and CO, wherein $R^1$ is selected from the group consisting of hydrogen, optionally substituted $C_1$-$C_8$ alkyl, optionally substituted $C_2$-$C_8$ alkenyl, optionally substituted $C_2$-$C_8$ alkynyl, optionally substituted —C=N—, optionally substituted —C(O)N—, optionally substituted $C_3$-$C_8$ carbocyclyl, optionally substituted 3-8 membered heterocyclyl, optionally substituted aryl, and optionally substituted heteroaryl; or R1 and $Ar^2$, together with the atom(s) and to which they are connected, optionally form an optionally substituted bicyclic heterocyclyl ring, or an bicyclic heteroaryl ring.

B is selected from null or O;

(ii-a) the Degradation Tag is a moiety of FORMULAE 6A, 6B, or 6C:

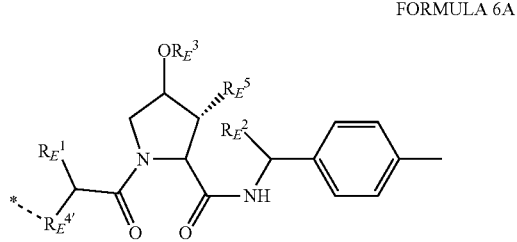

FORMULA 6A

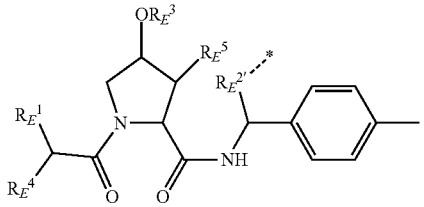

FORMULA 6B

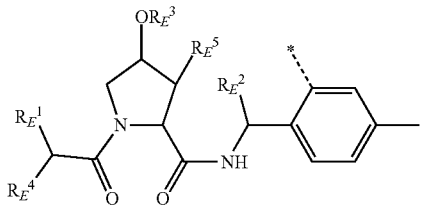

FORMULA 6C

*indicates the connection to the Linker moiety of the heterobifunctional compound;

$R_E^1$ and $R_E^2$ are independently selected from the group consisting of hydrogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl; optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted $C_3$-$C_{10}$ carbocyclyl, optionally substituted 3-10 membered heterocyclyl;

$R_E^{2'}$ is a divalent group selected from the group consisting of null, O, NH, optionally substituted $C_1$-$C_8$ alkylene, optionally substituted $C_2$-$C_8$ alkenylene, optionally substituted $C_2$-$C_8$ alkynylene; optionally substituted $C_1$-$C_8$alkoxy$C_1$-$C_8$alkylene, optionally substituted $C_1$-$C_8$ haloalkylene, optionally substituted $C_1$-$C_8$ hydroxyalkylene, optionally substituted $C_1$-$C_8$ aminoalkylene, optionally substituted $C_1$-$C_8$alkylamino$C_1$-$C_8$alkylene, optionally substituted $C_3$-$C_{10}$ carbocyclyl, and optionally substituted 3-10 membered heterocyclyl;

$R_E^3$ is selected from the group consisting of hydrogen, optionally substituted —$C(O)R_E^7$, —$C(O)OR_E^7$, —$C(O)NR_E^7R_E^8$, —$P(O)(OR_E^7)_2$, and —$CR_E^7R_E^8$—OP(O)(OR_E^9)_2$, wherein $R_E^7$, $R_E^8$ and $R_E^9$ are independently selected from the group consisting of hydrogen, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted $C_3$-$C_{10}$ carbocyclyl, optionally substituted 3-10 membered heterocyclyl, optionally substituted $C_2$-$C_8$ alkenyl, optionally substituted $C_2$-$C_8$ alkynyl, optionally substituted aryl and optionally substituted heteroaryl;

$R_E^4$ is selected from the group consisting of —$N(R_E^{10})R_E^{11}$, —$OR_E^{10}$, —$N(R_E^{10})C(O)R_E^{11}$, optionally substituted $C_3$-$C_{10}$ carbocyclyl, optionally substituted 3-10 membered heterocyclyl, optionally substituted aryl, and optionally substituted heteroaryl;

$R_E^{4'}$ is a divalent group selected from the group consisting of —$N(R_E^{10})$—, —O—, —$N(R_E^{10})C(O)R_E^{11'}$—, optionally substituted $C_3$-$C_{10}$ carbocyclyl, optionally substituted 3-10 membered heterocyclyl, optionally substituted aryl, and optionally substituted heteroaryl;

$R_E^{10}$ is selected from the group consisting of hydrogen, optionally substituted $C_1$-$C_8$alkyl, optionally substituted $C_3$-$C_8$cycloalkyl, optionally substituted $C_1$-$C_8$alkyl-CO, optionally substituted $C_1$-$C_8$cycloalkyl-CO, optionally substituted $C_3$-$C_8$cycloalkyl-$C_1$-$C_8$alkyl-CO, optionally substituted 3-10 membered heterocyclyl-CO, optionally substituted 3-10 membered heterocyclyl-$C_1$-$C_8$alkyl-CO, optionally substituted aryl-CO, optionally substituted aryl-$C_1$-$C_8$alkyl-CO, optionally substituted heteroaryl-CO, optionally substituted heteroaryl-$C_1$-$C_8$alkyl-CO, optionally substituted aryl, and optionally substituted heteroaryl;

$R_E^{11}$ is selected from the group consisting of hydrogen, optionally substituted $C_1$-$C_8$alkyl, optionally substituted $C_3$-$C_8$cycloalkyl, optionally substituted 3-8 membered heterocycloalkyl, optionally substituted $C_3$-$C_8$ carbocyclyl, and optionally substituted $C_3$-$C_8$ heterocyclyloyl;

$R_E^{11'}$, at each occurrence, is a divalent group independently selected from the group consisting of null, O, optionally substituted $C_1$-$C_8$alkylene, optionally substituted $C_3$-$C_8$ cycloalkylene, optionally substituted 3-8 membered heterocycloalkylene, optionally substituted $C_3$-$C_8$ carbocyclyl, and optionally substituted $C_3$-$C_8$ heterocyclyloyl;

$R_E^5$ is selected from the group consisting of hydrogen and halogen (such as F); and $R_E^6$ is selected from hydrogen, halogen, hydroxyl, amino, cyano, nitro, optionally substituted $C_1$-$C_8$alkyl, optionally substituted $C_1$-$C_8$cycloalkyl, optionally substituted $C_1$-$C_8$alkoxy, and optionally substituted $C_1$-$C_8$cycloalkoxy, optionally substituted $C_1$-$C_8$heterocycloalkyl, optionally substituted aryl, and optionally substituted heteroaryl;

Or, (ii-b) the Degradation Tag is a moiety of FORMULA 5, and the Degradation Tag is connected to the Linker moiety of the heterobifunctional compound via $Z_E$;

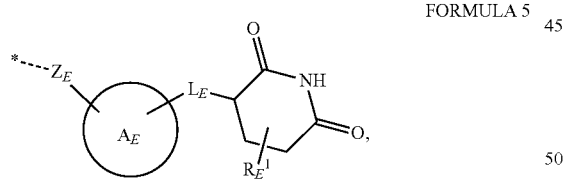

FORMULA 5 wherein $Z_E$ is a divalent group of —$(R_E^z)_{n_E}$—; wherein subscript $n_E$=0, 1, 2, 3, 4, 5 or 6; wherein $R_E^z$, at each occurrence, is independently $R_E^r$, or $R_E^w$; wherein $R_E^w$, at each occurrence, is a bond or selected from the group consisting of —CO—, —$CR_E^5R_E^6$—, —$NR_E^5$—, —O—, optionally substituted $C_1$-$C_{10}$ alkylene, optionally substituted $C_1$-$C_{10}$ alkenylene, optionally substituted $C_1$-$C_{10}$ alkynylene; and $R_E^r$, at each occurrence, is a bond, or selected from the group consisting of optionally substituted $C_3$-$C_{10}$ carbocyclyl such as 3-13 membered carbocyclyl, optionally substituted 3-13 membered heterocyclyl, optionally substituted aryl, and optionally substituted heteroaryl; with the proviso that —$R_E^z$-$R_E^z$— is not —O—O—;

$R_E^5$ and $R_E^6$, at each occurrence, are independently selected from the group consisting of hydrogen, halogen, oxo, hydroxy, amino, cyano, nitro, optionally substituted $C_1$-$C_6$ alkyl, optionally substituted 3 to 8 membered carbocyclyl, and optionally substituted 3 to 8 membered heterocyclyl; or $R_E^5$ and $R_E^6$ together with the atom(s) to which they are connected form an optionally substituted 3-8 membered cycloalkyl or heterocyclyl ring;

$R_E^1$ is selected from the group consisting of hydrogen, halogen, cyano, nitro, optionally substituted $C_1$-$C_6$ alkyl, optionally substituted 3-8 membered carbocyclyl, and optionally substituted 3-8 membered heterocyclyl;

$L_E$ is a divalent group selected from the group consisting of null, -$L_E^1$-, and -$L_E^1$-$L_E^2$-; wherein $L_E^1$ and $L_E^2$ are independently selected from the group consisting of —CO—, —O—, —$CR_E^{10}R_E^{11}$— and —$NR_E^{10}$—, with the proviso that -$L_E^1$-$L_E^2$— is not —O—O—; wherein $R_E^{10}$ and $R_E^{11}$ are independently selected from the group consisting of hydrogen, halogen, cyano, nitro, hydroxy, amino, optionally substituted $C_1$-$C_6$ alkyl, optionally substituted $C_1$-$C_6$ alkoxy, and optionally substituted $C_1$-$C_6$ alkylamino;

Ring $A_E$ is a divalent group selected from the group consisting of FORMULA $A_E$1, $A_E$2, $A_E$3, $A_E$4 and $A_E$5:

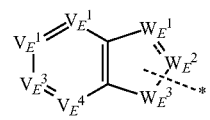

FORMULA $A_E$1

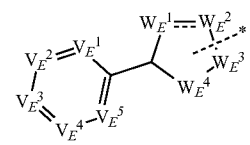

FORMULA $A_E$2

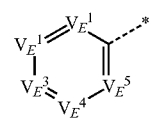

FORMULA $A_E$3

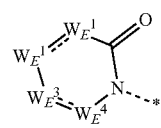

FORMULA $A_E$4

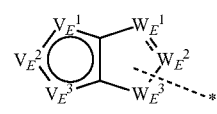

FORMULA $A_E$5 wherein

* indicates the attachment to $L_E$, and $Z_E$ is attached to any possible position on the Ring $A_E$;

⁓ indicates a single bond or a double bond;

$V_E^1$, $V_E^2$, $V_E^3$, $V_E^4$ and $V_E^5$, at each occurrence, are each independently selected from the group consisting of a bond, C, $CR_E^2$, S, N, and $NR_E^2$; or $V_E^1$ and $V_E^2$, $V_E^2$ and $V_E^3$, $V_E^3$ and $V_E^4$, or $V_E^4$ and $V_E^5$ are combined together to optionally form $C_6$ aryl ring or a 5 or 6 membered heteroaryl ring;

$R_E^2$, at each occurrence, is independently selected from the group consisting of absent, hydrogen, halogen, cyano, nitro, hydroxy, amino, optionally substituted $C_1$-$C_6$ alkyl, optionally substituted $C_1$-$C_6$ alkenyl, optionally substituted $C_1$-$C_6$ alkynyl, optionally substituted $C_1$-$C_6$ alkoxy, optionally substituted $C_1$-$C_6$ alkylamino, optionally substituted 3-8 membered carbocyclyl, and optionally substituted 3-8 membered heterocyclyl; or $R_E^2$ and another $R_E^2$ together with the atom(s) to which they are connected form optionally substituted 3-8 membered cycloalkyl, optionally substituted 3-8 membered heterocyclyl ring, optionally substituted aryl, and optionally substituted heteroaryl;

$W_E^1$, $W_E^2$, $W_E^3$ and $W_E^4$ are each independently selected from the group consisting of —N=, —C=, —$CR_E^3$=, —CO—, —O—, —$CR_E^3R_E^4$—, —$NR_E^3$—, —$CR_E^3$=$CR_E^4$—, —N=$CR_E^3$—, and —N=N—; or $W_E^1$ and $W_E^2$, $W_E^2$ and $W_E^3$, or $W_E^3$ and $W_E^4$ are combined together to optionally form $C_6$ aryl ring or a 5, 6 or 7 membered heteroaryl ring;

$R_E^3$ and $R_E^4$, at each occurrence, are independently selected from the group consisting of absent, hydrogen, halogen, cyano, nitro, hydroxy, amino, optionally substituted $C_1$-$C_6$ alkyl, optionally substituted 3 to 8 membered carbocyclyl, and optionally substituted 3 to 8 membered heterocyclyl; or $R_E^3$ and $R_E^4$, on the same atom or on the adjacent atoms, together with the atom(s) to which they are connected form an optionally substituted 3-8 membered cycloalkyl or heterocyclyl ring;

and, (iii) the Linker moiety is of FORMULA 9:

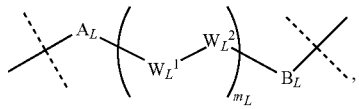

FORMULA 9 wherein $A_L$, $W_L^1$, $W_L^2$, and $B_L$, at each occurrence, are bivalent moieties independently selected from the group consisting of null, $R_L^d$—$R_L^e$, $R_L^dCOR_L^e$, $R_L^dC(O)OR_L^e$, $R_L^dC(O)N(R_L^1)R_L^e$, $R_L^dC(S)N(R_L^1)R_L^e$, $R_L^dOR_L^e$, $R_L^dSR_L^e$, $R_L^dSOR_L^e$, $R_L^dSO_2R_L^e$, $R_L^dSO_2N(R_L^1)R_L^e$, $R_L^dN(R_L^1)R_L^e$, $R_L^dN(R_L^1)COR_L^e$, $R_L^dN(R_L^1)CON(R_L^2)R_L^e$, $R_L^dN(R_L^1)SON(R_L^2)R_L^e$, $R_L^dN(R_L^1)SO_2N(R_L^2)R_L^e$, $R_L^dN(R_L^1)C(S)R_L^e$, optionally substituted $C_1$-$C_8$ alkylene, optionally substituted $C_2$-$C_8$ alkenylene, optionally substituted $C_2$-$C_8$ alkynylene, optionally substituted $C_1$-$C_8$alkoxy$C_1$-$C_8$alkylene, optionally substituted $C_1$-$C_8$ haloalkylene, optionally substituted $C_1$-$C_8$ hydroxyalkylene, optionally substituted $C_3$-$C_{13}$ cycloalkyl, optionally substituted 3-13 membered heterocyclyl, optionally substituted aryl, and optionally substituted heteroaryl, wherein $R_L^d$ and $R_L^e$, at each occurrence, are independently selected from null, $R_L^r$, optionally substituted ($C_1$-$C_8$ alkylene)-$R_L^r$, optionally substituted $R_L^r$-($C_1$-$C_8$ alkylene), optionally substituted ($C_1$-$C_8$ alkylene)-$R_L^r$-($C_1$-$C_8$ alkylene), or a bivalent moiety comprising of optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted $C_3$-$C_{13}$ cycloalkyl, optionally substituted 3-13 membered, optionally substituted aryl, and optionally substituted heteroaryl;

$R_L^r$, at each occurrence, is selected from optionally substituted $C_3$-$C_{10}$ carbocyclyl, optionally substituted 3-10 membered heterocyclyl, optionally substituted aryl, and optionally substituted heteroaryl;

$R_L^1$ and $R_L^2$, at each occurrence, are independently selected from the group consisting of hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_{10}$ carbocyclyl, optionally substituted 3-10 membered heterocyclyl, optionally substituted aryl, and optionally substituted heteroaryl;

$R_L^d$ and $R_L^e$, $R_L^1$ and $R_L^2$, $R_L^d$ and $R_L^1$, $R_L^d$ and $R_L^2$, $R_L^e$ and $R_L^1$, or $R_L^e$ and $R_L^2$ together with the atom(s) to which they are connected optionally form a $C_3$-$C_{20}$ carbocyclyl or 3-20 membered heterocyclyl ring; and $m_L$ is 1, 2, 3, 4, 5, 6, 7, 8, 9, 10, 11, 12, 13, 14, or 15.

In one embodiment, a heterobifunctional compound disclosed herein comprises a moiety of FORMULA I-2

FORMULA I-2

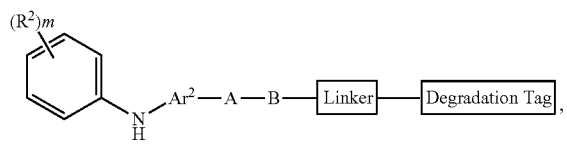

or a pharmaceutically acceptable salt, hydrate, solvate, prodrug, stereoisomer, tautomer, or analog thereof, wherein $Ar^2$, A, B, Linker and Degradation Tag are defined as in FORMULA I-1;

$R^2$, at each occurrence, is independently selected from hydrogen, halogen, cyano, nitro, azido, amino, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted aryl, or optionally substituted heteroaryl; and m is selected from 0, 1, 2, 3, 4, and 5.

In one embodiment, a heterobifunctional compound disclosed herein comprises a moiety of FORMULAE I-3, I-4, I-5, I-6, I-7 and I-8:

FORMULA I-3

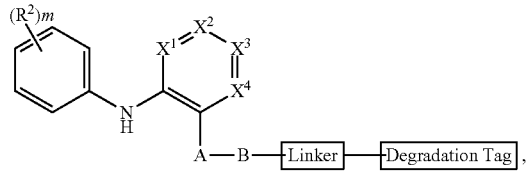

-continued

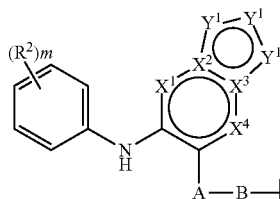
FORMULA I-4

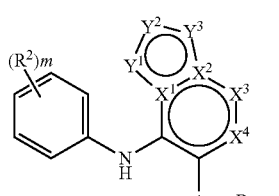
FORMULA I-5

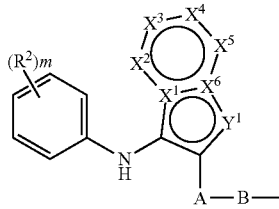
FORMULA I-6

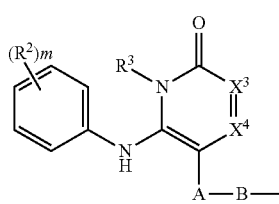
FORMULA I-7

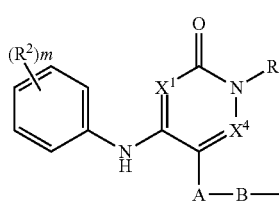
FORMULA I-8 or a pharmaceutically acceptable salt, hydrate, solvate, prodrug, stereoisomer, tautomer, or analog thereof, wherein A, B, Linker and Degradation Tag are defined as in FORMULA I-1;

$R^2$, and m are defined as in FORMULA I-2;

$Y^1$, $Y^2$, and $Y^3$ are independently selected from $NR^3$, $CR^4$, O, and S;

$X^1$, $X^2$, $X^3$, $X^4$, $X^5$, and $X^6$, are independently selected from $CR^5$ and N;

$R^3$, at each occurrence, is independently selected from null, hydrogen, optionally substituted $C_1$-$C_8$ alkyl, optionally substituted $C_3$-$C_8$ cycloalkyl, optionally substituted aryl, and optionally substituted heteroaryl.

$R^4$ and $R^5$, at each occurrence, are independently selected from the group consisting of null, hydrogen, halogen, cyano, nitro, azido, amino, $OR^6$, $SR^6$, $NR^6R^7$, $OCOR^6$, $OCO_2R^6$, $OCON(R^6)R^7$, $COR^6$, $CO_2R^6$, $CON(R^6)R^7$, $SOR^6$, $SO_2R^6$, $SO_2N(R^6)R^7$, $NR^8CO_2R^6$, $NR^8COR^6$, $NR^8C(O)N(R^6)R^7$, $NR^8SOR^6$, $NR^8SO_2R^6$, and $NR^8SO_2N(R^6)R^7$, optionally substituted $C_1$-$C_5$ alkyl, optionally substituted $C_2$-$C_5$ alkenyl, optionally substituted $C_2$-$C_5$ alkynyl, optionally substituted $C_1$-$C_8$alkoxy$C_1$-$C_8$alkyl, optionally substituted $C_1$-$C_8$alkylamino$C_1$-$C_8$alkyl, optionally substituted 3-10 membered heterocyclyl$C_1$-$C_8$alkyl, optionally substituted $C_3$-$C_{10}$ carbocyclyl$C_1$-$C_8$alkyl, optionally substituted $C_3$-$C_{10}$ carbocyclyl, optionally substituted 3-10 membered heterocyclyl, optionally substituted aryl, and optionally substituted heteroaryl, wherein $R^6$, $R^7$, and $R^8$ are independently selected from the group consisting of null, hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ carbocyclyl$C_1$-$C_8$alkyl, optionally substituted 3-10 membered heterocyclyl$C_1$-$C_8$alkyl, optionally substituted $C_3$-$C_{10}$ carbocyclyl, optionally substituted 3-10 membered heterocyclyl, optionally substituted aryl, and optionally substituted heteroaryl, or $R^6$ and $R^7$, $R^6$ and $R^8$ together with the atom to which they are connected form a 3-20 membered heterocyclyl ring;

In one embodiment, $Ar^2$ is selected the group consisting of:

In one embodiment, $Ar^2$ is selected from optionally substituted monocyclic aryl or heteroaryl groups comprising:

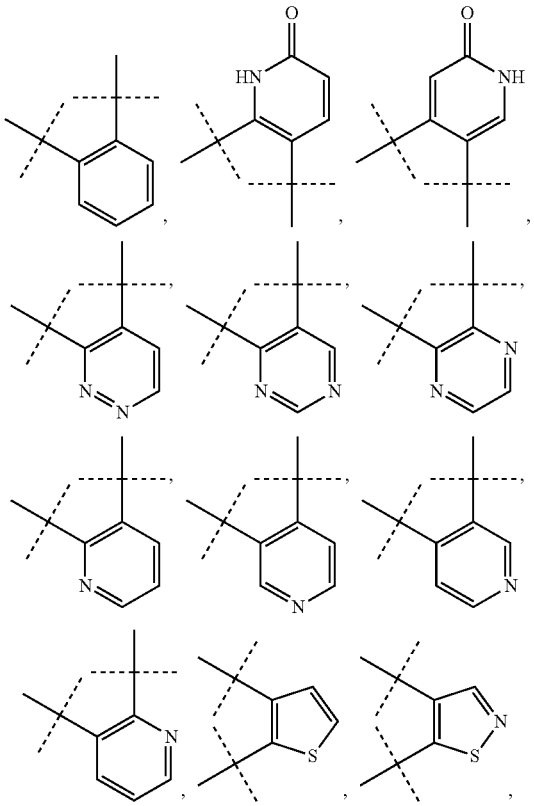

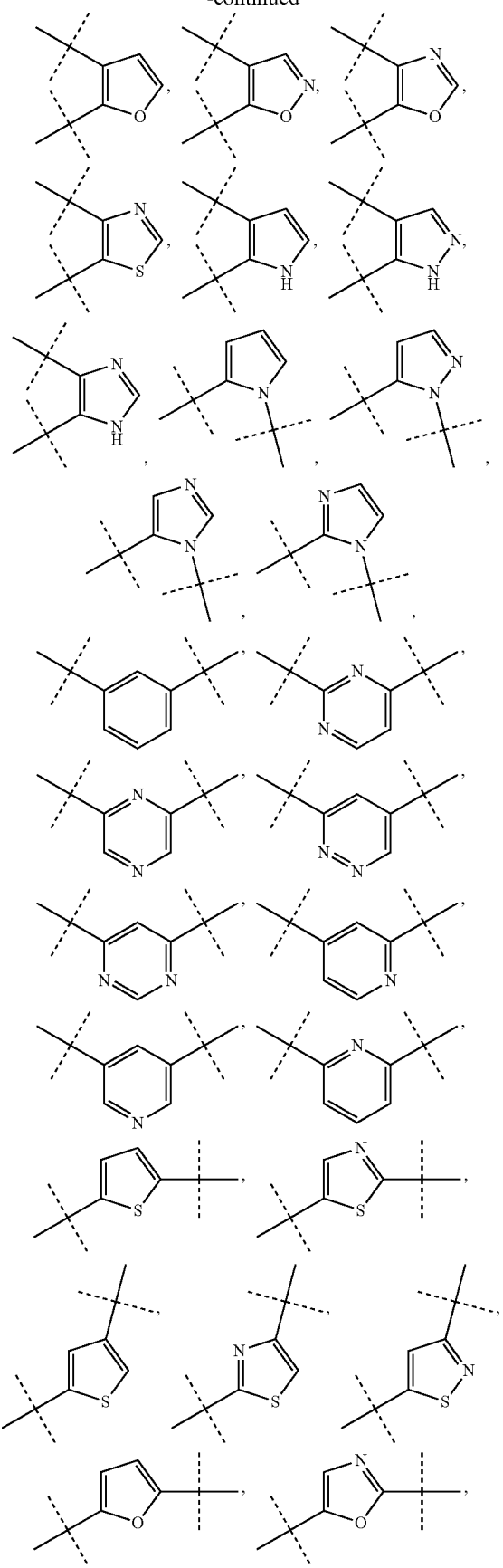
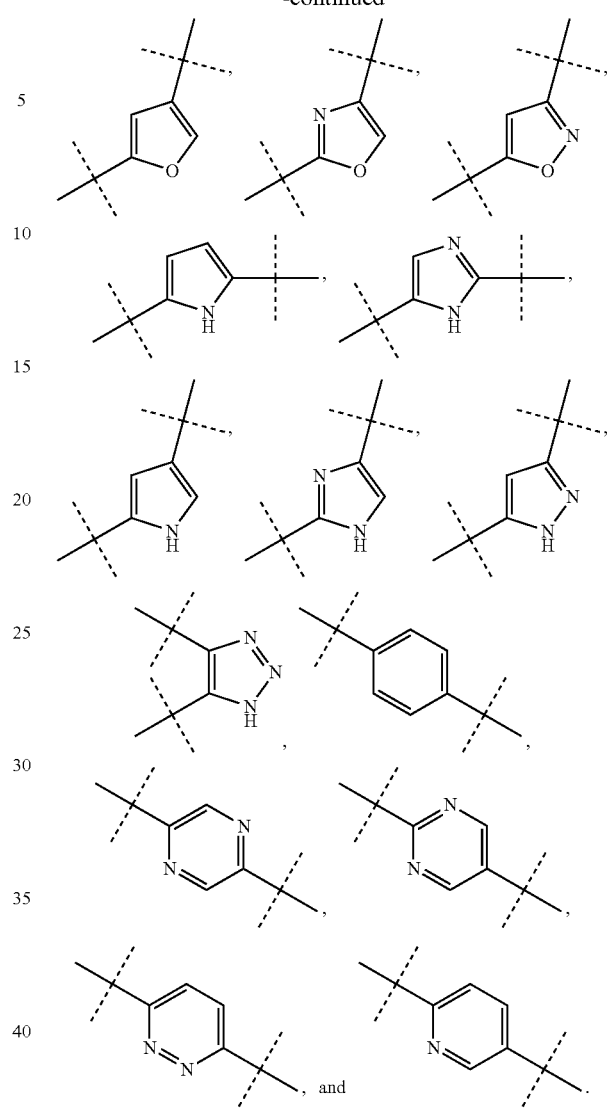
In one embodiment, Ar² is selected from optionally substituted bicyclic heteroaryl groups comprising:
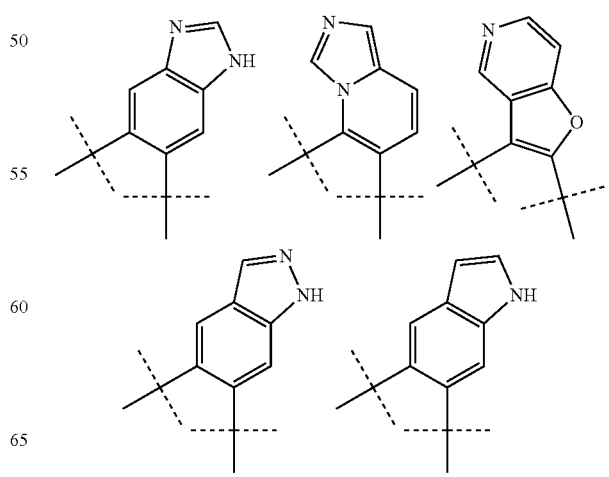

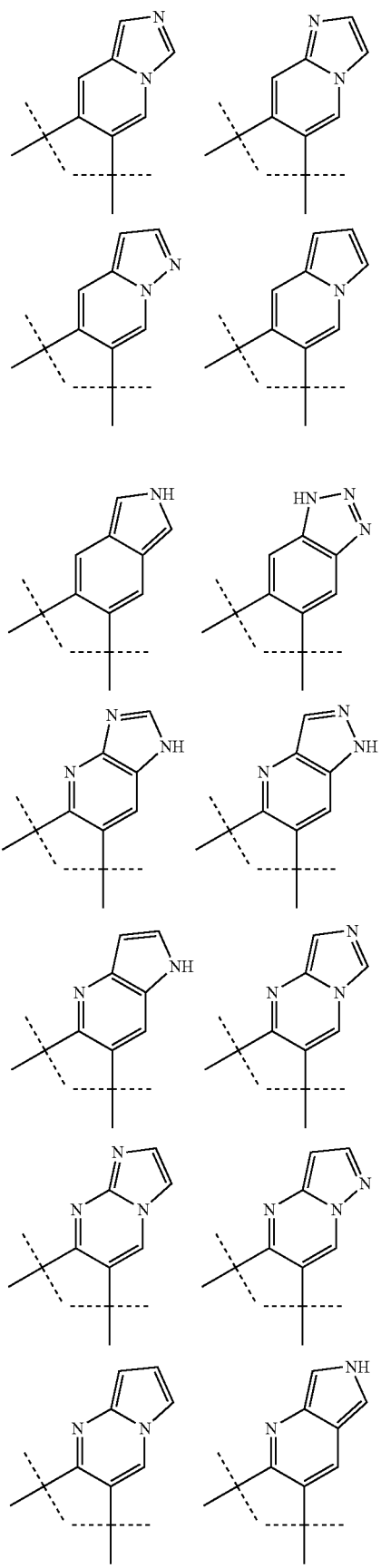
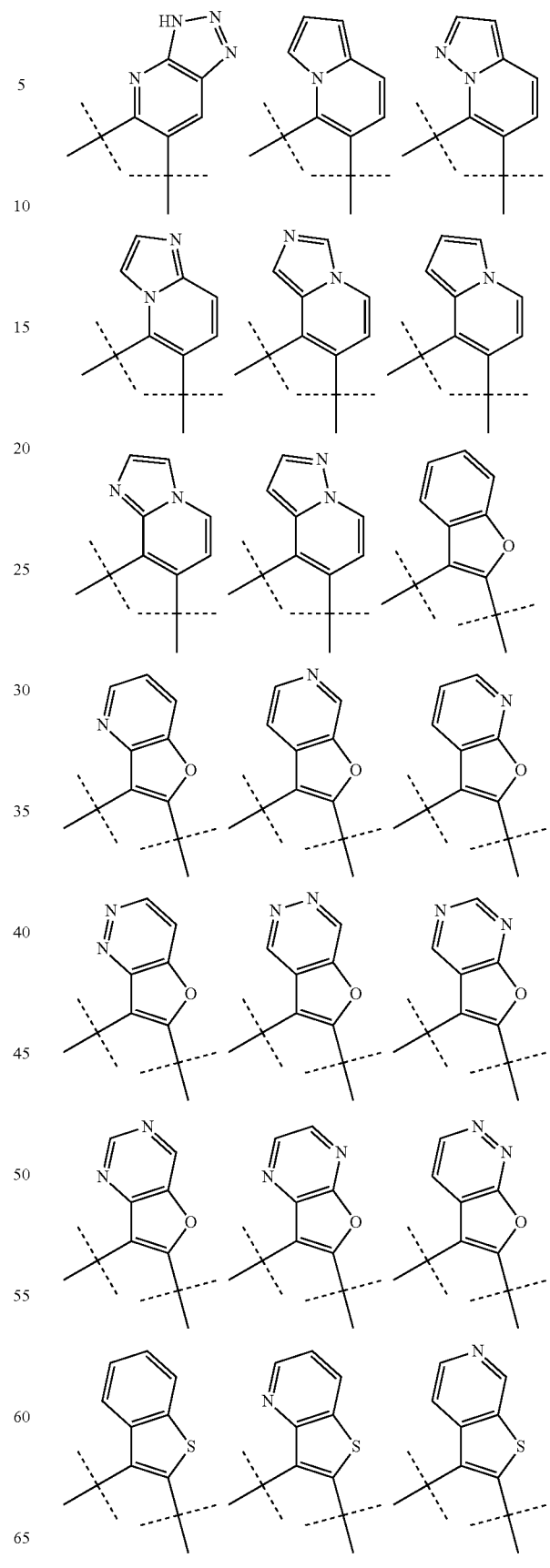

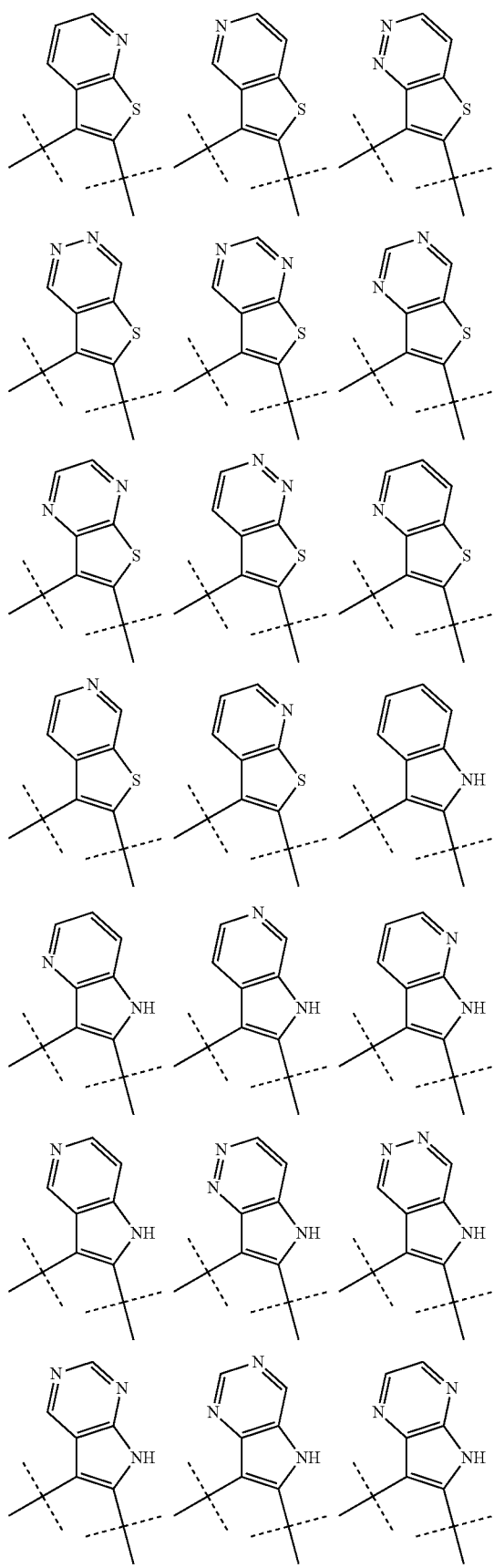
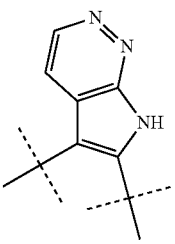
In one embodiment, a heterobifunctional compound disclosed herein comprises a moiety of FORMULA I-9, I-10, I-11, I-12, I-13, and I-14:
FORMULA I-9
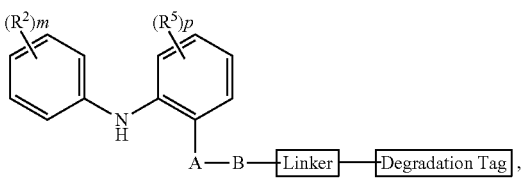
FORMULA I-10
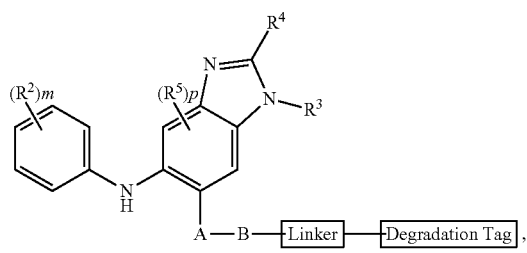
FORMULA I-11
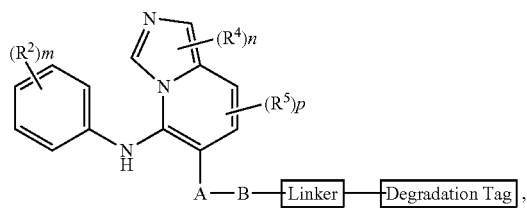
FORMULA I-12
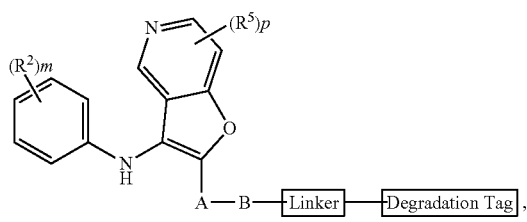
FORMULA I-13
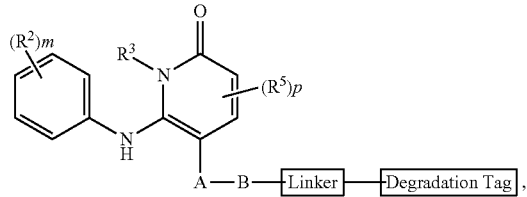

FORMULA I-14

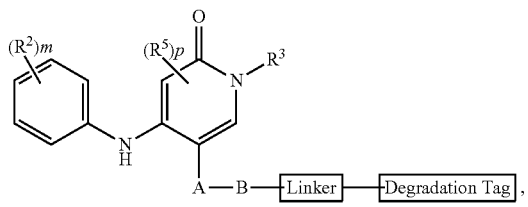

or a pharmaceutically acceptable salt, hydrate, solvate, prodrug, stereoisomer, tautomer, or analog thereof, wherein A, B, Linker and Degradation Tag are defined as in FORMULA I-1;

$R^2$, and m are defined as in FORMULA I-2;

$R^3$, $R^4$, and $R^5$ are defined as in FORMULAE I-3, I-4, I-5, I-6, I-7 and I-8;

n is 0, 1 or 2; and p is 0, 1, 2, 3 or 4.

In one embodiment, a heterobifunctional compound disclosed herein comprises a moiety of FORMULAE I-15, I-16, I-17, I-18, I-19 and I-20:

FORMULA I-15

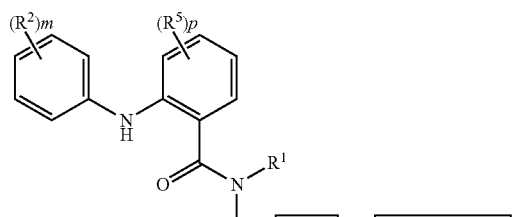

FORMULA I-16

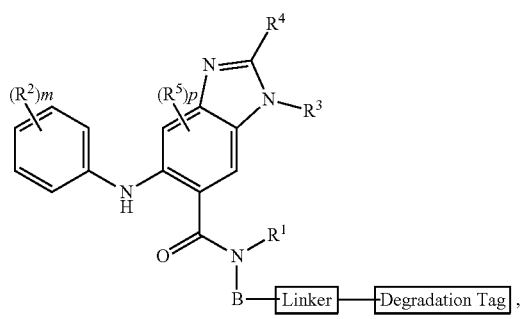

FORMULA I-17

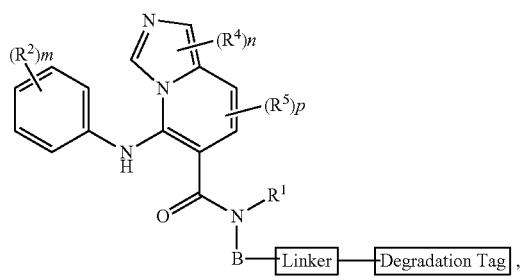

FORMULA I-18

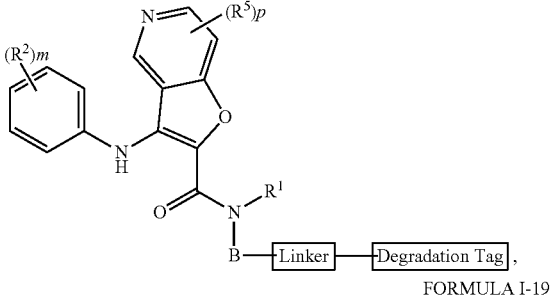

FORMULA I-19

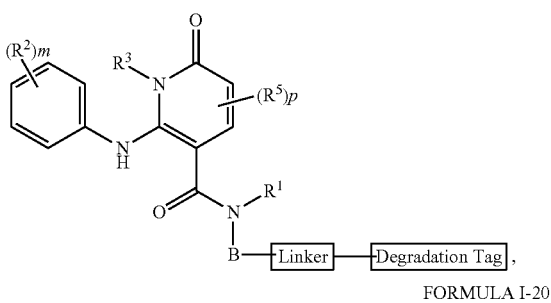

FORMULA I-20

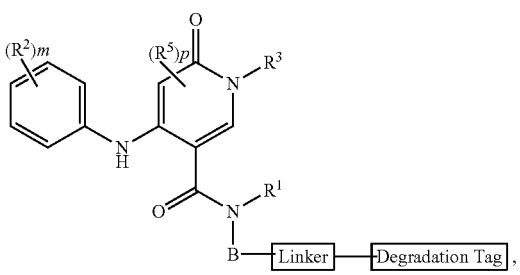

or a pharmaceutically acceptable salt, hydrate, solvate, prodrug, stereoisomer, tautomer, or analog thereof, wherein B, Linker and Degradation Tag are defined as in FORMULA I-1;

$R^2$, and m are defined as in FORMULA I-2;

$R^3$, $R^4$, and $R^5$ are defined as in FORMULAE I-3, I-4, I-5, I-6, I-7 and I-8;

n and p are defined as in FORMULAE I-9, I-10, I-11, I-12, I-13 and I-14.

In one embodiment, a heterobifunctional compound disclosed herein comprises a moiety of FORMULAE I-21, I-22, I-23, I-24, I-25 and I-26:

FORMULA I-21

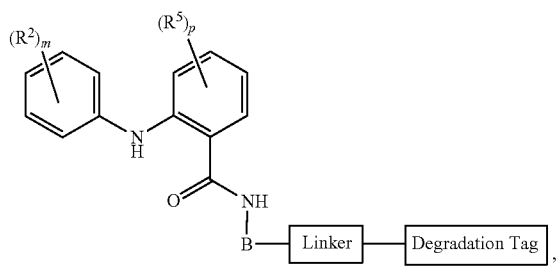

-continued

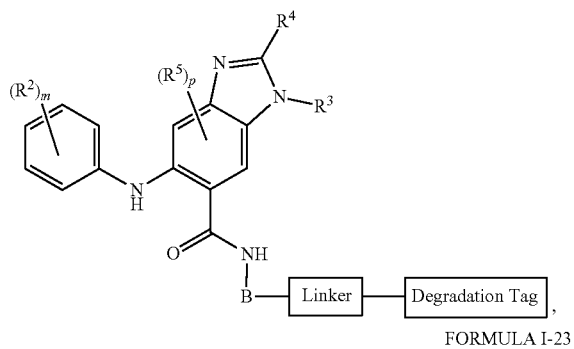
FORMULA I-22

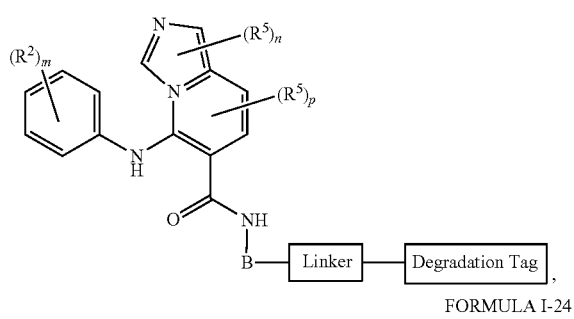
FORMULA I-23

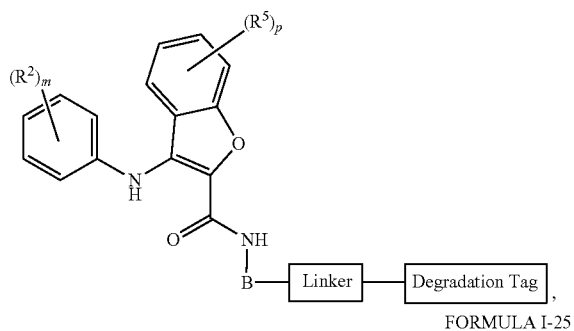
FORMULA I-24

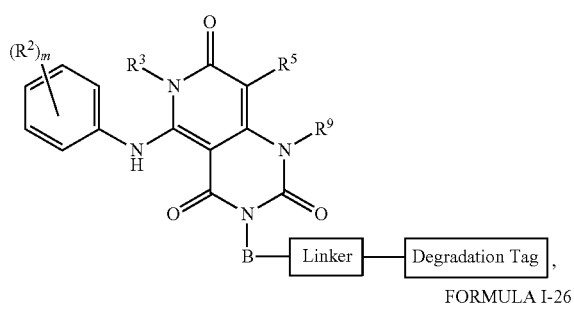
FORMULA I-25

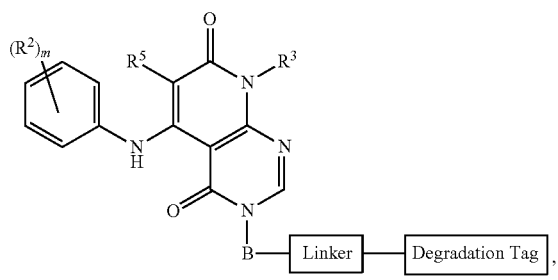
FORMULA I-26 or a pharmaceutically acceptable salt, hydrate, solvate, prodrug, stereoisomer, tautomer, or analog thereof, wherein B, Linker and Degradation Tag are defined as in FORMULA I-1;

$R^2$, and m are defined as in FORMULA I-2;

$R^3$, $R^4$, and $R^5$ are defined as in FORMULAE I-3, I-4, I-5, I-6, I-7 and I-8;

n and p are defined as in FORMULAE I-9, I-10, I-11, I-12, I-13 and I-14; and $R^9$ is selected from hydrogen, optionally substituted $C_1$-$C_8$ alkyl, optionally substituted $C_3$-$C_8$ cycloalkyl, optionally substituted aryl, or optionally substituted heteroaryl.

In one embodiment, a heterobifunctional compound disclosed herein comprises a moiety of FORMULAE I-27, I-28, I-29, I-30, I-31 and I-32:

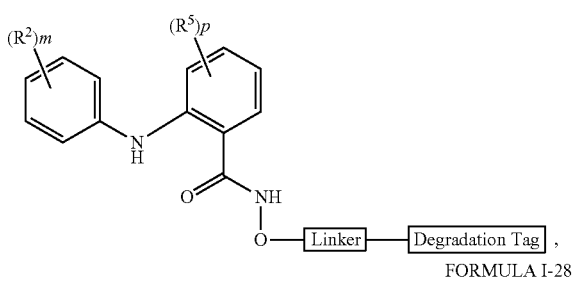
FORMULA I-27

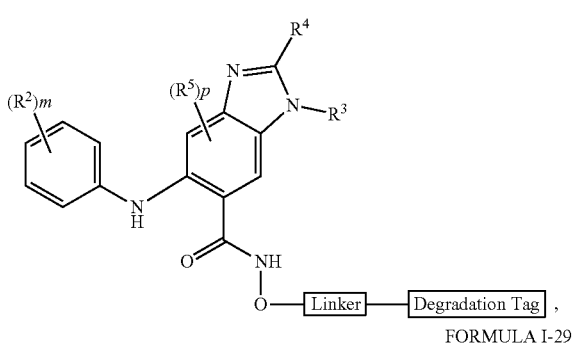
FORMULA I-28

FORMULA I-29

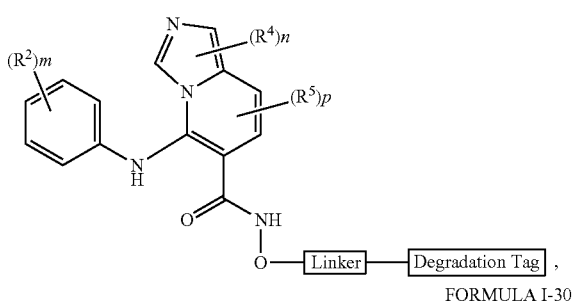
FORMULA I-30

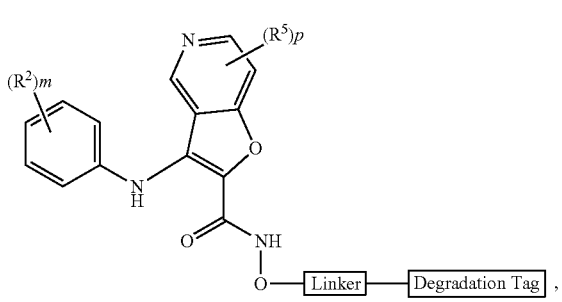

FORMULA I-31

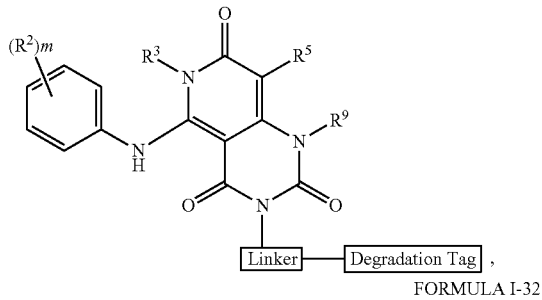

FORMULA I-32

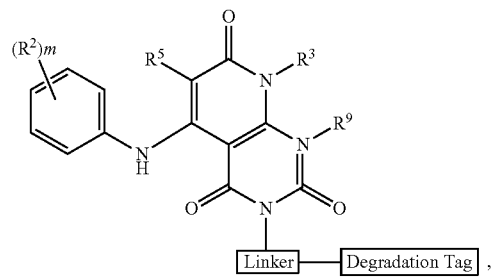

or a pharmaceutically acceptable salt, hydrate, solvate, prodrug, stereoisomer, tautomer, or analog thereof,
wherein
Linker and Degradation Tag are defined as in FORMULA I-1;
$R^2$, and m are defined as in FORMULA I-2;
$R^3$, $R^4$, and $R^5$ are defined as in FORMULAE I-3, I-4, I-5, I-6, I-7 and I-8;
n and p are defined as in FORMULAE I-9, I-10, I-11, I-12, I-13 and I-14.
$R^9$ is defined as in FORMULA I-19.

In one embodiment, a heterobifunctional compound disclosed herein comprises a moiety of FORMULAE I-33, I-34, I-35, I-36, I-37 and I-38:

FORMULA I-33

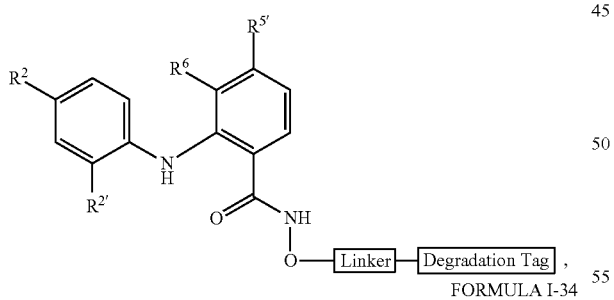

FORMULA I-34

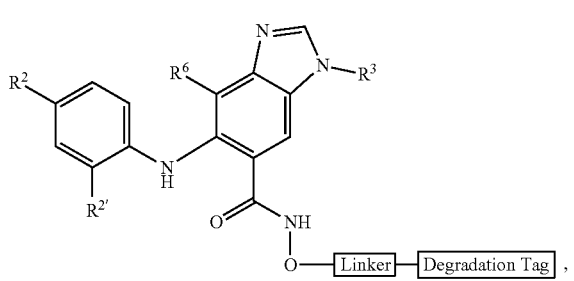

FORMULA I-35

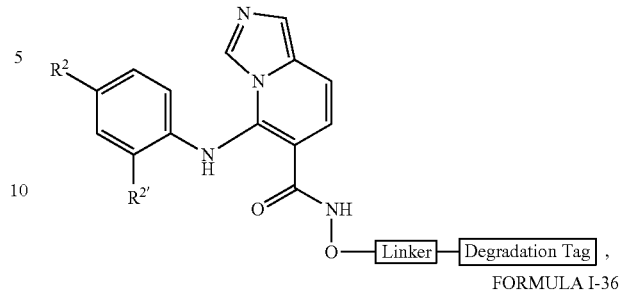

FORMULA I-36

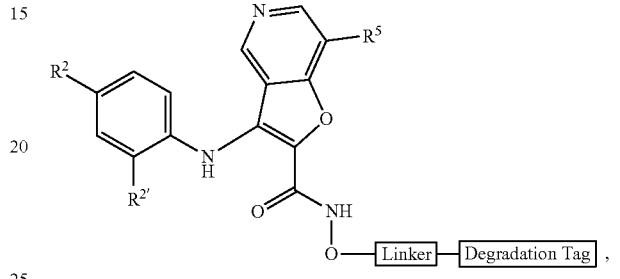

FORMULA I-37

FORMULA I-38 or a pharmaceutically acceptable salt, hydrate, solvate, prodrug, stereoisomer, tautomer, or analog thereof,
wherein
Linker and Degradation Tag are defined as in FORMULA I-1;
$R^2$, and m are defined as in FORMULA I-2;
$R^3$, $R^4$, and $R^5$ are defined as in FORMULAE I-3, I-4, I-5, I-6, I-7 and I-8;
$R^9$ is defined as in FORMULA I-19;
$R^{2'}$ is defined as $R^2$ in FORMULA I-2; and
$R^{5'}$ is defined as $R^5$ in FORMULAE I-3, I-4, I-5, I-6, I-7 and I-8.

In one embodiment, $R^2$, $R^{2'}$, $R^5$ and $R^{5'}$ are independently selected from hydrogen, halogen, optionally substituted $C_1$-$C_8$ alkyl, or optionally substituted $C_3$-$C_8$ cycloalkyl.

In one embodiment, $R^2$, $R^{2'}$, $R^5$ and $R^{5'}$ are independently selected from H, $CH_3$, F, Cl, Br, and Br.

In one embodiment, $R^2$ is Br or I.
In one embodiment, $R^2$ is I.
In one embodiment, $R^{2'}$ is F.
In one embodiment, $R^5$ and $R^{5'}$ are independently selected from F or $CH_3$.
In one embodiment, $R^3$ is selected from H, $CH_3$, isopropyl, and cyclopropyl.
In one embodiment, $R^3$ is $CH_3$.
In one embodiment, $R^9$ is selected from optionally substituted aryl, or optionally substituted heteroaryl.
In one embodiment, $R^9$ is optionally substituted phenyl.
In one embodiment, $R^9$ is

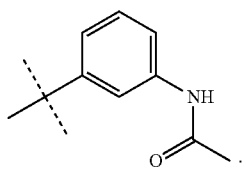

In one embodiment, a heterobifunctional compound disclosed herein comprises a moiety of FORMULAE II:

FORMULAE II

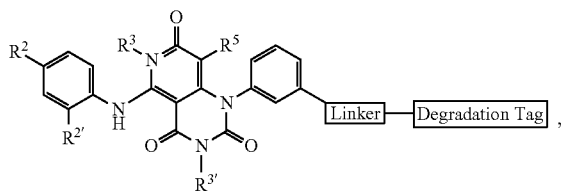

or a pharmaceutically acceptable salt, hydrate, solvate, prodrug, stereoisomer, tautomer, or analog thereof,
wherein
Linker and Degradation Tag are defined as in FORMULA I-1;
$R^2$, and m are defined as in FORMULA I-2;
$R^3$, and $R^5$ are defined as in FORMULAE I-3, I-4, I-5, I-6, I-7 and I-8;
$R^9$ is defined as in FORMULA I-19;
$R^{2'}$ is defined as $R^2$ in FORMULA I-2; and
$R^{3'}$ is defined as $R^3$ in FORMULAE I-3, I-4, I-5, I-6, I-7 and I-8.
In one embodiment, $R^2$, $R^{2'}$, and $R^5$ are independently selected from hydrogen, halogen, optionally substituted $C_1$-$C_8$ alkyl, or optionally substituted $C_3$-$C_5$ cycloalkyl.
In one embodiment, $R^2$, $R^{2'}$, and $R^5$ are independently selected from H, $CH_3$, F, Cl, Br, and Br.
In one embodiment, $R^2$ is Br or I.
In one embodiment, $R^2$ is I.
In one embodiment, $R^{2'}$ is F.
In one embodiment, $R^5$ and $R^{5'}$ are independently selected from F or $CH_3$.
In one embodiment, $R^3$ and $R^{3'}$ are independently selected from hydrogen, optionally substituted $C_1$-$C_8$ alkyl, or optionally substituted $C_3$-$C_8$ cycloalkyl; In one embodiment, $R^3$ and $R^{3'}$ are independently selected from H, $CH_3$, isopropyl, and cyclopropyl.
In one embodiment, $R^3$ is $CH_3$.
In one embodiment, $R^{3'}$ is cyclopropyl.

In one embodiment, a heterobifunctional compound disclosed herein comprises a moiety of FORMULAE III:

FORMULAE III

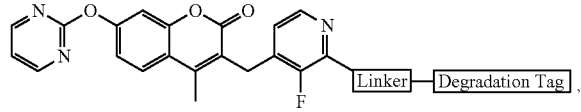

or a pharmaceutically acceptable salt, hydrate, solvate, prodrug, stereoisomer, tautomer, or analog thereof,
wherein
Linker and Degradation Tag are defined as in FORMULA I-1.
In one embodiment, a heterobifunctional compound disclosed herein comprises a moiety of FORMULAE IV:

FORMULAE IV

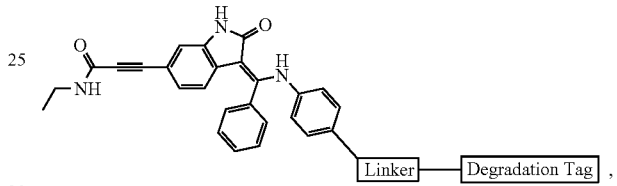

or a pharmaceutically acceptable salt, hydrate, solvate, prodrug, stereoisomer, tautomer, or analog thereof,
wherein
Linker and Degradation Tag are defined as in FORMULA I-1.
In some embodiments, heterobifunctional compound disclosed herein comprises FORMULAE I-1, I-2, I-3, I-9, I-15, I-21, I-27, or I-33.
In some embodiments, the Degradation Tag is a moiety of FORMULAE 6A, 6B, or 6C, wherein $R_E^1$ is selected from isopropyl and tert-butyl.
In some embodiments, the Degradation Tag is a moiety of FORMULAE 6A-1, 6B-1, 6C-1, 6A-2, 6B-2, or 6C-2:

FORMULA 6A-1

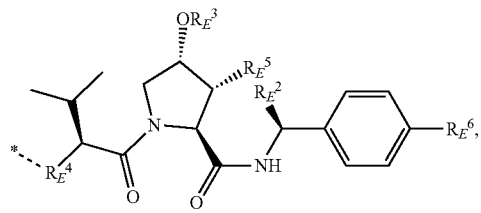

FORMULA 6B-1

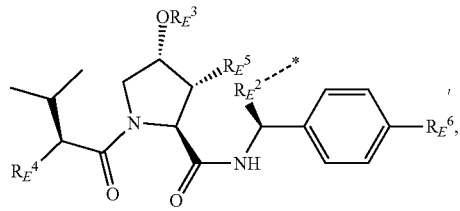

FORMULA 6C-1
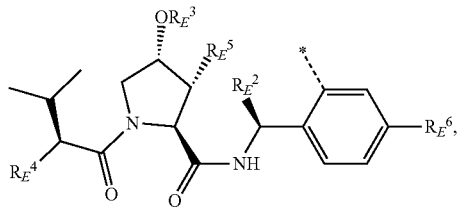

FORMULA 6A-2
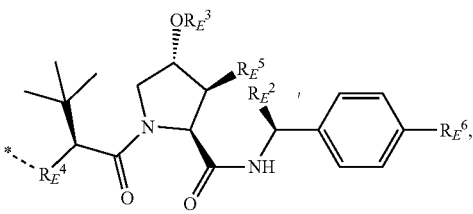

FORMULA 6B-2
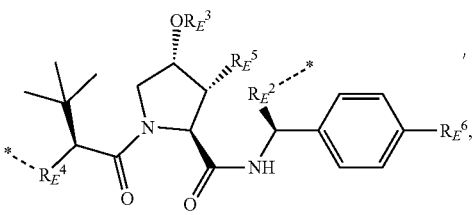

FORMULA 6C-2
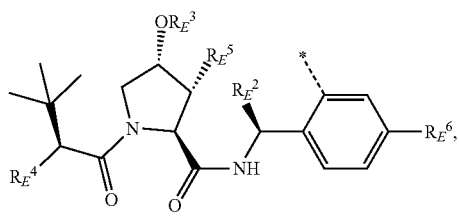

wherein $R_E^2$, $R_E^{2'}$, $R_E^3$, $R_E^4$, $R_E^{4'}$, $R_E^5$, and $R_E^6$ are defined as in FORMULAE 6A, 6B, or 6C.

In some embodiments, $R_E^2$ is H or Me.

In some embodiments, $R_E^{2'}$ is null or $CH_2$.

In some embodiments, the Degradation Tag is a moiety of FORMULAE 6A-3, 6B-3, 6C-3, 6A-4, 6B-4, or 6C-4:

FORMULA 6A-3
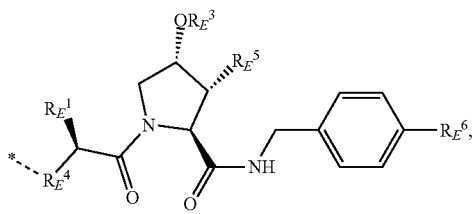

FORMULA 6B-3
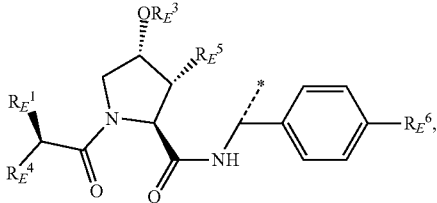

FORMULA 6C-3
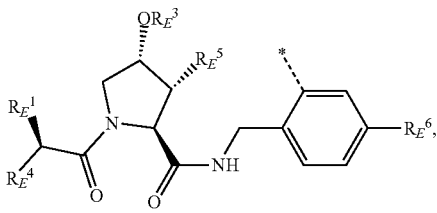

FORMULA 6A-4
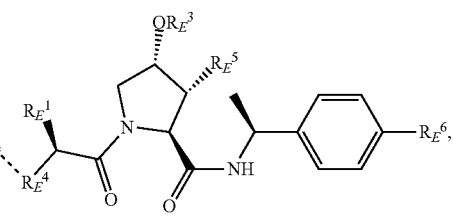

FORMULA 6B-4
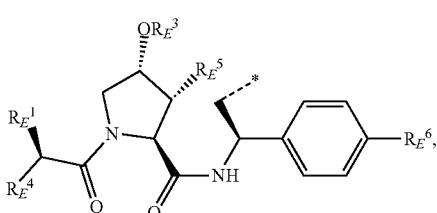

FORMULA 6C-4
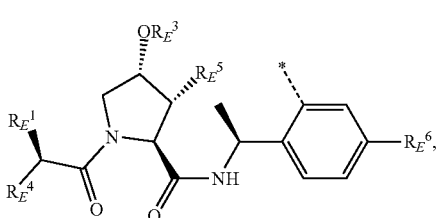

wherein $R_E^1$, $R_E^3$, $R_E^4$, $R_E^{4'}$, $R_E^5$, and $R_E^6$ are defined as in FORMULAE 6A, 6B, or 6C.

In some embodiments, $R_E^3$ is H.

In some embodiments, the Degradation Tag is a moiety of FORMULAE 6A-5, 6B-5, and 6C-5:

FORMULA 6A-5
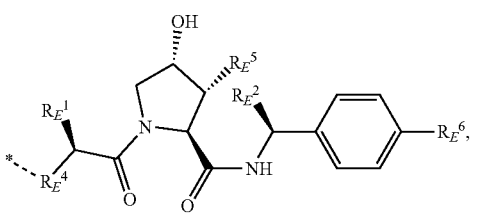

FORMULA 6B-5

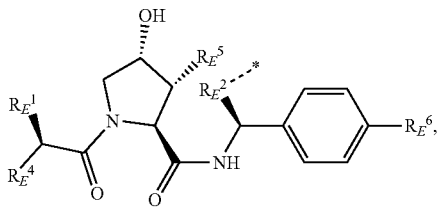

FORMULA 6C-5

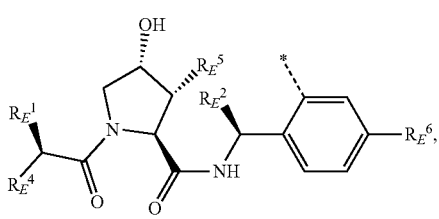

wherein
$R_E^1$, $R_E^2$, $R_E^{2'}$, $R_E^4$, $R_E^{4'}$, $R_E^5$, and $R_E^6$ are defined as in FORMULAE 6A, 6B, or 6C.

In some embodiments, $R_E^5$ is H or F.

In some embodiments, the Degradation Tag is a moiety of FORMULAE, 6A-6, 6B-6, 6C-6, 6A-7, 6B-7, and 6C-7:

FORMULA 6A-6

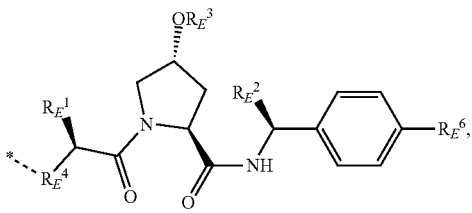

FORMULA 6B-6

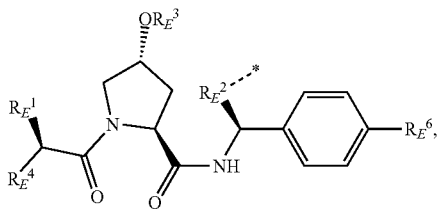

FORMULA 6C-6

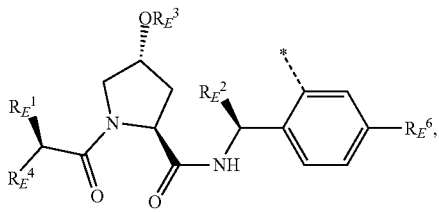

FORMULA 6A-7

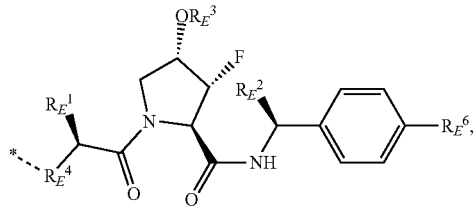

FORMULA 6B-7

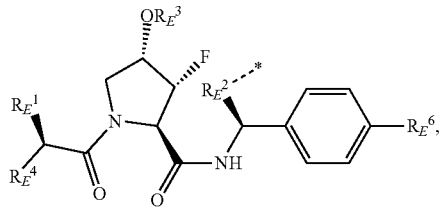

FORMULA 6C-7

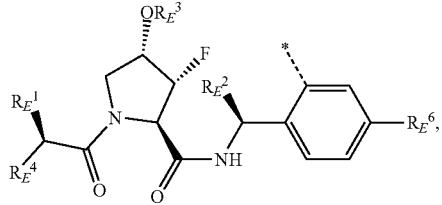

wherein
$R_E^1$, $R_E^2$, $R_E^{2'}$, $R_E^3$, $R_E^4$, $R_E^{4'}$, and $R_E^6$ are defined as in FORMULAE 6A, 6B, or 6C.

In some embodiments, $R_E^6$ is selected from hydrogen, halogen, cyano, optionally substituted aryl, and optionally substituted heteroaryl, In some embodiments, $R_E^6$ is selected from the group consisting of halogen, cyano, optionally substituted thiazole, optionally substituted oxazole, optionally substituted imidazole, optionally substituted pyrazole, optionally substituted oxadiazole, optionally substituted triazole, and optionally substituted isoxazole.

In some embodiments, $R_E^6$ is methyl thiazole.

In some embodiments, the Degradation Tag is a moiety of FORMULAE 6A-8, 6B-8, or 6C-8:

FORMULA 6A-8

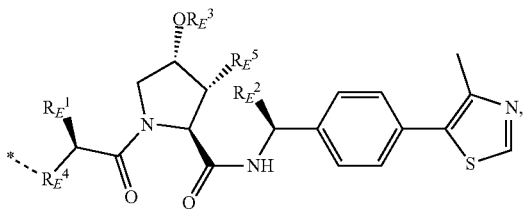

FORMULA 6B-8

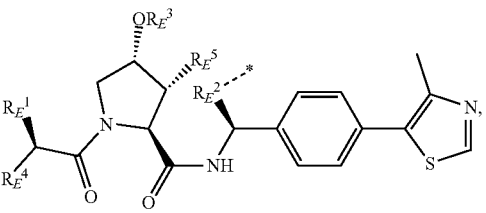

-continued

FORMULA 6C-8

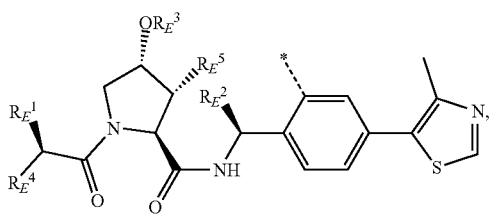

wherein
$R_E^1$, $R_E^2$, $R_E^{2'}$, $R_E^3$, $R_E^4$, $R_E^{4'}$, and $R_E^5$ are defined as in FORMULAE 6A, 6B, and 6C.

In some embodiments, $R_E^4$ is selected from —N($R_E^{10}$)$R_E^{11}$, —N($R_E^{10}$)C(O)$R_E^{11}$,

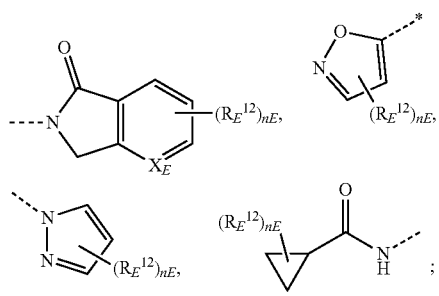

and/or $R_E^{4'}$ is selected from —N($R_E^{10}$)—, —N($R_E^{10}$)C(O)$R_E^{11'}$—,

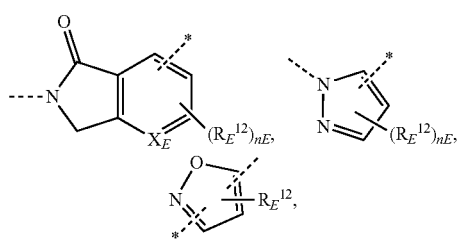

wherein
* indicates the connection to the Linker moiety of the heterobifunctional compound;
$R_E^{10}$ is selected from null, hydrogen, optionally substituted $C_1$-$C_8$alkyl, optionally substituted $C_1$-$C_8$cycloalkyl, optionally substituted $C_1$-$C_8$alkyl-CO, optionally substituted $C_3$-$C_8$cycloalkyl-CO, optionally substituted $C_3$-$C_8$cycloalkyl-$C_1$-$C_8$alkyl-CO, optionally substituted 3-10 membered heterocyclyl-CO, optionally substituted 3-10 membered heterocyclyl-$C_1$-$C_8$alkyl-CO, optionally substituted aryl-CO, optionally substituted aryl-$C_1$-$C_8$alkyl-CO, optionally substituted heteroaryl-CO, optionally substituted heteroaryl-$C_1$-$C_8$alkyl-CO, optionally substituted aryl, and optionally substituted heteroaryl;
$R_E^{11}$ is selected from null, hydrogen, optionally substituted $C_1$-$C_8$alkyl, and optionally substituted $C_3$-$C_8$cycloalkyl, and optionally substituted 3-8 membered heterocycloalkyl, optionally substituted $C_3$-$C_8$ carbocyclyl, and optionally substituted $C_3$-$C_8$ heterocyclyloyl;

$R_E^{11'}$, at each occurrence, is a divalent group independently selected from null, O, optionally substituted $C_1$-$C_8$alkylene, optionally substituted $C_3$-$C_8$ cycloalkylene, optionally substituted $C_3$-$C_8$ heterocycloalkylene, optionally substituted $C_3$-$C_5$ carbocyclyl, and optionally substituted $C_3$-$C_8$ heterocyclyloyl;

$R_E^{12}$, at each occurrence, is independently selected from hydrogen, halogen, cyano, optionally substituted $C_1$-$C_8$alkyl, optionally substituted $C_3$-$C_8$cycloalkyl, optionally substituted 3-8 membered heterocycloalkyl, optionally substituted $C_1$-$C_8$alkoxy, and optionally substituted $C_3$-$C_8$cycloalkoxy; and $n_E$ is 0, 1, 2, 3, or 4.

In some embodiments, the substituent(s) for $R_E^{11}$ and $R_E^{11'}$ are independently optionally substituted groups selected from $C_1$-$C_4$ alkyl, $C_1$-$C_4$ haloalkyl, halogen, and CN.

In some embodiments, $R_E^4$ is selected from NH$_2$, NHC(O)Me,

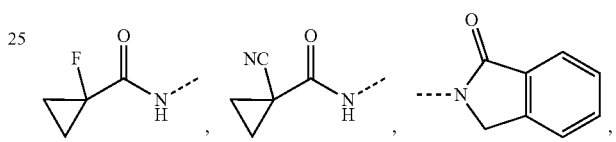

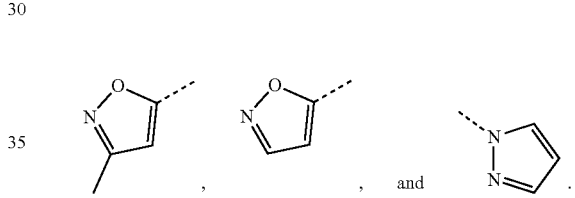

In some embodiments, $R_E^{4'}$ is selected from NH, C(O)NH, CH$_2$C(O)NH,

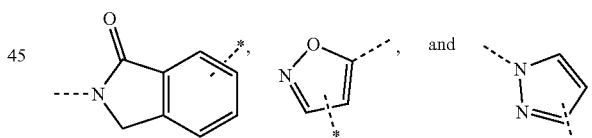

In some embodiments, the Degradation Tag is a moiety of FORMULAE 6A-9, 6A-10, 6A-11, 6A-12, 6A-13, 6B-9, 6B-10, 6B-11, 6B-12, 6B-13, 6B-14, 6B-15, 6C-9, 6C-10, 6C-11, 6C-12, 6C-13, 6C-14, or 6C-15:

FORMULA 6A-9

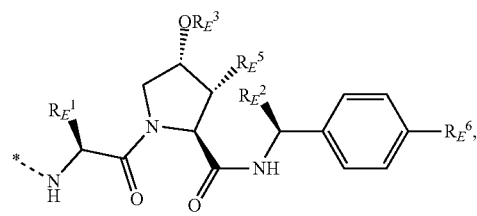

-continued
FORMULA 6A-10
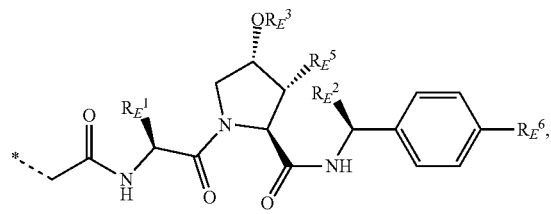
FORMULA 6A-11
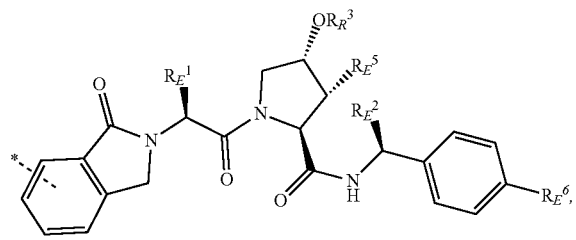
FORMULA 6A-12
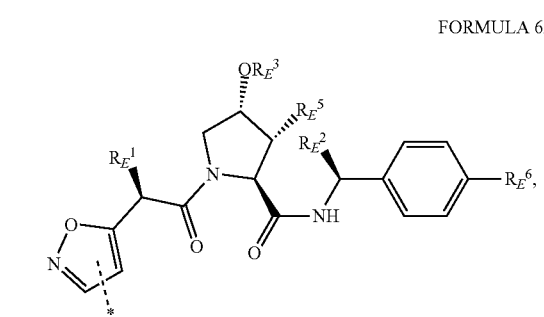
FORMULA 6A-13
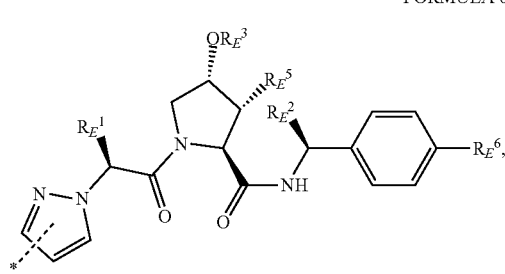
FORMULA 6B-9
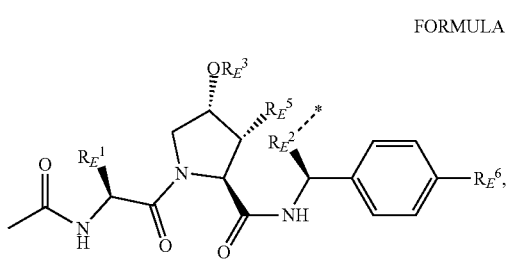
FORMULA 6B-10
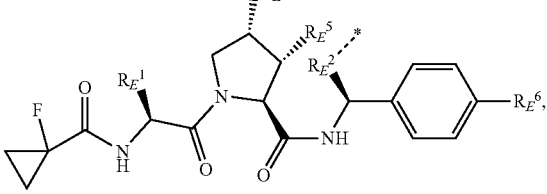
-continued
FORMULA 6B-11
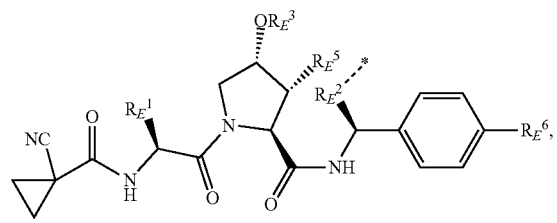
FORMULA 6B-12
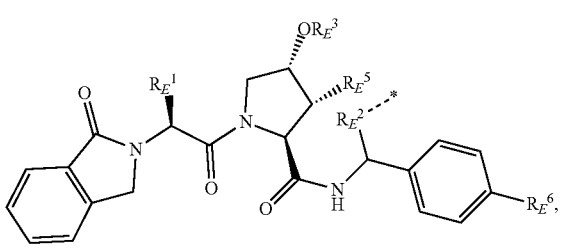
FORMULA 6B-13
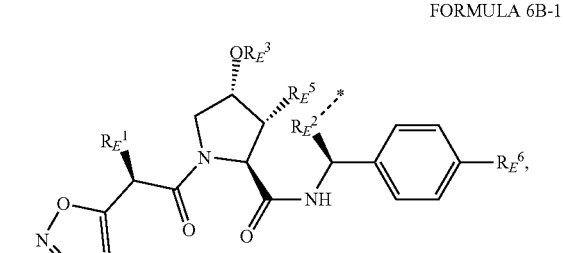
FORMULA 6B-14
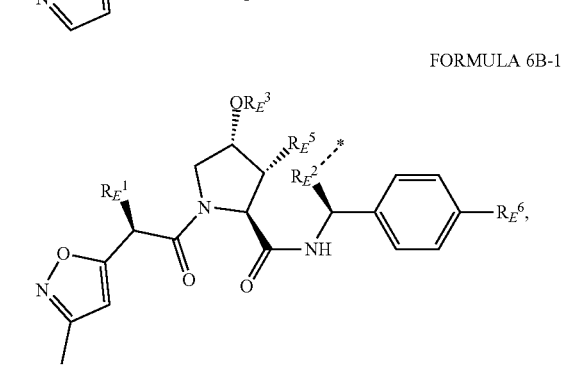
FORMULA 6B-15
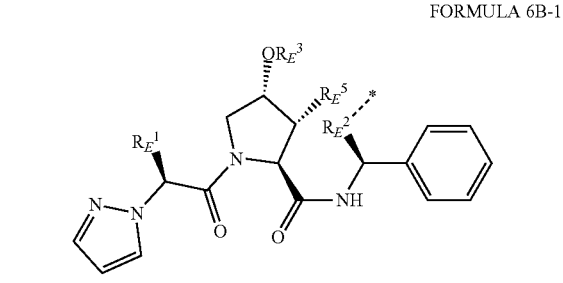
FORMULA 6C-9
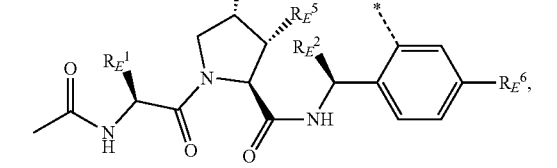

FORMULA 6C-10
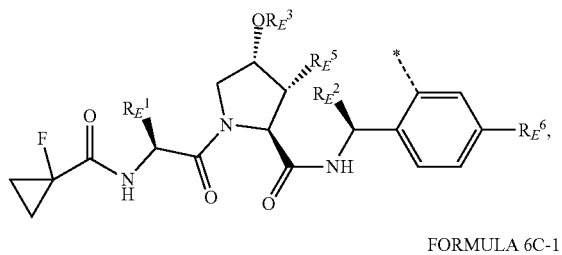
FORMULA 6C-11
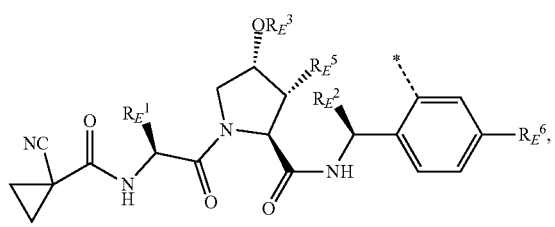
FORMULA 6C-12
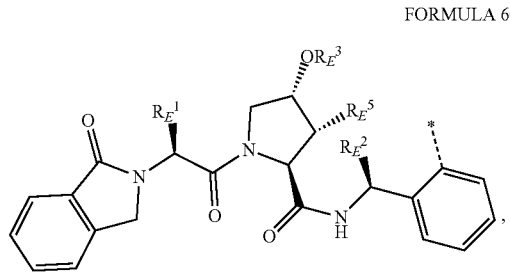
FORMULA 6C-13
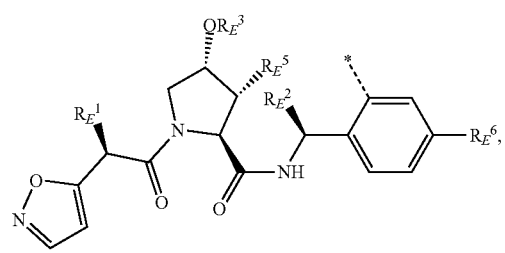
FORMULA 6C-14
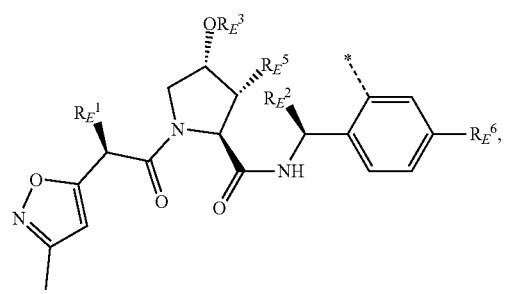
FORMULA 6C-15
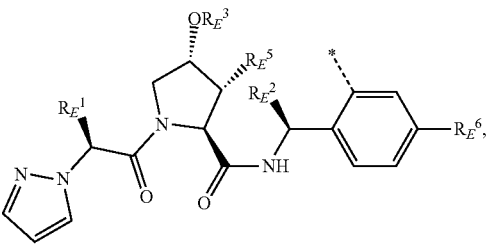
wherein $R_E^1$, $R_E^2$, $R_E^{2'}$, $R_E^3$, $R_E^5$, and $R_E^6$ are defined as in FORMULAE 6A, 6B, or 6C.
In some embodiments, the Degradation Tag is a moiety of any of FORMULAE 7A to 7BJ:
FORMULA 7A
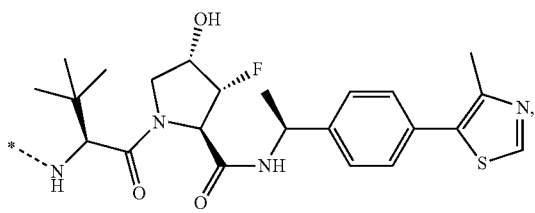
FORMULA 7B
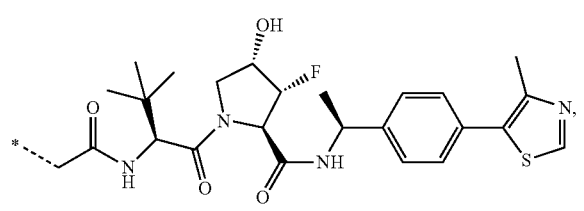
FORMULA 7C
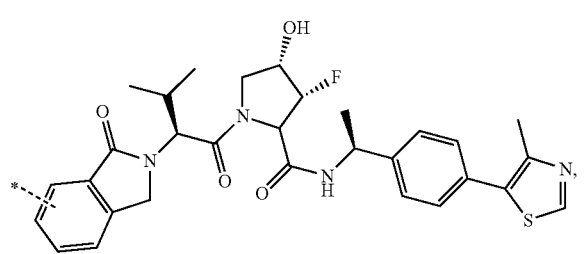
FORMULA 7D
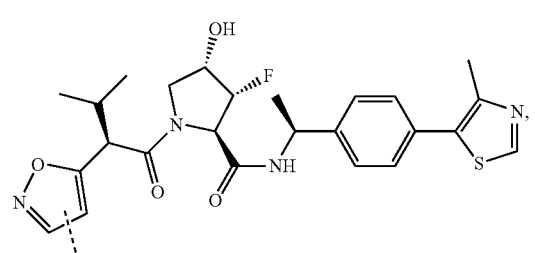

FORMULA 7E
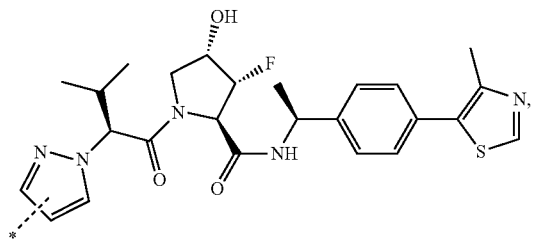
FORMULA 7F
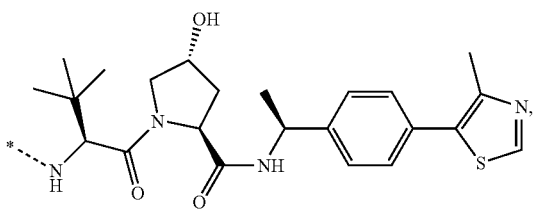
FORMULA 7G
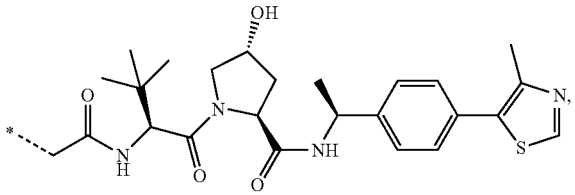
FORMULA 7H
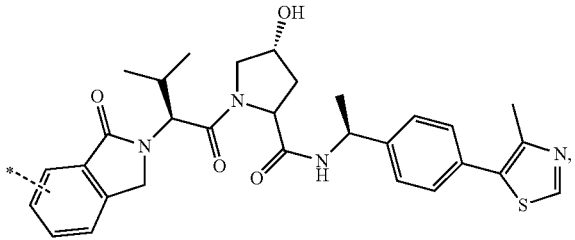
FORMULA 7I
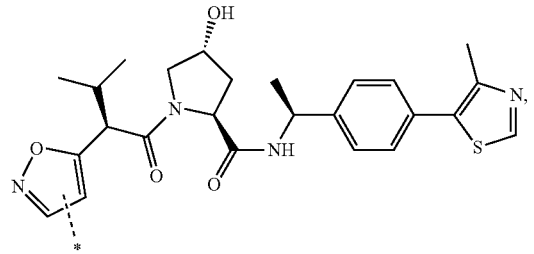
FORMULA 7J
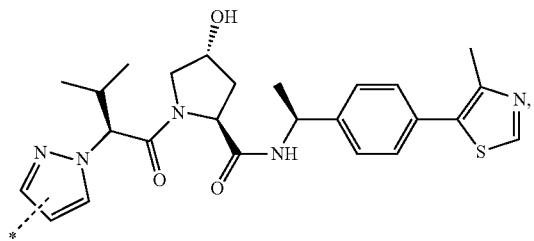
FORMULA 7K
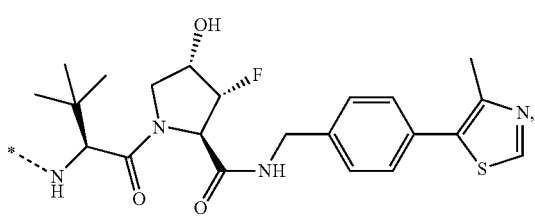
FORMULA 7L
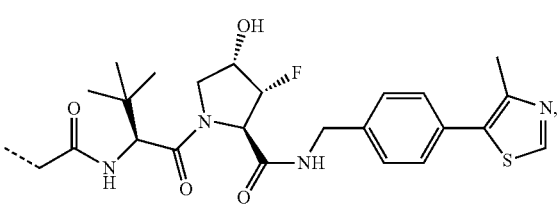
FORMULA 7M
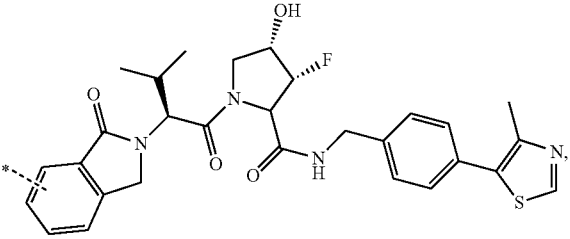
FORMULA 7N
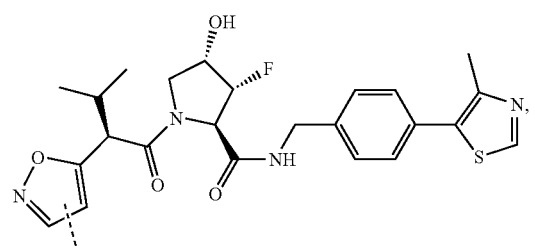
FORMULA 7O
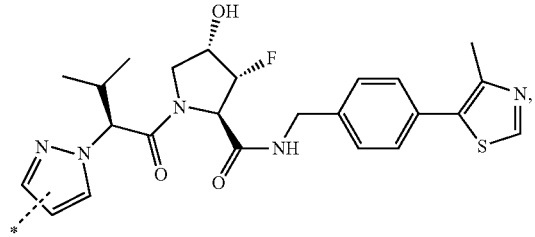
FORMULA 7P
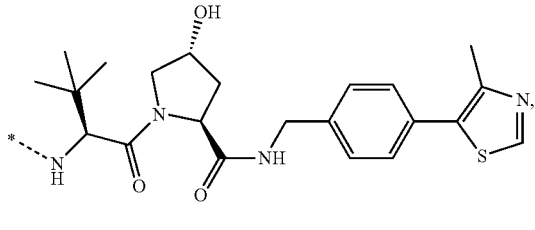

FORMULA 7Q
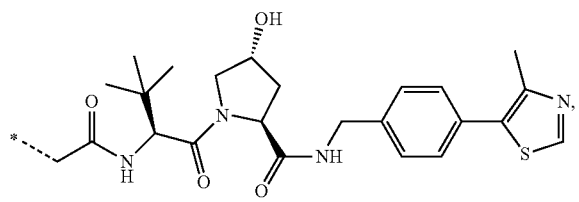
FORMULA 7R
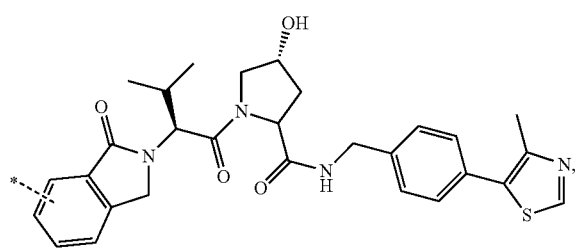
FORMULA 7S
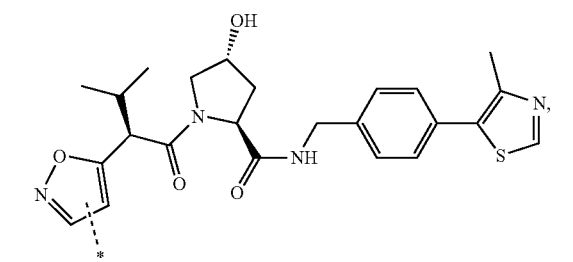
FORMULA 7T
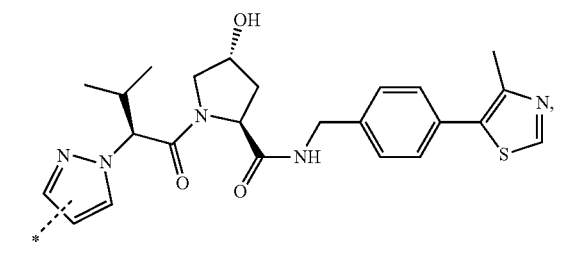
FORMULA 7U
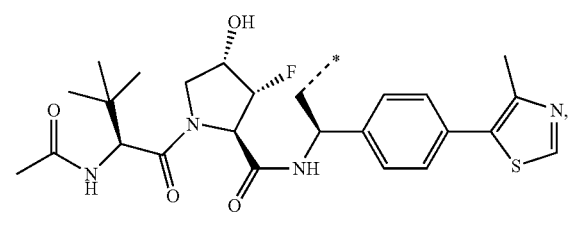
FORMULA 7V
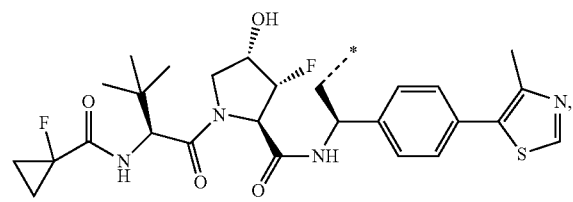
FORMULA 7W
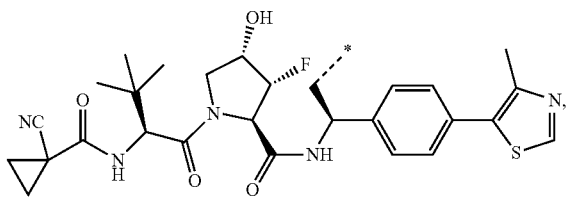
FORMULA 7X
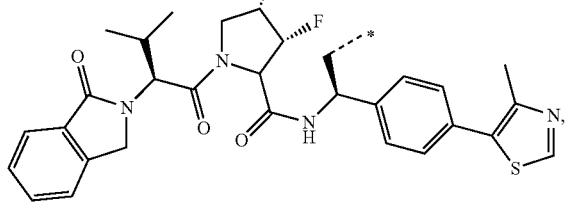
FORMULA 7Y
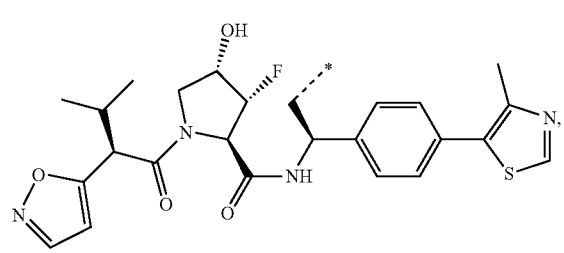
FORMULA 7Z
FORMULA 7AA
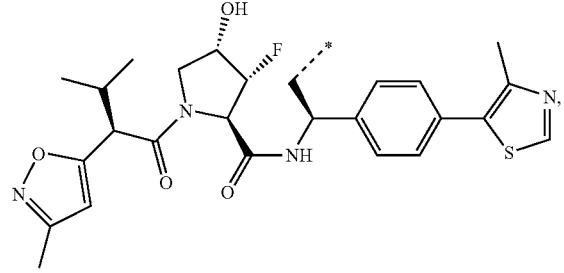

FORMULA 7AB

FORMULA 7AC

FORMULA 7AD

FORMULA 7AE

FORMULA 7AF

FORMULA 7AG

FORMULA 7AH

FORMULA 7AI

FORMULA AJ

FORMULA 7AK

FORMULA 7AL

FORMULA 7AM

FORMULA 7AN
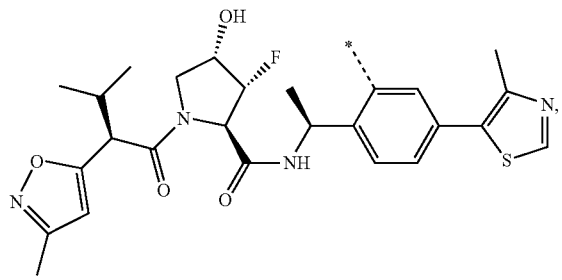
FORMULA 7AT
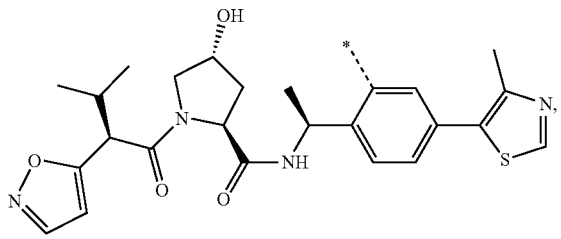
FORMULA 7AO
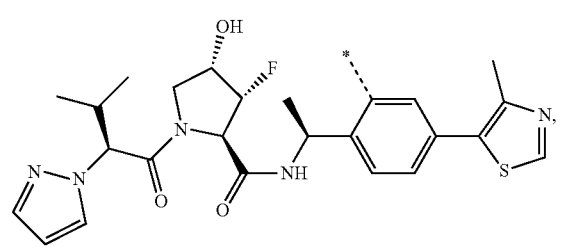
FORMULA 7AU
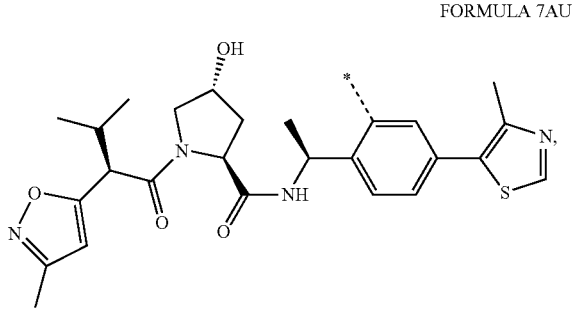
FORMULA 7AP
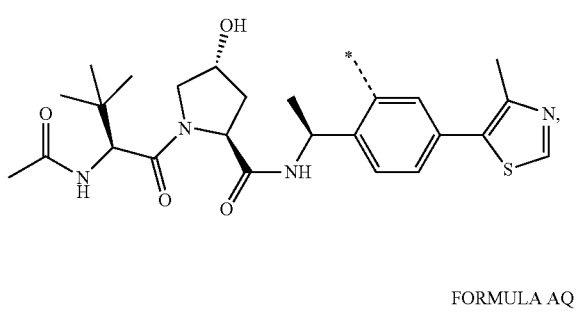
FORMULA 7AV
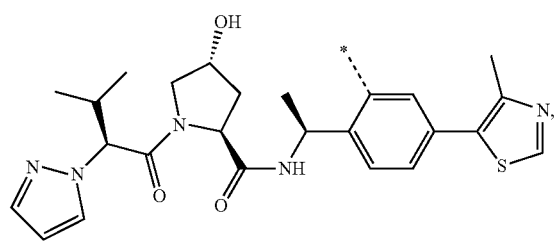
FORMULA AQ
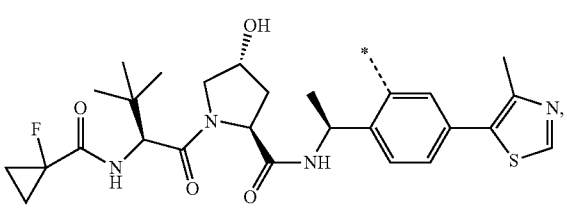
FORMULA 7AW
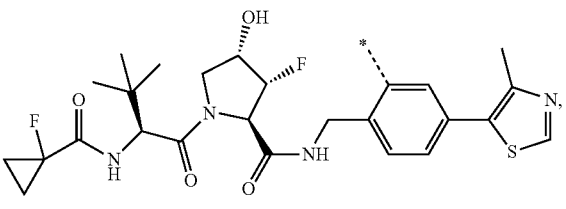
FORMULA 7AR
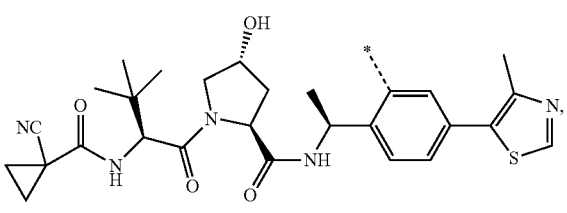
FORMULA AX
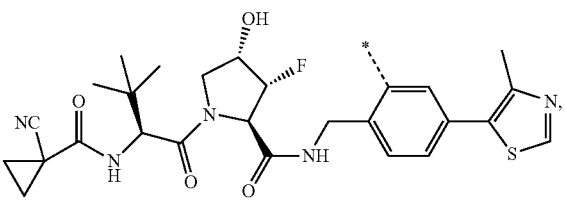
FORMULA 7AS
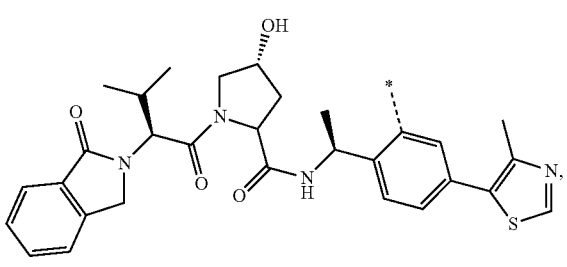
FORMULA 7AY

FORMULA 7AZ

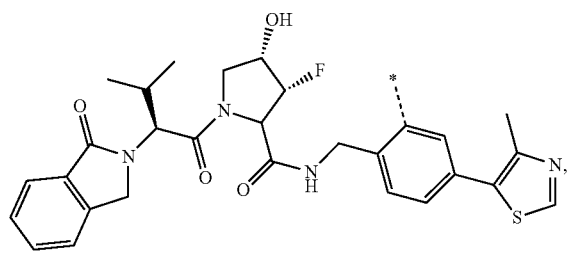

FORMULA 7BA

FORMULA 7BB

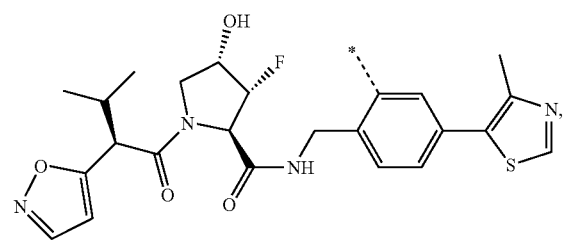

FORMULA 7BC

FORMULA 7BD

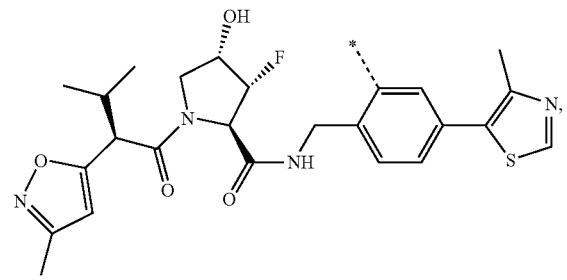

FORMULA BE

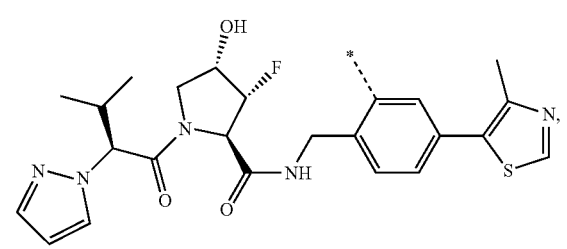

FORMULA 7BF

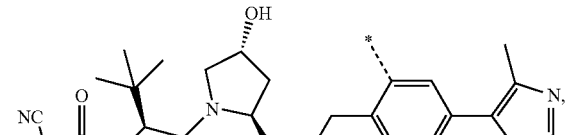

FORMULA 7BG

FORMULA 7BH

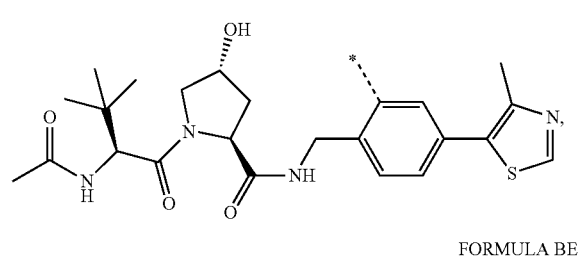

FORMULA 7BI

FORMULA 7BJ

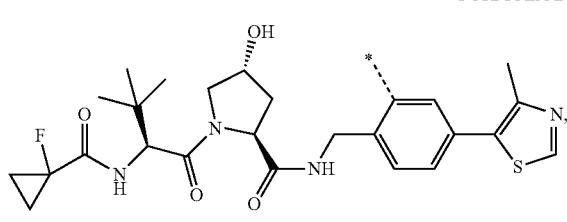

In another embodiment, the Degradation Tag is a moiety of FORMULA 5, wherein $R_E^2$ at each occurrence, is independently selected from the group consisting of absent, hydrogen, halogen, cyano, nitro, hydroxy, amino, optionally substituted $C_1$-$C_6$ alkyl, optionally substituted $C_1$-$C_6$ alkenyl, optionally substituted $C_1$-$C_6$ alkynyl, optionally substituted $C_1$-$C_6$ alkoxy, optionally substituted $C_1$-$C_6$ alkylamino, optionally substituted 3-8 membered carbocyclyl, and optionally substituted 3-8 membered heterocyclyl.

In another embodiment, the Degradation Tag is a moiety of FORMULA 5, and wherein $V_E^1$, $V_E^2$, $V_E^3$, $V_E^4$ and $V_E^5$, at each occurrence, are each independently selected from the group consisting of C, $CR_E^2$, S, N, and $NR_E^2$; or $V_E^1$ and $V_E^2$, $V_E^2$ and $V_E^3$, $V_E^3$ and $V_E^4$, or $V_E^4$ and $V_E^5$ are combined to optionally form $C_6$ aryl ring or a 5, 6 or 7 membered heteroaryl ring.

In another embodiment, the Degradation Tag is a moiety of FORMULA 5, and wherein Ring $A_E$ is a group consisting of FORMULA $A_E1$, and wherein $V_E^1$, $V_E^2$, $V_E^3$, and $V_E^4$ are each independently selected from the group consisting of C, $CR_E^2$, S, N, and $NR_E^2$.

In another embodiment, the Degradation Tag is a moiety of FORMULA 5, and wherein Ring $A_E$ is a group consisting of FORMULA $A_E2$, and wherein $V_E^1$, $V_E^2$, $V_E^3$, $V_E^4$ and $V_E^5$, at each occurrence, are each independently selected from the group consisting of C, $CR_E^2$, S, N, and $NR_E^2$.

In another embodiment, the Degradation Tag is a moiety of FORMULA 5, and wherein Ring $A_E$ is a group consisting of FORMULA $A_E3$, and wherein $V_E^1$, $V_E^2$, $V_E^3$, $V_E^4$ and $V_E^5$ are each independently selected from the group consisting of C, $CR_E^2$, S, N, and $NR_E^2$; or $V_E^1$ and $V_E^2$, $V_E^2$ and $V_E^3$, $V_E^3$ and $V_E^4$, or $V_E^4$ and $V_E^5$ are combined together to optionally form $C_6$ aryl ring or a 5, 6 or 7 membered heteroaryl ring.

In another embodiment, the Degradation Tag is a moiety of FORMULA 5, and wherein Ring $A_E$ is a group consisting of FORMULA $A_E4$, and wherein $\text{-----}$ is a single bond and $W_E^1$, $W_E^2$, $W_E^3$ and $W_E^4$ are each independently selected from the group consisting of —N=, —$CR_E^3$=, —CO—, —O—, —$CR_E^3R_E^4$—, and —$NR_E^3$—.

In another embodiment, the Degradation Tag is a moiety of FORMULA 5, and wherein Ring $A_E$ is a group consisting of FORMULA $A_E5$, and wherein $V_E^1$, $V_E^2$, and $V_E^3$ are each independently selected from the group consisting of $CR_E^2$, S, N, with the proviso that at least one of $V_E^1$, $V_E^2$, and $V_E^3$ is S, N or $NR_E^2$; or $V_E^1$ and $V_E^2$, $V_E^2$ and $V_E^3$ are combined together to optionally form 5 membered heteroaryl ring.

In another embodiment, the Degradation Tag is a moiety of FORMULA 5, and wherein $R_E^1$ is selected from hydrogen, halogen, cyano, nitro, optionally substituted $C_1$-$C_6$ alkyl, optionally substituted 3-8 membered carbocyclyl, and optionally substituted 3-8 membered heterocyclyl; preferably, $R_E^1$ is selected from hydrogen, halogen, cyano, nitro, and $C_1$-$C_5$ alkyl; more preferably, $R_E^1$ is selected from H, $CH_3$, or F.

In another embodiment, the Degradation Tag is a moiety of FORMULA 5, and wherein $R_E^2$ is selected from hydrogen, halogen, cyano, nitro, hydroxy, amino, optionally substituted $C_1$-$C_6$ alkyl, optionally substituted $C_1$-$C_6$ alkyl, optionally substituted $C_1$-$C_6$ alkoxyl, optionally substituted $C_1$-$C_6$ alkylamino, optionally substituted 3 to 8 membered carbocyclyl, and optionally substituted 3 to 8 membered heterocyclyl; preferably, $R_E^2$ is selected from hydrogen, halogen, cyano, nitro, and $C_1$-$C_6$ alkyl, optionally substituted $C_1$-$C_6$ alkoxyl, optionally substituted 3 to 8 membered carbocyclyl, and optionally substituted 3 to 8 membered heterocyclyl; more preferably, $R_E^2$ is selected from H, F, OMe, O-iPr, or O-cPr.

In another embodiment, the Degradation Tag is a moiety of FORMULA 5, and wherein $R_E^3$ and $R_E^4$ are independently selected from hydrogen, halogen, cyano, nitro, optionally substituted $C_1$-$C_6$ alkyl, optionally substituted 3 to 8 membered carbocyclyl, and optionally substituted 3 to 8 membered heterocyclyl; or $R_E^3$ and $R_E^4$ together with the atom(s) to which they are connected form a 3-8 membered carbocyclyl, or 3-8 membered heterocyclyl.

In another embodiment, $R_E^r$, at each occurrence, is selected from Group $R_E$, and Group $R_E$ consists of optionally substituted following cyclic groups

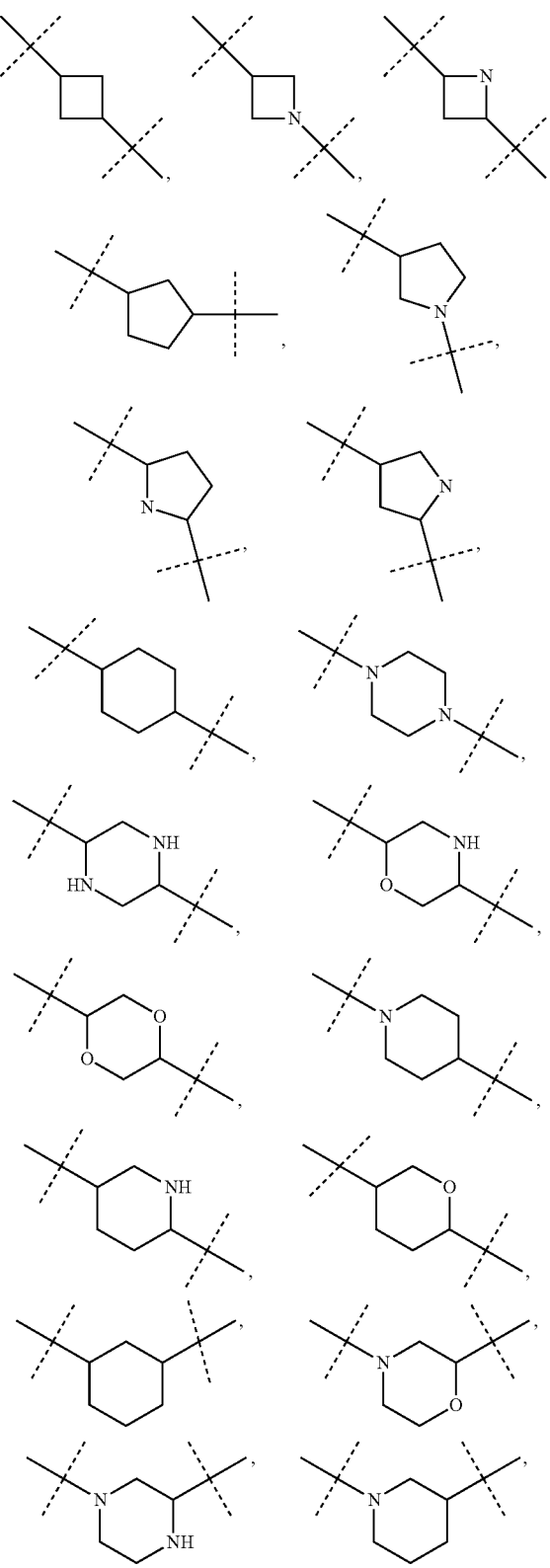

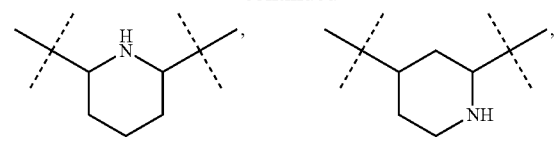
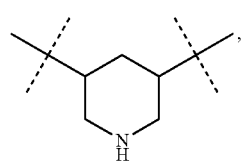 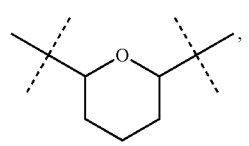 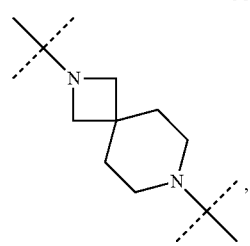 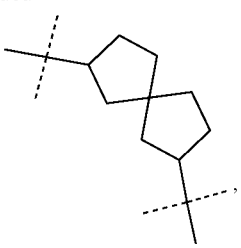
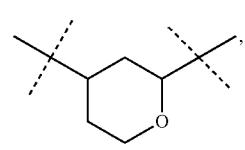 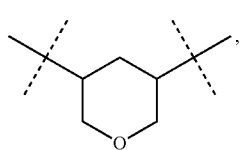 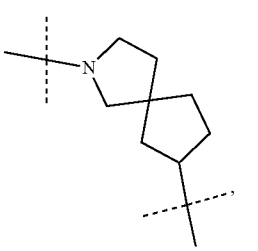 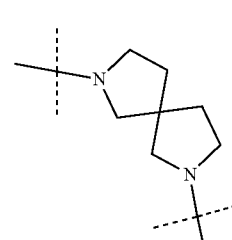
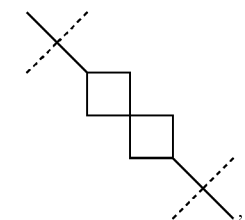 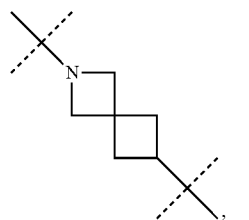 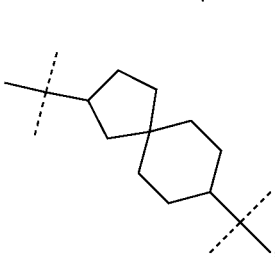 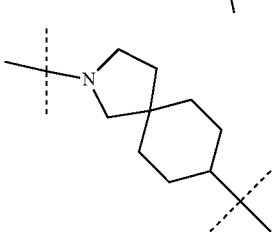
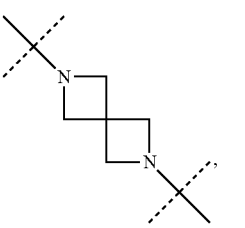 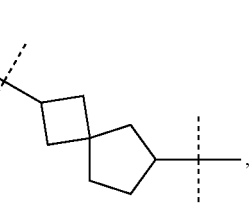 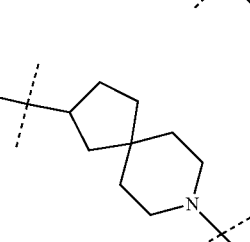 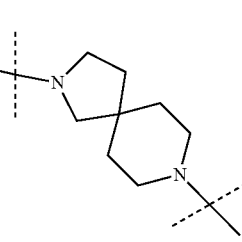
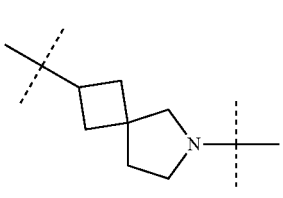 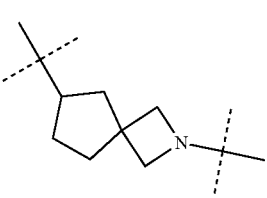 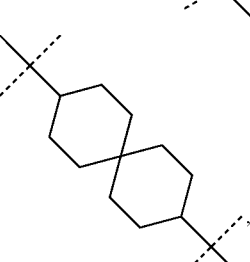 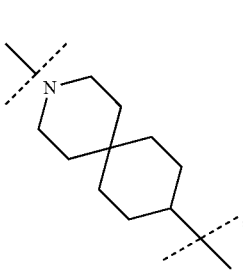
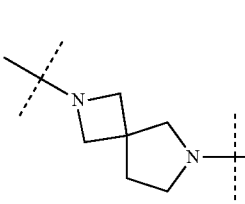 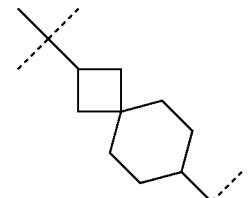 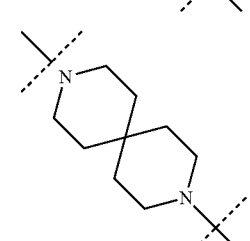 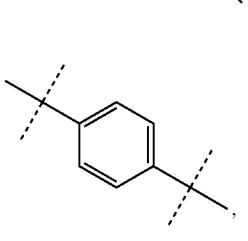
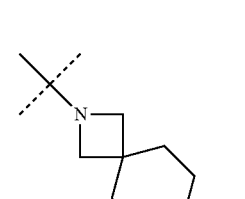 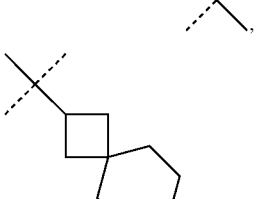 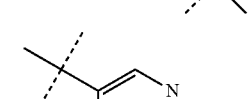 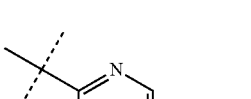
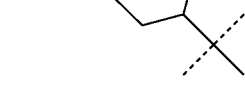 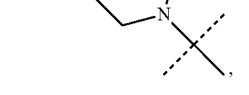 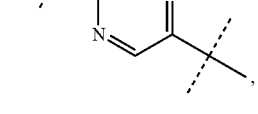 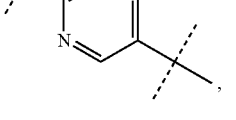

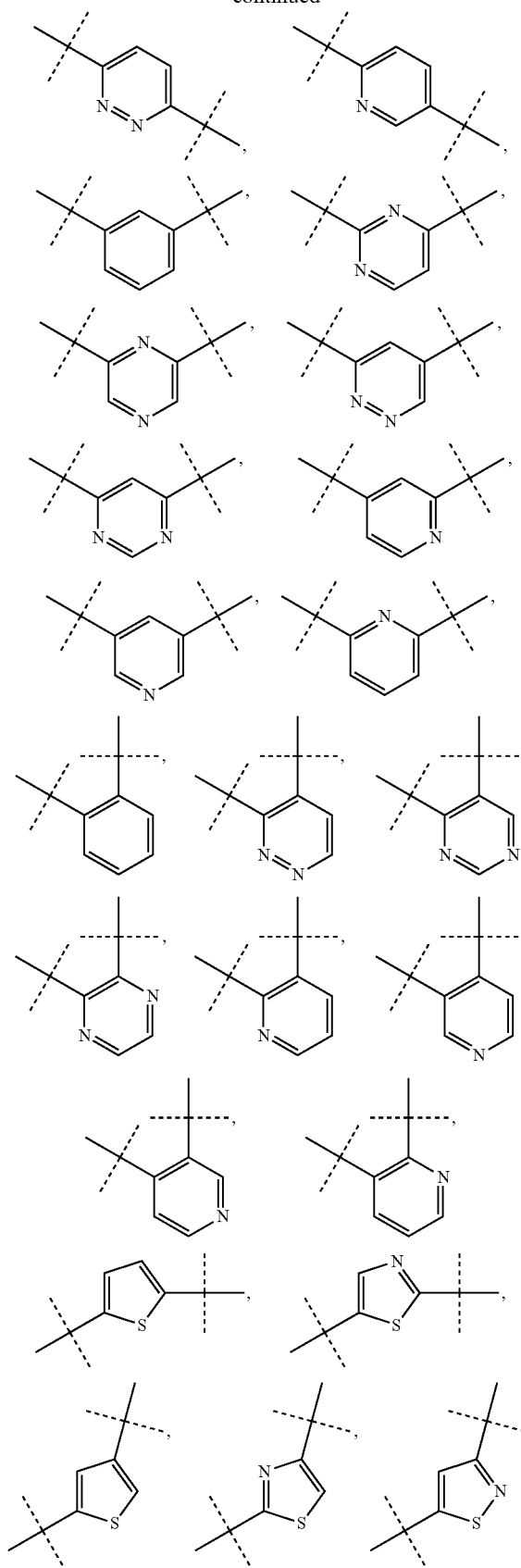
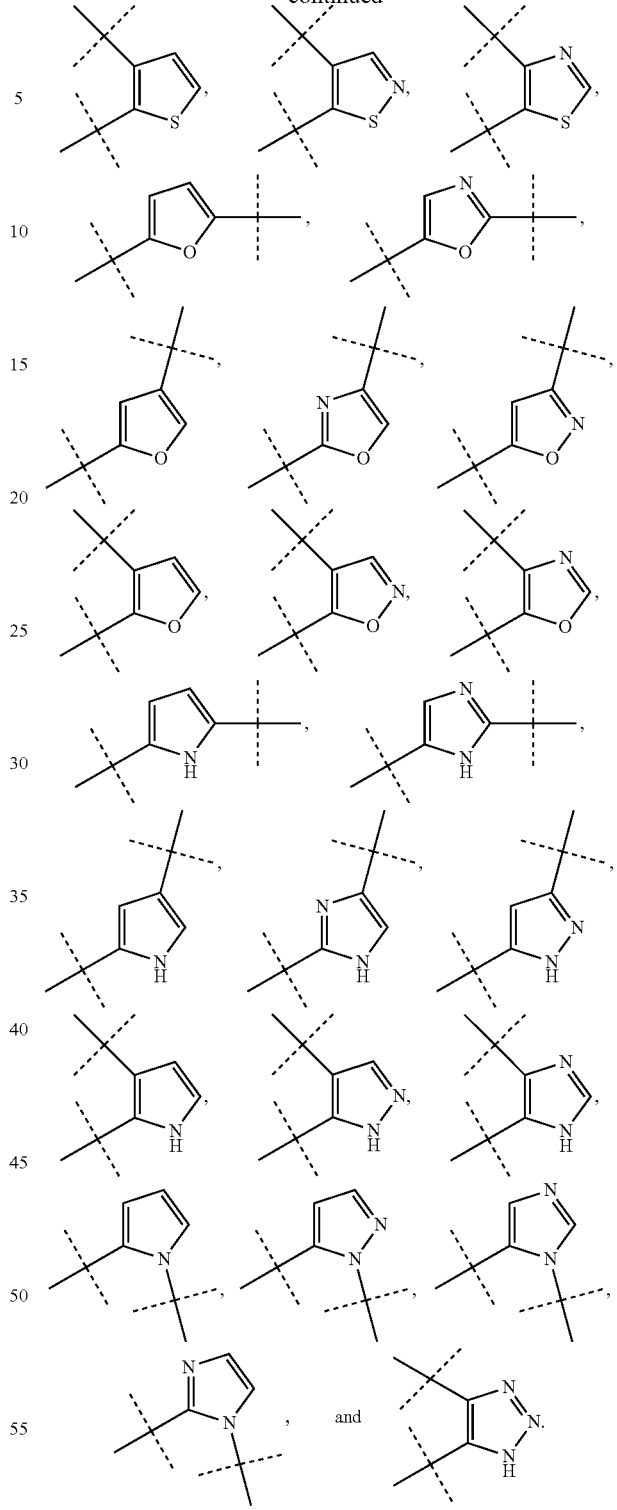
In another embodiment, the Degradation Tag is a moiety of FORMULA 5, and wherein in the group of $Z_E$, at most one $R_Ez$ is $R_E^r$.
In another embodiment, the Degradation Tag is a moiety of FORMULA 5, and wherein $n_E$=0, 1, 2 or 3.
In another embodiment, the Degradation Tag is a moiety of FORMULA 5, and wherein $Z_E$ is a divalent group selected from the group consisting of —$R_E^w$—, —$(R_E^w)_2$—, —$(R_E^w)_3$—, —$R_E^r$—, —$R_E^w$-$R_E^r$—$R_E^w$—, —$R_E^r$-$R_E^w$— and —$R_E^r$-$(R_E^w)_2$—.

In another embodiment, the Degradation Tag is a moiety of FORMULA 5, and wherein $R_E^5$ and $R_E^6$ at each occurrence are independently selected from a bond, hydrogen, halogen, oxo, hydroxyl, amino, cyano, nitro, optionally substituted $C_1$-$C_6$ alkyl, optionally substituted 3 to 8 membered carbocyclyl, and optionally substituted 3 to 8 membered heterocyclyl; or $R_E^5$ and $R_E^6$ together with the atom(s) to which they are connected form a 3-8 membered cycloalkyl or heterocyclyl ring.

In another embodiment, the Degradation Tag is a moiety of FORMULA 5, and wherein $R_E^Z$ is selected from —CO—, —$CR_E^5R_E^6$—, —$NR_E^5$—, —O—, optionally substituted $C_1$-$C_{10}$ alkylene, optionally substituted $C_1$-$C_{10}$ alkenylene, optionally substituted $C_1$-$C_{10}$ alkynylene, optionally substituted 3-8 membered carbocyclyl, optionally substituted 3-8 membered heterocyclyl.

In another embodiment, the Degradation Tag is a moiety of FORMULA 5, and wherein $Z_E$ is selected from a bond, $CH_2$, CH=CH, C≡C, NH, and O.

In another embodiment, the Degradation Tag is a moiety of FORMULA 5, and wherein Ring $A_E$ is of FORMULA $A_E$4 and $L_E$ is not null.

In another embodiment, the Degradation Tag is a moiety of FORMULA 5, and wherein Ring $A_E$ is of FORMULA $A_E$4 and $L_E$ is selected from the group consisting of —NH—, —N($C_1$-$C_4$ alkyl)-, —CO—, —NH—CO—, —N($C_1$-$C_4$ alkyl)-CO—, —CO—NH—, and —CO—N($C_1$-$C_4$ alkyl)-.

In another embodiment, the Degradation Tag is a moiety selected from the group consisting of FORMULA 5-1, 5-2, 5-3, 5-4, 5-5 and 5-6, and the Degradation Tag is connected to the Linker moiety of the heterobifunctional compound via a divalent group of $Z_E$;

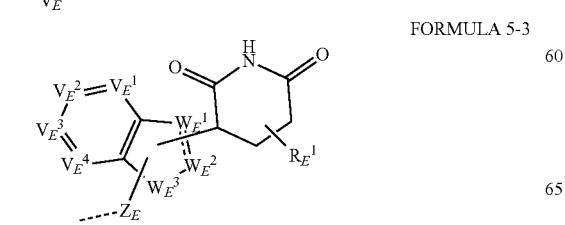

FORMULA 5-1

FORMULA 5-2

FORMULA 5-3

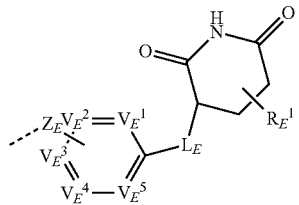

FORMULA 5-4

FORMULA 5-5

FORMULA 5-6 wherein $Z_E$, $R_E^1$, $L_E$, ⋯, $V_E^1$, $V_E^2$, $V_E^3$, $V_E^4$, $V_E^5$, $W_E^1$, $W_E^2$, $W_E^3$ and $W_E^4$ are defined as in FORMULA 5.

In another embodiment, the Degradation Tag is a moiety selected from the group consisting of FORMULAE 5A, 5B, 5C, 5D, 5E, 5F, 5G, 5H, 5I, 5J, 5K, 5L and 5M:

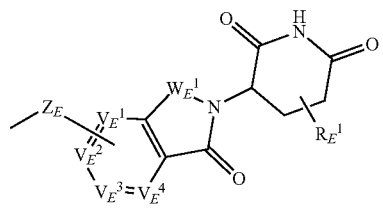

FORMULA 5A

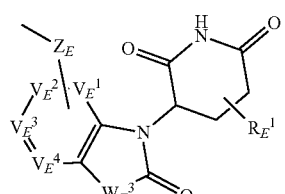

FORMULA 5B

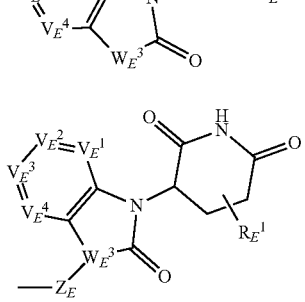

FORMULA 5C

FORMULA 5D

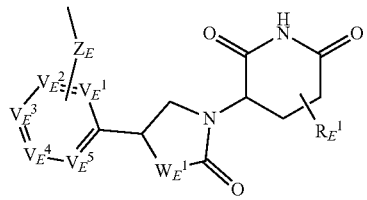

FORMULA 5E

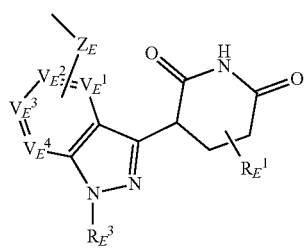

FORMULA 5F

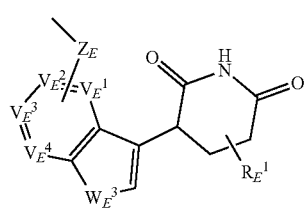

FORMULA 5G

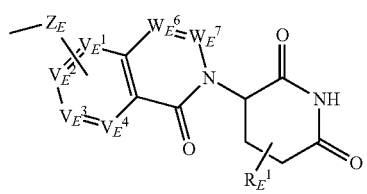

FORMULA 5H

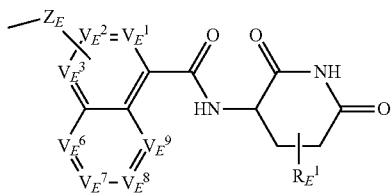

FORMULA 5I

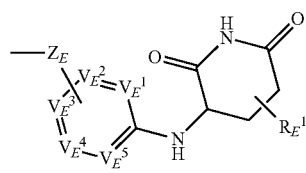

FORMULA 5J

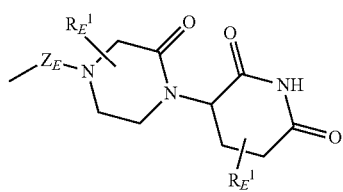

FORMULA 5K

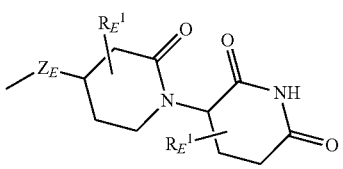

FORMULA 5L

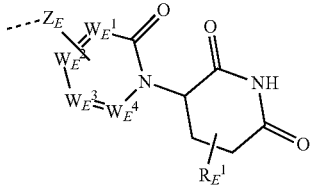

FORMULA 5M

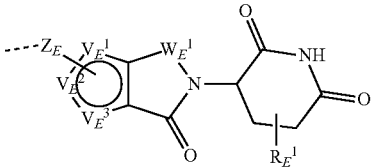

wherein, $V_E^6$, $V_E^7$, $V_E^8$, and $V_E^9$ are each independently selected from a bond, C, $CR_E^{12}$ and N; or $V_E^1$ and $V_E^2$, $V_E^2$ and $V_E^3$, $V_E^3$ and $V_E^4$, or $V_E^4$ and $V_E^5$ are combined together to optionally form $C_6$ aryl ring or a 5, 6 or 7 membered heteroaryl ring;

$R_E^{12}$, at each occurrence, is independently selected from the group consisting of hydrogen, halogen, cyano, nitro, hydroxy, amino, optionally substituted $C_1$-$C_6$ alkyl, optionally substituted $C_1$-$C_6$ alkenyl, optionally substituted $C_1$-$C_6$ alkynyl, optionally substituted $C_1$-$C_6$ alkoxy, optionally substituted $C_1$-$C_6$ alkylamino, optionally substituted 3-8 membered carbocyclyl, and optionally substituted 3-8 membered heterocyclyl;

$W_E^6$ and $W_E^7$ are each independently selected from —$CR_E^2$= and —N=;

$W_E^1$, $W_E^2$, $W_E^3$, $W_E^4$, $V_E^1$, $V_E^2$, $V_E^3$, $V_E^4$, $V_E^5$, $R_E^1$, $R_E^3$, and $Z_E$ are defined as in FORMULA 5.

In another embodiment, $W_E^1$ is selected from —CO—, —O—, —$CR_E^3R_E^4$—, —$NR_E^3$—, —$CR_E^3$=$CR_E^4$—, —N=$CR_E^3$—, and —N=N—.

In another embodiment, Ring $A_E$ is a divalent group of FORMULA $A_E$1 or $A_E$5; and Ring $A_E$ is attached to $L_E$ via $W_E^2$.

In another embodiment, Ring $A_E$ is a divalent group of FORMULA $A_E$1 or $A_E$5, wherein $W_E^1$ and $W_E^3$ are each independently selected from the group consisting of CO, O, $CR_E^3R_E^4$, $NR_E^3$; and $W_E^2$ is N.

In another embodiment, the Degradation Tag is a moiety of FORMULA 5-1 or 5-6, and the Degradation Tag is connected to the Linker moiety of the heterobifunctional compound via a divalent group of $Z_E$; wherein $W_E^1$ and $W_E^3$ are each independently selected from the group consisting of —CO—, —O—, —$CR_E^3R_E^4$—, —$NR_E^3$—;

$W_E^2$ is N, and connected to

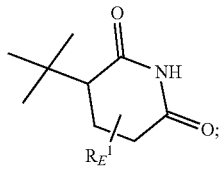

$Z_E$, $R_E^1$, $R_E^3$, $R_E^4$, $L_E$, ⋯, $V_E^1$, $V_E^2$, $V_E^3$, $V_E^4$, and $V_E^5$, are defined as in FORMULA 5.

In another embodiment, the Degradation Tag is a moiety of FORMULAE 5A or 5M; wherein $W_E$ is independently selected from the group consisting of —CO—, —O—, —$CR_E^3R_E^4$—, —$NR_E^3$—; and $V_E^1$, $V_E^2$, $V_E^3$, $V_E^4$, $R_E^1$, $R_E^3$, $R_E^4$ and $Z_E$ are defined as in FORMULA 5.

In another embodiment, $R_E^3$ and $R_E^4$, at each occurrence, are independently selected from the group consisting of absent, hydrogen, halogen, cyano, nitro, hydroxy, amino, optionally substituted $C_1$-$C_6$ alkyl.

In another embodiment, the Degradation Tag is a moiety of FORMULA 5-1, or FORMULA 5-3,

FORMULA 5-1

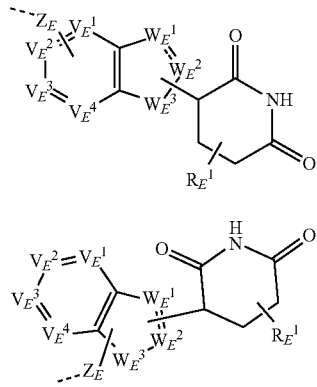

FORMULA 5-3

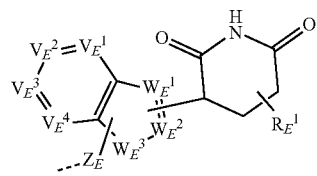

wherein
- $V_E^1$, $V_E^2$, $V_E^3$, and $V_E^4$ are each independently selected from a bond, C, $CR_E^2$, and N; or $V_E^1$ and $V_E^2$, $V_E^2$ and $V_E^3$, or $V_E^3$ and $V_E^4$ are combined together to optionally form 6 membered aryl ring or 5, 6 or 7 membered heteroaryl ring;
- ⋯ indicates a single bond or a double bond; wherein (i) when there is a single bond between $W_E^1$ and $W_E^2$ (i.e. the ⋯ between $W_E^1$ and $W_E^2$ indicates single bond), $W_E^1$, $W_E^2$ and $W_E^3$ are each independently selected from the group consisting of —N=, —$CR_E^3$=, —CO—, —O—, —$CR_E^3R_E^4$—, —$NR_E^3$—, —$CR_E^3$=$CR_E^4$—, —N=$CR_E^3$—, and —N=N—; or (ii) when there is a double bond between $W_E^1$ and $W_E^2$ (i.e. the ⋯ between $W_E^1$ and $W_E^2$ indicates a double bond), $W_E^1$ and $W_E^2$ are each independently selected from the group consisting of —N=, —C≡ and —$CR_E^3$=; $W_E^3$ is selected from the group consisting of —$CR_E^3R_E^4$—, —O—, —N=, —$NR_E^3$—, —C(O)$NR_E^3$—, —$CR_E^3$=$CR_E^4$—, and —$CR_E^3$=N—;
- $Z_E$, $R_E^2$, $R_E^3$, $R_E^4$ and $R_E^1$ are defined as in FORMULA 5.

In another embodiment, the Degradation Tag is a moiety of FORMULA 5-1 or 5-3, and wherein $V_E^1$, $V_E^2$, $V_E^3$, and $V_E^4$ are each independently selected from C, N, and $CR_E^2$.

In another embodiment, the Degradation Tag FORMULA 5-1 is moiety of FORMULA 5A, 5B, 5E, 5F or 5G

FORMULA 5A

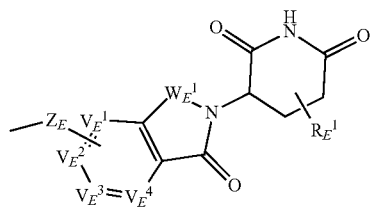

FORMULA 5B

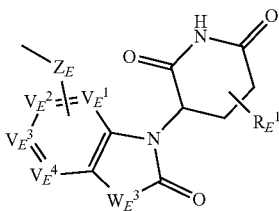

FORMULA 5E

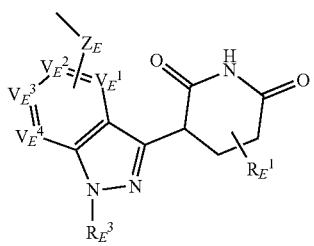

FORMULA 5F

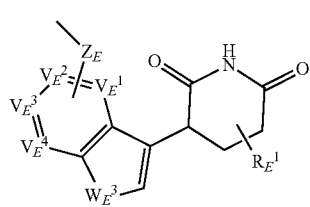

FORMULA 5G

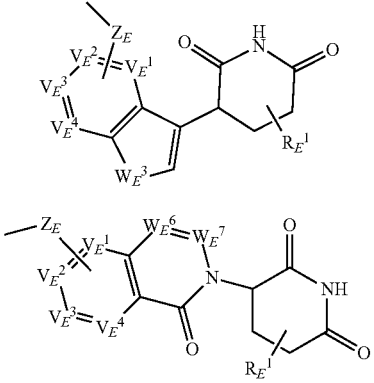

wherein $W_E^6$ and $W_E^7$ are each independently selected from —$CR_E^2$= and —N=; and $V_E^1$, $V_E^2$, $V_E^3$, $V_E^4$, $W_E^1$, $W_E^3$, $Z_E$, $R_E^3$ and $R_E^1$ are defined as in FORMULA 5-1.

In another embodiment, the Degradation Tag is a moiety of FORMULA 5A, 5B, 5E, 5F or 5G, and wherein $V_E^1$, $V_E^2$, $V_E^3$, and $V_E^4$ are each independently selected from a bond, C, $CR_E^2$ and N (preferably, C, $CR_E^2$ and N).

In another embodiment, the Degradation Tag is a moiety of FORMULA 5A, 5B, 5E, 5F or 5G, and wherein $W_E^1$ and $W_E^3$ are each independently selected from —CO—, —O—, —$CR_E^3R_E^4$—, —$NR_E^3$—, —$CR_E^3$=$CR_E^4$—, —N=$CR_E^3$—, and —N=N—; preferably, $W_E^1$ and $W_E^3$ are each independently selected from —CO—, —O—, —$CR_E^3R_E^4$—, and —$NR_E^3$—.

In another embodiment, the Degradation Tag FORMULA 5-3 is moiety of FORMULA 5C

FORMULA 5C

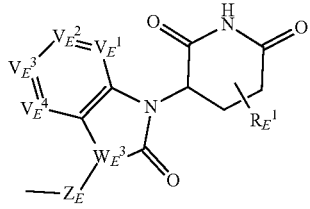

wherein $W_E^3$ is N or $CR_E^3$; and $V_E^1$, $V_E^2$, $V_E^3$, $V_E^4$, $Z_E$, and $R_E^1$ are defined as in FORMULA 5-3. In another embodiment, the Degradation Tag is a moiety of FORMULA 5C, wherein $V_E^1$, $V_E^2$, $V_E^3$, and $V_E^4$ are each independently selected from a bond, $CR_E^2$ and N.

In another embodiment, the Degradation Tag is a moiety of FORMULA 5-2,

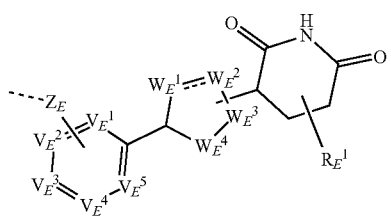

FORMULA 5-2

$V_E^1$, $V_E^2$, $V_E^3$, $V_E^4$ and $V_E^5$ are each independently selected from a bond, C, $CR_E^2$, and N; or $V_E^1$ and $V_E^2$, $V_E^2$ and $V_E^3$, $V_E^3$ and $V_E^4$, or $V_E^4$ and $V_E^5$ are combined together to optionally form $C_6$ aryl ring or 5, 6, or 7 heteroaryl ring;

⋯ indicates a single bond or a double bond; (i) when there is a single bond between $W_E^1$ and $W_E^2$ (i.e. the ⋯ between $W_E^1$ and $W_E^2$ indicates single bond), $W_E^1$ and $W_E^4$ are each independently selected from —N═, —$CR_E^3$═, —CO—, —O—, —$CR_E^3R_E^4$—, —$NR_E^3$—, —$CR_E^3$═$CR_E^4$—, —N═$CR_E^3$—, and —N═N—, and $W_E^2$ and $W_E^3$ are each independently selected from —N═, —$CR_E^3$═, —CO—, —O—, —$CR_E^3R_E^4$—, and —$NR_E^3$—; or (ii) when there is a double bond between $W_E^1$ and $W_E^2$ (i.e. the ⋯ between $W_E^1$ and $W_E^2$ indicates a double bond), $W_E^1$ and $W_E^2$ are each independently selected from —N═, C and —$CR_E^2$═; $W_E^3$ is selected from —N═, —$CR_E^3$═, —CO—, —O—, —$CR_E^3R_E^4$—, and —$NR_E^3$—; and $W_E^4$ is selected from —N═, —$CR_E^3$═, —CO—, —O—, —$CR_E^3R_E^4$—, —$NR_E^3$—, —$CR_E^3$═$CR_E$—, —N═$CR_E^3$—, and —N═N—;

$Z_E$, $R_E^2$, $R_E^3$, $R_E^4$ and $R_E^1$ are defined as in FORMULA 5.

In another embodiment, the Degradation Tag is a moiety of FORMULA 5-2, wherein $V_E^1$, $V_E^2$, $V_E^3$, $V_E^4$ and $V_E^5$ are each independently selected from a bond, C, $CR_E^2$, and N.

In another embodiment, the Degradation Tag is a moiety of FORMULA 5-2, wherein ⋯ indicates a single bond.

In another embodiment, the Degradation Tag is a moiety of FORMULA 5-2, wherein ⋯ indicates a single bond, $W_E^1$ and $W_E^4$ are each independently selected from —CO—, —O—, —$CR_E^3R_E^4$—, and —$NR_E^3$—, and $W_E^2$ and $W_E^3$ are each independently selected from —N═, —$CR_E^3$═, —CO—, —O—, —$CR_E^3R_E^4$—, and —$NR_E^3$—.

In another embodiment, the Degradation Tag FORMULA 5-2 is moiety of FORMULA 5D.

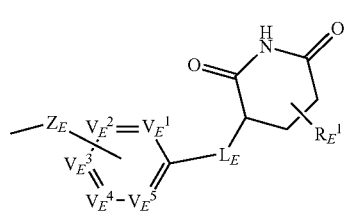

FORMULA 5D wherein $V_E^1$, $V_E^2$, $V_E^3$, $V_E^4$, $V_E^5$, $W_E^1$, $Z_E$, and $R_E^1$ are defined as in FORMULA 5-2.

In another embodiment, the Degradation Tag is a moiety of FORMULA 5D, wherein $W_E^1$ is selected from —CO—, —O—, —$CR_E^3R_E^4$—, —$NR_E^3$—, —$CR_E^3$═$CR_E^4$—, —N═$CR_E^3$—, and —N═N—; preferably, $W_E^1$ is selected from —CO—, —O—, —$CR_E^3R_E^4$—, and —$NR_E^3$—.

In another embodiment, the Degradation Tag is a moiety of FORMULA 5D, wherein $V_E^1$, $V_E^2$, $V_E^3$, $V_E^4$, and $V_E^5$ are each independently selected from a bond, C, $CR_E^2$ and N; or $V_E^1$ and $V_E^2$, $V_E^2$ and $V_E^3$, $V_E^3$ and $V_E^4$, or $V_E^4$ and $V_E^5$ are combined together to optionally form a $C_6$ aryl ring or 5, 6 or 7 heteroaryl ring; preferably, $V_E^1$, $V_E^2$, $V_E^3$, $V_E^4$, and $V_E^5$ are each independently selected from a bond, C, $CR_E^2$ and N.

In another embodiment, the Degradation Tag is a moiety of FORMULA 5-4,

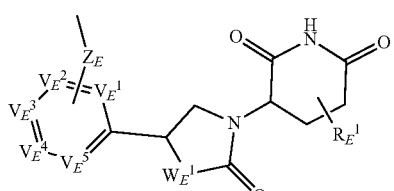

FORMULA 5-4 wherein $V_E^1$, $V_E^2$, $V_E^3$, $V_E^4$, $V_E^5$. $L_E$, $Z_E$, and $R_E^1$ are defined as in FORMULA 5.

In another embodiment, the Degradation Tag is a moiety of FORMULA 5-4, and wherein $L_E$ is not null.

In another embodiment, the Degradation Tag is a moiety of FORMULA 5-4, and wherein $L_E$ is selected from the group consisting of —NH—, —N($C_1$-$C_4$ alkyl)-, —CO—, —NH—CO—, —N($C_1$-$C_4$ alkyl)-CO—, —CO—NH—, and —CO—N($C_1$-$C_4$ alkyl)-.

In another embodiment, the Degradation Tag is a moiety of FORMULA 5-4, and wherein
$V_E^1$, $V_E^2$, $V_E^3$, $V_E^4$ and $V_E^5$, at each occurrence, are each independently selected from the group consisting of C, $CR_E^2$ and N; or
$V_E^1$ and $V_E^2$, $V_E^2$ and $V_E^3$, $V_E^3$ and $V_E^4$; or $V_E^4$ and $V_E^5$ are combined together to optionally form a ring of

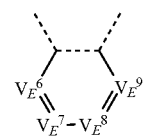

wherein $V_E^6$, $V_E^7$, $V_E^8$, and $V_E^9$ are each independently selected from the group consisting of C, $CR_E^{12}$ and N;
$R_E^{12}$, at each occurrence, is independently selected from the group consisting of hydrogen, halogen, cyano, nitro, hydroxy, amino, optionally substituted $C_1$-$C_6$ alkyl, optionally substituted $C_1$-$C_6$ alkenyl, optionally substituted $C_1$-$C_6$ alkynyl, optionally substituted $C_1$-$C_6$ alkoxy, optionally substituted $C_1$-$C_6$ alkylamino, optionally substituted 3-8 membered carbocyclyl, and optionally substituted 3-8 membered heterocyclyl.

In another embodiment, the Degradation Tag is a moiety of FORMULA 5-4, and wherein $V_E^6$, $V_E^7$, $V_E^1$, and $V_E^9$ are each independently selected from the group consisting of $CR_E^{12}$ and N.

In another embodiment, the Degradation Tag is a moiety of FORMULA 5-4, and wherein $R_E^{12}$, at each occurrence, is independently selected from the group consisting of hydrogen, halogen, cyano, nitro, hydroxy, amino, optionally substituted $C_1$-$C_6$ alkyl.

In another embodiment, the Degradation Tag is a moiety of FORMULA 5-4, and wherein

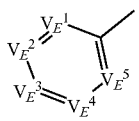

is selected from the group consisting of

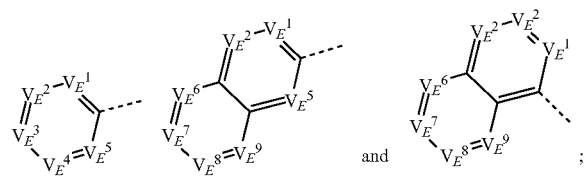

wherein
$V_E^1$, $V_E^2$, $V_E^3$, $V_E^4$ and $V_E^5$ are each independently selected from the group consisting of C, $CR_E^2$ and N; and $V_E^6$, $V_E^7$, $V_E^8$, and $V_E^9$ are each independently selected from the group consisting of $CR_E^{12}$ and N.

In another embodiment, the Degradation Tag is a moiety of FORMULA 5-4, and wherein $Z_E$ is null, —$CH_2$—, —O—, or —NH—.

In another embodiment, the Degradation Tag FORMULA 5-4 is moiety of FORMULA 5H, or 5I;

FORMULA 5H

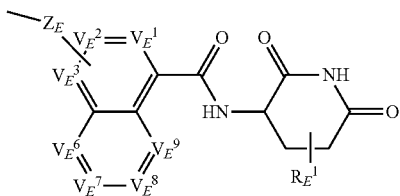

FORMULA 5I

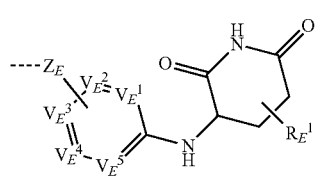

wherein $V_E^1$, $V_E^2$, $V_E^3$, $V_E^4$, $V_E^5$, $V_E^6$, $V_E^7$, $V_E^8$, and $V_E^9$ are each independently selected from a bond, C, $CR_E^2$ and N; and $Z_E$ and $R_E^1$ are defined as in FORMULA 5-4.

In another embodiment, the Degradation Tag is a moiety of FORMULA 5-5,

FORMULA 5-5

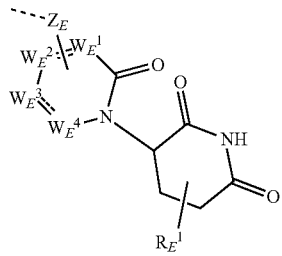

wherein ⋯, $W_E^1$, $W_E^2$, $W_E^3$, $W_E^4$, $Z_E$ and $R_E^1$ are defined as in FORMULA 5.

In another embodiment, the Degradation Tag is a moiety of FORMULA 5-5, and wherein $W_E^1$, $W_E^2$, $W_E^3$ and $W_E^4$ are each independently selected from the group consisting of —N=, —C=, —$CR_E^3$=, —CO—, —O—, —$CR_E^3R_E^4$—, and —$NR_E^3$—.

In another embodiment, the Degradation Tag is a moiety of FORMULA 5-5, and wherein $W_E^1$, $W_E^2$, $W_E^3$ and $W_E^4$ are each independently selected from the group consisting of —N=, —C=, —CH=, —CO—, —O—, —N—, —$CH_2$—, and —NH—.

In another embodiment, the Degradation Tag FORMULA 5-5 is moiety of FORMULA 5J, 5K or 5L;

FORMULA 5J

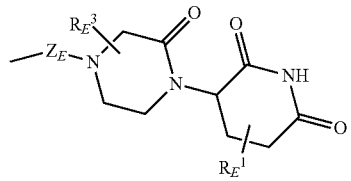

FORMULA 5K

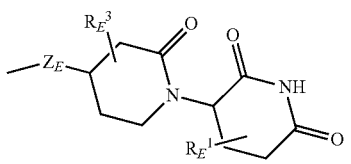

FORMULA 5L

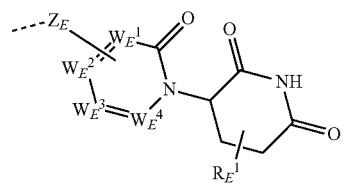

wherein $W_E^1$, $W_E^2$, $W_E^3$, $W_E^4$, $Z_E$, $R_E^3$ and $R_E^1$ are defined as in FORMULA 5-5.

In another embodiment, the Degradation Tag is a moiety of FORMULA 5-6,

FORMULA 5-6

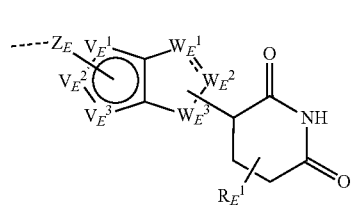

wherein $V_E^1$, $V_E^2$, and $V_E^3$ are each independently selected from C, $CR_E^2$, S, N, and $NR_E^2$; or $V_E^1$ and $V_E^2$, or $V_E^2$ and $V_E^3$ are combined together to optionally form 5 membered heteroaryl ring;

⋯ indicates a single bond or a double bond; wherein (i) when there is a single bond between $W_E^1$ and $W_E^2$ (i.e. the ⋯ between $W_E^1$ and $W_E^2$ indicates single bond), $W_E^1$, $W_E^2$ and $W_E^3$ are each independently selected from the group consisting of —N=, —$CR_E^3$=, —CO—, —O—, —$CR_E^3R_E^4$—, —$NR_E^3$— $CR_E^3$=$CR_E^4$—, —N=$CR_E^3$—, and —N=N—; or (ii) when there is a double bond between $W_E^1$ and $W_E^2$ (i.e. the ⋯ between $W_E^1$ and $W_E^2$ indicates a double bond), $W_E^1$ and $W_E^2$ are each independently selected from the group consisting of —N—, —C= and —$CR_E^3$=; $W_E^3$ is selected from the group consisting of —O—, —N=, —$NR_E^3$—, —C(O)$NR_E^3$—, —$CR_E^3R_E^4$—, —$CR_E^3$=$CR_E^4$—, and —$CR_E^3$=N—;

$Z_E$, $R_E^2$, $R_E^3$, $R_E^4$ and $R_E^1$ are defined as in FORMULA 5.

In another embodiment, the Degradation Tag is a moiety of FORMULA 5-6, and wherein $V_E^1$, $V_E^2$, $V_E^3$, and $V_E^4$ are each independently selected from C, $CR_E^2$, S, N, and $NR_E^2$.

In another embodiment, the Degradation Tag FORMULA 5-6 is moiety of FORMULA 5M:

FORMULA 5M

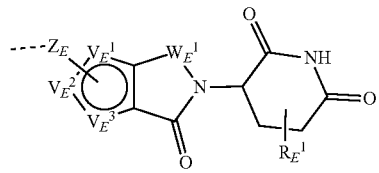

wherein $V_E^1$, $V_E^2$, $V_E^3$, $W_E^1$, $Z_E$ and $R_E^1$ are defined as in FORMULA 5-6.

In another embodiment, the Degradation Tag is a moiety of FORMULA 5M, and wherein $V_E^1$, $V_E^2$, and $V_E^3$ are each independently selected from C, $CR_E^2$, S, N, and $NR_E^2$ (preferably, one of $V_E^1$, $V_E^2$, and $V_E^3$ is S).

In another embodiment, the Degradation Tag is a moiety of FORMULA 5M, and wherein $W_E^1$ is selected from —CO—, —O—, —$CR_E^3R_E^4$—, —$NR_E^3$—, —$CR_E^3$=$CR_E^4$—, —N=$CR_E^3$—, and —N=N—; preferably, $W_E^1$ is selected from —CO—, —O—, —$CR_E^3R_E^4$—, and —$NR_E^3$—.

In another embodiment, the Degradation Tag is a moiety of FORMULAE 8A to:

FORMULA 8A

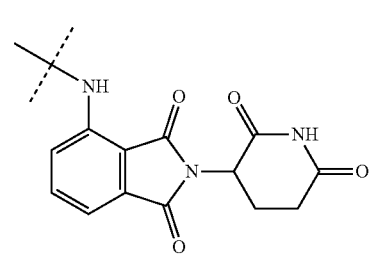

FORMULA 8B

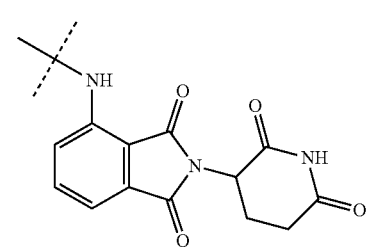

FORMULA 8C

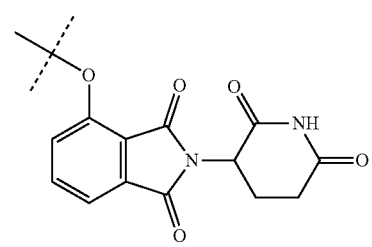

FORMULA 8D

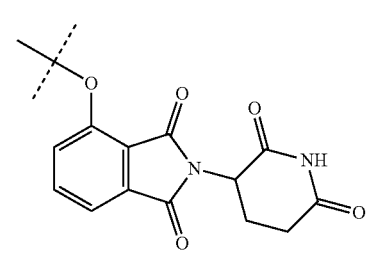

FORMULA 8E

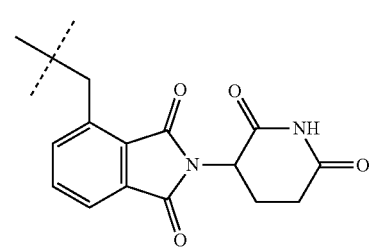

FORMULA 8F

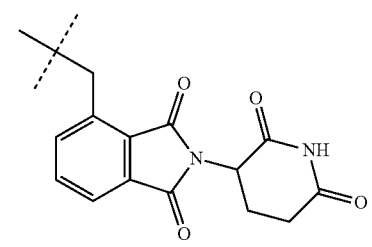

FORMULA 8G
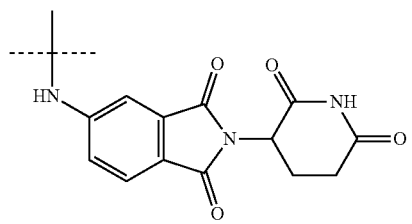
FORMULA 8H
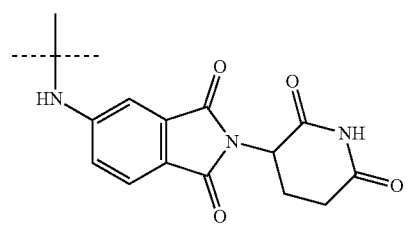
FORMULA 8I
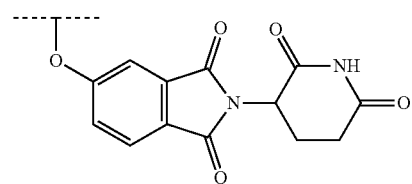
FORMULA 8J
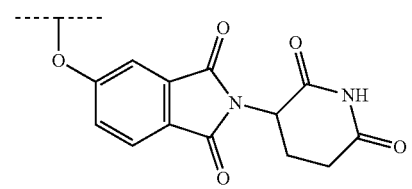
FORMULA 8K
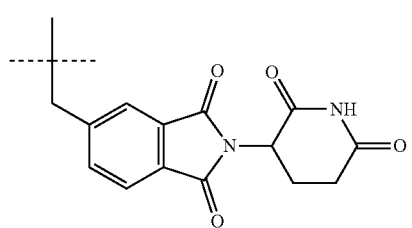
FORMULA 8L
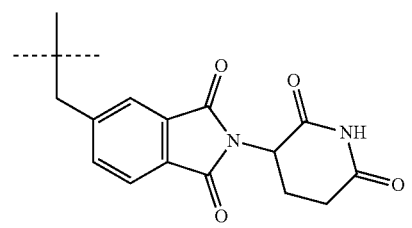
FORMULA 8M
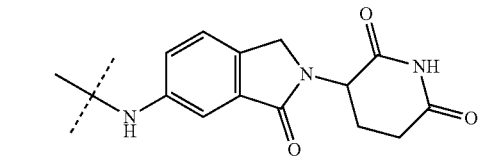
FORMULA 8N
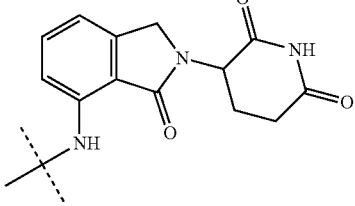
FORMULA 8O
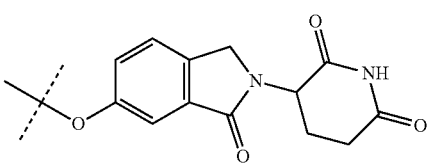
FORMULA 8P
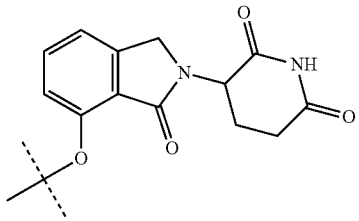
FORMULA 8Q
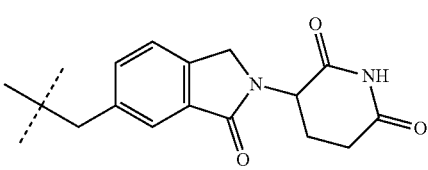
FORMULA 8R
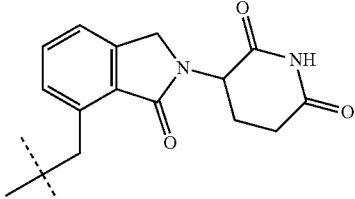
FORMULA 8S
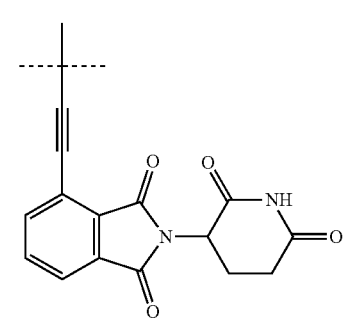
FORMULA 8T
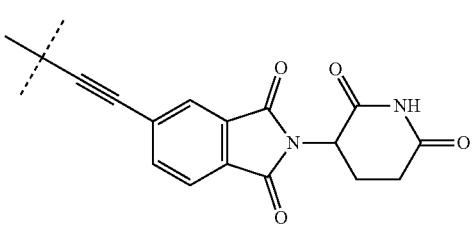

FORMULA 8U
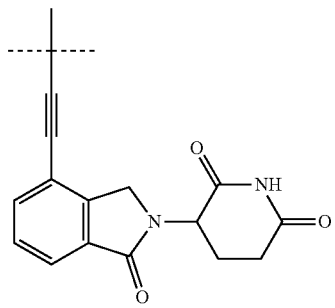
FORMULA 8V
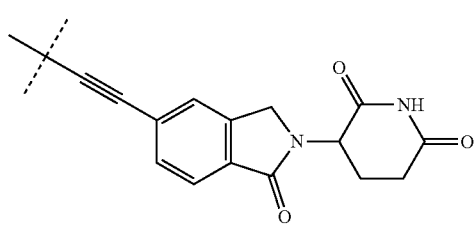
FORMULA 8W
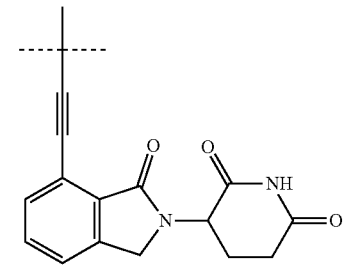
FORMULA 8X
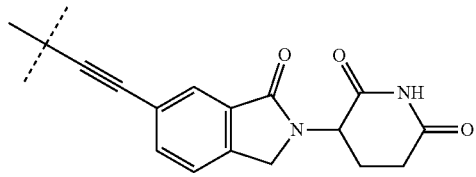
FORMULA 8Y
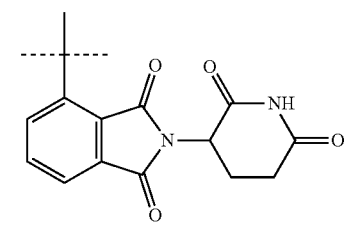
FORMULA 8Z
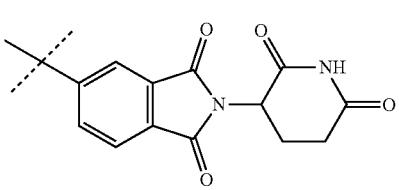
FORMULA 8AA
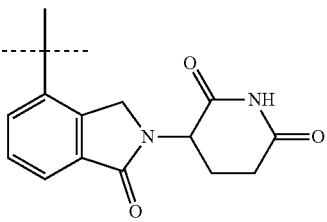
FORMULA 8AB
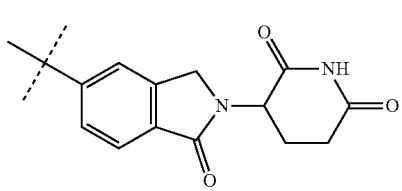
FORMULA 8AC
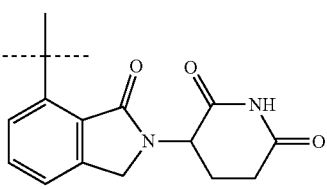
FORMULA 8AD
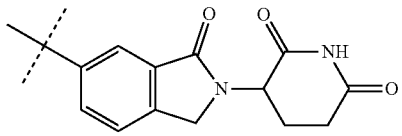
FORMULA 8AE
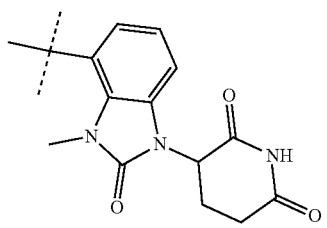
FORMULA 8AF
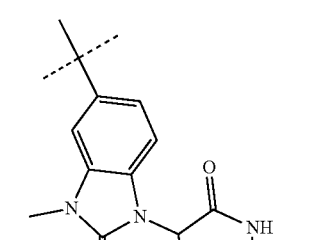
FORMULA 8AG
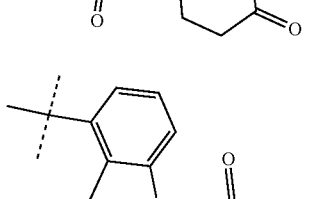

-continued
FORMULA 8AH
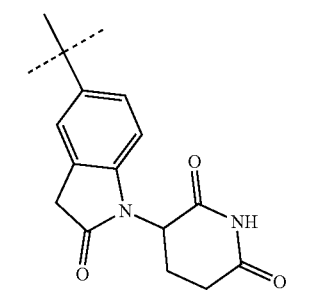
FORMULA 8AI
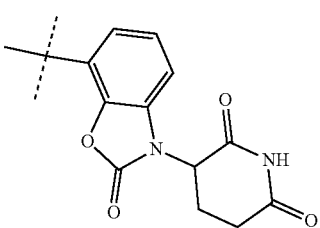
FORMULA 8AJ
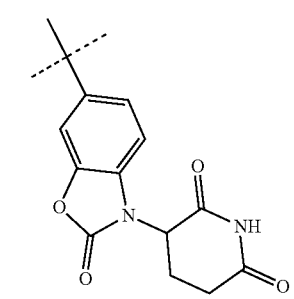
FORMULA 8AK
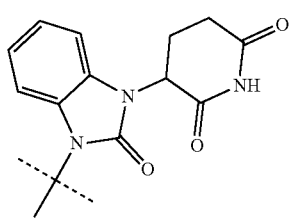
FORMULA 8AL
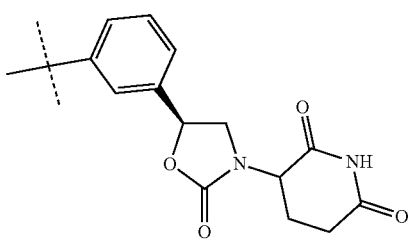
FORMULA 8AM
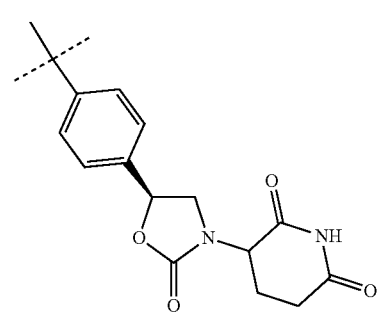
-continued
FORMULA 8AN
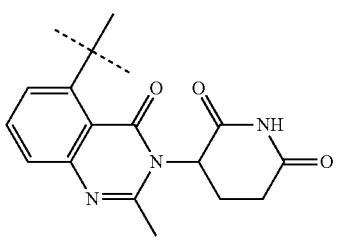
FORMULA 8AO
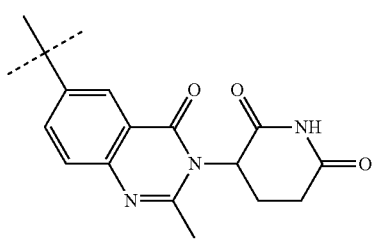
FORMULA 8AP
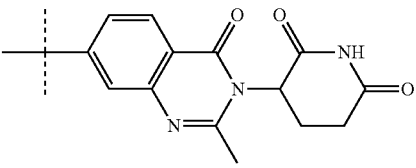
FORMULA 8AQ
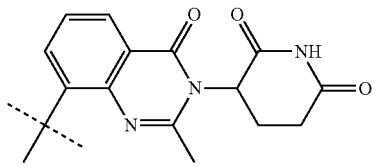
FORMULA 8AR
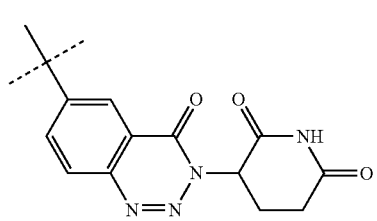
FORMULA 8AS
FORMULA 8AT
FORMULA 8AU
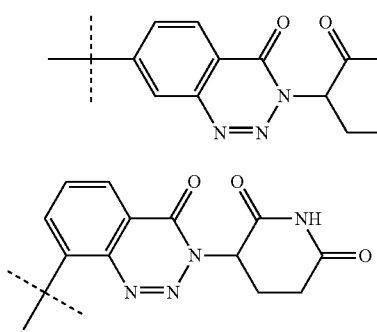

FORMULA 8AV
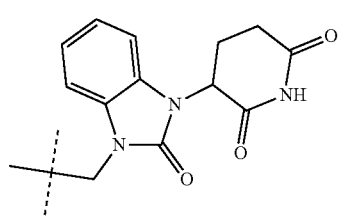
FORMULA 8AW
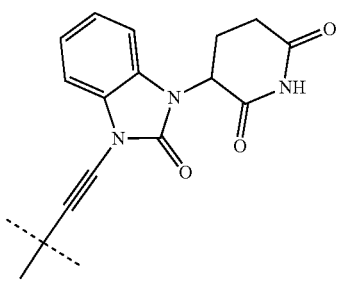
FORMULA 8AX
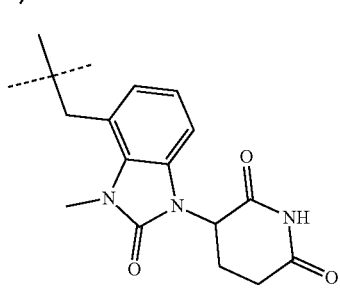
FORMULA 8AY
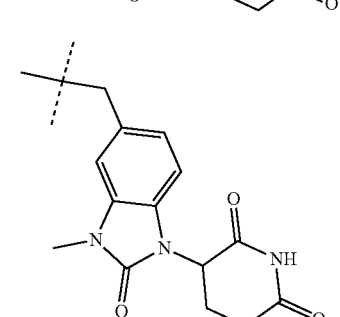
FORMULA 8AZ
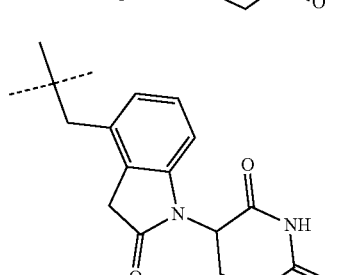
FORMULA 8BA
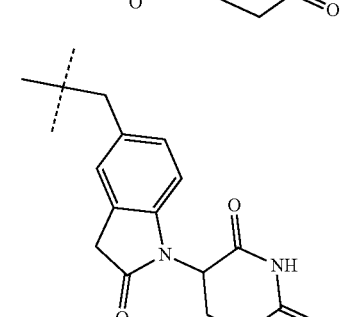
FORMULA 8BB
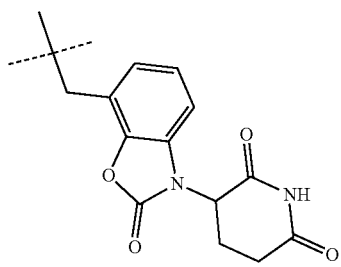
FORMULA 8BC
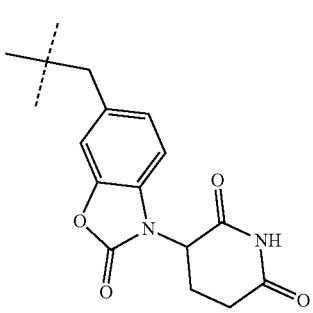
FORMULA 8BD
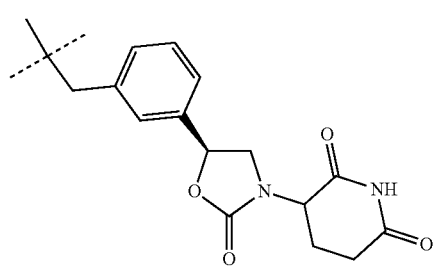
FORMULA 8BE
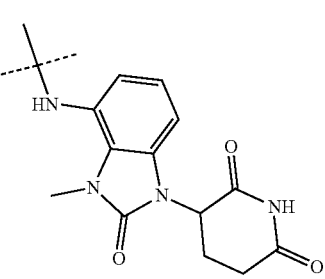
FORMULA 8BF
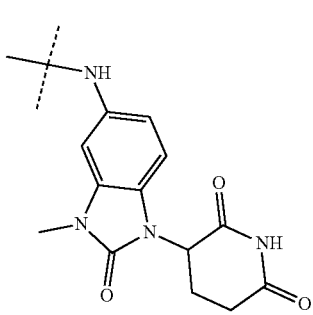

FORMULA 8BG
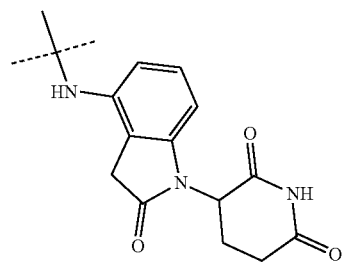
FORMULA 8BL
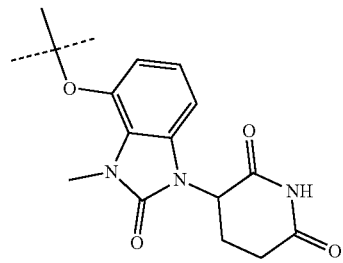
FORMULA 8BH
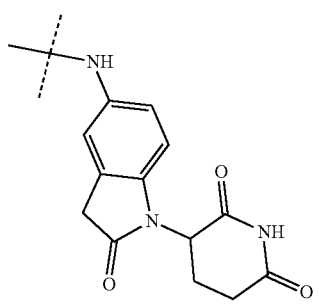
FORMULA 8BM
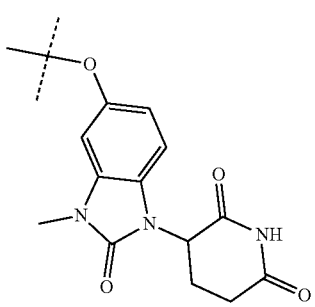
FORMULA 8BI
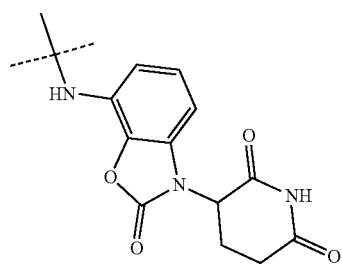
FORMULA 8BN
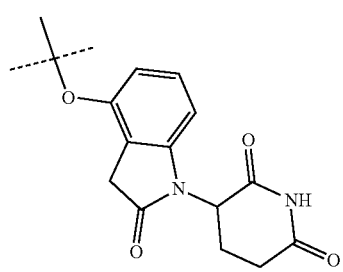
FORMULA 8BJ
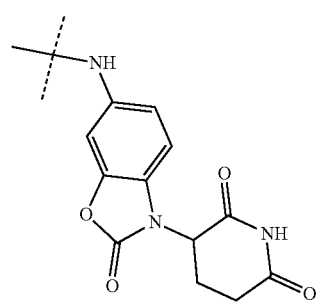
FORMULA 8BO
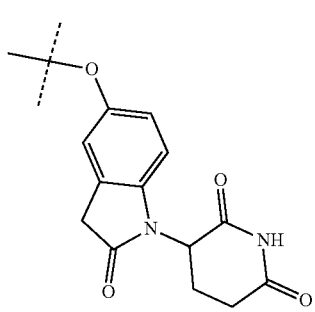
FORMULA 8BK
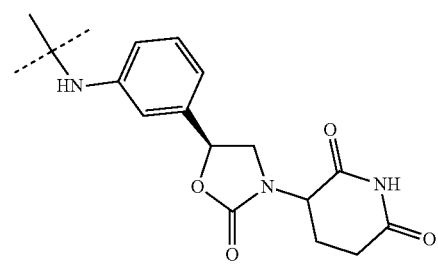
FORMULA 8BP
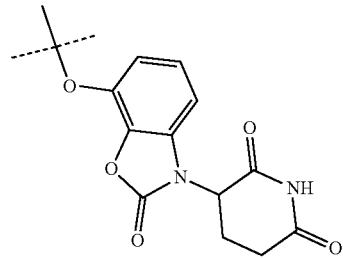

-continued
FORMULA 8BQ
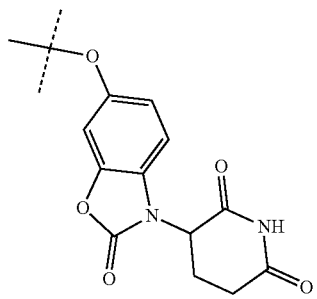
FORMULA 8BR
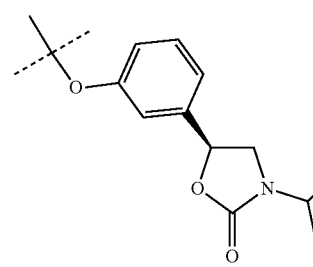
FORMULA 8BS
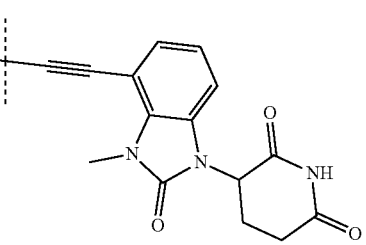
FORMULA 8BT
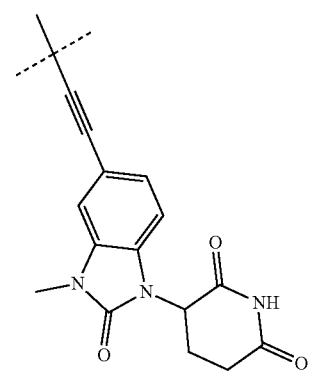
FORMULA 8BU
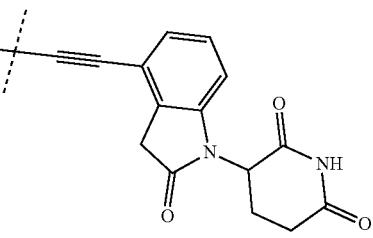
-continued
FORMULA 8BV
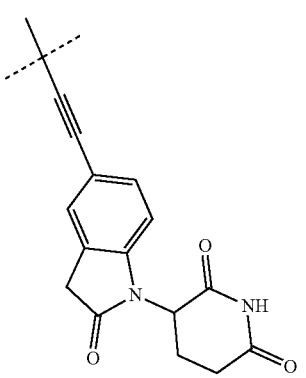
FORMULA 8BW
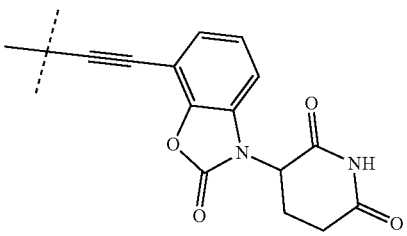
FORMULA 8BX
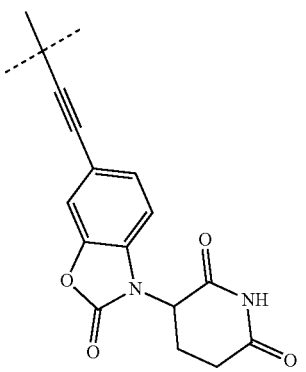
FORMULA 8BY
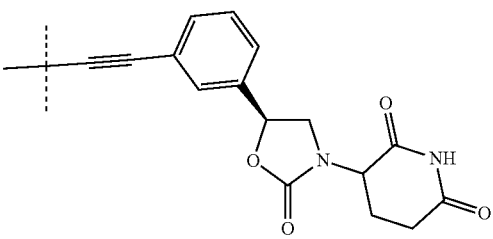
FORMULA 8BZ
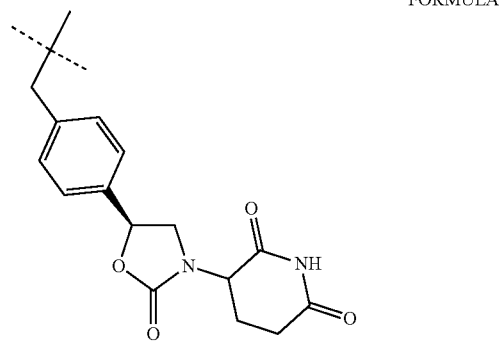

FORMULA 8CA
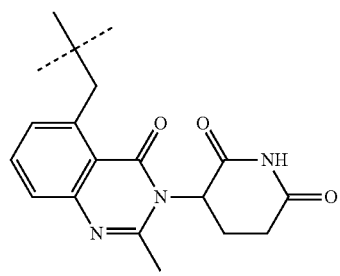
FORMULA 8CB
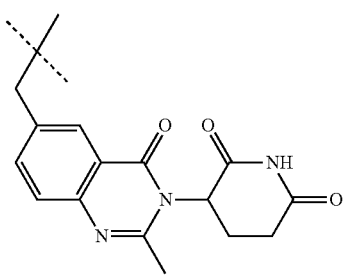
FORMULA 8CC
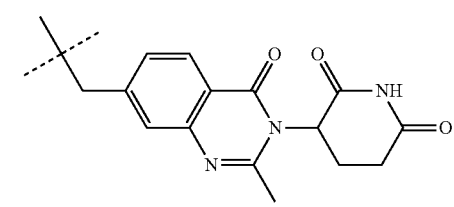
FORMULA 8CD
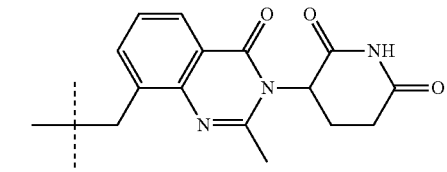
FORMULA 8CE
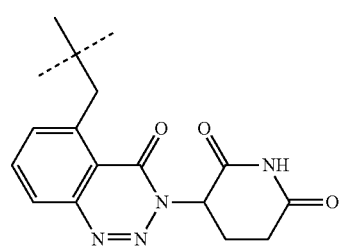
FORMULA 8CF
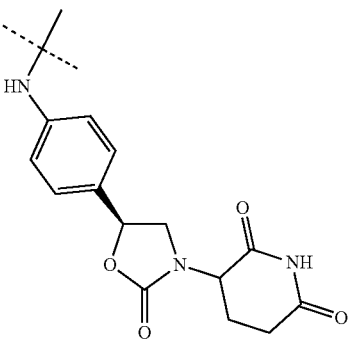
FORMULA 8CG
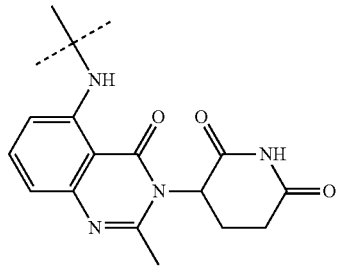
FORMULA 8CH
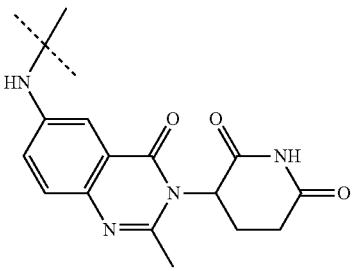
FORMULA 8CI
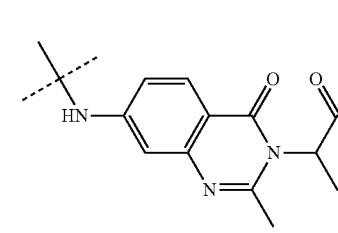
FORMULA 8CJ
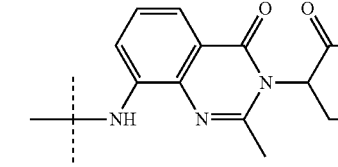
FORMULA 8CK
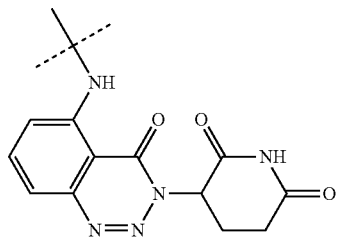
FORMULA 8CL
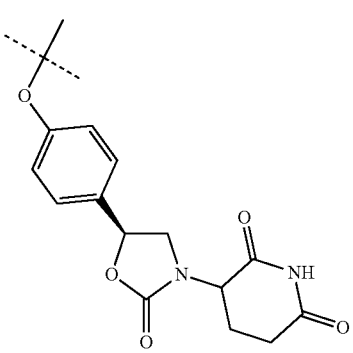

FORMULA 8CM
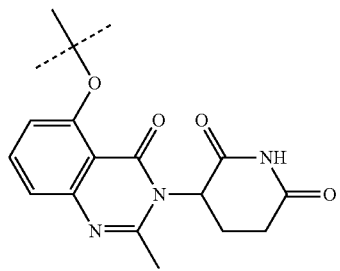
FORMULA 8CN
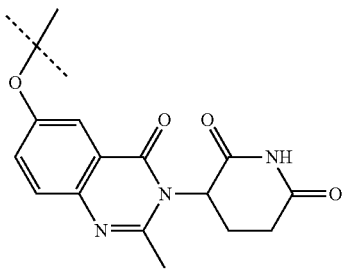
FORMULA 8CO
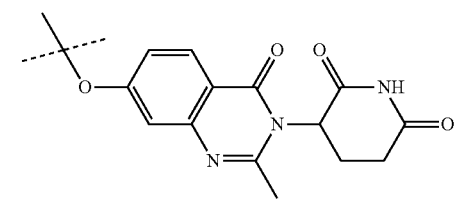
FORMULA 8CP
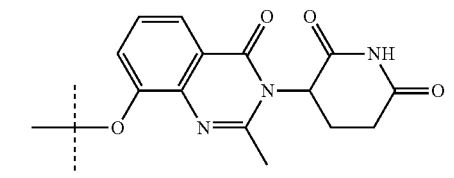
FORMULA 8CQ
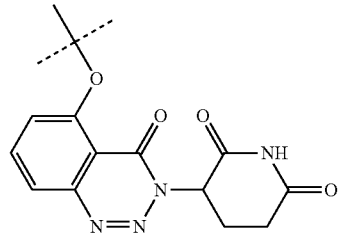
FORMULA 8CR
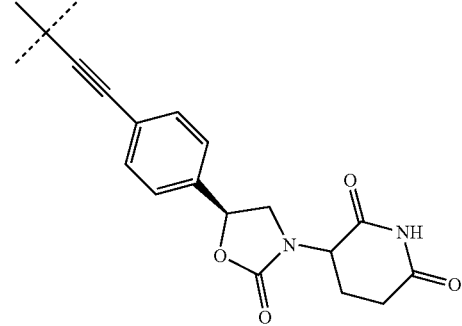
FORMULA 8CS
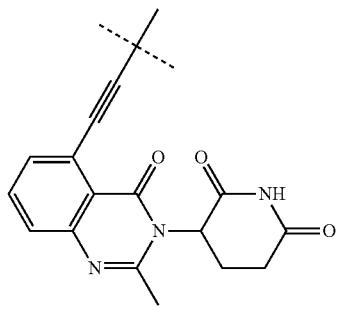
FORMULA 8CT
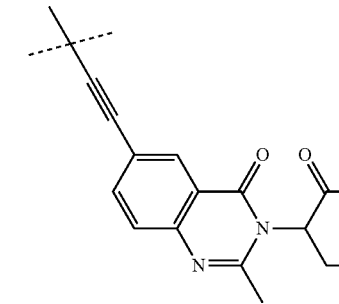
FORMULA 8CU
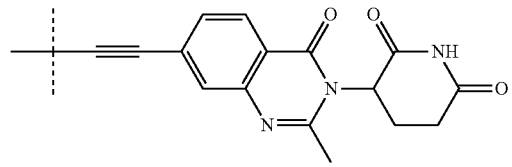
FORMULA 8CV
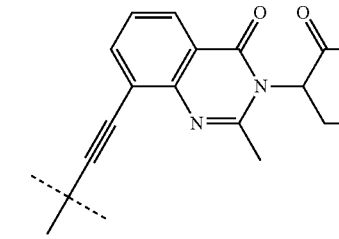
FORMULA 8CW
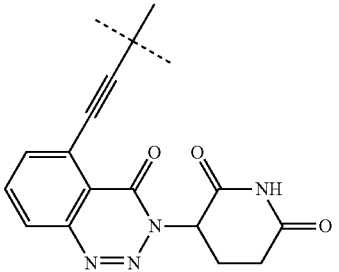
FORMULA 8CX
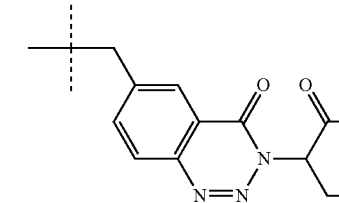

FORMULA 8CY
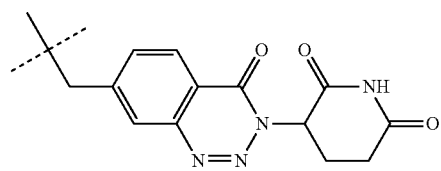
FORMULA 8CZ
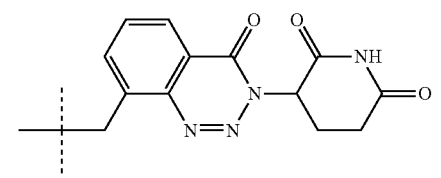
FORMULA 8DA
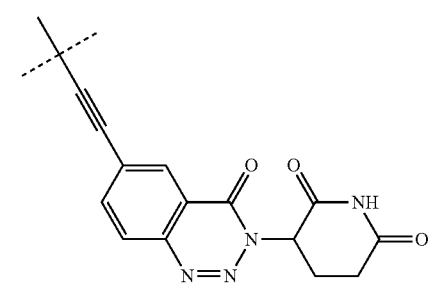
FORMULA 8DB
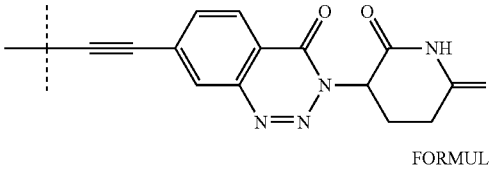
FORMULA 8DC
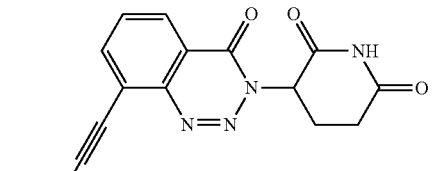
FORMULA 8DD
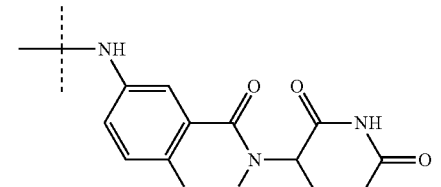
FORMULA 8DE
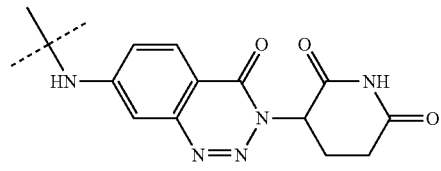
FORMULA 8DF
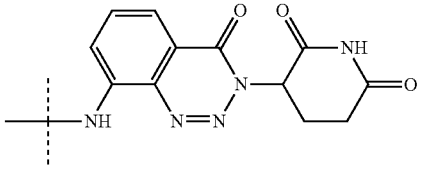
FORMULA 8DG
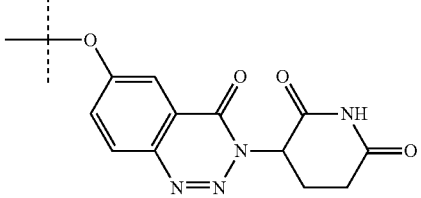
FORMULA 8DH
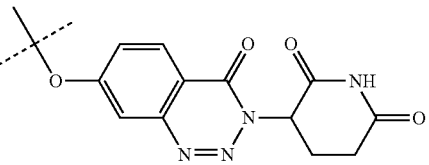
FORMULA 8DI
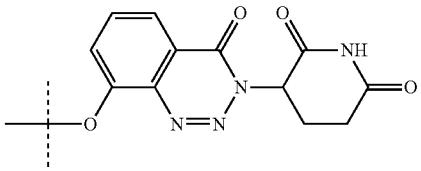
FORMULA 8DJ
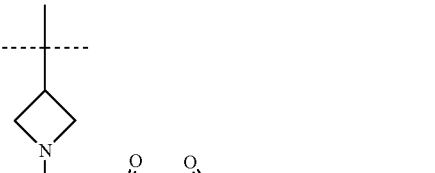
FORMULA 8DK
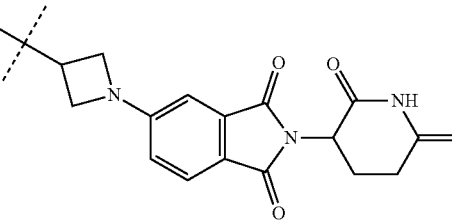

FORMULA 8DL
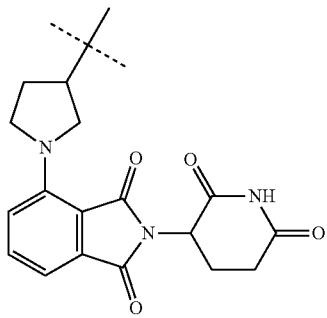
FORMULA 8DM
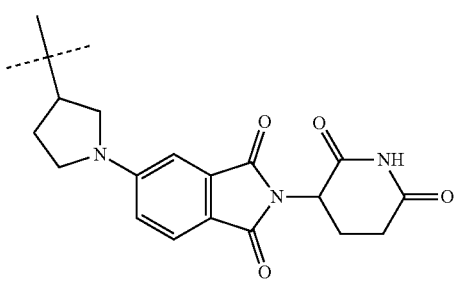
FORMULA 8DN
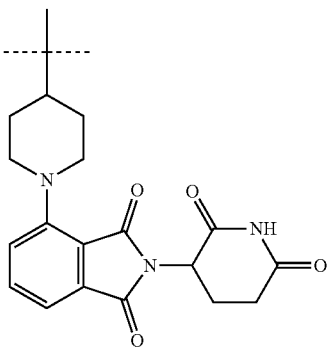
FORMULA 8DO
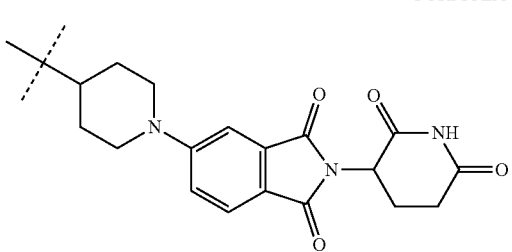
FORMULA 8DP
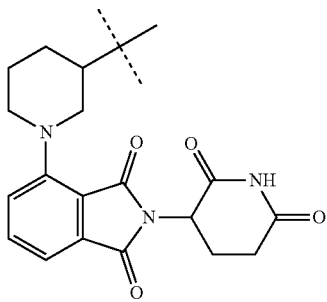
FORMULA 8DQ
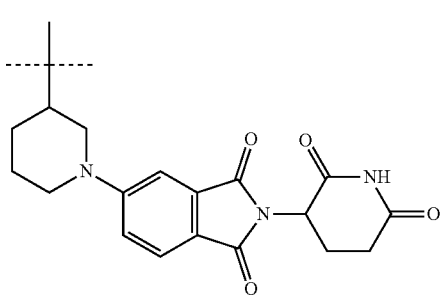
FORMULA 8DR
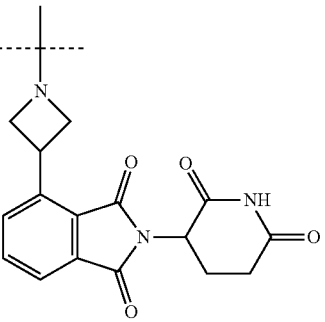
FORMULA 8DS
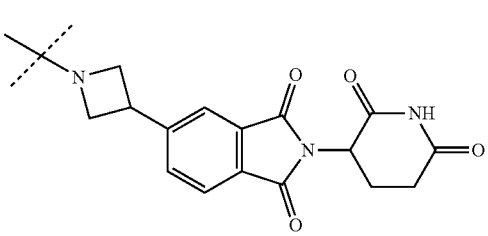
FORMULA 8DT
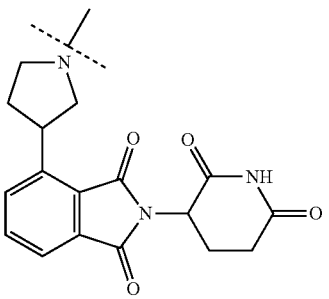
FORMULA 8DU
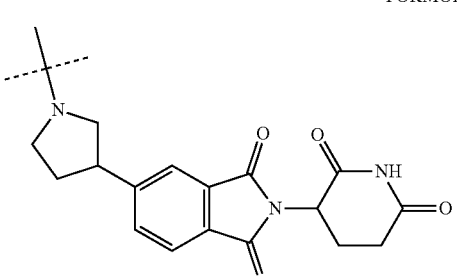

FORMULA 8DV
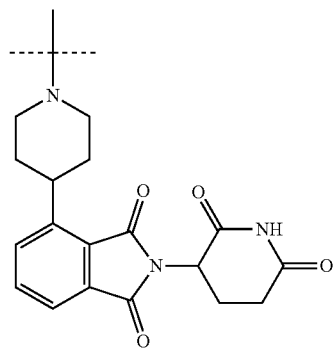
FORMULA 8DW
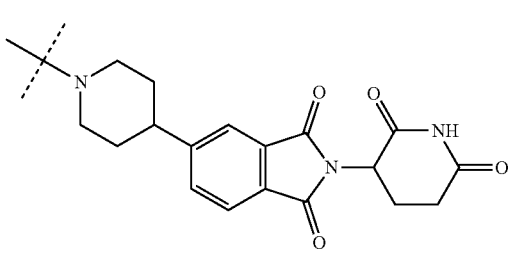
FORMULA 8DX
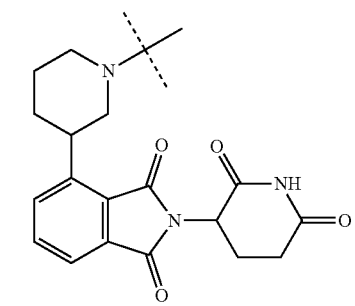
FORMULA 8DY
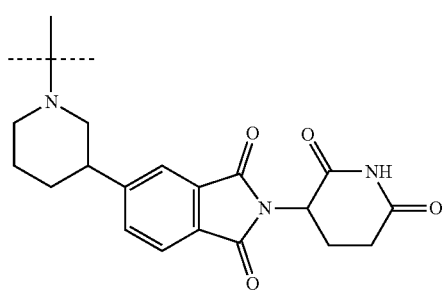
FORMULA 8DZ
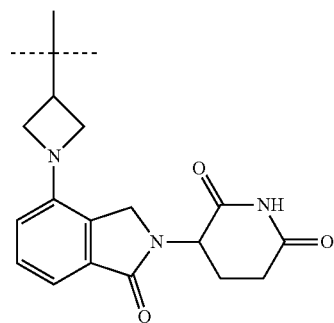
FORMULA 8EA
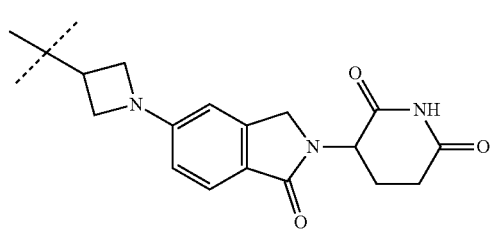
FORMULA 8EB
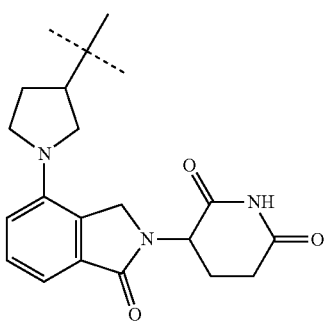
FORMULA 8EC
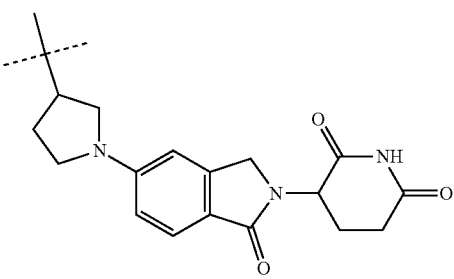
FORMULA 8ED
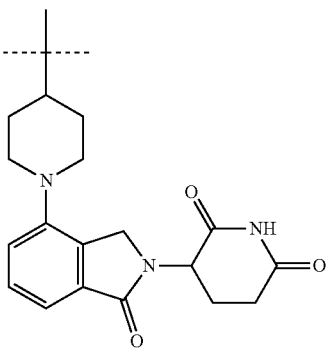
FORMULA 8EE
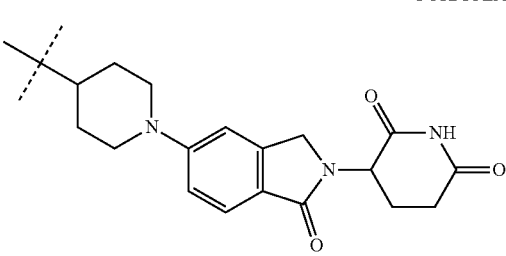

FORMULA 8EF
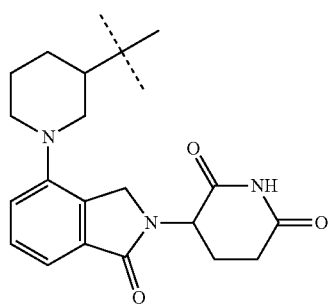
FORMULA 8EG
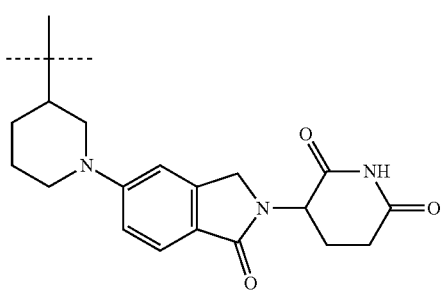
FORMULA 8EH
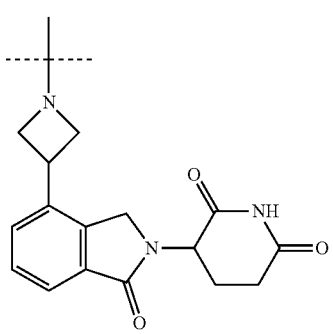
FORMULA 8EI
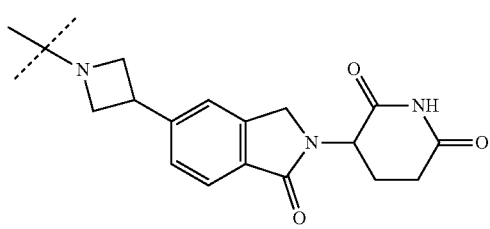
FORMULA 8EJ
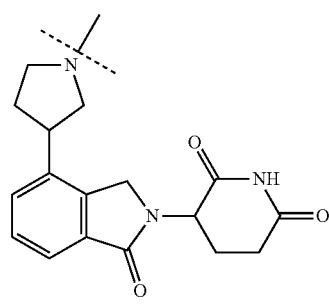
FORMULA 8EK
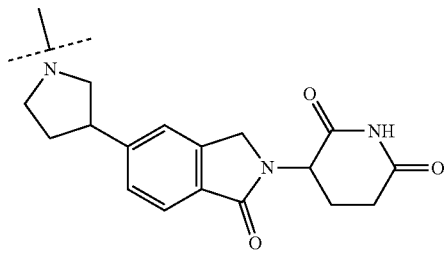
FORMULA 8EL
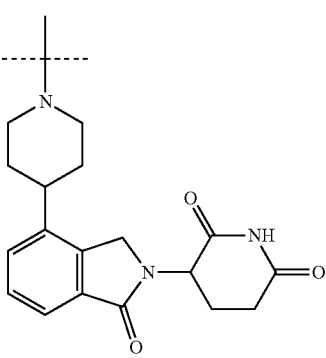
FORMULA 8EM
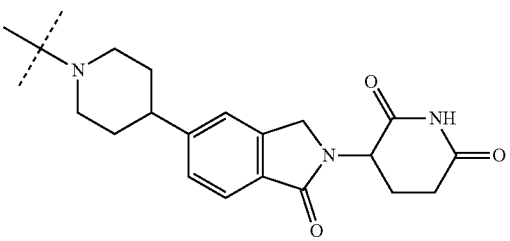
FORMULA 8EN
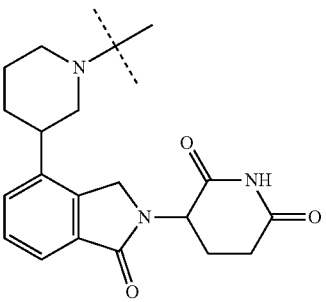
FORMULA 8EO
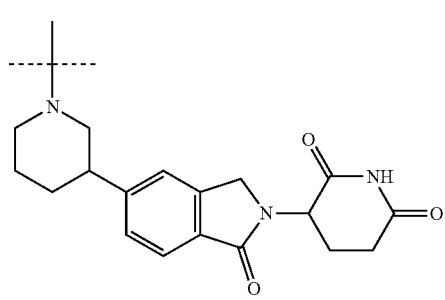

FORMULA 8EP
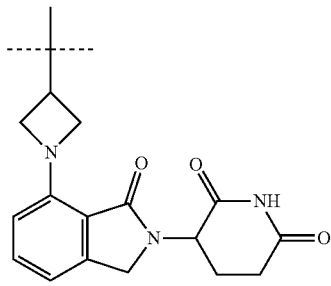
FORMULA 8EQ
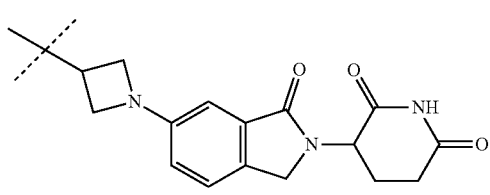
FORMULA 8ER
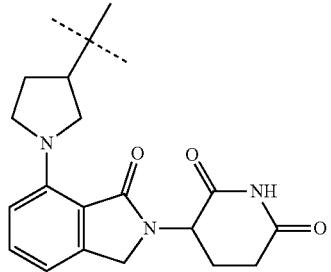
FORMULA 8ES
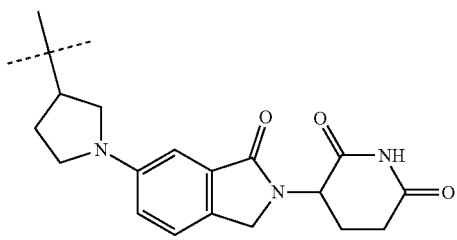
FORMULA 8ET
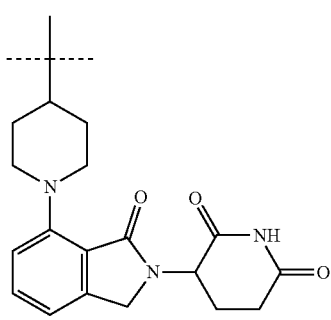
FORMULA 8EU
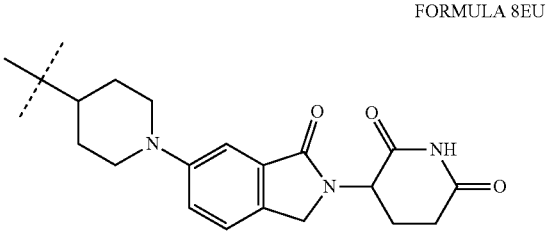
FORMULA 8EV
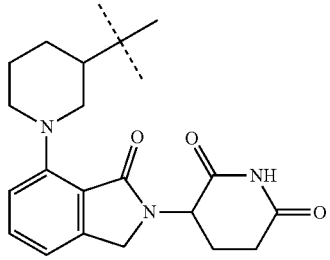
FORMULA 8EW
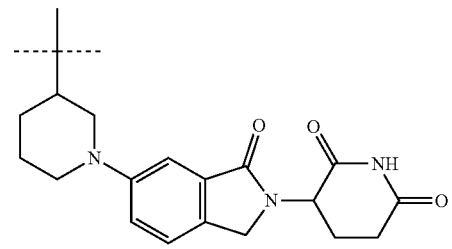
FORMULA 8EX
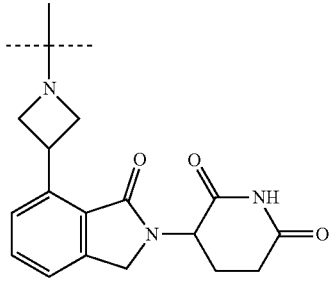
FORMULA 8EY
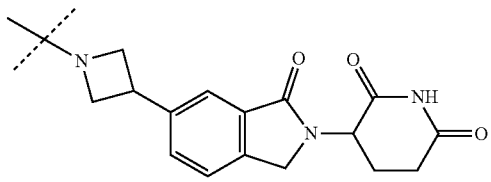
FORMULA 8EZ
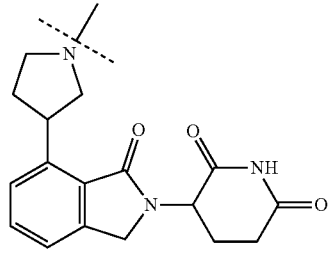
FORMULA 8FA
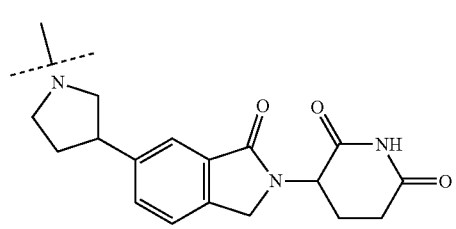

FORMULA 8FB
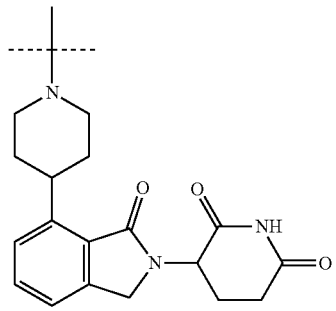
FORMULA 8FC
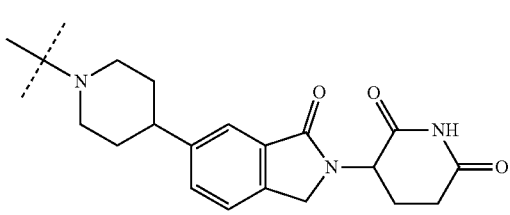
FORMULA 8FD
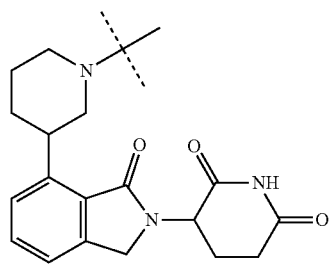
FORMULA 8FE
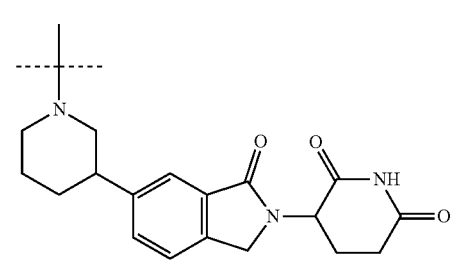
FORMULA 8FF
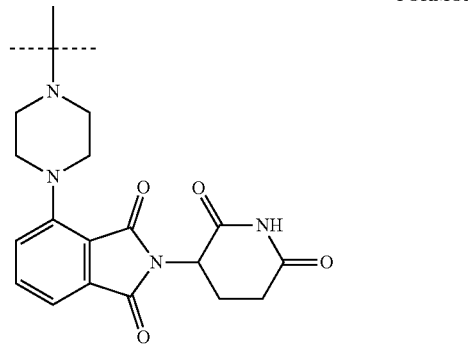
FORMULA 8FG
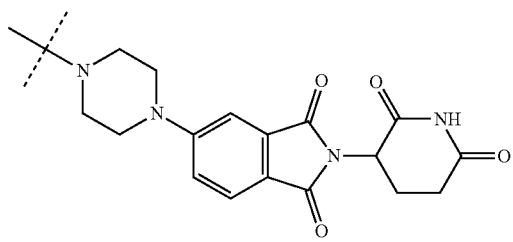
FORMULA 8FH
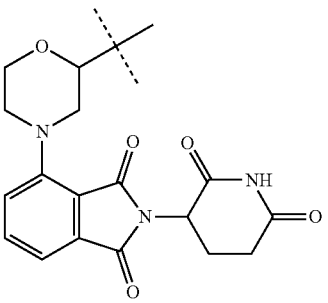
FORMULA 8FI
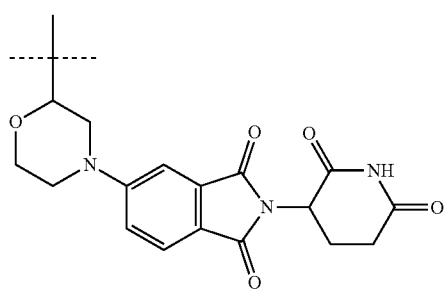
FORMULA 8FJ
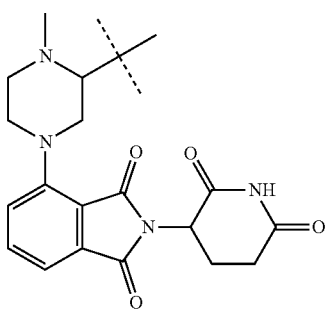
FORMULA 8FK
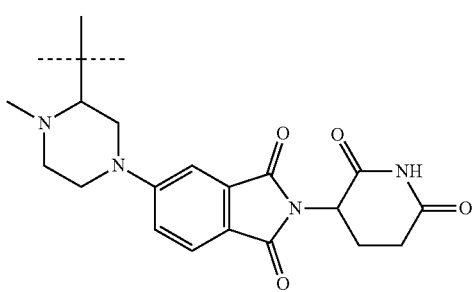

FORMULA 8FL
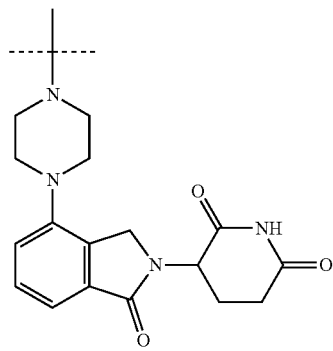
FORMULA 8FM
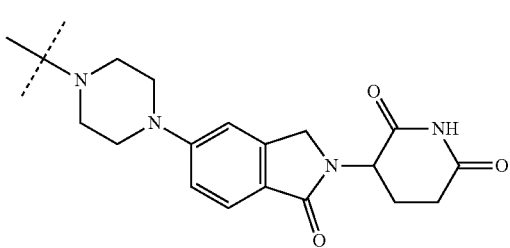
FORMULA 8FN
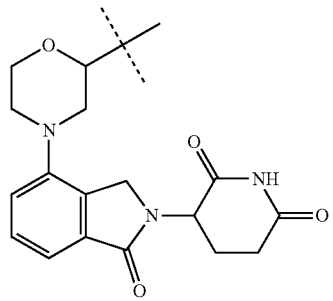
FORMULA 8FO
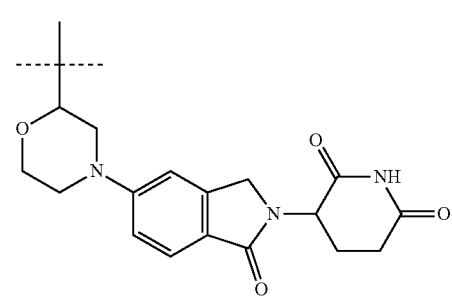
FORMULA 8FP
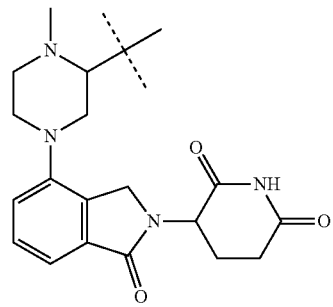
FORMULA 8FQ
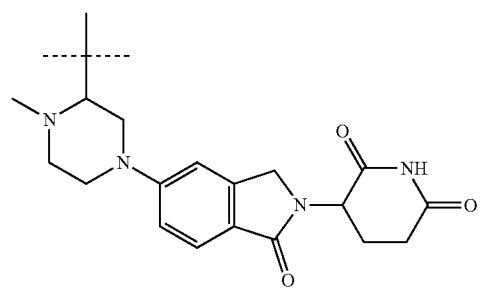
FORMULA 8FR
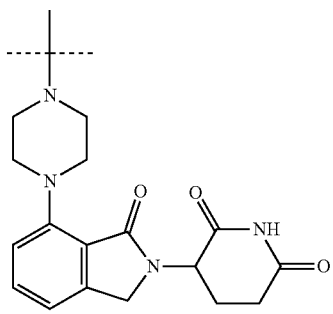
FORMULA 8FS
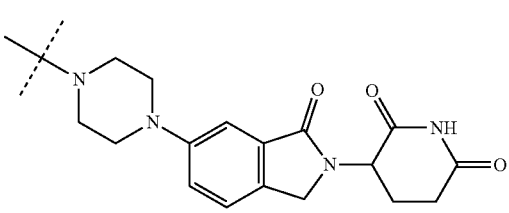
FORMULA 8FT
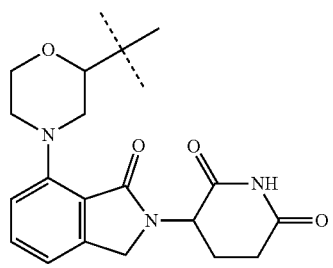
FORMULA 8FU
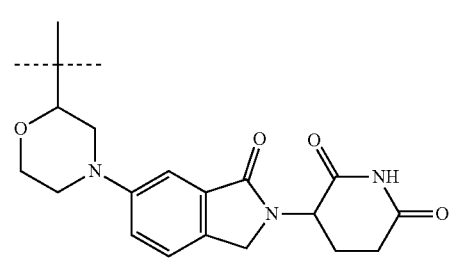

FORMULA 8FV
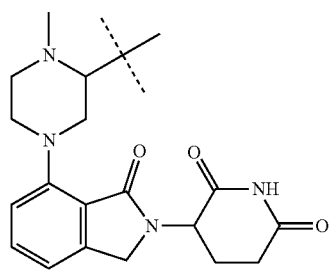
FORMULA 8FW
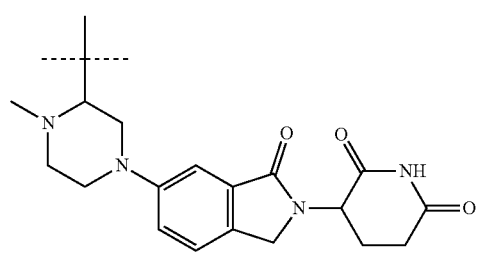
FORMULA 8FX
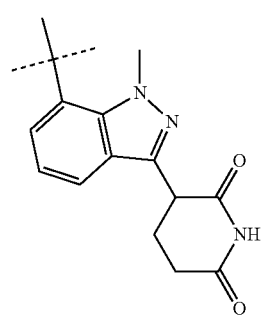
FORMULA 8FY
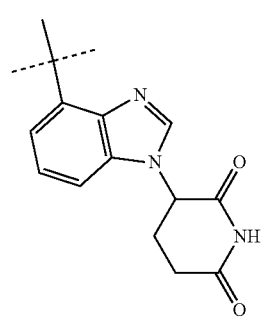
FORMULA 8FZ
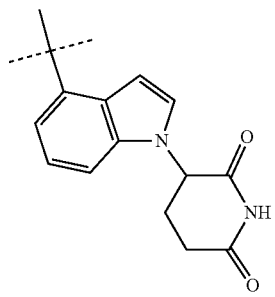
FORMULA 8GA
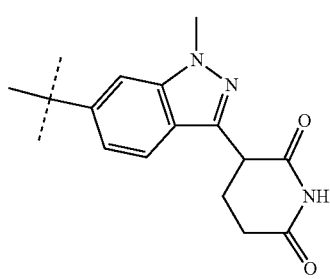
FORMULA 8GB
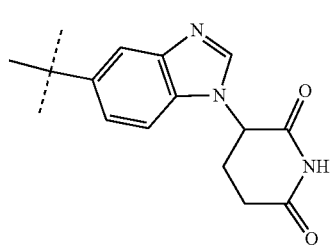
FORMULA 8GC
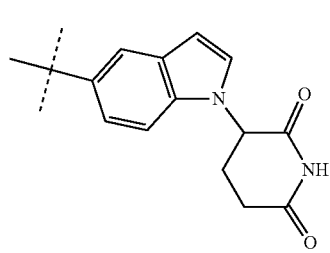
FORMULA 8GD
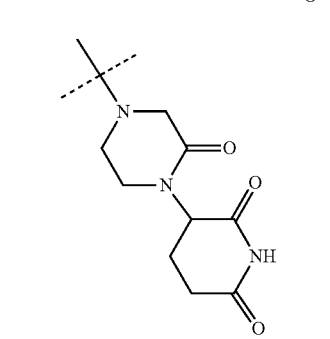
FORMULA 8GE
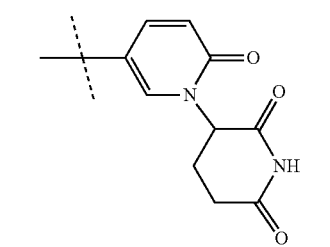
FORMULA 8GF
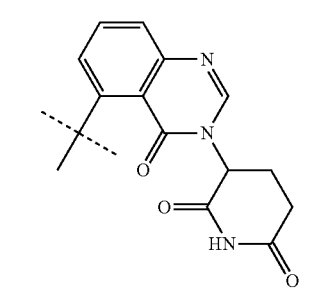

FORMULA 8GG
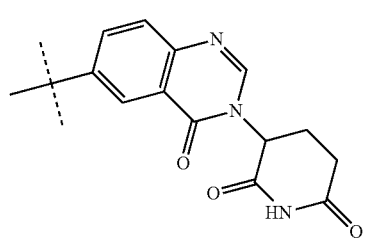
FORMULA 8GH
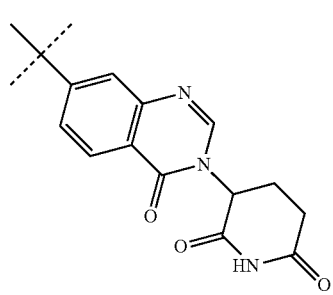
FORMULA 8GI
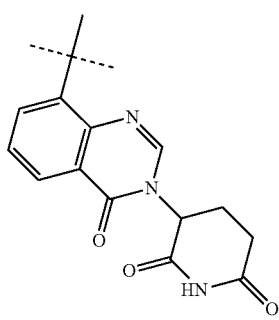
FORMULA 8GJ
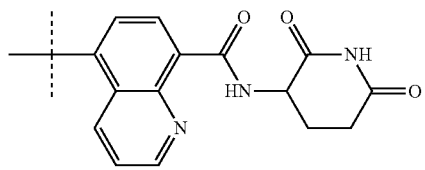
FORMULA 8GK
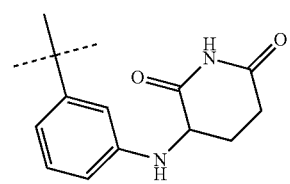
FORMULA 8GL
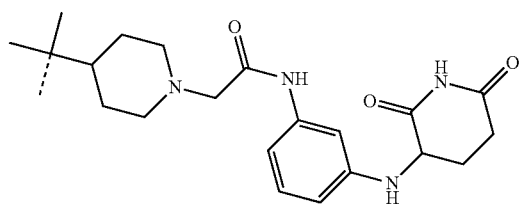
FORMULA 8GM
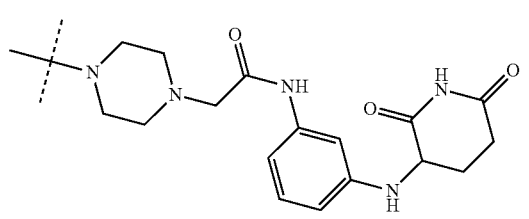
FORMULA 8GN
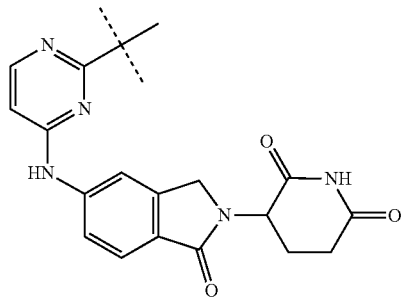
FORMULA 8GO
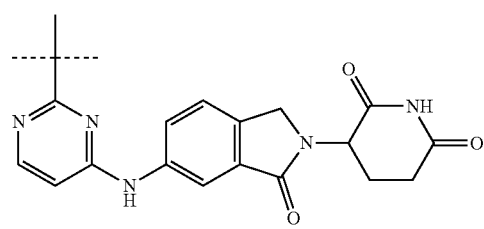
FORMULA 8GP
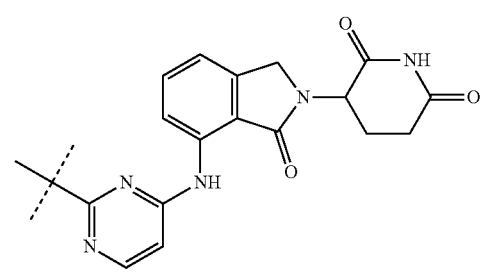
FORMULA 8GQ FORMULA 8GR
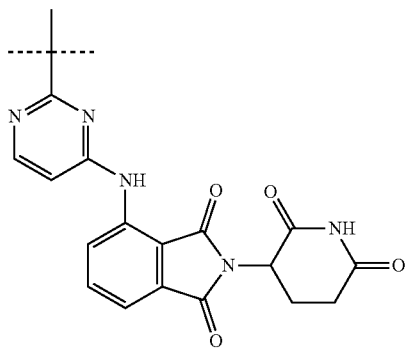
FORMULA 8GS
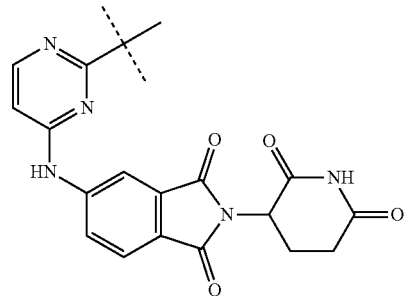
FORMULA 8GT
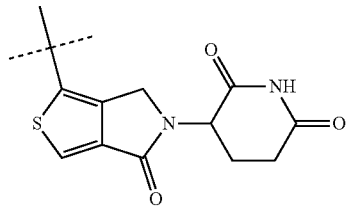
FORMULA 8GU
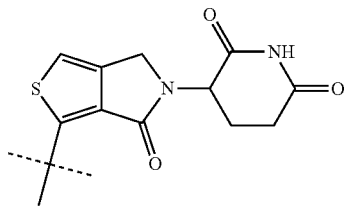
FORMULA 8GV
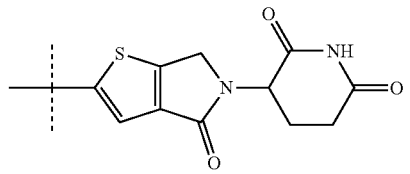
FORMULA 8GW
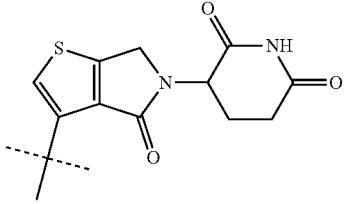
FORMULA 8GX
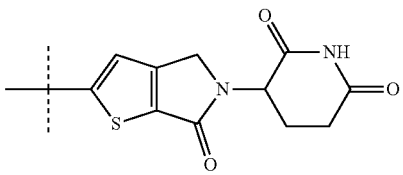
FORMULA 8GY
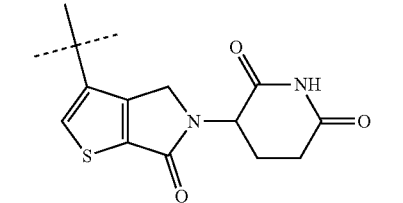
FORMULA 8GZ
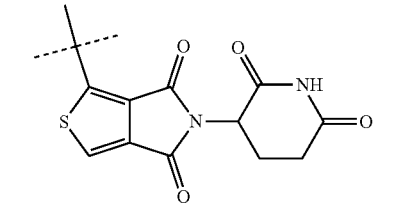
FORMULA 8HA
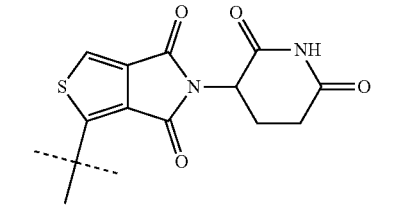
FORMULA 8HB
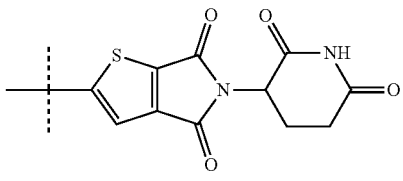
FORMULA 8HC
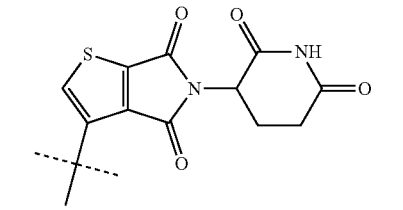
FORMULA 8HD
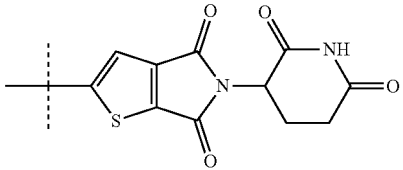

-continued

FORMULA 8HE

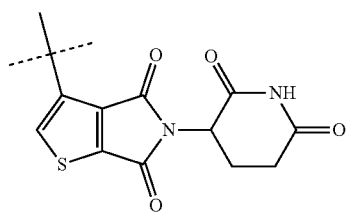

In another embodiment, the Degradation Tag is a moiety of FORMULA 4A:

FORMULA 4A

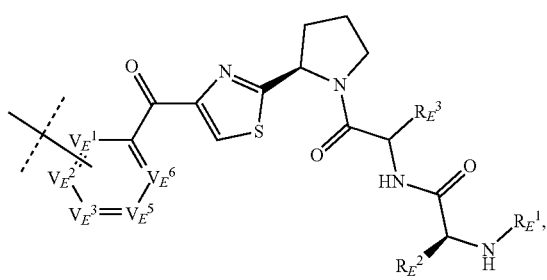

wherein
$V_E^1$, $V_E^2$, $V_E^3$, $V_E^4$, and $V_E^5$, are independently selected from $CR_E^4$ and N; and
$R_E^1$, $R_E^2$, $R_E^3$, and $R_E^4$ are independently selected from hydrogen, halogen, cyano, nitro, optionally substituted $C_1$-$C_8$ alkyl, optionally substituted $C_2$-$C_8$ alkenyl, and optionally substituted $C_2$-$C_8$ alkynyl; optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkoxy, optionally substituted $C_1$-$C_8$alkylamino, optionally substituted $C_3$-$C_{10}$ carbocyclyl, and optionally substituted 3-10 membered heterocyclyl.

In another embodiment, the Degradation Tag is a moiety of FORMULA 4B:

FORMULA 4B

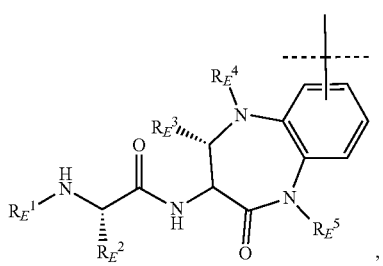

wherein
$R_E^1$, $R_E^2$, and $R_E^3$ are independently selected from hydrogen, halogen, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl;

$R_E^4$ and $R_E^5$ are independently selected from hydrogen, $COR_E^6$, $CO_2R_E^6$, $CONR_E^6R_E^7$, $SOR_E^6$, $SO_2R_E^6$, $SO_2NR_E^6R_E^7$, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted aryl-$C_1$-$C_8$alkyl, optionally substituted 3-8 membered cycloalkyl, optionally substituted 3-8 membered heterocyclyl, optionally substituted aryl, and optionally substituted heteroaryl, wherein $R_E^6$ and $R_E^7$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted 3-8 membered heterocyclyl, optionally substituted aryl, and optionally substituted heteroaryl, or $R_E^6$ and $R_E^7$ together with the atom(s) to which they are connected form a 3-8 membered cycloalkyl or heterocyclyl ring.

In another embodiment, the Degradation Tag is a moiety of FORMULA 6A, 6B, and 6C.
In another embodiment, the Degradation Tag is a moiety of FORMULA 6A.
In another embodiment, the Degradation Tag is a moiety of FORMULA 6B.
In another embodiment, the Degradation Tag is a moiety of FORMULA 6C.
In another embodiment, the Degradation Tag is a moiety of FORMULA 6A-1 to 6A-13.
In another embodiment, the Degradation Tag is a moiety of FORMULA 6B-1 to 6A-15.
In another embodiment, the Degradation Tag is a moiety of FORMULA 6C-1 to 6C-15.
In another embodiment, the Degradation Tag is a moiety of FORMULA 7A to 7BJ.
In another embodiment, the Degradation Tag is a moiety of FORMULA 7F, 7P, 7AC, 7AQ, and 7BE.
In another embodiment, the Degradation Tag is a moiety of FORMULA 5.
In another embodiment, the Degradation Tag is a moiety of FORMULA 5-1 to 5-6.
In another embodiment, the Degradation Tag is a moiety of FORMULA 5-1.
In another embodiment, the Degradation Tag is a moiety of FORMULA 5A to 5M.
In another embodiment, the Degradation Tag is a moiety of FORMULA 5A.
In another embodiment, the Degradation Tag is a moiety of FORMULA 8A to 8HE.
In another embodiment, the Degradation Tag is a moiety of FORMULA 8A to 8AD.
In another embodiment, the Degradation Tag is a moiety of FORMULA 8DJ to 8FW.
In another embodiment, the Degradation Tag is a moiety of FORMULA 8A and 8G.

In some embodiments, the Linker comprises acyclic or cyclic saturated or unsaturated carbon, ethylene glycol, amide, amino, ether, urea, carbamate, aromatic, heteroaromatic, heterocyclic or carbonyl groups.

In certain embodiments, the length of the Linker is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more atoms.

In another embodiment, $A_L$ and $B_L$, at each occurrence, are independently selected from the group consisting of null, $R_L^d$-$R_L^e$, $R_L^dCOR_L^e$, $R_L^dC(O)OR_L^e$, $R_L^dC(O)N(R_L^1)R_L^e$, $R_L^dOR_L^e$, $R_L^dSR_L^e$, $R_L^dN(R_L^1)R_L^e$, $R_L^dN(R_L^1)COR_Lc$, $R_L^dN(R_L^1)CON(R_L^2)R_L^e$, $R_L^dN(R_L^1)SON(R_L^2)R_L^e$, and $R_L^dN(R_L^1)SO_2N(R_L^2)R_L^e$, wherein $R_L^d$ and $R_L^e$, at each occurrence, are independently selected from the group consisting of null, optionally substituted $C_1$, $C_2$ or $C_3$ alkylene, $R_L^r$, $R_L^r$—($C_1$, $C_2$ or $C_3$ alkylene), ($C_1$, $C_2$ or $C_3$ alkylene)-$R_L^r$, and ($C_1$, $C_2$ or $C_3$ alkylene)-$R_L^r$-($C_1$, $C_2$ or $C_3$ alkylene).

In another embodiment, $A_L$ and $B_L$, at each occurrence, are independently selected from the group consisting of null, $R_L^d$—$R_L^e$, $R_L^dCOR_L^e$, $R_L^dC(O)OR_L^e$, $R_L^dC(O)N(R_L^1)R_L^e$, $R_L^dOR_L^e$, $R_L^dSR_L^e$, $R_L^dN(R_L^1)R_L^e$, $R_L^dN(R_L^1)COR_L^e$, $R_L^dN(R_L^1)CON(R_L^2)R_L^e$, $R_L^dN(R_L^1)SON(R_L^2)R_L^e$, and $R_L^dN(R_L^1)SO_2N(R_L^2)R_L^e$, wherein $R_L^d$ and $R_L^e$, at each occurrence, are independently selected from the group consisting of null, $R_L^r$, and optionally substituted $C_1$, $C_2$ or $C_3$ alkylene.

In another embodiment, $W_L^1$ and $W_L^2$, at each occurrence, are independently selected from null, O, S, $NR_L^1$, $R_L^r$, optionally substituted $C_1$-$C_3$ alkylene, with the proviso that at least one of $W_L^1$ and $W_L^2$ is not null.

In another embodiment, none of $W_L^1$-$W_L^2$, $A_L$-$W_L^1$ and $W_L^2$—$B_L$ is a moiety of —O—O—.

In another embodiment, $W_L^2$, at each occurrence, is independently null, O, or $NR_L^1$; and $W_L^1$, at each occurrence, is independently selected from $R_L^r$, and optionally substituted $C_1$, $C_2$ or $C_3$ alkylene.

In another embodiment, $W_L^1$, at each occurrence, is independently null, O, or $NR_L^1$; and $W_L^2$, at each occurrence, is independently selected from $R_L^r$, and optionally substituted $C_1$, $C_2$ or $C_3$ alkylene.

In another embodiment, $A_L$ is the attachment to the MEK Ligand;
  $A_L$ is selected from the group consisting of $R_L^d$-$R_L^e$, $R_L^dC(O)R_L^e$, $R_L^dC(O)NHR_L^e$, $R_L^dNHC(O)R_Lc$, $R_L^dNHC(O)NHR_L^e$, $R_L^dN(R_L^1)SON(R_L^2)R_L^e$, and $R_L^dN(R_L^e)SO_2N(R_L^2)R_L^e$;
  $B_L$ is selected from the group consisting of null, $R_L^dC(O)NHR_L^e$, $R_L^dC(O)R_L^e$, $R_L^dNHC(O)R_L$, and $R_L^dNHR_L^e$, $R_L^dOR_L^1$, and $R_L^d$—$R_L^e$;
  $R_L^d$ and $R_L^e$, at each occurrence, are independently selected from the group consisting of null, optionally substituted $C_1$, $C_2$ or $C_3$ alkylene, $R_L^r$, $R_L^r$-($C_1$, $C_2$ or $C_3$ alkylene), ($C_1$, $C_2$ or $C_3$ alkylene)-$R_L^r$, and ($C_1$, $C_2$ or $C_3$ alkylene)-$R_L^r$-($C_1$, $C_2$ or $C_3$ alkylene);
  $W_L^2$, at each occurrence, is independently selected from null, O, or $NR_L^1$, and $W_L^1$, at each occurrence, is independently selected from $R_L^r$, and optionally substituted $C_1$, $C_2$ or $C_3$ alkylene.

In another embodiment, $A_L$ is the attachment to the MEK Ligand;
  $A_L$ is selected from the group consisting of $R_L^d$—$R_L^e$, $R_L^dC(O)R_L^e$, $R_L^dC(O)NHR_L^e$, $R_L^dNHC(O)R_L^e$, $R_L^dNHC(O)NHR_L^e$, $R_L^dN(R_L^1)SON(R_L^2)R_Lc$, and $R_L^dN(R_L^1)SO_2N(R_L^2)R_L^e$;
  $B_L$ is selected from the group consisting of null, $R_L^dC(O)NHR_Lc$, $R_L^dC(O)R_Lc$, $R_L^dNHC(O)R_Lc$, $R_L^dNHR_L^e$, $R_L^dOR_L^e$, and $R_L^d$-$R_L^e$;
  $R_L^d$ and $R_L^e$, at each occurrence, are independently selected from the group consisting of null, $R_L^r$, optionally substituted $C_1$, $C_2$ or $C_3$ alkylene;
  $W_L^2$ is O, or $NR_L^1$; and $W_L^1$, at each occurrence, is optionally independently selected from $R_L^r$, optionally substituted $C_1$, $C_2$ or $C_3$ alkylene;
  $m_L$ is 0, 1, 2, 3, 4, 5, 6, 7, 8, 9, 10, 11, 12, 13, 14, or 15.

In another refinement, the length of the Linker is 3 to 30 chain atoms.

In another refinement, the length of the Linker is 6 to 25 chain atoms.

In another embodiment, $R_L^r$, at each occurrence, is selected from FORMULAE C1, C2, C3, C4, and C5

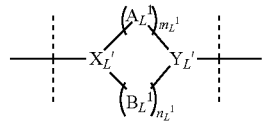

FORMULA C1

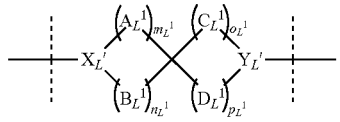

FORMULA C2

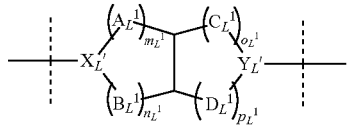

FORMULA C3

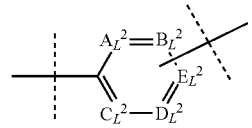

FORMULA C4

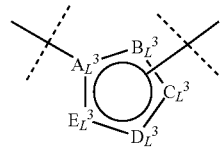

FORMULA C5 wherein $A_L^1$, $B_L^1$, $C_L^1$ and $D_L^1$, at each occurrence, are independently selected from the group consisting of null, O, CO, SO, $SO_2$, $NR_L^b$, $CR_L^bR_L^c$;

$X_L'$, $Y_L'$, $A_L^2$, $B_L^2$, $C_L^2$, $D_L^2$ and $E_L^2$, at each occurrence, are independently selected from N, $CR_L^b$;

$A_L^3$, $B_L^3$, $C_L^3$, $D_L^3$, and $E_L^3$, at each occurrence, are independently selected from N, O, S, $NR_L^b$, $CR_L^b$;

$R_L^b$ and $R_L^c$, at each occurrence, are independently selected from hydrogen, halogen, hydroxyl, amino, cyano, nitro, optionally substituted $C_1$-$C_8$alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl, optionally substituted $C_3$-$C_{10}$ carbocyclyl, optionally substituted $C_3$-$C_{10}$ cycloalkoxy, optionally substituted $C_3$-$C_{10}$ carbocyclylamino, optionally substituted 3-10 membered heterocyclyl, optionally substituted aryl, and optionally substituted heteroaryl; and $m_L^1$, $n_L^1$, $o_L^1$ and $p_L^1$ are independently selected from 0, 1, 2, 3, 4 and 5.

In another embodiment, $R_L^r$, at each occurrence, is selected from Group $R_L^{r1}$ and Group $R_L^{r2}$, and
Group $R_L^{r1}$ consists of optionally substituted following cyclic groups
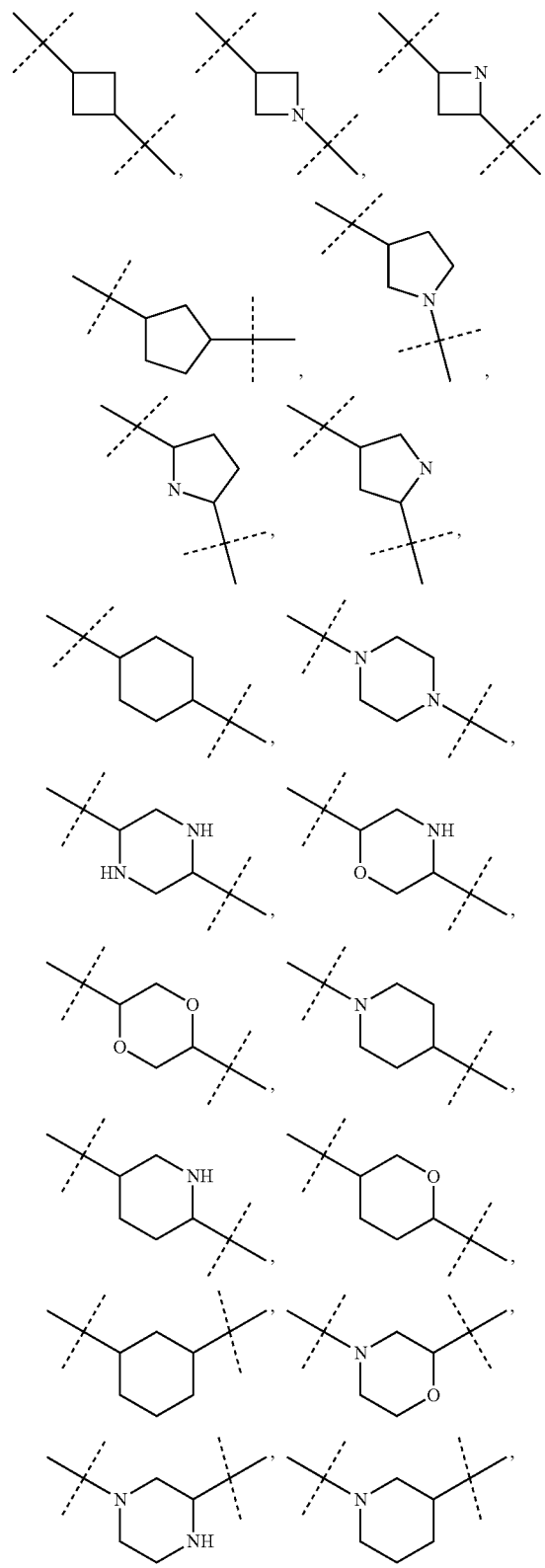
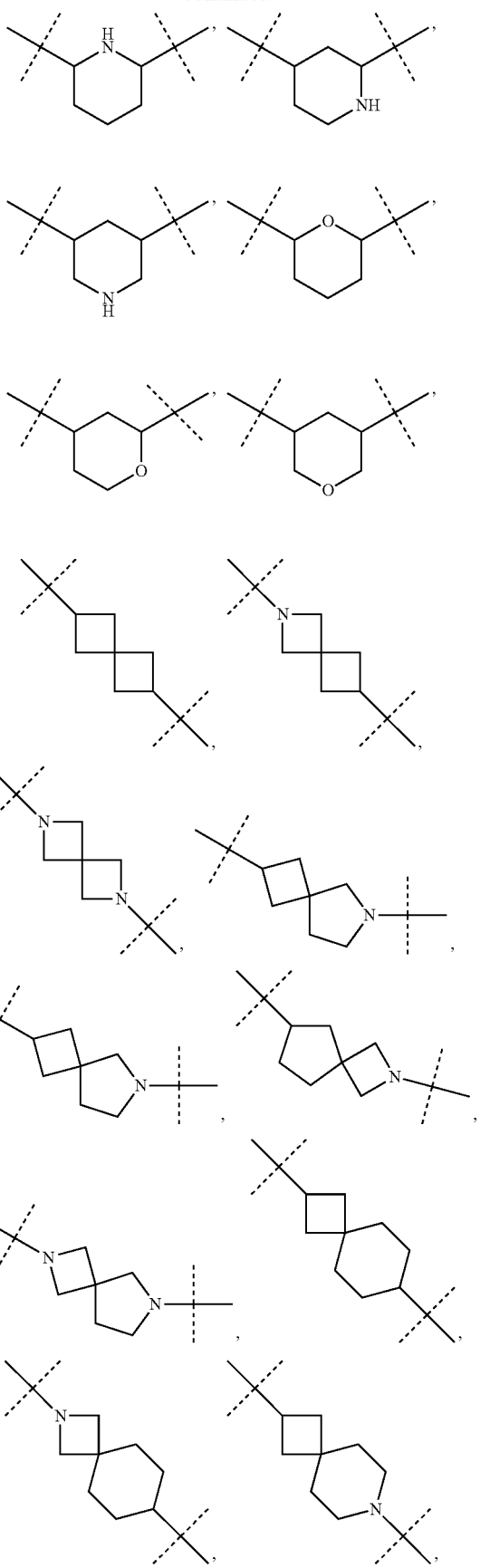

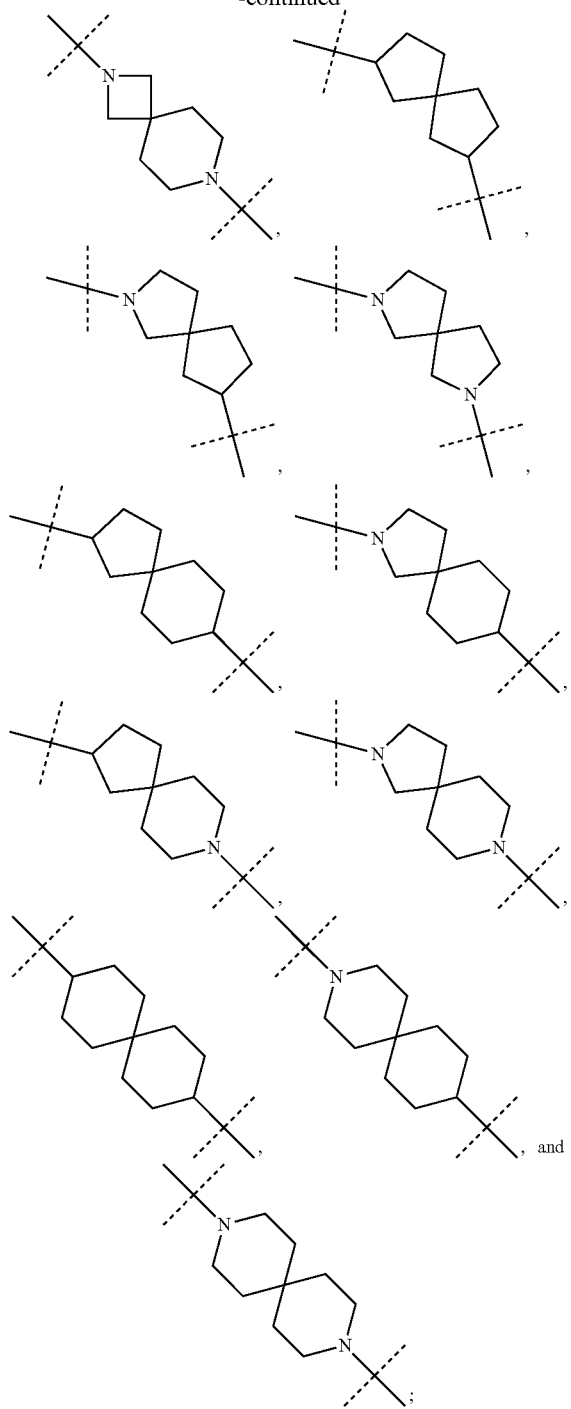
Group $R_L^{r2}$ consists of optionally substituted following cyclic groups
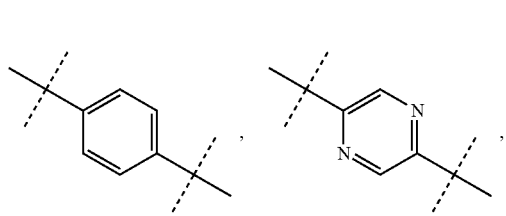
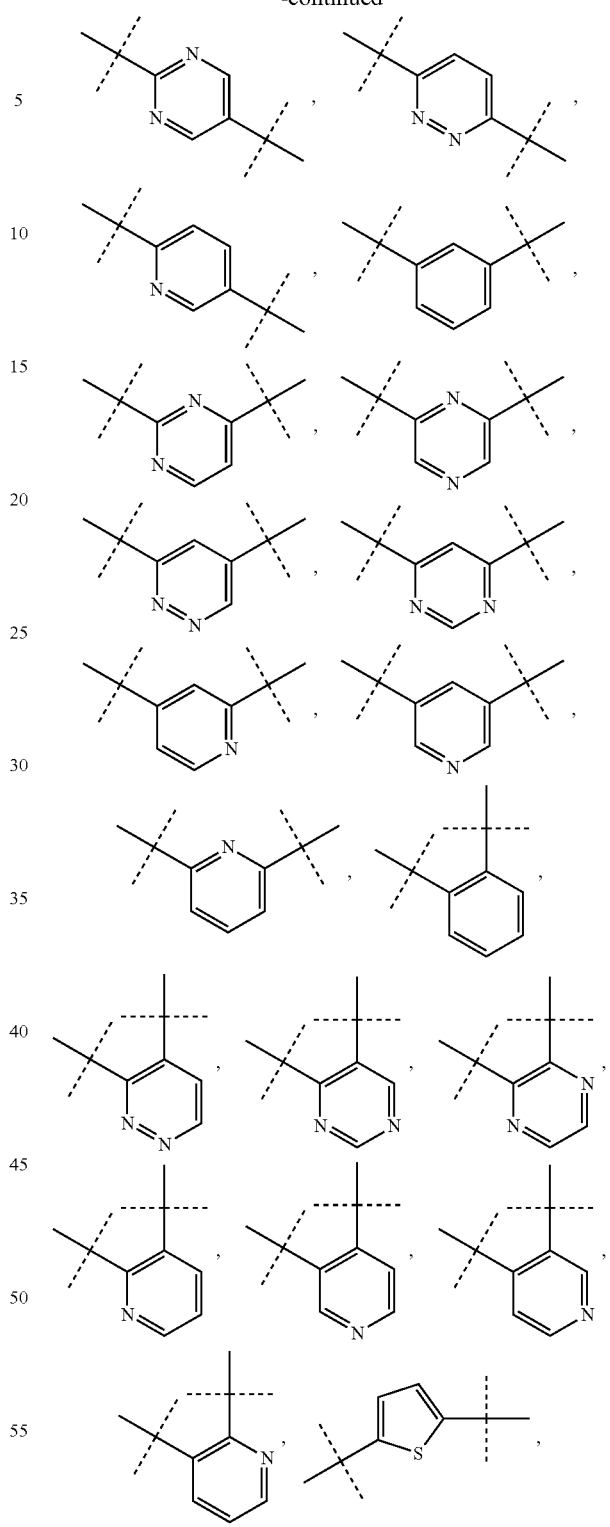
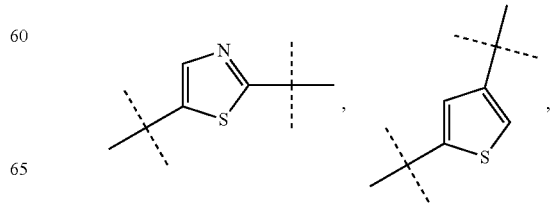

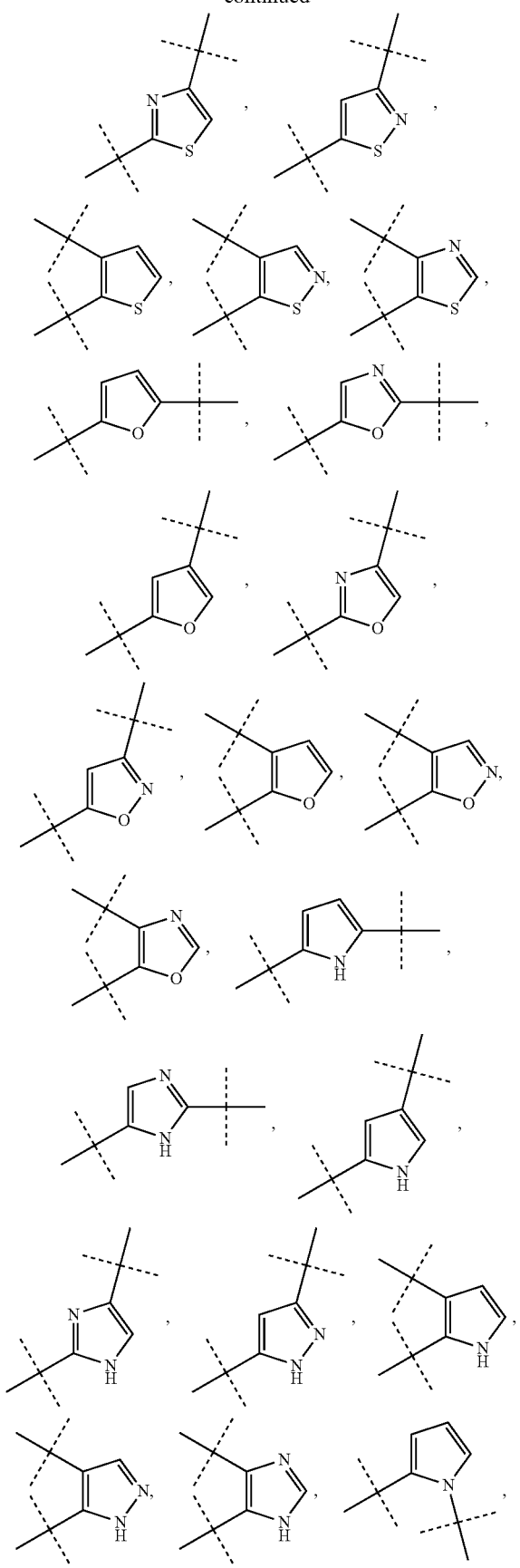

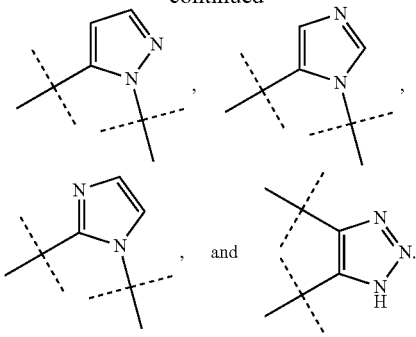

In one embodiment, the Linker moiety is of FORMULA 9A:

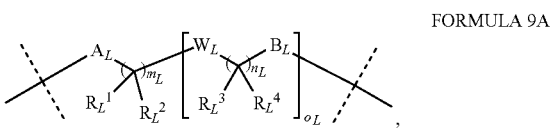

FORMULA 9A wherein $R_L^1$, $R_L^2$, $R_L^3$ and $R_L^4$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl, optionally substituted $C_3$-$C_{10}$ carbocyclyl, optionally substituted $C_3$-$C_{10}$ cycloalkoxy, optionally substituted $C_3$-$C_{10}$ carbocyclylamino, optionally substituted 3-10 membered heterocyclyl, optionally substituted aryl, and optionally substituted heteroaryl, or $R_L^1$ and $R_L^2$, $R_L^3$ and $R_L^4$ together with the atom(s) to which they are connected form a 3-20 membered cycloalkyl or 3-20 membered heterocyclyl ring;

$A_L$, $W_L$ and $B_L$, at each occurrence, are bivalent moieties independently selected from null, $R_L^d$-$R_L^e$, $R_L^dCOR_L^e$, $R_L^dC(O)OR_L^e$, $R_L^dC(O)N(R_L^5)R_L^e$, $R_L^dC(S)N(R_L^5)R_L^e$, $R_L^dOR_L^e$, $R_L^dSR_L^e$, $R_L^dSOR_L^e$, $R_L^dSO_2R_L^e$, $R_L^dSO_2N(R_L^5)R_L^e$, $R_L^dN(R_L^5)R_L^e$, $R_L^dN(R_L^5)COR_L^e$, $R_L^dN(R_L^5)CON(R_L^6)R_L^e$, $R_L^dN(R_L^1)SON(R_L^2)R_L^e$, $R_L^dN(R_L^1)SO_2N(R_L^2)R_L^e$, $R_L^dN(R_L^5)C(S)R_L^e$, optionally substituted $C_1$-$C_8$ alkylene, optionally substituted $C_2$-$C_5$ alkenylene, optionally substituted $C_2$-$C_8$ alkynylene, optionally substituted $C_1$-$C_8$alkoxy$C_1$-$C_8$alkylene, optionally substituted $C_1$-$C_8$ haloalkylene, optionally substituted $C_1$-$C_8$ hydroxyalkylene, optionally substituted $C_3$-$C_{13}$ carbocyclyl, optionally substituted 3-13 membered heterocyclyl, optionally substituted aryl, and optionally substituted heteroaryl, wherein $R_L^d$ and $R_L^e$, at each occurrence, are independently selected from null, optionally substituted $(C_1$-$C_8$ alkyl)-$R_L^r$, optionally substituted $R_L^r$—$(C_1$-$C_8$ alkylene), optionally substituted $(C_1$-$C_8$ alkylene)-$R_L^r$-$(C_1$-$C_8$ alkylene), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted $C_3$-$C_{13}$ carbocyclyl, optionally substituted 3-13 membered heterocyclyl, optionally substituted aryl, and optionally substituted heteroaryl;

$R_L^r$ is defined as in FORMULA 9;

$R_L^5$ and $R_L^6$, at each occurrence, are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_{10}$ carbocyclyl, optionally substituted 3-10 membered heterocyclyl, optionally substituted aryl, and optionally substituted heteroaryl;

$R_L^d$ and $R_L^e$, $R_L^5$ and $R_L^6$, $R_L^d$ and $R_L^5$, $R_L^d$ and $R_L^6$, $R_L^e$ and $R_L^5$, $R_L^e$ and $R_L^6$ together with the atom(s) to which they are connected form a 3-20 membered cycloalkyl or 3-20 membered heterocyclyl ring;

$m_L$ is 0, 1, 2, 3, 4, 5, 6, 7, 8, 9, 10, 11, 12, 13, 14, or 15;

$n_L$, at each occurrence, is 0, 1, 2, 3, 4, 5, 6, 7, 8, 9, 10, 11, 12, 13, 14, or 15; and $o_L$ is 0, 1, 2, 3, 4, 5, 6, 7, 8, 9, 10, 11, 12, 13, 14, or 15.

In another embodiment, the Linker moiety is of FORMULA 9B:

FORMULA 9B

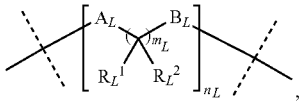

wherein $R_L^1$ and $R_L^2$, at each occurrence, are independently selected from hydrogen, halogen, hydroxyl, amino, cyano, nitro, and optionally substituted $C_1$-$C_8$ alkyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, $C_1$-$C_8$alkylamino$C_1$-$C_8$alkyl, optionally substituted $C_3$-$C_{10}$ carbocyclyl, optionally substituted $C_3$-$C_{10}$ cycloalkoxy, optionally substituted $C_3$-$C_{10}$ carbocyclylamino, optionally substituted 3-10 membered heterocyclyl, optionally substituted aryl, and optionally substituted heteroaryl, or $R_L^1$ and $R_L^2$ together with the atom(s) to which they are connected form a 3-20 membered cycloalkyl or 3-20 membered heterocyclyl ring;

$A_L$ and $B_L$, at each occurrence, are independently selected from null, or bivalent moiety selected from $R_L^d$-$R_L^e$, $R_L^d COR_L^e$, $R_L^d CO_2R_L^e$, $R_L^d C(O)N(R_L^3)R_L^e$, $R_L^d C(S)N(R_L^3)R_L^e$, $R_L^d OR_L^e$, $R_L^d SR_L^e$, $R_L^d SOR_L^e$, $R_L^d SO_2R_L^e$, $R_L^d SO_2N(R_L^3)R_L^e$, $R_L^d N(R_L^3)R_L^e$, $R_L^d N(R_L^3)COR_L^e$, $R_L^d N(R_L^3)CON(R_L^4)R_L^e$, $R_L^d N(R_L^1)SON(R_L^2)R_L^e$, $R_L^d N(R_L^1)SO_2N(R_L^2)R_L^e$, $R_L^d N(R_L^3)C(S)R_L^e$, optionally substituted $C_1$-$C_8$ alkylene, optionally substituted $C_2$-$C_8$ alkenylene, optionally substituted $C_2$-$C_8$ alkynylene, optionally substituted $C_1$-$C_8$alkoxy$C_1$-$C_8$alkylene, optionally substituted $C_1$-$C_8$ haloalkylene, optionally substituted $C_1$-$C_8$ hydroxyalkylene, optionally substituted $C_3$-$C_{13}$ carbocyclyl, optionally substituted 3-13 membered heterocyclyl, optionally substituted aryl, and optionally substituted heteroaryl, wherein $R_L^d$ and $R_L^e$, at each occurrence, are independently selected from null, optionally substituted ($C_1$-$C_8$ alkylene)-$R_L^r$, optionally substituted $R_L^r$—($C_1$-$C_8$ alkylene), optionally substituted ($C_1$-$C_8$ alkylene)-$R_L^r$, ($C_1$-$C_8$ alkylene), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_5$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted $C_3$-$C_{13}$ carbocyclyl, optionally substituted 3-13 membered heterocyclyl, optionally substituted aryl, and optionally substituted heteroaryl;

$R_L^r$ is defined as in FORMULA 9;

$R_L^3$ and $R_L^4$, at each occurrence, are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_{10}$ carbocyclyl, optionally substituted 3-10 membered heterocyclyl, optionally substituted aryl, and optionally substituted heteroaryl;

$R_L^d$ and $R_L^e$, $R_L^3$ and $R_L^4$, $R_L^d$ and $R_L^3$, $R_L^d$ and $R_L^4$, $R_L^e$ and $R_L^3$, $R_L^e$ and $R_L^4$ together with the atom(s) to which they are connected form a 3-20 membered cycloalkyl or 3-20 membered heterocyclyl ring;

each $m_L$ is 0, 1, 2, 3, 4, 5, 6, 7, 8, 9, 10, 11, 12, 13, 14, or 15; and $n_L$ is 0, 1, 2, 3, 4, 5, 6, 7, 8, 9, 10, 11, 12, 13, 14, or 15.

In another embodiment, the Linker moiety is of FORMULA 9C:

FORMULA 9C

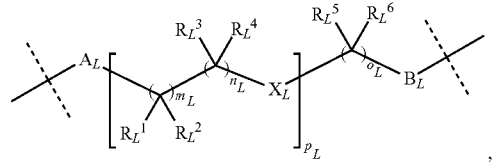

wherein $X_L$, at each occurrence, is selected from O and $NR_L^7$;

$R_L^1$, $R_L^2$, $R_L^3$, $R_L^4$, $R_L^5$, and $R_L^6$, at each occurrence, are independently selected from the group consisting of hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, optionally substituted $C_1$-$C_8$ alkylamino$C_1$-$C_8$ alkyl, optionally substituted $C_3$-$C_{10}$ carbocyclyl, optionally substituted $C_3$-$C_{10}$ cycloalkoxy, optionally substituted 3-10 membered heterocyclyl, optionally substituted aryl, and optionally substituted heteroaryl;

$A_L$ and $B_L$, at each occurrence, are independently selected from null, or bivalent moiety selected from $R_L^d$-$R_L^e$, $R_L^d COR_L^e$, $R_L^d CO_2 R_L^e$, $R_L^d C(O)N(R_L^5)R_L^e$, $R_L^d C(S)N(R_L^8)R_L^e$, $R_L^d OR_L^e$, $R_L^d SR_L^e$, $R_L^d SOR_L^e$, $R_L^d SO_2 R_L^e$, $R_L^d SO_2 N(R_L^8)R_L^e$, $R_L^d N(R_L^5)R_L^e$, $R_L^d N(R_L^8)COR_L^e$, $R_L^d N(R_L^8)CON(R_L^9)R_L^e$, $R_L^d N(R_L^1)SON(R_L^2)R_L^e$, $R_L^d N(R_L^1)SO_2N(R_L^2)R_L^e$, $R_L^d N(R_L^8)C(S)R_L^e$, optionally substituted $C_1$-$C_8$ alkylene, optionally substituted $C_2$-$C_8$ alkenylene, optionally substituted $C_2$-$C_8$ alkynylene, optionally substituted $C_1$-$C_8$alkoxy$C_1$-$C_8$alkylene, optionally substituted $C_1$-$C_8$ haloalkylene, optionally substituted $C_1$-$C_8$ hydroxyalkylene, optionally substituted 4-13 membered fused cycloalkyl, optionally substituted 5-13 membered fused heterocyclyl, optionally substituted 5-13 membered bridged cycloalkyl, optionally substituted 5-13 membered bridged heterocyclyl, optionally substituted 5-13 membered spiro cycloalkyl, optionally substituted 5-13 membered spiro heterocyclyl, optionally substituted $C_3$-$C_{10}$ carbocyclyl, optionally substituted 3-10 membered heterocyclyl, optionally substituted aryl, and optionally substituted heteroaryl, wherein $R_L^d$ and $R_L^e$, at each occurrence, are independently selected from null, optionally substituted ($C_1$-$C_8$ alkylene)-$R_L^r$, optionally substituted $R_L^r$—($C_1$-$C_8$ alkylene), optionally substituted ($C_1$-$C_8$ alkylene)-$R_L^r$-($C_1$-$C_8$ alkylene), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted $C_3$-$C_{13}$ carbocyclyl, optionally substituted 3-13 membered heterocyclyl, optionally substituted aryl, and optionally substituted heteroaryl;

$R_L^r$ is defined as in FORMULA 9;

$R_L^7$, $R_L^8$ and $R_L^9$, at each occurrence, are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_{10}$ carbocyclyl, optionally substituted 3-10 membered heterocyclyl, optionally substituted aryl, and optionally substituted heteroaryl;

$R_L^d$ and $R_L^e$, $R_L^5$ and $R_L^9$, $R_L^d$ and $R_L^5$, $R_L^d$ and $R_L^9$, $R_L^e$ and $R_L^8$, $R_L^e$ and $R_L^9$ together with the atom(s) to which they are connected form a 3-20 membered cycloalkyl or 3-20 membered heterocyclyl ring;

$m_L$, at each occurrence, is 0, 1, 2, 3, 4, 5, 6, 7, 8, 9, 10, 11, 12, 13, 14, or 15;

$n_L$, at each occurrence, is 0, 1, 2, 3, 4, 5, 6, 7, 8, 9, 10, 11, 12, 13, 14, or 15;

$o_L$ is 0, 1, 2, 3, 4, 5, 6, 7, 8, 9, 10, 11, 12, 13, 14, or 15; and $p_L$ is 0, 1, 2, 3, 4, 5, 6, 7, 8, 9, 10, 11, 12, 13, 14, or 15.

In another refinement, the length of the Linker is 3 to 30 chain atoms.

In another refinement, the length of the Linker is 6 to 25 chain atoms.

Without wishing to be bound by any particular theory, it is contemplated herein that, in some embodiments, attaching VHL-1 or pomalidomide to either portion of the molecule can recruit the VHL E3 ligase or cereblon E3 ligase to MEK.

The heterobifunctional compounds disclosed herein can selectively affect MEK-mediated disease cells compared to WT (wild type) cells (i.e., an heterobifunctional compound able to kill or inhibit the growth of an MEK-mediated disease cell while also having a relatively low ability to lyse or inhibit the growth of a WT cell), e.g., possess a $GI_{50}$ for one or more MEK-mediated disease cells more than 1.5-fold lower, more than 2-fold lower, more than 2.5-fold lower, more than 3-fold lower, more than 4-fold lower, more than 5-fold lower, more than 6-fold lower, more than 7-fold lower, more than 8-fold lower, more than 9-fold lower, more than 10-fold lower, more than 15-fold lower, or more than 20-fold lower than its $GI_{50}$ for one or more WT cells, e.g., WT cells of the same species and tissue type as the MEK-mediated disease cells.

In some aspects, provided herein is a method for identifying a heterobifunctional compound which mediates degradation or reduction of MEK, the method comprising: providing a heterobifunctional test compound comprising an MEK Ligand conjugated to a Degradation Tag through a Linker; contacting the heterobifunctional test compound with a cell comprising a ubiquitin ligase and MEK; determining whether MEK level is decreased in the cell; and identifying the heterobifunctional test compound as a heterobifunctional compound which mediates degradation or reduction of MEK. In certain embodiments, the cell is a cancer cell. In certain embodiments, the cancer cell is a MEK-mediated cancer cell.

Synthesis and Testing of Heterobifunctional Compounds

The binding affinity of novel synthesized heterobifunctional compounds can be assessed using standard biophysical assays known in the art (e.g., isothermal titration calorimetry (ITC), surface plasmon resonance (SPR)). Cellular assays can then be used to assess the heterobifunctional compound's ability to induce MEK degradation and inhibit cancer cell proliferation. Besides evaluating a heterobifunctional compound's induced changes in the protein levels of MEK, MEK mutants, MEK deletions, or MEK fusion proteins, protein-protein interaction or kinase enzymatic activity can also be assessed. Assays suitable for use in any or all of these steps are known in the art, and include, e.g., western blotting, quantitative mass spectrometry (MS) analysis, flow cytometry, enzymatic activity assay, ITC, SPR, cell growth inhibition, xenograft, orthotopic, and patient-derived xenograft models. Suitable cell lines for use in any or all of these steps are known in the art and include HT-29 and SK-MEL-28 cells. Suitable mouse models for use in any or all of these steps are known in the art and include subcutaneous xenograft models, orthotopic models, patient-derived xenograft models, and patient-derived orthotopic models.

By way of non-limiting example, detailed synthesis protocols are described in the Examples for specific exemplary heterobifunctional compounds.

Pharmaceutically acceptable isotopic variations of the compounds disclosed herein are contemplated and can be synthesized using conventional methods known in the art or methods corresponding to those described in the Examples (substituting appropriate reagents with appropriate isotopic variations of those reagents). Specifically, an isotopic variation is a compound in which at least one atom is replaced by an atom having the same atomic number, but an atomic mass different from the atomic mass usually found in nature. Useful isotopes are known in the art and include, for example, isotopes of hydrogen, carbon, nitrogen, oxygen, phosphorus, sulfur, fluorine, and chlorine. Exemplary isotopes thus include, e.g., $^2H$, $^3H$, $^{13}C$, $^{14}C$, $^{15}N$, $^{17}O$, $^{18}O$, $^{32}P$, $^{35}S$, $^{18}F$, and $^{36}Cl$.

Isotopic variations (e.g., isotopic variations containing $^2H$) can provide therapeutic advantages resulting from greater metabolic stability, e.g., increased in vivo half-life or reduced dosage requirements. In addition, certain isotopic variations (particularly those containing a radioactive isotope) can be used in drug or substrate tissue distribution studies. The radioactive isotopes tritium ($^3H$) and carbon-14 ($^{14}C$) are particularly useful for this purpose in view of their ease of incorporation and ready means of detection.

Pharmaceutically acceptable solvates of the compounds disclosed herein are contemplated. A solvate can be generated, e.g., by substituting a solvent used to crystallize a compound disclosed herein with an isotopic variation (e.g., $D_2O$ in place of $H_2O$, $d_6$-acetone in place of acetone, or $d_6$-DMSO in place of DMSO).

Pharmaceutically acceptable fluorinated variations of the compounds disclosed herein are contemplated and can be synthesized using conventional methods known in the art or methods corresponding to those described in the Examples (substituting appropriate reagents with appropriate fluorinated variations of those reagents). Specifically, a fluorinated variation is a compound in which at least one hydrogen atom is replaced by a fluoro atom. Fluorinated variations can provide therapeutic advantages resulting from greater metabolic stability, e.g., increased in vivo half-life or reduced dosage requirements.

Pharmaceutically acceptable prodrugs of the compounds disclosed herein are contemplated and can be synthesized using conventional methods known in the art or methods corresponding to those described in the Examples (e.g., converting hydroxyl groups or carboxylic acid groups to ester groups). As used herein, a "prodrug" refers to a compound that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

Definition of Terms

As used herein, the terms "comprising" and "including" are used in their open, non-limiting sense.

As used herein, the term "heterobifunctional compound(s)" and "bivalent compound(s)" can be used interchangeably.

As used herein, the terms "Tyrosine Kinase 2 ligand" and "MEK ligand", or "MEK targeting moiety" are to be construed to encompass any molecules ranging from small molecules to large proteins that associate with or bind to MEK proteins. The MEK ligand is capable of binding to a MEK protein comprising MEK, a MEK mutant, a MEK deletion, or a MEK fusion protein. The MEK ligand can be, for example but not limited to, a small molecule compound (i.e., a molecule of molecular weight less than about 1.5 kilodaltons (kDa)), a peptide or polypeptide, nucleic acid or oligonucleotide, carbohydrate such as oligosaccharides, or an antibody or fragment thereof.

"Alkyl" refers to a straight or branched hydrocarbon chain radical consisting solely of carbon and hydrogen atoms, containing no unsaturation. An alkyl may comprise one, two, three, four, five, six, seven, eight, nine, ten, eleven, twelve, thirteen, fourteen, fifteen, or sixteen carbon atoms. In certain embodiments, an alkyl comprises one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl (nPr), 1-methylethyl (iso-propyl, iPr), n-butyl, n-pentyl, 1,1-dimethylethyl (t-butyl), pentyl, 3-methylhexyl, 2-methylhexyl, and the like.

"Alkenyl" refers to a straight or branched hydrocarbon chain radical group consisting solely of carbon and hydrogen atoms, containing at least one double bond. An alkenyl may comprise two, three, four, five, six, seven, eight, nine, ten, eleven, twelve, thirteen, fourteen, fifteen, or sixteen carbon atoms. In certain embodiments, an alkenyl comprises two to twelve carbon atoms (e.g., $C_2$-$C_{12}$ alkenyl). In certain embodiments, an alkenyl comprises two to eight carbon atoms (e.g., $C_2$-$C_8$ alkenyl). In certain embodiments, an alkenyl comprises two to six carbon atoms (e.g., $C_2$-$C_6$ alkenyl). In other embodiments, an alkenyl comprises two to four carbon atoms (e.g., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

The term "allyl," as used herein, means a —$CH_2CH=CH_2$ group.

As used herein, the term "alkynyl" refers to a straight or branched hydrocarbon chain radical group consisting solely of carbon and hydrogen atoms, containing at least one triple bond. An alkynyl may comprise two, three, four, five, six, seven, eight, nine, ten, eleven, twelve, thirteen, fourteen, fifteen, or sixteen carbon atoms. In certain embodiments, an alkynyl comprises two to twelve carbon atoms (e.g., $C_2$-$C_{12}$ alkynyl). In certain embodiments, an alkynyl comprises two to eight carbon atoms (e.g., $C_2$-$C_8$ alkynyl). In other embodiments, an alkynyl has two to six carbon atoms (e.g., $C_2$-$C_6$ alkynyl). In other embodiments, an alkynyl has two to four carbon atoms (e.g., $C_2$-$C_4$ alkynyl). The alkynyl is attached to the rest of the molecule by a single bond. Examples of such groups include, but are not limited to, ethynyl, propynyl, 1-butynyl, 2-butynyl, 1-pentynyl, 2-pentynyl, 1-hexynyl, 2-hexynyl, 3-hexynyl, and the like.

The term "alkoxy", as used herein, means an alkyl group as defined herein which is attached to the rest of the molecule via an oxygen atom. Examples of such groups include, but are not limited to, methoxy, ethoxy, n-propyloxy, iso-propyloxy, n-butoxy, iso-butoxy, tert-butoxy, pentyloxy, hexyloxy, and the like.

The term "aryl", as used herein, "refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon atoms. An aryl may comprise from six to eighteen carbon atoms, where at least one of the rings in the ring system is fully unsaturated, i.e., it contains a cyclic, delocalized (4n+2) π-electron system in accordance with the Hückel theory. In certain embodiments, an aryl comprises six to fourteen carbon atoms ($C_6$-$C_{14}$ aryl or 6-14 membered aryl). In certain embodiments, an aryl comprises six to ten carbon atoms ($C_6$-$C_{10}$ aryl or 6-10 membered aryl). Examples of such groups include, but are not limited to, phenyl, fluorenyl and naphthyl. The terms "Ph" and "phenyl," as used herein, mean a —$C_6H_5$ group.

The term "heteroaryl", refers to a radical derived from a 3- to 18-membered aromatic ring radical (i.e. 3-18 membered heteroaryl) that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. In certain embodiments, a heteroaryl refers to a radical derived from a 3- to 10-membered aromatic ring radical (3-10 membered heteroaryl). In certain embodiments, a heteroaryl refers to a radical derived from 5- to 7-membered aromatic ring (5-7 membered heteroaryl). Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of such groups include, but not limited to, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. In certain embodiments, a heteroaryl is attached to the rest of the molecule via a ring carbon atom. In certain embodiments, an heteroaryl is attached to the rest of the molecule via a nitrogen atom (N-attached) or a carbon atom (C-attached). For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

The term "heterocyclyl", as used herein, means a non-aromatic, monocyclic, bicyclic, tricyclic, or tetracyclic radical having a total of from 4, 5, 6, 7, 8, 9, 10, 11, 12, 13, 14, 15, or 16 atoms in its ring system, and containing from 3 to 12 (such as 3, 4, 5, 6, 7, 8, 9, 10, 11, or 12) carbon atoms and from 1 to 4 (such as 1, 2. 3 or 4) heteroatoms each independently selected from O, S and N, and with the proviso that the ring of said group does not contain two adjacent O atoms or two adjacent S atoms. A heterocyclyl group may include fused, bridged or spirocyclic ring systems. In certain embodiments, a heterocyclyl group comprises 3 to 10 ring atoms (3-10 membered heterocyclyl). In certain embodiments, a heterocyclyl group comprises 3 to 8 ring atoms (3-8 membered heterocyclyl). In certain embodiments, a heterocyclyl group comprises 3 to 10 ring atoms (3-10 membered heterocyclyl). In certain embodiments, a heterocyclyl group comprises 3 to 8 ring atoms (3-8 membered heterocyclyl). A heterocyclyl group may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a heterocyclyl group contains a sulfur atom, said sulfur atom may be oxidized with one or two oxygen atoms to afford either a sulfoxide or sulfone. An example of a 4 membered heterocyclyl group is azetidinyl (derived from azetidine). An example of a 5 membered cycloheteroalkyl group is pyrrolidinyl. An example of a 6 membered cycloheteroalkyl group is piperidinyl. An example of a 9 membered cycloheteroalkyl group is indolinyl. An example of a 10 membered cycloheteroalkyl group is 4H-quinolizinyl. Further examples of such heterocyclyl groups include, but are not limited to, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, 3-oxopiperazinyl, 4-methylpiperazinyl, 4-ethylpiperazinyl, and 1-oxo-2,8,diazaspiro[4.5]dec-8-yl. A heteroaryl group may be attached to the rest of molecular via a carbon atom (C-attached) or a nitrogen atom (N-attached). For instance, a group derived from piperazine may be piperazin-1-yl (N-attached) or piperazin-2-yl (C-attached).

The term "cycloalkyl" or "carbocyclyl" means a saturated, monocyclic, bicyclic, tricyclic, or tetracyclic radical having a total of from 3, 4, 5, 6, 7, 8, 9, 10, 11, 12, or 13 carbon atoms in its ring system. A cycloalkyl may be fused, bridged or spirocyclic. In certain embodiments, a cycloalkyl comprises 3 to 8 carbon ring atoms (3-8 membered or $C_3$-$C_8$carbocyclyl). In certain embodiments, a cycloalkyl comprises 3 to 10 carbon ring atoms ($C_3$-$C_{10}$ cycloalkyl). Examples of such groups include, but are not limited to, cyclopropyl(cPr), cyclobutyl, cyclopentyl, cyclopentenyl, cyclohexyl, cycloheptyl, adamantyl, and the like.

The term "spirocyclic" as used herein has its conventional meaning, that is, any ring system containing two or more rings wherein two of the rings have one ring carbon in common. Each ring of the spirocyclic ring system, as herein defined, independently comprises 3 to 20 ring atoms. Preferably, they have 3 to 10 ring atoms. Non-limiting examples of a spirocyclic system include spiro[3.3]heptane, spiro[3.4]octane, and spiro[4.5]decane.

The term cyano" refers to a —C≡N group.

An "aldehyde" group refers to a —C(O)H group.

An "alkoxy" group refers to both an —O-alkyl, as defined herein.

An "alkoxycarbonyl" refers to a —C(O)-alkoxy, as defined herein.

An "alkylaminoalkyl" group refers to an -alkyl-NR-alkyl group, as defined herein.

An "alkylsulfonyl" group refer to a —SO$_2$alkyl, as defined herein.

An "amino" group refers to an optionally substituted —NH$_2$.

An "aminoalkyl" group refers to an -alkyl-amino group (such as —CH$_2$(NH$_2$)), as defined herein.

An "alkylamino" group refers to an -amino-alkyl group (such as —NH(CH$_3$)), as defined herein.

An "cycloalkylamino" group refers to an -amino-cycloalkyl group (such as

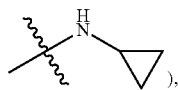

), as defined herein.

An "aminocarbonyl" refers to a —C(O)-amino, as defined herein.

An "arylalkyl" group refers to -alkylaryl, where alkyl and aryl are defined herein.

An "aryloxy" group refers to both an —O-aryl and an —O-heteroaryl group, as defined herein.

An "aryloxycarbonyl" refers to —C(O)-aryloxy, as defined herein.

An "arylsulfonyl" group refers to a —SO$_2$aryl, as defined herein.

A "carbonyl" group refers to a —C(O)— group, as defined herein.

A "carboxylic acid" group refers to a —C(O)OH group.

A "cycloalkoxy" refers to a —O-cycloalkyl group, as defined herein.

A "halo" or "halogen" group refers to fluorine, chlorine, bromine or iodine.

A "haloalkyl" group refers to an alkyl group substituted with one or more halogen atoms.

A "hydroxy" group refers to an —OH group.

A "nitro" group refers to a —NO$_2$ group.

An "oxo" group refers to the =O substituent.

A "trihalomethyl" group refers to a methyl substituted with three halogen atoms.

The term "alkylene" is a bidentate radical obtained by removing a hydrogen atom from a alkyl group as defined above. Examples of such groups include, but are not limited to, —CH$_2$—, —CH$_2$CH$_2$—, etc. The term "cycloalkylene" or "carbocyclylene" is a bidentate radical obtained by removing a hydrogen atom from a cycloalkyl ring as defined above. Examples of such groups include, but are not limited to, cyclopropylene, cyclobutylene, cyclopentylene, cyclopentenylene, cyclohexylene, cycloheptylene, and the like. Similarly, the terms "alkenylene", "alkynylene", "alkoxyalkylene", "haloalkylene", "hydroxyalkylene", "aminoalkylene", "alkylaminoalkylene", and "heterocyclylene" are bidentate radicals obtained by removing a hydrogen atom from an alkenyl radical, an alkynyl radical, an alkoxyalkyl radical, a haloalkyl radical, an hydroxyalkylene", "aminoalkyl radical, and an alkylaminoalkyl radical, respectively.

The term "length" when refers to a moiety means the smallest number of carbon and/or hetero atoms from one end to the other end of the moiety. When it refers to the Linker, it means the smallest number of atoms from the end connects to the MEK ligand and the end connects to the Degradation Tag. It applies to both situations where the Linker is linear or branched, and where the Linker comprises a ring system.

The term "substituted", unless otherwise stated, means that the specified group or moiety bears one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$—$C_4$ alkyl, —O$C_1$—$C_4$ alkylphenyl, —$C_1$-$C_4$ alkyl-OH, —O$C_1$—$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo, —CO$_2$H, —C(O)O$C_1$—$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The term "null" means the absence of an atom or moiety, and there is a bond between adjacent atoms in the structure.

The term "optionally substituted" means that the specified group may be either unsubstituted or substituted by one or more substituents as defined herein. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a C$_6$ aryl group, also called "phenyl" herein, is substituted with one additional substituent, one of ordinary skill in the art would understand that such a group has 4 open positions left on carbon atoms of the C$_6$ aryl ring (6 initial positions, minus one at which the remainder of the compound of the present invention is attached to and an additional substituent, remaining 4 positions open). In such cases, the remaining 4 carbon atoms are each bound to one hydrogen atom to fill their valencies. Similarly, if a C$_6$ aryl group in the present compounds is said to be "disubstituted," one of ordinary skill in the art would understand it to mean that the C$_6$ aryl has 3 carbon atoms remaining that are unsubstituted. Those three unsubstituted carbon atoms are each bound to one hydrogen atom to fill their valencies. Unless otherwise specified, an optionally substituted radical may be a radical unsubstituted or substituted with one or more substituents selected from halogen, CN, NO$_2$, OR'", SR$^1$, NR"R°, COR'", CO$_2$R'", CONR"R°, SOR'", SO$_2$R'", SO$_2$NR"R°, NR"COR°, NR'"C(O)NR"R°, NR"SOR°, NR$_n$SO$_2$R°, $C_1$-$C_8$ alkyl, $C_1$-$C_8$alkoxy$C_1$-$C_8$alkyl, $C_1$-$C_8$ haloalkyl, $C_1$-$C_8$ hydroxyalkyl, $C_1$-$C_8$alkylamino$C_1$-$C_5$ alkyl, $C_3$-$C_7$ cycloalkyl, 3-7 membered heterocyclyl, $C_2$-$C_8$ alkenyl, $C_2$-$C_8$ alkynyl, aryl, and heteroaryl, wherein R'", R", and R° are independently selected from null, hydrogen, $C_1$-$C_8$ alkyl, $C_2$-$C_8$ alkenyl, $C_2$-$C_8$ alkynyl, $C_3$-$C_7$ cycloalkyl, 3-7 membered heterocyclyl, aryl, and heteroaryl, or $R''$ and $R^\circ$ together with the atom to which they are connected form a 3-8 membered cycloalkyl or heterocyclyl ring.

As used herein, the same symbol in different FORMULA means different definition, for example, the definition of R1 in FORMULA 1 is as defined with respect to FORMULA 1 and the definition of R1 in FORMULA 6 is as defined with respect to FORMULA 6.

As used herein, each unit in the Linker moiety (e.g., —($W_L^1$-$W_L^2$)—,

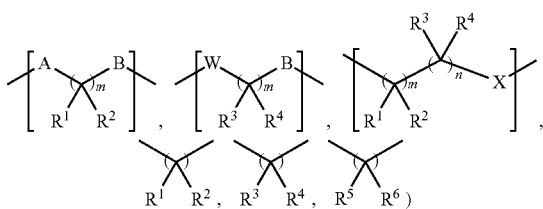

can be the same as or different from each other. In certain embodiments, each unit in the Linker moiety is the same as each other.

As used herein, when m (or n or o or p) is defined by a range, for example, "m is 0 to 15" or "m=0-3" mean that m is an integer from 0 to 15 (i.e. m is 0, 1, 2, 3, 4, 5, 6, 7, 8, 9, 10, 11, 12, 13, 14, or 15) or m is an integer from 0 to 3 (i.e. m is 0, 1, 2, or 3) or is any integer in the defined range.

"Pharmaceutically acceptable salt" includes both acid and base addition salts. A pharmaceutically acceptable salt of any one of the heterobifunctional compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

Pharmaceutical Compositions

In some aspects, the compositions and methods described herein include the manufacture and use of pharmaceutical compositions and medicaments that include one or more heterobifunctional compounds as disclosed herein. Also included are the pharmaceutical compositions themselves.

In some aspects, the compositions disclosed herein can include other compounds, drugs, or agents used for the treatment of cancer. For example, in some instances, pharmaceutical compositions disclosed herein can be combined with one or more (e.g., one, two, three, four, five, or less than ten) compounds. Such additional compounds can include, e.g., conventional chemotherapeutic agents or any other cancer treatment known in the art. When co-administered, heterobifunctional compounds disclosed herein can operate in conjunction with conventional chemotherapeutic agents or any other cancer treatment known in the art to produce mechanistically additive or synergistic therapeutic effects.

In some aspects, the pH of the compositions disclosed herein can be adjusted with pharmaceutically acceptable acids, bases, or buffers to enhance the stability of the heterobifunctional compound or its delivery form.

Pharmaceutical compositions typically include a pharmaceutically acceptable excipient, adjuvant, or vehicle. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human. A pharmaceutically acceptable excipient, adjuvant, or vehicle is a substance that can be administered to a patient, together with a compound of the invention, and which does not compromise the pharmacological activity thereof and is nontoxic when administered in doses sufficient to deliver a therapeutic amount of the compound. Exemplary conventional nontoxic pharmaceutically acceptable excipients, adjuvants, and vehicles include, but not limited to, saline, solvents, dispersion media, coatings, antibacterial and antifungal agents, isotonic and absorption delaying agents, and the like, compatible with pharmaceutical administration.

In particular, pharmaceutically acceptable excipients, adjuvants, and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

Depending on the dosage form selected to deliver the heterobifunctional compounds disclosed herein, different pharmaceutically acceptable excipients, adjuvants, and vehicles may be used. In the case of tablets for oral use, pharmaceutically acceptable excipients, adjuvants, and vehicles may be used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient may be suspended or dissolved in an oily phase is combined with emulsifying or suspending agents. If desired, certain sweetening, flavoring, or coloring agents can be added.

As used herein, the heterobifunctional compounds disclosed herein are defined to include pharmaceutically acceptable derivatives or prodrugs thereof. A "pharmaceutically acceptable derivative" means any pharmaceutically acceptable salt, solvate, or prodrug, e.g., carbamate, ester, phosphate ester, salt of an ester, or other derivative of a compound or agent disclosed herein, which upon administration to a recipient is capable of providing (directly or indirectly) a compound described herein, or an active metabolite or residue thereof. Particularly favored derivatives and prodrugs are those that increase the bioavailability of the compounds disclosed herein when such compounds are administered to a subject (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to the structure of formulae described herein. Such derivatives are recognizable to those skilled in the art without undue experimentation. Nevertheless, reference is made to the teaching of Burger's Medicinal Chemistry and Drug Discovery, 5$^{th}$ Edition, Vol. 1: Principles and Practice, which is incorporated herein by reference to the extent of teaching such derivatives.

The heterobifunctional compounds disclosed herein include pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, morphological forms, or deuterated derivatives thereof.

In some aspects, the pharmaceutical compositions disclosed herein can include an effective amount of one or more heterobifunctional compounds. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment or prevention of cell growth, cell proliferation, or cancer). In some aspects, pharmaceutical compositions can further include one or more additional compounds, drugs, or agents used for the treatment of cancer (e.g., conventional chemotherapeutic agents) in amounts effective for causing an intended effect or physiological outcome (e.g., treatment or prevention of cell growth, cell proliferation, or cancer).

In some aspects, the pharmaceutical compositions disclosed herein can be formulated for sale in the United States, import into the United States, or export from the United States.

Administration of Pharmaceutical Compositions

The pharmaceutical compositions disclosed herein can be formulated or adapted for administration to a subject via any route, e.g., any route approved by the Food and Drug Administration (FDA). Exemplary methods are described in the FDA Data Standards Manual (DSM) (available at http://www.fda.gov/Drugs/DevelopmentApprovalProcess/Forms-SubmissionRequirements/ElectronicSubmissions/DataStandardsManualmonographs). In particular, the pharmaceutical compositions can be formulated for and administered via oral, parenteral, or transdermal delivery. The term "parenteral" as used herein includes subcutaneous, intracutaneous, intravenous, intramuscular, intraperitoneal, intra-articular, intra-arterial, intrasynovial, intrasternal, intrathecal, intralesional, and intracranial injection or infusion techniques.

For example, the pharmaceutical compositions disclosed herein can be administered, e.g., topically, rectally, nasally (e.g., by inhalation spray or nebulizer), buccally, vaginally, subdermally (e.g., by injection or via an implanted reservoir), or ophthalmically.

For example, pharmaceutical compositions of this invention can be orally administered in any orally acceptable dosage form including, but not limited to, capsules, tablets, emulsions and aqueous suspensions, dispersions and solutions.

For example, the pharmaceutical compositions of this invention can be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

For example, the pharmaceutical compositions of this invention can be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, or other solubilizing or dispersing agents known in the art.

For example, the pharmaceutical compositions of this invention can be administered by injection (e.g., as a solution or powder). Such compositions can be formulated according to techniques known in the art using suitable dispersing or wetting agents (such as, for example, Tween 80) and suspending agents. The sterile injectable preparation may also be a sterile injectable solution or suspension in a nontoxic parenterally acceptable diluent or solvent, e.g., as a solution in 1,3-butanediol. Among the acceptable vehicles and solvents that may be employed are mannitol, water, Ringers solution, and isotonic sodium chloride solution. In addition, sterile, fixed oils are conventionally employed as a solvent or suspending medium. For this purpose, any bland fixed oil can be employed, including synthetic mono- or diglycerides. Fatty acids, such as oleic acid and its glyceride derivatives are useful in the preparation of injectables, as are natural pharmaceutically-acceptable oils, e.g., olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens, Spans, or other similar emulsifying agents or bioavailability enhancers which are commonly used in the manufacture of pharmaceutically acceptable solid, liquid, or other dosage forms can also be used for the purposes of formulation.

In some aspects, an effective dose of a pharmaceutical composition of this invention can include, but is not limited to, e.g., about 0.00001, 0.0001, 0.001, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.5, 3, 4, 5, 6, 7, 8, 9, 10, 15, 20, 30, 40, 50, 60, 70, 80, 90, 100, 200, 300, 400, 500, 600, 700, 800, 900, 1000, 2500, 5000, or 10000 mg/kg/day, or according to the requirements of the particular pharmaceutical composition.

When the pharmaceutical compositions disclosed herein include a combination of the heterobifunctional compounds described herein and one or more additional compounds (e.g., one or more additional compounds, drugs, or agents used for the treatment of cancer or any other condition or disease, including conditions or diseases known to be associated with or caused by cancer, inflammation, and/or auto-immune diseases), both the heterobifunctional compounds and the additional compounds may be present at dosage levels of between about 1 to 100%, and more preferably between about 5 to 95% of the dosage normally administered in a monotherapy regimen. The additional agents can be administered separately, as part of a multiple dose regimen, from the compounds of this invention. Alternatively, those agents can be part of a single dosage form, mixed together with the compounds of this invention in a single composition.

In some aspects, the pharmaceutical compositions disclosed herein can be included in a container, pack, or dispenser together with instructions for administration.

Methods of Treatment

The methods disclosed herein contemplate administration of an effective amount of a compound or composition to achieve the desired or stated effect. Typically, the compounds or compositions of the invention will be administered from about 1 to about 6 times per day or, alternately or in addition, as a continuous infusion. Such administration can be used as a chronic or acute therapy. The amount of active ingredient that can be combined with the carrier materials to produce a single dosage form will vary depending upon the host treated and the particular mode of administration. A typical preparation will contain from about 5% to about 95% active compound (w/w). Alternatively, such preparations can contain from about 20% to about 80% active compound.

In some aspects, provided herein are a heterobifunctional compound described herein for preventing or treating a disease or condition.

In some aspects, provided herein are a heterobifunctional compound described herein for treating or preventing one or more diseases or conditions disclosed herein in a subject in need thereof. In certain embodiments, the disease or condition is a MEK-mediated disease or condition. In certain embodiments, the disease or condition is resulted from MEK expression, mutation, deletion, or fusion. In certain embodiments, the diseases or conditions are cancer, hyperproliferative disorder, inflammation, auto-immune disease, dermatological disorders, viral infections, dry eye disorders, bone remodeling disorders, organ transplant associated immunological complications, relapsed cancer, and immunological diseases. In one embodiment, the MEK-mediated cancer is selected from the group consisting of brain cancer, stomach cancer, squamous cell cancer, gastrointestinal tract cancer, liver cancer, biliary passage cancer, breast cancer, ovary cancer, cervix cancer, prostate cancer, testis cancer, penile cancer, genitourinary tract cancer, esophagus cancer, larynx cancer, skin cancer, lung cancer, pancreas cancer, thyroid cancer, gland cancer, bladder cancer, kidney cancer, muscle cancer, bone cancer, head cancer, neck cancer, renal cancer, colorectal cancer, gynecological cancer, cancers of the hematopoietic system, myeloproliferative neoplasms, essential thrombocythemia, polycythemia vera, primary myelofibrosis, chronic neutrophilic leukemia, acute lymphoblastic leukemia, Hodgkin's lymphoma, chronic myelomonocytic leukemia, systemic mast cell disease, hyper eosinophilic syndrome, cutaneous T-cell lymphoma, B-cell lymphoma, and myeloma. In one embodiment, the MEK-mediated non-cancerous hyperproliferative disorder is selected from benign hyperplasia of the skin (e.g., psoriasis), restenosis, or prostate (e.g., benign prostatic hypertrophy (BPH)). In one embodiment, the MEK-mediated disorder is selected from benign hyperplasia of the skin (e.g., psoriasis), restenosis, or prostate (e.g., benign prostatic hypertrophy (BPH)). In one embodiment, the MEK-mediated disorder is selected from pancreatitis or kidney disease (including proliferative glomemlonephritis and diabetes-induced renal disease). In one embodiment, the MEK-mediated disorder is pain. In one embodiment, the MEK-mediated inflammatory disorders are selected from the group consisting of ankylosing spondylitis, Crohn's disease, inflammatory bowel disease, ulcerative colitis, and ischemia reperfusion injuries. In one embodiment, the MEK-mediated auto-immune diseases are selected from the group consisting of multiple sclerosis, scleroderma, rheumatoid arthritis, psoriatic arthritis, juvenile idiopathic arthritis, psoriasis, myasthenia gravis, type I diabetes, diabetic retinopathy, systemic lupus erythematosus, IgA nephropathy, autoimmune thyroid disorders, alopecia areata, and bullous pemphigoid. In one embodiment, the MEK-mediated dermatological disorders are selected from the group consisting of atopic dermatitis, pruritus, alopecia areata, psoriasis, skin rash, skin irritation, skin sensitization, chronic mucocutaneous candidiasis, dermatomyositis, erythema multiforme, palmoplantar pustulosis, vitiligo, polyarteritis nodosa, and STING-associated vasculopathy. In one embodiment, the MEK-mediated diseases are selected from retinopathy of prematurity, age-related macular degeneration, and hemangioma. In some aspects, provided herein are use of a heterobifunctional compound in manufacture of a medicament for preventing or treating one or more diseases or conditions disclosed herein.

In some aspects, the methods disclosed include the administration of a therapeutically effective amount of one or more of the compounds or compositions described herein to a subject (e.g., a mammalian subject, e.g., a human subject) who is in need of, or who has been determined to be in need of, such treatment. In some aspects, the methods disclosed include selecting a subject and administering to the subject an effective amount of one or more of the compounds or compositions described herein, and optionally repeating administration as required for the prevention or treatment of cancer.

In some aspects, subject selection can include obtaining a sample from a subject (e.g., a candidate subject) and testing the sample for an indication that the subject is suitable for selection. In some aspects, the subject can be confirmed or identified, e.g. by a health care professional, as having had, having an elevated risk to have, or having a condition or disease. In some aspects, suitable subjects include, for example, subjects who have or had a condition or disease but that resolved the disease or an aspect thereof, present reduced symptoms of disease (e.g., relative to other subjects (e.g., the majority of subjects) with the same condition or disease), or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease). In some aspects, exhibition of a positive immune response towards a condition or disease can be made from patient records, family history, or detecting an indication of a positive immune response. In some aspects, multiple parties can be included in subject selection. For example, a first party can obtain a sample from a candidate subject and a second party can test the sample. In some aspects, subjects can be selected or referred by a medical practitioner (e.g., a general practitioner). In some aspects, subject selection can include obtaining a sample from a selected subject and storing the sample or using the in the methods disclosed herein. Samples can include, e.g., cells or populations of cells.

In some aspects, methods of treatment can include a single administration, multiple administrations, and repeating administration of one or more compounds disclosed herein as required for the prevention or treatment of the disease or condition disclosed herein (e.g., an MEK-mediated disease). In some aspects, methods of treatment can include assessing a level of disease in the subject prior to treatment, during treatment, or after treatment. In some aspects, treatment can continue until a decrease in the level of disease in the subject is detected.

The term "subject," as used herein, refers to any animal. In some instances, the subject is a mammal. In some instances, the term "subject," as used herein, refers to a human (e.g., a man, a woman, or a child).

The terms "administer," "administering," or "administration," as used herein, refer to implanting, ingesting, injecting, inhaling, or otherwise absorbing a compound or composition, regardless of form. For example, the methods disclosed herein include administration of an effective amount of a compound or composition to achieve the desired or stated effect.

The terms "treat", "treating," or "treatment," as used herein, refer to partially or completely alleviating, inhibiting, ameliorating, or relieving the disease or condition from which the subject is suffering. This means any manner in which one or more of the symptoms of a disease or disorder (e.g., cancer) are ameliorated or otherwise beneficially altered. As used herein, amelioration of the symptoms of a particular disorder (e.g., cancer) refers to any lessening, whether permanent or temporary, lasting or transient that can be attributed to or associated with treatment by the heterobifunctional compounds, compositions and methods of the present invention. In some embodiments, treatment can promote or result in, for example, a decrease in the number of tumor cells (e.g., in a subject) relative to the number of tumor cells prior to treatment; a decrease in the viability (e.g., the average/mean viability) of tumor cells (e.g., in a subject) relative to the viability of tumor cells prior to treatment; a decrease in the rate of growth of tumor cells; a decrease in the rate of local or distant tumor metastasis; or reductions in one or more symptoms associated with one or more tumors in a subject relative to the subject's symptoms prior to treatment.

The terms "prevent," "preventing," and "prevention," as used herein, shall refer to a decrease in the occurrence of a disease or decrease in the risk of acquiring a disease or its associated symptoms in a subject. The prevention may be complete, e.g., the total absence of disease or pathological cells in a subject. The prevention may also be partial, such that the occurrence of the disease or pathological cells in a subject is less than, occurs later than, or develops more slowly than that which would have occurred without the present invention. In certain embodiments, the subject has an elevated risk of developing one or more MEK-mediated diseases. Exemplary MEK-mediated diseases that can be treated with heterobifunctional compounds include, for example, cancer (e.g. cancers of brain, stomach, gastrointestinal tracts, liver, biliary passage, breast, ovary, cervix, prostate, testis, penile, genitourinary tract, esophagus, larynx, skin, lung, pancreas, thyroid, glands, bladder, kidney, muscle, bone, and cancers of the hematopoietic system, such as myeloproliferative neoplasms, including essential thrombocythemia, polycythemia vera, primary myelofibrosis, chronic neutrophilic leukemia, acute lymphoblastic leukemia, Hodgkin's lymphoma, chronic myelomonocytic leukemia, systemic mast cell disease, hypereosinophilic syndrome, cutaneous T-cell lymphoma, B-cell lymphoma, myeloma, and other hematologic malignancies, particularly cancers that involve inflammation, mutations or other aberrations that activate the MEK pathway); inflammation (e.g. ankylosing spondylitis, Crohn's disease, inflammatory bowel disease, ulcerative colitis, and ischemia reperfusion injuries, which are conditions related to inflammatory ischemic events such as stroke or cardiac arrest); auto-immune diseases (e.g. multiple sclerosis, rheumatoid arthritis, psoriatic arthritis, juvenile idiopathic arthritis, psoriasis, myasthenia gravis, type I diabetes, systemic lupus erythematosus, IgA nephropathy, autoimmune thyroid disorders, alopecia areata, and bullous pemphigoid); dermatological disorders (e.g. atopic dermatitis, pruritus, alopecia areata, psoriasis, skin rash, skin irritation, skin sensitization, chronic mucocutaneous candidiasis, dermatomyositis, erythema multiforme, palmoplantar pustulosis, vitiligo, polyarteritis nodosa, and STING-associated vasculopathy); viral infections (e.g. viral infections and consequent complications, such as infections of Hepatitis B, Hepatitis C, Human Immunodeficiency Virus (HIV), Human T-lymphotropic Virus (HTLV1), Epstein Barr Virus (EBV), Varicella-Zoster Virus (VZV) and Human Papilloma Virus (HPV)); dry eye disorder, also known as dry eye syndrome (DES) or keratoconjunctivitis sicca (KCS); bone remodeling disorders (e.g. osteoporosis and osteoarthritis); organ transplant associated immunological complications (e.g. graft-versus-host diseases).

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. Moreover, treatment of a subject with a therapeutically effective amount of the compounds or compositions described herein can include a single treatment or a series of treatments. For example, effective amounts can be administered at least once. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health or age of the subject, and other diseases present.

Following administration, the subject can be evaluated to detect, assess, or determine their level of disease. In some instances, treatment can continue until a change (e.g., reduction) in the level of disease in the subject is detected. Upon improvement of a patient's condition (e.g., a change (e.g., decrease) in the level of disease in the subject), a maintenance dose of a compound, or composition disclosed herein can be administered, if necessary. Subsequently, the dosage or frequency of administration, or both, can be reduced, e.g., as a function of the symptoms, to a level at which the improved condition is retained. Patients may, however, require intermittent treatment on a long-term basis upon any recurrence of disease symptoms.

The present disclosure is also described and demonstrated by way of the following examples. However, the use of these and other examples anywhere in the specification is illustrative only and in no way limits the scope and meaning of the invention or of any exemplified term. Likewise, the invention is not limited to any particular preferred embodiment or aspect described herein. Indeed, many modifications and variations may be apparent to those skilled in the art upon reading this specification, and such variations can be made without departing from the invention in spirit or in scope. The invention is therefore to be limited only by the terms of the appended claims along with the full scope of equivalents to which those claims are entitled.

EXAMPLES

Example 1: 3,4-Difluoro-2-((2-fluoro-4-iodophenyl)amino)-N-(3-oxopropoxy)benzamide (Z5)

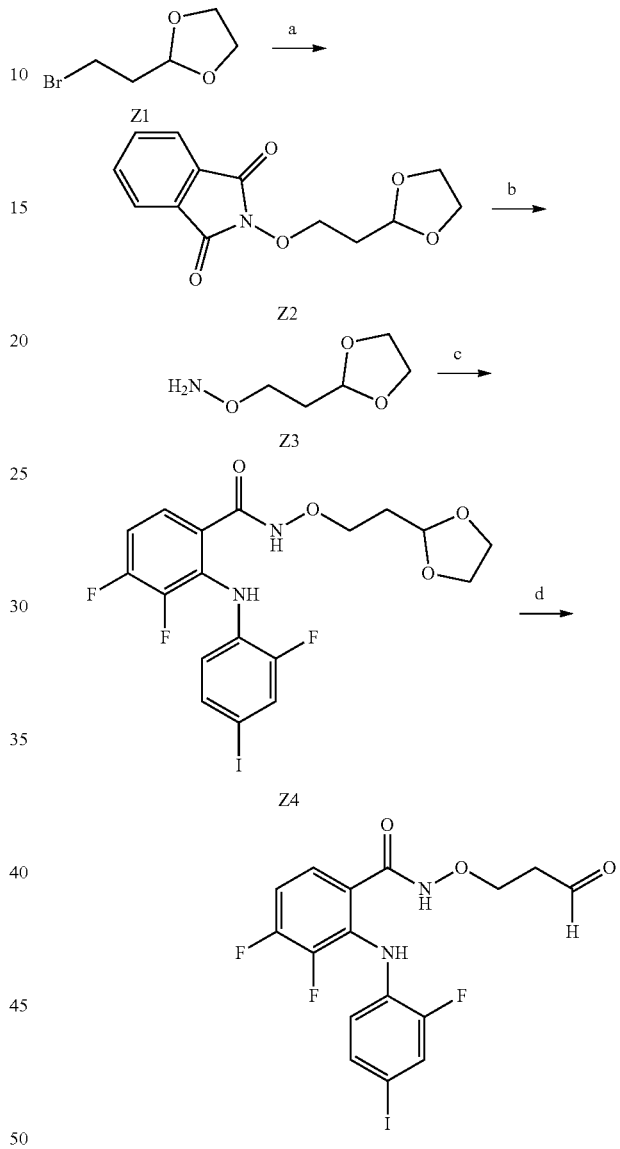

Reagents and conditions: (a) DBU, DMF, 50° C., 4 h; (b) N$_2$H$_4$•H$_2$O, MeOH, DCM, rt, 2 h; (c) HOAt, EDCI, NMM, DMSO, rt, overnight; (d) 3M HCl, THF, rt, 6 h.

Step 1. Synthesis of 2-(2-(1,3-dioxolan-2-yl)ethoxy)isoindoline-1,3-dione (Z2)

To a solution of compound Z1 (1 g, 5.5 mmol) in DMF (5 mL) were added 2-hydroxyisoindoline-1,3-dione (0.9 g, 5.5 mmol) and DBU (1.6 mL, 11.0 mmol). The reaction mixture was heated to 50° C. for 4 h. The reaction was monitored by UPLC. Upon completion, the reaction mixture was purified by reverse column chromatography to give compound Z2 (1.2 g, 4.5 mmol, 82% yield) as yellow solid. $^1$H NMR (600 MHz, Methanol-d$_4$) δ 8.36-7.40 (m, 4H), 5.10 (t, J=4.7 Hz, 1H), 4.31 (t, J=6.6 Hz, 2H), 3.98-3.93 (m, 2H), 3.87-3.82

(m, 2H), 2.09 (td, J=6.6, 4.6 Hz, 2H). UPLC>95%, $t_R$=1.12 min. MS (ESI) [M+H]$^+$=264.1638.

Step 2. Synthesis of O-(2-(1,3-dioxolan-2-yl)ethyl) hydroxylamine (Z3)

A solution of compound Z2 (1.2 g, 4.5 mmol) and hydrazine monohydrate (0.66 mL, 13.5 mmol) in MeOH (4 mL) and DCM (2 mL) was stirred at room temperature for 2 h. The reaction was monitored by UPLC. Upon completion, the solvent was evaporated, water (20 mL) was added to the residue, and then extracted with DCM (20 mL×3). The combined organic layers were washed with 5% NaHCO$_3$ solution and brine, then dried over anhydrous Na$_2$SO$_4$, filtered, and concentrated to obtain compound Z3 (0.53 g, 4.0 mmol, 89% yield) as colorless liquid without further purification.

Step 3. Synthesis of N-(2-(1,3-dioxolan-2-yl)ethoxy)-3,4-difluoro-2-((2-fluoro-4-iodophenyl) amino) benzamide (Z4)

To a solution of compound Z3 (0.53 g, 4.0 mmol) and 3,4-difluoro-2-((2-fluoro-4-iodophenyl)amino)benzoic acid (1.6 g, 4.0 mmol) in DMSO (5 mL) were added HOAt (0.8 g, 6.0 mmol), EDCI (1.2 g, 6.0 mmol), and 4-methylmorpholine (1.3 mL, 12.0 mmol). The reaction mixture was stirred at room temperature overnight. The reaction was monitored by UPLC. Upon completion, the reaction mixture was purified by reverse column chromatography to give compound Z4 (1.5 g, 3.0 mmol, 75% yield) as white solid. $^1$H NMR (600 MHz, Methanol-d$_4$) δ 7.45 (dd, J=10.6, 1.9 Hz, 1H), 7.38 (t, J=7.0 Hz, 1H), 7.35 (dt, J=8.5, 1.5 Hz, 1H), 7.03 (td, J=9.2, 7.0 Hz, 1H), 6.60 (td, J=8.7, 4.2 Hz, 1H), 4.97 (t, J=4.9 Hz, 1H), 3.96 (t, J=6.7 Hz, 2H), 3.95-3.90 (m, 2H), 3.86-3.78 (m, 2H), 1.97 (td, J=6.7, 4.7 Hz, 2H). UPLC>95%, $t_R$=1.95 min. MS (ESI) [M−H]$^+$=507.0261.

Step 4. Synthesis of 3,4-Difluoro-2-((2-fluoro-4-iodophenyl)amino)-N-(3-oxopropoxy)benzamide (Z5)

To a solution of compound Z4 (0.5 g, 1.0 mmol) in THF (3 mL) was added 3M HCl (5 mL). The reaction mixture was stirred at room temperature for 6 h. The reaction was monitored by UPLC. Upon completion, the reaction mixture was cooled to 0° C., neutralized with saturated NaHCO$_3$ to pH 7~8, and then extracted with EtOAc (30 mL×3) to obtain compound Z5 (0.37 g, 0.8 mmol, 80% yield) as colorless liquid without further purification.

Example 2: (2S,4R)-1-((S)-2-((6-Aminohexyl)amino)-3,3-dimethylbutanoyl)-4-hydroxy-N-(4-(4-methylthiazol-5-yl)benzyl)pyrrolidine-2-carboxamide (Z7)

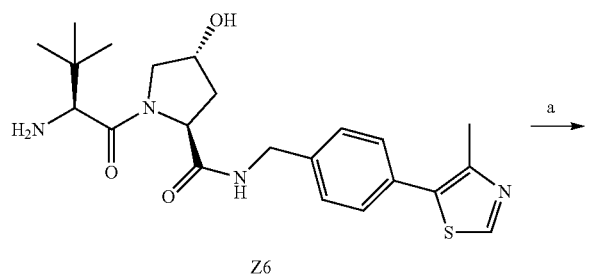

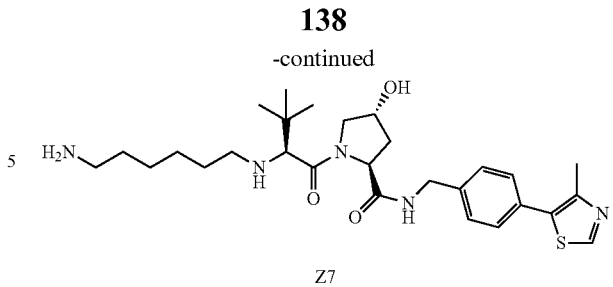

Reagents and conditions: (a) 1. Z5, HOAt, EDCI, NMM, DMSO, rt, overnight, 2. TFA, DCM, rt, 2 h.

To a solution of compound Z6 (0.5 g, 1.2 mmol) and 7-((tert-butoxycarbonyl)amino)heptanoic acid (0.3 g, 1.2 mmol) in DMSO (5 mL) were added HOAt (0.2 g, 1.8 mmol), EDCI (0.4 g, 1.8 mmol), and 4-methylmorpholine (0.4 mL, 3.6 mmol). The reaction mixture was stirred at room temperature overnight. The reaction was monitored by UPLC. Upon completion, the reaction mixture was purified by reverse column chromatography to give the desired intermediate (0.7 g, 1.1 mmol, 92% yield) as a white solid. This intermediate (0.7 g, 1.1 mmol) then was dissolved in DCM (2 mL), and trifluoroacetic acid (2 mL) was added. The reaction mixture was stirred at room temperature for 2 h. The reaction was monitored by UPLC. Once completion, the solvent was evaporated, and the residue was purified by reverse column chromatography to obtain compound Z7 (0.6 g, 1.0 mmol, 91% yield) as a white solid. 1H NMR (600 MHz, methanol-d4) δ 9.80 (s, 1H), 7.56 (dd, J=8.2, 4.1 Hz, 2H), 7.51 (d, J=7.9 Hz, 2H), 4.65-4.60 (m, 1H), 4.58-4.56 (m, 1H), 4.55-4.52 (m, 1H), 4.52-4.49 (m, 1H), 4.41 (d, J=15.7 Hz, 1H), 3.91 (d, J=11.0 Hz, 1H), 3.81 (dd, J=11.0, 3.9 Hz, 1H), 2.92 (t, J=7.7 Hz, 2H), 2.59 (s, 3H), 2.35-2.27 (m, 2H), 2.27-2.22 (m, 1H), 2.12-2.04 (m, 1H), 1.70-1.60 (m, 4H), 1.51-1.34 (m, 4H), 1.04 (s, 9H).

Example 3: (2S,4R)-1-((S)-16-(tert-Butyl)-1-(3,4-difluoro-2-((2-fluoro-4-iodophenyl)amino)phenyl)-1,14-dioxo-3-oxa-2,7,15-triazaheptadecan-17-oyl)-4-hydroxy-N-(4-(4-methylthiazol-5-yl)benzyl)pyrrolidine-2-carboxamide (CPD-001)

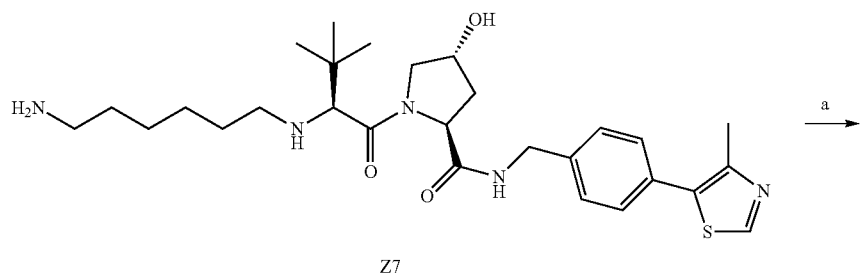

Z7

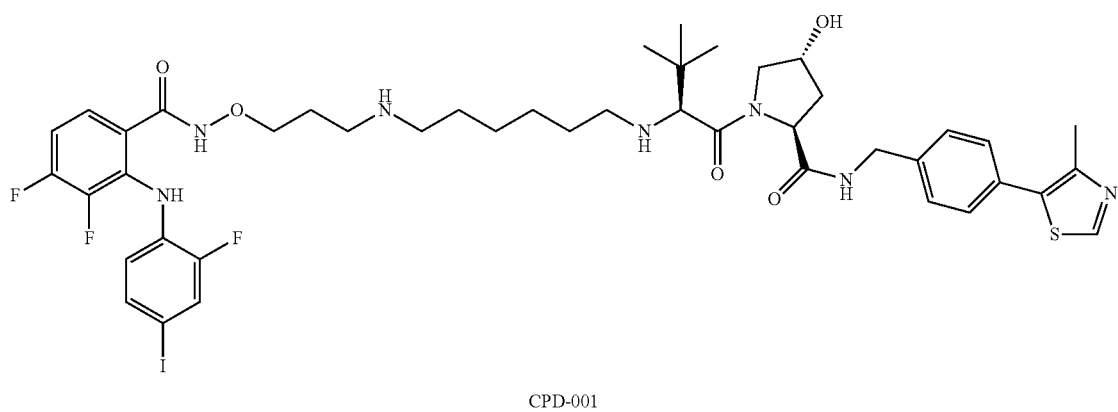

CPD-001

Reagents and conditions: (a) Z5, NaBH₃CN, DCM, MeOH, rt, overnight.

To a solution of compound Z7 (0.1 g, 0.2 mmol) and compound Z5 (0.1 g, 0.2 mmol) in DCM (2 mL) and MeOH (1 mL) was added NaBH$_3$CN (19 mg, 0.3 mmol). The reaction mixture was stirred at room temperature overnight. The reaction was monitored by UPLC. Upon completion, the reaction mixture was purified by preparative HPLC to give CPD-001 (0.1 g, 0.1 mmol, 50% yield) as a white solid. $^1$H NMR (600 MHz, Methanol-d$_4$) δ 8.94 (d, J=6.0 Hz, 1H), 7.51-7.45 (m, 3H), 7.44-7.39 (m, 3H), 7.38 (d, J=8.8 Hz, 1H), 7.07 (q, J=8.9 Hz, 1H), 6.63 (td, J=8.6, 4.0 Hz, 1H), 4.67-4.63 (m, 1H), 4.58-4.55 (m, 1H), 4.53 (d, J=10.4 Hz, 1H), 4.51-4.49 (m, 1H), 4.36 (d, J=15.4 Hz, 1H), 4.05 (t, J=5.1 Hz, 2H), 3.90 (d, J=11.0 Hz, 1H), 3.81 (dd, J=10.9, 4.0 Hz, 1H), 3.23 (t, J=5.9 Hz, 2H), 3.10-2.99 (m, 2H), 2.48 (s, 3H), 2.31 (dt, J=14.9, 7.6 Hz, 1H), 2.28-2.25 (m, 1H), 2.25-2.19 (m, 1H), 2.08 (ddd, J=13.3, 9.1, 4.4 Hz, 1H), 2.05-1.99 (m, 2H), 1.73 (p, J=7.8 Hz, 2H), 1.61 (dt, J=13.7, 6.9 Hz, 2H), 1.42 (p, J=7.1 Hz, 2H), 1.37 (q, J=7.2 Hz, 2H), 1.03 (s, 9H).

Example 4: (2S,4R)-1-((S)-14-(tert-Butyl)-1-(3,4-difluoro-2-((2-fluoro-4-iodophenyl)amino)phenyl)-1,12-dioxo-3,10-dioxa-2,7,13-triazapentadecan-15-oyl)-4-hydroxy-N-(4-(4-methylthiazol-5-yl)benzyl)pyrrolidine-2-carboxamide (CPD-002)

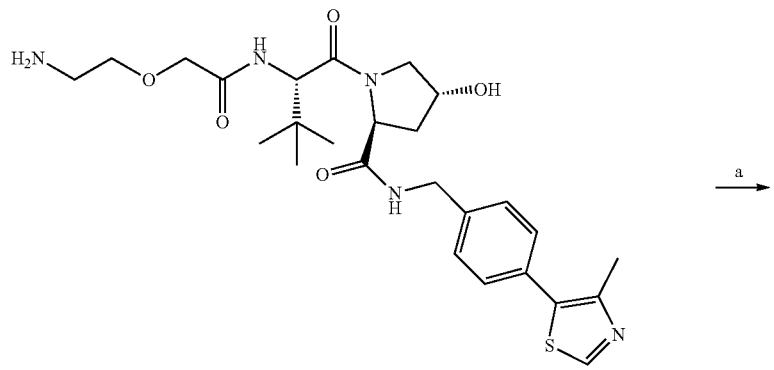

Z8

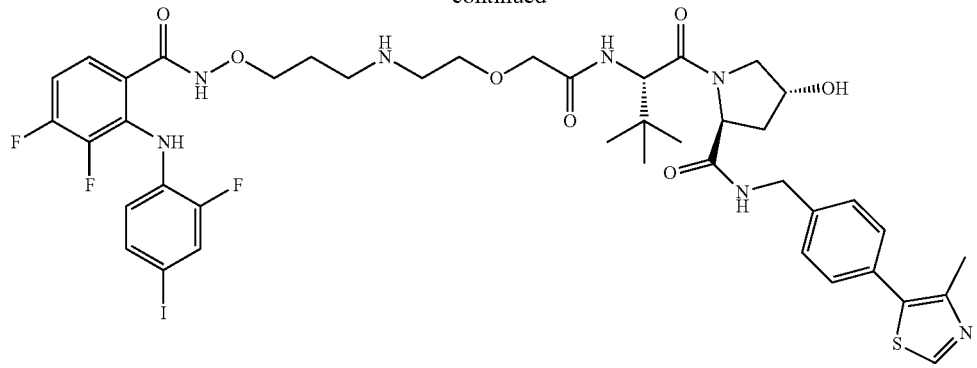

CPD-002

Reagents and conditions: (a) Z5, NaBH₃CN, DCM, MeOH, rt, overnight.

CPD-002 was synthesized following the same procedures as CPD-001 as described in Example 3 (0.1 g, yield: 49%). $^1$H NMR (600 MHz, Methanol-$d_4$) δ 8.98 (s, 1H), 7.50-7.44 (m, 3H), 7.42 (d, J=8.3 Hz, 2H), 7.40-7.35 (m, 2H), 7.06 (q, J=8.8 Hz, 1H), 6.62 (td, J=8.8, 4.0 Hz, 1H), 4.67 (s, 1H), 4.59-4.55 (m, 1H), 4.54 (d, J=3.3 Hz, 1H), 4.51 (d, J=10.2 Hz, 1H), 4.35 (d, J=15.4 Hz, 1H), 4.12 (s, 1H), 4.09 (s, 1H), 4.07-4.03 (m, 3H), 3.91-3.84 (m, 3H), 3.80 (dd, J=11.0, 3.7 Hz, 1H), 3.36-3.34 (m, 1H), 3.28 (p, J=1.7 Hz, 1H), 2.48 (s, 3H), 2.24 (dd, J=13.1, 7.7 Hz, 1H), 2.12-2.02 (m, 4H), 1.01 (s, 9H).

Example 5: (2S,4R)-1-((S)-15-(tert-Butyl)-1-(3,4-difluoro-2-((2-fluoro-4-iodophenyl)amino)phenyl)-1,13-dioxo-3,10-dioxa-2,7,14-triazahexadecan-16-oyl)-4-hydroxy-N-(4-(4-methylthiazol-5-yl)benzyl)pyrrolidine-2-carboxamide (CPD-003)

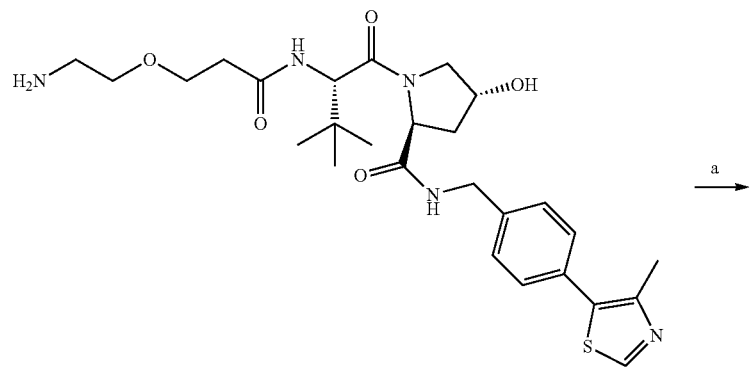

Z9

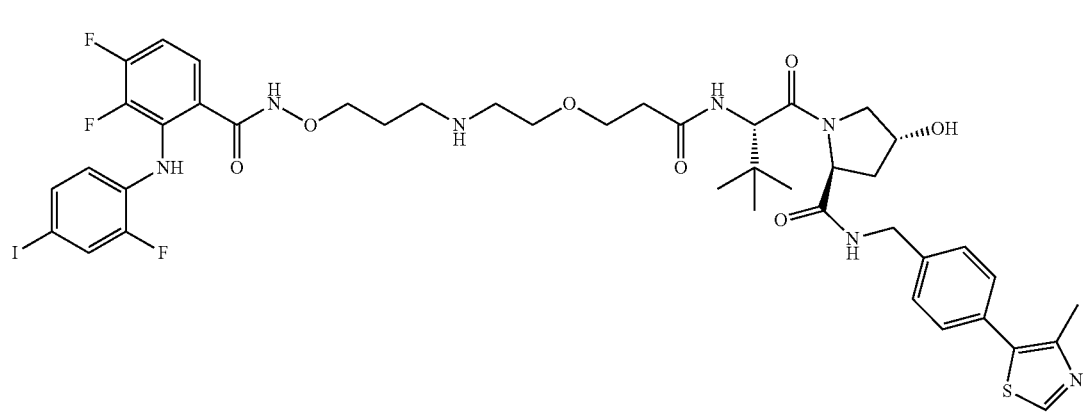

CPD-003

Reagents and conditions: (a) Z5, NaBH₃CN, DCM, MeOH, rt, overnight.

CPD-003 was synthesized following the same procedures as CPD-001 as described in Example 3. (0.06 g, yield: 42%). ¹H NMR (600 MHz, Methanol-d₄) δ 9.73 (s, 1H), 7.50 (t, J=6.7 Hz, 2H), 7.46 (d, J=8.2 Hz, 2H), 7.43 (dd, J=10.6, 2.0 Hz, 1H), 7.39 (t, J=7.2 Hz, 1H), 7.34 (d, J=8.1 Hz, 1H), 7.01 (d, J=7.7 Hz, 1H), 6.68-6.54 (m, 1H), 4.63-4.55 (m, 2H), 4.50 (d, J=14.8 Hz, 2H), 4.43 (d, J=15.6 Hz, 1H), 4.04 (t, J=5.4 Hz, 2H), 3.98-3.89 (m, 2H), 3.85-3.68 (m, 6H), 2.57 (s, 6H), 2.26 (t, J=10.6 Hz, 1H), 2.07 (q, J=6.3, 5.3 Hz, 4H), 1.01 (s, 9H).

Example 6: (2S,4R)-1-((S)-18-(tert-Butyl)-1-(3,4-difluoro-2-((2-fluoro-4-iodophenyl)amino)phenyl)-1,16-dioxo-3,10,13-trioxa-2,7,17-triazanonadecan-19-oyl)-4-hydroxy-N-(4-(4-methylthiazol-5-yl)benzyl)pyrrolidine-2-carboxamide (CPD-004)

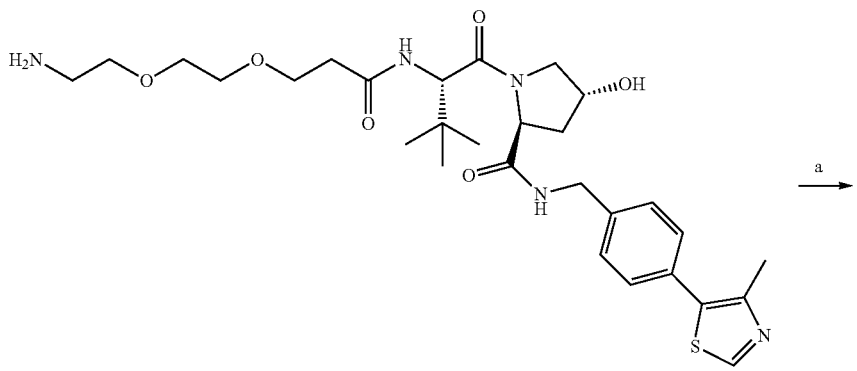

Z10

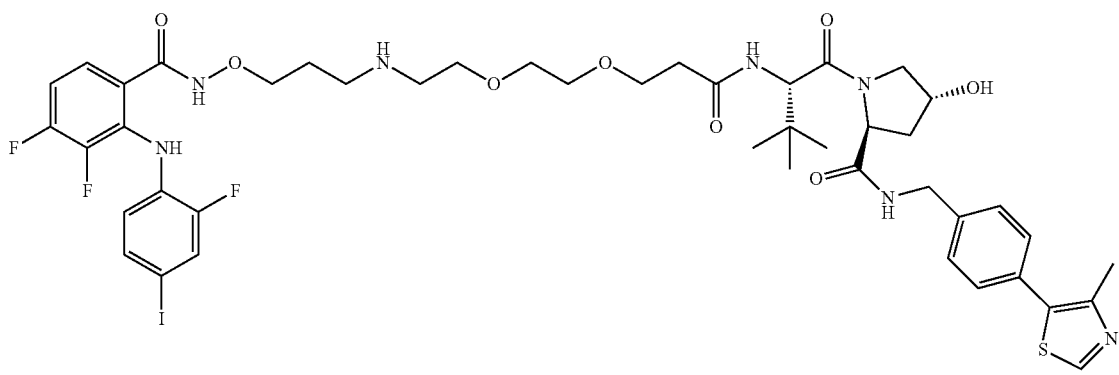

CPD-004

Reagents and conditions: (a) Z5, NaBH₃CN, DCM, MeOH, rt, overnight.

CPD-004 was synthesized following the same procedures as CPD-001 as described in Example 3. (0.08 g, yield: 42%). $^1$H NMR (600 MHz, Methanol-$d_4$) δ 9.28 (s, 1H), 7.51-7.47 (m, 3H), 7.45 (d, J=8.1 Hz, 2H), 7.41 (t, J=6.9 Hz, 1H), 7.38-7.35 (m, 1H), 7.05 (q, J=8.6 Hz, 1H), 6.63 (td, J=8.6, 4.1 Hz, 1H), 4.64 (s, 1H), 4.58-4.53 (m, 1H), 4.52-4.49 (m, 2H), 4.40 (d, J=15.6 Hz, 1H), 4.07 (t, J=5.2 Hz, 2H), 3.96-3.88 (m, 1H), 3.83-3.76 (m, 3H), 3.74-3.63 (m, 3H), 3.58 (t, J=4.5 Hz, 2H), 3.56-3.52 (m, 2H), 3.30-3.23 (m, 3H), 2.57-2.52 (m, 1H), 2.52 (s, 3H), 2.50-2.43 (m, 1H), 2.24 (dd, J=13.2, 7.6 Hz, 1H), 2.14-2.00 (m, 3H), 1.02 (s, 9H).

Example 7: (2S,4R)-1-((S)-11-(tert-Butyl)-1-(3,4-difluoro-2-((2-fluoro-4-iodophenyl)amino)phenyl)-1,9-dioxo-3-oxa-2,7,10-triazadodecan-12-oyl)-4-hydroxy-N-(4-(4-methylthiazol-5-yl)benzyl)pyrrolidine-2-carboxamide (CPD-005)

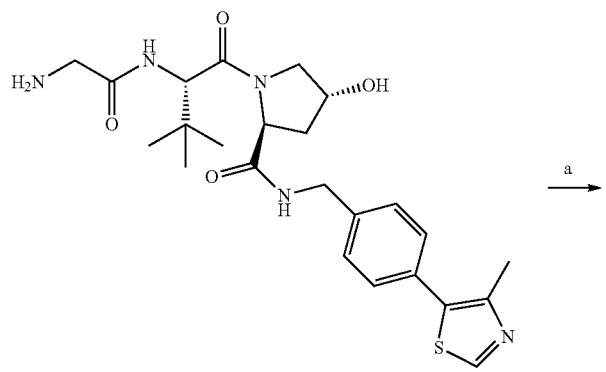

Z11

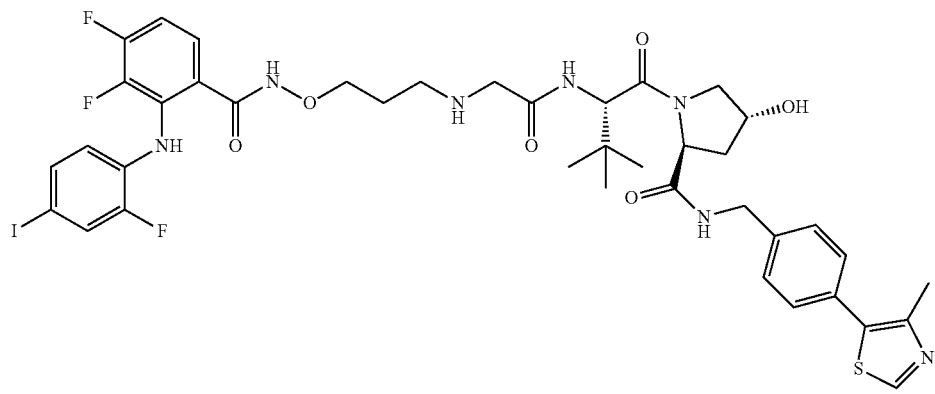

CPD-005

Reagents and conditions: (a) Z5, NaBH$_3$CN, DCM, MeOH, rt, overnight.

CPD-005 was synthesized following the same procedures as CPD-001 as described in Example 3. (0.07 g, yield: 42%). ¹H NMR (600 MHz, Methanol-$d_4$) δ 9.30 (d, J=4.2 Hz, 1H), 7.53-7.47 (m, 3H), 7.47-7.44 (m, 2H), 7.40-7.36 (m, 2H), 7.01 (td, J=9.1, 6.9 Hz, 1H), 6.68 (td, J=8.7, 3.8 Hz, 1H), 4.58-4.55 (m, 2H), 4.53 (d, J=8.4 Hz, 2H), 4.51-4.48 (dt, J=4.5, 2.5 Hz, 1H), 4.37 (d, J=15.6 Hz, 1H), 4.08 (dt, J=9.8, 5.0 Hz, 1H), 4.03 (dq, J=9.9, 5.3 Hz, 1H), 3.98 (d, J=15.8 Hz, 1H), 3.87 (d, J=15.8 Hz, 1H), 3.81 (d, J=11.0 Hz, 1H), 3.76 (dd, J=10.9, 3.8 Hz, 1H), 2.52 (s, 3H), 2.25-2.20 (m, 1H), 2.11-2.03 (m, 4H), 1.03 (s, 9H).

Example 8: (2S,4R)-1-((S)-12-(tert-Butyl)-1-(3,4-difluoro-2-((2-fluoro-4-iodophenyl)amino)phenyl)-1,10-dioxo-3-oxa-2,7,11-triazatridecan-13-oyl)-4-hydroxy-N-(4-(4-methylthiazol-5-yl)benzyl)pyrrolidine-2-carboxamide (CPD-006)

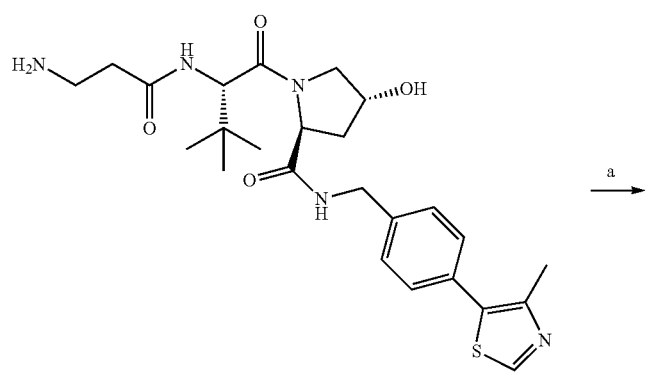

Z12

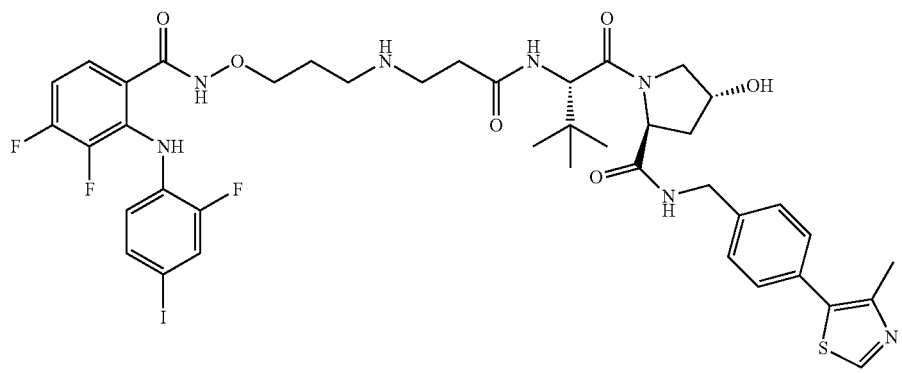

CPD-006

Reagents and conditions: (a) Z5, NaBH₃CN, DCM, MeOH, rt, overnight.

CPD-006 was synthesized following the same procedures as CPD-001 as described in Example 3. (0.05 g, yield: 41%). ¹H NMR (600 MHz, Methanol-d₄) δ 8.96 (s, 1H), 7.51-7.45 (m, 3H), 7.44-7.40 (m, 3H), 7.38 (dt, J=8.3, 1.4 Hz, 1H), 7.05 (td, J=9.1, 6.9 Hz, 1H), 6.66 (td, J=8.7, 3.9 Hz, 1H), 4.59-4.53 (m, 3H), 4.50-4.47 (m, 1H), 4.34 (d, J=15.5 Hz, 1H), 4.03 (t, J=5.2 Hz, 2H), 3.90 (d, J=10.9 Hz, 11H), 3.75 (dd, J=10.9, 3.9 Hz, 1H), 3.35-3.32 (m, 2H), 3.27-3.22 (m, 2H), 2.78 (t, J=6.6 Hz, 2H), 2.47 (s, 3H), 2.25-2.20 (m, 1H), 2.08 (ddd, J=13.4, 9.3, 4.3 Hz, 1H), 2.05-1.99 (m, 2H), 1.02 (s, 9H).

Example 9: (2S,4R)-1-((S)-14-(tert-Butyl)-1-(3,4-difluoro-2-((2-fluoro-4-iodophenyl)amino)phenyl)-1,12-dioxo-3-oxa-2,7,13-triazapentadecan-15-oyl)-4-hydroxy-N-(4-(4-methylthiazol-5-yl)benzyl)pyrrolidine-2-carboxamide (CPD-007)

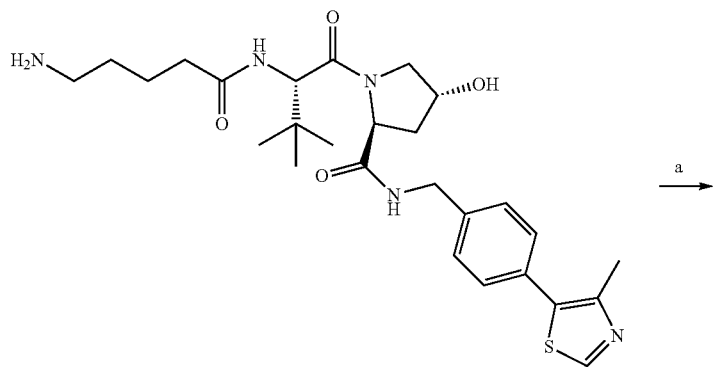

Z13

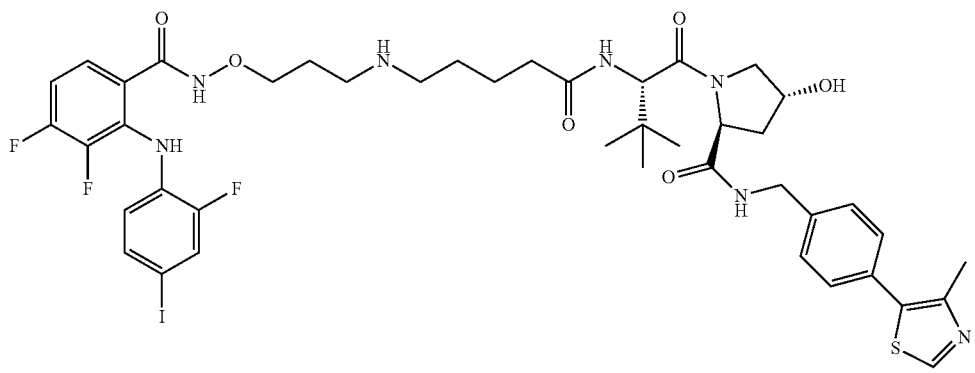

CPD-007

Reagents and conditions: (a) Z5, NaBH₃CN, DCM, MeOH, rt, overnight.

CPD-007 was synthesized following the same procedures as CPD-001 as described in Example 3. (0.05 g, yield: 40%).
$^1$H NMR (600 MHz, Methanol-$d_4$) δ 8.88 (s, 1H), 7.49 (dd, J=10.7, 1.9 Hz, 1H), 7.46 (d, J=8.2 Hz, 2H), 7.43-7.39 (m, 2H), 7.39-7.33 (m, 2H), 7.07 (td, J=9.2, 7.1 Hz, 1H), 6.64 (td, J=8.7, 3.9 Hz, 1H), 4.61 (s, 1H), 4.55 (dq, J=14.0, 6.7 Hz, 2H), 4.50 (dd, J=4.2, 2.2 Hz, 1H), 4.35 (d, J=15.5 Hz, 1H), 4.07-3.99 (m, 2H), 3.89 (dt, J=11.1, 1.7 Hz, 1H), 3.80 (dd, J=10.9, 3.9 Hz, 11H), 3.66-3.62 (m, 1H), 3.59 (dd, J=12.6, 3.9 Hz, 1H), 3.22 (t, J=5.9 Hz, 2H), 3.05 (t, J=7.3 Hz, 2H), 2.47 (s, 2H), 2.34 (tt, J=15.0, 7.6 Hz, 2H), 2.24-2.19 (m, 11H), 2.09 (ddd, J=13.3, 9.2, 4.5 Hz, 1H), 2.04-1.98 (m, 2H), 1.81-1.65 (m, 4H), 1.03 (s, 9H).

Example 10: (2S,4R)-1-((S)-13-(tert-Butyl)-1-(3,4-difluoro-2-((2-fluoro-4-iodophenyl)amino)phenyl)-1,11-dioxo-3-oxa-2,7,12-triazatetradecan-14-oyl)-4-hydroxy-N-(4-(4-methylthiazol-5-yl)benzyl)pyrrolidine-2-carboxamide (CPD-008)

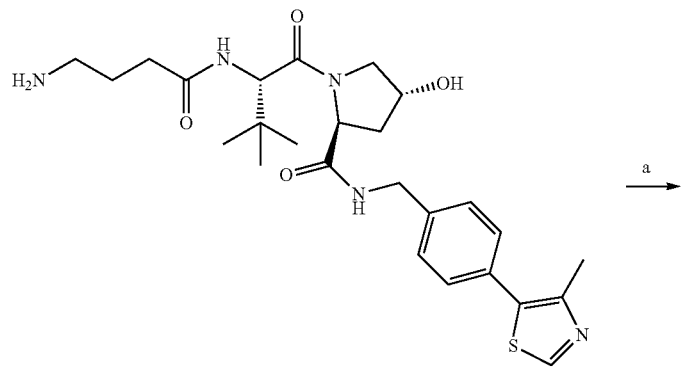

Z14

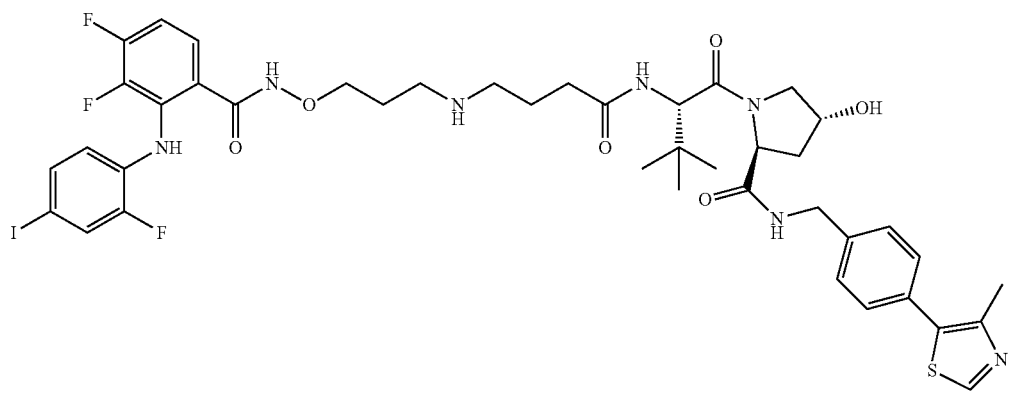

CPD-008

Reagents and conditions: (a) Z5, NaBH$_3$CN, DCM, MeOH, rt, overnight.

CPD-008 was synthesized following the same procedures as CPD-001 as described in Example 3. (0.03 g, yield: 39%). $^1$H NMR (600 MHz, Methanol-$d_4$) δ 8.98 (s, 1H), 7.50-7.45 (m, 3H), 7.44-7.38 (m, 3H), 7.37 (dt, J=8.5, 1.3 Hz, 11H), 7.06 (td, J=9.2, 7.0 Hz, 1H), 6.64 (td, J=8.8, 3.9 Hz, 11H), 4.58 (d, J=6.8 Hz, 11H), 4.56 (dd, J=3.0, 1.4 Hz, 11H), 4.53 (d, J=9.7 Hz, 11H), 4.51-4.49 (m, 1H), 4.36 (d, J=15.5 Hz, 11H), 4.03 (dp, J=11.8, 4.2 Hz, 2H), 3.91 (d, J=10.9 Hz, 11H), 3.79 (dd, J=10.9, 3.9 Hz, 11H), 3.22 (t, J=5.9 Hz, 2H), 3.08 (td, J=7.5, 1.8 Hz, 2H), 2.48 (s, 3H), 2.48-2.44 (m, 2H), 2.22 (ddt, J=13.2, 7.6, 1.9 Hz, 1H), 2.08 (ddd, J=13.3, 9.3, 4.4 Hz, 1H), 2.04-1.97 (m, 4H), 1.03 (s, 9H).

Example 11: (2S,4R)-1-((S)-15-(tert-butyl)-1-(3,4-difluoro-2-((2-fluoro-4-iodophenyl)amino)phenyl)-1,13-dioxo-3-oxa-2,7,14-triazahexadecan-16-oyl)-4-hydroxy-N-(4-(4-methylthiazol-5-yl)benzyl)pyrrolidine-2-carboxamide (CPD-009)

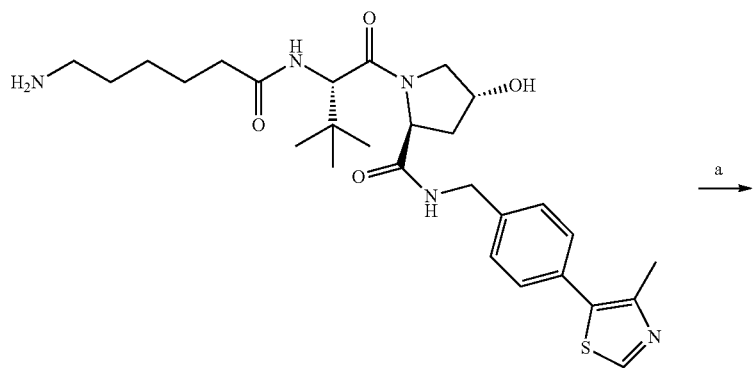

Z15

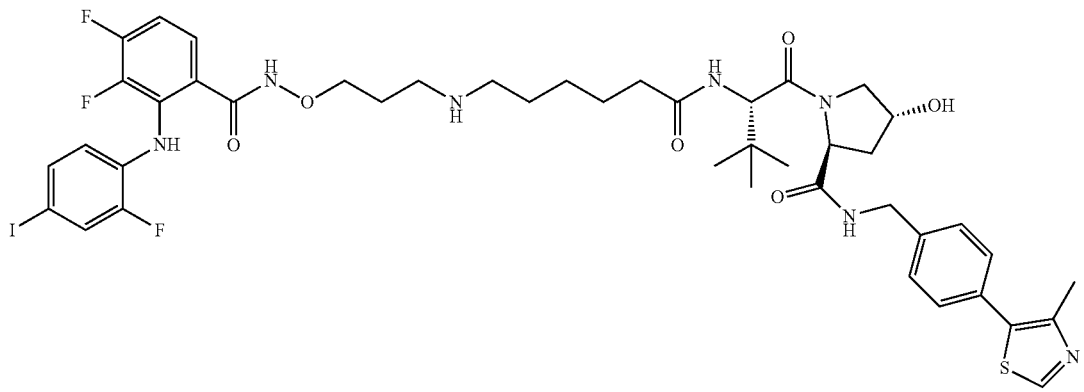

CPD-009

Reagents and conditions: (a) Z5, NaBH$_3$CN, DCM, MeOH, rt, overnight.

CPD-009 was synthesized following the same procedures as CPD-001 as described in Example 3. (0.03 g, yield: 38%). $^1$H NMR (600 MHz, Methanol-$d_4$) δ 8.93 (s, 1H), 7.51-7.45 (m, 3H), 7.42 (d, J=7.8 Hz, 3H), 7.37 (d, J=9.1 Hz, 1H), 7.07 (q, J=8.6 Hz, 1H), 6.63 (td, J=8.7, 4.0 Hz, 1H), 4.64 (s, 1H), 4.61-4.52 (m, 2H), 4.50 (s, 1H), 4.36 (d, J=15.5 Hz, 1H), 4.04 (t, J=5.2 Hz, 2H), 3.91 (d, J=11.0 Hz, 1H), 3.81 (dd, J=11.0, 3.9 Hz, 1H), 3.23 (t, J=5.9 Hz, 2H), 3.04 (t, J=7.9 Hz, 2H), 2.48 (s, 3H), 2.35-2.26 (m, 2H), 2.22 (dd, J=13.2, 7.8 Hz, 1H), 2.09 (ddd, J=13.3, 9.1, 4.4 Hz, 1H), 2.02 (dd, J=11.0, 5.3 Hz, 2H), 1.74 (p, J=7.8 Hz, 2H), 1.65 (p, J=7.2 Hz, 2H), 1.42 (p, J=7.8 Hz, 2H), 1.03 (s, 9H).

Example 12: (2S,4R)-1-((S)-18-(tert-butyl)-1-(3,4-difluoro-2-((2-fluoro-4-iodophenyl)amino)phenyl)-1,16-dioxo-3-oxa-2,7,17-triazanonadecan-19-oyl)-4-hydroxy-N-(4-(4-methylthiazol-5-yl)benzyl)pyrrolidine-2-carboxamide (CPD-010)

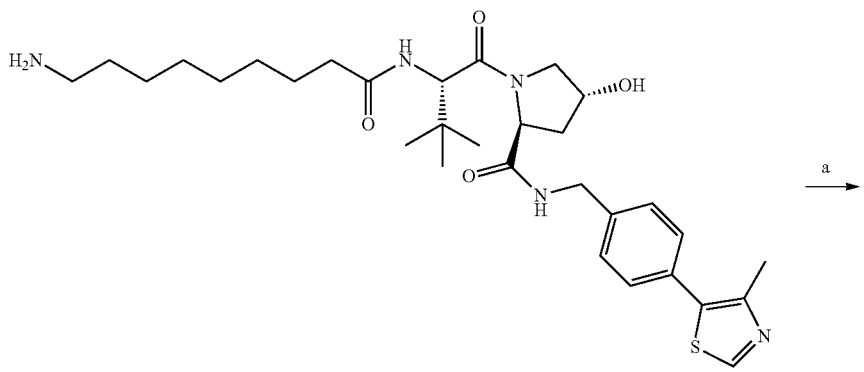

Z16

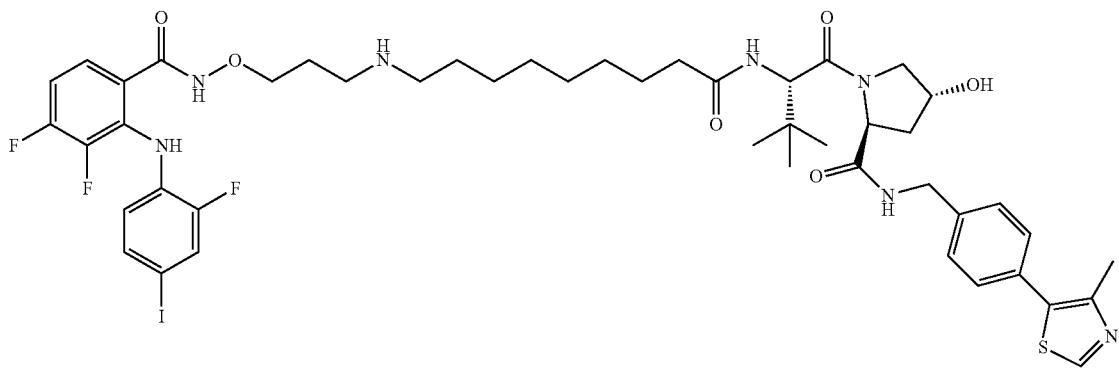

CPD-010

Reagents and conditions: (a) Z5, NaBH$_3$CN, DCM, MeOH, rt, overnight.

CPD-010 was synthesized following the same procedures as CPD-001 as described in Example 3. (0.03 g, yield: 35%). $^1$H NMR (600 MHz, Methanol-$d_4$) δ 8.97 (s, 1H), 7.51-7.45 (m, 3H), 7.45-7.39 (m, 3H), 7.37 (dt, J=8.5, 1.3 Hz, 1H), 7.07 (td, J=9.2, 7.0 Hz, 1H), 6.64 (td, J=8.7, 4.3 Hz, 1H), 4.64 (s, 1H), 4.60-4.55 (m, 1H), 4.54-4.52 (m, 1H), 4.50 (dq, J=4.1, 2.1 Hz, 1H), 4.36 (d, J=15.5 Hz, 1H), 4.07 (dd, J=5.8, 4.5 Hz, 2H), 3.90 (dt, J=11.2, 1.7 Hz, 1H), 3.81 (dd, J=10.9, 3.9 Hz, 1H), 3.23 (t, J=5.8 Hz, 2H), 3.10-2.90 (m, 2H), 2.48 (s, 3H), 2.33-2.26 (m, 1H), 2.25-2.18 (m, 2H), 2.08 (ddd, J=13.3, 9.1, 4.5 Hz, 1H), 2.02 (dt, J=10.2, 5.1 Hz, 2H), 1.72 (p, J=7.8 Hz, 2H), 1.59 (q, J=7.2 Hz, 2H), 1.42-1.36 (d, J=7.9 Hz, 2H), 1.35-1.29 (m, 6H), 1.03 (s, 9H).

Example 13: (2S,4R)-1-((S)-17-(tert-butyl)-1-(3,4-difluoro-2-((2-fluoro-4-iodophenyl)amino)phenyl)-1,15-dioxo-3-oxa-2,7,16-triazaoctadecan-18-oyl)-4-hydroxy-N-(4-(4-methylthiazol-5-yl)benzyl)pyrrolidine-2-carboxamide (CPD-011)

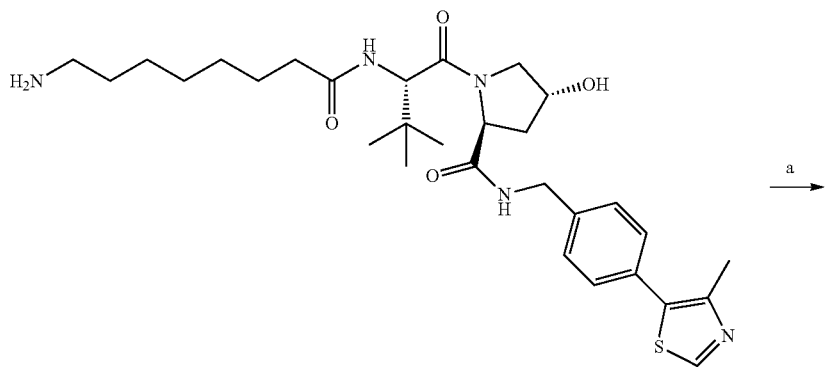

Z17

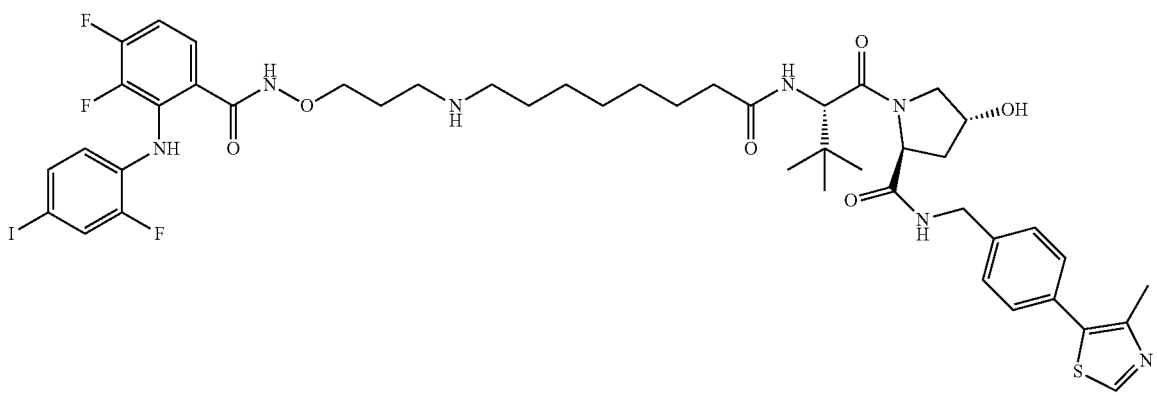

CPD-011

Reagents and conditions: (a) Z5, NaBH$_3$CN, DCM, MeOH, rt, overnight.

CPD-011 was synthesized following the same procedures as CPD-001 as described in Example 3. (0.03 g, yield: 39%). $^1$H NMR (600 MHz, Methanol-$d_4$) δ 8.92 (s, 1H), 7.52-7.45 (m, 3H), 7.44-7.39 (m, 3H), 7.38 (dt, J=8.6, 1.3 Hz, 1H), 7.07 (td, J=9.2, 7.0 Hz, 1H), 6.63 (td, J=8.7, 4.3 Hz, 1H), 4.67-4.62 (m, 1H), 4.60-4.55 (m, 1H), 4.54 (d, J=12.9 Hz, 1H), 4.51-4.48 (m, 1H), 4.36 (d, J=15.5 Hz, 1H), 4.06 (t, J=5.1 Hz, 2H), 3.90 (d, J=11.0 Hz, 1H), 3.81 (dd, J=11.0, 3.9 Hz, 1H), 3.23 (t, J=5.9 Hz, 2H), 3.09-2.97 (m, 2H), 2.48 (s, 3H), 2.32-2.27 (m, 1H), 2.26-2.20 (m, 2H), 2.08 (ddd, J=13.3, 9.2, 4.5 Hz, 1H), 2.02 (dt, J=10.1, 5.0 Hz, 2H), 1.72 (p, J=7.7 Hz, 2H), 1.61 (dp, J=14.5, 7.1 Hz, 2H), 1.43-1.38 (m, 2H), 1.38-1.28 (m, 4H), 1.03 (s, 9H).

Example 14: (2S,4R)-1-((S)-17-(tert-butyl)-1-(3,4-difluoro-2-((2-fluoro-4-iodophenyl)amino)phenyl)-1,15-dioxo-3,10,13-trioxa-2,7,16-triazaoctadecan-18-oyl)-4-hydroxy-N-(4-(4-methylthiazol-5-yl)benzyl)pyrrolidine-2-carboxamide (CPD-012)

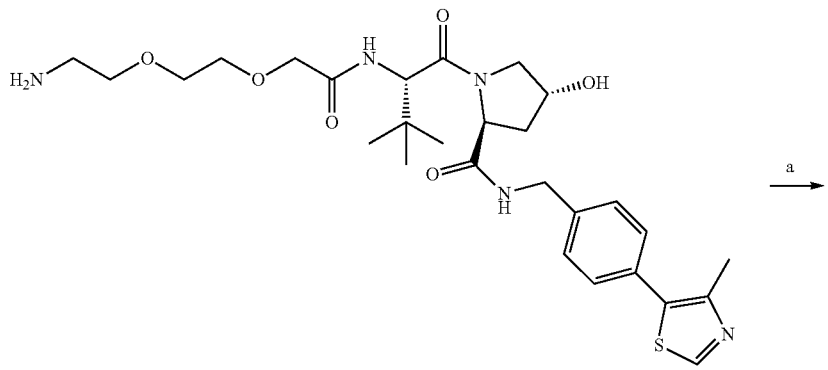

Z18

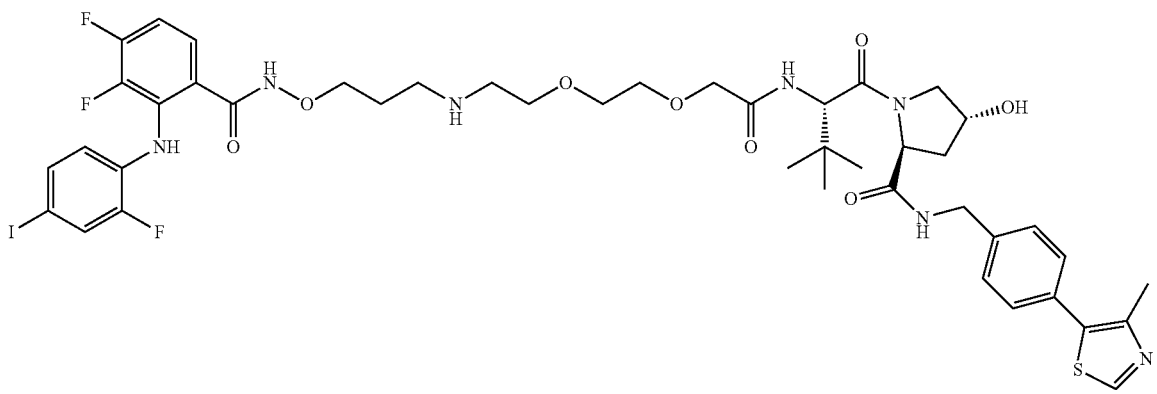

CPD-012

Reagents and conditions: (a) Z5, NaBH$_3$CN, DCM, MeOH, rt, overnight.

CPD-012 was synthesized following the same procedures as CPD-001 as described in Example 3. (0.03 g, yield: 46%). ¹H NMR (600 MHz, Methanol-$d_4$) δ 8.95 (s, 1H), 7.50-7.45 (m, 2H), 7.45-7.41 (m, 3H), 7.40-7.35 (m, 2H), 7.16-6.99 (m, 1H), 6.63 (td, J=8.8, 4.0 Hz, 1H), 4.77-4.70 (m, 1H), 4.59-4.53 (m, 1H), 4.50 (d, J=6.0 Hz, 1H), 4.48-4.38 (m, 2H), 4.08-4.00 (m, 3H), 3.96 (d, J=15.8 Hz, 1H), 3.88 (d, J=11.2 Hz, 1H), 3.81 (dt, J=9.8, 3.8 Hz, 3H), 3.67-3.61 (m, 4H), 3.30-3.23 (m, 3H), 2.47 (s, 3H), 2.33-2.21 (m, 1H), 2.14-2.06 (m, 2H), 2.04 (d, J=14.1 Hz, 2H), 1.03 (s, 9H).

Example 15: (2S,4R)-1-((S)-19-(tert-butyl)-1-(3,4-difluoro-2-((2-fluoro-4-iodophenyl)amino)phenyl)-1,17-dioxo-3-oxa-2,7,18-triazaicosan-20-oyl)-4-hydroxy-N-(4-(4-methylthiazol-5-yl)benzyl)pyrrolidine-2-carboxamide (CPD-013)

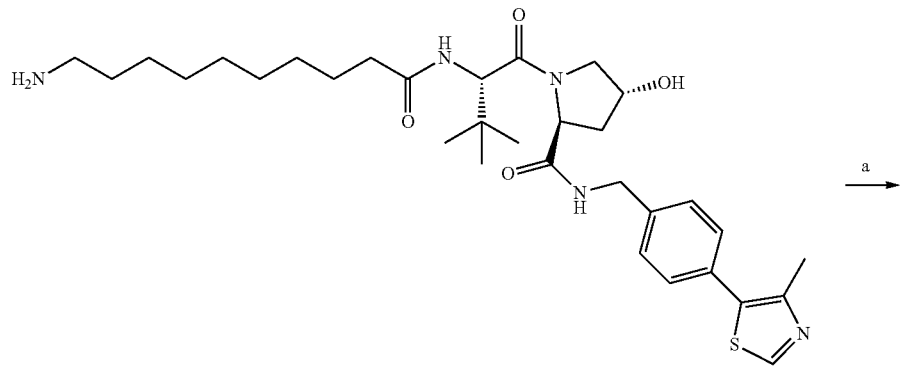

Z19

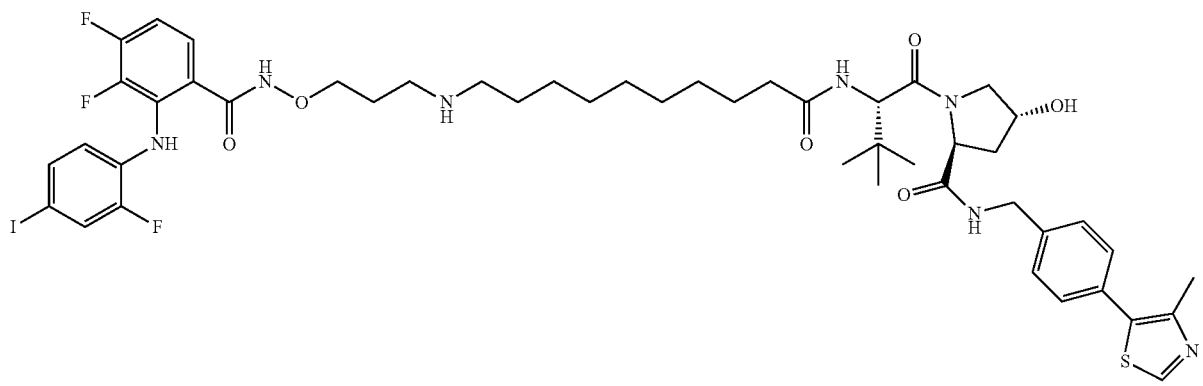

CPD-013

Reagents and conditions: (a) Z5, NaBH₃CN, DCM, MeOH, rt, overnight.

CPD-013 was synthesized following the same procedures as CPD-001 as described in Example 3. (0.09 g, yield: 46%). ¹H NMR (600 MHz, Methanol-$d_4$) δ 8.96 (s, 1H), 7.50-7.44 (m, 3H), 7.44-7.39 (m, 3H), 7.38 (dt, J=8.5, 1.3 Hz, 1H), 7.07 (td, J=9.2, 7.0 Hz, 1H), 6.64 (td, J=8.7, 4.3 Hz, 1H), 4.63 (s, 1H), 4.59-4.55 (m, 1H), 4.54 (d, J=12.1 Hz, 1H), 4.50 (dd, J=4.3, 2.2 Hz, 1H), 4.36 (d, J=15.5 Hz, 1H), 4.11-4.02 (m, 2H), 3.90 (d, J=11.0 Hz, 1H), 3.80 (dd, J=11.0, 3.9 Hz, 1H), 3.24 (t, J=5.9 Hz, 2H), 3.08-2.99 (m, 2H), 2.48 (s, 3H), 2.29 (ddd, J=15.2, 8.4, 7.0 Hz, 1H), 2.26-2.19 (m, 2H), 2.08 (ddd, J=13.3, 9.1, 4.5 Hz, 1H), 2.02 (dt, J=10.3, 5.1 Hz, 2H), 1.71 (p, J=7.7 Hz, 2H), 1.65-1.53 (m, 2H), 1.42-1.36 (m, 2H), 1.34-1.25 (m, 8H), 1.03 (s, 9H).

Example 16: (2S,4R)-1-((S)-20-(tert-butyl)-1-(3,4-difluoro-2-((2-fluoro-4-iodophenyl)amino)phenyl)-1,18-dioxo-3-oxa-2,7,19-triazahenicosan-21-oyl)-4-hydroxy-N-(4-(4-methylthiazol-5-yl)benzyl)pyrrolidine-2-carboxamide (CPD-014)

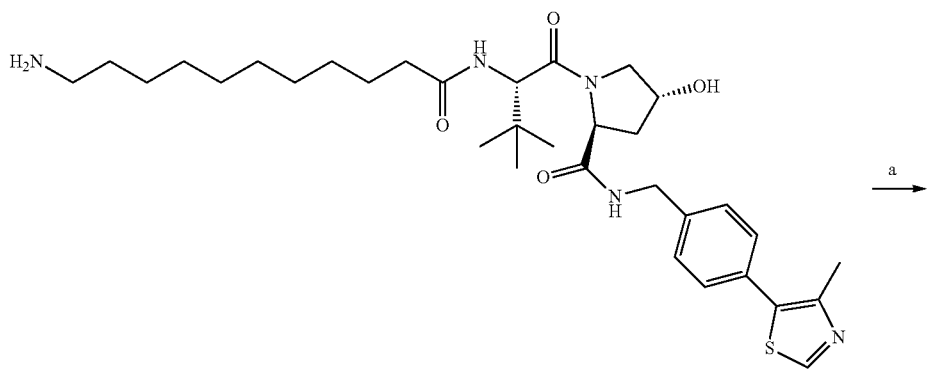

Z20

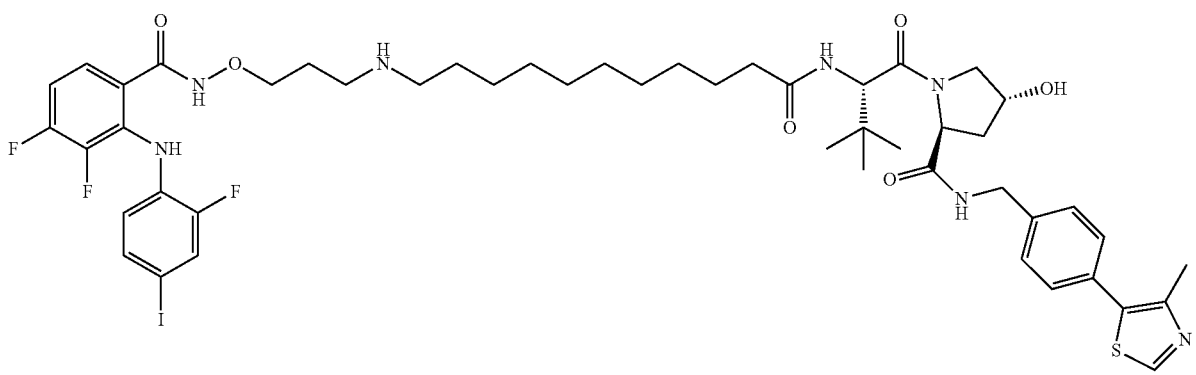

CPD-014

Reagents and conditions: (a) Z5, NaBH₃CN, DCM, MeOH, rt, overnight.

CPD-014 was synthesized following the same procedures as CPD-001 as described in Example 3. (0.08 g, yield: 40%). ¹H NMR (600 MHz, Methanol-$d_4$) δ 8.94 (s, 1H), 7.50-7.44 (m, 3H), 7.44-7.39 (m, 3H), 7.38 (dt, J=8.5, 1.3 Hz, 1H), 7.07 (td, J=9.2, 6.9 Hz, 1H), 6.64 (td, J=8.7, 4.3 Hz, 1H), 4.64 (s, 1H), 4.59-4.55 (m, 1H), 4.54 (d, J=12.6 Hz, 1H), 4.51-4.49 (m, 1H), 4.36 (d, J=15.5 Hz, 1H), 4.13-4.03 (m, 2H), 3.90 (d, J=11.0 Hz, 1H), 3.81 (dd, J=11.0, 3.9 Hz, 1H), 3.24 (t, J=5.8 Hz, 2H), 3.10-2.97 (m, 2H), 2.48 (s, 3H), 2.32-2.26 (m, 1H), 2.26-2.19 (m, 2H), 2.08 (ddd, J=13.4, 9.2, 4.5 Hz, 1H), 2.05-1.99 (m, 2H), 1.71 (p, J=7.7 Hz, 2H), 1.59 (tq, J=14.3, 6.9 Hz, 2H), 1.44-1.35 (m, 2H), 1.32-1.29 (m, 6H), 1.29-1.26 (m, 4H), 1.03 (s, 9H).

Example 17: (2S,4R)-1-((S)-20-(tert-butyl)-1-(3,4-difluoro- Example 17: 2-((2-fluoro-4-iodophenyl)amino)phenyl)-1,18-dioxo-3,10,13,16-tetraoxa-2,7,19-triazahenicosan-21-oyl)-4-hydroxy-N-(4-(4-methylthiazol-5-yl)benzyl)pyrrolidine-2-carboxamide (CPD-015)

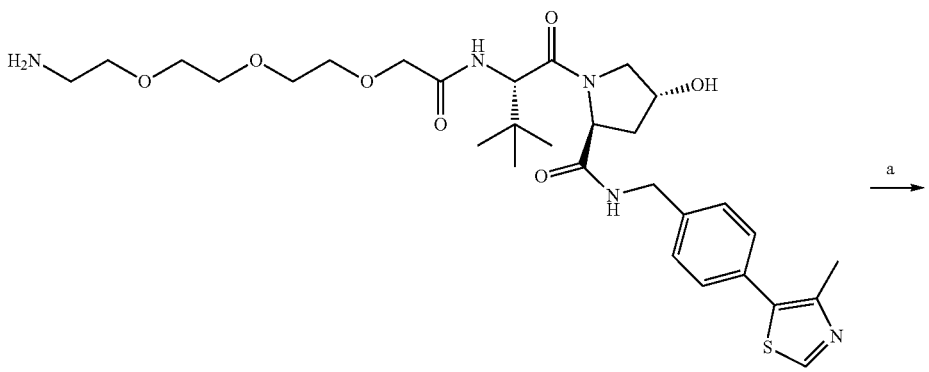

Z21

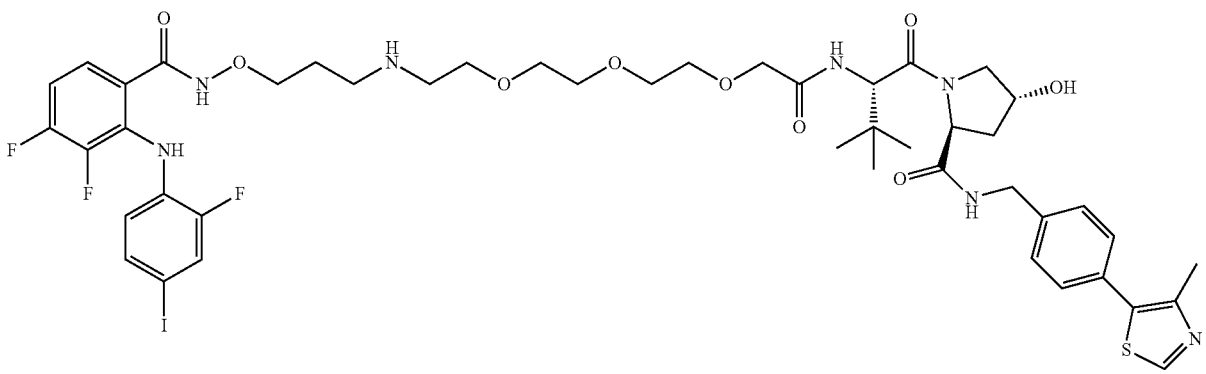

CPD-015

Reagents and conditions: (a) Z5, NaBH₃CN, DCM, MeOH, rt, overnight.

CPD-015 was synthesized following the same procedures as CPD-001 as described in Example 3. (0.06 g, yield: 47%). $^1$H NMR (600 MHz, Methanol-$d_4$) δ 8.99 (s, 1H), 7.49-7.45 (m, 3H), 7.42 (d, J=8.2 Hz, 2H), 7.41-7.38 (m, 1H), 7.37 (dt, J=8.4, 1.3 Hz, 1H), 7.05 (td, J=9.2, 7.0 Hz, 1H), 6.64 (td, J=8.8, 4.2 Hz, 1H), 4.68 (s, 1H), 4.56 (dd, J=7.9, 1.7 Hz, 1H), 4.53 (d, J=11.4 Hz, 1H), 4.51-4.48 (m, 1H), 4.39 (d, J=15.5 Hz, 1H), 4.14-4.00 (m, 4H), 3.88 (d, J=11.1 Hz, 1H), 3.81 (dd, J=10.9, 3.8 Hz, 1H), 3.77 (dd, J=5.7, 4.3 Hz, 2H), 3.71-3.65 (m, 2H), 3.63-3.58 (m, 4H), 3.58-3.55 (m, 2H), 3.30-3.23 (m, 4H), 2.48 (s, 3H), 2.24 (ddt, J=13.2, 7.5, 1.8 Hz, 1H), 2.08 (ddd, J=13.4, 9.5, 4.3 Hz, 1H), 2.05-2.00 (m, 2H), 1.04 (s, 9H).

Example 18: (2S,4R)-1-((S)-21-(tert-butyl)-1-(3,4-difluoro-2-((2-fluoro-4-iodophenyl)amino)phenyl)-1,19-dioxo-3,10,13,16-tetraoxa-2,7,20-triazadocosan-22-oyl)-4-hydroxy-N-(4-(4-methylthiazol-5-yl)benzyl)pyrrolidine-2-carboxamide (CPD-016)

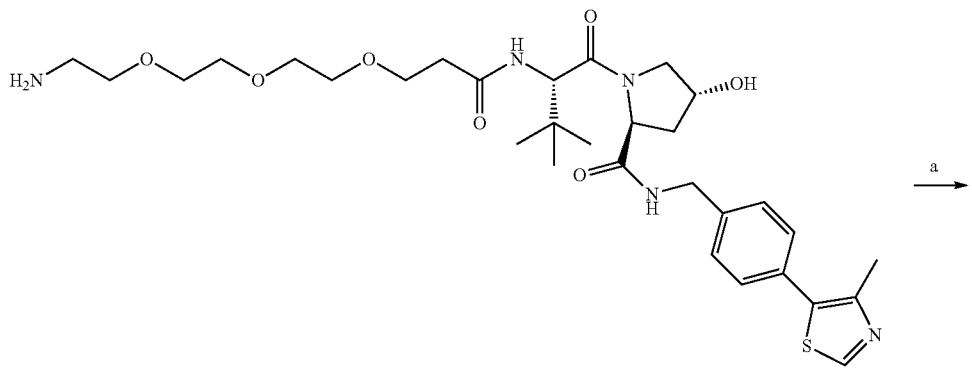

Z22

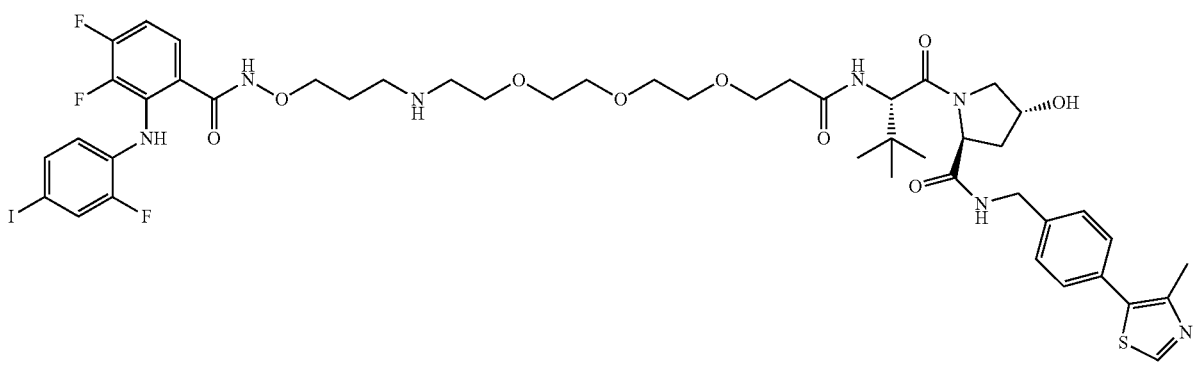

CPD-016

Reagents and conditions: (a) Z5, NaBH$_3$CN, DCM, MeOH, rt, overnight.

CPD-016 was synthesized following the same procedures as CPD-001 as described in Example 3. (0.05 g, yield: 51%). $^1$H NMR (600 MHz, Methanol-$d_4$) δ 9.02 (s, 1H), 7.51-7.44 (m, 3H), 7.43-7.39 (m, 3H), 7.38 (dt, J=8.5, 1.3 Hz, 1H), 7.18-6.99 (m, 1H), 6.64 (td, J=8.7, 4.2 Hz, 1H), 4.64 (s, 1H), 4.59-4.55 (m, 1H), 4.53 (d, J=15.4 Hz, 1H), 4.49 (d, J=3.3 Hz, 1H), 4.37 (d, J=15.5 Hz, 1H), 4.15-4.02 (m, 2H), 3.89 (d, J=11.0 Hz, 1H), 3.80 (dd, J=11.0, 3.9 Hz, 1H), 3.78-3.75 (m, 2H), 3.74-3.66 (m, 2H), 3.60-3.57 (dd, J=5.8, 2.2 Hz, 3H), 3.56-3.53 (m, 5H), 3.30-3.25 (m, 4H), 2.61-2.52 (m, 1H), 2.51-2.39 (m, 4H), 2.27-2.19 (m, 1H), 2.09 (dt, J=8.3, 4.3 Hz, 1H), 2.05 (td, J=6.7, 4.5 Hz, 2H), 1.03 (s, 9H).

Example 19: (2S,4R)-1-((S)-24-(tert-butyl)-1-(3,4-difluoro-2-((2-fluoro-4-iodophenyl)amino)phenyl)-1,22-dioxo-3,10,13,16,19-pentaoxa-2,7,23-triazapentacosan-25-oyl)-4-hydroxy-N-(4-(4-methylthiazol-5-yl)benzyl)pyrrolidine-2-carboxamide (CPD-017)

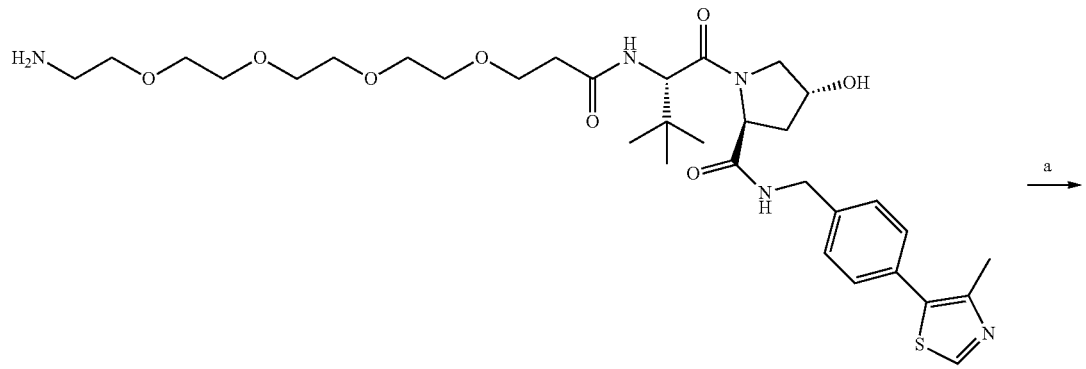

Z23

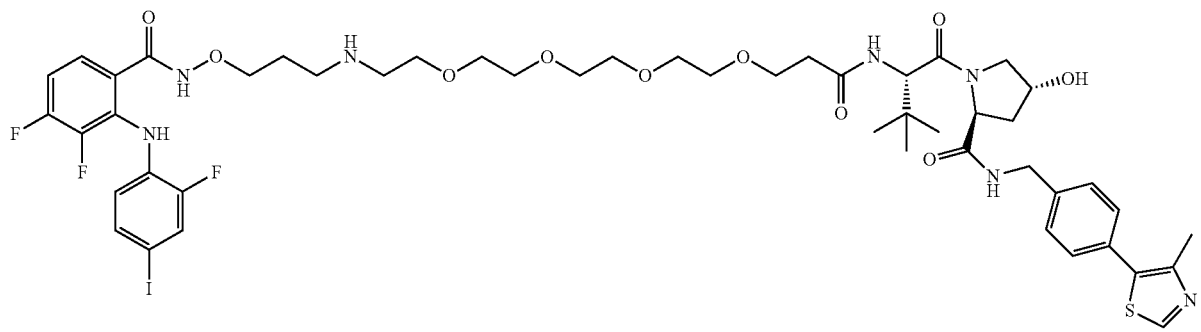

CPD-017

Reagents and conditions: (a) Z5, NaBH$_3$CN, DCM, MeOH, rt, overnight.

CPD-017 was synthesized following the same procedures as CPD-001 as described in Example 3. (0.07 g, yield: 52%). ¹H NMR (600 MHz, Methanol-$d_4$) δ 8.93 (s, 1H), 7.50-7.44 (m, 3H), 7.43-7.39 (m, 3H), 7.38 (dt, J=8.5, 1.3 Hz, 1H), 7.06 (td, J=9.1, 6.8 Hz, 1H), 6.64 (td, J=8.7, 4.0 Hz, 1H), 4.68-4.63 (m, 1H), 4.58-4.54 (m, 1H), 4.54-4.51 (m, 1H), 4.51-4.48 (m, 1H), 4.39-4.33 (m, 1H), 4.11-4.03 (m, 2H), 3.93-3.86 (m, 1H), 3.83-3.76 (m, 3H), 3.75-3.67 (m, 2H), 3.63-3.58 (m, 6H), 3.57 (dq, J=5.7, 3.2, 2.6 Hz, 6H), 3.30-3.25 (m, 4H), 2.57 (ddd, J=15.2, 7.2, 5.2 Hz, 1H), 2.50-2.41 (m, 4H), 2.26-2.19 (m, 1H), 2.09 (dt, J=8.4, 4.2 Hz, 11H), 2.07-2.02 (m, 2H), 1.03 (s, 9H).

Example 20: (2S,4R)-1-((S)-27-(tert-butyl)-1-(3,4-difluoro-2-((2-fluoro-4-iodophenyl)amino)phenyl)-1,25-dioxo-3,10,13,16,19,22-hexaoxa-2,7,26-triazaoctacosan-28-oyl)-4-hydroxy-N-(4-(4-methylthiazol-5-yl)benzyl)pyrrolidine-2-carboxamide (CPD-018)

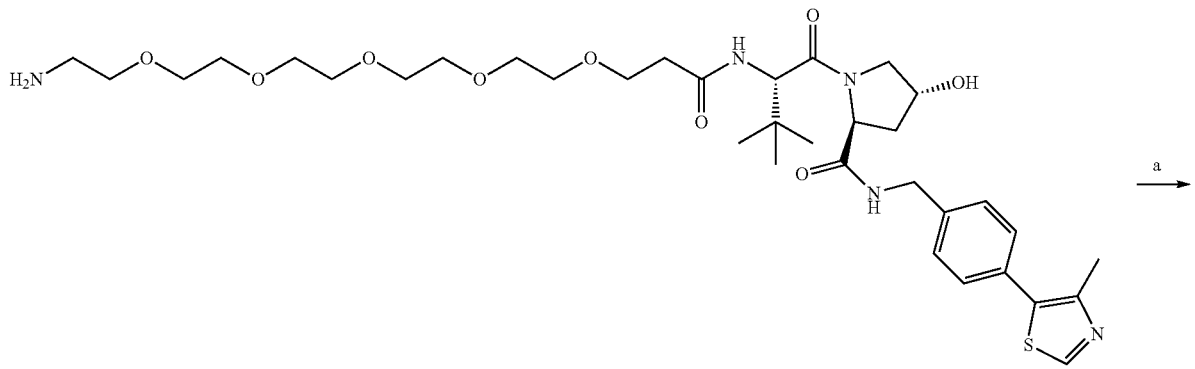

Z24

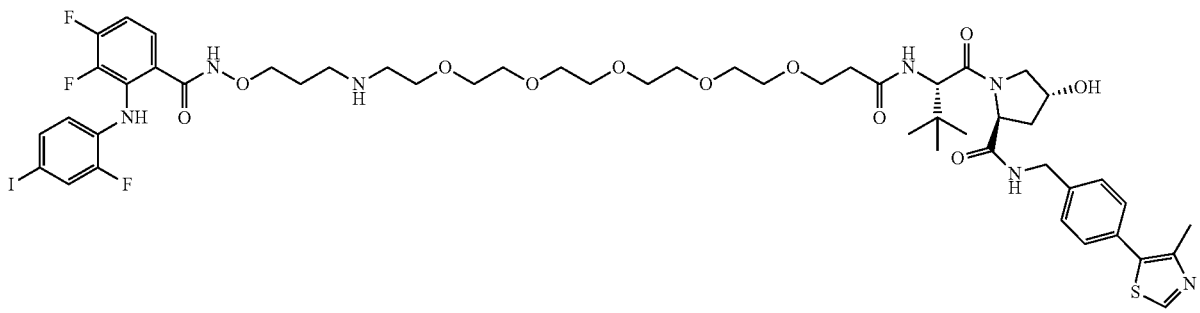

CPD-018

Reagents and conditions: (a) Z5, NaBH₃CN, DCM, MeOH, rt, overnight.

CPD-018 was synthesized following the same procedures as CPD-001 as described in Example 3. (0.07 g, yield: 52%). $^1$H NMR (600 MHz, Methanol-$d_4$) δ 8.94 (s, 1H), 7.50-7.44 (m, 3H), 7.43-7.39 (m, 3H), 7.39-7.36 (m, 1H), 7.06 (q, J=8.7 Hz, 1H), 6.65 (td, J=8.7, 4.2 Hz, 1H), 4.64 (s, 1H), 4.59-4.55 (m, 1H), 4.53 (d, J=10.7 Hz, 1H), 4.51-4.48 (m, 1H), 4.36 (d, J=15.5 Hz, 1H), 4.06 (t, J=5.1 Hz, 2H), 3.99-3.92 (m, 1H), 3.89 (d, J=11.0 Hz, 1H), 3.84-3.76 (m, 3H), 3.75-3.68 (m, 2H), 3.65-3.58 (m, 10H), 3.57-3.54 (m, 6H), 3.29-3.24 (m, 2H), 2.61-2.54 (m, 1H), 2.51-2.43 (m, 4H), 2.22 (dd, J=13.2, 7.8 Hz, 1H), 2.09 (dt, J=8.4, 4.3 Hz, 1H), 2.07-2.01 (m, 2H), 1.39-1.27 (m, 1H), 1.03 (s, 9H).

Example 21: N-(3-((2-(2-((2-(2,6-dioxopiperidin-3-yl)-1,3-dioxoisoindolin-4-yl)amino)ethoxy)ethyl)amino)propoxy)-3,4-difluoro-2-((2-fluoro-4-iodophenyl)amino)benzamide

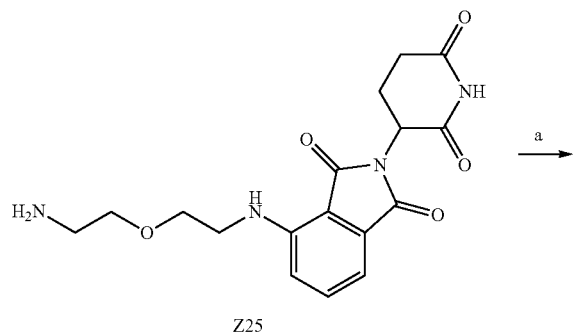

Z25

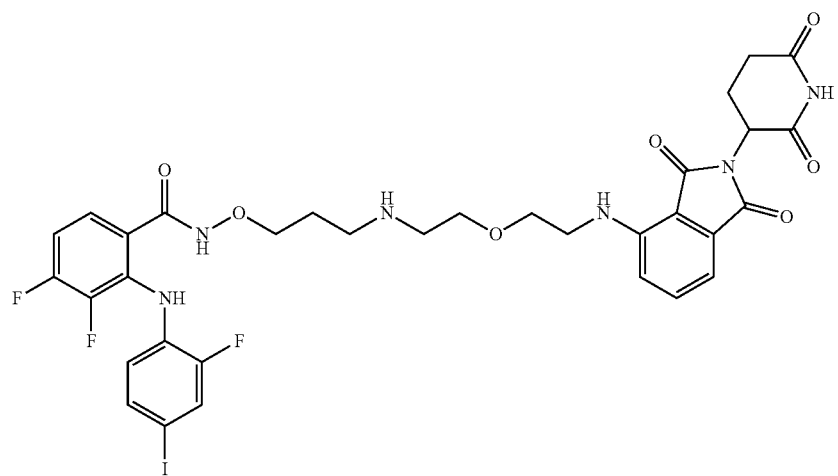

CPD-019

Reagents and conditions: (a) Z5, NaBH$_3$CN, DCM, MeOH, rt, overnight.

CPD-019 was synthesized following the same procedures as CPD-001 as described in Example 3. (0.07 g, yield: 52%). ¹H NMR (600 MHz, Methanol-$d_4$) δ 7.46 (dd, J=8.6, 7.1 Hz, 1H), 7.38 (dd, J=10.7, 2.0 Hz, 1H), 7.35 (dd, J=7.7, 2.3 Hz, 1H), 7.26 (dt, J=8.3, 1.3 Hz, 1H), 6.96 (d, J=7.0 Hz, 1H), 6.95-6.88 (m, 2H), 6.57 (td, J=8.8, 4.7 Hz, 1H), 4.98-4.93 (m, 1H), 4.15-4.07 (m, 2H), 3.93-3.83 (m, 2H), 3.77 (ddd, J=6.0, 4.5, 1.9 Hz, 2H), 3.45 (dd, J=5.7, 4.2 Hz, 2H), 3.34 (t, J=5.2 Hz, 4H), 2.82 (ddd, J=17.5, 13.8, 5.3 Hz, 1H), 2.71 (ddd, J=17.5, 4.5, 2.7 Hz, 1H), 2.60 (qd, J=13.1, 4.5 Hz, 1H), 2.09-2.03 (m, 2H), 2.00 (dtd, J=13.1, 5.3, 3.0 Hz, 1H).

Example 22: N-(3-((2-(2-(2-((2-(2,6-dioxopiperidin-3-yl)-1,3-dioxoisoindolin-4-yl)amino)ethoxy)ethoxy)ethyl)amino)propoxy)-3,4-difluoro-2-((2-fluoro-4-iodophenyl)amino)benzamide (CPD-020)

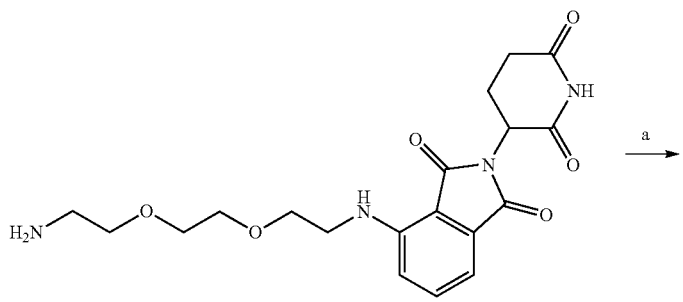

Z26

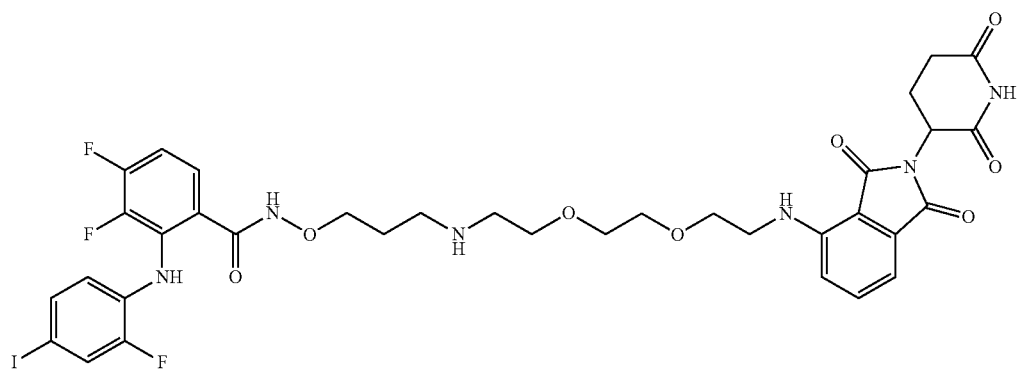

CPD-020

Reagents and conditions: (a) Z5, NaBH₃CN, DCM, MeOH, rt, overnight.

CPD-020 was synthesized following the same procedures as CPD-001 as described in Example 3. (0.05 g, yield: 48%). ¹H NMR (600 MHz, Methanol-d₄) δ 7.54 (dd, J=8.6, 7.1 Hz, 1H), 7.44 (dd, J=10.7, 1.9 Hz, 1H), 7.39-7.31 (m, 2H), 7.09-6.97 (m, 3H), 6.63 (td, J=8.7, 4.1 Hz, 1H), 5.03 (dd, J=12.8, 5.5 Hz, 1H), 4.04 (t, J=5.0 Hz, 2H), 3.81 (t, J=5.0 Hz, 2H), 3.67 (t, J=5.1 Hz, 2H), 3.66-3.58 (m, 4H), 3.45 (dd, J=5.8, 4.5 Hz, 2H), 3.27 (t, J=6.0 Hz, 2H), 3.24 (t, J=5.1 Hz, 2H), 2.83 (ddd, J=17.5, 13.9, 5.3 Hz, 1H), 2.76-2.56 (m, 2H), 2.12-2.04 (m, 1H), 2.01 (dt, J=10.5, 5.2 Hz, 2H).

Example 23: N-((1-((2-(2,6-dioxopiperidin-3-yl)-1,3-dioxoisoindolin-4-yl)amino)-3,6,9-trioxa-12-azapentadecan-15-yl)oxy)-3,4-difluoro-2-((2-fluoro-4-iodophenyl)amino)benzamide (CPD-021)

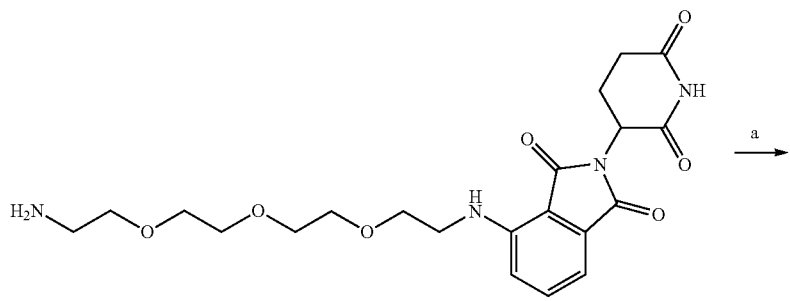

Z27

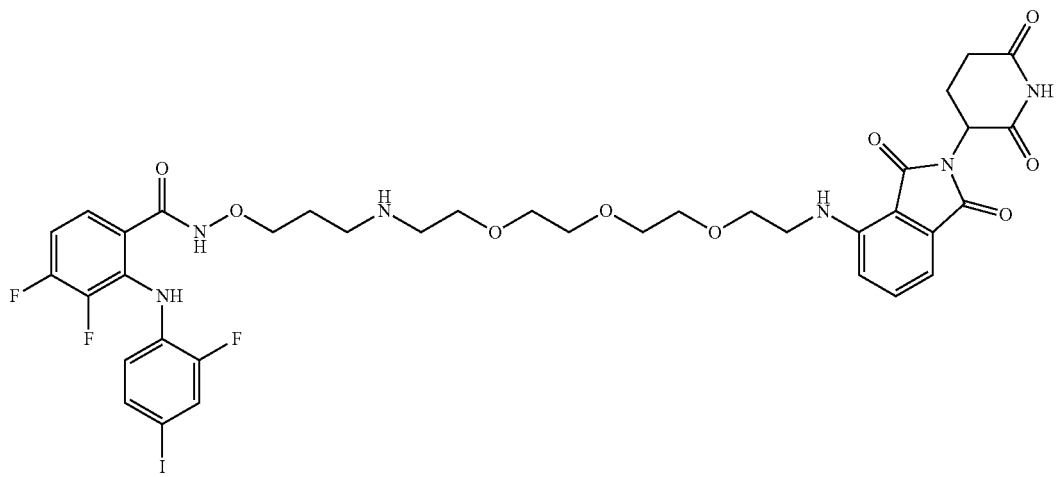

CPD-021

Reagents and conditions: (a) Z5, NaBH₃CN, DCM, MeOH, rt, overnight.

CPD-021 was synthesized following the same procedures as CPD-001 as described in Example 3. (0.05 g, yield: 44%). $^1$H NMR (600 MHz, Methanol-$d_4$) δ 7.54 (dd, J=8.5, 7.0 Hz, 1H), 7.46 (dd, J=10.6, 1.9 Hz, 1H), 7.40-7.31 (m, 2H), 7.04 (dt, J=15.9, 8.7 Hz, 3H), 6.63 (td, J=8.7, 4.1 Hz, 1H), 5.04 (dd, J=12.8, 5.5 Hz, 1H), 4.03 (t, J=5.1 Hz, 2H), 3.78-3.74 (m, 2H), 3.70 (t, J=5.2 Hz, 2H), 3.65-3.60 (m, 4H), 3.60 (s, 4H), 3.48 (t, J=5.1 Hz, 2H), 3.26 (t, J=6.0 Hz, 2H), 3.24 (t, J=5.0 Hz, 2H), 2.84 (ddd, J=17.6, 14.0, 5.3 Hz, 1H), 2.73 (ddd, J=17.5, 4.3, 2.6 Hz, 1H), 2.71-2.65 (m, 1H), 2.17-2.05 (m, 1H), 2.04-1.97 (m, 2H).

Example 24: N-((1-((2-(2,6-dioxopiperidin-3-yl)-1,3-dioxoisoindolin-4-yl)amino)-3,6,9,12-tetraoxa-15-azaoctadecan-18-yl)oxy)-3,4-difluoro-2-((2-fluoro-4-iodophenyl)amino)benzamide (CPD-022)

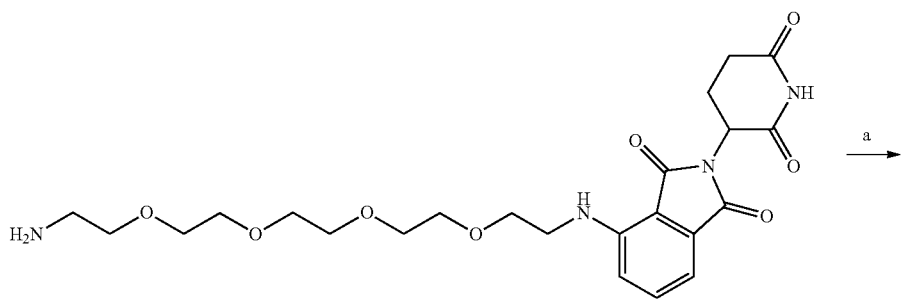

Z28

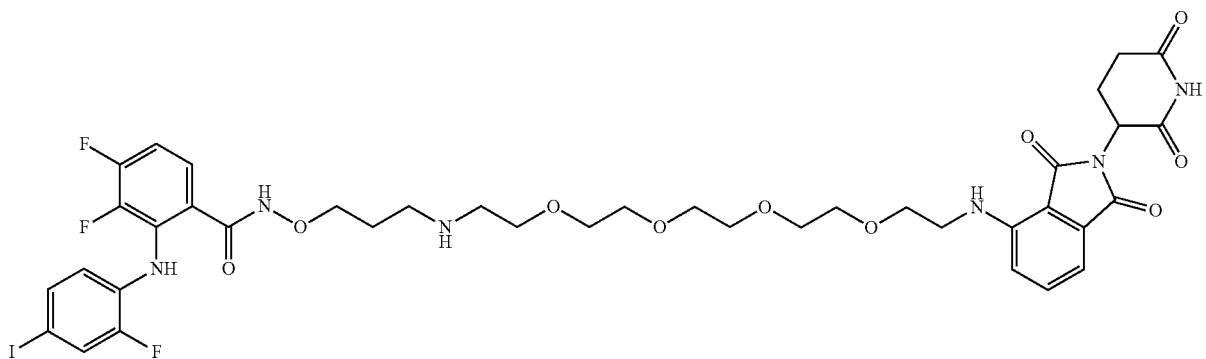

CPD-022

Reagents and conditions: (a) Z5, NaBH$_3$CN, DCM, MeOH, rt, overnight.

CPD-022 was synthesized following the same procedures as CPD-001 as described in Example 3. (0.05 g, yield: 40%). ¹H NMR (600 MHz, Methanol-d₄) δ 7.54 (dd, J=8.6, 7.1 Hz, 1H), 7.47 (dd, J=10.7, 1.9 Hz, 1H), 7.43-7.31 (m, 2H), 7.10-6.98 (m, 3H), 6.64 (td, J=8.7, 4.1 Hz, 1H), 5.04 (dd, J=12.7, 5.6 Hz, 1H), 4.04 (t, J=5.2 Hz, 2H), 3.80-3.74 (m, 2H), 3.71 (t, J=5.2 Hz, 2H), 3.67-3.62 (m, 4H), 3.60 (dt, J=3.8, 2.6 Hz, 2H), 3.59-3.54 (m, 6H), 3.49 (t, J=5.2 Hz, 2H), 3.28 (t, J=6.0 Hz, 2H), 3.25 (t, J=5.0 Hz, 2H), 2.85 (ddd, J=17.6, 14.0, 5.3 Hz, 1H), 2.76-2.72 (m, 1H), 2.69 (td, J=13.3, 4.5 Hz, 1H), 2.09 (ddt, J=13.1, 5.5, 2.8 Hz, 1H), 2.02 (dt, J=10.5, 5.2 Hz, 2H).

Example 25: N-((1-((2-(2,6-dioxopiperidin-3-yl)-1,3-dioxoisoindolin-4-yl)amino)-3,6,9,12,15-pentaoxa-18-azahenicosan-21-yl)oxy)-3,4-difluoro-2-((2-fluoro-4-iodophenyl)amino)benzamide (CPD-023)

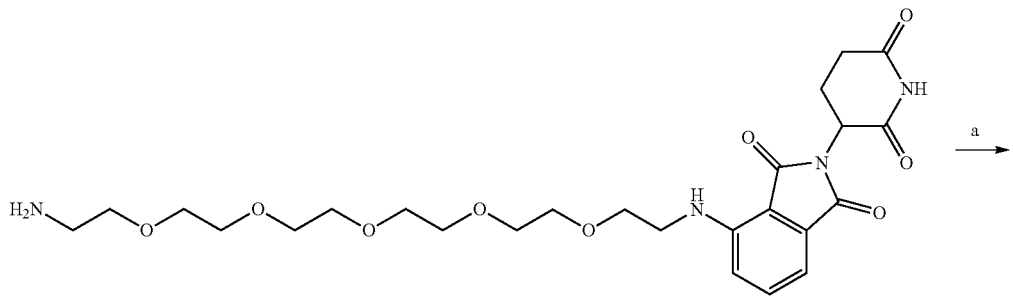

Z29

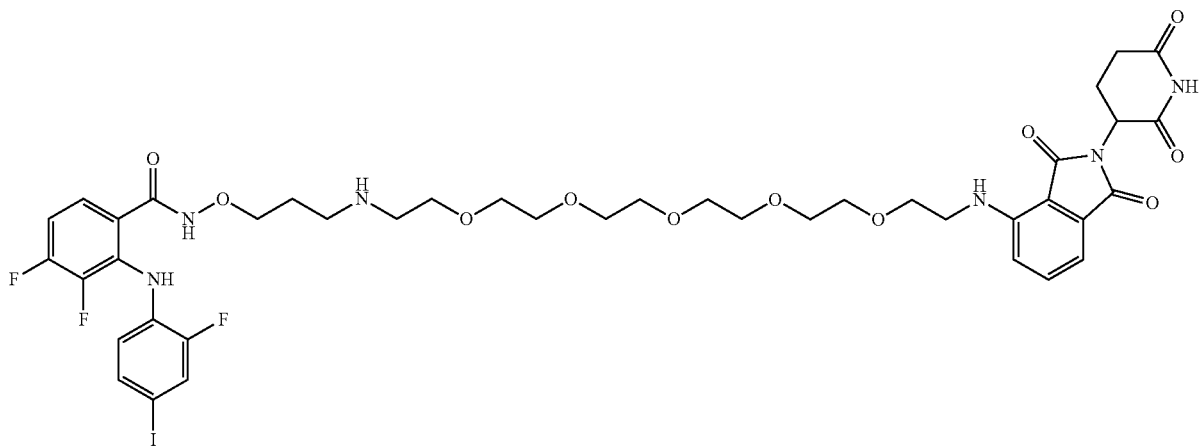

CPD-023

Reagents and conditions: (a) Z5, NaBH₃CN, DCM, MeOH, rt, overnight.

CPD-023 was synthesized following the same procedures as CPD-001 as described in Example 3. (0.05 g, yield: 38%). ¹H NMR (600 MHz, Methanol-$d_4$) δ 7.54 (dd, J=8.5, 7.1 Hz, 1H), 7.47 (dd, J=10.7, 1.9 Hz, 1H), 7.40 (ddd, J=9.0, 5.3, 1.7 Hz, 1H), 7.37 (ddd, J=8.5, 2.0, 1.0 Hz, 1H), 7.11-6.99 (m, 3H), 6.64 (td, J=8.7, 4.2 Hz, 1H), 5.04 (dd, J=12.8, 5.5 Hz, 1H), 4.05 (t, J=5.2 Hz, 2H), 3.79-3.75 (m, 2H), 3.71 (t, J=5.2 Hz, 2H), 3.65 (s, 4H), 3.64-3.61 (m, 2H), 3.60-3.58 (m, 2H), 3.58-3.56 (m, 4H), 3.54 (dd, J=6.0, 2.7 Hz, 3H), 3.48 (t, J=5.2 Hz, 2H), 3.29 (t, J=6.1 Hz, 2H), 3.26 (t, J=5.1 Hz, 2H), 2.85 (ddd, J=17.6, 14.0, 5.3 Hz, 1H), 2.75 (dd, J=4.4, 2.6 Hz, 1H), 2.74-2.70 (m, 1H), 2.70-2.66 (m, 1H), 2.15-2.07 (m, 1H), 2.06-1.99 (m, 2H).

Example 26: N-(3-((2-((2-(2,6-dioxopiperidin-3-yl)-1,3-dioxoisoindolin-4-yl)amino)ethyl)amino)propoxy)-3,4-difluoro-2-((2-fluoro-4-iodophenyl)amino)benzamide (CPD-024)

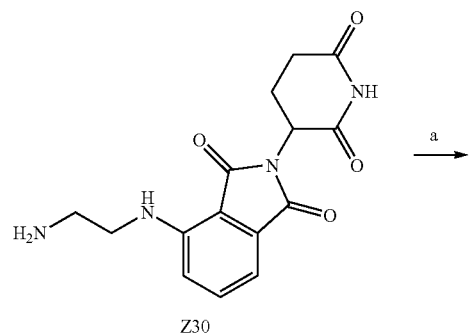

Z30

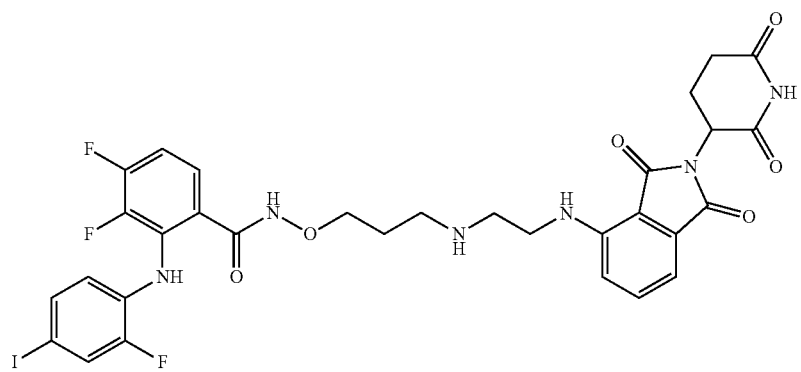

CPD-024

Reagents and conditions: (a) Z5, NaBH₃CN, DCM, MeOH, rt, overnight.

CPD-024 was synthesized following the same procedures as CPD-001 as described in Example 3. (0.05 g, yield: 37%). ¹H NMR (600 MHz, Methanol-$d_4$) δ 7.54 (dd, J=8.6, 7.1 Hz, 1H), 7.37-7.34 (m, 1H), 7.32 (dd, J=10.7, 1.9 Hz, 1H), 7.29 (dt, J=8.6, 1.2 Hz, 1H), 7.09 (d, J=8.5 Hz, 1H), 7.06-7.00 (m, 2H), 6.58 (td, J=8.7, 4.6 Hz, 1H), 4.95-4.91 (m, 1H), 4.19-4.02 (m, 2H), 3.77 (td, J=5.7, 2.3 Hz, 2H), 3.37 (t, J=5.8 Hz, 2H), 3.33 (t, J=5.9 Hz, 2H), 2.79 (ddd, J=17.5, 13.9, 5.4 Hz, 1H), 2.67 (ddd, J=17.5, 4.6, 2.6 Hz, 1H), 2.52 (qd, J=13.1, 4.5 Hz, 11H), 2.11-2.00 (m, 2H), 1.94 (dtd, J=13.1, 5.3, 2.5 Hz, 1H).

Example 27: N-(3-((3-((2-(2,6-dioxopiperidin-3-yl)-1,3-dioxoisoindolin-4-yl)amino)propyl)amino)propoxy)-3,4-difluoro-2-((2-fluoro-4-iodophenyl)amino)benzamide (CPD-025)

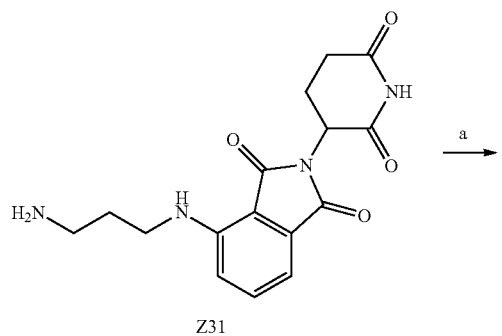

Z31

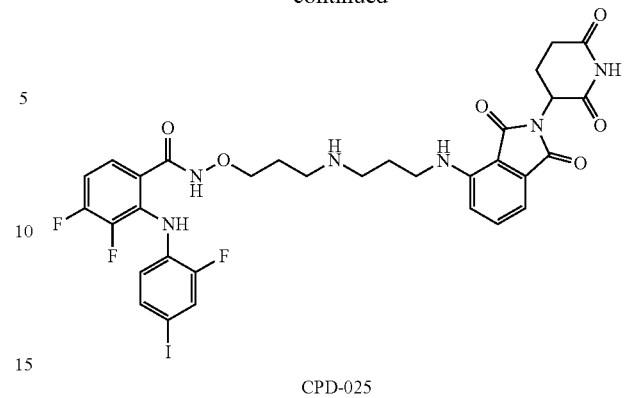

CPD-025

Reagents and conditions: (a) Z5, NaBH₃CN, DCM, MeOH, rt, overnight.

CPD-025 was synthesized following the same procedures as CPD-001 as described in Example 3. (0.04 g, yield: 33%). ¹H NMR (600 MHz, Methanol-$d_4$) δ 7.50 (dd, J=8.6, 7.1 Hz, 1H), 7.40-7.37 (m, 1H), 7.35 (dd, J=10.8, 1.9 Hz, 1H), 7.27 (dt, J=8.5, 1.3 Hz, 1H), 7.06 (dd, J=9.3, 7.0 Hz, 1H), 7.03 (d, J=2.4 Hz, 1H), 7.02 (d, J=3.9 Hz, 1H), 6.56 (td, J=8.7, 4.3 Hz, 1H), 5.01 (dd, J=12.8, 5.5 Hz, 1H), 4.08 (dd, J=5.7, 4.4 Hz, 2H), 3.49 (t, J=6.5 Hz, 2H), 3.27 (t, J=5.7 Hz, 2H), 3.21 (t, J=7.2 Hz, 2H), 2.84 (ddd, J=17.5, 13.9, 5.3 Hz, 1H), 2.73 (ddd, J=17.4, 4.4, 2.6 Hz, 1H), 2.66 (qd, J=13.1, 4.5 Hz, 1H), 2.13-2.07 (m, 2H), 2.06-1.99 (m, 3H).

Example 28: N-(3-((4-((2-(2,6-dioxopiperidin-3-yl)-1,3-dioxoisoindolin-4-yl)amino)butyl)amino)propoxy)-3,4-difluoro-2-((2-fluoro-4-iodophenyl)amino)benzamide (CPD-026)

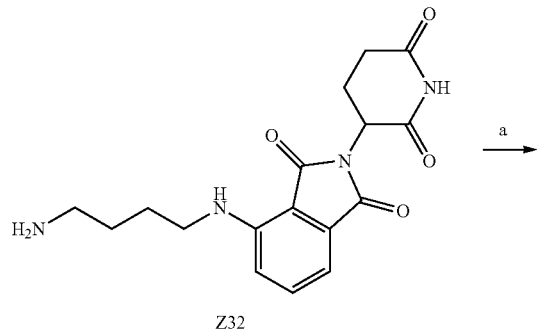

Z32

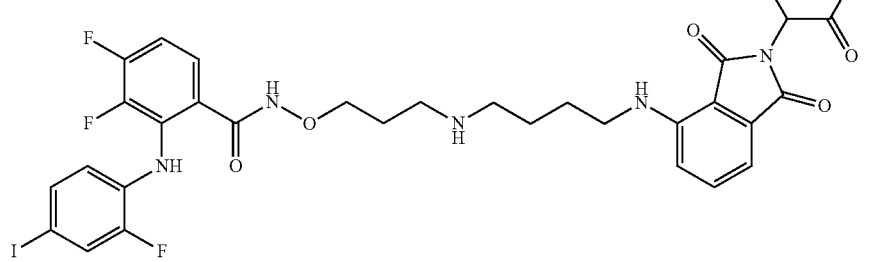

CPD-026

Reagents and conditions: (a) Z5, NaBH₃CN, DCM, MeOH, rt, overnight.

CPD-026 was synthesized following the same procedures as CPD-001 as described in Example 3. (0.04 g, yield: 33%). ¹H NMR (600 MHz, Methanol-d₄) δ 7.52 (dd, J=8.6, 7.1 Hz, 1H), 7.40 (dd, J=10.7, 1.9 Hz, 1H), 7.38-7.35 (m, 1H), 7.27 (dt, J=8.5, 1.3 Hz, 1H), 7.09-7.03 (m, 1H), 7.02 (d, J=7.1 Hz, 1H), 6.99 (d, J=8.5 Hz, 1H), 6.60 (td, J=8.7, 4.6 Hz, 1H), 5.01-4.93 (m, 1H), 4.17-4.01 (m, 2H), 3.35 (td, J=6.6, 1.6 Hz, 2H), 3.25 (t, J=5.8 Hz, 2H), 3.13 (t, J=7.4 Hz, 2H), 2.82 (ddd, J=17.5, 13.9, 5.3 Hz, 1H), 2.72 (ddd, J=17.5, 4.5, 2.6 Hz, 1H), 2.63 (qd, J=13.1, 4.5 Hz, 1H), 2.08-1.97 (m, 3H), 1.89 (p, J=7.3 Hz, 2H), 1.83-1.75 (m, 2H).

Example 29: N-(3-((5-((2-(2,6-dioxopiperidin-3-yl)-1,3-dioxoisoindolin-4-yl)amino)pentyl)amino)propoxy)-3,4-difluoro-2-((2-fluoro-4-iodophenyl)amino)benzamide (CPD-027)

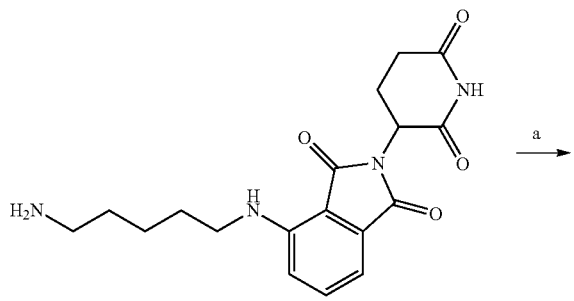

Z33

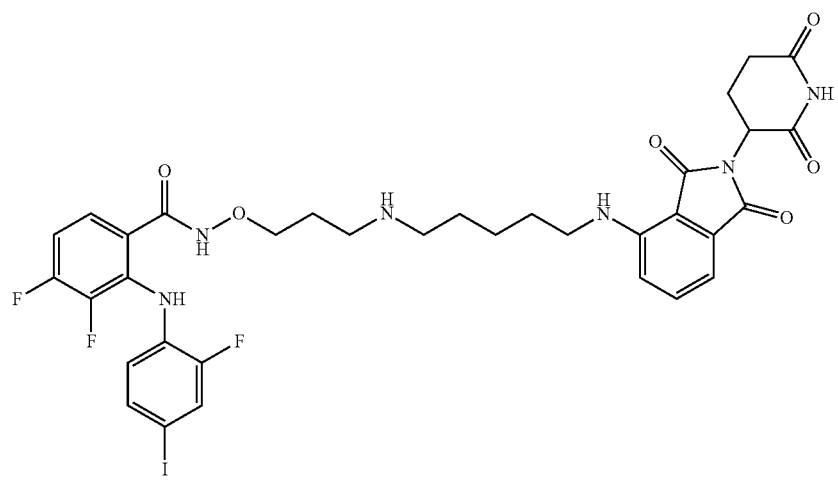

CPD-027

Reagents and conditions: (a) Z5, NaBH₃CN, DCM, MeOH, rt, overnight.

CPD-027 was synthesized following the same procedures as CPD-001 as described in Example 3. (0.02 g, yield: 33%). $^1$H NMR (600 MHz, Methanol-$d_4$) δ 7.51 (dd, J=8.6, 7.1 Hz, 1H), 7.42 (dd, J=10.7, 1.9 Hz, 1H), 7.40-7.37 (m, 1H), 7.31 (dt, J=8.4, 1.3 Hz, 1H), 7.07-7.00 (m, 2H), 6.98 (d, J=8.6 Hz, 1H), 6.60 (td, J=8.8, 4.6 Hz, 1H), 5.00 (dd, J=12.7, 5.5 Hz, 1H), 4.08 (t, J=5.3 Hz, 2H), 3.32-3.28 (m, 2H), 3.25 (t, J=5.7 Hz, 2H), 3.09 (t, J=7.6 Hz, 2H), 2.84 (ddd, J=17.4, 13.8, 5.3 Hz, 1H), 2.78-2.71 (m, 1H), 2.70-2.62 (m, 1H), 2.09-1.95 (m, 3H), 1.82 (p, J=7.8 Hz, 2H), 1.71 (p, J=7.0 Hz, 2H), 1.56 (tt, J=10.0, 6.3 Hz, 2H).

Example 30: N-(3-((6-((2-(2,6-dioxopiperidin-3-yl)-1,3-dioxoisoindolin-4-yl)amino)hexyl)amino)propoxy)-3,4-difluoro-2-((2-fluoro-4-iodophenyl)amino)benzamide (CPD-028)

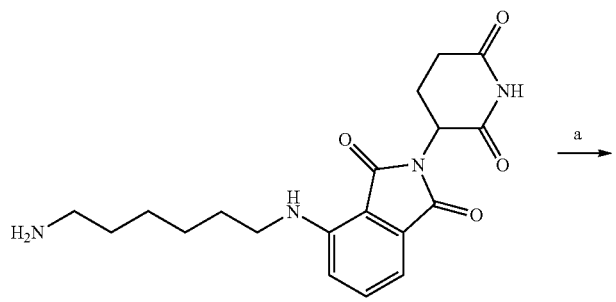

Z34

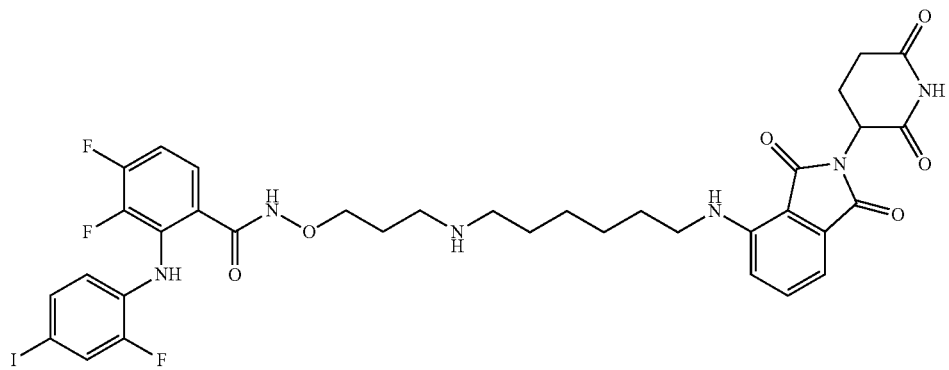

CPD-028

Reagents and conditions: (a) Z5, NaBH$_3$CN, DCM, MeOH, rt, overnight.

CPD-028 was synthesized following the same procedures as CPD-001 as described in Example 3. (0.02 g, yield: 30%). ¹H NMR (600 MHz, Methanol-d₄) δ 7.52 (dd, J=8.6, 7.0 Hz, 1H), 7.43 (dd, J=10.6, 1.9 Hz, 1H), 7.39 (ddd, J=8.9, 5.3, 1.7 Hz, 1H), 7.34 (dt, J=8.4, 1.3 Hz, 1H), 7.05 (dd, J=9.3, 7.1 Hz, 1H), 7.03 (d, J=7.0 Hz, 1H), 7.00 (d, J=8.5 Hz, 1H), 6.61 (td, J=8.7, 4.4 Hz, 1H), 5.03 (dd, J=12.7, 5.4 Hz, 1H), 4.08 (t, J=5.1 Hz, 2H), 3.30-3.28 (m, 2H), 3.24 (t, J=5.8 Hz, 2H), 3.10-3.02 (m, 2H), 2.88-2.80 (m, 1H), 2.73 (ddd, J=16.2, 4.0, 2.1 Hz, 1H), 2.67 (td, J=13.3, 4.4 Hz, 1H), 2.10-2.05 (m, 1H), 2.05-2.00 (m, 2H), 1.76 (q, J=7.4 Hz, 2H), 1.64 (q, J=6.9 Hz, 2H), 1.47 (t, J=3.7 Hz, 4H).

Example 31: N-(3-((7-((2-(2,6-dioxopiperidin-3-yl)-1,3-dioxoisoindolin-4-yl)amino)heptyl)amino)propoxy)-3,4-difluoro-2-((2-fluoro-4-iodophenyl)amino)benzamide (CPD-029)

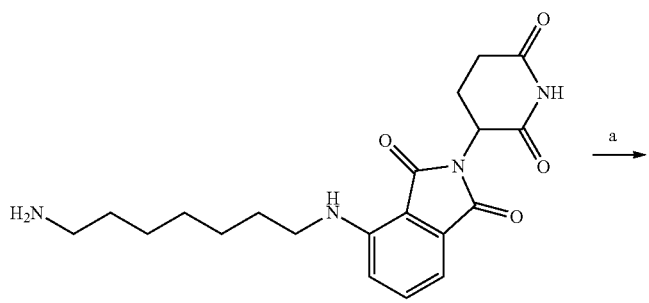

Z35

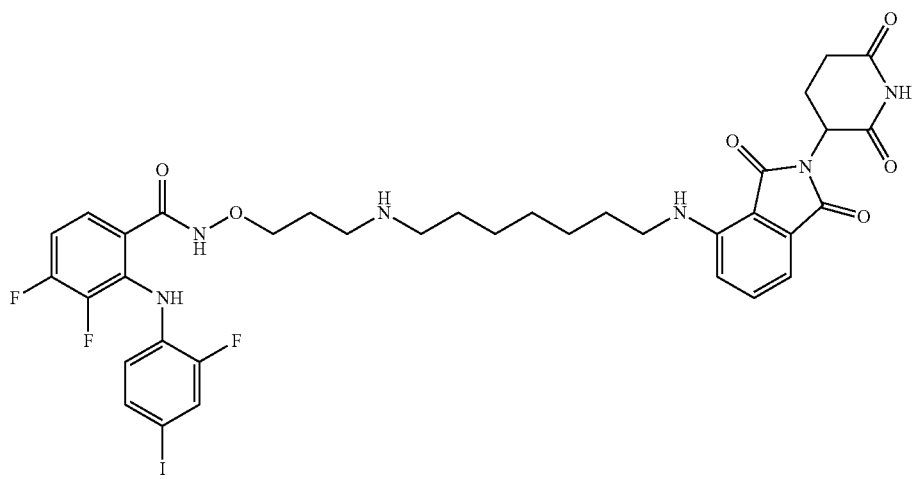

CPD-029

Reagents and conditions: (a) Z5, NaBH₃CN, DCM, MeOH, rt, overnight.

CPD-029 was synthesized following the same procedures as CPD-001 as described in Example 3. (0.02 g, yield: 30%). ¹H NMR (600 MHz, Methanol-$d_4$) δ 7.52 (dd, J=8.6, 7.0 Hz, 1H), 7.44 (dd, J=10.7, 1.9 Hz, 1H), 7.39 (ddd, J=8.7, 5.3, 1.7 Hz, 1H), 7.35 (dt, J=8.6, 1.4 Hz, 1H), 7.07-7.01 (m, 2H), 7.00 (d, J=8.5 Hz, 1H), 6.62 (td, J=8.7, 4.4 Hz, 1H), 5.03 (dd, J=12.8, 5.4 Hz, 1H), 4.20-3.95 (m, 2H), 3.29 (t, J=7.1 Hz, 2H), 3.23 (t, J=5.8 Hz, 2H), 3.07-3.02 (m, 2H), 2.85 (ddd, J=17.5, 14.0, 5.4 Hz, 1H), 2.76-2.71 (m, 1H), 2.71-2.66 (m, 1H), 2.12-2.06 (m, 1H), 2.03 (td, J=6.0, 4.4 Hz, 2H), 1.74 (p, J=7.6 Hz, 2H), 1.65 (p, J=6.9 Hz, 2H), 1.51-1.35 (m, 6H).

Example 32: N-(3-((8-((2-(2,6-dioxopiperidin-3-yl)-1,3-dioxoisoindolin-4-yl)amino)octyl)amino)propoxy)-3,4-difluoro-2-((2-fluoro-4-iodophenyl)amino)benzamide (CPD-030)

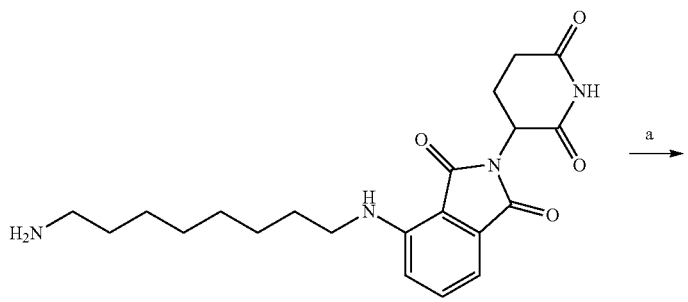

Z36

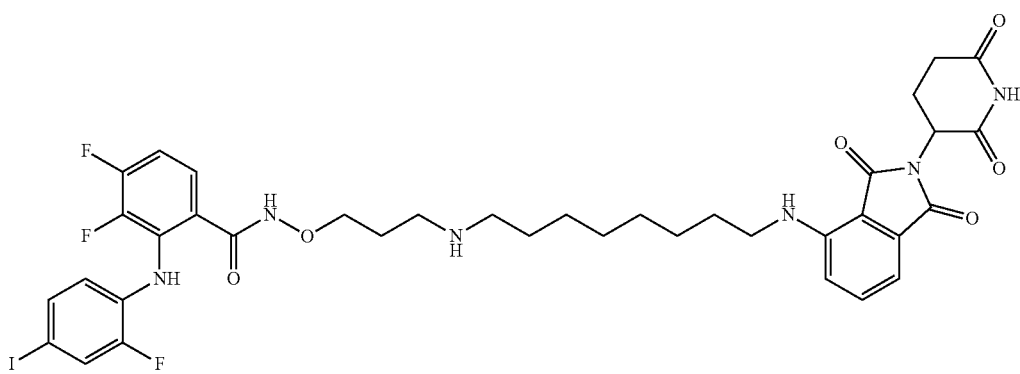

CPD-030

Reagents and conditions: (a) Z5, NaBH₃CN, DCM, MeOH, rt, overnight.

CPD-030 was synthesized following the same procedures as CPD-001 as described in Example 3. (0.02 g, yield: 38%). $^1$H NMR (600 MHz, Methanol-$d_4$) δ 7.53 (dd, J=8.6, 7.1 Hz, 1H), 7.45 (dd, J=10.6, 1.9 Hz, 1H), 7.40 (dd, J=8.6, 5.5 Hz, 1H), 7.36 (dt, J=8.4, 1.3 Hz, 1H), 7.05 (dd, J=9.2, 7.1 Hz, 1H), 7.03 (d, J=7.1 Hz, 1H), 7.01 (d, J=8.5 Hz, 1H), 6.63 (td, J=8.7, 4.4 Hz, 1H), 5.04 (dd, J=12.8, 5.5 Hz, 1H), 4.08 (dd, J=5.8, 4.5 Hz, 2H), 3.30-3.28 (m, 2H), 3.23 (t, J=5.8 Hz, 2H), 3.08-3.00 (m, 2H), 2.85 (ddd, J=17.5, 13.9, 5.3 Hz, 1H), 2.78-2.60 (m, 2H), 2.09 (dtd, J=10.2, 5.7, 2.5 Hz, 1H), 2.05-1.99 (m, 2H), 1.72 (p, J=7.6 Hz, 2H), 1.64 (p, J=7.0 Hz, 2H), 1.41 (d, J=5.4 Hz, 4H), 1.38-1.33 (m, 4H).

Example 33: (2S,4R)-1-((S)-20-(tert-butyl)-1-(3,4-difluoro-2-((2-fluoro-4-iodophenyl)amino)phenyl)-1,18-dioxo-3-oxa-2,7,19-triazahenicosan-21-oyl)-4-hydroxy-N—((S)-1-(4-(4-methylthiazol-5-yl)phenyl)ethyl)pyrrolidine-2-carboxamide (CPD-031)

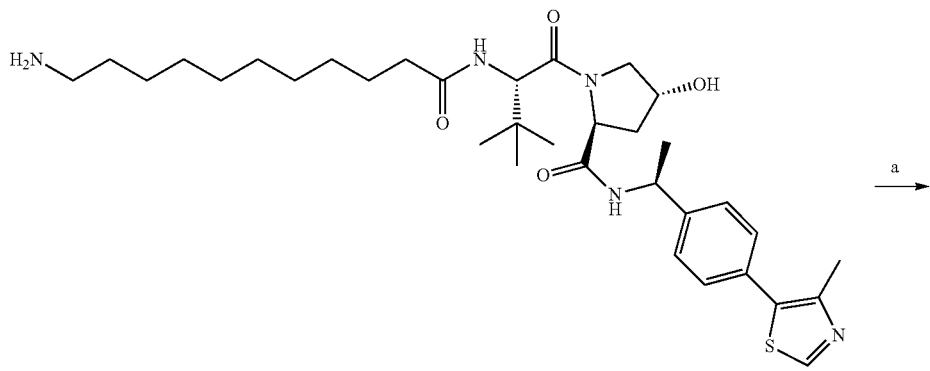

Z37

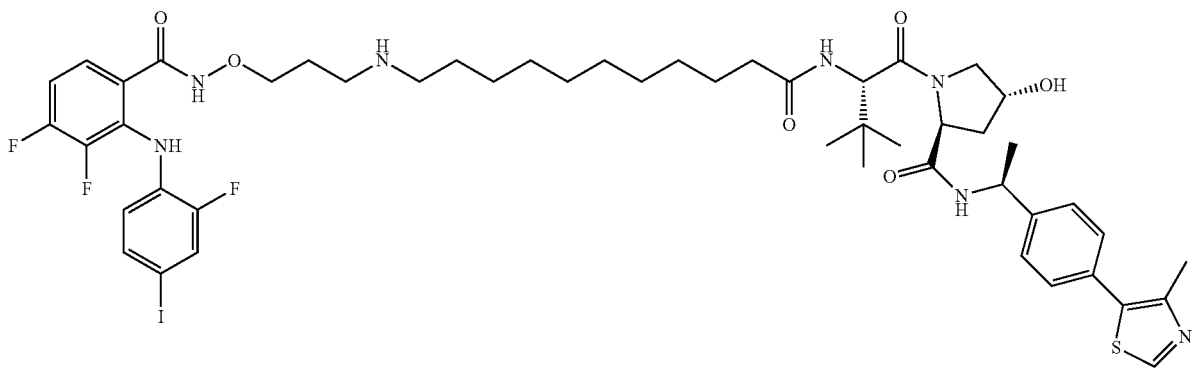

CPD-031

Reagents and conditions: (a) Z5, NaBH$_3$CN, DCM, MeOH, rt, overnight.

CPD-031 was synthesized following the same procedures as CPD-001 as described in Example 3. (0.02 g, yield: 38%). ¹H NMR (800 MHz, Methanol-$d_4$) δ 8.97 (s, 1H), 7.43 (dq, J=17.7, 10.2 Hz, 6H), 7.37 (d, J=8.6 Hz, 1H), 7.06 (q, J=8.5 Hz, 1H), 6.64 (td, J=8.8, 4.0 Hz, 1H), 5.00 (q, J=6.9 Hz, 1H), 4.62 (s, 1H), 4.57 (t, J=8.3 Hz, 1H), 4.43 (d, J=5.2 Hz, 1H), 4.08 (t, J=5.2 Hz, 2H), 3.88 (d, J=11.1 Hz, 1H), 3.75 (dd, J=11.1, 3.9 Hz, 1H), 3.23 (q, J=9.5, 7.7 Hz, 2H), 3.04 (q, J=7.1, 6.3 Hz, 2H), 2.49 (s, 3H), 2.29 (dt, J=15.0, 7.7 Hz, 1H), 2.22 (ddd, J=27.3, 13.7, 8.1 Hz, 2H), 2.03 (p, J=5.5 Hz, 2H), 1.95 (ddd, J=13.3, 9.1, 4.5 Hz, 1H), 1.72 (p, J=7.9 Hz, 2H), 1.63-1.55 (m, 2H), 1.51 (d, J=7.0 Hz, 3H), 1.38 (q, J=7.6 Hz, 2H), 1.33-1.25 (m, 10H), 1.04 (s, 9H).

Example 34: (2S,4R)-1-((S)-21-(tert-butyl)-1-(3,4-difluoro-2-((2-fluoro-4-iodophenyl)amino)phenyl)-1,19-dioxo-3-oxa-2,7,20-triazadocosan-22-oyl)-4-hydroxy-N-(4-(4-methylthiazol-5-yl)benzyl)pyrrolidine-2-carboxamide (CPD-032)

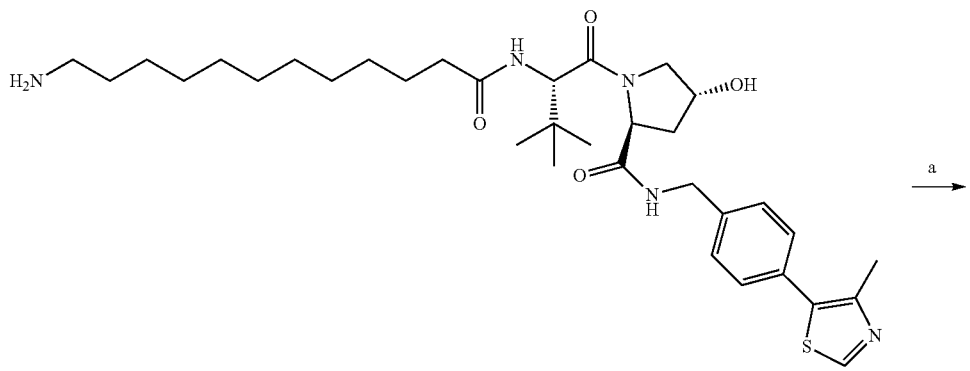

Z38

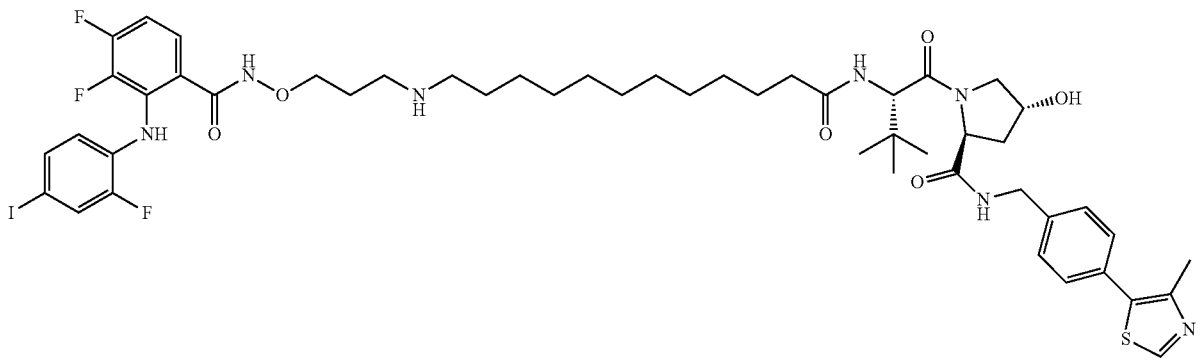

CPD-032

Reagents and conditions: (a) Z5, NaBH₃CN, DCM, MeOH, rt, overnight.

CPD-032 was synthesized following the same procedures as CPD-001 as described in Example 3. (0.02 g, yield: 34%). ¹H NMR (600 MHz, Methanol-$d_4$) δ 9.05 (s, 1H), 7.50-7.47 (m, 2H), 7.44 (td, J=6.9, 6.2, 1.8 Hz, 3H), 7.41-7.39 (m, 1H), 7.39-7.36 (m, 1H), 7.10-7.03 (m, 1H), 6.64 (td, J=8.7, 4.3 Hz, 1H), 4.63 (s, 1H), 4.59-4.52 (m, 2H), 4.50 (dtt, J=3.8, 2.6, 1.3 Hz, 1H), 4.36 (d, J=15.7 Hz, 1H), 4.08 (t, J=5.1 Hz, 2H), 3.90 (d, J=11.3 Hz, 1H), 3.81 (dd, J=10.9, 4.0 Hz, 1H), 3.24 (t, J=5.8 Hz, 2H), 3.07-3.01 (m, 2H), 2.49 (s, 3H), 2.30 (dt, J=14.0, 7.9 Hz, 1H), 2.26-2.19 (m, 2H), 2.08 (ddd, J=13.3, 9.1, 4.5 Hz, 1H), 2.03 (dd, J=6.3, 4.4 Hz, 2H), 1.72 (p, J=7.7 Hz, 2H), 1.64-1.54 (m, 2H), 1.38 (q, J=7.4 Hz, 2H), 1.29 (d, J=18.3 Hz, 12H), 1.03 (s, 9H).

Example 35: (2S,4R)-1-((S)-21-(tert-butyl)-1-(3,4-difluoro-2-((2-fluoro-4-iodophenyl)amino)phenyl)-1,19-dioxo-3-oxa-2,7,20-triazadocosan-22-oyl)-4-hydroxy-N—((S)-1-(4-(4-methylthiazol-5-yl)phenyl)ethyl)pyrrolidine-2-carboxamide (CPD-033)

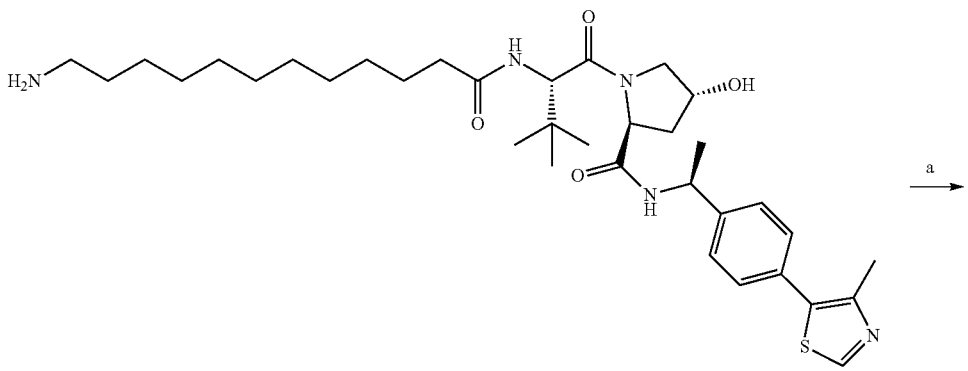

Z39

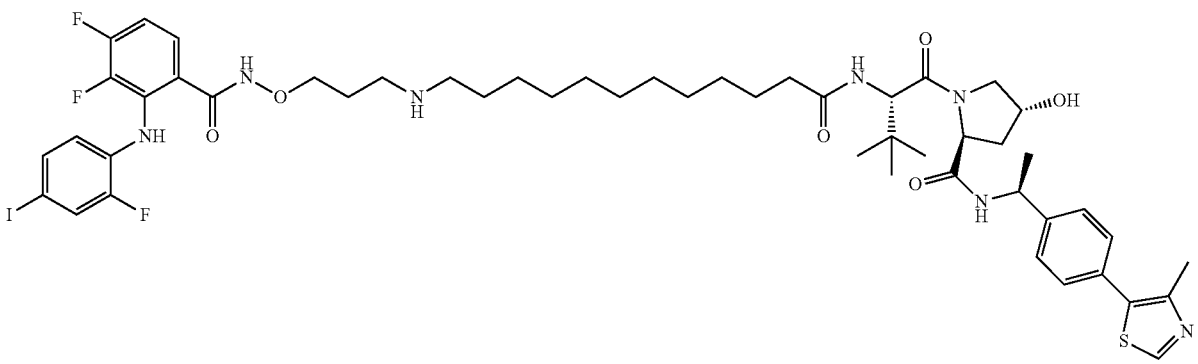

CPD-033

Reagents and conditions: (a) Z5, NaBH₃CN, DCM, MeOH, rt, overnight.

CPD-033 was synthesized following the same procedures as CPD-001 as described in Example 3. (0.02 g, yield: 34%). $^1$H NMR (600 MHz, Methanol-d$_4$) δ 9.12 (d, J=1.7 Hz, 1H), 7.49-7.42 (m, 5H), 7.39 (dd, J=16.6, 8.0 Hz, 2H), 7.07 (q, J=8.5, 8.0 Hz, 1H), 6.70-6.57 (m, 1H), 4.64-4.60 (m, 1H), 4.59-4.54 (m, 1H), 4.45-4.41 (m, 1H), 4.15-4.03 (m, 2H), 3.88 (d, J=10.9 Hz, 1H), 3.79-3.72 (m, 1H), 3.24 (t, J=5.8 Hz, 2H), 3.04 (t, J=7.8 Hz, 2H), 2.55-2.46 (m, 3H), 2.30 (dt, J=15.6, 8.0 Hz, 1H), 2.26-2.17 (m, 2H), 2.06-2.00 (m, 3H), 1.98-1.90 (m, 1H), 1.75-1.68 (m, 2H), 1.65-1.54 (m, 2H), 1.51 (dd, J=7.1, 1.7 Hz, 3H), 1.42-1.36 (m, 2H), 1.35-1.24 (m, 12H), 1.04 (s, 9H).

Example 36: (2R,4S)-1-((S)-20-(tert-butyl)-1-(3,4-difluoro-2-((2-fluoro-4-iodophenyl)amino)phenyl)-1,18-dioxo-3-oxa-2,7,19-triazahenicosan-21-oyl)-4-hydroxy-N—((S)-1-(4-(4-methylthiazol-5-yl)phenyl)ethyl)pyrrolidine-2-carboxamide (CPD-034)

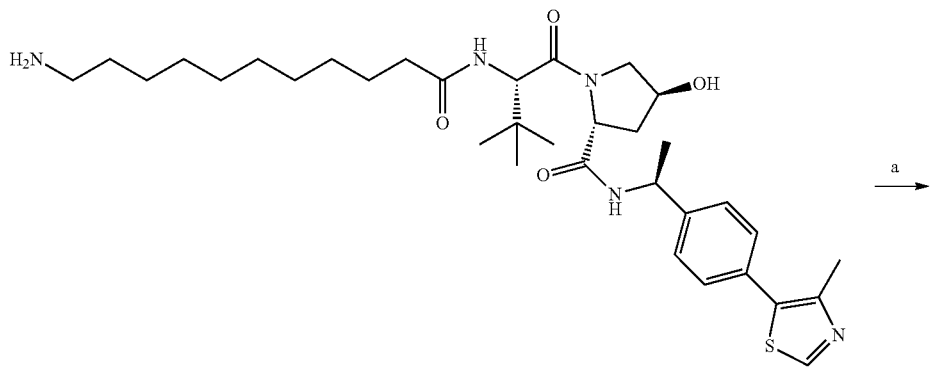

Z40

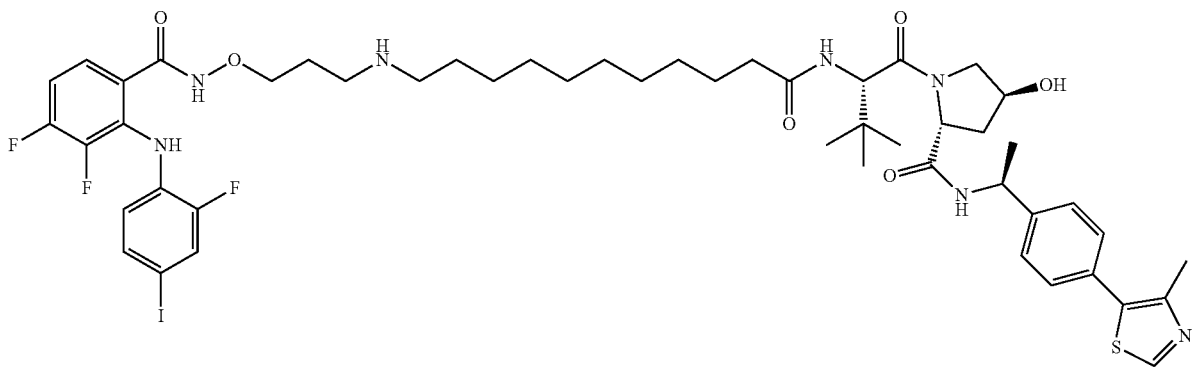

CPD-034

Reagents and conditions: (a) Z5, NaBH$_3$CN, DCM, MeOH, rt, overnight.

CPD-034 was synthesized following the same procedures as CPD-001 as described in Example 3. (0.02 g, yield: 34%). ¹H NMR (800 MHz, Methanol-$d_4$) δ 8.98 (s, 1H), 7.52 (d, J=7.9 Hz, 2H), 7.46-7.42 (m, 3H), 7.41 (dd, J=8.8, 5.1 Hz, 1H), 7.35 (d, J=8.6 Hz, 1H), 7.05 (q, J=8.6 Hz, 1H), 6.62 (td, J=8.7, 4.1 Hz, 1H), 5.02 (q, J=7.9, 7.1 Hz, 1H), 4.55 (t, J=7.4 Hz, 1H), 4.49 (s, 1H), 4.45 (p, J=4.5 Hz, 1H), 4.08 (t, J=5.1 Hz, 2H), 3.94 (dd, J=10.8, 4.9 Hz, 1H), 3.69 (dd, J=10.9, 3.5 Hz, 1H), 3.23 (t, J=5.8 Hz, 2H), 3.02 (t, J=7.8 Hz, 2H), 2.49 (s, 3H), 2.28 (dt, J=15.1, 7.9 Hz, 1H), 2.23-2.16 (m, 2H), 2.10 (dt, J=12.5, 5.8 Hz, 1H), 2.02 (dd, J=11.0, 5.6 Hz, 2H), 1.70 (p, J=7.8 Hz, 2H), 1.59-1.51 (m, 2H), 1.45 (d, J=7.0 Hz, 3H), 1.36 (p, J=7.5 Hz, 2H), 1.30-1.26 (m, 4H), 1.25-1.21 (m, 6H), 1.05 (s, 9H).

Example 37: (2S,4R)-1-((S)-20-(tert-butyl)-1-(3,4-difluoro-2-((2-fluoro-4-iodophenyl)amino)phenyl)-1,18-dioxo-3-oxa-2,8,19-triazahenicosan-21-oyl)-4-hydroxy-N—((S)-1-(4-(4-methylthiazol-5-yl)phenyl)ethyl)pyrrolidine-2-carboxamide (CPD-035)

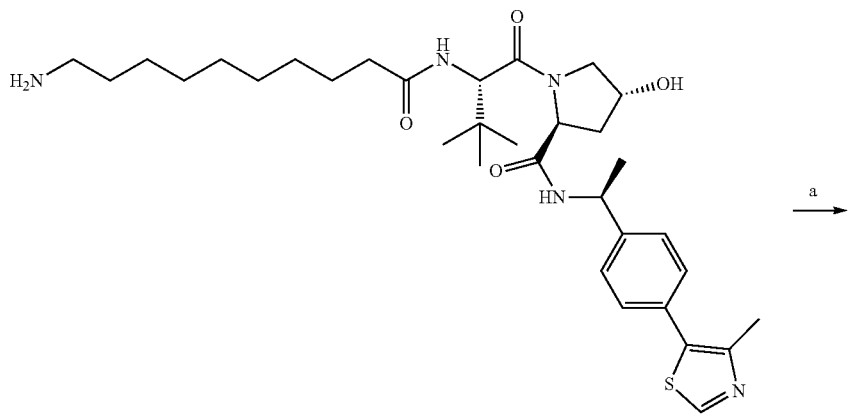

Z41

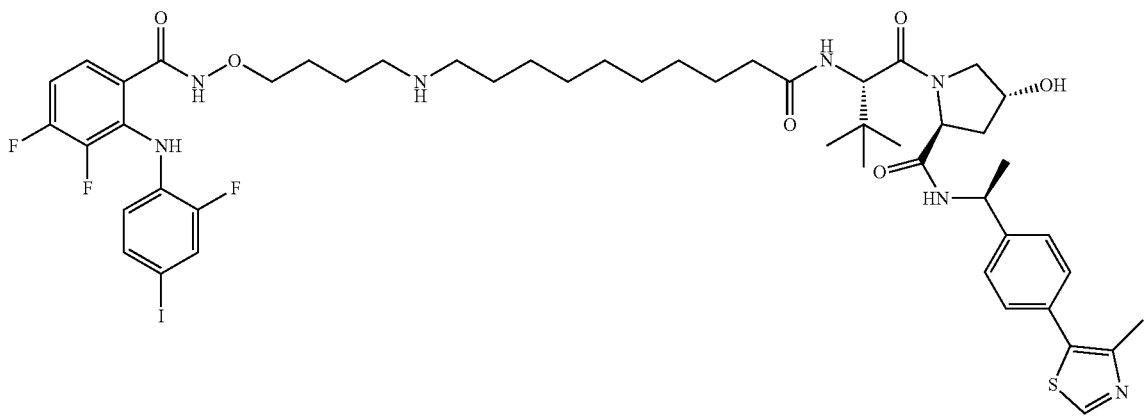

CPD-035

Reagents and conditions: (a) Z5, NaBH₃CN, DCM, MeOH, rt, overnight.

CPD-035 was synthesized following the same procedures as CPD-001 as described in Example 3. (0.02 g, yield: 34%). ¹H NMR (600 MHz, Methanol-d₄) δ 9.03 (s, 1H), 7.52-7.42 (m, 5H), 7.41-7.33 (m, 2H), 7.06 (q, J=8.7 Hz, 1H), 6.61 (td, J=8.8, 4.3 Hz, 1H), 5.00 (q, J=6.8 Hz, 1H), 4.63 (s, 1H), 4.57 (t, J=8.3 Hz, 1H), 4.43 (s, 1H), 3.93 (t, J=5.5 Hz, 2H), 3.87 (d, J=11.0 Hz, 1H), 3.75 (dd, J=11.0, 3.9 Hz, 1H), 3.10 (t, J=7.4 Hz, 2H), 3.05-2.95 (m, 2H), 2.50 (s, 3H), 2.30 (dt, J=15.0, 7.7 Hz, 1H), 2.25 (dd, J=8.1, 6.3 Hz, 1H), 2.22-2.17 (m, 1H), 1.95 (ddd, J=13.3, 9.0, 4.6 Hz, 1H), 1.88 (p, J=7.0 Hz, 2H), 1.76 (q, J=6.1 Hz, 2H), 1.68 (p, J=7.6 Hz, 2H), 1.63-1.55 (m, 2H), 1.51 (d, J=7.0 Hz, 3H), 1.42-1.28 (m, 10H), 1.04 (s, 9H).

Example 38: (2S,4R)-1-((S)-19-(tert-butyl)-1-(3,4-difluoro-2-((2-fluoro-4-iodophenyl)amino)phenyl)-1,17-dioxo-3-oxa-2,7,18-triazaicosan-20-oyl)-4-hydroxy-N—((S)-1-(4-(4-methylthiazol-5-yl)phenyl)ethyl)pyrrolidine-2-carboxamide (CPD-036)

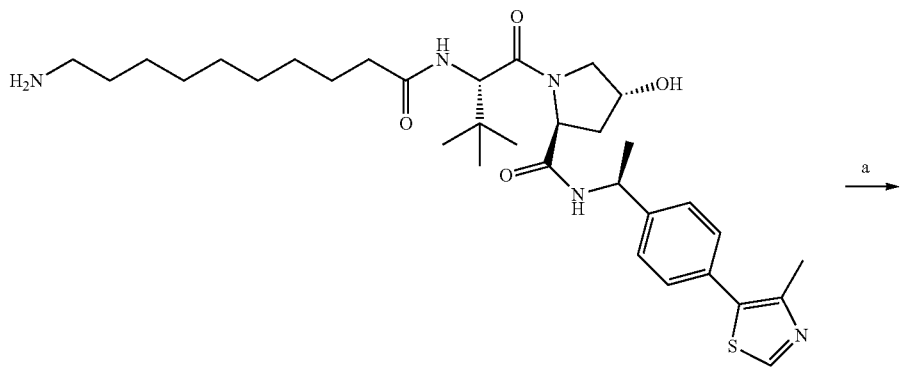

Z42

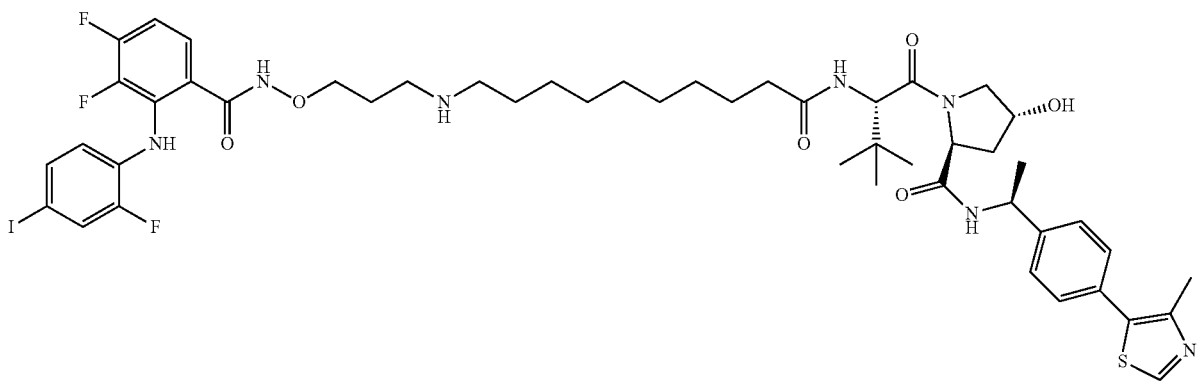

CPD-036

Reagents and conditions: (a) Z5, NaBH₃CN, DCM, MeOH, rt, overnight.

CPD-036 was synthesized following the same procedures as CPD-001 as described in Example 3. (0.02 g, yield: 32%). ¹H NMR (600 MHz, Methanol-$d_4$) δ 9.03 (s, 1H), 7.48-7.44 (m, 3H), 7.43 (d, J=8.2 Hz, 2H), 7.40-7.36 (m, 2H), 7.07 (td, J=9.2, 6.9 Hz, 1H), 6.64 (td, J=8.7, 4.3 Hz, 1H), 5.03-4.98 (m, 1H), 4.62 (s, 1H), 4.59-4.53 (m, 1H), 4.43 (td, J=4.2, 2.0 Hz, 1H), 4.14-4.04 (m, 2H), 3.87 (d, J=11.0 Hz, 1H), 3.75 (dd, J=11.0, 4.0 Hz, 1H), 3.24 (t, J=5.9 Hz, 2H), 3.12-2.98 (m, 2H), 2.49 (s, 3H), 2.33-2.27 (m, 1H), 2.24 (dd, J=8.2, 6.3 Hz, 1H), 2.22-2.17 (m, 1H), 2.03 (dt, J=10.3, 5.0 Hz, 2H), 1.95 (ddd, J=13.3, 9.0, 4.5 Hz, 1H), 1.72 (p, J=7.8 Hz, 2H), 1.65-1.55 (m, 2H), 1.51 (d, J=7.0 Hz, 3H), 1.42-1.37 (m, 2H), 1.35-1.26 (m, 8H), 1.03 (s, 9H).

Example 39: (2S,4R)-1-((S)-22-(tert-butyl)-1-(3,4-difluoro-2-((2-fluoro-4-iodophenyl)amino)phenyl)-1,20-dioxo-3-oxa-2,8,21-triazatricosan-23-oyl)-4-hydroxy-N—((S)-1-(4-(4-methylthiazol-5-yl)phenyl)ethyl)pyrrolidine-2-carboxamide (CPD-038)

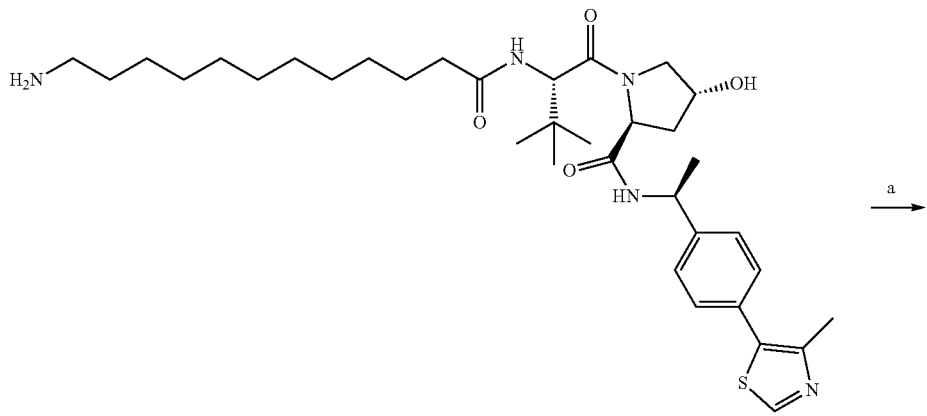

Z43

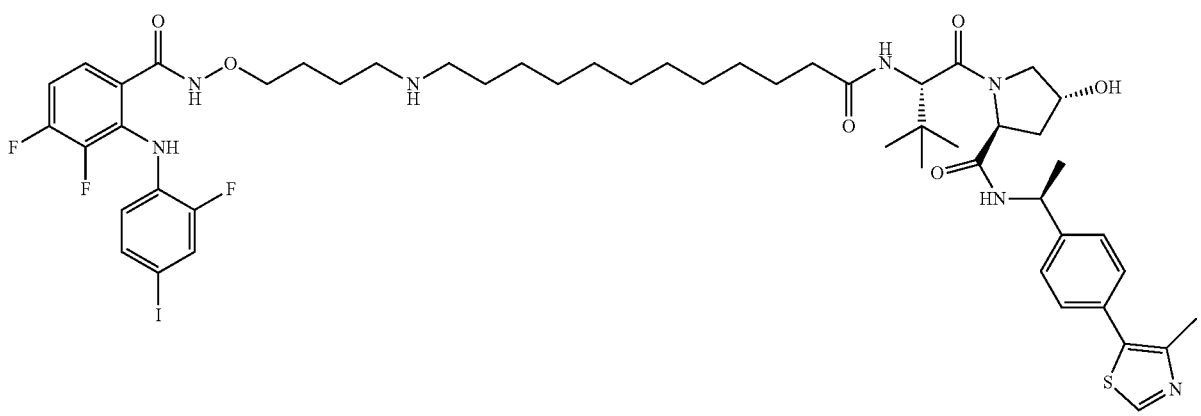

CPD-038

Reagents and conditions: (a) Z5, NaBH₃CN, DCM, MeOH, rt, overnight.

CPD-038 was synthesized following the same procedures as CPD-001 as described in Example 3. (0.02 g, yield: 35%). $^1$H NMR (600 MHz, Methanol-$d_4$) δ 9.00 (s, 1H), 7.47-7.41 (m, 5H), 7.39 (td, J=6.4, 3.0 Hz, 1H), 7.37-7.34 (m, 1H), 7.05 (td, J=9.1, 6.9 Hz, 1H), 6.61 (td, J=8.7, 4.3 Hz, 1H), 5.00 (q, J=7.0 Hz, 1H), 4.62 (s, 1H), 4.57 (dd, J=9.1, 7.5 Hz, 1H), 4.44 (dp, J=4.3, 2.0 Hz, 1H), 3.93 (t, J=5.6 Hz, 2H), 3.88 (dt, J=11.3, 1.8 Hz, 1H), 3.75 (dd, J=11.0, 4.0 Hz, 1H), 3.10 (t, J=7.3 Hz, 2H), 3.02-2.95 (m, 2H), 2.49 (s, 3H), 2.33-2.27 (m, 1H), 2.26-2.23 (m, 1H), 2.23-2.17 (m, 1H), 1.96 (ddd, J=13.3, 9.0, 4.5 Hz, 1H), 1.88 (p, J=7.1 Hz, 2H), 1.75 (h, J=5.5, 5.0 Hz, 2H), 1.68 (p, J=7.9 Hz, 2H), 1.63-1.56 (m, 2H), 1.51 (d, J=7.0 Hz, 3H), 1.41-1.25 (m, 14H), 1.04 (s, 9H).

Example 40: (2S,4R)-1-((S)-21-(tert-butyl)-1-(3,4-difluoro-2-((2-fluoro-4-iodophenyl)amino)phenyl)-1,19-dioxo-3-oxa-2,8,20-triazadocosan-22-oyl)-4-hydroxy-N—((S)-1-(4-(4-methylthiazol-5-yl)phenyl)ethyl)pyrrolidine-2-carboxamide (CPD-039)

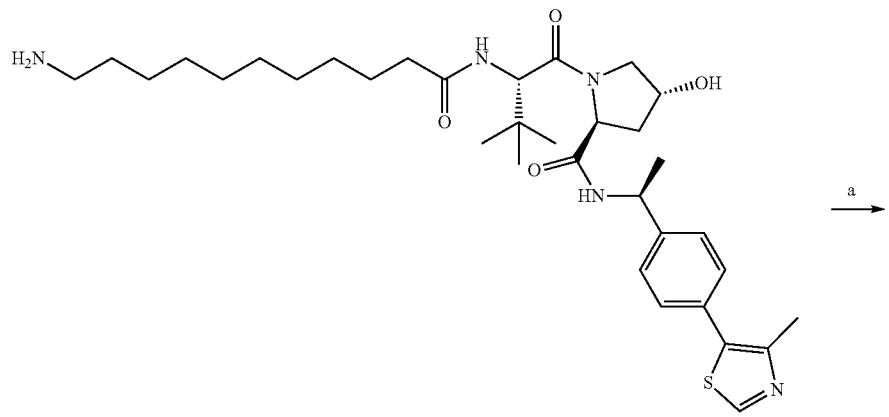

Z44

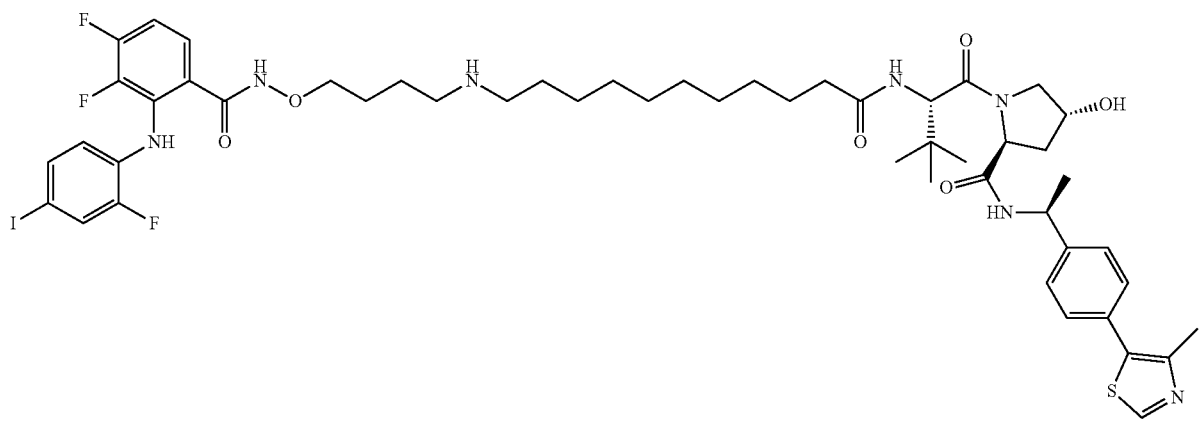

CPD-039

Reagents and conditions: (a) Z5, NaBH$_3$CN, DCM, MeOH, rt, overnight.

CPD-039 was synthesized following the same procedures as CPD-001 as described in Example 3. (0.02 g, yield: 34%). $^1$H NMR (600 MHz, Methanol-$d_4$) δ 8.93 (s, 1H), 7.50-7.41 (m, 5H), 7.37 (dd, J=8.5, 6.6 Hz, 2H), 7.06 (q, J=8.8 Hz, 1H), 6.62 (td, J=8.7, 4.2 Hz, 1H), 5.02-4.98 (m, 1H), 4.65-4.61 (m, 1H), 4.58-4.55 (m, 1H), 4.45-4.42 (m, 1H), 3.93 (t, J=5.6 Hz, 2H), 3.87 (d, J=11.1 Hz, 1H), 3.75 (dd, J=11.0, 4.0 Hz, 1H), 3.10 (t, J=7.3 Hz, 2H), 3.04-2.95 (m, 2H), 2.48 (s, 3H), 2.30 (dt, J=15.0, 7.6 Hz, 1H), 2.26-2.23 (m, 1H), 2.22-2.17 (m, 1H), 1.95 (ddd, J=13.4, 9.1, 4.6 Hz, 1H), 1.88 (t, J=7.1 Hz, 2H), 1.76 (q, J=6.1 Hz, 2H), 1.68 (p, J=7.6 Hz, 2H), 1.63-1.56 (m, 2H), 1.51 (d, J=7.0 Hz, 3H), 1.39-1.35 (m, 2H), 1.34-1.27 (m, 10H), 1.04 (s, 9H).

Example 41: N-(3-((2-((2-(2,6-dioxopiperidin-3-yl)-1,3-dioxoisoindolin-5-yl)amino)ethyl)amino)propoxy)-3,4-difluoro-2-((2-fluoro-4-iodophenyl)amino)benzamide (CPD-040)

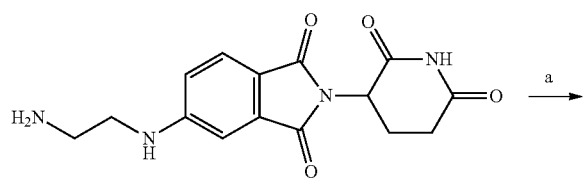

Z45

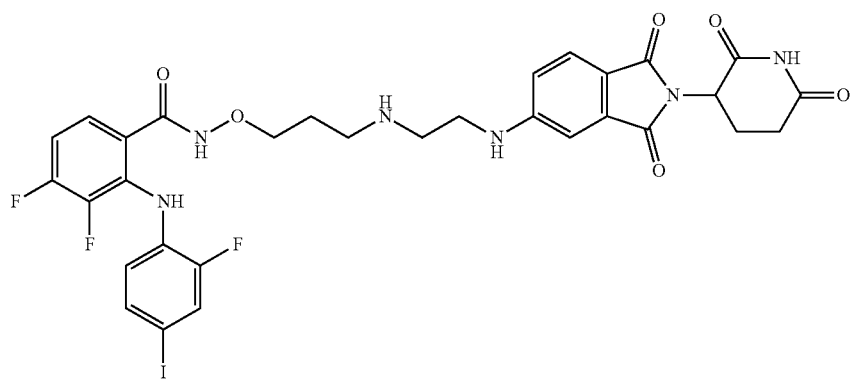

CPD-040

Reagents and conditions: (a) Z5, NaBH$_3$CN, DCM, MeOH, rt, overnight.

CPD-040 was synthesized following the same procedures as CPD-001 as described in Example 3. (0.02 g, yield: 31%). $^1$H NMR (600 MHz, Methanol-$d_4$) δ 7.50 (d, J=8.3 Hz, 1H), 7.37-7.33 (m, 2H), 7.32-7.29 (m, 1H), 7.06 (q, J=8.8 Hz, 1H), 6.98 (d, J=2.2 Hz, 1H), 6.86 (dd, J=8.4, 2.3 Hz, 1H), 6.57 (td, J=8.7, 4.1 Hz, 1H), 5.06-4.98 (m, 1H), 4.05 (t, J=5.1 Hz, 2H), 3.67 (t, J=6.2 Hz, 2H), 3.35-3.32 (m, 3H), 2.84 (ddd, J=17.3, 13.8, 5.4 Hz, 1H), 2.73 (ddd, J=17.5, 4.5, 2.6 Hz, 1H), 2.66 (qd, J=13.1, 4.4 Hz, 1H), 2.05 (q, J=5.5, 5.0 Hz, 4H).

Example 42: N-(3-((3-((2-(2,6-dioxopiperidin-3-yl)-1,3-dioxoisoindolin-5-yl)amino)propyl)amino)propoxy)-3,4-difluoro-2-((2-fluoro-4-iodophenyl)amino)benzamide (CPD-041)

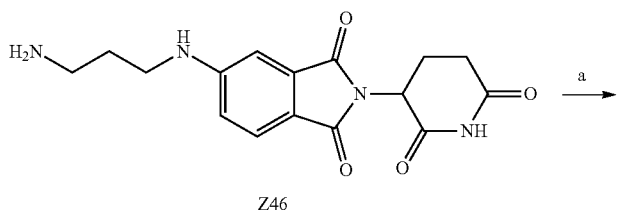

Z46

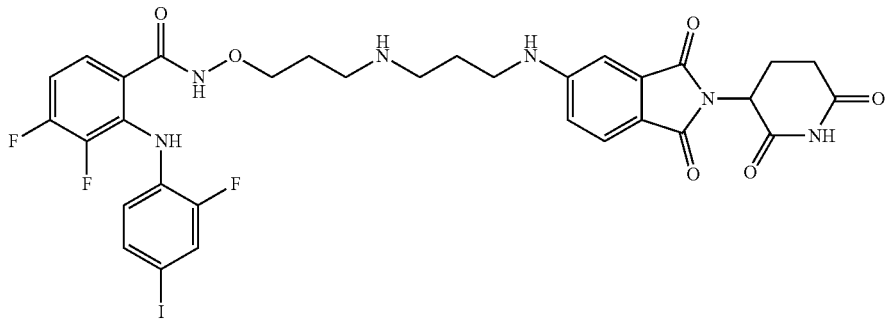

CPD-041

Reagents and conditions: (a) Z5, NaBH$_3$CN, DCM, MeOH, rt, overnight.

CPD-041 was synthesized following the same procedures as CPD-001 as described in Example 3. (0.02 g, yield: 31%). $^1$H NMR (600 MHz, Methanol-$d_4$) δ 7.50 (d, J=8.3 Hz, 1H), 7.36 (dd, J=10.7, 1.9 Hz, 1H), 7.31 (d, J=6.6 Hz, 1H), 7.30 (dt, J=8.5, 1.2 Hz, 1H), 7.04 (td, J=9.2, 7.0 Hz, 1H), 6.94 (d, J=2.2 Hz, 1H), 6.81 (dd, J=8.4, 2.2 Hz, 1H), 6.58 (td, J1=8.7, 4.2 Hz, 1H), 5.02 (dd, J=12.8, 5.5 Hz, 1H), 4.13-4.02 (m, 2H), 3.36 (t, J=6.9 Hz, 2H), 3.27 (t, J=5.7 Hz, 2H), 3.22 (t, J=7.3 Hz, 2H), 2.85 (ddd, J=17.4, 13.9, 5.4 Hz, 1H), 2.73 (ddd, J=17.4, 4.5, 2.6 Hz, 1H), 2.66 (qd, J=13.1, 4.5 Hz, 1H), 2.13-2.07 (m, 2H), 2.07-2.02 (m, 3H).

Example 43: N-(3-((4-((2-(2,6-dioxopiperidin-3-yl)-1,3-dioxoisoindolin-5-yl)amino)butyl)amino)propoxy)-3,4-difluoro-2-((2-fluoro-4-iodophenyl)amino)benzamide (CPD-042)

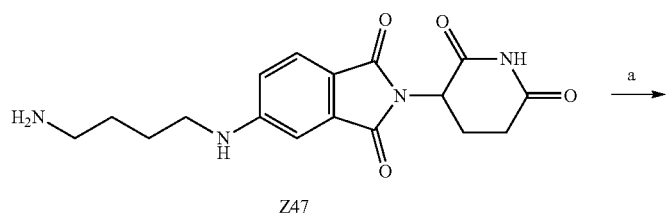

Z47

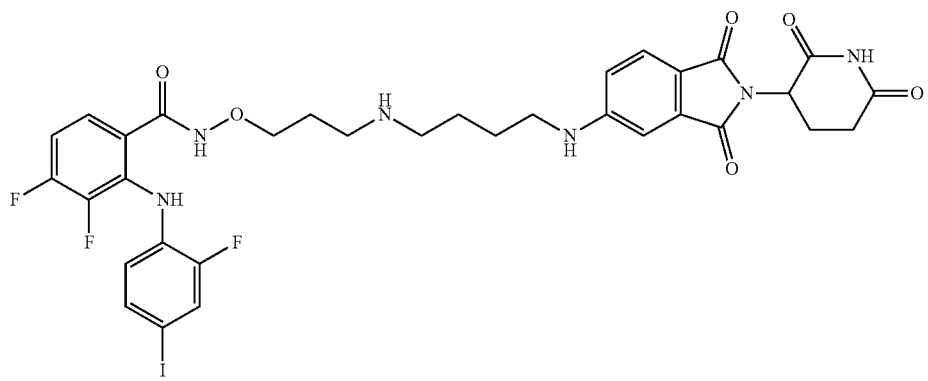

CPD-042

Reagents and conditions: (a) Z5, NaBH$_3$CN, DCM, MeOH, rt, overnight.

CPD-042 was synthesized following the same procedures as CPD-001 as described in Example 3. (0.02 g, yield: 31%). ¹H NMR (600 MHz, Acetone-d₆) δ 9.88 (s, 1H), 9.34 (s, 1H), 8.80 (s, 1H), 7.65-7.57 (m, 1H), 7.54 (d, J=8.4 Hz, 1H), 7.47 (dd, J=10.7, 2.0 Hz, 1H), 7.40 (dd, J=8.5, 1.9 Hz, 1H), 7.08 (td, J=9.3, 7.1 Hz, 1H), 6.98 (d, J=2.1 Hz, 1H), 6.90 (dd, J=8.4, 2.2 Hz, 1H), 6.76 (td, J=8.8, 5.2 Hz, 1H), 5.04 (dd, J=12.6, 5.4 Hz, 1H), 4.19 (t, J=5.2 Hz, 2H), 3.40 (s, 3H), 3.32 (t, J=6.8 Hz, 3H), 3.00-2.90 (m, 1H), 2.85-2.67 (m, 2H), 2.20-2.11 (m, 3H), 2.04-1.98 (m, 2H), 1.84 (p, J=7.0 Hz, 2H).

Example 44: N-(3-((5-((2-(2,6-dioxopiperidin-3-yl)-1,3-dioxoisoindolin-5-yl)amino)pentyl)amino)propoxy)-3,4-difluoro-2-((2-fluoro-4-iodophenyl)amino)benzamide (CPD-043)

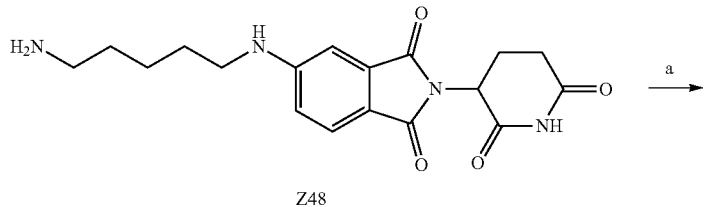

Z48

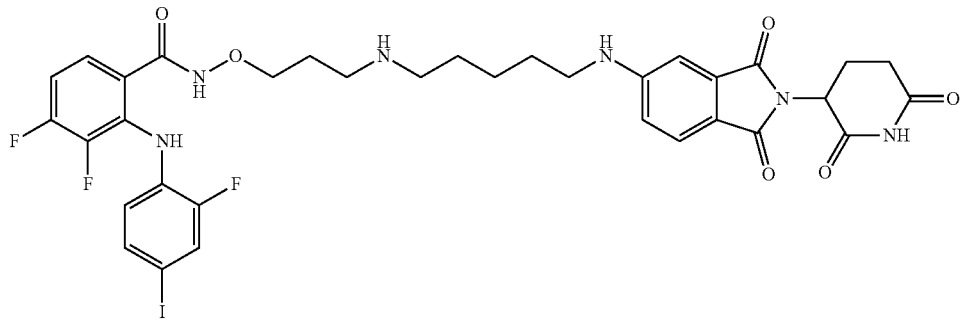

CPD-043

Reagents and conditions: (a) Z5, NaBH₃CN, DCM, MeOH, rt, overnight.

CPD-043 was synthesized following the same procedures as CPD-001 as described in Example 3. (0.02 g, yield: 35%). ¹H NMR (600 MHz, Methanol-d₄) δ 7.53 (d, J=8.4 Hz, 1H), 7.41 (dd, J=10.7, 1.9 Hz, 1H), 7.39-7.36 (m, 1H), 7.35-7.31 (m, 1H), 7.05 (q, J=8.7 Hz, 1H), 6.93 (d, J=2.1 Hz, 1H), 6.81 (dd, J=8.4, 2.2 Hz, 1H), 6.61 (td, J=8.7, 4.2 Hz, 1H), 5.03 (dd, J=12.6, 5.4 Hz, 1H), 4.07 (t, J=5.1 Hz, 2H), 3.24 (t, J=5.8 Hz, 2H), 3.20 (t, J=7.0 Hz, 2H), 3.10-3.03 (m, 2H), 2.91-2.81 (m, 1H), 2.78-2.71 (m, 1H), 2.68 (td, J=13.3, 4.4 Hz, 1H), 2.12-2.06 (m, 1H), 2.05-1.99 (m, 2H), 1.81 (p, J=7.9 Hz, 2H), 1.70 (p, J=7.1 Hz, 2H), 1.54 (p, J=7.7, 7.3 Hz, 2H).

Example 45: N-(3-((6-((2-(2,6-dioxopiperidin-3-yl)-1,3-dioxoisoindolin-5-yl)amino)hexyl)amino)propoxy)-3,4-difluoro-2-((2-fluoro-4-iodophenyl)amino)benzamide (CPD-044)

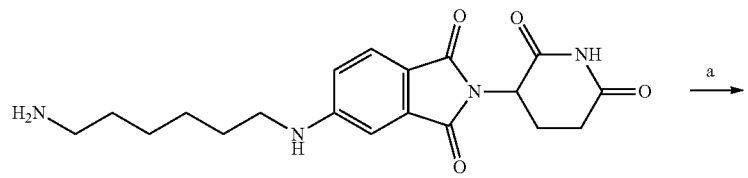

Z49

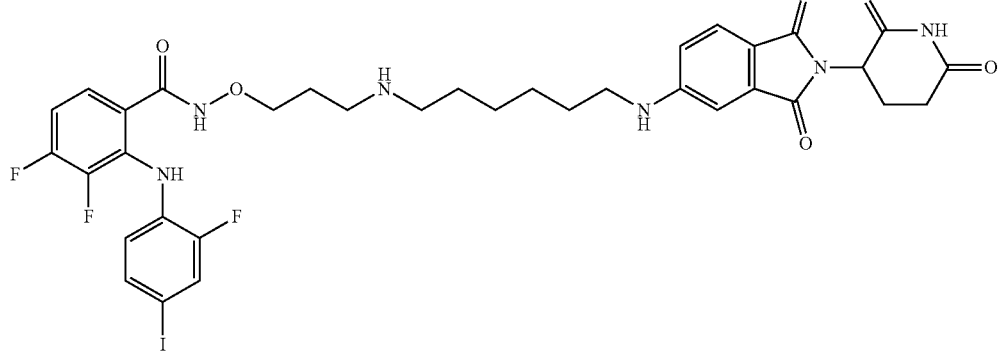

CPD-044

Reagents and conditions: (a) Z5, NaBH₃CN, DCM, MeOH, rt, overnight.

CPD-044 was synthesized following the same procedures as CPD-001 as described in Example 3. (0.02 g, yield: 31%). $^1$H NMR (600 MHz, Methanol-$d_4$) δ 7.53 (d, J=8.4 Hz, 1H), 7.43 (dd, J=10.6, 1.9 Hz, 1H), 7.39 (t, J=7.1 Hz, 1H), 7.35 (dd, J=8.5, 1.5 Hz, 1H), 7.05 (q, J=8.7 Hz, 1H), 6.94 (d, J=2.3 Hz, 1H), 6.81 (dd, J=8.4, 2.2 Hz, 1H), 6.62 (td, J=8.7, 4.3 Hz, 1H), 5.08-4.99 (m, 1H), 4.07 (t, J=5.1 Hz, 2H), 3.24 (t, J=5.8 Hz, 2H), 3.19 (t, J=7.1 Hz, 2H), 3.09-3.02 (m, 2H), 2.86 (ddd, J=22.7, 12.4, 5.4 Hz, 1H), 2.78-2.71 (m, 1H), 2.68 (td, J=13.3, 4.5 Hz, 1H), 2.13-2.05 (m, 1H), 2.06-1.99 (m, 2H), 1.80-1.73 (m, 2H), 1.65 (t, J=7.0 Hz, 2H), 1.55-1.42 (m, 4H).

Example 46: N-(3-((7-((2-(2,6-dioxopiperidin-3-yl)-1,3-dioxoisoindolin-5-yl)amino)heptyl)amino)propoxy)-3,4-difluoro-2-((2-fluoro-4-iodophenyl)amino)benzamide (CPD-045)

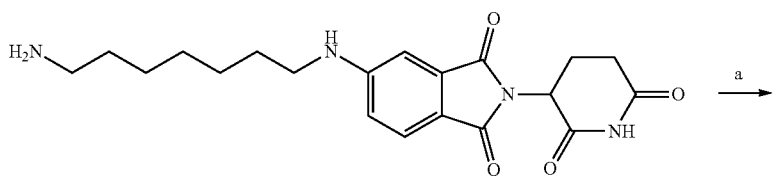

Z50

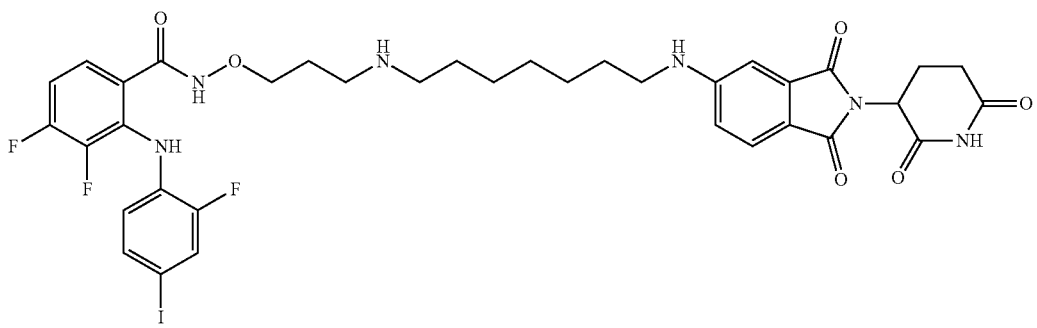

CPD-045

Reagents and conditions: (a) Z5, NaBH₃CN, DCM, MeOH, rt, overnight.

CPD-045 was synthesized following the same procedures as CPD-001 as described in Example 3. (0.02 g, yield: 32%). $^1$H NMR (600 MHz, Methanol-$d_4$) δ 7.53 (d, J=8.3 Hz, 1H), 7.43 (dd, J=10.6, 1.9 Hz, 1H), 7.41-7.38 (m, 1H), 7.35 (dt, J=8.4, 1.3 Hz, 1H), 7.05 (td, J=9.2, 7.0 Hz, 1H), 6.93 (d, J=2.2 Hz, 1H), 6.80 (dd, J=8.4, 2.1 Hz, 1H), 6.62 (td, J=8.7, 4.3 Hz, 1H), 5.03 (dd, J=12.8, 5.5 Hz, 1H), 4.07 (t, J=5.1 Hz, 2H), 3.23 (t, J=5.8 Hz, 2H), 3.18 (t, J=7.1 Hz, 2H), 3.08-3.02 (m, 2H), 2.85 (ddd, J=17.7, 14.0, 5.3 Hz, 1H), 2.77-2.71 (m, 1H), 2.68 (td, J=13.3, 4.4 Hz, 1H), 2.08 (dtd, J=14.9, 5.2, 4.3, 2.5 Hz, 1H), 2.03 (dt, J=6.5, 3.1 Hz, 2H), 1.74 (q, J=7.7 Hz, 2H), 1.64 (q, J=7.1 Hz, 2H), 1.47-1.35 (m, 6H).

Example 47: N-(3-((8-((2-(2,6-dioxopiperidin-3-yl)-1,3-dioxoisoindolin-5-yl)amino)octyl)amino)propoxy)-3,4-difluoro-2-((2-fluoro-4-iodophenyl)amino)benzamide (CPD-046)

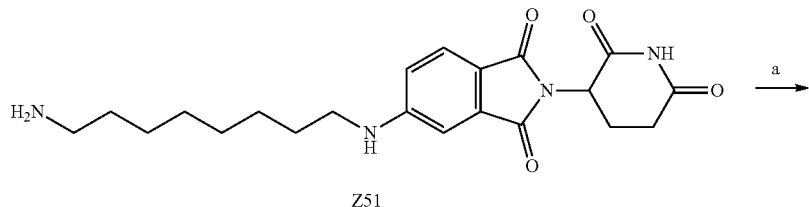

Z51

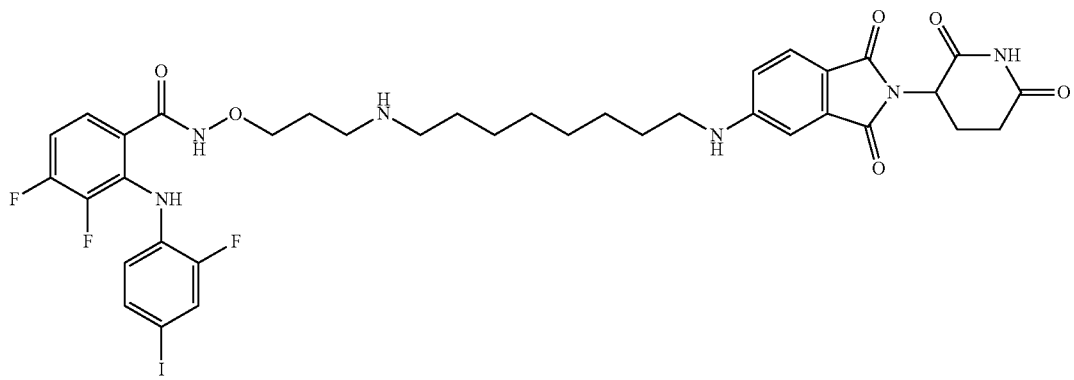

CPD-046

Reagents and conditions: (a) Z5, NaBH$_3$CN, DCM, MeOH, rt, overnight.

CPD-046 was synthesized following the same procedures as CPD-001 as described in Example 3. (0.02 g, yield: 31%). $^1$H NMR (600 MHz, Methanol-$d_4$) δ 7.54 (d, J=8.4 Hz, 1H), 7.45 (dd, J=10.6, 1.9 Hz, 1H), 7.40 (d, J=7.4 Hz, 1H), 7.36 (d, J=8.7 Hz, 1H), 7.09-7.02 (m, 1H), 6.94 (d, J=2.2 Hz, 1H), 6.81 (dd, J=8.4, 2.2 Hz, 1H), 6.63 (q, J=4.5 Hz, 1H), 5.03 (dd, J=12.7, 5.6 Hz, 1H), 4.07 (t, J=5.1 Hz, 2H), 3.23 (t, J=5.8 Hz, 2H), 3.19 (t, J=7.1 Hz, 2H), 3.04 (t, J=7.9 Hz, 2H), 2.90-2.81 (m, 1H), 2.78-2.71 (m, 1H), 2.72-2.65 (m, 1H), 2.12-2.06 (m, 1H), 2.06-2.00 (m, 2H), 1.73 (d, J=7.9 Hz, 2H), 1.68-1.61 (m, 2H), 1.46-1.40 (m, 4H), 1.39-1.33 (m, 4H).

Example 48: N-(3-((2-(2-((2-(2,6-dioxopiperidin-3-yl)-1,3-dioxoisoindolin-5-yl)amino)ethoxy)ethyl)amino)propoxy)-3,4-difluoro-2-((2-fluoro-4-iodophenyl)amino)benzamide (CPD-047)

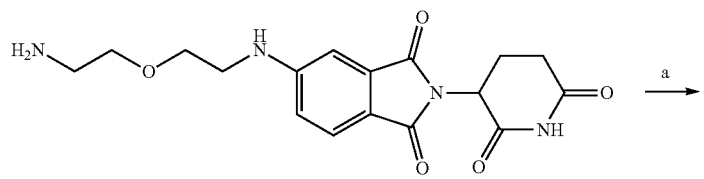

Z52

-continued

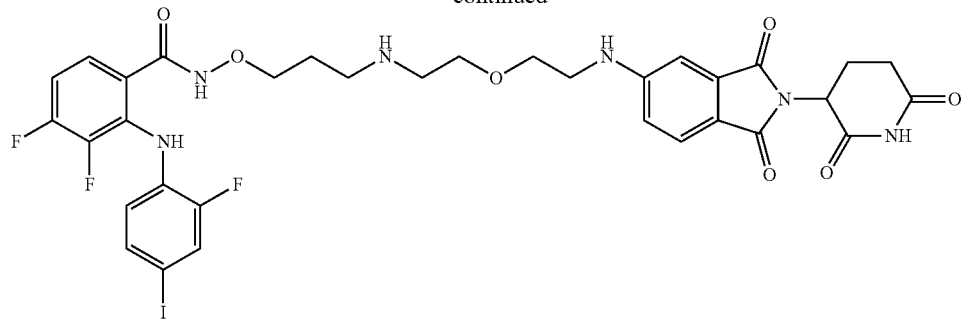

CPD-047

Reagents and conditions: (a) Z5, NaBH₃CN, DCM, MeOH, rt, overnight.

CPD-047 was synthesized following the same procedures as CPD-001 as described in Example 3. (0.02 g, yield: 31%). ¹H NMR (600 MHz, Methanol-$d_4$) δ 7.50-7.40 (m, 2H), 7.33 (dd, J=8.5, 1.6 Hz, 1H), 7.29 (t, J=7.2 Hz, 1H), 7.00 (q, J=8.6 Hz, 1H), 6.86 (d, J=2.2 Hz, 1H), 6.74 (dd, J=8.4, 2.2 Hz, 1H), 6.59 (td, J=8.7, 4.4 Hz, 1H), 5.03 (dd, J=12.7, 5.5 Hz, 1H), 4.06 (t, J=5.0 Hz, 2H), 3.87-3.77 (m, 2H), 3.70 (t, J=5.3 Hz, 2H), 3.33 (t, J=5.4 Hz, 2H), 3.32-3.30 (m, 4H), 2.85 (ddd, J=17.2, 13.8, 5.3 Hz, 1H), 2.77-2.72 (m, 1H), 2.68 (qd, J=13.1, 4.4 Hz, 1H), 2.11-2.07 (m, 1H), 2.05 (t, J=5.8 Hz, 2H).

Example 49: N-(3-((2-(2-(2-((2-(2,6-dioxopiperidin-3-yl)-1,3-dioxoisoindolin-5-yl)amino)ethoxy)ethoxy)ethyl)amino)propoxy)-3,4-difluoro-2-((2-fluoro-4-iodophenyl)amino)benzamide (CPD-048)

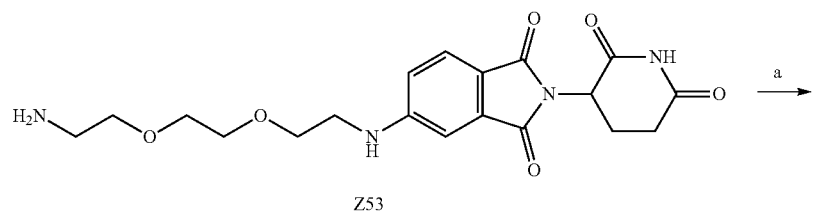

Z53

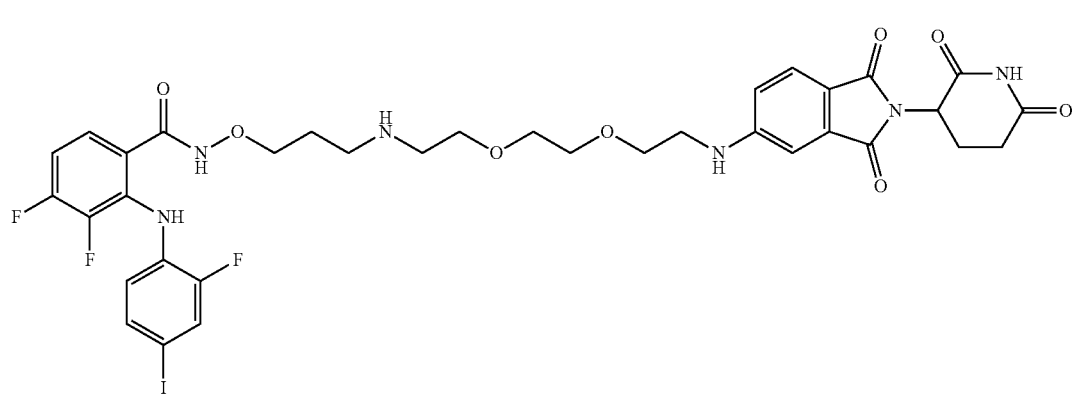

CPD-048

Reagents and conditions: (a) Z5, NaBH₃CN, DCM, MeOH, rt, overnight.

CPD-048 was synthesized following the same procedures as CPD-001 as described in Example 3. (0.02 g, yield: 31%). ¹H NMR (600 MHz, Methanol-d₄) δ 7.54 (d, J=8.4 Hz, 1H), 7.46 (dd, J=10.7, 1.9 Hz, 1H), 7.37 (t, J=8.8 Hz, 2H), 7.09-7.02 (m, 1H), 7.01 (d, J=2.2 Hz, 1H), 6.84 (dd, J=8.4, 2.2 Hz, 1H), 6.63 (td, J=8.7, 4.1 Hz, 1H), 5.09-5.00 (m, 1H), 4.04 (t, J=5.2 Hz, 2H), 3.77 (t, J=5.0 Hz, 2H), 3.69-3.56 (m, 6H), 3.38 (t, J=5.4 Hz, 2H), 3.27 (t, J=6.0 Hz, 2H), 3.23 (t, J=5.0 Hz, 2H), 2.85 (ddd, J=18.6, 14.0, 5.4 Hz, 1H), 2.77-2.71 (m, 1H), 2.69 (dd, J=13.4, 4.3 Hz, 1H), 2.12-2.07 (m, 1H), 2.02 (dd, J=11.5, 5.9 Hz, 2H).

Example 50: N-((1-((2-(2,6-dioxopiperidin-3-yl)-1,3-dioxoisoindolin-5-yl)amino)-3,6,9-trioxa-12-azapentadecan-15-yl)oxy)-3,4-difluoro-2-((2-fluoro-4-iodophenyl)amino)benzamide (CPD-049)

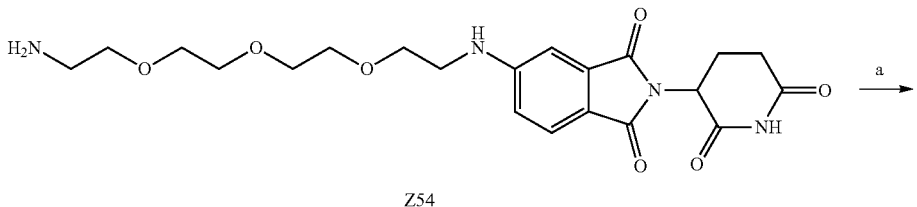

Z54

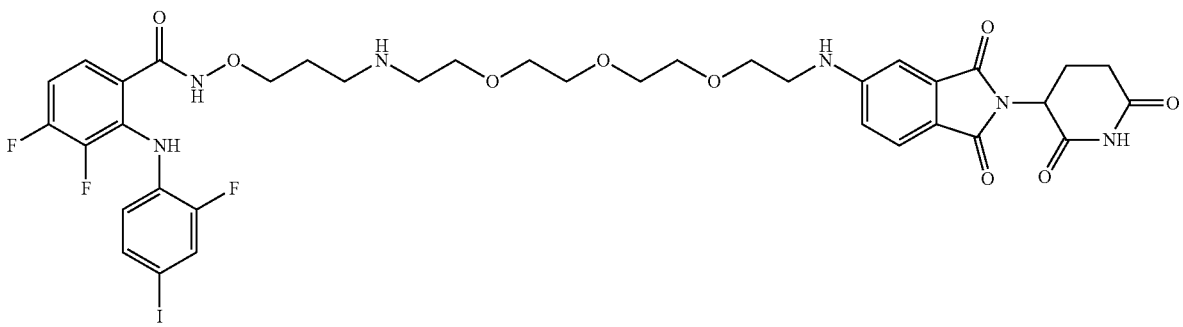

CPD-049

Reagents and conditions: (a) Z5, NaBH₃CN, DCM, MeOH, rt, overnight.

CPD-049 was synthesized following the same procedures as CPD-001 as described in Example 3. (0.02 g, yield: 31%). ¹H NMR (600 MHz, Methanol-d₄) δ 7.55 (d, J=8.4 Hz, 1H), 7.46 (dd, J=10.7, 2.0 Hz, 1H), 7.38 (d, J=8.0 Hz, 1H), 7.35 (dd, J=8.5, 1.6 Hz, 1H), 7.07-7.02 (m, 1H), 7.01 (d, J=2.1 Hz, 1H), 6.86 (dd, J=8.3, 2.2 Hz, 1H), 6.63 (td, J=8.7, 4.1 Hz, 1H), 5.03 (dd, J=12.7, 5.5 Hz, 1H), 4.04 (t, J=5.2 Hz, 2H), 3.81-3.73 (m, 2H), 3.68 (t, J=5.3 Hz, 2H), 3.62 (qd, J=3.4, 1.6 Hz, 4H), 3.59 (s, 4H), 3.40 (t, J=5.3 Hz, 2H), 3.25 (dt, J=10.1, 5.5 Hz, 4H), 2.84 (ddd, J=17.1, 13.8, 5.3 Hz, 1H), 2.78-2.71 (m, 1H), 2.67 (td, J=13.2, 4.3 Hz, 1H), 2.12-2.04 (m, 1H), 2.04-1.99 (m, 2H).

Example 51: N-((1-((2-(2,6-dioxopiperidin-3-yl)-1,3-dioxoisoindolin-5-yl)amino)-3,6,9,12-tetraoxa-15-azaoctadecan-18-yl)oxy)-3,4-difluoro-2-((2-fluoro-4-iodophenyl)amino)benzamide (CPD-050)

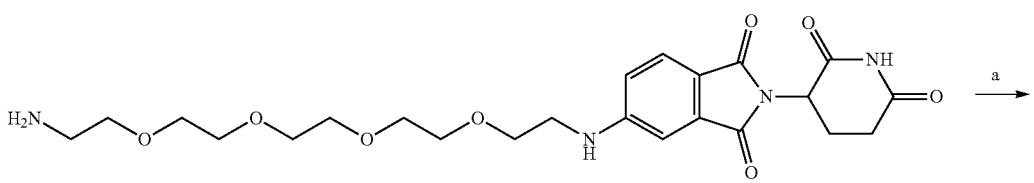

Z55

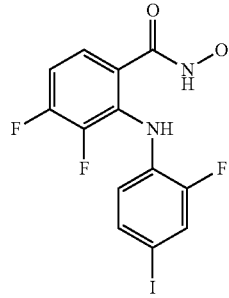

CPD-050

Reagents and conditions: (a) Z5, NaBH₃CN, DCM, MeOH, rt, overnight.

CPD-050 was synthesized following the same procedures as CPD-001 as described in Example 3. (0.02 g, yield: 31%). $^1$H NMR (600 MHz, Methanol-$d_4$) δ 7.55 (d, J=8.3 Hz, 1H), 7.46 (dd, J=10.6, 1.9 Hz, 1H), 7.39 (d, J=8.2 Hz, 1H), 7.36 (dt, J=8.5, 1.3 Hz, 1H), 7.09-7.02 (m, 1H), 7.02 (d, J=2.1 Hz, 1H), 6.86 (dd, J=8.4, 2.2 Hz, 1H), 6.64 (td, J=8.7, 4.1 Hz, 1H), 5.03 (dd, J=12.8, 5.4 Hz, 1H), 4.04 (t, J=5.2 Hz, 2H), 3.81-3.73 (m, 2H), 3.69 (t, J=5.3 Hz, 2H), 3.66-3.62 (m, 4H), 3.61-3.59 (m, 2H), 3.58-3.55 (m, 6H), 3.40 (t, J=5.3 Hz, 2H), 3.26 (t, J=6.1 Hz, 2H), 3.24 (t, J=5.1 Hz, 2H), 2.84 (ddd, J=17.7, 14.0, 5.4 Hz, 1H), 2.76-2.70 (m, 1H), 2.70-2.64 (m, 1H), 2.11-2.05 (m, 1H), 2.02 (dt, J=10.5, 5.2 Hz, 2H).

Example 52: N-((1-((2-(2,6-dioxopiperidin-3-yl)-1,3-dioxoisoindolin-5-yl)amino)-3,6,9,12,15-pentaoxa-18-azahenicosan-21-yl)oxy)-3,4-difluoro-2-((2-fluoro-4-iodophenyl)amino)benzamide (CPD-051)

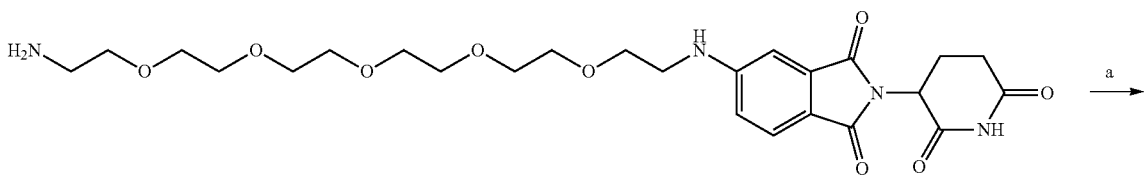

Z56

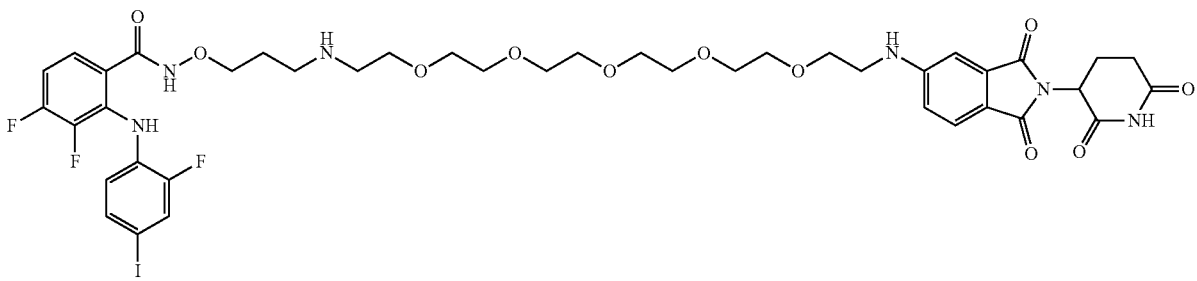

CPD-051

Reagents and conditions: (a) Z5, NaBH₃CN, DCM, MeOH, rt, overnight.

CPD-051 was synthesized following the same procedures as CPD-001 as described in Example 3. (0.02 g, yield: 36%). ¹H NMR (600 MHz, Methanol-$d_4$) δ 7.44 (d, J=8.4 Hz, 1H), 7.35 (dd, J=10.6, 2.0 Hz, 1H), 7.30 (ddd, J=9.0, 5.3, 1.7 Hz, 1H), 7.27-7.24 (m, 1H), 6.94 (td, J=9.2, 6.9 Hz, 1H), 6.90 (d, J=2.2 Hz, 1H), 6.75 (dd, J=8.4, 2.2 Hz, 1H), 6.53 (td, J=8.7, 4.2 Hz, 1H), 4.92 (dd, J=12.7, 5.5 Hz, 1H), 3.95 (t, J=5.2 Hz, 2H), 3.72-3.62 (m, 2H), 3.58 (t, J=5.3 Hz, 2H), 3.53 (s, 4H), 3.52-3.50 (m, 2H), 3.50-3.48 (m, 2H), 3.47 (td, J=4.7, 4.0, 1.6 Hz, 3H), 3.44 (dt, J=4.9, 2.1 Hz, 4H), 3.28 (t, J=5.3 Hz, 2H), 3.21 (p, J=1.7 Hz, 1H), 3.18 (t, J=6.1 Hz, 2H), 3.15 (t, J=5.0 Hz, 2H), 2.74 (ddd, J=17.1, 13.7, 5.2 Hz, 1H), 2.67-2.61 (m, 1H), 2.57 (td, J=13.3, 4.4 Hz, 1H), 1.98 (dtd, J=10.5, 5.6, 4.8, 2.9 Hz, 1H), 1.93 (dt, J=10.7, 5.2 Hz, 2H).

Example 53: (2R,4S)-1-((S)-22-(tert-butyl)-1-(3,4-difluoro-2-((2-fluoro-4-iodophenyl)amino)phenyl)-1,20-dioxo-3-oxa-2,8,21-triazatricosan-23-oyl)-4-hydroxy-N—((S)-1-(4-(4-methylthiazol-5-yl)phenyl)ethyl)pyrrolidine-2-carboxamide (CPD-052)

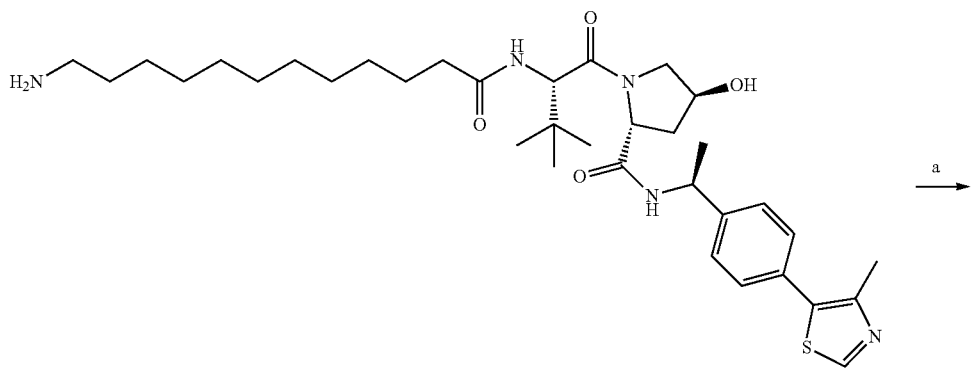

Z57

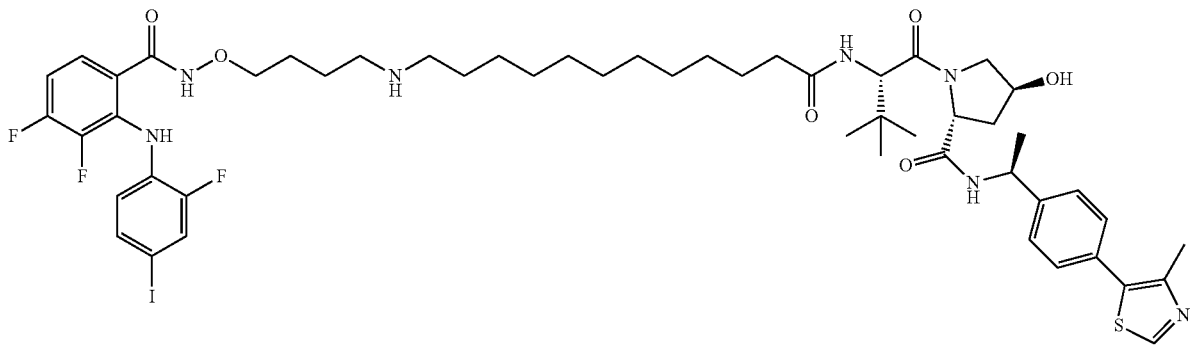

CPD-052

Reagents and conditions: (a) Z5, NaBH₃CN, DCM, MeOH, rt, overnight.

CPD-052 was synthesized following the same procedures as CPD-001 as described in Example 3. (0.02 g, yield: 46%). ¹H NMR (600 MHz, Methanol-$d_4$) δ 9.01 (s, 1H), 7.52 (d, J=8.0 Hz, 2H), 7.47-7.42 (m, 3H), 7.40-7.37 (m, 1H), 7.35 (dd, J=8.6, 1.7 Hz, 1H), 7.13-6.98 (m, 1H), 6.61 (td, J=8.7, 4.3 Hz, 1H), 5.02 (q, J=7.0 Hz, 1H), 4.55 (dd, J=8.2, 6.5 Hz, 1H), 4.49 (s, 1H), 4.45 (q, J=4.6 Hz, 1H), 3.93 (q, J=5.2 Hz, 3H), 3.69 (dd, J=10.8, 3.5 Hz, 1H), 3.10 (t, J=7.3 Hz, 2H), 3.02-2.93 (m, 2H), 2.50 (s, 3H), 2.33-2.25 (m, 1H), 2.19 (dt, J=14.4, 7.9 Hz, 2H), 2.10 (dt, J=12.6, 5.8 Hz, 1H), 1.88 (p, J=7.2 Hz, 2H), 1.75 (p, J=6.5 Hz, 2H), 1.66 (p, J=7.7 Hz, 2H), 1.55 (dt, J=22.0, 7.1 Hz, 2H), 1.45 (d, J=7.1 Hz, 3H), 1.38-1.31 (m, 2H), 1.31-1.21 (m, 12H), 1.06 (s, 9H).

Example 54: (2S,4R)—N—((S)-1-(3,4-difluoro-2-((2-fluoro-4-iodophenyl)amino)phenyl)-13-(4-(4-methylthiazol-5-yl)phenyl)-1,11-dioxo-3-oxa-2,7,10-triazatridecan-13-yl)-1-(2-(1-fluorocyclopropane-1-carboxamido)-3,3-dimethylbutanoyl)-4-hydroxypyrrolidine-2-carboxamide (CPD-054)

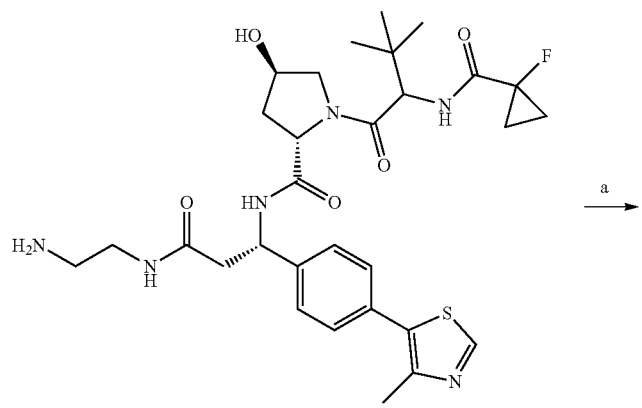

Z58

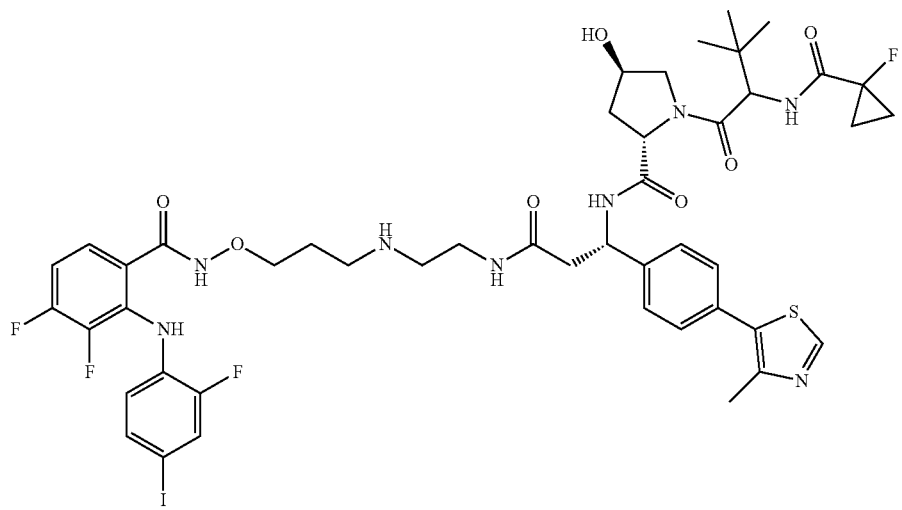

CPD-054

Reagents and conditions: (a) Z5, NaBH₃CN, DCM, MeOH, rt, overnight.

CPD-054 was synthesized following the same procedures as CPD-001 as described in Example 3. (0.02 g, yield: 46%). ¹H NMR (600 MHz, Methanol-$d_4$) δ 8.95 (s, 1H), 7.44-7.41 (m, 3H), 7.39-7.33 (m, 4H), 7.02 (td, J=9.2, 7.0 Hz, 1H), 6.63 (td, J=8.7, 3.5 Hz, 1H), 5.31 (dd, J=7.9, 6.6 Hz, 1H), 4.72 (dd, J=9.3, 1.2 Hz, 1H), 4.55 (dd, J=9.4, 7.6 Hz, 1H), 4.44 (tt, J=3.7, 1.6 Hz, 1H), 4.06-3.98 (m, 2H), 3.84 (dt, J=11.3, 1.7 Hz, 1H), 3.76 (dd, J=11.1, 3.8 Hz, 1H), 3.55-3.49 (m, 2H), 3.25 (t, J=5.8 Hz, 2H), 3.17 (q, J=5.5 Hz, 2H), 2.80 (dd, J=14.7, 8.0 Hz, 1H), 2.71 (dd, J=14.7, 6.7 Hz, 1H), 2.47 (s, 3H), 2.19 (ddt, J=13.2, 7.0, 1.9 Hz, 1H), 2.01 (qt, J=5.6, 2.9 Hz, 2H), 1.93 (ddd, J=13.4, 9.5, 4.4 Hz, 1H), 1.40-1.26 (m, 4H), 1.04 (s, 9H).

Example 55: (2S,4R)—N—((S)-1-(3,4-difluoro-2-((2-fluoro-4-iodophenyl)amino)phenyl)-14-(4-(4-methylthiazol-5-yl)phenyl)-1,12-dioxo-3-oxa-2,7,11-triazatetradecan-14-yl)-1-(2-(1-fluorocyclopropane-1-carboxamido)-3,3-dimethylbutanoyl)-4-hydroxypyrrolidine-2-carboxamide (CPD-055)

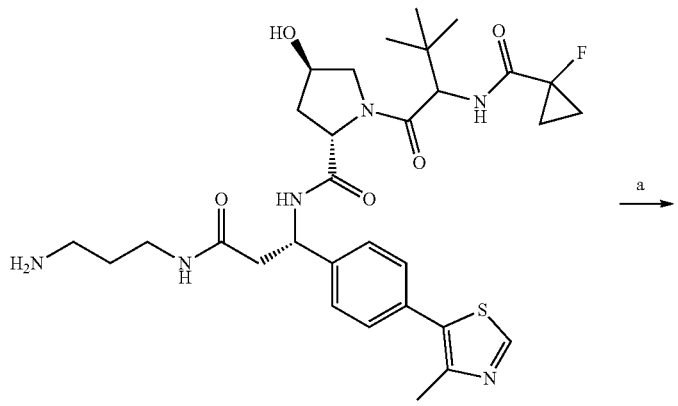

Z59

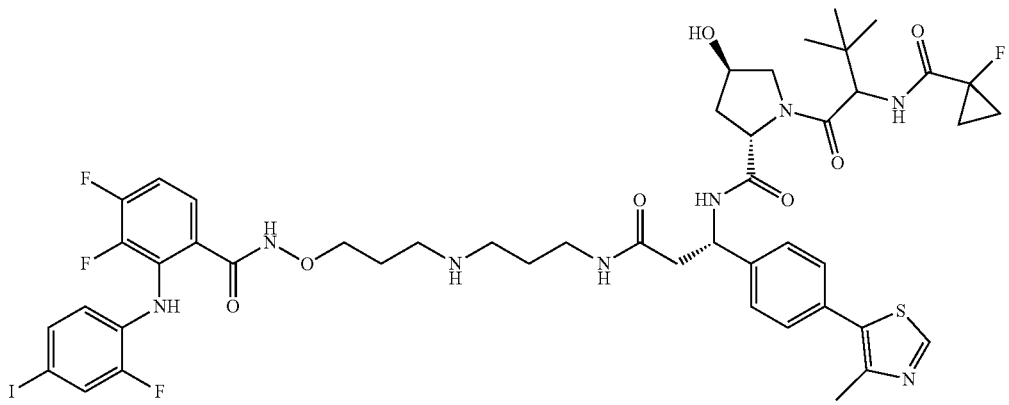

CPD-055

Reagents and conditions: (a) Z5, NaBH₃CN, DCM, MeOH, rt, overnight.

CPD-055 was synthesized following the same procedures as CPD-001 as described in Example 3. (0.02 g, yield: 46%). ¹H NMR (600 MHz, Methanol-d₄) δ 8.92 (s, 1H), 7.53-7.42 (m, 5H), 7.40-7.37 (m, 1H), 7.35 (dt, J=8.6, 1.4 Hz, 1H), 7.06 (td, J=9.2, 7.0 Hz, 1H), 6.61 (td, J=8.8, 3.9 Hz, 1H), 5.34 (t, J=7.4 Hz, 1H), 4.75-4.71 (m, 1H), 4.56 (dd, J=9.3, 7.6 Hz, 1H), 4.44 (tt, J=3.8, 1.6 Hz, 1H), 4.03 (t, J=5.3 Hz, 2H), 3.83 (dt, J=11.5, 1.7 Hz, 1H), 3.75 (dd, J=11.1, 3.8 Hz, 1H), 3.27 (t, J=6.5 Hz, 2H), 3.14 (t, J=6.1 Hz, 2H), 2.92 (dt, J=13.6, 7.1 Hz, 1H), 2.87 (ddt, J=9.5, 6.0, 3.4 Hz, 2H), 2.78 (dd, J=14.6, 7.8 Hz, 1H), 2.47 (s, 3H), 2.20 (ddt, J=13.2, 7.7, 2.0 Hz, 1H), 1.99 (tt, J=8.7, 4.4 Hz, 2H), 1.92 (ddd, J=13.4, 9.4, 4.4 Hz, 1H), 1.84 (pd, J=6.8, 3.7 Hz, 2H), 1.41-1.25 (m, 4H), 1.05 (s, 9H).

Example 56: (2S,4R)—N—((S)-1-(3,4-difluoro-2-((2-fluoro-4-iodophenyl)amino)phenyl)-15-(4-(4-methylthiazol-5-yl)phenyl)-1,13-dioxo-3-oxa-2,7,12-triazapentadecan-15-yl)-1-(2-(1-fluorocyclopropane-1-carboxamido)-3,3-dimethylbutanoyl)-4-hydroxypyrrolidine-2-carboxamide (CPD-056)

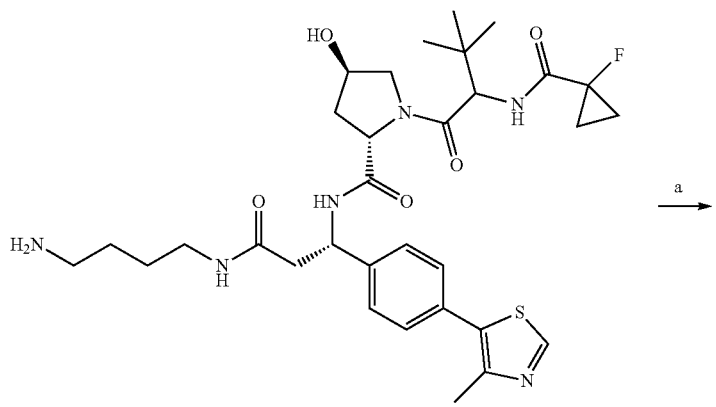

Z60

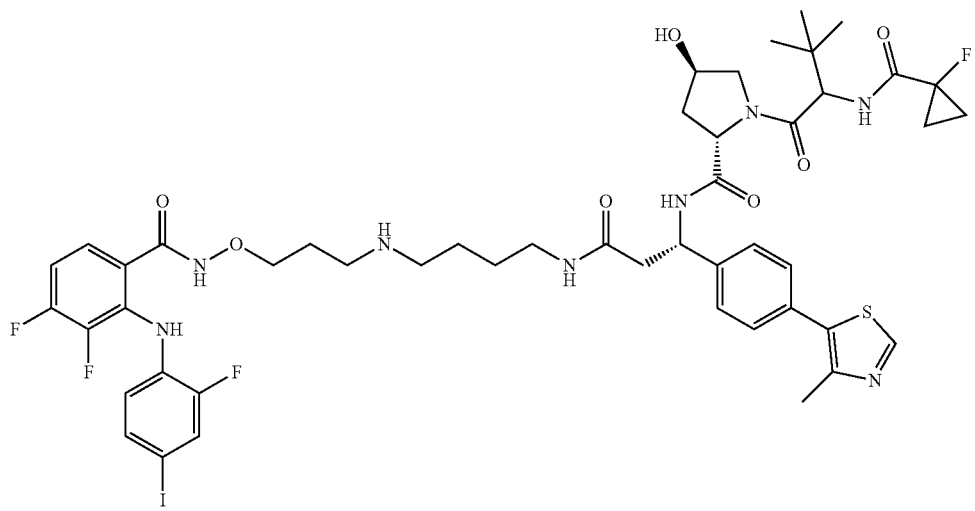

CPD-056

Reagents and conditions: (a) Z5, NaBH₃CN, DCM, MeOH, rt, overnight.

CPD-056 was synthesized following the same procedures as CPD-001 as described in Example 3. (0.02 g, yield: 36%). ¹H NMR (600 MHz, Methanol-$d_4$) δ 8.97 (s, 1H), 7.46 (dd, J=10.5, 1.8 Hz, 5H), 7.40-7.37 (m, 1H), 7.37-7.34 (m, 1H), 7.05 (td, J=9.1, 7.0 Hz, 1H), 6.61 (td, J=8.7, 4.1 Hz, 1H), 5.32 (dd, J=7.9, 6.5 Hz, 1H), 4.77-4.69 (m, 1H), 4.58 (dd, J=9.3, 7.6 Hz, 1H), 4.44 (tt, J=3.9, 1.7 Hz, 1H), 4.08-3.99 (m, 2H), 3.83 (dt, J=11.4, 1.7 Hz, 1H), 3.76 (dd, J=11.1, 3.8 Hz, 1H), 3.20 (t, J=6.0 Hz, 2H), 3.15 (td, J=6.9, 5.3 Hz, 2H), 3.06-3.00 (m, 2H), 2.85 (dd, J=14.3, 6.6 Hz, 1H), 2.74 (dd, J=14.2, 8.0 Hz, 1H), 2.47 (s, 3H), 2.20 (ddt, J=13.0, 7.5, 1.8 Hz, 1H), 2.01 (tt, J=7.9, 3.9 Hz, 2H), 1.95 (ddd, J=13.4, 9.3, 4.4 Hz, 1H), 1.70-1.63 (m, 2H), 1.52 (p, J=7.4 Hz, 2H), 1.40-1.26 (m, 4H), 1.05 (s, 9H).

Example 57: (2S,4R)—N—((S)-1-(3,4-difluoro-2-((2-fluoro-4-iodophenyl)amino)phenyl)-16-(4-(4-methylthiazol-5-yl)phenyl)-1,14-dioxo-3-oxa-2,7,13-triazahexadecan-16-yl)-1-(2-(1-fluorocyclopropane-1-carboxamido)-3,3-dimethylbutanoyl)-4-hydroxypyrrolidine-2-carboxamide (CPD-057)

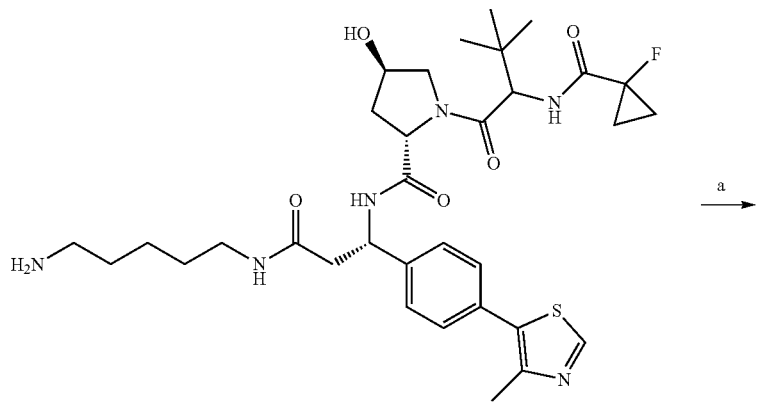

Z61

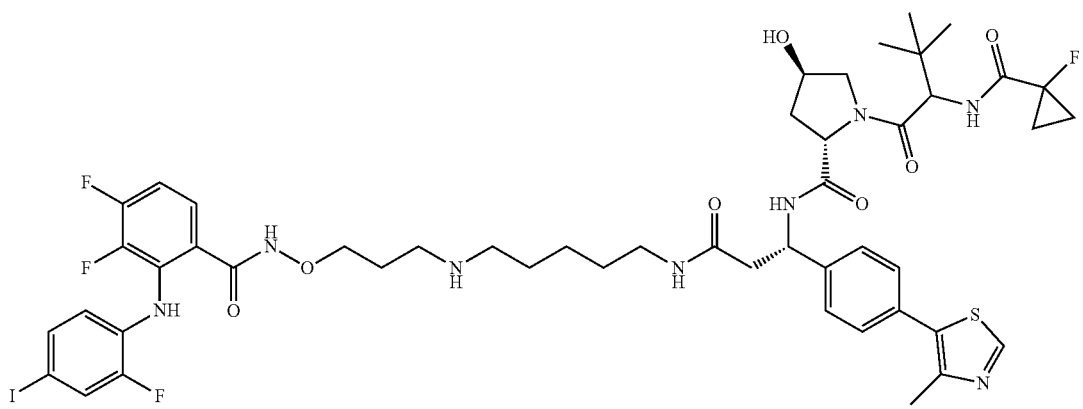

CPD-057

Reagents and conditions: (a) Z5, NaBH₃CN, DCM, MeOH, rt, overnight.

CPD-057 was synthesized following the same procedures as CPD-001 as described in Example 3. (0.02 g, yield: 46%). $^1$H NMR (600 MHz, Methanol-$d_4$) δ 8.86 (d, J=5.6 Hz, 1H), 7.48-7.45 (m, 2H), 7.44 (d, J=4.1 Hz, 2H), 7.43-7.41 (m, 1H), 7.40-7.38 (m, 1H), 7.35 (ddd, J=8.5, 2.0, 1.0 Hz, 1H), 7.06 (td, J=9.2, 7.0 Hz, 1H), 6.60 (td, J=8.7, 4.1 Hz, 1H), 5.32 (dd, J=8.5, 6.0 Hz, 1H), 4.73 (dd, J=9.4, 1.2 Hz, 1H), 4.57 (dd, J=9.3, 7.6 Hz, 1H), 4.44 (dq, J=4.0, 2.1 Hz, 1H), 4.09-3.97 (m, 2H), 3.83 (dt, J=11.4, 1.7 Hz, 1H), 3.77 (dd, J=11.1, 3.8 Hz, 1H), 3.18 (t, J=5.8 Hz, 2H), 3.11 (q, J=6.9 Hz, 1H), 3.06 (dd, J=13.5, 6.8 Hz, 1H), 2.99-2.93 (m, 2H), 2.85 (dd, J=14.2, 6.0 Hz, 1H), 2.75 (dd, J=14.2, 8.6 Hz, 1H), 2.45 (s, 3H), 2.19 (ddt, J=13.2, 7.5, 1.9 Hz, 1H), 2.04-1.98 (m, 2H), 1.95 (ddd, J=13.4, 9.4, 4.4 Hz, 1H), 1.73-1.62 (m, 2H), 1.45-1.38 (m, 2H), 1.38-1.24 (m, 6H), 1.05 (s, 9H).

Example 58: (2S,4R)—N—((S)-1-(3,4-difluoro-2-((2-fluoro-4-iodophenyl)amino)phenyl)-17-(4-(4-methylthiazol-5-yl)phenyl)-1,15-dioxo-3-oxa-2,7,14-triazaheptadecan-17-yl)-1-(2-(1-fluorocyclopropane-1-carboxamido)-3,3-dimethylbutanoyl)-4-hydroxypyrrolidine-2-carboxamide (CPD-058)

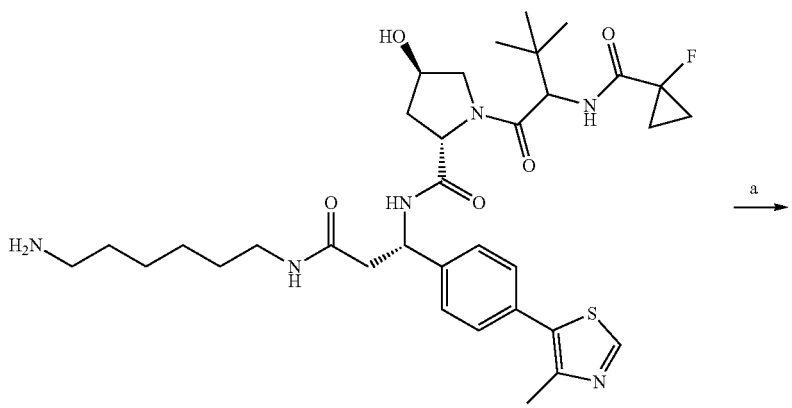

Z62

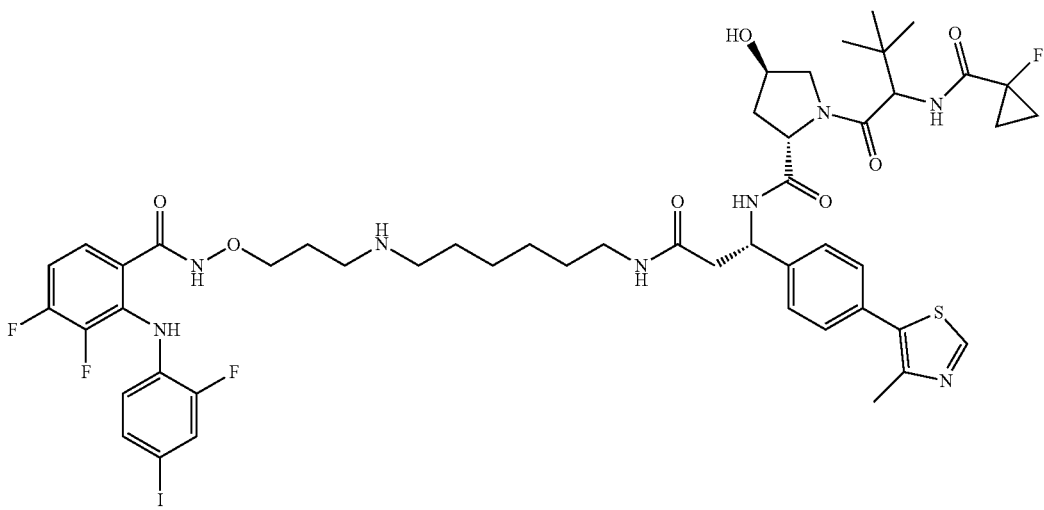

CPD-058

Reagents and conditions: (a) Z5, NaBH$_3$CN, DCM, MeOH, rt, overnight.

CPD-058 was synthesized following the same procedures as CPD-001 as described in Example 3. (0.02 g, yield: 39%). $^1$H NMR (600 MHz, Methanol-$d_4$) δ 8.94 (s, 1H), 7.48-7.43 (m, 5H), 7.42-7.38 (m, 1H), 7.36 (ddd, J=8.5, 1.9, 1.0 Hz, 1H), 7.06 (td, J=9.2, 7.0 Hz, 1H), 6.62 (td, J=8.7, 4.1 Hz, 1H), 5.32 (dd, J=8.4, 6.0 Hz, 1H), 4.77-4.71 (m, 1H), 4.57 (dd, J=9.3, 7.7 Hz, 1H), 4.45 (tt, J=4.0, 1.7 Hz, 1H), 4.05 (t, J=5.1 Hz, 2H), 3.83 (dt, J=11.3, 1.7 Hz, 1H), 3.76 (dd, J=11.1, 3.8 Hz, 1H), 3.21 (t, J=5.8 Hz, 2H), 3.11 (dt, J=14.0, 7.1 Hz, 1H), 3.06 (dt, J=13.5, 7.0 Hz, 1H), 3.01-2.96 (m, 2H), 2.85 (dd, J=14.1, 6.1 Hz, 1H), 2.74 (dd, J=14.1, 8.4 Hz, 1H), 2.47 (s, 3H), 2.19 (ddt, J=13.2, 7.6, 1.9 Hz, 1H), 2.02 (dt, J=9.9, 5.0 Hz, 2H), 1.95 (ddd, J=13.4, 9.3, 4.4 Hz, 1H), 1.72-1.63 (m, 2H), 1.42-1.27 (m, 8H), 1.26-1.18 (m, 2H), 1.05 (s, 9H).

Example 59: (2S,4R)—N—((S)-1-(3,4-difluoro-2-((2-fluoro-4-iodophenyl)amino)phenyl)-18-(4-(4-methylthiazol-5-yl)phenyl)-1,16-dioxo-3-oxa-2,7,15-triazaoctadecan-18-yl)-1-(2-(1-fluorocyclopropane-1-carboxamido)-3,3-dimethylbutanoyl)-4-hydroxypyrrolidine-2-carboxamide (CPD-059)

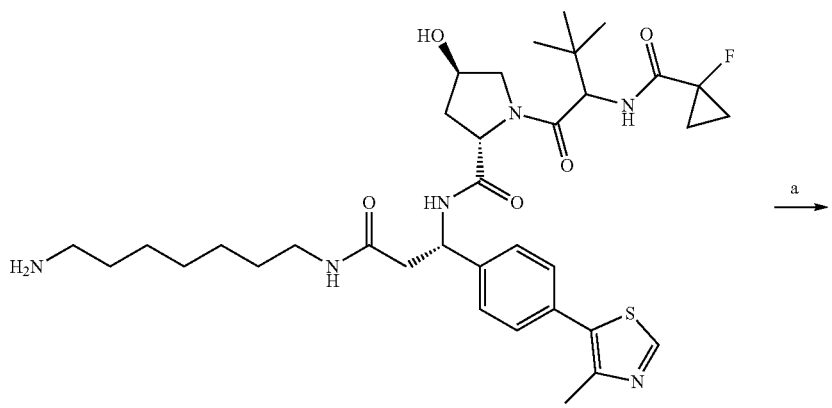

Z63

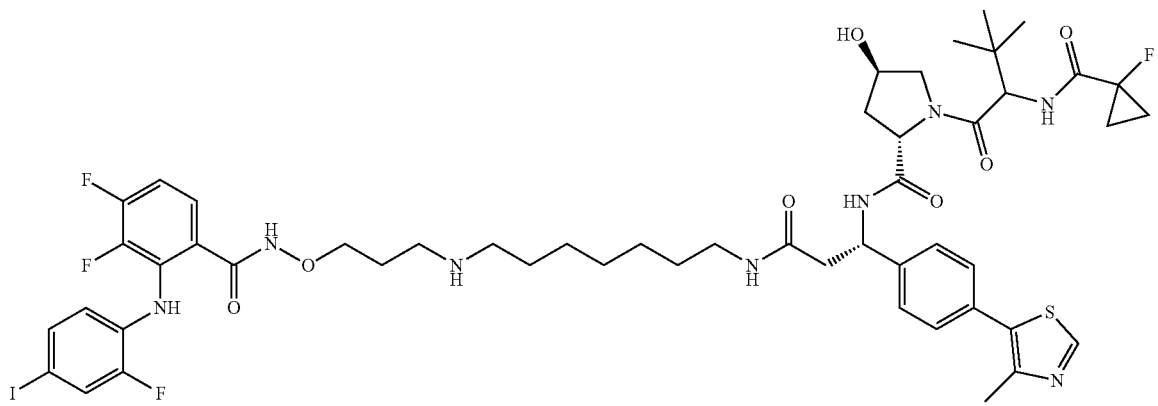

CPD-059

Reagents and conditions: (a) Z5, NaBH$_3$CN, DCM, MeOH, rt, overnight.

CPD-059 was synthesized following the same procedures as CPD-001 as described in Example 3. (0.02 g, yield: 38%). $^1$H NMR (600 MHz, Methanol-$d_4$) δ 8.90 (s, 1H), 7.48-7.42 (m, 5H), 7.42-7.38 (m, 1H), 7.36 (ddd, J=8.5, 1.9, 1.0 Hz, 1H), 7.06 (td, J=9.2, 7.0 Hz, 1H), 6.62 (td, J=8.7, 4.2 Hz, 1H), 5.31 (dd, J=8.6, 5.9 Hz, 1H), 4.74 (dd, J=9.4, 1.3 Hz, 1H), 4.58 (dd, J=9.3, 7.6 Hz, 1H), 4.45 (tt, J=4.0, 1.7 Hz, 1H), 4.13-4.01 (m, 2H), 3.83 (dt, J=11.4, 1.7 Hz, 1H), 3.77 (dd, J=11.1, 3.8 Hz, 1H), 3.22 (t, J=5.8 Hz, 2H), 3.10 (dt, J=13.9, 7.1 Hz, 1H), 3.06-3.00 (m, 1H), 2.99-2.94 (m, 2H), 2.87-2.80 (m, 1H), 2.74 (dd, J=14.1, 8.5 Hz, 1H), 2.47 (d, J=2.5 Hz, 3H), 2.19 (ddt, J=13.2, 7.6, 1.9 Hz, 1H), 2.02 (dt, J=10.1, 4.9 Hz, 2H), 1.95 (ddd, J=13.4, 9.3, 4.4 Hz, 1H), 1.69-1.62 (m, 2H), 1.40-1.20 (m, 10H), 1.16 (q, J=8.3 Hz, 2H), 1.06 (s, 9H).

Example 60: (2S,4R)—N—((S)-1-(3,4-difluoro-2-((2-fluoro-4-iodophenyl)amino)phenyl)-19-(4-(4-methylthiazol-5-yl)phenyl)-1,17-dioxo-3-oxa-2,7,16-triazanonadecan-19-yl)-1-((S)-2-(1-fluorocyclopropane-1-carboxamido)-3,3-dimethylbutanoyl)-4-hydroxypyrrolidine-2-carboxamide (CPD-060)

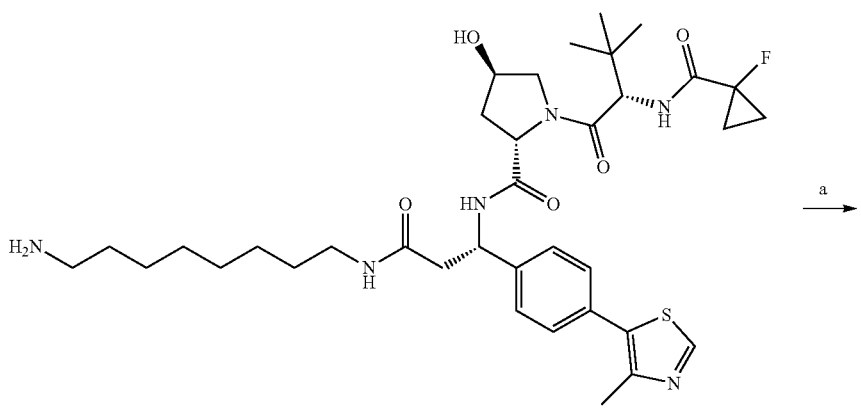

Z64

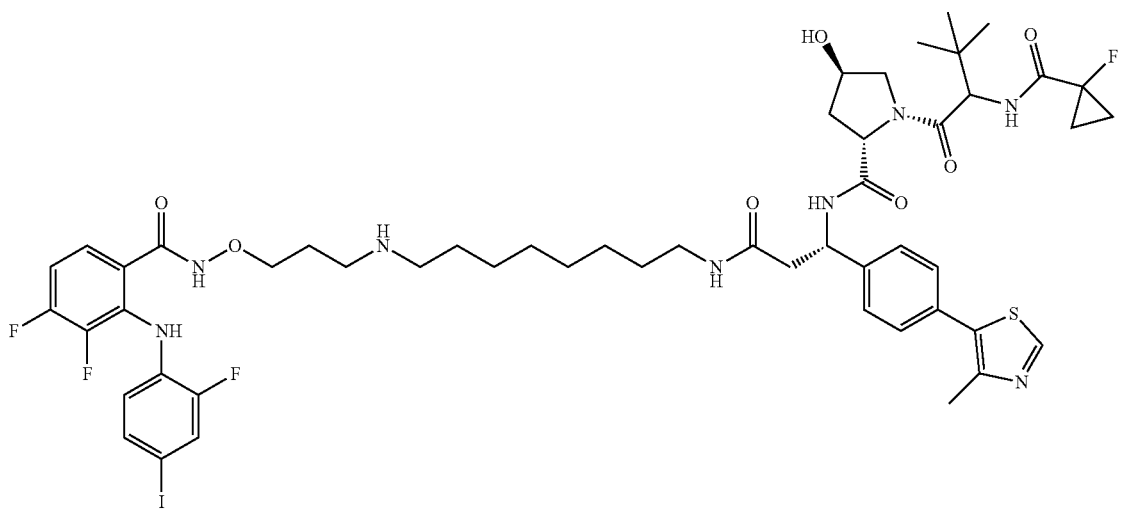

CPD-060

Reagents and conditions: (a) Z5, NaBH$_3$CN, DCM, MeOH, rt, overnight.

CPD-060 was synthesized following the same procedures as CPD-001 as described in Example 3. (0.07 g, yield: 30%). ¹H NMR (600 MHz, Methanol-$d_4$) δ 8.93 (s, 1H), 7.48-7.43 (m, 5H), 7.42-7.39 (m, 1H), 7.36 (dd, J=8.2, 1.8 Hz, 1H), 7.06 (q, J=8.6 Hz, 1H), 6.63 (td, J=8.7, 4.1 Hz, 1H), 5.31 (dd, J=8.6, 5.8 Hz, 1H), 4.74 (dt, J=8.7, 1.2 Hz, 1H), 4.57 (dd, J=9.1, 7.7 Hz, 1H), 4.44 (s, 1H), 4.07 (t, J=5.1 Hz, 2H), 3.83 (d, J=11.1 Hz, 1H), 3.76 (dd, J=11.1, 3.8 Hz, 1H), 3.23 (t, J=5.8 Hz, 2H), 3.10 (dt, J=13.8, 7.0 Hz, 1H), 3.02 (dt, J=16.7, 7.5 Hz, 3H), 2.84 (dd, J=14.1, 5.8 Hz, 1H), 2.73 (dd, J=14.1, 8.6 Hz, 1H), 2.48 (s, 3H), 2.19 (dd, J=13.1, 7.8 Hz, 1H), 2.08-2.00 (m, 2H), 1.95 (ddd, J=13.4, 9.3, 4.3 Hz, 1H), 1.66 (p, J=7.8 Hz, 2H), 1.38-1.26 (m, 8H), 1.25-1.17 (m, 4H), 1.16-1.11 (m, 2H), 1.06 (s, 9H).

Example 61: (2S,4R)—N—((S)-1-(3,4-difluoro-2-((2-fluoro-4-iodophenyl)amino)phenyl)-20-(4-(4-methylthiazol-5-yl)phenyl)-1,18-dioxo-3-oxa-2,7,17-triazaicosan-20-yl)-1-(2-(1-fluorocyclopropane-1-carboxamido)-3,3-dimethylbutanoyl)-4-hydroxypyrrolidine-2-carboxamide (CPD-061)

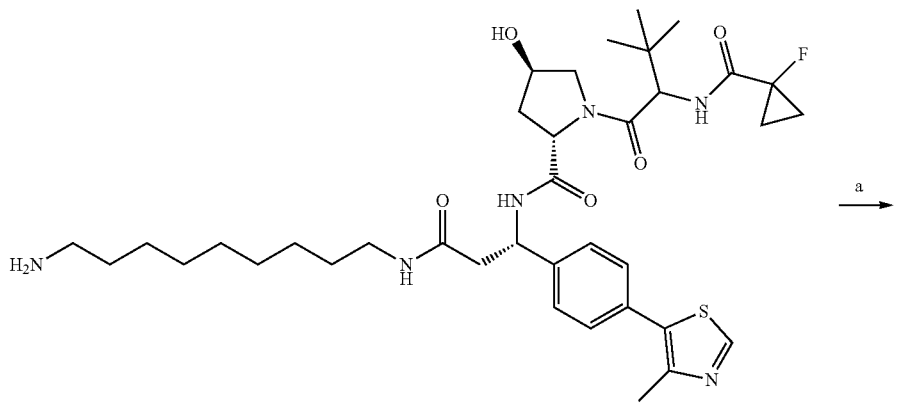

Z65

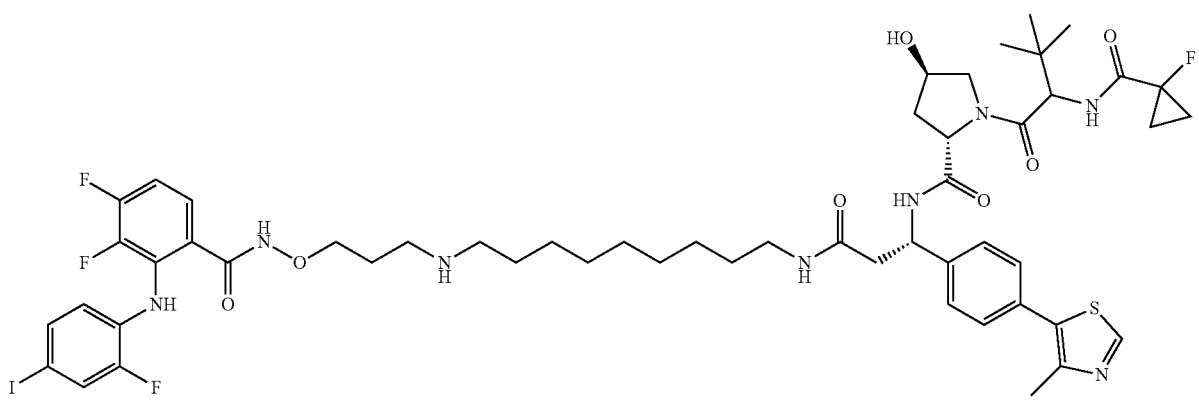

CPD-061

Reagents and conditions: (a) Z5, NaBH₃CN, DCM, MeOH, rt, overnight.

CPD-061 was synthesized following the same procedures as CPD-001 as described in Example 3. (0.07 g, yield: 30%). $^1$H NMR (600 MHz, Methanol-$d_4$) δ 8.90 (s, 1H), 7.47-7.42 (m, 5H), 7.41 (td, J=6.0, 2.8 Hz, 1H), 7.36 (ddd, J=8.5, 2.0, 1.0 Hz, 1H), 7.06 (td, J=9.2, 7.0 Hz, 1H), 6.63 (td, J=8.7, 4.3 Hz, 1H), 5.31 (dd, J=8.7, 5.7 Hz, 1H), 4.74 (dd, J=9.3, 1.2 Hz, 1H), 4.58 (dd, J=9.3, 7.5 Hz, 1H), 4.45 (tt, J=4.0, 1.7 Hz, 1H), 4.12-4.03 (m, 2H), 3.83 (dt, J=11.3, 1.7 Hz, 1H), 3.77 (dd, J=11.1, 3.8 Hz, 1H), 3.24 (t, J=5.8 Hz, 2H), 3.10 (dt, J=13.8, 7.0 Hz, 1H), 3.05-2.97 (m, 3H), 2.84 (dd, J=14.0, 5.8 Hz, 1H), 2.73 (dd, J=14.0, 8.7 Hz, 1H), 2.48 (d, J=1.9 Hz, 3H), 2.20 (ddt, J=13.2, 7.7, 1.9 Hz, 1H), 2.08-2.01 (m, 2H), 1.95 (ddd, J=13.4, 9.3, 4.4 Hz, 1H), 1.73-1.66 (m, 2H), 1.38-1.28 (m, 8H), 1.24-1.15 (m, 6H), 1.13-1.09 (m, 2H), 1.06 (s, 9H).

Example 62: (2S,4R)—N—((S)-1-(3,4-difluoro-2-((2-fluoro-4-iodophenyl)amino)phenyl)-21-(4-(4-methylthiazol-5-yl)phenyl)-1,19-dioxo-3-oxa-2,7,18-triazahenicosan-21-yl)-1-((S)-2-(1-fluorocyclopropane-1-carboxamido)-3,3-dimethylbutanoyl)-4-hydroxypyrrolidine-2-carboxamide (CPD-062)

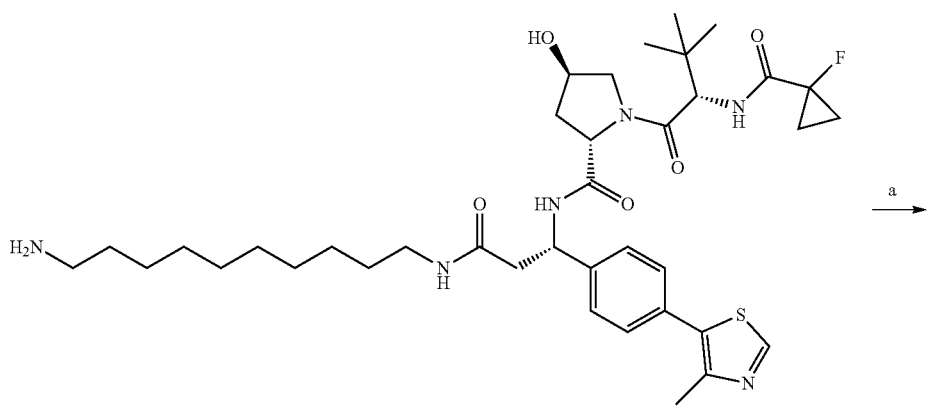

Z66

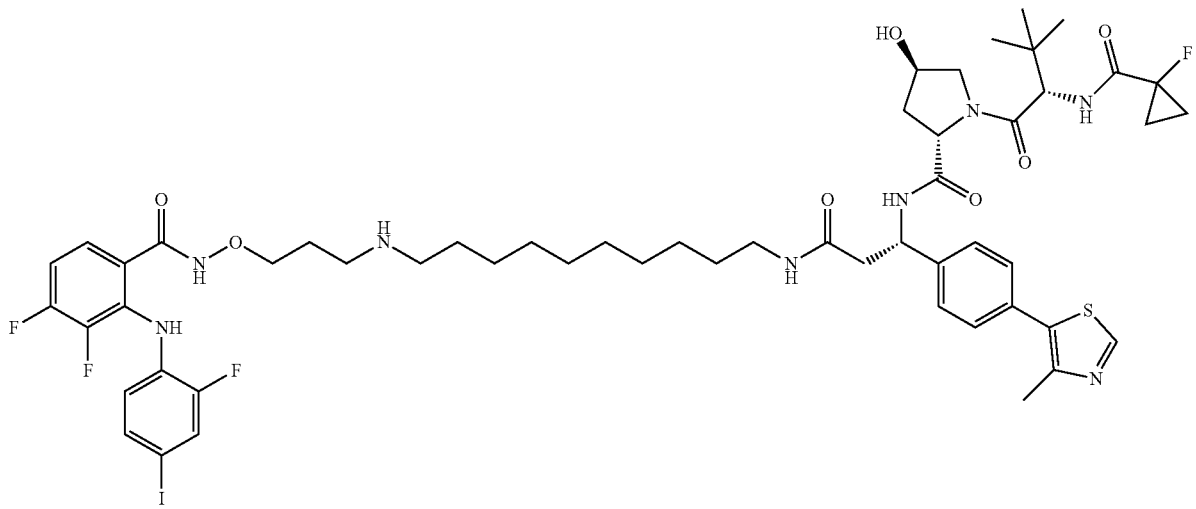

CPD-062

Reagents and conditions: (a) Z5, NaBH$_3$CN, DCM, MeOH, rt, overnight.

CPD-062 was synthesized following the same procedures as CPD-001 as described in Example 3. (0.07 g, yield: 30%). $^1$H NMR (600 MHz, Methanol-$d_4$) δ 8.93 (s, 1H), 7.48-7.43 (m, 5H), 7.42-7.39 (m, 1H), 7.36 (d, J=8.5 Hz, 1H), 7.06 (q, J=8.6 Hz, 1H), 6.63 (td, J=8.8, 4.3 Hz, 1H), 5.31 (dd, J=8.7, 5.7 Hz, 1H), 4.77-4.71 (m, 1H), 4.57 (dd, J=9.1, 7.7 Hz, 1H), 4.46-4.43 (m, 1H), 4.08 (t, J=5.1 Hz, 2H), 3.83 (d, J=11.2 Hz, 1H), 3.77 (dd, J=11.1, 3.8 Hz, 1H), 3.24 (t, J=5.8 Hz, 2H), 3.10 (dt, J=13.8, 7.1 Hz, 1H), 3.06-2.98 (m, 3H), 2.84 (dd, J=14.0, 5.8 Hz, 1H), 2.73 (dd, J=14.0, 8.6 Hz, 1H), 2.48 (s, 3H), 2.27-2.13 (m, 1H), 2.10-2.01 (m, 2H), 1.95 (ddd, J=13.4, 9.3, 4.4 Hz, 1H), 1.70 (p, J=7.8 Hz, 2H), 1.44-1.27 (m, 8H), 1.25-1.15 (m, 8H), 1.14-1.09 (m, 2H), 1.06 (s, 9H).

Example 63: (2S,4R)—N—((S)-1-(3,4-difluoro-2-((2-fluoro-4-iodophenyl)amino)phenyl)-22-(4-(4-methylthiazol-5-yl)phenyl)-1,20-dioxo-3-oxa-2,7,19-triazadocosan-22-yl)-1-(2-(1-fluorocyclopropane-1-carboxamido)-3,3-dimethylbutanoyl)-4-hydroxypyrrolidine-2-carboxamide (CPD-063)

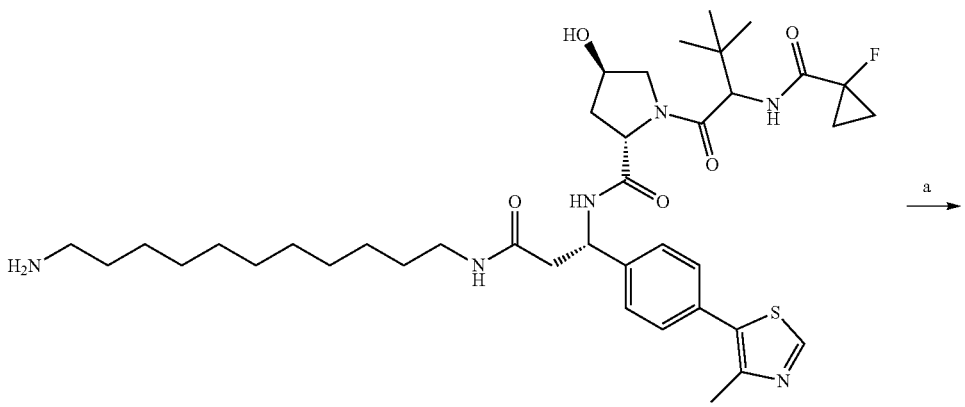

Z67

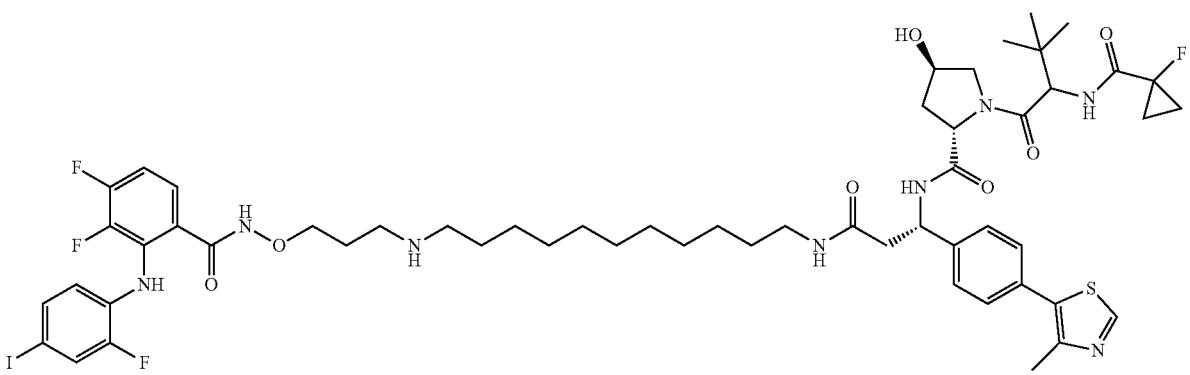

CPD-063

Reagents and conditions: (a) Z5, NaBH$_3$CN, DCM, MeOH, rt, overnight.

CPD-063 was synthesized following the same procedures as CPD-001 as described in Example 3. (0.07 g, yield: 30%). $^1$H NMR (600 MHz, Methanol-$d_4$) δ 8.91 (s, 1H), 7.48-7.42 (m, 5H), 7.42-7.39 (m, 11H), 7.36 (ddd, J=8.4, 1.9, 1.0 Hz, 11H), 7.05 (td, J=9.2, 7.0 Hz, 11H), 6.64 (td, J=8.7, 4.3 Hz, 1H), 5.31 (dd, J=8.6, 5.8 Hz, 11H), 4.74 (dd, J=9.4, 1.3 Hz, 11H), 4.58 (dd, J=9.2, 7.5 Hz, 11H), 4.45 (dt, J=4.1, 2.1 Hz, 1H), 4.13-4.03 (m, 2H), 3.83 (dt, J=11.2, 1.7 Hz, 1H), 3.77 (dd, J=11.1, 3.8 Hz, 1H), 3.24 (t, J=5.8 Hz, 2H), 3.10 (dt, J=13.7, 7.0 Hz, 1H), 3.06-2.98 (m, 3H), 2.84 (dd, J=14.0, 5.8 Hz, 11H), 2.74 (dd, J=14.0, 8.6 Hz, 1H), 2.48 (d, J=1.8 Hz, 3H), 2.20 (ddt, J=13.2, 7.7, 2.0 Hz, 11H), 2.06-2.01 (m, 2H), 1.96 (ddd, J=13.4, 9.3, 4.4 Hz, 11H), 1.74-1.68 (m, 2H), 1.43-1.23 (m, 10H), 1.21-1.14 (m, 8H), 1.11 (q, J=7.3, 6.3 Hz, 2H), 1.06 (s, 9H).

Example 64: (2S,4R)—N—((S)-1-(3,4-difluoro-2-((2-fluoro-4-iodophenyl)amino)phenyl)-16-(4-(4-methylthiazol-5-yl)phenyl)-1,14-dioxo-3,10-dioxa-2,7,13-triazahexadecan-16-yl)-1-(2-(1-fluorocyclopropane-1-carboxamido)-3,3-dimethylbutanoyl)-4-hydroxypyrrolidine-2-carboxamide (CPD-064)

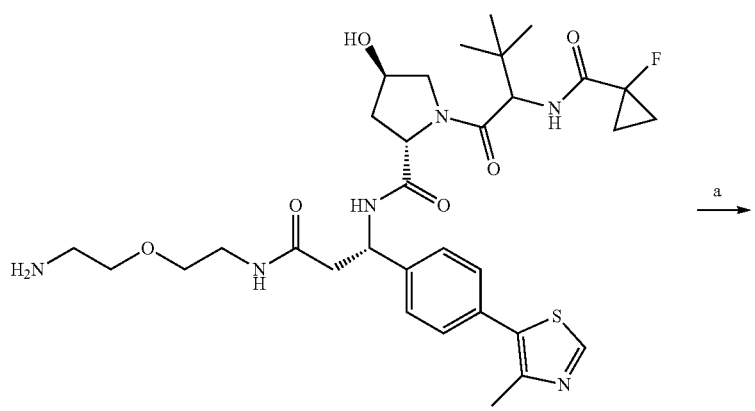

Z68

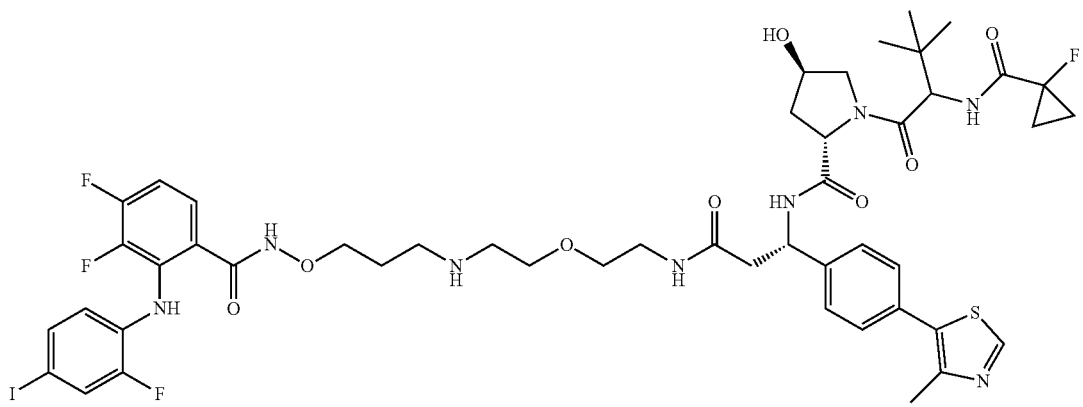

CPD-064

Reagents and conditions: (a) Z5, NaBH$_3$CN, DCM, MeOH, rt, overnight.

CPD-064 was synthesized following the same procedures as CPD-001 as described in Example 3. (0.07 g, yield: 31%). ¹H NMR (600 MHz, Methanol-$d_4$) δ 9.14 (s, 1H), 7.47-7.42 (m, 5H), 7.39 (ddd, J=8.9, 5.4, 1.7 Hz, 1H), 7.33 (ddd, J=8.4, 2.0, 1.0 Hz, 1H), 7.03 (td, J=9.2, 6.9 Hz, 1H), 6.58 (td, J=8.7, 4.1 Hz, 1H), 5.31 (dd, J=7.9, 6.6 Hz, 1H), 4.75-4.70 (m, 1H), 4.59-4.53 (m, 1H), 4.44 (tt, J=3.9, 1.7 Hz, 1H), 4.05 (ddt, J=8.8, 6.1, 2.9 Hz, 2H), 3.83 (d, J=11.4 Hz, 1H), 3.76 (dd, J=11.2, 3.9 Hz, 1H), 3.72 (ddd, J=9.0, 5.8, 4.5 Hz, 2H), 3.46 (t, J=5.8 Hz, 2H), 3.29-3.25 (m, 4H), 3.25-3.21 (m, 2H), 2.84 (dd, J=14.4, 6.6 Hz, 1H), 2.73 (dd, J=14.4, 7.9 Hz, 1H), 2.49 (s, 3H), 2.21 (ddt, J=13.2, 7.6, 1.9 Hz, 1H), 2.05 (dq, J=7.5, 5.5 Hz, 2H), 1.94 (ddd, J=13.5, 9.4, 4.4 Hz, 1H), 1.41-1.25 (m, 4H), 1.05 (s, 9H).

Example 65: (2S,4R)—N—((S)-1-(3,4-difluoro-2-((2-fluoro-4-iodophenyl)amino)phenyl)-23-(4-(4-methylthiazol-5-yl)phenyl)-1,21-dioxo-3-oxa-2,7,20-triazatricosan-23-yl)-1-(2-(1-fluorocyclopropane-1-carboxamido)-3,3-dimethylbutanoyl)-4-hydroxypyrrolidine-2-carboxamide (CPD-065)

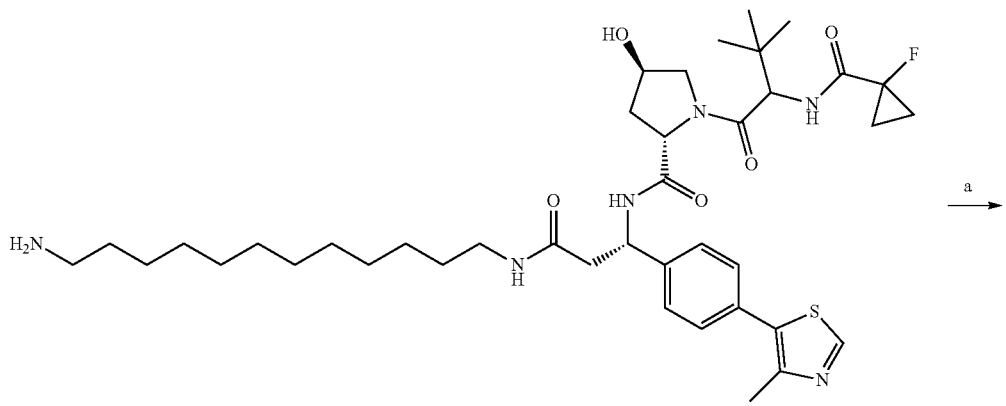

Z69

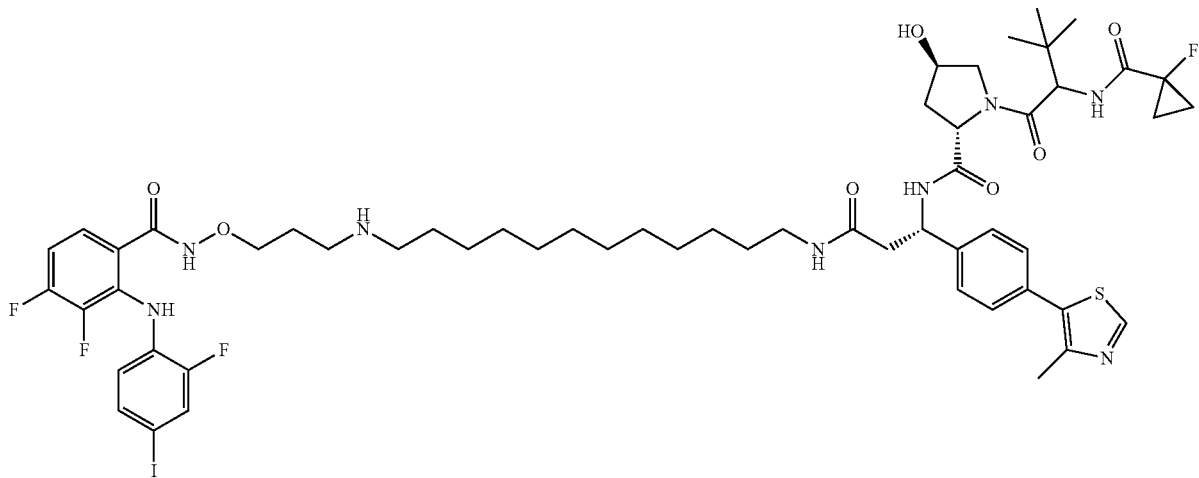

CPD-065

Reagents and conditions: (a) Z5, NaBH₃CN, DCM, MeOH, rt, overnight.

CPD-065 was synthesized following the same procedures as CPD-001 as described in Example 3. (0.07 g, yield: 37%). $^{1}$H NMR (600 MHz, Methanol-$d_4$) δ 8.97 (s, 1H), 7.49-7.43 (m, 5H), 7.41 (ddd, J=8.8, 4.4, 1.6 Hz, 1H), 7.37 (ddd, J=8.4, 2.0, 1.0 Hz, 1H), 7.05 (td, J=9.3, 7.0 Hz, 1H), 6.64 (td, J=8.7, 4.4 Hz, 1H), 5.31 (dd, J=8.6, 5.8 Hz, 1H), 4.74 (dd, J=9.3, 1.3 Hz, 1H), 4.58 (dd, J=9.2, 7.5 Hz, 1H), 4.45 (tt, J=4.0, 1.7 Hz, 1H), 4.08 (dd, J=5.7, 4.5 Hz, 2H), 3.88-3.81 (m, 1H), 3.77 (dd, J=11.1, 3.8 Hz, 1H), 3.24 (t, J=5.8 Hz, 2H), 3.10 (dt, J=13.8, 7.0 Hz, 1H), 3.06-2.98 (m, 3H), 2.84 (dd, J=14.0, 5.8 Hz, 1H), 2.74 (dd, J=14.0, 8.6 Hz, 1H), 2.49 (d, J=1.8 Hz, 3H), 2.20 (ddt, J=13.3, 7.7, 2.0 Hz, 1H), 2.03 (dt, J=10.2, 5.0 Hz, 2H), 1.96 (ddd, J=13.4, 9.4, 4.5 Hz, 1H), 1.72 (ddd, J=13.0, 10.3, 6.9 Hz, 2H), 1.41-1.35 (m, 3H), 1.35-1.26 (m, 7H), 1.26-1.16 (m, 10H), 1.15-1.10 (m, 2H), 1.06 (s, 9H).

Example 66: (2S,4R)—N—((S)-1-(3,4-difluoro-2-((2-fluoro-4-iodophenyl)amino)phenyl)-19-(4-(4-methylthiazol-5-yl)phenyl)-1,17-dioxo-3,10,13-trioxa-2,7,16-triazanonadecan-19-yl)-1-(2-(1-fluorocyclopropane-1-carboxamido)-3,3-dimethylbutanoyl)-4-hydroxypyrrolidine-2-carboxamide (CPD-066)

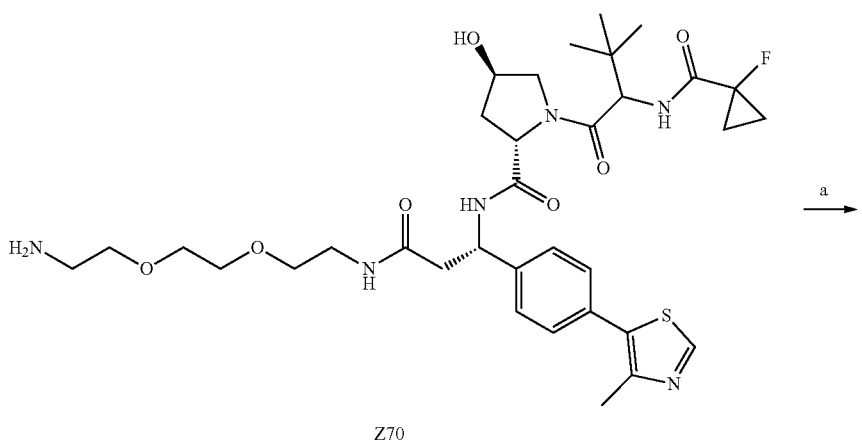

Z70

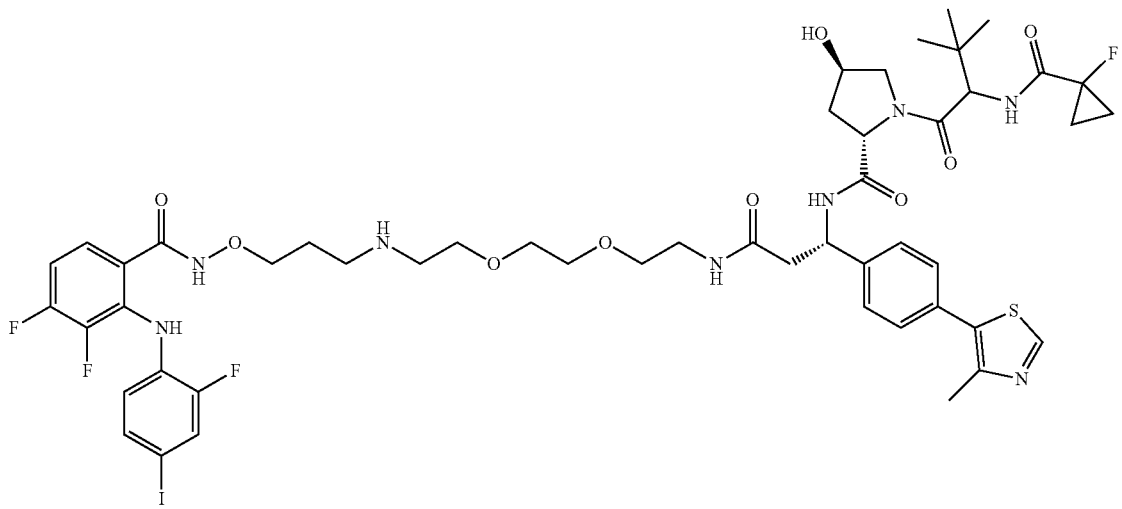

CPD-066

Reagents and conditions: (a) Z5, NaBH$_3$CN, DCM, MeOH, rt, overnight.

CPD-066 was synthesized following the same procedures as CPD-001 as described in Example 3. (0.08 g, yield: 40%). ¹H NMR (600 MHz, Methanol-$d_4$) δ 8.92 (s, 1H), 7.49-7.42 (m, 5H), 7.39 (ddd, J=8.7, 6.0, 1.8 Hz, 1H), 7.36 (ddd, J=8.4, 2.0, 1.0 Hz, 1H), 7.05 (td, J=9.3, 7.0 Hz, 1H), 6.62 (td, J=8.7, 4.1 Hz, 1H), 5.32 (dd, J=8.3, 6.2 Hz, 1H), 4.73 (dd, J=9.3, 1.2 Hz, 1H), 4.57 (dd, J=9.3, 7.6 Hz, 1H), 4.44 (tt, J=4.0, 1.7 Hz, 1H), 4.06 (t, J=5.3 Hz, 2H), 3.83 (dt, J=11.3, 1.7 Hz, 1H), 3.78-3.71 (m, 3H), 3.52 (td, J=3.7, 3.3, 1.8 Hz, 2H), 3.47 (dd, J=5.1, 3.8 Hz, 2H), 3.37 (qt, J=10.0, 5.8 Hz, 2H), 3.27 (dq, J=9.6, 5.0, 4.1 Hz, 5H), 2.85 (dd, J=14.3, 6.2 Hz, 1H), 2.75 (dd, J=14.3, 8.4 Hz, 1H), 2.47 (s, 3H), 2.20 (ddt, J=13.3, 7.7, 2.0 Hz, 1H), 2.04 (dt, J=10.8, 5.3 Hz, 2H), 1.95 (ddd, J=13.4, 9.4, 4.4 Hz, 1H), 1.42-1.24 (m, 5H), 1.05 (s, 9H).

Example 67: (2S,4R)—N—((S)-1-(3,4-difluoro-2-((2-fluoro-4-iodophenyl)amino)phenyl)-22-(4-(4-methylthiazol-5-yl)phenyl)-1,20-dioxo-3,10,13,16-tetraoxa-2,7,19-triazadocosan-22-yl)-1-(2-(1-fluorocyclopropane-1-carboxamido)-3,3-dimethylbutanoyl)-4-hydroxypyrrolidine-2-carboxamide (CPD-067)

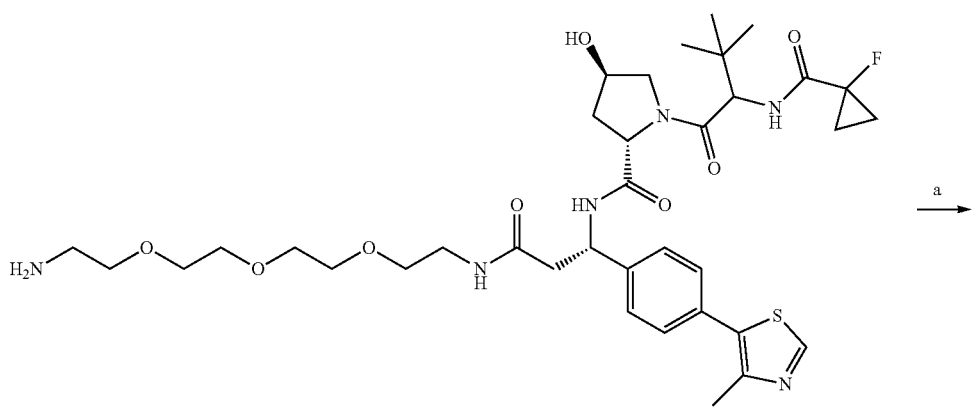

Z71

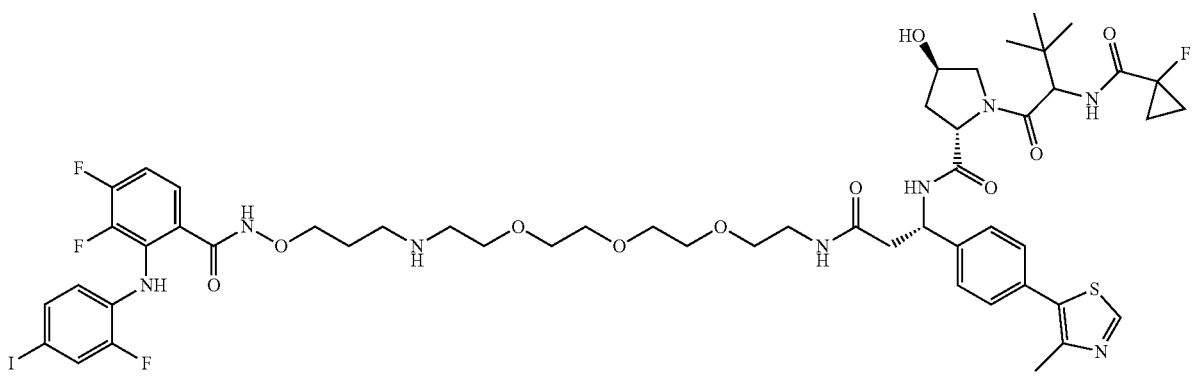

CPD-067

Reagents and conditions: (a) Z5, NaBH₃CN, DCM, MeOH, rt, overnight.

CPD-067 was synthesized following the same procedures as CPD-001 as described in Example 3. (0.08 g, yield: 40%). ¹H NMR (600 MHz, Methanol-$d_4$) δ 9.00 (s, 1H), 7.50-7.42 (m, 5H), 7.42-7.38 (m, 1H), 7.36 (ddd, J=8.5, 1.9, 1.0 Hz, 1H), 7.05 (td, J=9.1, 6.9 Hz, 1H), 6.63 (td, J=8.7, 4.1 Hz, 1H), 5.32 (dd, J=8.2, 6.2 Hz, 1H), 4.76-4.71 (m, 1H), 4.57 (dd, J=9.3, 7.6 Hz, 1H), 4.44 (tt, J=4.0, 1.8 Hz, 1H), 4.06 (dd, J=5.8, 4.5 Hz, 2H), 3.83 (dt, J=11.3, 1.7 Hz, 1H), 3.79-3.73 (m, 3H), 3.60-3.56 (m, 2H), 3.56-3.53 (m, 2H), 3.53-3.51 (m, 2H), 3.50-3.48 (m, 2H), 3.42 (dt, J=9.9, 5.8 Hz, 1H), 3.38 (ddd, J=9.9, 6.3, 5.1 Hz, 1H), 3.30-3.25 (m, 6H), 2.85 (dd, J=14.2, 6.2 Hz, 1H), 2.79-2.72 (m, 1H), 2.49 (s, 3H), 2.20 (ddt, J=13.2, 7.6, 1.9 Hz, 1H), 2.04 (dt, J=10.9, 5.3 Hz, 2H), 1.95 (ddd, J=13.4, 9.3, 4.4 Hz, 1H), 1.42-1.25 (m, 4H), 1.05 (s, 9H).

Example 68: (2S,4R)—N—((S)-1-(3,4-difluoro-2-((2-fluoro-4-iodophenyl)amino)phenyl)-25-(4-(4-methylthiazol-5-yl)phenyl)-1,23-dioxo-3,10,13,16,19-pentaoxa-2,7,22-triazapentacosan-25-yl)-1-(2-(1-fluorocyclopropane-1-carboxamido)-3,3-dimethylbutanoyl)-4-hydroxypyrrolidine-2-carboxamide (CPD-068)

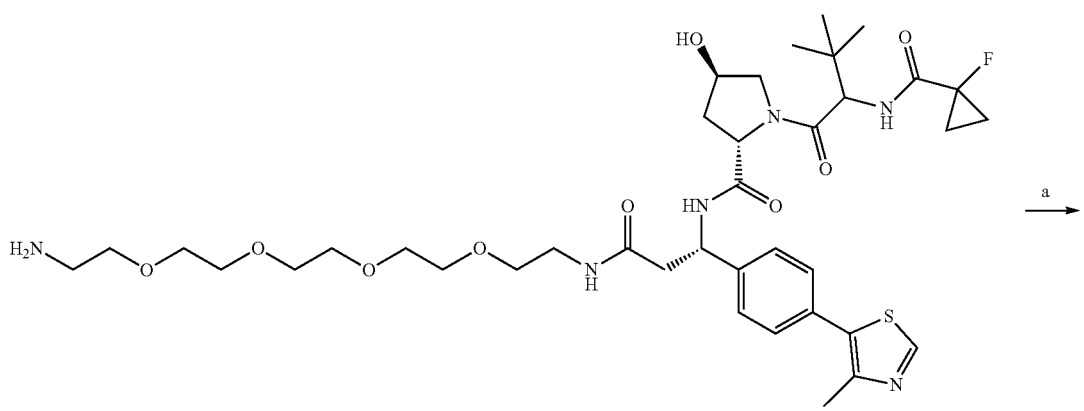

Z72

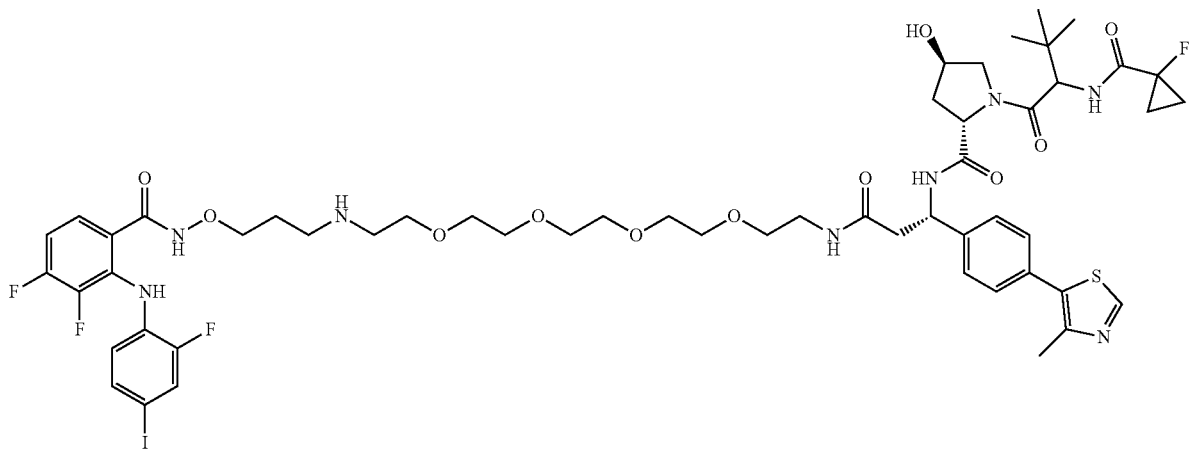

CPD-068

Reagents and conditions: (a) Z5, NaBH₃CN, DCM, MeOH, rt, overnight.

CPD-068 was synthesized following the same procedures as CPD-001 as described in Example 3. (0.08 g, yield: 43%). $^1$H NMR (600 MHz, Methanol-$d_4$) δ 8.99 (s, 1H), 7.49-7.44 (m, 5H), 7.40 (ddd, J=10.1, 4.6, 2.0 Hz, 1H), 7.37 (ddd, J=8.5, 2.0, 1.0 Hz, 1H), 7.05 (td, J=9.2, 7.0 Hz, 1H), 6.64 (td, J=8.7, 4.2 Hz, 1H), 5.32 (dd, J=8.2, 6.1 Hz, 1H), 4.78-4.70 (m, 1H), 4.61-4.53 (m, 1H), 4.45 (tt, J=3.9, 1.7 Hz, 1H), 4.09-4.03 (m, 2H), 3.86-3.81 (m, 1H), 3.79-3.74 (m, 3H), 3.60-3.57 (m, 2H), 3.55 (qd, J=4.7, 3.7, 2.1 Hz, 8H), 3.53-3.49 (m, 2H), 3.44 (ddd, J=9.9, 6.2, 5.3 Hz, 1H), 3.39 (ddd, J=9.9, 6.4, 4.8 Hz, 1H), 3.30-3.24 (m, 6H), 2.84 (dd, J=14.2, 6.2 Hz, 1H), 2.76 (dd, J=14.2, 8.1 Hz, 1H), 2.49 (s, 3H), 2.20 (ddt, J=13.2, 7.6, 1.9 Hz, 1H), 2.04 (dt, J=10.5, 5.2 Hz, 2H), 1.95 (ddd, J=13.4, 9.3, 4.4 Hz, 1H), 1.42-1.25 (m, 4H), 1.06 (s, 9H).

Example 69: (2S,4R)—N—((S)-1-(3,4-difluoro-2-((2-fluoro-4-iodophenyl)amino)phenyl)-28-(4-(4-methylthiazol-5-yl)phenyl)-1,26-dioxo-3,10,13,16,19,22-hexaoxa-2,7,25-triazaoctacosan-28-yl)-1-(2-(1-fluorocyclopropane-1-carboxamido)-3,3-dimethylbutanoyl)-4-hydroxypyrrolidine-2-carboxamide (CPD-069)

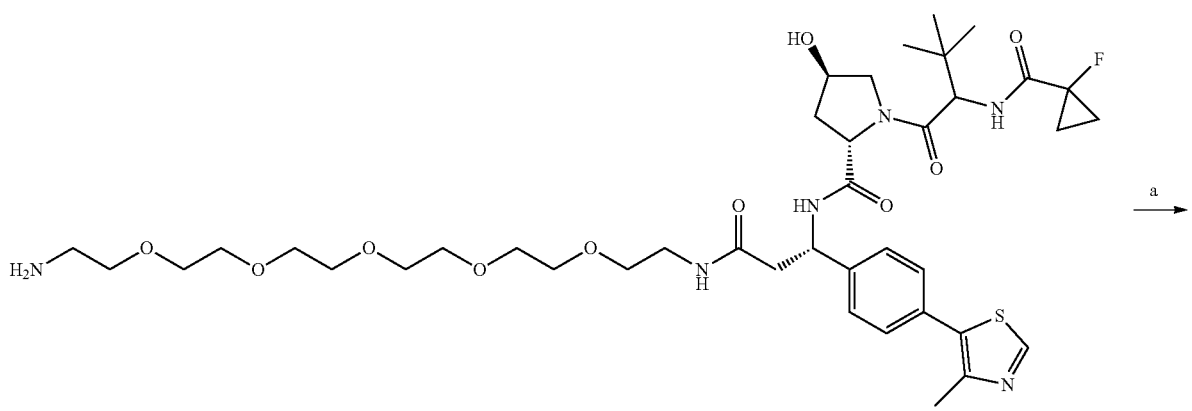

Z73

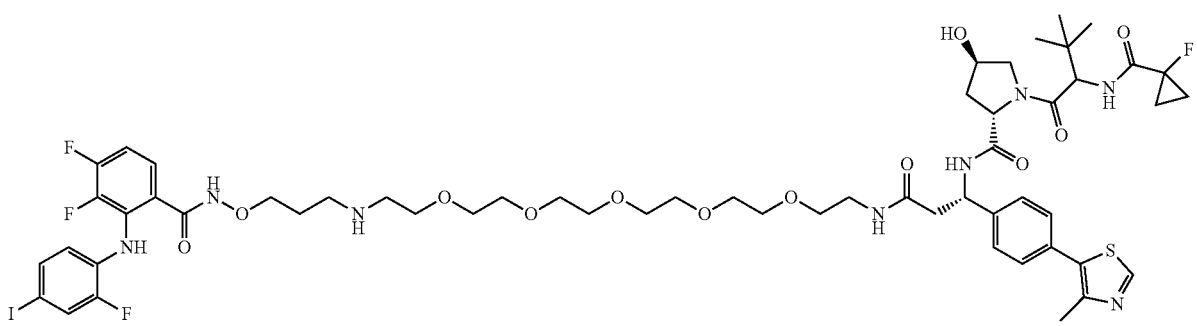

CPD-069

Reagents and conditions: (a) Z5, NaBH$_3$CN, DCM, MeOH, rt, overnight.

CPD-069 was synthesized following the same procedures as CPD-001 as described in Example 3. (0.08 g, yield: 44%). $^1$H NMR (600 MHz, Methanol-$d_4$) δ 8.96 (s, 1H), 7.48 (dd, J=10.6, 2.0 Hz, 2H), 7.46 (d, J=1.0 Hz, 3H), 7.42-7.39 (m, 1H), 7.37 (ddd, J=8.4, 2.0, 1.0 Hz, 1H), 7.06 (td, J=9.2, 7.0 Hz, 1H), 6.64 (td, J=8.7, 4.1 Hz, 1H), 5.32 (dd, J=8.2, 6.1 Hz, 1H), 4.74 (dd, J=9.4, 1.3 Hz, 1H), 4.57 (dd, J=9.3, 7.6 Hz, 1H), 4.44 (dq, J=3.9, 2.1 Hz, 1H), 4.12-4.03 (m, 2H), 3.86-3.81 (m, 1H), 3.79-3.74 (m, 3H), 3.60-3.54 (m, 14H), 3.51 (td, J=4.2, 2.8 Hz, 2H), 3.44 (ddd, J=9.9, 6.3, 5.1 Hz, 1H), 3.39 (ddd, J=9.9, 6.4, 4.8 Hz, 1H), 3.30-3.25 (m, 5H), 2.85 (dd, J=14.1, 6.1 Hz, 1H), 2.76 (dd, J=14.2, 8.2 Hz, 1H), 2.49 (s, 3H), 2.20 (ddt, J=13.3, 7.6, 1.9 Hz, 1H), 2.04 (dt, J=10.3, 5.2 Hz, 2H), 1.96 (ddd, J=13.4, 9.3, 4.4 Hz, 1H), 1.43-1.25 (m, 5H), 1.06 (s, 9H).

Example 70: (2R,4R)—N-(2-((1-(3,4-difluoro-2-((2-fluoro-4-iodophenyl)amino)phenyl)-1,11-dioxo-3-oxa-2,7,10-triazadodecan-12-yl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide (CPD-070)

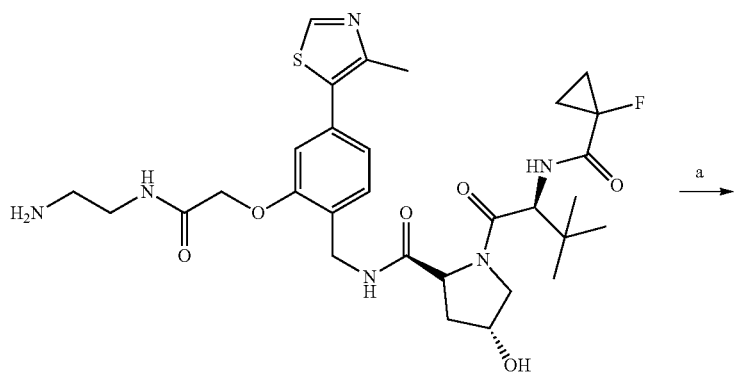

Z74

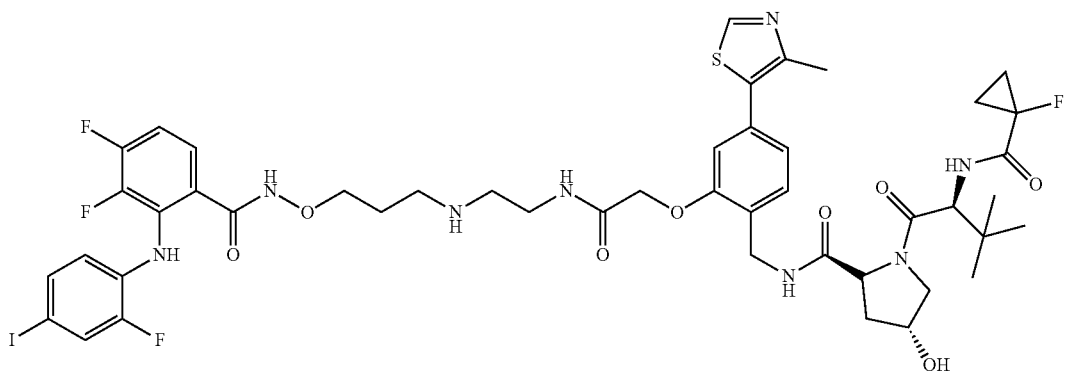

CPD-070

Reagents and conditions: (a) Z5, NaBH$_3$CN, DCM, MeOH, rt, overnight.

CPD-070 was synthesized following the same procedures as CPD-001 as described in Example 3. (0.08 g, yield: 47%).
¹H NMR (600 MHz, Methanol-d₄) δ 8.99 (s, 1H), 7.47 (dd, J=9.3, 3.2 Hz, 1H), 7.44 (dd, J=10.6, 1.9 Hz, 1H), 7.39 (d, J=7.7 Hz, 1H), 7.34 (ddd, J=8.5, 2.0, 0.9 Hz, 1H), 7.24-7.20 (m, 1H), 7.07 (dd, J=7.7, 1.6 Hz, 1H), 6.78 (d, J=1.7 Hz, 1H), 6.62 (td, J=8.7, 3.7 Hz, 1H), 4.74-4.68 (m, 1H), 4.62 (d, J=14.8 Hz, 1H), 4.53 (dd, J=9.4, 7.5 Hz, 1H), 4.49-4.45 (m, 2H), 4.42 (d, J=14.5 Hz, 1H), 4.34 (d, J=14.8 Hz, 1H), 4.06-4.01 (m, 2H), 3.85 (d, J=10.8 Hz, 1H), 3.78 (dd, J=11.0, 3.8 Hz, 1H), 3.75 (q, J=5.6, 4.8 Hz, 1H), 3.70 (dt, J=14.9, 4.9 Hz, 1H), 3.35 (t, J=5.5 Hz, 2H), 2.47 (s, 3H), 2.20 (ddt, J=13.5, 7.8, 2.0 Hz, 1H), 2.05 (qt, J=8.0, 4.4 Hz, 3H), 1.42-1.22 (m, 6H), 0.97 (s, 9H).

Example 71: (2R,4R)—N-(2-((1-(3,4-difluoro-2-((2-fluoro-4-iodophenyl)amino)phenyl)-1,12-dioxo-3-oxa-2,7,11-triazatridecan-13-yl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide (CPD-071)

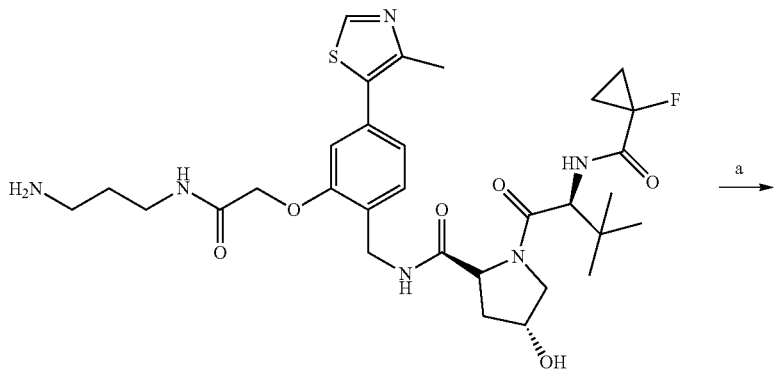

Z75

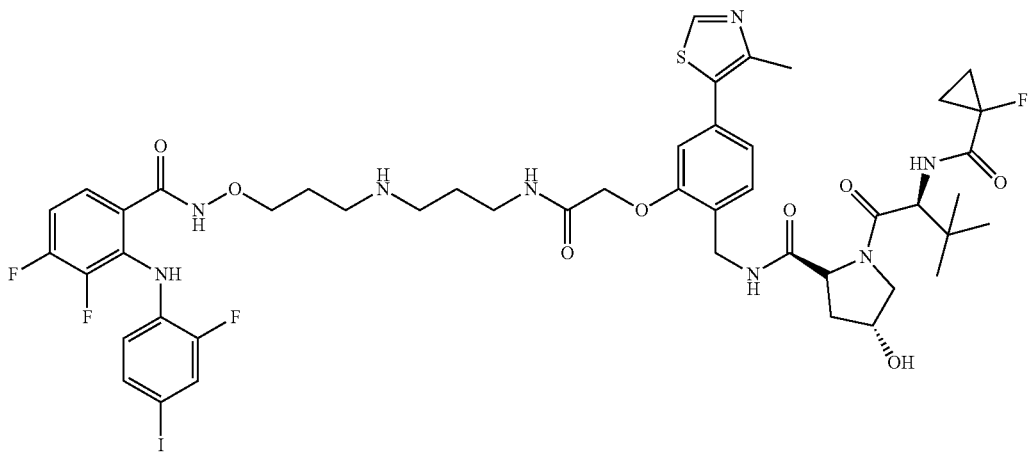

CPD-071

Reagents and conditions: (a) Z5, NaBH₃CN, DCM, MeOH, rt, overnight.

CPD-071 was synthesized following the same procedures as CPD-001 as described in Example 3. (0.08 g, yield: 47%). ¹H NMR (600 MHz, Methanol-$d_4$) δ 9.00 (s, 1H), 7.49-7.45 (m, 1H), 7.42-7.39 (m, 1H), 7.38 (dd, J=5.2, 1.6 Hz, 1H), 7.35-7.32 (m, 1H), 7.11 (dd, J=7.7, 1.6 Hz, 1H), 7.07-7.01 (m, 1H), 6.98 (d, J=1.6 Hz, 1H), 6.61 (td, J=8.7, 4.1 Hz, 1H), 4.73-4.69 (m, 1H), 4.66-4.59 (m, 3H), 4.58-4.54 (m, 11H), 4.48 (tt, J=3.8, 1.7 Hz, 1H), 4.40 (d, J=15.0 Hz, 11H), 4.09-4.03 (m, 2H), 3.84 (d, J=10.9 Hz, 1H), 3.78 (dd, J=11.1, 3.7 Hz, 1H), 3.46 (td, J=6.7, 5.2 Hz, 2H), 3.22 (t, J=5.9 Hz, 2H), 3.12 (t, J=7.4 Hz, 2H), 2.49 (s, 3H), 2.21 (ddt, J=13.2, 7.6, 1.9 Hz, 1H), 2.10-1.98 (m, 5H), 1.41-1.20 (m, 4H), 0.97 (s, 9H).

Example 72: (2R,4R)—N-(2-((1-(3,4-difluoro-2-((2-fluoro-4-iodophenyl)amino)phenyl)-1,12-dioxo-3-oxa-2,7,11-triazatridecan-13-yl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide (CPD-072)

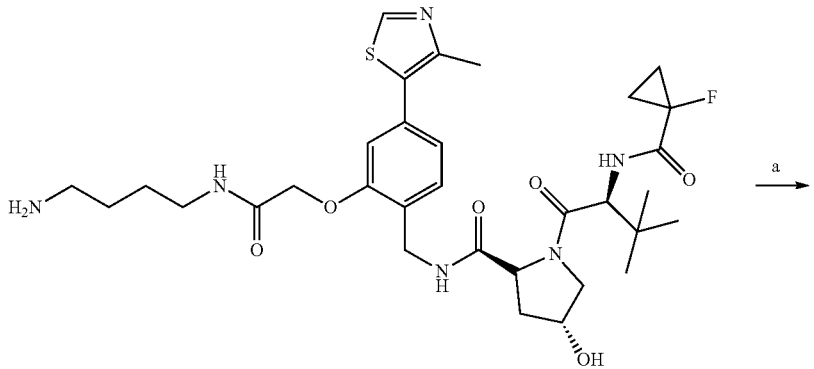

Z76

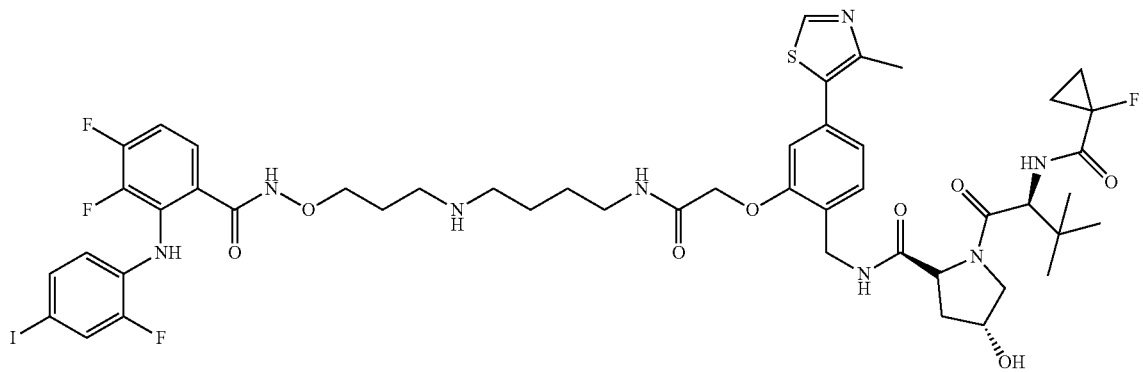

CPD-072

Reagents and conditions: (a) Z5, NaBH₃CN, DCM, MeOH, rt, overnight.

CPD-072 was synthesized following the same procedures as CPD-001 as described in Example 3. (0.08 g, yield: 47%). ¹H NMR (600 MHz, Methanol-$d_4$) δ 8.97 (s, 1H), 7.45 (dd, J=10.6, 2.0 Hz, 1H), 7.41 (d, J=7.7 Hz, 11H), 7.38-7.32 (m, 2H), 7.08 (dd, J=7.7, 1.6 Hz, 11H), 7.04-6.97 (m, 11H), 6.94 (d, J=1.6 Hz, 11H), 6.59 (td, J=8.7, 4.3 Hz, 11H), 4.74-4.68 (m, 11H), 4.64-4.52 (m, 4H), 4.48 (tt, J=4.0, 1.8 Hz, 11H), 4.36 (d, J=14.8 Hz, 11H), 4.05 (t, J=5.7 Hz, 2H), 3.84 (d, J=11.0 Hz, 11H), 3.77 (dd, J=11.1, 3.8 Hz, 1H), 3.41 (dt, J=13.4, 6.7 Hz, 1H), 3.36-3.32 (m, 1H), 3.23 (t, J=5.8 Hz, 2H), 3.11 (td, J=7.5, 4.1 Hz, 2H), 2.48 (s, 3H), 2.22-2.14 (m, 1H), 2.07-2.00 (m, 3H), 1.83 (p, J=7.7 Hz, 2H), 1.72 (ddd, J=12.9, 10.3, 6.1 Hz, 2H), 1.40-1.23 (m, 4H), 0.99 (s, 9H).

Example 73: (2R,4R)—N-(2-((1-(3,4-difluoro-2-((2-fluoro-4-iodophenyl)amino)phenyl)-1,14-dioxo-3-oxa-2,7,13-triazapentadecan-15-yl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide (CPD-073)

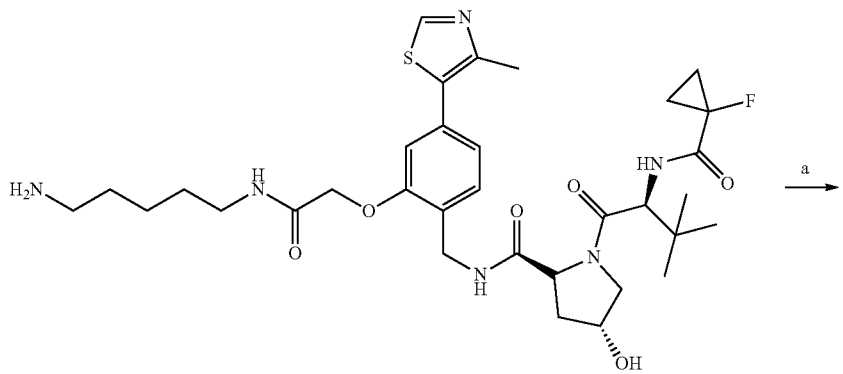

Z77

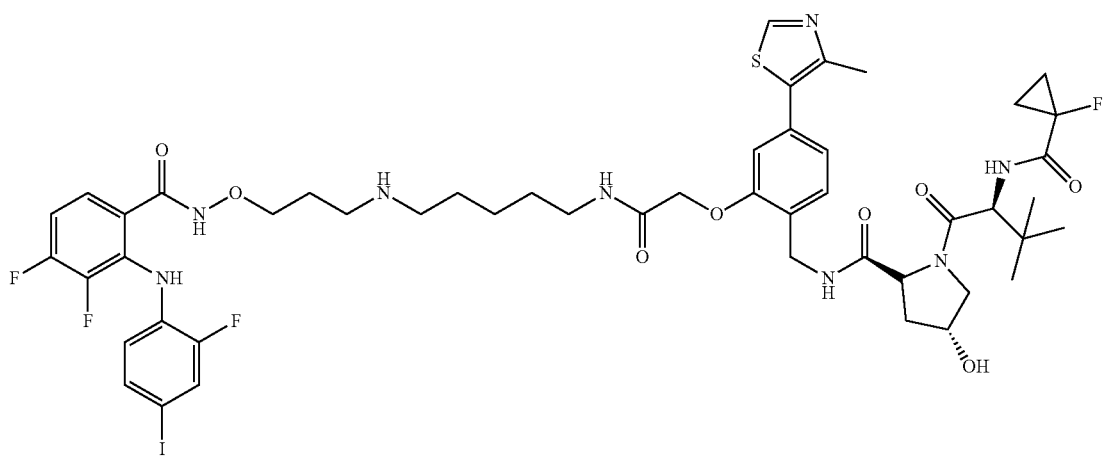

CPD-073

Reagents and conditions: (a) Z5, NaBH₃CN, DCM, MeOH, rt, overnight.

CPD-073 was synthesized following the same procedures as CPD-001 as described in Example 3. (0.08 g, yield: 47%). $^1$H NMR (600 MHz, Methanol-$d_4$) δ 8.92 (s, 1H), 7.50-7.45 (m, 1H), 7.40 (td, J=9.7, 6.3 Hz, 1H), 7.35 (dt, J=9.2, 1.9 Hz, 1H), 7.10 (dd, J=7.7, 1.6 Hz, 1H), 7.05 (td, J=9.2, 6.9 Hz, 1H), 6.96 (d, J=1.6 Hz, 1H), 6.62 (td, J=8.7, 4.2 Hz, 1H), 6.56 (td, J=8.8, 5.0 Hz, 1H), 4.75-4.69 (m, 1H), 4.65-4.59 (m, 2H), 4.58-4.55 (m, 1H), 4.49-4.46 (m, 1H), 4.43 (d, J=15.0 Hz, 1H), 4.11 (t, J=5.0 Hz, 1H), 4.06 (t, J=5.1 Hz, 1H), 3.84 (d, J=11.1 Hz, 1H), 3.77 (dd, J=11.1, 3.8 Hz, 1H), 3.27 (t, J=5.8 Hz, 1H), 3.23 (t, J=5.8 Hz, 1H), 3.12-3.06 (m, 1H), 3.05-2.98 (m, 2H), 2.48 (s, 3H), 2.23-2.17 (m, 1H), 2.09-2.00 (m, 4H), 1.87 (p, J=8.1 Hz, 1H), 1.76 (p, J=8.0 Hz, 2H), 1.62 (p, J=7.2 Hz, 2H), 1.57-1.51 (m, 1H), 1.43 (p, J=7.7 Hz, 2H), 1.38-1.24 (m, 3H), 1.00 (s, 9H).

Example 74: (2R,4R)—N-(2-((1-(3,4-difluoro-2-((2-fluoro-4-iodophenyl)amino)phenyl)-1,16-dioxo-3-oxa-2,7,15-triazaheptadecan-17-yl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide (CPD-074)

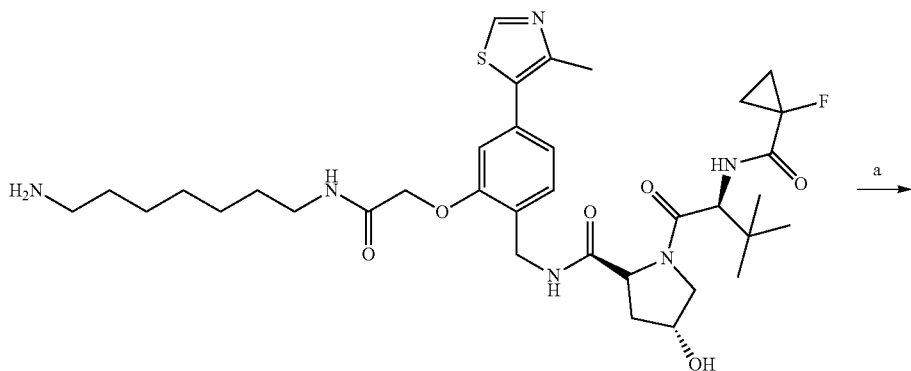

Z78

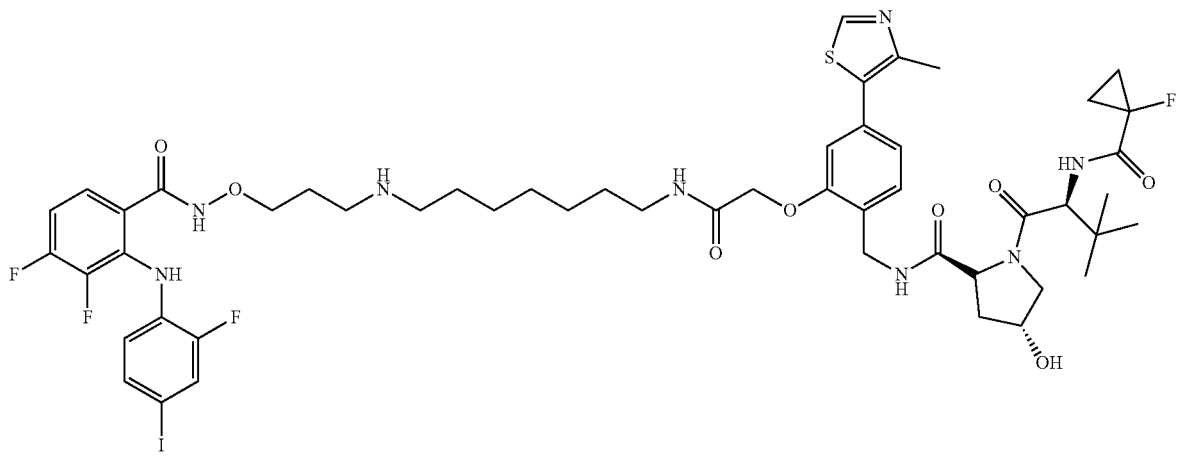

CPD-074

Reagents and conditions: (a) Z5, NaBH$_3$CN, DCM, MeOH, rt, overnight.

CPD-074 was synthesized following the same procedures as CPD-001 as described in Example 3. (0.08 g, yield: 42%). ¹H NMR (600 MHz, Methanol-d₄) δ 8.96 (s, 1H), 7.49 (d, J=7.7 Hz, 1H), 7.45 (dd, J=10.6, 2.0 Hz, 1H), 7.40 (ddt, J=9.9, 4.6, 2.3 Hz, 1H), 7.36 (ddd, J=8.5, 2.0, 1.0 Hz, 1H), 7.10 (dd, J=7.7, 1.6 Hz, 1H), 7.06 (td, J=9.2, 7.1 Hz, 1H), 6.96 (d, J=1.6 Hz, 1H), 6.62 (td, J=8.7, 4.2 Hz, 1H), 4.75-4.69 (m, 1H), 4.64-4.60 (m, 2H), 4.59-4.55 (m, 2H), 4.48 (tt, J=3.9, 1.7 Hz, 1H), 4.44 (d, J=15.0 Hz, 1H), 4.07 (dd, J=5.7, 4.5 Hz, 2H), 3.88-3.81 (m, 1H), 3.78 (dd, J=11.1, 3.8 Hz, 1H), 3.27 (dd, J=12.5, 7.1 Hz, 2H), 3.23 (t, J=5.9 Hz, 2H), 3.07-2.98 (m, 2H), 2.49 (s, 3H), 2.21 (ddt, J=13.2, 7.6, 1.9 Hz, 1H), 2.07 (dt, J=8.4, 4.3 Hz, 1H), 2.05-2.00 (m, 2H), 1.70 (p, J=7.6 Hz, 2H), 1.55 (p, J=6.6 Hz, 2H), 1.43-1.22 (m, 10H), 1.00 (s, 9H).

Example 75: (2R,4R)—N-(2-((1-(3,4-difluoro-2-((2-fluoro-4-iodophenyl)amino)phenyl)-1,17-dioxo-3-oxa-2,7,16-triazaoctadecan-18-yl)oxy)-4-(4-methyl-thiazol-5-yl)benzyl)-1-((S)-2-(1-fluorocyclopropane-1-carboxamido)-3,3-dimethylbutanoyl)-4-hydroxypyrrolidine-2-carboxamide (CPD-075)

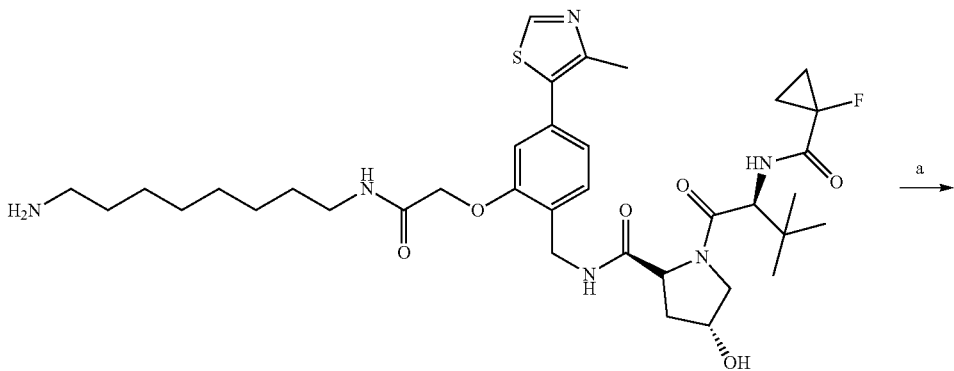

Z79

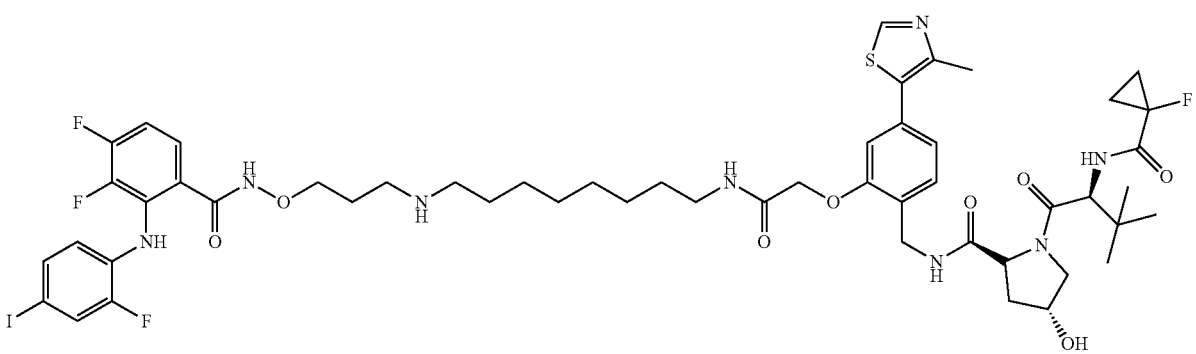

CPD-075

Reagents and conditions: (a) Z5, NaBH₃CN, DCM, MeOH, rt, overnight.

CPD-075 was synthesized following the same procedures as CPD-001 as described in Example 3. (0.06 g, yield: 47%). ¹H NMR (600 MHz, Methanol-$d_4$) δ 8.94 (s, 1H), 7.48 (d, J=7.7 Hz, 1H), 7.47-7.43 (m, 1H), 7.42-7.39 (m, 1H), 7.36 (ddd, J=8.5, 2.0, 1.0 Hz, 1H), 7.09 (dd, J=7.7, 1.5 Hz, 1H), 7.07-7.03 (m, 1H), 6.96 (d, J=1.6 Hz, 1H), 6.63 (td, J=8.7, 4.3 Hz, 1H), 4.76-4.70 (m, 1H), 4.65-4.59 (m, 2H), 4.59-4.55 (m, 2H), 4.48 (dq, J=4.1, 2.1 Hz, 1H), 4.44 (d, J=15.0 Hz, 1H), 4.10-4.02 (m, 2H), 3.88-3.82 (m, 1H), 3.78 (dd, J=11.1, 3.8 Hz, 1H), 3.28 (dt, J=9.7, 7.1 Hz, 2H), 3.24 (t, J=5.9 Hz, 2H), 3.06-3.00 (m, 2H), 2.49 (s, 3H), 2.20 (ddq, J=11.5, 5.9, 2.0 Hz, 1H), 2.07 (dt, J=8.4, 4.3 Hz, 1H), 2.03 (td, J=7.1, 6.3, 4.4 Hz, 2H), 1.74-1.67 (m, 2H), 1.54 (dd, J=10.0, 4.0 Hz, 2H), 1.42-1.34 (m, 3H), 1.34-1.30 (m, 2H), 1.30-1.25 (m, 7H), 1.01 (s, 9H).

Example 76: (2S,4R)-1-((S)-2-(1-cyanocyclopropane-1-carboxamido)-3,3-dimethylbutanoyl)-N—((S)-1-(3,4-difluoro-2-((2-fluoro-4-iodophenyl)amino)phenyl)-19-(4-(4-methylthiazol-5-yl)phenyl)-1,17-dioxo-3-oxa-2,7,16-triazanonadecan-19-yl)-4-hydroxypyrrolidine-2-carboxamide (CPD-076)

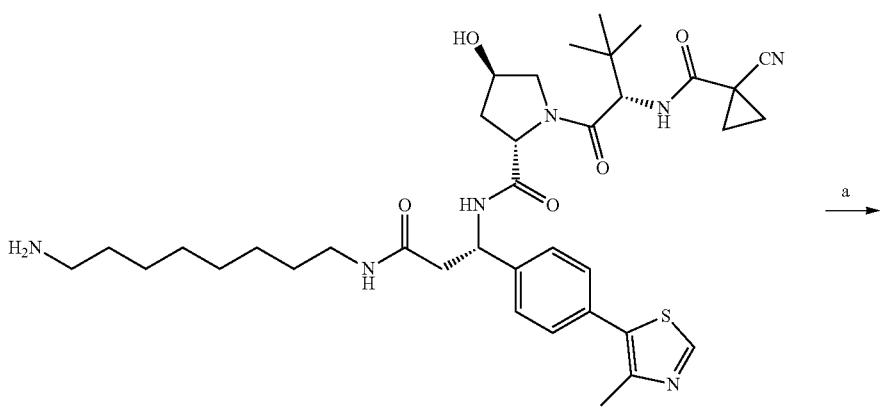

Z80

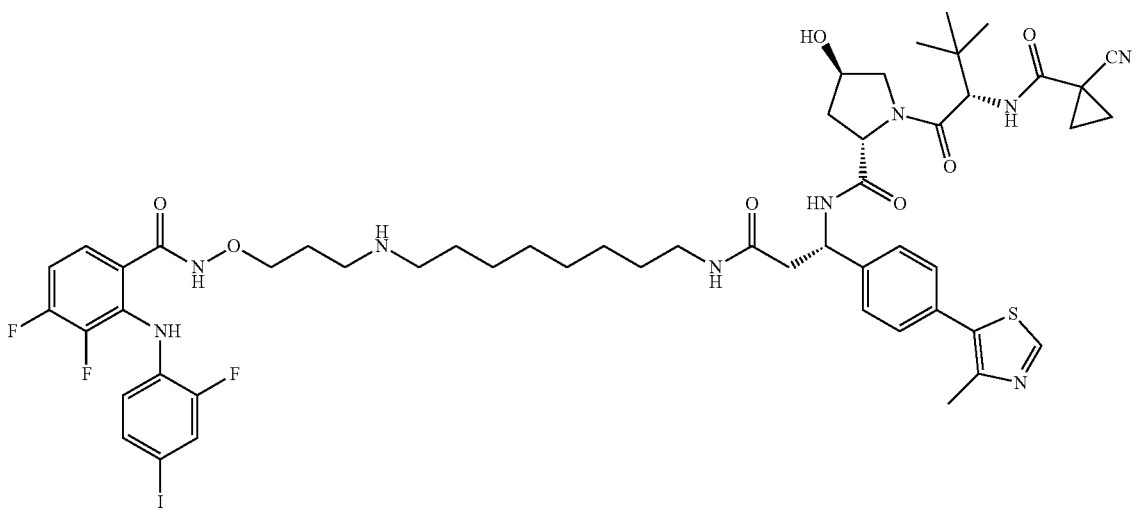

CPD-076

Reagents and conditions: (a) Z5, NaBH₃CN, DCM, MeOH, rt, overnight.

CPD-076 was synthesized following the same procedures as CPD-001 as described in Example 3. (0.08 g, yield: 42%). ¹H NMR (600 MHz, Methanol-$d_4$) δ 8.94 (s, 1H), 7.46 (dd, J=8.5, 2.2 Hz, 4H), 7.41 (s, 1H), 7.36 (dd, J=8.8, 6.2 Hz, 2H), 7.06 (q, J=8.6 Hz, 1H), 6.63 (td, J=8.6, 4.2 Hz, 1H), 5.33-5.28 (m, 1H), 4.69-4.64 (m, 1H), 4.60-4.55 (m, 1H), 4.45-4.43 (m, 1H), 4.07 (t, J=5.1 Hz, 2H), 3.80 (d, J=11.1 Hz, 1H), 3.74 (dd, J=11.2, 3.7 Hz, 1H), 3.23 (t, J=5.8 Hz, 2H), 3.11 (dt, J=13.8, 7.0 Hz, 1H), 3.05 (t, J=6.9 Hz, 1H), 3.01 (t, J=7.8 Hz, 2H), 2.90-2.82 (m, 1H), 2.74 (dd, J=14.0, 8.5 Hz, 1H), 2.48 (s, 3H), 2.23-2.15 (m, 1H), 2.08-2.00 (m, 2H), 1.95 (ddd, J=13.4, 9.4, 4.3 Hz, 1H), 1.70-1.61 (m, 3H), 1.61-1.54 (m, 3H), 1.39-1.28 (m, 4H), 1.26-1.18 (m, 4H), 1.17-1.12 (m, 2H), 1.05 (s, 9H).

Example 77: (2S,4R)-1-((S)-2-(1-cyanocyclopropane-1-carboxamido)-3,3-dimethylbutanoyl)-N—((S)-1-(3,4-difluoro-2-((2-fluoro-4-iodophenyl)amino)phenyl)-21-(4-(4-methylthiazol-5-yl)phenyl)-1,19-dioxo-3-oxa-2,7,18-triazahenicosan-21-yl)-4-hydroxypyrrolidine-2-carboxamide (CPD-077)

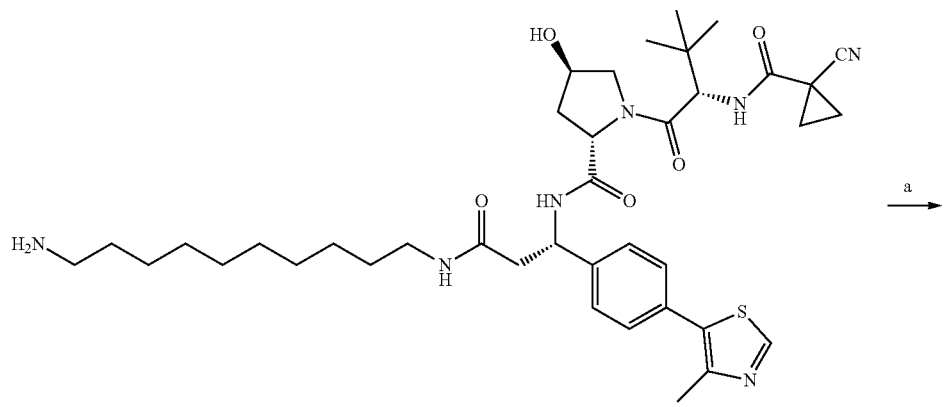

Z81

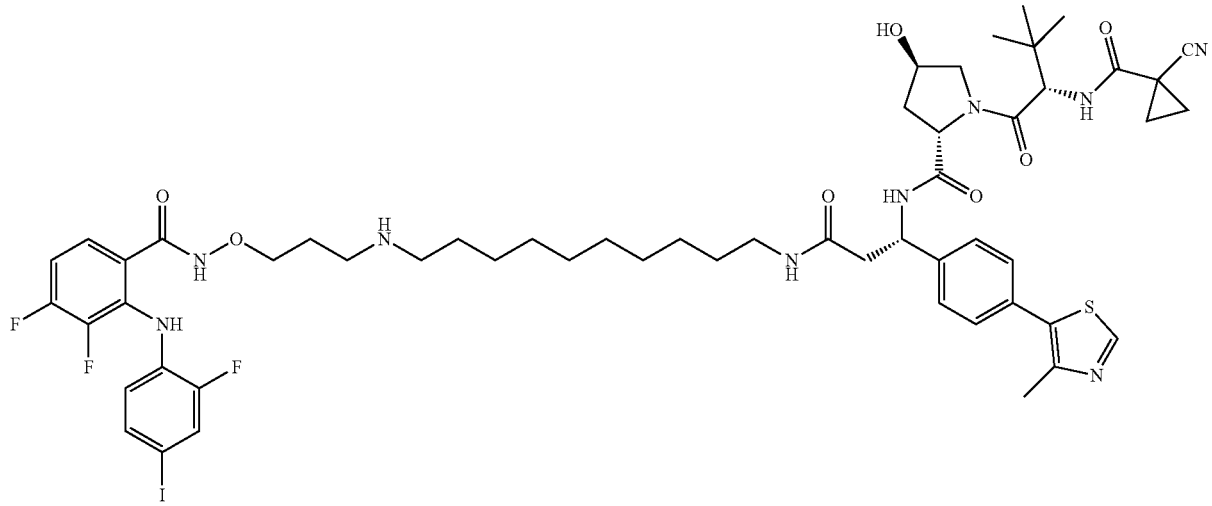

CPD-077

Reagents and conditions: (a) Z5, NaBH₃CN, DCM, MeOH, rt, overnight.

CPD-077 was synthesized following the same procedures as CPD-001 as described in Example 3. (0.08 g, yield: 41%). ¹H NMR (600 MHz, Methanol-$d_4$) δ 8.93 (s, 1H), 7.48-7.43 (m, 4H), 7.42-7.39 (m, 1H), 7.36 (dd, J=8.6, 4.9 Hz, 2H), 7.06 (q, J=8.6 Hz, 1H), 6.64 (td, J=8.7, 4.2 Hz, 1H), 5.38-5.26 (m, 1H), 4.72-4.63 (m, 1H), 4.61-4.53 (m, 1H), 4.45-4.42 (m, 1H), 4.08 (t, J=5.2 Hz, 2H), 3.80 (d, J=11.1 Hz, 1H), 3.74 (dd, J=11.2, 3.7 Hz, 1H), 3.24 (t, J=5.9 Hz, 2H), 3.11 (dt, J=14.0, 7.2 Hz, 1H), 3.07-2.97 (m, 3H), 2.85 (dd, J=14.0, 5.7 Hz, 1H), 2.74 (dd, J=14.0, 8.7 Hz, 1H), 2.48 (s, 3H), 2.24-2.14 (m, 1H), 2.07-2.01 (m, 2H), 1.95 (ddd, J=13.5, 9.3, 4.3 Hz, 1H), 1.70 (p, J=7.9 Hz, 2H), 1.64 (dt, J=12.8, 6.0 Hz, 1H), 1.61-1.53 (m, 3H), 1.36-1.28 (m, 4H), 1.26-1.15 (m, 8H), 1.14-1.09 (m, 2H), 1.06 (s, 9H).

Example 78: (2S,4R)—N—((S)-1-(3,4-difluoro-2-((2-fluoro-4-iodophenyl)amino)phenyl)-19-(4-(4-methylthiazol-5-yl)phenyl)-1,17-dioxo-3-oxa-2,7,16-triazanonadecan-19-yl)-4-hydroxy-1-((R)-3-methyl-2-(3-methylisoxazol-5-yl)butanoyl)pyrrolidine-2-carboxamide (CPD-078)

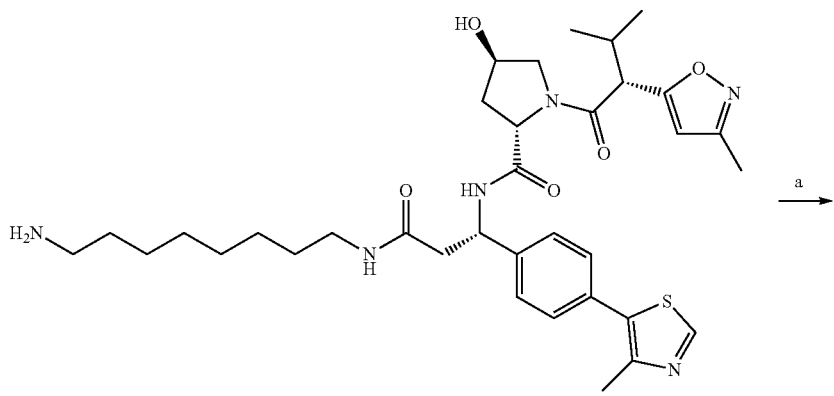

Z82

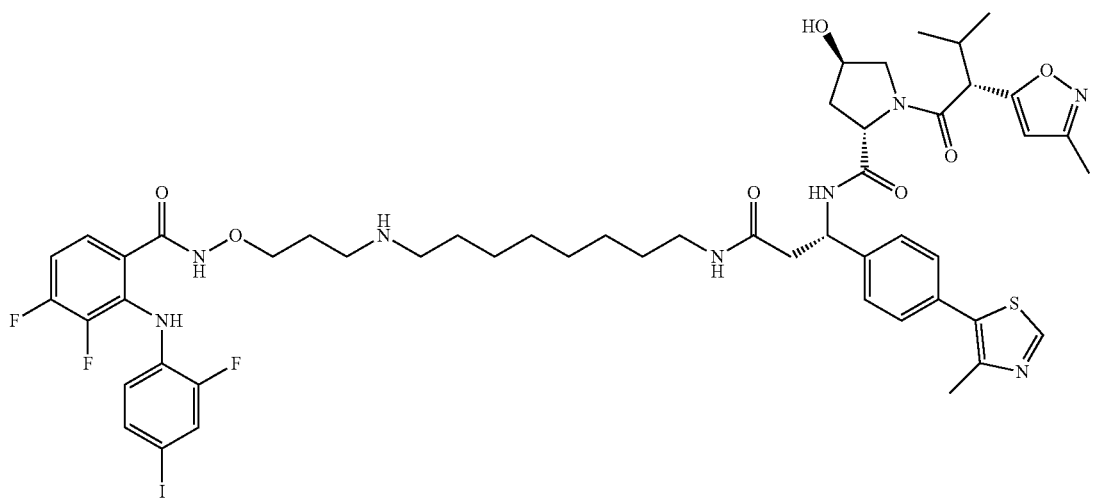

CPD-078

Reagents and conditions: (a) Z5, NaBH₃CN, DCM, MeOH, rt, overnight.

CPD-078 was synthesized following the same procedures as CPD-001 as described in Example 3. (0.08 g, yield: 40%). Two isomers of this spectrum. ¹H NMR (600 MHz, Methanol-d₄) δ 8.94 (d, J=2.9 Hz, 1H), 7.49-7.42 (m, 4H), 7.42-7.39 (m, 2H), 7.38-7.34 (m, 1H), 7.06 (q, J=8.7 Hz, 1H), 6.63 (td, J=8.7, 4.2 Hz, 1H), 6.23 (d, J=19.1 Hz, 1H), 5.37-5.24 (m, 1H), 4.59-4.46 (m, 1H), 4.45-4.41 (m, 1H), 4.07 (t, J=5.2 Hz, 2H), 3.92-3.83 (m, 1H), 3.78 (d, J=9.8 Hz, 1H), 3.75-3.64 (m, 1H), 3.59 (t, J=10.5 Hz, 1H), 3.23 (t, J=5.8 Hz, 2H), 3.13-3.05 (m, 1H), 3.05-2.98 (m, 3H), 2.91-2.80 (m, 1H), 2.79-2.68 (m, 1H), 2.48 (s, 3H), 2.45-2.34 (m, 1H), 2.24 (d, J=15.5 Hz, 3H), 2.21-2.11 (m, 1H), 2.02 (dd, J=10.7, 5.3 Hz, 2H), 1.96 (ddd, J=13.2, 8.8, 4.4 Hz, 1H), 1.72-1.61 (m, 2H), 1.36-1.29 (m, 4H), 1.26-1.18 (m, 4H), 1.15 (t, J=7.3 Hz, 2H), 1.06 (dd, J=6.6, 3.2 Hz, 3H), 0.89 (d, J=6.7 Hz, 1H), 0.85 (d, J=6.7 Hz, 1H).

Example 79: (2S,4R)—N—((S)-1-(3,4-difluoro-2-((2-fluoro-4-iodophenyl)amino)phenyl)-21-(4-(4-methylthiazol-5-yl)phenyl)-1,19-dioxo-3-oxa-2,7,18-triazahenicosan-21-yl)-4-hydroxy-1-((R)-3-methyl-2-(3-methylisoxazol-5-yl)butanoyl)pyrrolidine-2-carboxamide (CPD-079)

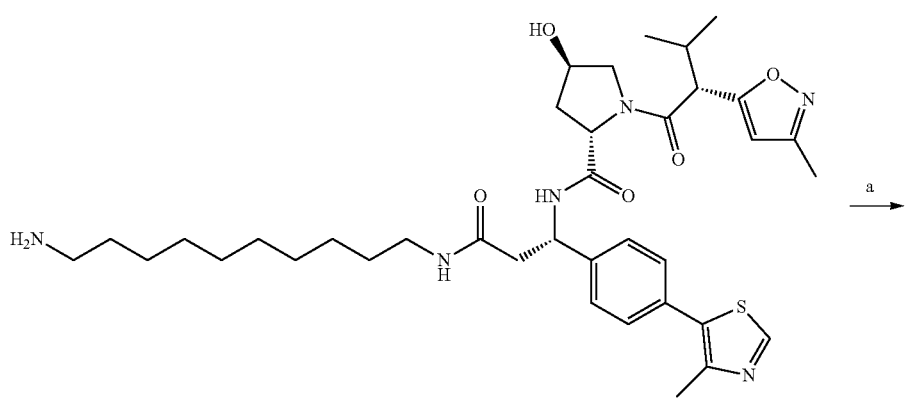

Z83

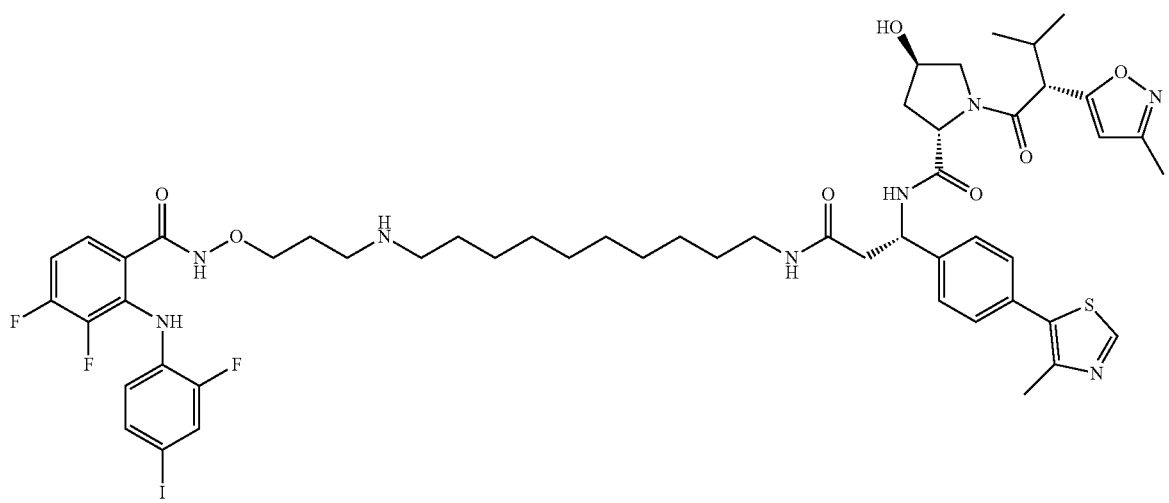

CPD-079

Reagents and conditions: (a) Z5, NaBH₃CN, DCM, MeOH, rt, overnight.

CPD-079 was synthesized following the same procedures as CPD-001 as described in Example 3. (0.08 g, yield: 49%). Two isomers of this spectrum. $^1$H NMR (600 MHz, Methanol-$d_4$) δ 8.91 (s, 1H), 7.48-7.42 (m, 4H), 7.42-7.38 (m, 2H), 7.37 (dd, J=9.7, 2.4 Hz, 1H), 7.06 (q, J=8.7 Hz, 1H), 6.64 (td, J=8.7, 4.3 Hz, 1H), 6.23 (d, J=19.9 Hz, 1H), 5.37-5.25 (m, 1H), 4.52 (dt, J=43.6, 8.1 Hz, 1H), 4.44 (s, 1H), 4.08 (t, J=5.2 Hz, 2H), 3.93-3.84 (m, 1H), 3.78 (d, J=9.8 Hz, 1H), 3.75-3.65 (m, 1H), 3.64-3.56 (m, 1H), 3.24 (t, J=5.9 Hz, 2H), 3.09 (dt, J=14.0, 6.7 Hz, 1H), 3.02 (dt, J=14.1, 7.5 Hz, 3H), 2.93-2.78 (m, 1H), 2.78-2.67 (m, 1H), 2.48 (s, 3H), 2.40 (dt, J=16.3, 6.8 Hz, 1H), 2.27-2.22 (m, 3H), 2.21-2.11 (m, 1H), 2.03 (t, J=5.4 Hz, 2H), 1.95 (td, J=13.4, 5.4 Hz, 1H), 1.70 (p, J=8.0 Hz, 2H), 1.45-1.27 (m, 4H), 1.26-1.09 (m, 10H), 1.06 (dd, J=6.5, 1.9 Hz, 3H), 0.89 (d, J=6.7 Hz, 1H), 0.86 (d, J=6.7 Hz, 1H).

Example 80: (2R,4R)—N-(2-((1-(3,4-difluoro-2-((2-fluoro-4-iodophenyl)amino)phenyl)-1,15-dioxo-3-oxa-2,7,14-triazahexadecan-16-yl)oxy)-4-(4-methyl-thiazol-5-yl)benzyl)-1-((S)-2-(1-fluorocyclopropane-1-carboxamido)-3,3-dimethylbutanoyl)-4-hydroxypyrrolidine-2-carboxamide (CPD-080)

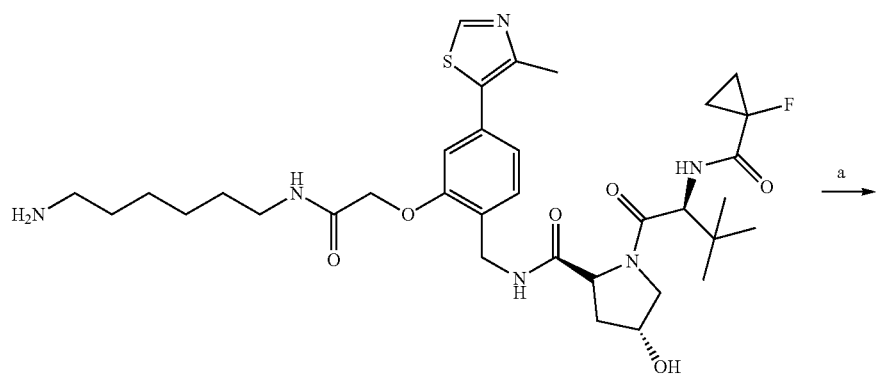

Z84

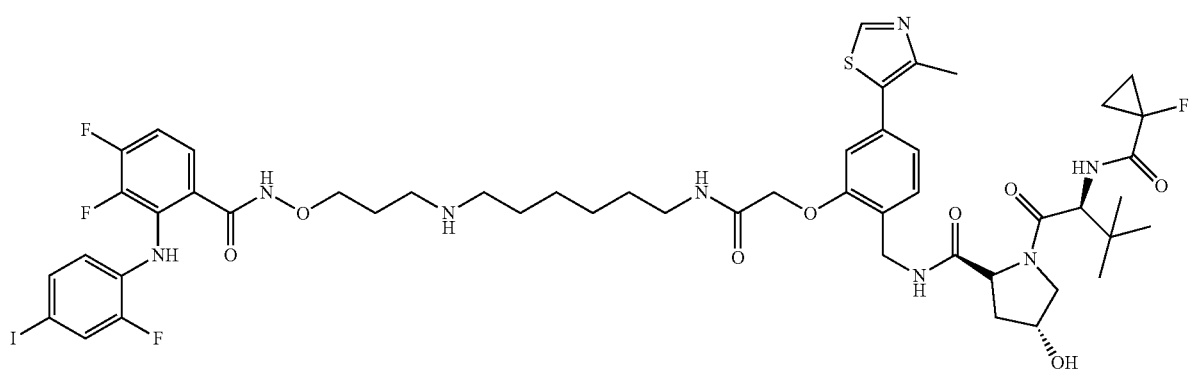

CPD-080

Reagents and conditions: (a) Z5, NaBH$_3$CN, DCM, MeOH, rt, overnight.

CPD-080 was synthesized following the same procedures as CPD-001 as described in Example 3. (0.08 g, yield: 45%). ¹H NMR (600 MHz, Methanol-d₄) δ 9.02 (s, 1H), 7.50-7.43 (m, 2H), 7.40 (ddd, J=8.9, 5.3, 1.7 Hz, 1H), 7.35 (ddd, J=8.5, 1.9, 0.9 Hz, 1H), 7.09 (dd, J=7.7, 1.6 Hz, 1H), 7.06 (td, J=9.2, 7.0 Hz, 1H), 6.96 (d, J=1.6 Hz, 1H), 6.61 (td, J=8.7, 4.2 Hz, 1H), 4.74-4.70 (m, 1H), 4.63-4.54 (m, 4H), 4.48 (dq, J=4.0, 2.0 Hz, 1H), 4.44 (d, J=15.0 Hz, 1H), 4.09-4.03 (m, 2H), 3.84 (dt, J=11.3, 1.7 Hz, 1H), 3.78 (dd, J=11.1, 3.8 Hz, 1H), 3.30-3.26 (m, 2H), 3.23 (t, J=5.9 Hz, 2H), 3.06-3.00 (m, 2H), 2.49 (s, 3H), 2.20 (ddt, J=13.2, 7.6, 1.9 Hz, 1H), 2.07 (dt, J=8.4, 4.3 Hz, 1H), 2.03 (td, J=7.1, 6.4, 4.5 Hz, 2H), 1.71 (td, J=10.3, 9.1, 6.6 Hz, 2H), 1.58 (p, J=7.2 Hz, 2H), 1.42 (tt, J=9.9, 4.7 Hz, 2H), 1.36 (tdd, J=7.0, 4.7, 1.7 Hz, 2H), 1.34-1.23 (m, 4H), 1.00 (s, 9H).

Example 81: (2S,4R)—N—((S)-1-(3,4-difluoro-2-((2-fluoro-4-iodophenyl)amino)phenyl)-13-(4-(4-methylthiazol-5-yl)phenyl)-1,11-dioxo-3-oxa-2,7,10-triazatridecan-13-yl)-4-hydroxy-1-((R)-3-methyl-2-(3-methylisoxazol-5-yl)butanoyl)pyrrolidine-2-carboxamide (CPD-081)

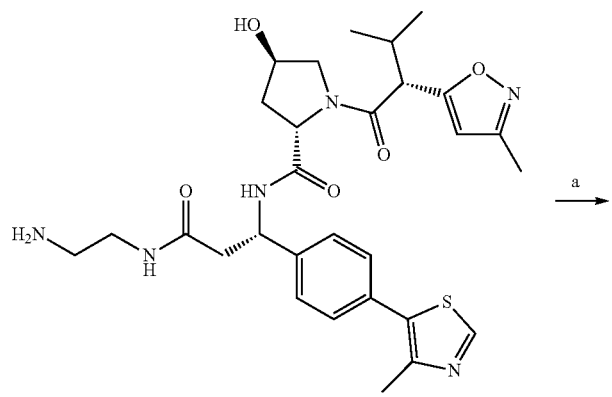

Z85

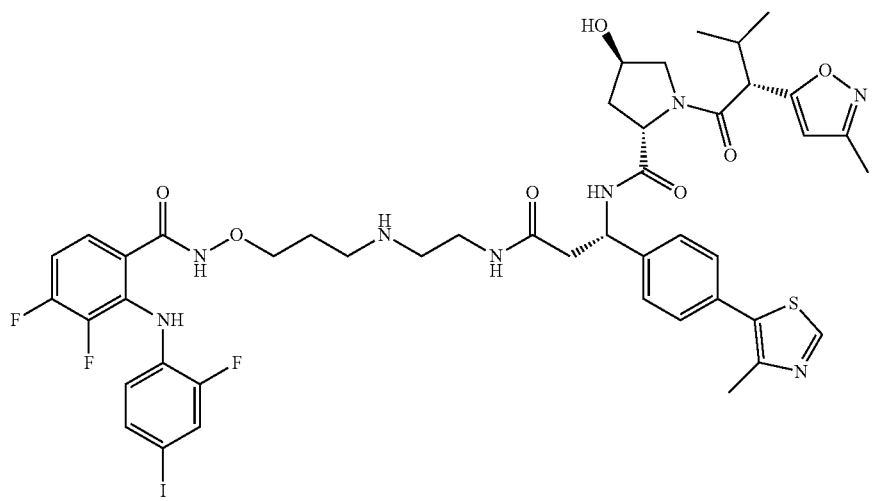

CPD-081

Reagents and conditions: (a) Z5, NaBH₃CN, DCM, MeOH, rt, overnight.

CPD-081 was synthesized following the same procedures as CPD-001 as described in Example 3. (0.08 g, yield: 42%). Two isomers of this spectrum. $^1$H NMR (600 MHz, Methanol-$d_4$) δ 9.02 (s, 1H), 7.46-7.41 (m, 3H), 7.39-7.33 (m, 3H), 7.31 (d, J=8.2 Hz, 1H), 7.01 (tt, J=9.1, 7.2 Hz, 1H), 6.63 (tt, J=8.6, 4.0 Hz, 1H), 6.23 (d, J=18.7 Hz, 1H), 5.32 (ddd, J=34.1, 8.6, 5.5 Hz, 1H), 4.60-4.39 (m, 2H), 4.04 (dp, J=9.9, 4.8 Hz, 2H), 3.92-3.83 (m, 1H), 3.76 (dd, J=24.6, 10.4 Hz, 1H), 3.70-3.61 (m, 1H), 3.59-3.54 (m, 1H), 3.53-3.44 (m, 1H), 3.28 (t, J=5.8 Hz, 1H), 3.26-3.21 (m, 2H), 3.18-3.10 (m, 1H), 2.81-2.75 (m, 1H), 2.74-2.70 (m, 1H), 2.67 (dd, J=14.6, 5.1 Hz, 1H), 2.48 (s, 3H), 2.45-2.36 (m, 1H), 2.25 (s, 1H), 2.23 (s, 1H), 2.18-2.11 (m, 1H), 2.07-1.99 (m, 2H), 1.97-1.92 (m, 1H), 1.04 (dd, J=10.9, 6.6 Hz, 3H), 0.85 (dd, J=15.6, 6.7 Hz, 3H).

Example 82: (2S,4R)—N—((S)-1-(3,4-difluoro-2-((2-fluoro-4-iodophenyl)amino)phenyl)-14-(4-(4-methylthiazol-5-yl)phenyl)-1,12-dioxo-3-oxa-2,7,11-triazatetradecan-14-yl)-4-hydroxy-1-((R)-3-methyl-2-(3-methylisoxazol-5-yl)butanoyl)pyrrolidine-2-carboxamide (CPD-082)

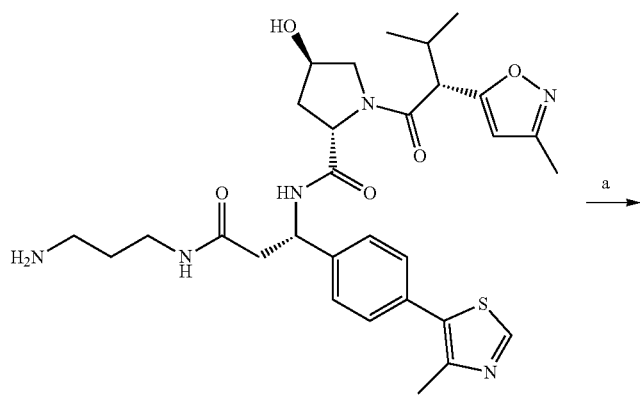

Z86

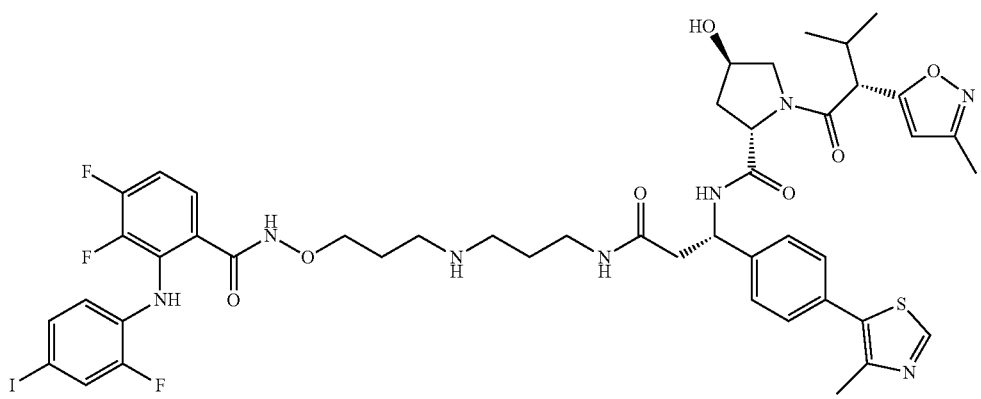

CPD-082

Reagents and conditions: (a) Z5, NaBH$_3$CN, DCM, MeOH, rt, overnight.

CPD-082 was synthesized following the same procedures as CPD-001 as described in Example 3. (0.08 g, yield: 47%). Two isomers of this spectrum. $^1$H NMR (600 MHz, Methanol-$d_4$) δ 9.02 (s, 1H), 7.50-7.43 (m, 4H), 7.42-7.37 (m, 2H), 7.35 (dq, J=8.5, 1.6 Hz, 1H), 7.05 (td, J=9.1, 6.9 Hz, 1H), 6.61 (td, J=8.7, 4.0 Hz, 1H), 6.22 (d, J=8.8 Hz, 1H), 5.41-5.29 (m, 1H), 4.51 (dt, J=52.4, 8.1 Hz, 1H), 4.42 (ddt, J=9.0, 6.9, 3.4 Hz, 1H), 4.09-3.99 (m, J=4.6 Hz, 2H), 3.90-3.81 (m, 1H), 3.81-3.70 (m, 1H), 3.67-3.60 (m, 1H), 3.29-3.25 (m, 1H), 3.18 (td, J=6.7, 6.2, 3.2 Hz, 2H), 3.02-2.87 (m, 2H), 2.86-2.68 (m, 2H), 2.48 (d, J=1.4 Hz, 3H), 2.45-2.35 (m, 1H), 2.23 (d, J=14.5 Hz, 3H), 2.16 (s, 1H), 2.04-1.98 (m, 3H), 1.95-1.82 (m, 3H), 1.05 (dd, J=6.6, 3.9 Hz, 3H), 0.85 (dd, J=14.9, 6.7 Hz, 3H).

Example 83: (2S,4R)—N—((S)-1-(3,4-difluoro-2-((2-fluoro-4-iodophenyl)amino)phenyl)-15-(4-(4-methylthiazol-5-yl)phenyl)-1,13-dioxo-3-oxa-2,7,12-triazapentadecan-15-yl)-4-hydroxy-1-((R)-3-methyl-2-(3-methylisoxazol-5-yl)butanoyl)pyrrolidine-2-carboxamide (CPD-083)

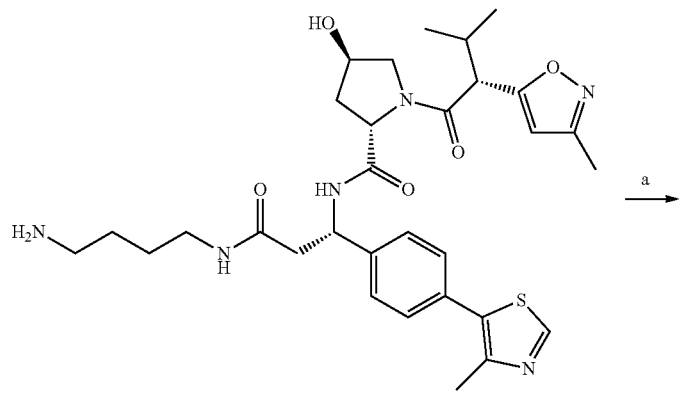

Z87

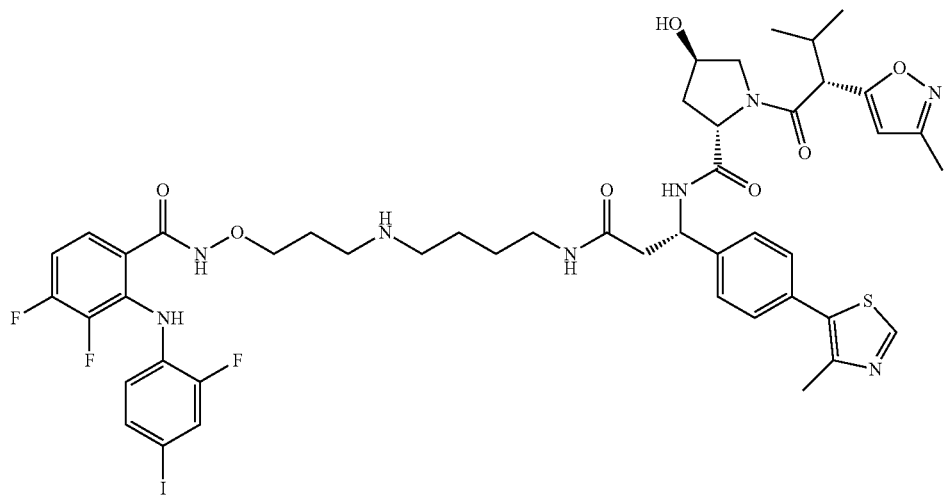

CPD-083

Reagents and conditions: (a) Z5, NaBH$_3$CN, DCM, MeOH, rt, overnight.

CPD-083 was synthesized following the same procedures as CPD-001 as described in Example 3. (0.08 g, yield: 39%). Two isomers of this spectrum. $^1$H NMR (600 MHz, Methanol-d$_4$) δ 9.00 (d, J=2.1 Hz, 1H), 7.49-7.41 (m, 4H), 7.41-7.37 (m, 2H), 7.35 (dt, J=8.4, 1.4 Hz, 1H), 7.05 (tdd, J=9.3, 6.9, 2.6 Hz, 1H), 6.62 (td, J=8.7, 4.1 Hz, 1H), 6.22 (d, J=14.3 Hz, 1H), 5.38-5.25 (m, 1H), 4.51 (dt, J=45.9, 8.1 Hz, 1H), 4.45-4.41 (m, 1H), 4.04 (t, J=5.3 Hz, 2H), 3.91-3.82 (m, 1H), 3.80-3.70 (m, 1H), 3.69-3.59 (m, 1H), 3.22 (t, J=5.8 Hz, 2H), 3.19-3.14 (m, 2H), 3.08-3.02 (m, 2H), 2.86-2.80 (m, 1H), 2.79-2.68 (m, 2H), 2.48 (d, J=1.2 Hz, 3H), 2.41 (dtd, J=9.9, 6.7, 5.1 Hz, 1H), 2.24 (d, J=2.6 Hz, 2H), 2.22 (s, 1H), 2.05-1.98 (m, 2H), 1.97-1.90 (m, 1H), 1.73-1.64 (m, 2H), 1.54 (tt, J=9.7, 4.6 Hz, 2H), 1.05 (dd, J=6.6, 5.5 Hz, 3H), 0.85 (dd, J=19.4, 6.7 Hz, 3H).

Example 84: (2S,4R)—N—((S)-1-(3,4-difluoro-2-((2-fluoro-4-iodophenyl)amino)phenyl)-16-(4-(4-methylthiazol-5-yl)phenyl)-1,14-dioxo-3-oxa-2,7,13-triazahexadecan-16-yl)-4-hydroxy-1-((R)-3-methyl-2-(3-methylisoxazol-5-yl)butanoyl)pyrrolidine-2-carboxamide (CPD-084)

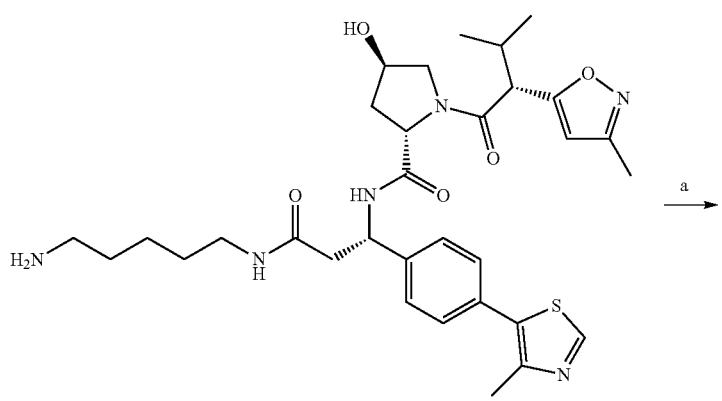

Z88

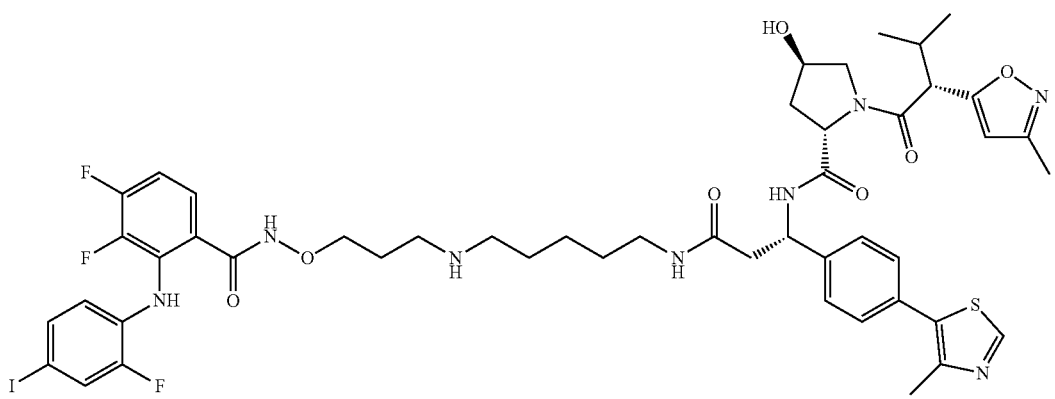

CPD-084

Reagents and conditions: (a) Z5, NaBH$_3$CN, DCM, MeOH, rt, overnight.

CPD-084 was synthesized following the same procedures as CPD-001 as described in Example 3. (0.08 g, yield: 58%). Two isomers of this spectrum. $^1$H NMR (600 MHz, Methanol-d4) δ 8.91 (d, J=2.4 Hz, 1H), 7.48-7.42 (m, 4H), 7.42-7.37 (m, 2H), 7.35 (ddt, J=8.4, 1.9, 1.0 Hz, 1H), 7.06 (td, J=9.3, 7.0 Hz, 1H), 6.60 (tdd, J=8.8, 4.3, 2.9 Hz, 1H), 6.23 (d, J=14.7 Hz, 1H), 5.37-5.25 (m, 1H), 4.51 (dt, J=48.1, 8.1 Hz, 1H), 4.43 (qd, J=3.7, 3.3, 1.5 Hz, 1H), 4.05 (ddd, J=6.9, 4.7, 2.2 Hz, 2H), 3.91-3.84 (m, 1H), 3.80-3.70 (m, 1H), 3.68-3.59 (m, 1H), 3.19 (dq, J=6.0, 3.4 Hz, 2H), 3.09 (ddd, J=15.0, 13.3, 6.9 Hz, 2H), 3.01-2.95 (m, 2H), 2.89-2.82 (m, 1H), 2.81-2.68 (m, 2H), 2.46 (s, 3H), 2.43-2.36 (m, 1H), 2.25 (d, J=7.2 Hz, 2H), 2.22 (s, 1H), 2.05-1.99 (m, 2H), 1.95 (ddt, J=12.9, 8.4, 4.1 Hz, 1H), 1.69 (ddd, J=15.5, 9.1, 6.8 Hz, 2H), 1.48-1.39 (m, 2H), 1.34-1.24 (m, 2H), 1.08-1.01 (m, 3H), 0.86 (dd, J=18.8, 6.7 Hz, 3H).

Example 85: (2S,4R)—N—((S)-1-(3,4-difluoro-2-((2-fluoro-4-iodophenyl)amino)phenyl)-17-(4-(4-methylthiazol-5-yl)phenyl)-1,15-dioxo-3-oxa-2,7,14-triazaheptadecan-17-yl)-4-hydroxy-1-((R)-3-methyl-2-(3-methylisoxazol-5-yl)butanoyl)pyrrolidine-2-carboxamide (CPD-085)

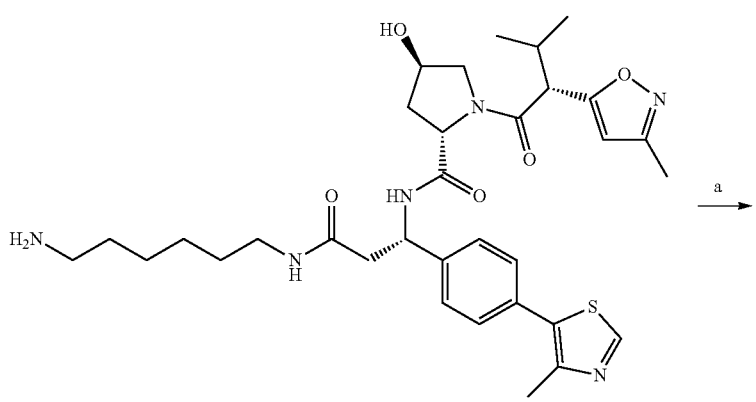

Z89

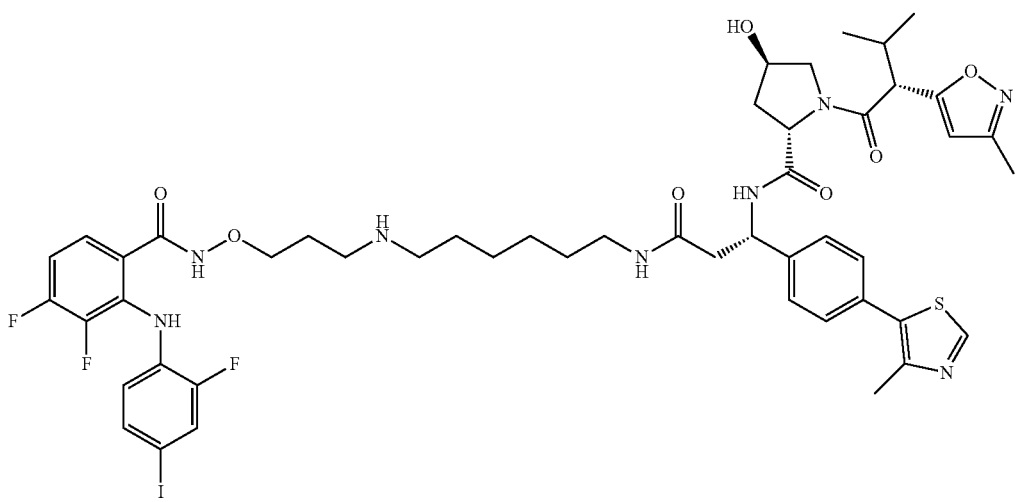

CPD-085

Reagents and conditions: (a) Z5, NaBH$_3$CN, DCM, MeOH, rt, overnight.

CPD-085 was synthesized following the same procedures as CPD-001 as described in Example 3. (0.08 g, yield: 49%). Two isomers of this spectrum. ¹H NMR (600 MHz, Methanol-$d_4$) δ 8.91 (d, J=1.9 Hz, 1H), 7.49-7.42 (m, 4H), 7.41-7.38 (m, 2H), 7.38-7.35 (m, 1H), 7.06 (tdd, J=9.8, 7.9, 1.4 Hz, 1H), 6.62 (td, J=8.7, 4.1 Hz, 1H), 6.23 (d, J=17.0 Hz, 1H), 5.37-5.24 (m, 1H), 4.51 (dt, J=45.0, 8.1 Hz, 1H), 4.44 (tq, J=4.8, 2.3 Hz, 1H), 4.05 (t, J=5.2 Hz, 2H), 3.90-3.84 (m, 1H), 3.79-3.70 (m, 1H), 3.68-3.58 (m, 1H), 3.21 (t, J=5.9 Hz, 2H), 3.15-3.04 (m, 2H), 3.03-2.97 (m, 2H), 2.85 (dd, J=14.2, 6.1 Hz, 1H), 2.81-2.67 (m, 2H), 2.47 (d, J=0.7 Hz, 3H), 2.43-2.37 (m, 1H), 2.25 (d, J=6.4 Hz, 2H), 2.22 (s, 1H), 2.07-1.99 (m, 2H), 1.95 (dddd, J=13.0, 7.9, 4.7, 3.5 Hz, 1H), 1.68 (ddt, J=8.6, 5.9, 3.1 Hz, 2H), 1.43-1.32 (m, 4H), 1.23 (tq, J=7.9, 3.9 Hz, 2H), 1.05 (dd, J=6.6, 5.3 Hz, 3H), 0.87 (dd, J=19.4, 6.7 Hz, 3H).

Example 86: (2S,4R)—N—((S)-1-(3,4-difluoro-2-((2-fluoro-4-iodophenyl)amino)phenyl)-18-(4-(4-methylthiazol-5-yl)phenyl)-1,16-dioxo-3-oxa-2,7,15-triazaoctadecan-18-yl)-4-hydroxy-1-((R)-3-methyl-2-(3-methylisoxazol-5-yl)butanoyl)pyrrolidine-2-carboxamide (CPD-086)

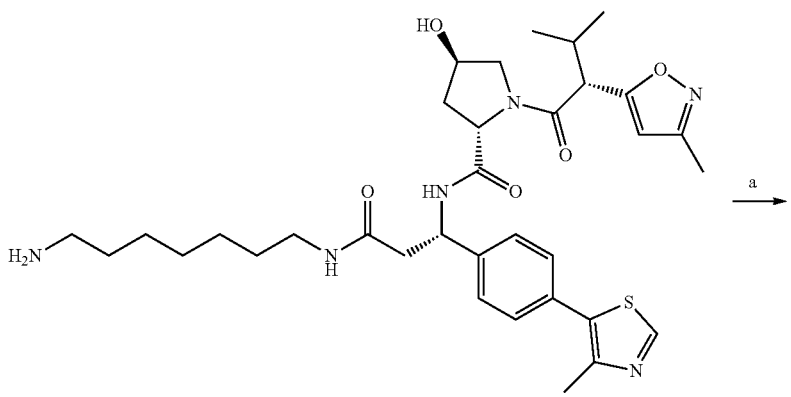

Z90

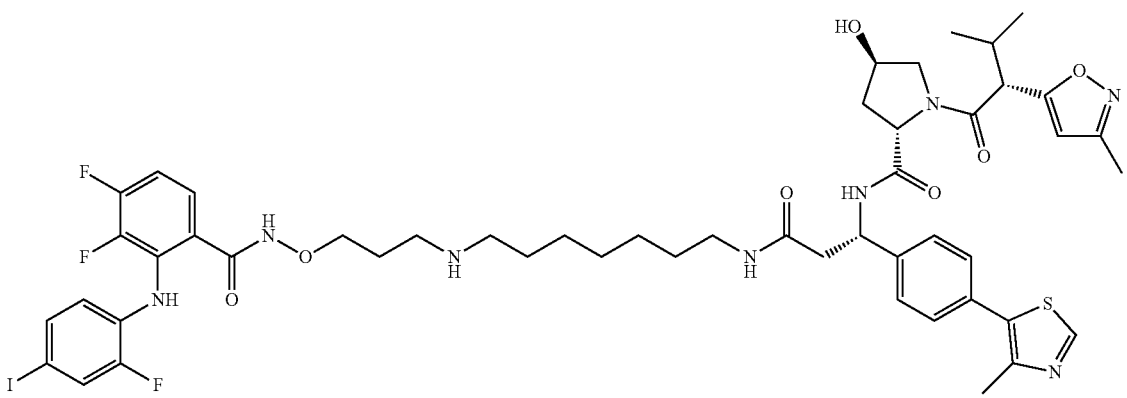

CPD-086

Reagents and conditions: (a) Z5, NaBH₃CN, DCM, MeOH, rt, overnight.

CPD-086 was synthesized following the same procedures as CPD-001 as described in Example 3. (0.08 g, yield: 43%). Two isomers of this spectrum. ¹H NMR (600 MHz, Methanol-d₄) δ 8.91 (d, J=2.5 Hz, 1H), 7.48-7.43 (m, 4H), 7.42-7.39 (m, 2H), 7.38-7.34 (m, 1H), 7.10-7.03 (m, 1H), 6.62 (td, J=8.7, 4.2 Hz, 1H), 6.23 (d, J=18.8 Hz, 1H), 5.31 (ddd, J=35.8, 8.2, 6.1 Hz, 1H), 4.51 (dt, J=44.2, 8.1 Hz, 1H), 4.44 (tq, J=4.8, 2.4 Hz, 1H), 4.11-4.02 (m, 2H), 3.91-3.83 (m, 1H), 3.80-3.70 (m, 1H), 3.68-3.58 (m, 1H), 3.22 (t, J=5.8 Hz, 2H), 3.07 (ddqd, J=20.3, 13.3, 6.9, 2.5 Hz, 2H), 2.98 (td, J=8.4, 7.9, 4.7 Hz, 2H), 2.85 (dd, J=14.0, 5.8 Hz, 1H), 2.81-2.68 (m, 2H), 2.48 (d, J=0.9 Hz, 3H), 2.44-2.37 (m, 1H), 2.26-2.24 (m, 2H), 2.23 (s, 1H), 2.06-2.00 (m, 2H), 1.95 (ddt, J=12.9, 8.5, 4.4 Hz, 1H), 1.71-1.62 (m, 2H), 1.34 (tt, J=15.6, 7.7 Hz, 4H), 1.28-1.22 (m, 2H), 1.20-1.13 (m, 2H), 1.05 (dd, J=6.6, 2.9 Hz, 3H), 0.87 (dd, J=19.0, 6.7 Hz, 3H).

Example 87: (2S,4R)—N—((S)-1-(3,4-difluoro-2-((2-fluoro-4-iodophenyl)amino)phenyl)-20-(4-(4-methylthiazol-5-yl)phenyl)-1,18-dioxo-3-oxa-2,7,17-triazaicosan-20-yl)-4-hydroxy-1-((R)-3-methyl-2-(3-methylisoxazol-5-yl)butanoyl)pyrrolidine-2-carboxamide (CPD-087)

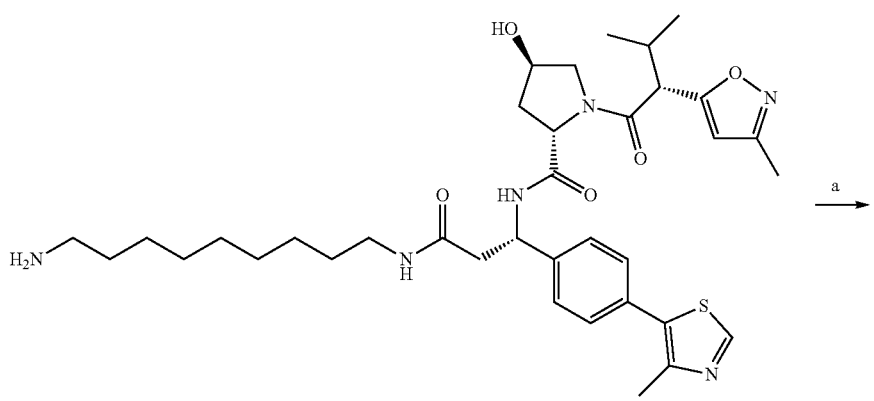

Z91

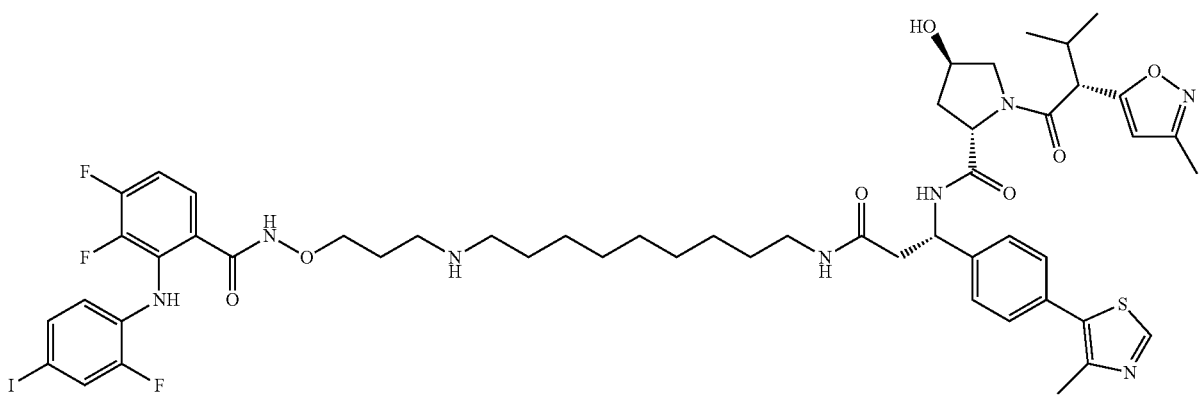

CPD-087

Reagents and conditions: (a) Z5, NaBH₃CN, DCM, MeOH, rt, overnight.

CPD-087 was synthesized following the same procedures as CPD-001 as described in Example 3. (0.08 g, yield: 42%). Two isomers of this spectrum. $^1$H NMR (600 MHz, Methanol-d$_4$) δ 8.95 (d, J=3.1 Hz, 1H), 7.49-7.43 (m, 4H), 7.42-7.39 (m, 2H), 7.38-7.35 (m, 1H), 7.06 (td, J=9.1, 7.0 Hz, 1H), 6.63 (td, J=8.7, 4.3 Hz, 1H), 6.23 (d, J=20.6 Hz, 1H), 5.30 (ddd, J=35.1, 8.1, 5.9 Hz, 1H), 4.52 (dt, J=43.6, 8.1 Hz, 1H), 4.45-4.42 (m, 1H), 4.08 (t, J=5.4 Hz, 2H), 3.90-3.85 (m, 1H), 3.80-3.70 (m, 1H), 3.68-3.56 (m, 1H), 3.24 (t, J=5.8 Hz, 2H), 3.09 (dtd, J=13.8, 7.0, 1.8 Hz, 1H), 3.05-2.98 (m, 3H), 2.88-2.82 (m, 1H), 2.81-2.74 (m, 1H), 2.70 (dt, J=20.9, 7.5 Hz, 1H), 2.48 (d, J=1.0 Hz, 3H), 2.44-2.38 (m, 1H), 2.25 (d, J=5.2 Hz, 2H), 2.23 (s, 1H), 2.03 (tt, J=6.5, 3.4 Hz, 2H), 1.96 (ddt, J=13.1, 8.2, 4.8 Hz, 1H), 1.73-1.64 (m, 2H), 1.32 (qd, J=8.0, 7.3, 3.7 Hz, 4H), 1.27-1.16 (m, 6H), 1.15-1.09 (m, 2H), 1.06 (dd, J=6.6, 2.6 Hz, 3H), 0.87 (dd, J=18.7, 6.7 Hz, 3H).

Example 88: (2S,4R)—N—((S)-1-(3,4-difluoro-2-((2-fluoro-4-iodophenyl)amino)phenyl)-23-(4-(4-methylthiazol-5-yl)phenyl)-1,21-dioxo-3-oxa-2,7,20-triazatricosan-23-yl)-4-hydroxy-1-((R)-3-methyl-2-(3-methylisoxazol-5-yl)butanoyl)pyrrolidine-2-carboxamide (CPD-088)

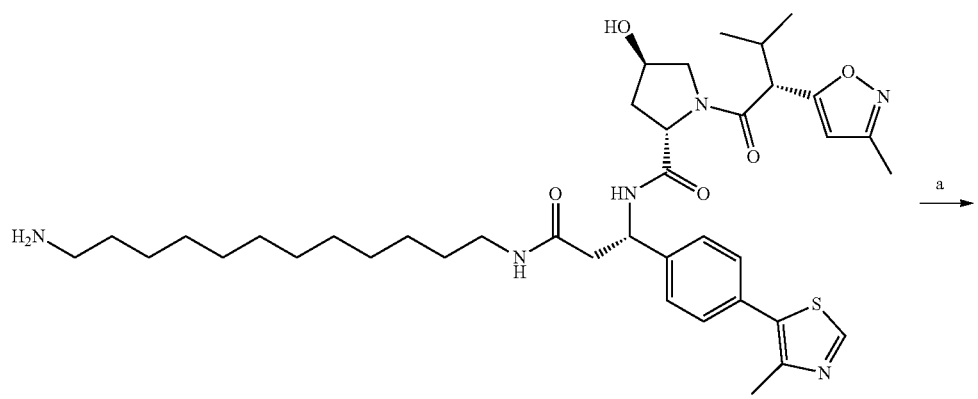

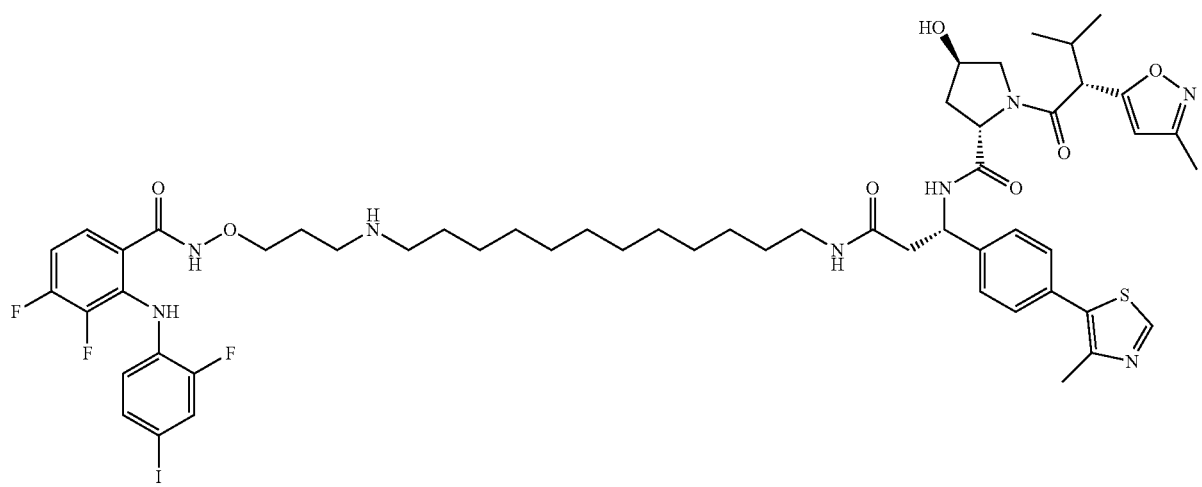

CPD-088

Reagents and conditions: (a) Z5, NaBH$_3$CN, DCM, MeOH, rt, overnight.

CPD-088 was synthesized following the same procedures as CPD-001 as described in Example 3. (0.08 g, yield: 41%). Two isomers of this spectrum. ¹H NMR (600 MHz, Methanol-d₄) δ 8.97 (d, J=4.2 Hz, 1H), 7.49-7.43 (m, 4H), 7.43-7.39 (m, 2H), 7.39-7.35 (m, 1H), 7.06 (td, J=9.2, 7.0 Hz, 1H), 6.64 (td, J=8.7, 4.3 Hz, 1H), 6.23 (d, J=21.0 Hz, 1H), 5.30 (ddd, J=35.2, 8.1, 5.9 Hz, 1H), 4.52 (dt, J=43.4, 8.1 Hz, 1H), 4.44 (tt, J=4.6, 2.3 Hz, 1H), 4.08 (t, J=5.1 Hz, 2H), 3.91-3.85 (m, 1H), 3.80-3.70 (m, 1H), 3.68-3.58 (m, 2H), 3.24 (t, J=5.7 Hz, 2H), 3.13-3.07 (m, 11H), 3.03 (ddd, J=13.3, 8.9, 7.0 Hz, 3H), 2.87-2.77 (m, 1H), 2.77-2.68 (m, 1H), 2.49 (s, 3H), 2.45-2.37 (m, 1H), 2.25 (d, J=4.5 Hz, 2H), 2.23 (s, 1H), 2.03 (tt, J=6.3, 3.3 Hz, 2H), 1.99-1.92 (m, 1H), 1.76-1.68 (m, 2H), 1.38 (p, J=7.8, 7.4 Hz, 2H), 1.35-1.26 (m, 4H), 1.19 (q, J=6.3, 4.2 Hz, 10H), 1.12 (d, J=5.5 Hz, 2H), 1.06 (dd, J=6.6, 1.6 Hz, 3H), 0.87 (dd, J=18.0, 6.7 Hz, 3H).

Example 89: (2S,4R)—N—((S)-1-(3,4-difluoro-2-((2-fluoro-4-iodophenyl)amino)phenyl)-16-(4-(4-methylthiazol-5-yl)phenyl)-1,14-dioxo-3,10-dioxa-2,7,13-triazahexadecan-16-yl)-4-hydroxy-1-((R)-3-methyl-2-(3-methylisoxazol-5-yl)butanoyl)pyrrolidine-2-carboxamide (CPD-089)

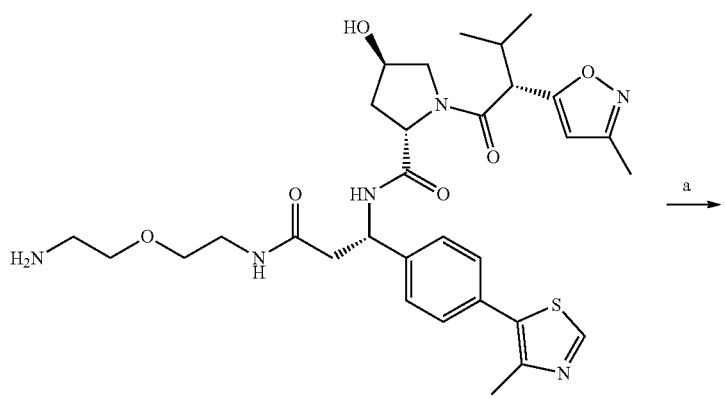

Z93

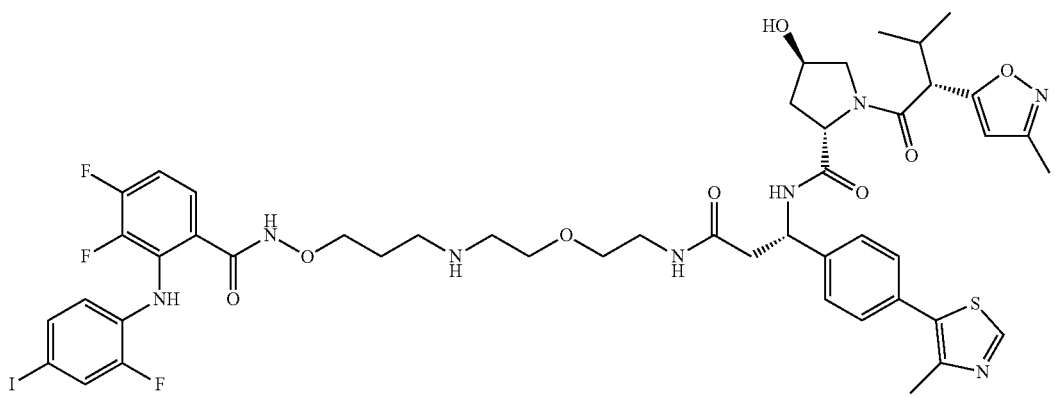

CPD-089

Reagents and conditions: (a) Z5, NaBH₃CN, DCM, MeOH, rt, overnight.

CPD-089 was synthesized following the same procedures as CPD-001 as described in Example 3. (0.08 g, yield: 44%). Two isomers of this spectrum. $^1$H NMR (600 MHz, Methanol-d$_4$) δ 9.05 (d, J=2.0 Hz, 1H), 7.48-7.40 (m, 4H), 7.40-7.36 (m, 2H), 7.36-7.32 (m, 1H), 7.06-6.99 (m, 11H), 6.60 (tt, J=8.5, 3.9 Hz, 1H), 6.22 (d, J=9.7 Hz, 11H), 5.32 (dt, J=27.8, 7.2 Hz, 11H), 4.56-4.37 (m, 2H), 4.09-4.02 (m, 2H), 3.91-3.83 (m, 1H), 3.80-3.70 (m, 3H), 3.68-3.60 (m, 1H), 3.47 (dt, J=7.8, 5.4 Hz, 2H), 3.29 (t, J=5.9 Hz, 2H), 3.26-3.18 (m, 3H), 2.82 (dd, J=14.5, 6.7 Hz, 1H), 2.77-2.67 (m, 2H), 2.48 (d, J=1.1 Hz, 3H), 2.43-2.37 (m, 1H), 2.24 (d, J=11.1 Hz, 2H), 2.21 (s, 1H), 2.19-2.12 (m, 1H), 2.06 (tt, J=6.5, 3.9 Hz, 2H), 1.93 (ddt, J=13.1, 8.5, 4.5 Hz, 1H), 1.04 (dd, J=8.5, 6.6 Hz, 3H), 0.86 (dd, J=17.3, 6.7 Hz, 3H).

Example 90: (2S,4R)—N—((S)-1-(3,4-difluoro-2-((2-fluoro-4-iodophenyl)amino)phenyl)-19-(4-(4-methylthiazol-5-yl)phenyl)-1,17-dioxo-3,10,13-trioxa-2,7,16-triazanonadecan-19-yl)-4-hydroxy-1-((R)-3-methyl-2-(3-methylisoxazol-5-yl)butanoyl)pyrrolidine-2-carboxamide (CPD-090)

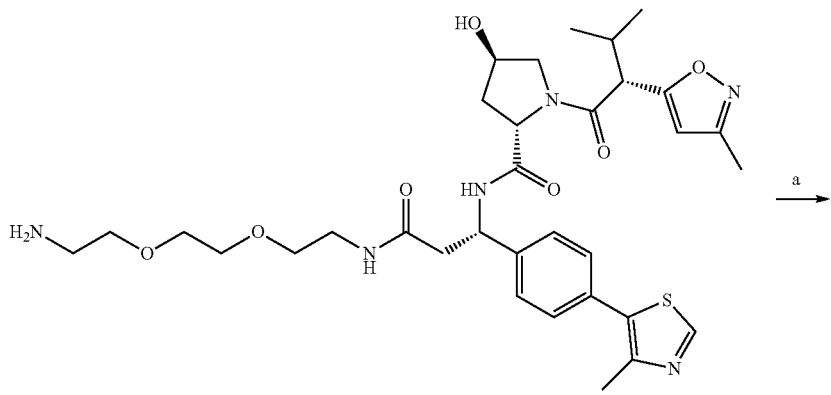

Z94

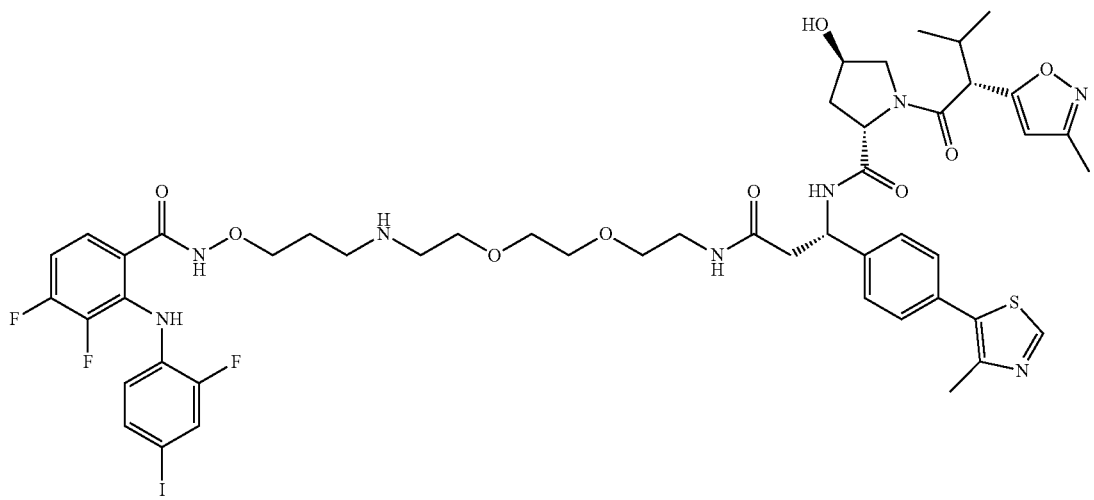

CPD-090

Reagents and conditions: (a) Z5, NaBH$_3$CN, DCM, MeOH, rt, overnight.

CPD-090 was synthesized following the same procedures as CPD-001 as described in Example 3. (0.08 g, yield: 43%). Two isomers of this spectrum. $^1$H NMR (600 MHz, Methanol-$d_4$) δ 9.05 (d, J=2.1 Hz, 1H), 7.49-7.42 (m, 4H), 7.41-7.38 (m, 2H), 7.36 (dt, J=8.5, 1.4 Hz, 1H), 7.04 (tdd, J=9.6, 7.0, 3.1 Hz, 1H), 6.63 (td, J=8.7, 4.1 Hz, 1H), 6.23 (d, J=16.4 Hz, 1H), 5.37-5.22 (m, 1H), 4.51 (dt, J=45.8, 8.1 Hz, 1H), 4.44 (dp, J=4.8, 2.4 Hz, 1H), 4.06 (q, J=5.5 Hz, 2H), 3.91-3.83 (m, 1H), 3.80-3.71 (m, 3H), 3.69-3.58 (m, 1H), 3.54 (dtd, J=6.0, 3.6, 2.9, 1.2 Hz, 2H), 3.49 (td, J=4.6, 3.9, 2.0 Hz, 2H), 3.43-3.36 (m, 2H), 3.30-3.27 (m, 2H), 3.26 (dd, J=6.2, 1.9 Hz, 3H), 2.92-2.82 (m, 1H), 2.80-2.68 (m, 2H), 2.49 (d, J=1.7 Hz, 3H), 2.41 (ddt, J=16.5, 13.6, 6.7 Hz, 1H), 2.25 (d, J=5.4 Hz, 2H), 2.22 (s, 1H), 2.20-2.12 (m, 1H), 2.08-2.02 (m, 2H), 1.95 (ddt, J=13.0, 8.6, 4.5 Hz, 1H), 1.05 (t, J=6.4 Hz, 3H), 0.86 (dd, J=18.3, 6.7 Hz, 3H).

Example 91: (2S,4R)—N—((S)-1-(3,4-difluoro-2-((2-fluoro-4-iodophenyl)amino)phenyl)-22-(4-(4-methylthiazol-5-yl)phenyl)-1,20-dioxo-3,10,13,16-tetraoxa-2,7,19-triazadocosan-22-yl)-4-hydroxy-1-((R)-3-methyl-2-(3-methylisoxazol-5-yl)butanoyl)pyrrolidine-2-carboxamide (CPD-091)

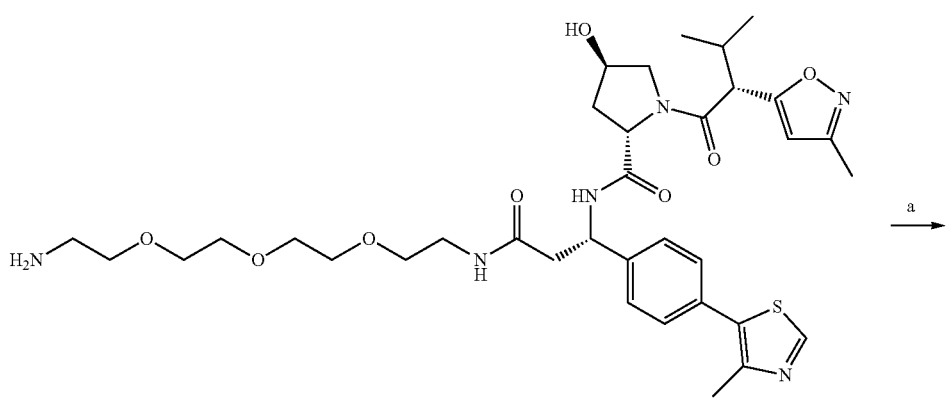

Z95

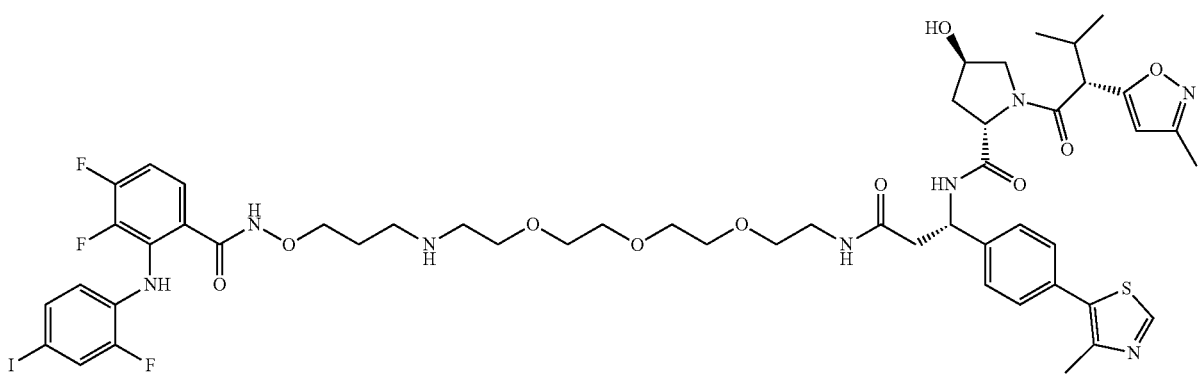

CPD-091

Reagents and conditions: (a) Z5, NaBH$_3$CN, DCM, MeOH, rt, overnight.

CPD-091 was synthesized following the same procedures as CPD-001 as described in Example 3. (0.08 g, yield: 34%). Two isomers of this spectrum. $^1$H NMR (600 MHz, Methanol-$d_4$) δ 8.96 (s, 1H), 7.49-7.46 (m, 1H), 7.45 (s, 2H), 7.44-7.41 (m, 1H), 7.40-7.35 (m, 3H), 7.05 (tdd, J=9.2, 6.9, 2.2 Hz, 1H), 6.63 (td, J=8.7, 4.1 Hz, 1H), 6.23 (d, J=15.8 Hz, 1H), 5.38-5.23 (m, 1H), 4.51 (dt, J=45.8, 8.1 Hz, 1H), 4.44 (dd, J=4.8, 2.6 Hz, 1H), 4.08-4.03 (m, 2H), 3.90-3.84 (m, 1H), 3.77 (td, J=6.3, 5.4, 2.6 Hz, 2H), 3.74-3.65 (m, 1H), 3.62-3.57 (m, 3H), 3.55 (ddd, J=5.6, 3.9, 1.5 Hz, 2H), 3.51 (ttd, J=5.8, 4.1, 3.6, 2.6 Hz, 4H), 3.45-3.37 (m, 2H), 3.27 (dt, J=10.4, 5.8 Hz, 5H), 2.91-2.82 (m, 1H), 2.81-2.69 (m, 2H), 2.48 (d, J=1.1 Hz, 3H), 2.44-2.37 (m, 1H), 2.25 (d, J=6.9 Hz, 2H), 2.22 (s, 1H), 2.20-2.13 (m, 11H), 2.07-2.01 (m, 2H), 1.95 (ddt, J=12.9, 8.2, 4.3 Hz, 11H), 1.05 (dd, J=6.6, 4.5 Hz, 3H), 0.87 (dd, J=17.6, 6.7 Hz, 3H).

Example 92: (2S,4R)—N—((S)-1-(3,4-difluoro-2-((2-fluoro-4-iodophenyl)amino)phenyl)-25-(4-(4-methylthiazol-5-yl)phenyl)-1,23-dioxo-3,10,13,16,19-pentaoxa-2,7,22-triazapentacosan-25-yl)-4-hydroxy-1-((R)-3-methyl-2-(3-methylisoxazol-5-yl)butanoyl)pyrrolidine-2-carboxamide (CPD-092)

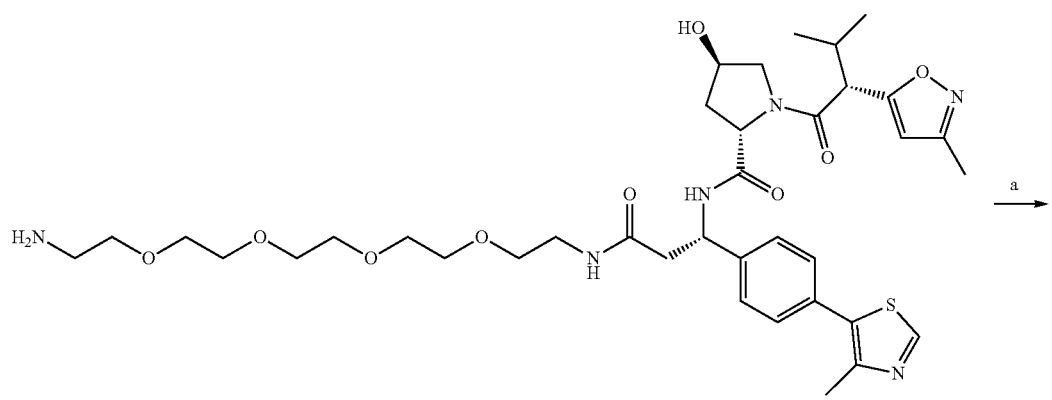

Z96

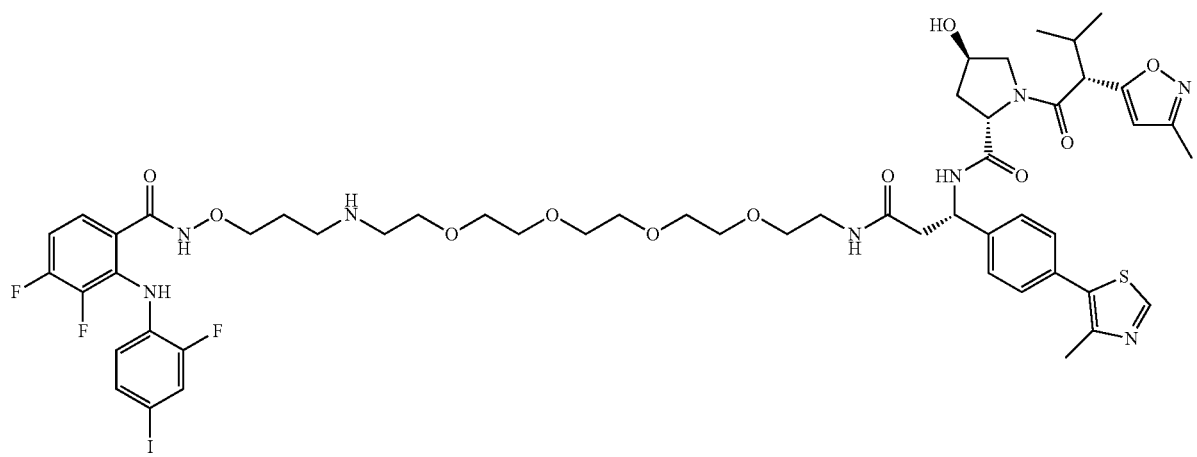

CPD-092

Reagents and conditions: (a) Z5, NaBH$_3$CN, DCM, MeOH, rt, overnight.

CPD-092 was synthesized following the same procedures as CPD-001 as described in Example 3. (0.08 g, yield: 44%). Two isomers of this spectrum. $^1$H NMR (600 MHz, Methanol-d$_4$) δ 9.00 (s, 1H), 7.49-7.46 (m, 11H), 7.45 (s, 2H), 7.44-7.42 (m, 11H), 7.42-7.35 (m, 3H), 7.05 (tdd, J=9.1, 6.9, 2.1 Hz, 11H), 6.64 (td, J=8.7, 4.0 Hz, 11H), 6.23 (d, J=16.5 Hz, 11H), 5.37-5.26 (m, 1H), 4.51 (dt, J=45.2, 8.1 Hz, 1H), 4.44 (tt, J=4.8, 2.4 Hz, 1H), 4.06 (dt, J=5.4, 3.7 Hz, 2H), 3.91-3.83 (m, 1H), 3.77 (dt, J=7.5, 2.3 Hz, 2H), 3.75-3.65 (m, 1H), 3.62-3.57 (m, 3H), 3.57-3.54 (m, 8H), 3.54-3.50 (m, 2H), 3.46-3.38 (m, 2H), 3.30-3.24 (m, 5H), 2.91-2.81 (m, 1H), 2.80-2.70 (m, 2H), 2.49 (d, J=1.0 Hz, 3H), 2.41 (tdq, J=10.0, 6.5, 3.6, 3.1 Hz, 11H), 2.25 (d, J=6.7 Hz, 2H), 2.22 (s, 1H), 2.20-2.13 (m, 1H), 2.07-2.02 (m, 2H), 1.99-1.91 (m, 1H), 1.05 (dd, J=6.6, 5.2 Hz, 3H), 0.87 (dd, J=18.5, 6.7 Hz, 3H).

Example 93: (2S,4R)—N—((S)-1-(3,4-difluoro-2-((2-fluoro-4-iodophenyl)amino)phenyl)-28-(4-(4-methylthiazol-5-yl)phenyl)-1,26-dioxo-3,10,13,16,19,22-hexaoxa-2,7,25-triazaoctacosan-28-yl)-4-hydroxy-1-((R)-3-methyl-2-(3-methylisoxazol-5-yl)butanoyl)pyrrolidine-2-carboxamide (CPD-093)

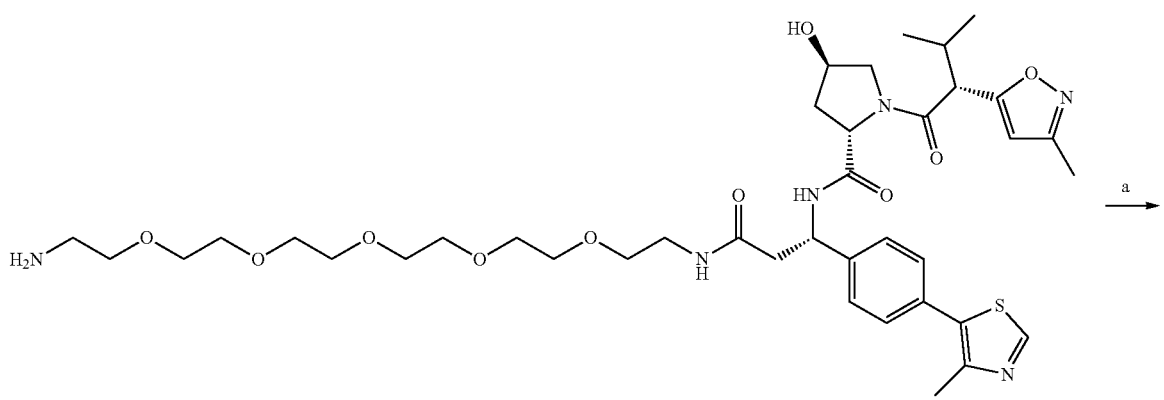

Z97

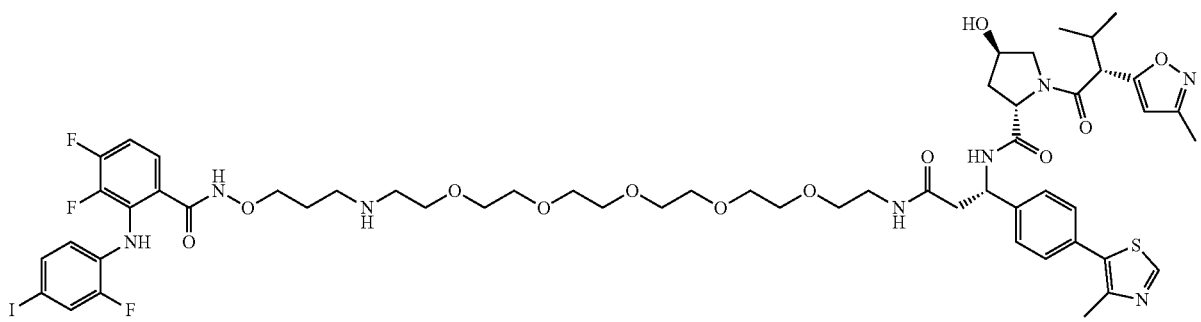

CPD-093

Reagents and conditions: (a) Z5, NaBH$_3$CN, DCM, MeOH, rt, overnight.

CPD-093 was synthesized following the same procedures as CPD-001 as described in Example 3. (0.08 g, yield: 41%). Two isomers of this spectrum. $^1$H NMR (600 MHz, Methanol-$d_4$) δ 8.98 (d, J=1.7 Hz, 11H), 7.50-7.46 (m, 1H), 7.46 (s, 2H), 7.43 (d, J=8.3 Hz, 2H), 7.40-7.35 (m, 2H), 7.09-7.02 (m, 1H), 6.64 (td, J=8.7, 4.0 Hz, 1H), 6.23 (d, J=17.0 Hz, 1H), 5.36-5.25 (m, 1H), 4.52 (dt, J=44.7, 8.1 Hz, 1H), 4.45-4.41 (m, 1H), 4.06 (q, J=4.4, 3.8 Hz, 2H), 3.91-3.84 (m, 1H), 3.80-3.75 (m, 3H), 3.73 (d, J=11.6 Hz, 1H), 3.67 (dd, J=11.0, 4.3 Hz, 1H), 3.63-3.53 (m, 14H), 3.52 (qd, J=4.9, 4.3, 2.4 Hz, 2H), 3.47-3.37 (m, 2H), 3.28 (td, J=7.8, 2.7 Hz, 4H), 2.88-2.82 (m, 1H), 2.80-2.70 (m, 2H), 2.49 (s, 3H), 2.41 (dtd, J=13.5, 6.8, 3.1 Hz, 1H), 2.25 (d, J=6.5 Hz, 2H), 2.22 (s, 1H), 2.14 (d, J=13.6 Hz, 1H), 2.08-2.02 (m, 2H), 1.99-1.93 (m, 1H), 1.05 (dd, J=6.6, 5.1 Hz, 3H), 0.87 (dd, J=18.5, 6.7 Hz, 3H).

Example 94: 3,4-difluoro-2-((2-fluoro-4-iodophenyl)amino)-N-((1-((2-(1-methyl-2,6-dioxopiperidin-3-yl)-1,3-dioxoisoindolin-5-yl)amino)-3,6,9,12,15-pentaoxa-18-azahenicosan-21-yl)oxy)benzamide (CPD-097)

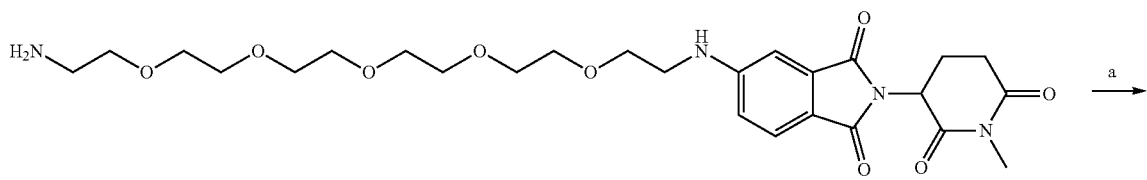

Z98

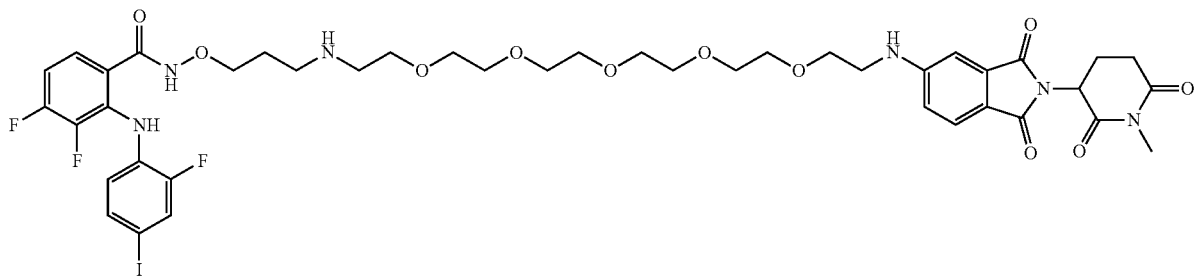

CPD-097

Reagents and conditions: (a) Z5, NaBH$_3$CN, DCM, MeOH, rt, overnight.

CPD-094 was synthesized following the same procedures as CPD-001 as described in Example 3. (0.08 g, yield: 44%). ¹H NMR (600 MHz, Methanol-$d_4$) δ 7.45 (d, J=8.4 Hz, 1H), 7.36 (dd, J=10.6, 1.9 Hz, 1H), 7.30 (ddd, J=9.0, 5.3, 1.8 Hz, 1H), 7.26 (dt, J=8.5, 1.4 Hz, 1H), 6.94 (td, J=9.3, 7.0 Hz, 1H), 6.91 (d, J=2.2 Hz, 1H), 6.76 (dd, J=8.4, 2.2 Hz, 1H), 6.53 (td, J=8.7, 4.2 Hz, 1H), 4.95 (dd, J=12.9, 5.5 Hz, 1H), 3.95 (t, J=5.2 Hz, 2H), 3.65 (dd, J=5.7, 4.3 Hz, 2H), 3.59 (t, J=5.3 Hz, 2H), 3.54 (s, 4H), 3.52-3.51 (m, 1H), 3.49 (dd, J=5.9, 2.5 Hz, 2H), 3.48-3.46 (m, 3H), 3.46-3.43 (m, 4H), 3.29 (t, J=5.3 Hz, 2H), 3.21 (p, J=1.6 Hz, 2H), 3.18 (t, J=6.1 Hz, 2H), 3.15 (t, J=5.0 Hz, 2H), 3.03 (s, 3H), 2.79-2.76 (m, 1H), 2.76 (d, J=4.0 Hz, 1H), 2.62-2.48 (m, 1H), 1.97 (ddd, J=9.9, 5.0, 2.9 Hz, 1H), 1.95-1.91 (m, 2H).

Example 95: (2S,4R)-1-((S)-20-(tert-butyl)-1-(3,4-difluoro-2-((2-fluoro-4-iodophenyl)amino)phenyl)-7-methyl-1,18-dioxo-3-oxa-2,7,19-triazahenicosan-21-oyl)-4-hydroxy-N—((S)-1-(4-(4-methylthiazol-5-yl)phenyl)ethyl)pyrrolidine-2-carboxamide (CPD-037)

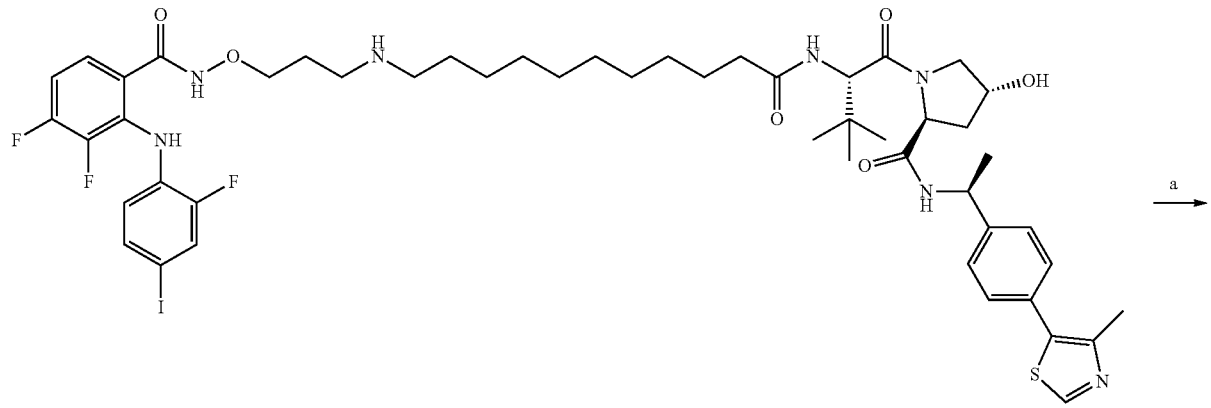

CPD-031

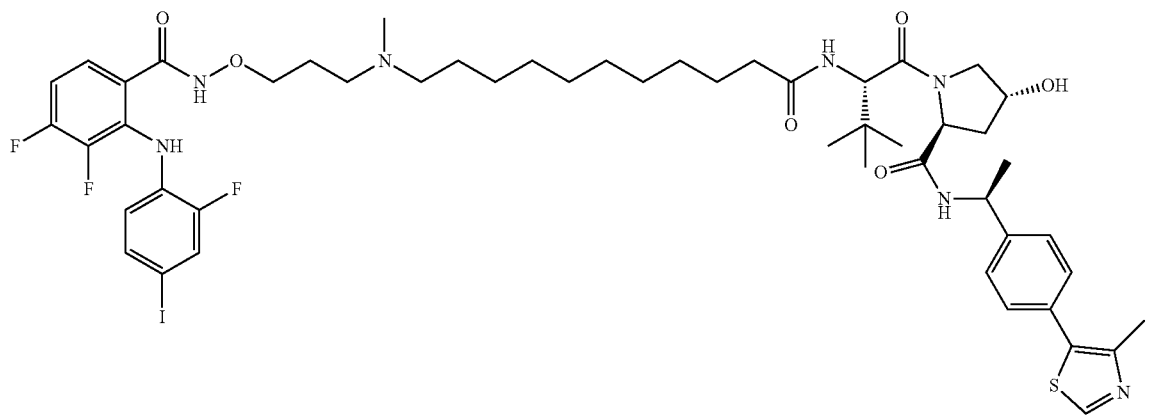

CPD-037

Reagents and conditions: (a) HCHO, NaBH₃CN, DCM, MeOH, rt, overnight.

To a solution of CPD-031 (0.1 g, 0.09 mmol) and formaldehyde (3 mg, 0.1 mmol) in MeOH (1 mL) was added NaBH$_3$CN (9 mg, 0.14 mmol). The reaction mixture was stirred at room temperature overnight. The reaction was monitored by UPLC. Upon completion, the reaction mixture was purified by preparative HPLC to give CPD-037 (0.05 g, 0.05 mmol, 56% yield) as a white solid. $^1$H NMR (800 MHz, Methanol-d$_4$) δ 8.89 (s, 1H), 7.51 (d, J=7.9 Hz, 2H), 7.45 (t, J=10.7 Hz, 3H), 7.39 (s, 1H), 7.36 (d, J=8.7 Hz, 1H), 7.06 (q, J=8.3 Hz, 1H), 6.62 (td, J=8.7, 3.8 Hz, 1H), 5.02 (q, J=7.2 Hz, 1H), 4.55 (t, J=7.4 Hz, 1H), 4.49 (s, 1H), 4.47-4.43 (m, 1H), 4.11 (t, J=7.6 Hz, 1H), 4.06-4.01 (m, 1H), 3.93 (dd, J=10.8, 5.0 Hz, 1H), 3.68 (dd, J=11.1, 3.6 Hz, 1H), 3.45 (q, J=7.7, 6.6 Hz, 1H), 3.04 (td, J=11.9, 5.0 Hz, 1H), 2.89 (s, 3H), 2.49 (s, 3H), 2.27 (dt, J=14.7, 7.9 Hz, 1H), 2.20 (ddd, J=13.7, 9.0, 4.8 Hz, 2H), 2.10 (dt, J=12.8, 5.8 Hz, 3H), 1.80-1.67 (m, 2H), 1.59-1.52 (m, 2H), 1.45 (d, J=7.1 Hz, 3H), 1.36-1.18 (m, 14H), 1.05 (s, 9H).

Example 96: (2R,4S)-1-((S)-20-(tert-butyl)-1-(3,4-difluoro-2-((2-fluoro-4-iodophenyl)amino)phenyl)-7-methyl-1,18-dioxo-3-oxa-2,7,19-triazahenicosan-21-oyl)-4-hydroxy-N—((S)-1-(4-(4-methylthiazol-5-yl)phenyl)ethyl)pyrrolidine-2-carboxamide (CPD-053)

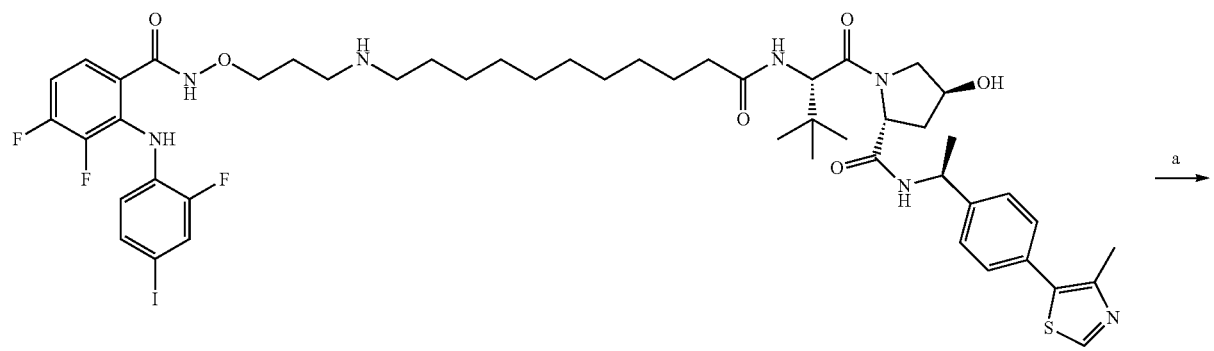

CPD-034

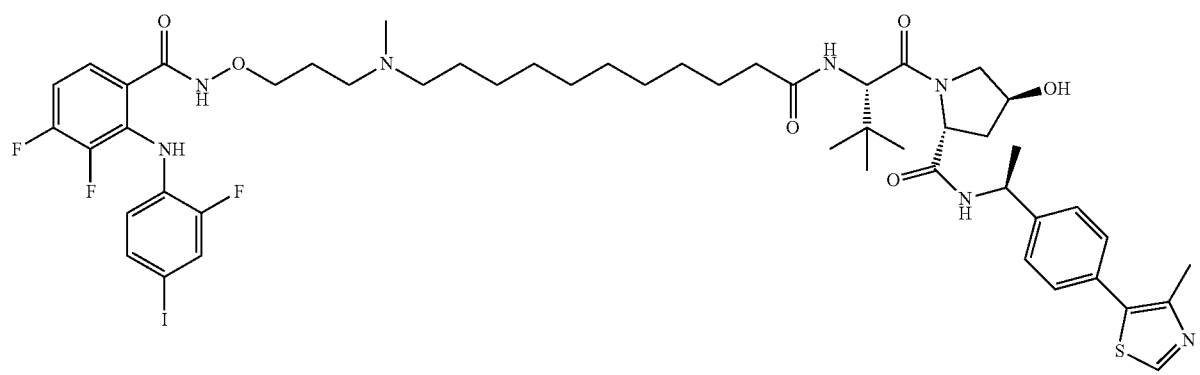

CPD-053

Reagents and conditions: (a) HCHO, NaBH$_3$CN, DCM, MeOH, rt, overnight.

CPD-053 was synthesized following the same procedures as CPD-037 as described in Example 95. (0.08 g, yield: 44%). ¹H NMR (800 MHz, Methanol-$d_4$) δ 8.89 (s, 1H), 7.48 (d, J=10.6 Hz, 1H), 7.44 (d, J=8.0 Hz, 2H), 7.42 (d, J=7.9 Hz, 2H), 7.38 (t, J=7.3 Hz, 2H), 7.07 (q, J=8.5 Hz, 1H), 6.64 (td, J=8.7, 3.8 Hz, 1H), 5.00 (q, J=7.2 Hz, 1H), 4.63 (s, 1H), 4.57 (t, J=8.3 Hz, 1H), 4.44 (s, 1H), 4.10 (s, 1H), 4.04 (s, 1H), 3.87 (d, J=11.0 Hz, 1H), 3.75 (dd, J=11.2, 4.1 Hz, 1H), 3.45 (d, J=6.6 Hz, 1H), 3.10-3.00 (m, 1H), 2.90 (s, 3H), 2.48 (s, 3H), 2.29 (dt, J=15.0, 7.7 Hz, 1H), 2.23 (t, J=7.2 Hz, 1H), 2.21-2.17 (m, 1H), 2.13-2.08 (m, 2H), 1.96 (ddd, J=13.3, 8.9, 4.6 Hz, 1H), 1.77 (s, 1H), 1.73 (s, 1H), 1.62-1.55 (m, 2H), 1.51 (d, J=7.1 Hz, 3H), 1.39-1.24 (m, 14H), 1.04 (s, 9H).

Example 97: (2S,4R)-1-((S)-20-(tert-butyl)-1-(3,4-difluoro-2-((2-fluoro-4-iodophenyl)amino)phenyl)-8-methyl-1,18-dioxo-3-oxa-2,8,19-triazahenicosan-21-oyl)-4-hydroxy-N—((S)-1-(4-(4-methylthiazol-5-yl)phenyl)ethyl)pyrrolidine-2-carboxamide (CPD-094)

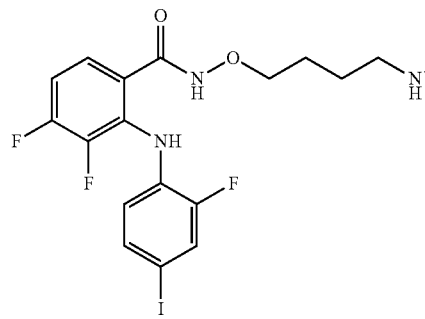
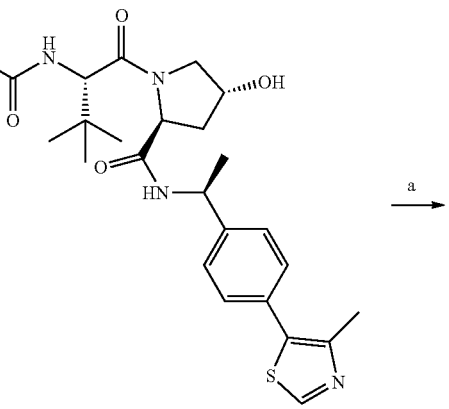

CPD-035

→ a

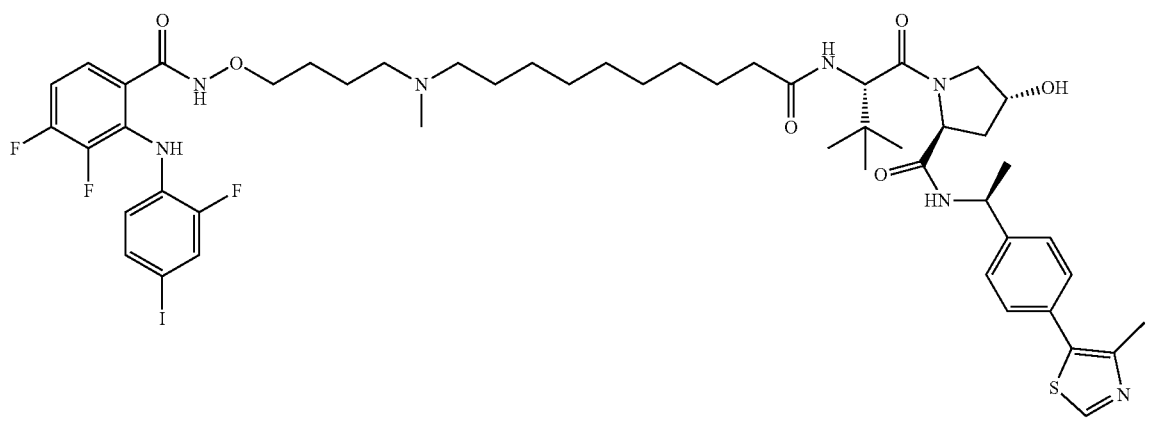

CPD-094

Reagents and conditions: (a) HCHO, NaBH₃CN, DCM, MeOH, rt, overnight.

CPD-094 was synthesized following the same procedures as CPD-037 as described in Example 95. (0.08 g, yield: 44%). ¹H NMR (600 MHz, Methanol-d₄) δ 8.97 (s, 1H), 7.49-7.41 (m, 5H), 7.40-7.34 (m, 2H), 7.06 (td, J=9.2, 7.0 Hz, 1H), 6.61 (td, J=8.8, 4.3 Hz, 1H), 5.00 (q, J=6.9 Hz, 1H), 4.63 (d, J=6.4 Hz, 1H), 4.59-4.54 (m, 1H), 4.43 (dp, J=4.3, 2.0 Hz, 1H), 3.92 (p, J=5.0 Hz, 2H), 3.87 (d, J=11.1 Hz, 1H), 3.75 (dd, J=11.0, 4.0 Hz, 1H), 3.34 (ddd, J=9.1, 7.0, 4.5 Hz, 1H), 3.23-3.13 (m, 2H), 3.07 (ddd, J=12.6, 10.3, 6.2 Hz, 1H), 2.87 (s, 3H), 2.49 (s, 3H), 2.29 (ddd, J=14.1, 8.3, 7.1 Hz, 11H), 2.26-2.22 (m, 1H), 2.22-2.15 (m, 2H), 1.99-1.88 (m, 3H), 1.73 (p, J=6.2 Hz, 4H), 1.65-1.56 (m, 2H), 1.51 (d, J=7.0 Hz, 2H), 1.39-1.26 (m, 10H), 1.04 (s, 9H).

Example 98: (2S,4R)-1-((S)-22-(tert-butyl)-1-(3,4-difluoro-2-((2-fluoro-4-iodophenyl)amino)phenyl)-8-methyl-1,20-dioxo-3-oxa-2,8,21-triazatricosan-23-oyl)-4-hydroxy-N—((S)-1-(4-(4-methylthiazol-5-yl)phenyl)ethyl)pyrrolidine-2-carboxamide (CPD-095)

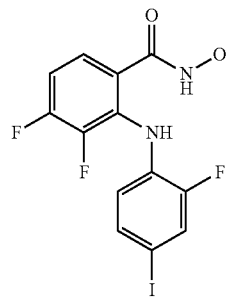
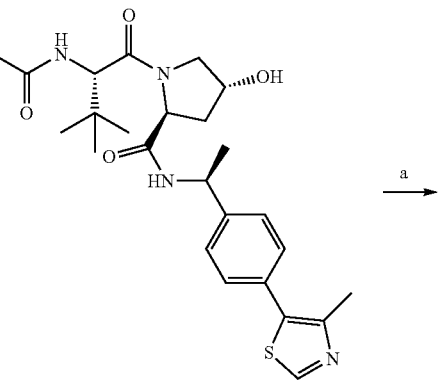

CPD-038

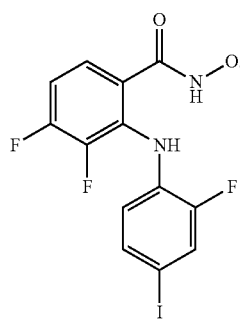

CPD-095

Reagents and conditions: (a) HCHO, NaBH₃CN, DCM, MeOH, rt, overnight.

CPD-095 was synthesized following the same procedures as CPD-037 as described in Example 95. (0.07 g, yield: 41%). ¹H NMR (600 MHz, Methanol-d₄) δ 8.95 (s, 1H), 7.50-7.40 (m, 5H), 7.40-7.35 (m, 2H), 7.06 (td, J=9.3, 7.0 Hz, 1H), 6.61 (td, J=8.7, 4.3 Hz, 1H), 5.00 (q, J=7.0 Hz, 1H), 4.63 (s, 11H), 4.56 (t, J=8.3 Hz, 11H), 4.43 (dp, J=4.3, 1.9 Hz, 1H), 3.93 (q, J=5.1 Hz, 2H), 3.87 (dt, J=11.2, 1.7 Hz, 1H), 3.75 (dd, J=11.0, 4.0 Hz, 11H), 3.35 (td, J=10.0, 9.2, 4.9 Hz, 1H), 3.18 (dtt, J=12.7, 9.4, 5.9 Hz, 2H), 3.07 (ddd, J=12.8, 10.2, 6.4 Hz, 1H), 2.87 (s, 3H), 2.49 (s, 3H), 2.29 (ddd, J=14.1, 8.3, 7.1 Hz, 11H), 2.24 (dd, J=8.2, 6.3 Hz, 1H), 2.22-2.15 (m, 2H), 1.99-1.88 (m, 3H), 1.73 (p, J=6.2 Hz, 4H), 1.65-1.55 (m, 3H), 1.51 (d, J=7.0 Hz, 2H), 1.42-1.23 (m, 13H), 1.04 (s, 9H).

Example 99: (2S,4R)-1-((S)-21-(tert-butyl)-1-(3,4-difluoro-2-((2-fluoro-4-iodophenyl)amino)phenyl)-8-methyl-1,19-dioxo-3-oxa-2,8,20-triazadocosan-22-oyl)-4-hydroxy-N—((S)-1-(4-(4-methylthiazol-5-yl)phenyl)ethyl)pyrrolidine-2-carboxamide (CPD-096)

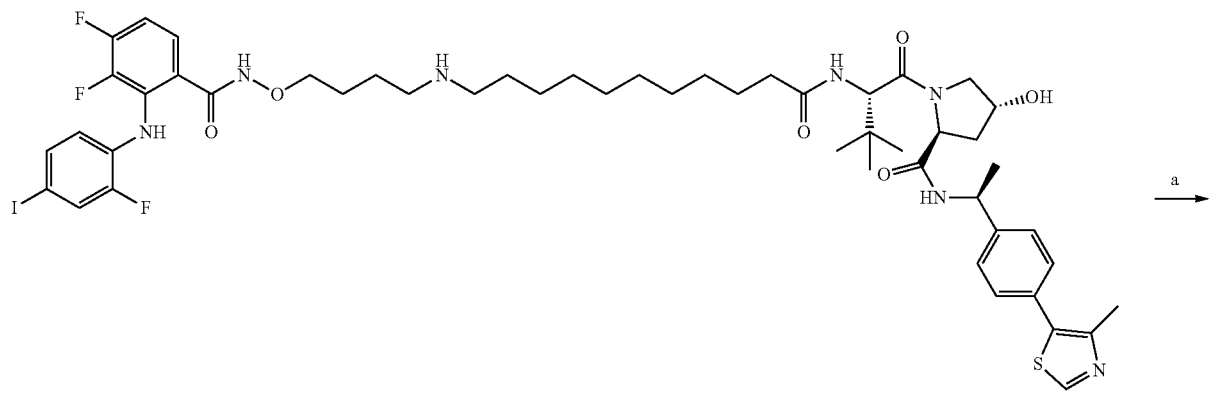

CPD-039

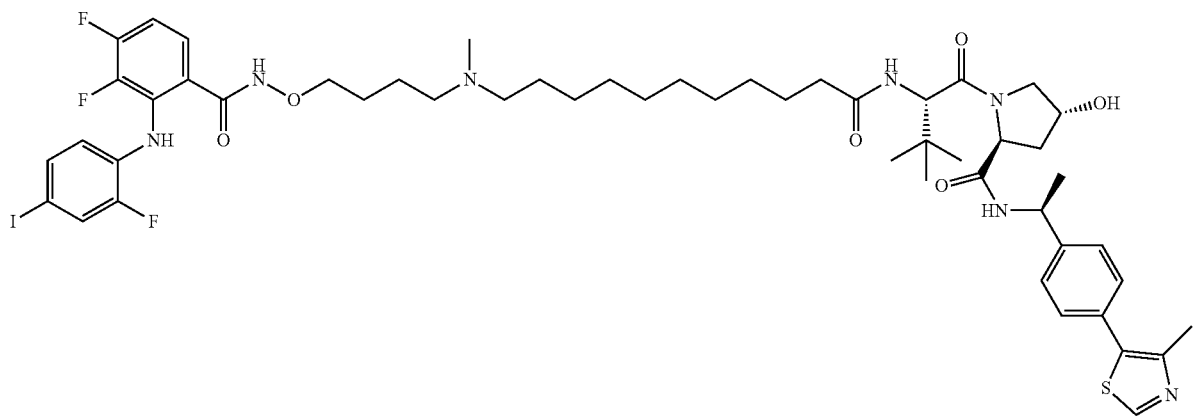

CPD-096

Reagents and conditions: (a) HCHO, NaBH₃CN, DCM, MeOH, rt, overnight.

CPD-096 was synthesized following the same procedures as CPD-037 as described in Example 95. (0.08 g, yield: 40%). $^1$H NMR (600 MHz, Methanol-d$_4$) δ 8.93 (s, 1H), 7.50-7.40 (m, 5H), 7.40-7.34 (m, 2H), 7.06 (td, J=9.3, 7.0 Hz, 1H), 6.61 (td, J=8.7, 4.3 Hz, 1H), 5.00 (q, J=6.9 Hz, 1H), 4.63 (s, 1H), 4.56 (dd, J=9.1, 7.6 Hz, 1H), 4.43 (dp, J=4.2, 1.9 Hz, 1H), 3.92 (d, J=4.8 Hz, 2H), 3.89-3.85 (m, 1H), 3.75 (dd, J=11.0, 4.0 Hz, 1H), 3.38-3.33 (m, 1H), 3.23-3.12 (m, 2H), 3.07 (ddd, J=12.7, 10.2, 6.2 Hz, 11H), 2.87 (s, 3H), 2.48 (s, 3H), 2.29 (ddd, J=14.1, 8.3, 7.1 Hz, 1H), 2.24 (dd, J=8.1, 6.4 Hz, 1H), 2.22-2.15 (m, 2H), 1.95 (ddt, J=13.2, 8.7, 4.4 Hz, 3H), 1.77-1.69 (m, 4H), 1.65-1.56 (m, 2H), 1.51 (d, J=7.0 Hz, 2H), 1.40-1.26 (m, 12H), 1.04 (s, 9H).

Certain compounds disclosed herein have the structures shown in Table 1.

TABLE 1

| CPD | Structure |
|---|---|
| CPD-001 | 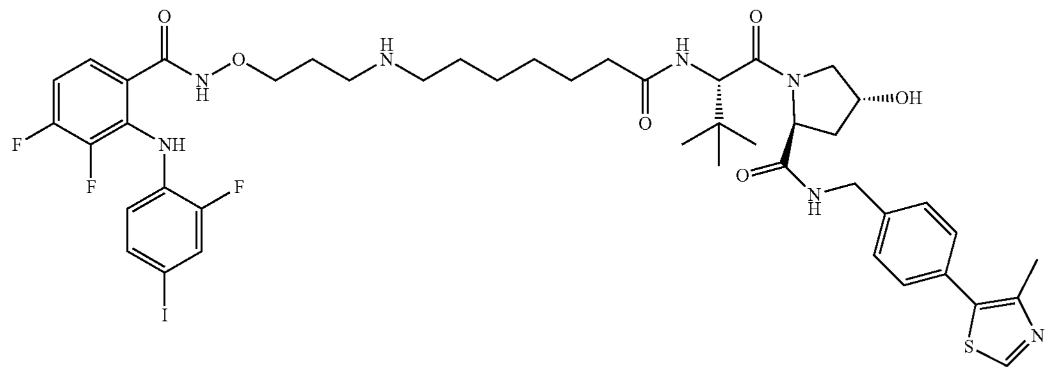 [SMILES: Cc1ncsc1-c1ccc(CNC(=O)[C@@H]2C[C@@H](O)CN2C(=O)[C@@H](NC(=O)CCCCCCNCCCONC(=O)c2ccc(F)c(F)c2Nc2ccc(I)cc2F)C(C)(C)C)cc1] |
| CPD-002 | 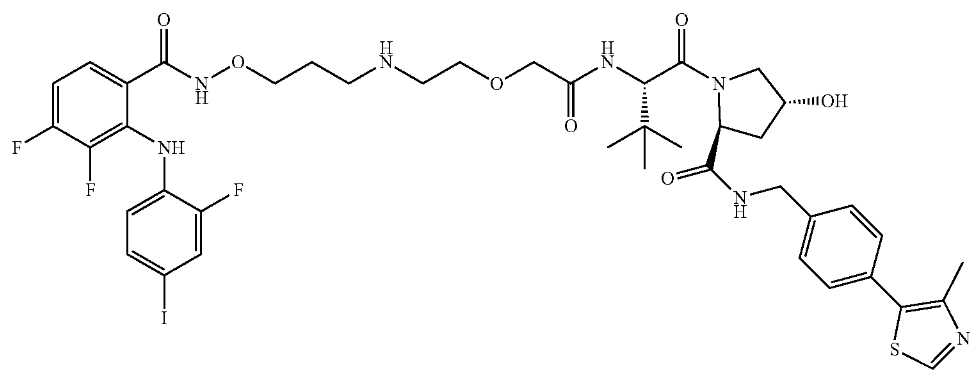 [SMILES: Cc1ncsc1-c1ccc(CNC(=O)[C@@H]2C[C@@H](O)CN2C(=O)[C@@H](NC(=O)COCCNCCCONC(=O)c2ccc(F)c(F)c2Nc2ccc(I)cc2F)C(C)(C)C)cc1] |
| CPD-003 | 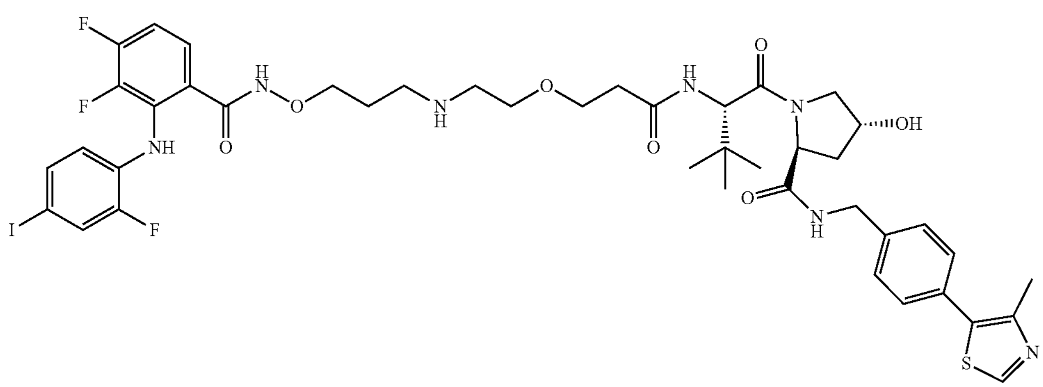 [SMILES: Cc1ncsc1-c1ccc(CNC(=O)[C@@H]2C[C@@H](O)CN2C(=O)[C@@H](NC(=O)CCOCCNCCCONC(=O)c2ccc(F)c(F)c2Nc2ccc(I)cc2F)C(C)(C)C)cc1] |

TABLE 1-continued

| CPD | Structure |
|---|---|
| CPD-004 | 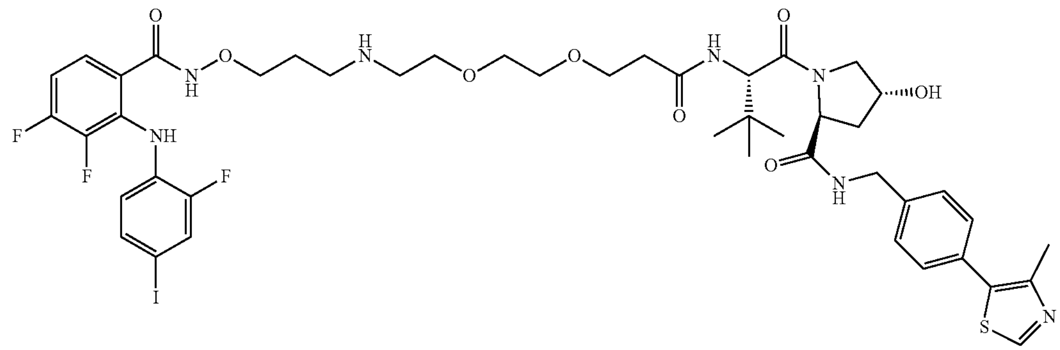 [SMILES: Cc1ncsc1-c1ccc(CNC(=O)[C@@H]2C[C@@H](O)CN2C(=O)[C@@H](NC(=O)CCOCCOCCNCCCONC(=O)c2ccc(F)c(F)c2Nc2ccc(I)cc2F)C(C)(C)C)cc1] |
| CPD-005 | 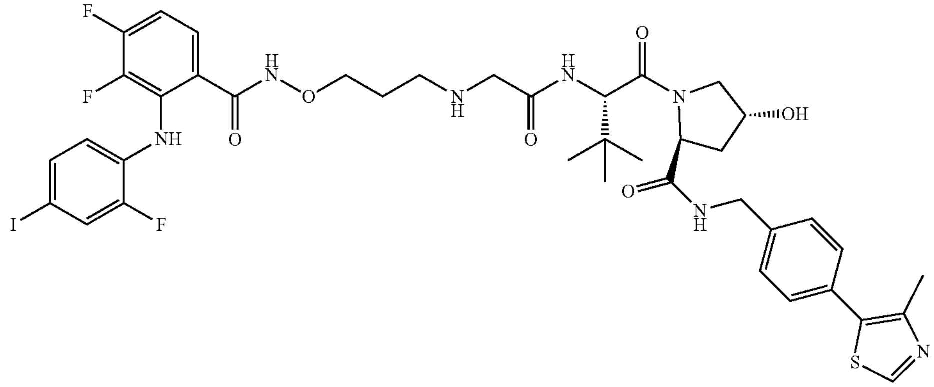 [SMILES: Cc1ncsc1-c1ccc(CNC(=O)[C@@H]2C[C@@H](O)CN2C(=O)[C@@H](NC(=O)CNCCCONC(=O)c2ccc(F)c(F)c2Nc2ccc(I)cc2F)C(C)(C)C)cc1] |
| CPD-006 | 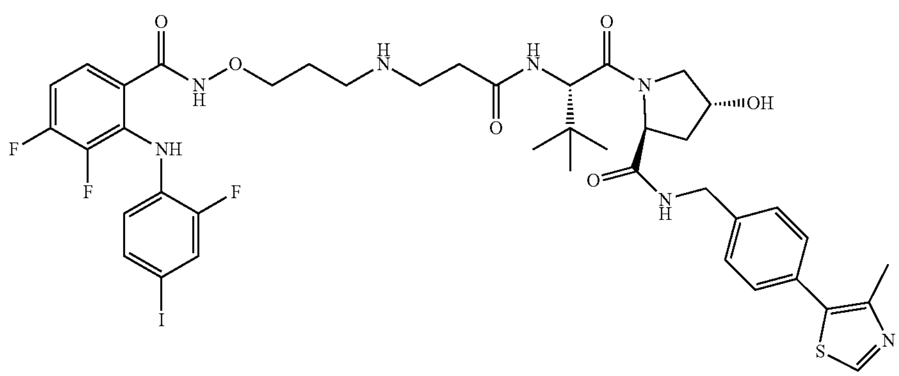 [SMILES: Cc1ncsc1-c1ccc(CNC(=O)[C@@H]2C[C@@H](O)CN2C(=O)[C@@H](NC(=O)CCNCCCONC(=O)c2ccc(F)c(F)c2Nc2ccc(I)cc2F)C(C)(C)C)cc1] |
| CPD-007 | 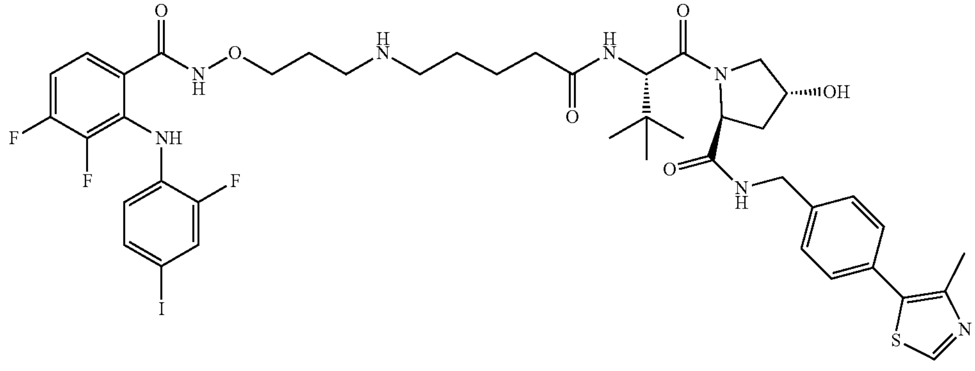 [SMILES: Cc1ncsc1-c1ccc(CNC(=O)[C@@H]2C[C@@H](O)CN2C(=O)[C@@H](NC(=O)CCCCNCCCONC(=O)c2ccc(F)c(F)c2Nc2ccc(I)cc2F)C(C)(C)C)cc1] |

TABLE 1-continued

| CPD | Structure |
|---|---|
| CPD-008 | 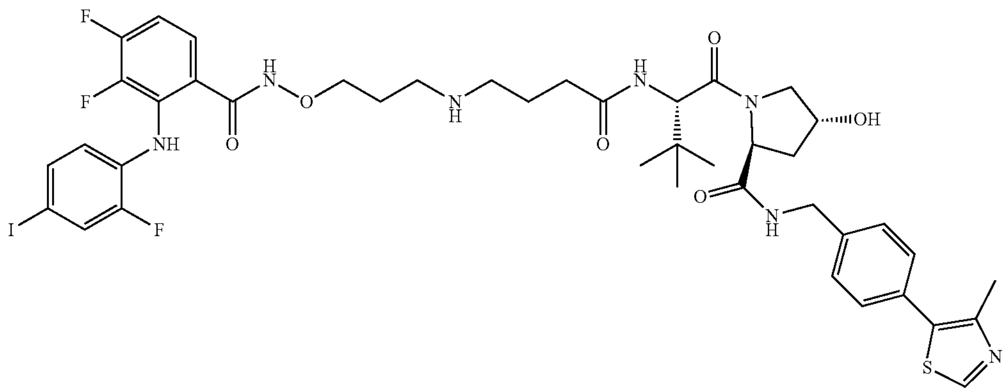 [SMILES: Cc1ncsc1-c1ccc(CNC(=O)[C@@H]2C[C@@H](O)CN2C(=O)[C@@H](NC(=O)CCCNCCCONC(=O)c2ccc(F)c(F)c2Nc2ccc(I)cc2F)C(C)(C)C)cc1] |
| CPD-009 | 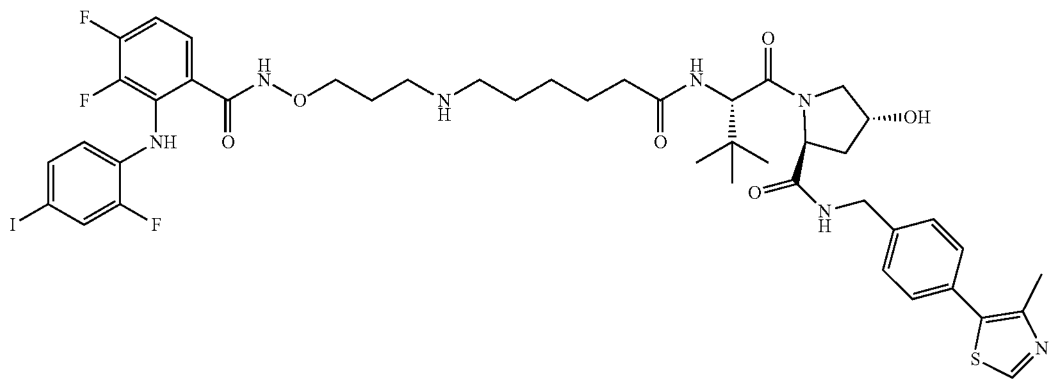 [SMILES: Cc1ncsc1-c1ccc(CNC(=O)[C@@H]2C[C@@H](O)CN2C(=O)[C@@H](NC(=O)CCCCCNCCCONC(=O)c2ccc(F)c(F)c2Nc2ccc(I)cc2F)C(C)(C)C)cc1] |
| CPD-010 | 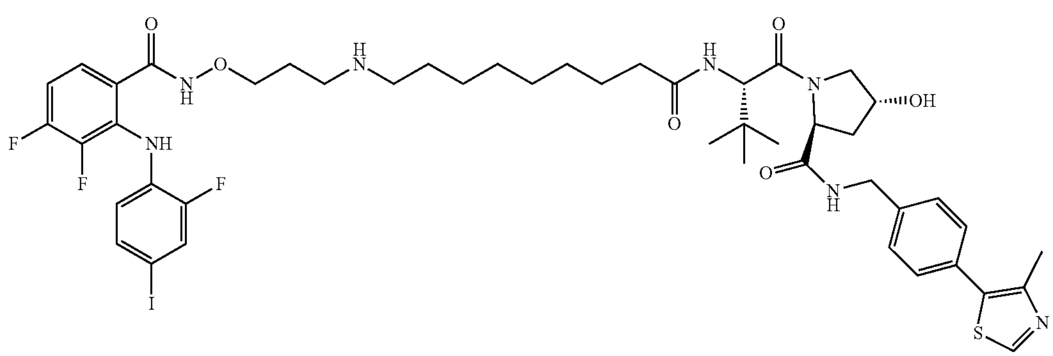 [SMILES: Cc1ncsc1-c1ccc(CNC(=O)[C@@H]2C[C@@H](O)CN2C(=O)[C@@H](NC(=O)CCCCCCCCNCCCONC(=O)c2ccc(F)c(F)c2Nc2ccc(I)cc2F)C(C)(C)C)cc1] |
| CPD-011 | 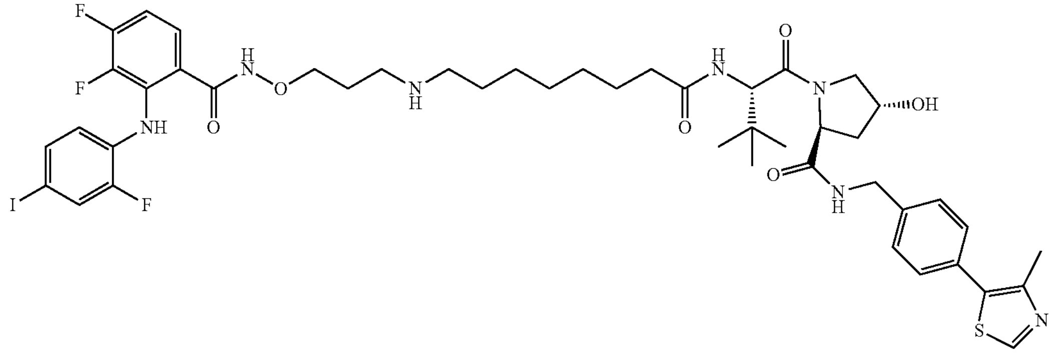 [SMILES: Cc1ncsc1-c1ccc(CNC(=O)[C@@H]2C[C@@H](O)CN2C(=O)[C@@H](NC(=O)CCCCCCCNCCCONC(=O)c2ccc(F)c(F)c2Nc2ccc(I)cc2F)C(C)(C)C)cc1] |

TABLE 1-continued
| CPD | Structure |
|---|---|
| CPD-012 | 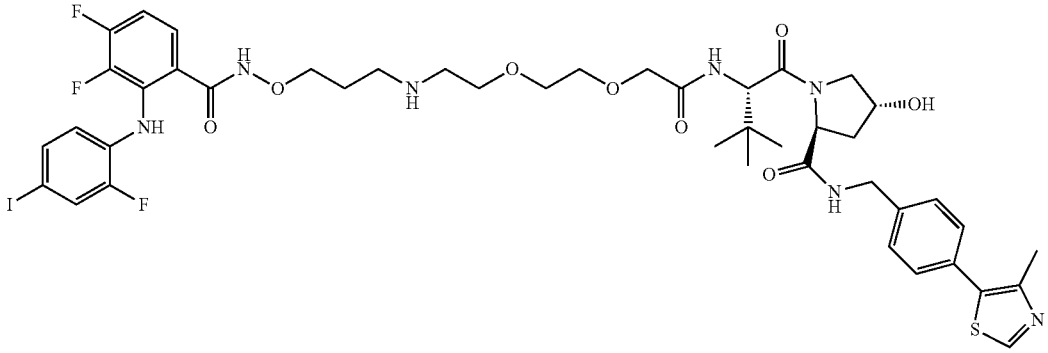 [SMILES: Cc1ncsc1-c1ccc(CNC(=O)[C@@H]2C[C@@H](O)CN2C(=O)[C@@H](NC(=O)COCCOCCNCCCONC(=O)c2ccc(F)c(F)c2Nc2ccc(I)cc2F)C(C)(C)C)cc1] |
| CPD-013 | 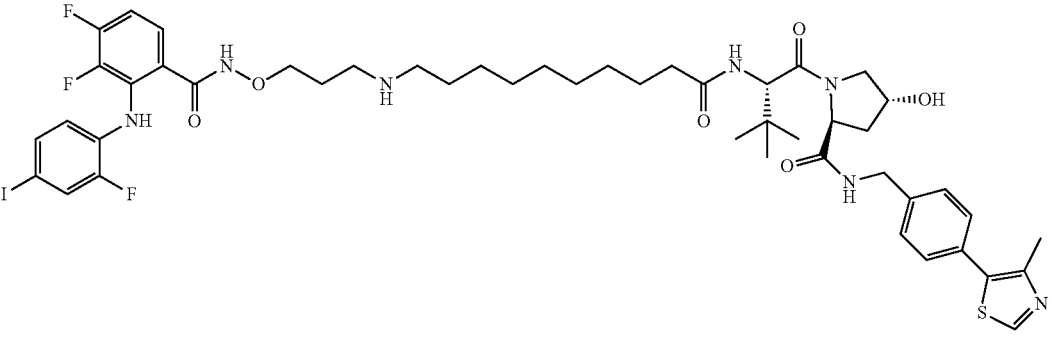 [SMILES: Cc1ncsc1-c1ccc(CNC(=O)[C@@H]2C[C@@H](O)CN2C(=O)[C@@H](NC(=O)CCCCCCCCCNCCCONC(=O)c2ccc(F)c(F)c2Nc2ccc(I)cc2F)C(C)(C)C)cc1] |
| CPD-014 | 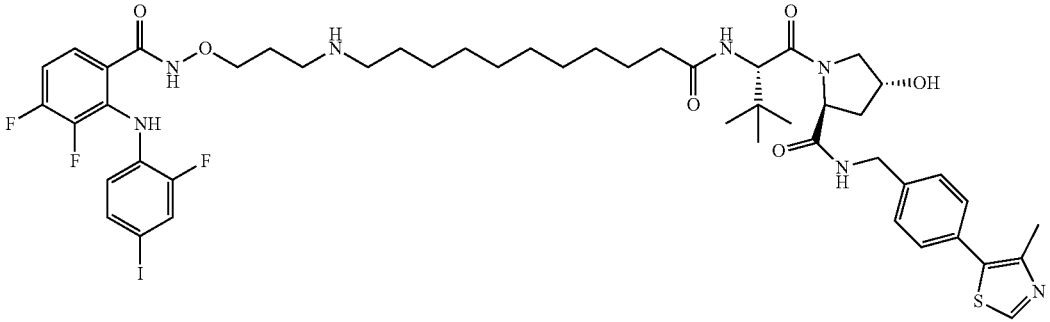 [SMILES: Cc1ncsc1-c1ccc(CNC(=O)[C@@H]2C[C@@H](O)CN2C(=O)[C@@H](NC(=O)CCCCCCCCCCNCCCONC(=O)c2ccc(F)c(F)c2Nc2ccc(I)cc2F)C(C)(C)C)cc1] |
| CPD-015 | 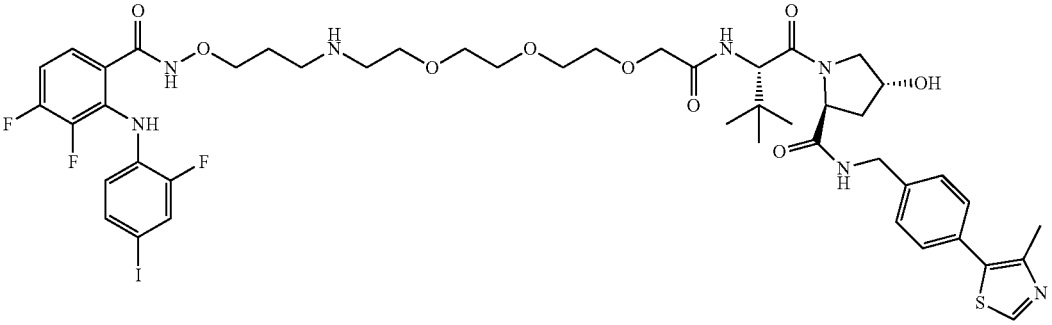 [SMILES: Cc1ncsc1-c1ccc(CNC(=O)[C@@H]2C[C@@H](O)CN2C(=O)[C@@H](NC(=O)COCCOCCOCCNCCCONC(=O)c2ccc(F)c(F)c2Nc2ccc(I)cc2F)C(C)(C)C)cc1] |

TABLE 1-continued

| CPD | Structure |
|---|---|
| CPD-016 | 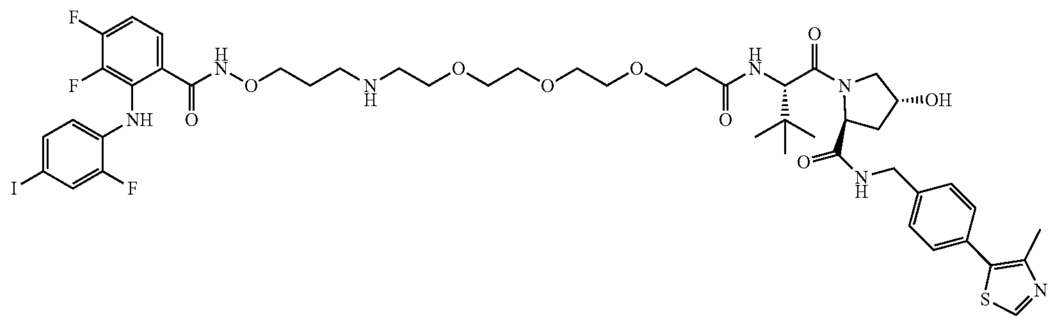 [SMILES: Cc1ncsc1-c1ccc(CNC(=O)[C@@H]2C[C@@H](O)CN2C(=O)[C@@H](NC(=O)CCOCCOCCOCCNCCCONC(=O)c2ccc(F)c(F)c2Nc2ccc(I)cc2F)C(C)(C)C)cc1] |
| CPD-017 | 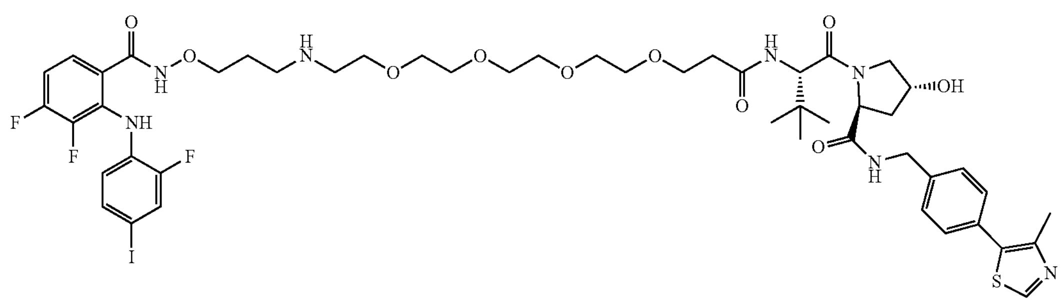 [SMILES: Cc1ncsc1-c1ccc(CNC(=O)[C@@H]2C[C@@H](O)CN2C(=O)[C@@H](NC(=O)CCOCCOCCOCCOCCNCCCONC(=O)c2ccc(F)c(F)c2Nc2ccc(I)cc2F)C(C)(C)C)cc1] |
| CPD-018 | 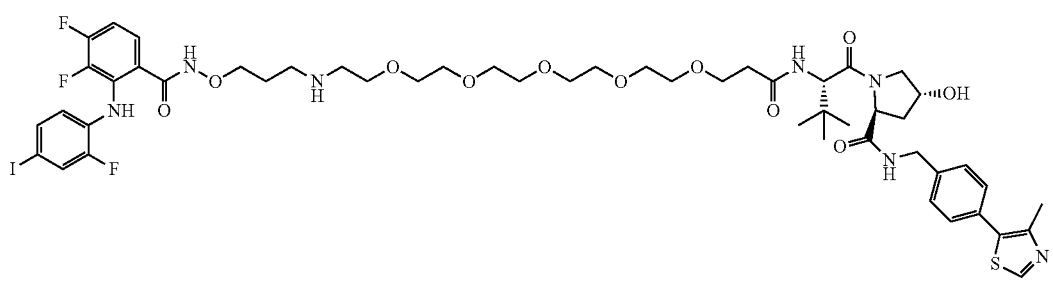 [SMILES: Cc1ncsc1-c1ccc(CNC(=O)[C@@H]2C[C@@H](O)CN2C(=O)[C@@H](NC(=O)CCOCCOCCOCCOCCOCCNCCCONC(=O)c2ccc(F)c(F)c2Nc2ccc(I)cc2F)C(C)(C)C)cc1] |
| CPD-019 | 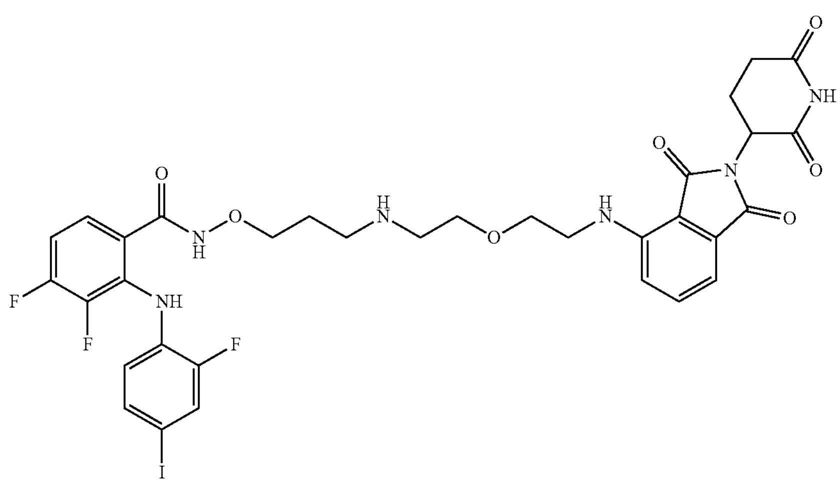 [SMILES: O=C1CCC(N2C(=O)c3cccc(NCCOCCNCCCONC(=O)c4ccc(F)c(F)c4Nc4ccc(I)cc4F)c3C2=O)C(=O)N1] |

TABLE 1-continued

| CPD | Structure |
|---|---|
| CPD-020 | 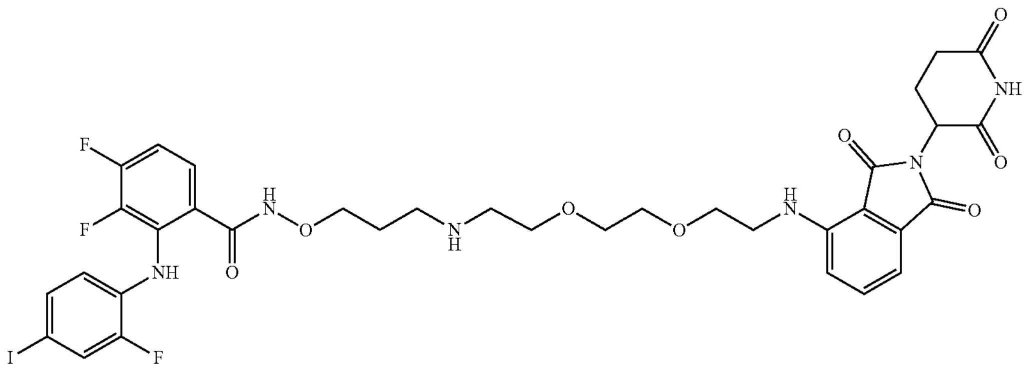 [SMILES: O=C1CCC(N2C(=O)c3cccc(NCCOCCOCCNCCCONC(=O)c4ccc(F)c(F)c4Nc4ccc(I)cc4F)c3C2=O)C(=O)N1] |
| CPD-021 | 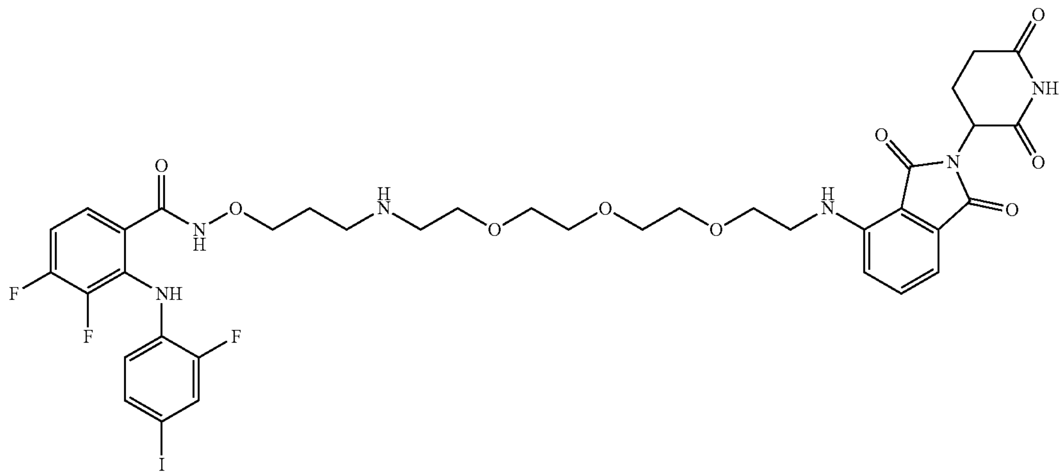 [SMILES: O=C1CCC(N2C(=O)c3cccc(NCCOCCOCCOCCNCCCONC(=O)c4ccc(F)c(F)c4Nc4ccc(I)cc4F)c3C2=O)C(=O)N1] |
| CPD-022 | 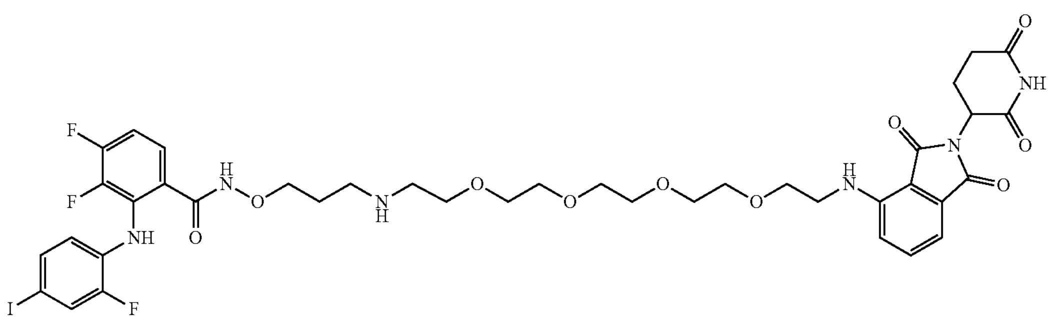 [SMILES: O=C1CCC(N2C(=O)c3cccc(NCCOCCOCCOCCOCCNCCCONC(=O)c4ccc(F)c(F)c4Nc4ccc(I)cc4F)c3C2=O)C(=O)N1] |
| CPD-023 | 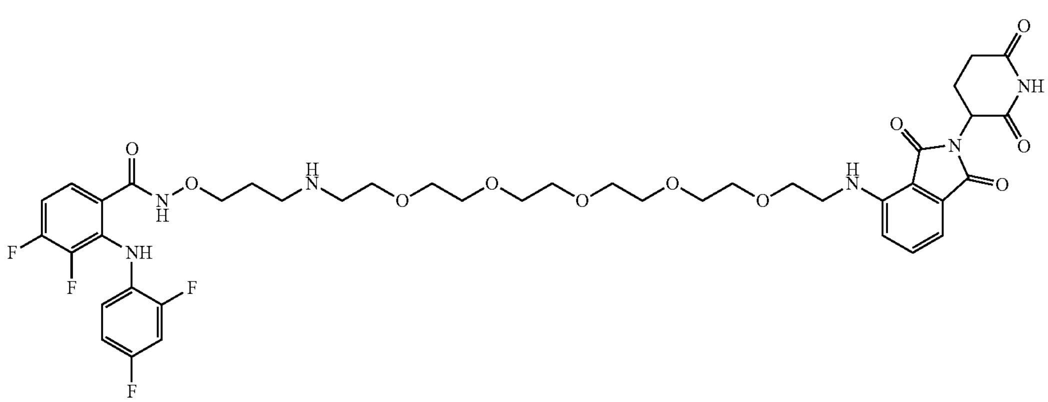 [SMILES: O=C1CCC(N2C(=O)c3cccc(NCCOCCOCCOCCOCCOCCNCCCONC(=O)c4ccc(F)c(F)c4Nc4ccc(F)cc4F)c3C2=O)C(=O)N1] |

TABLE 1-continued
| CPD | Structure |
|---|---|
| CPD-024 | 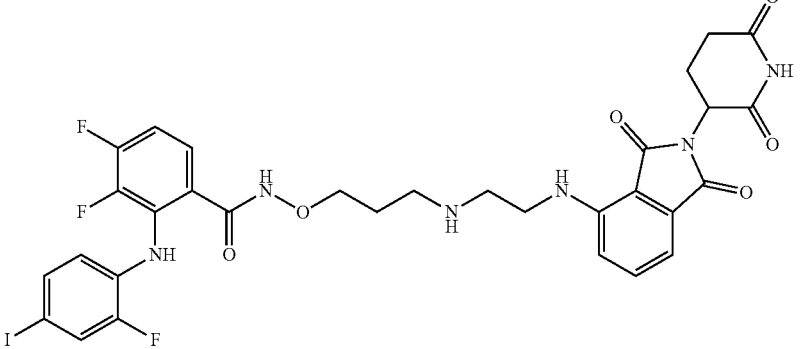 |
| CPD-025 | 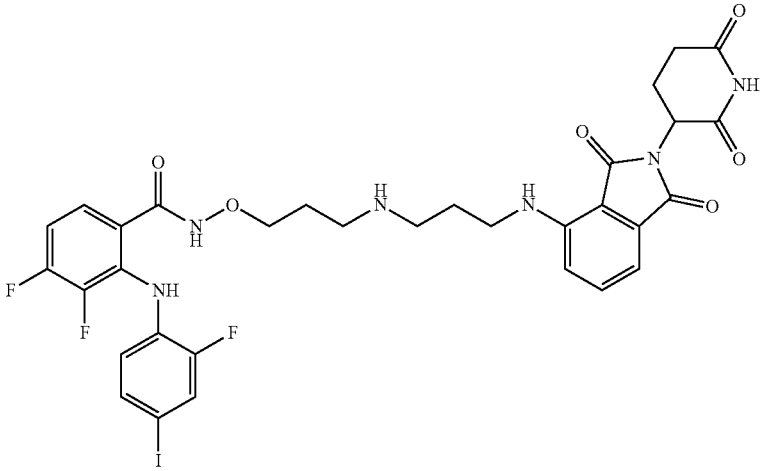 [SMILES: O=C1CCC(N2C(=O)c3cccc(NCCCNCCCONC(=O)c4ccc(F)c(F)c4Nc4ccc(I)cc4F)c3C2=O)C(=O)N1] |
| CPD-026 | 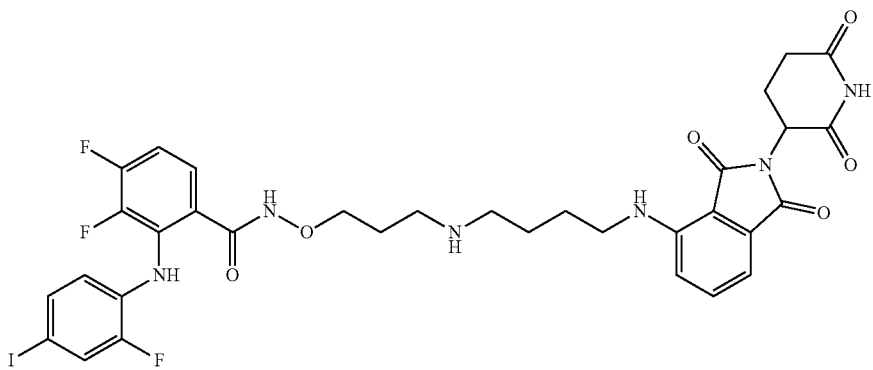 [SMILES: O=C1CCC(N2C(=O)c3cccc(NCCCCNCCCONC(=O)c4ccc(F)c(F)c4Nc4ccc(I)cc4F)c3C2=O)C(=O)N1] |

TABLE 1-continued
| CPD | Structure |
|---|---|
| CPD-027 | 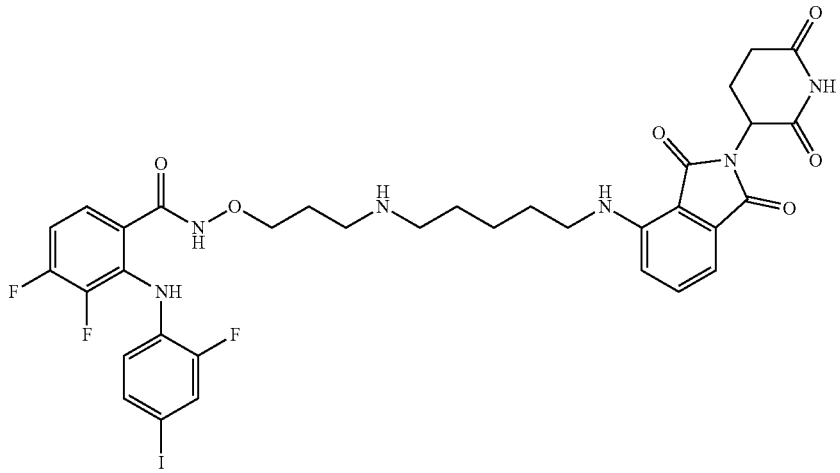 [SMILES: O=C1CCC(N2C(=O)c3cccc(NCCCCCNCCCONC(=O)c4ccc(F)c(F)c4Nc4ccc(I)cc4F)c3C2=O)C(=O)N1] |
| CPD-028 | 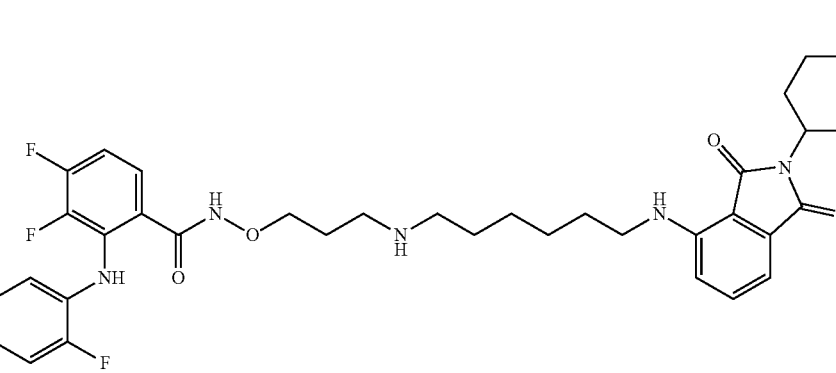 |
| CPD-029 | 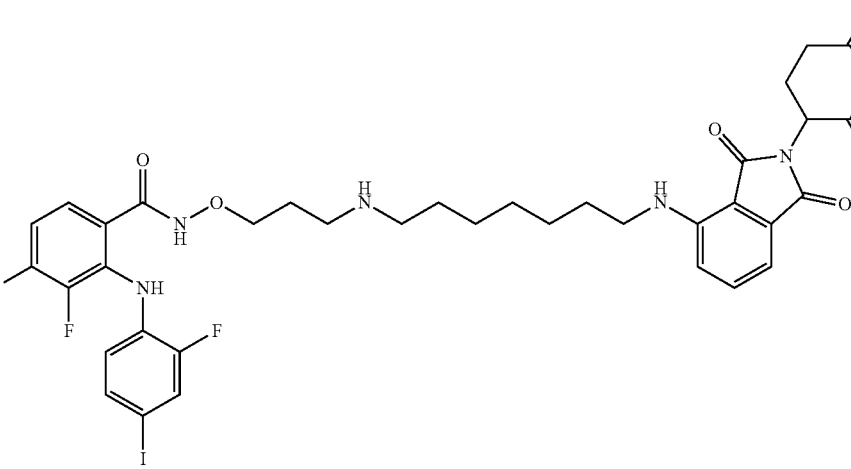 |

TABLE 1-continued
| CPD | Structure |
|---|---|
| CPD-030 | 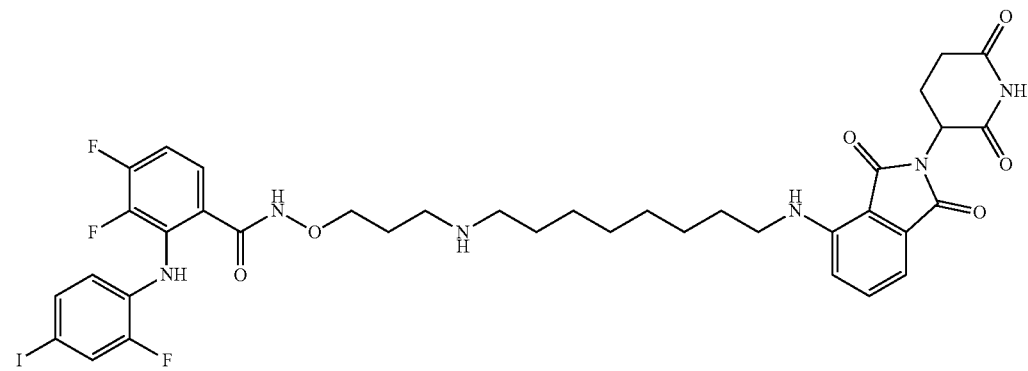 [SMILES: O=C1CCC(N2C(=O)c3cccc(NCCCCCCCCNCCCONC(=O)c4ccc(F)c(F)c4Nc4ccc(I)cc4F)c3C2=O)C(=O)N1] |
| CPD-031 | 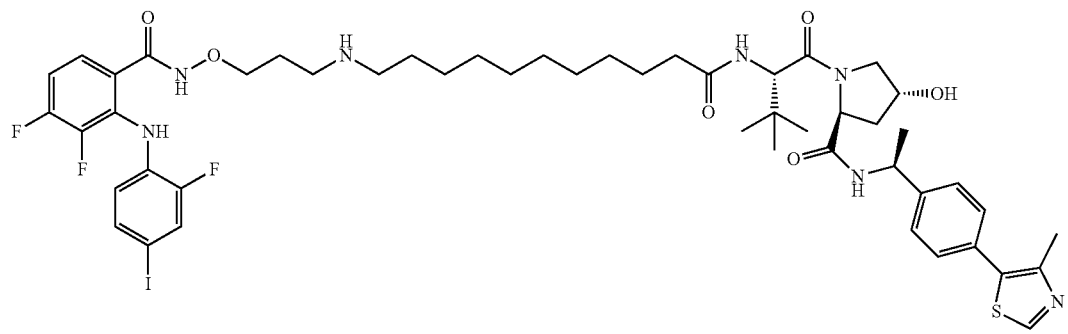 [SMILES: Cc1ncsc1-c1ccc([C@H](C)NC(=O)[C@@H]2C[C@@H](O)CN2C(=O)[C@@H](NC(=O)CCCCCCCCCCNCCCONC(=O)c2ccc(F)c(F)c2Nc2ccc(I)cc2F)C(C)(C)C)cc1] |
| CPD-032 | 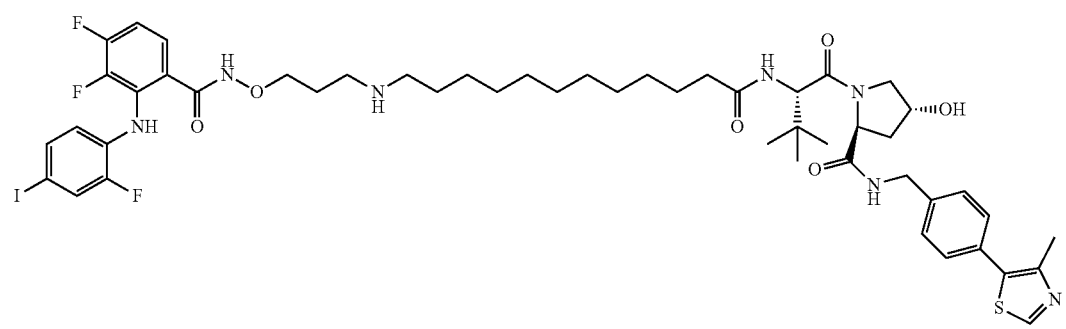 [SMILES: Cc1ncsc1-c1ccc(CNC(=O)[C@@H]2C[C@@H](O)CN2C(=O)[C@@H](NC(=O)CCCCCCCCCCCNCCCONC(=O)c2ccc(F)c(F)c2Nc2ccc(I)cc2F)C(C)(C)C)cc1] |
| CPD-033 | 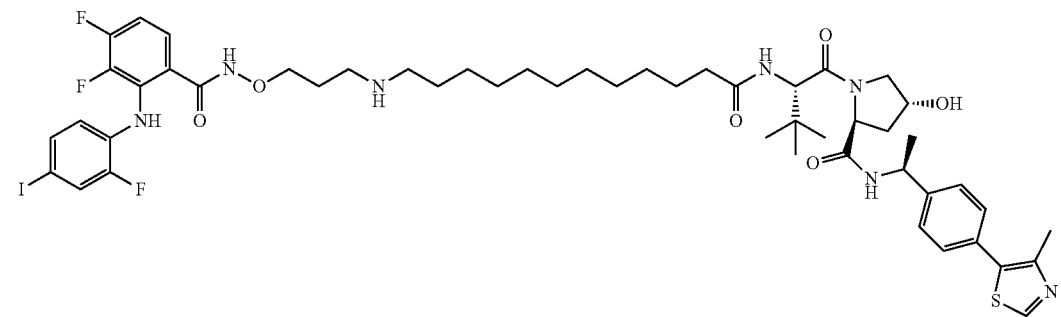 [SMILES: Cc1ncsc1-c1ccc([C@H](C)NC(=O)[C@@H]2C[C@@H](O)CN2C(=O)[C@@H](NC(=O)CCCCCCCCCCCNCCCONC(=O)c2ccc(F)c(F)c2Nc2ccc(I)cc2F)C(C)(C)C)cc1] |

TABLE 1-continued
| CPD | Structure |
|---|---|
| CPD-034 | 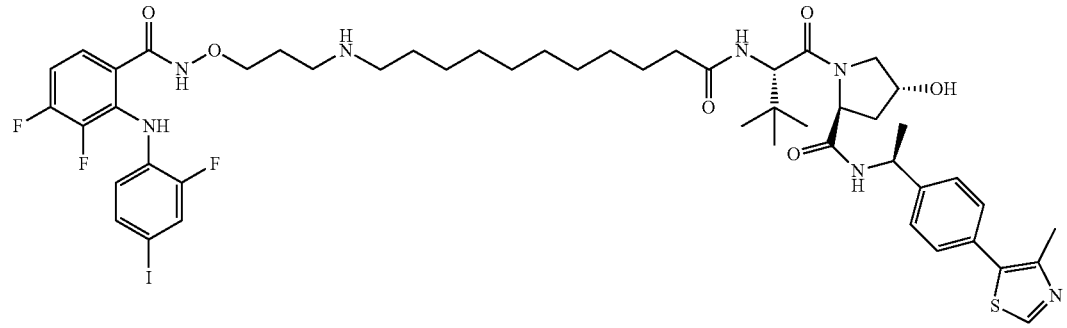 [SMILES: Cc1ncsc1-c1ccc([C@H](C)NC(=O)[C@@H]2C[C@@H](O)CN2C(=O)[C@@H](NC(=O)CCCCCCCCCCNCCCONC(=O)c2ccc(F)c(F)c2Nc2ccc(I)cc2F)C(C)(C)C)cc1] |
| CPD-035 | 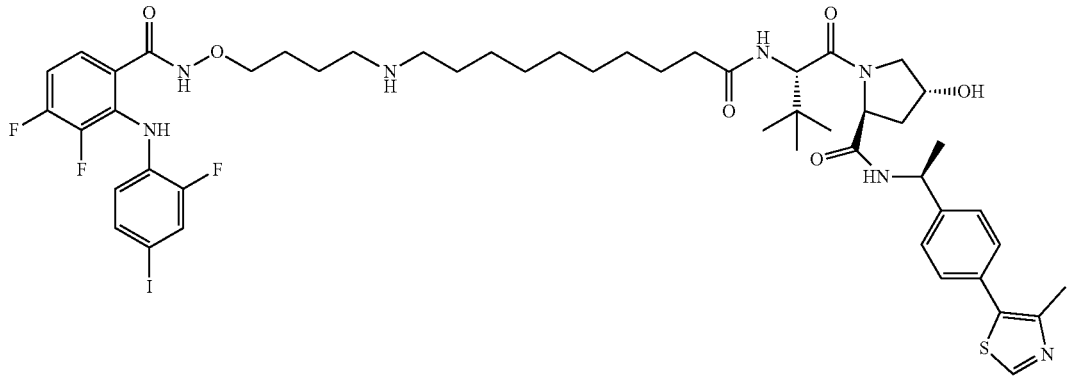 [SMILES: Cc1ncsc1-c1ccc([C@H](C)NC(=O)[C@@H]2C[C@@H](O)CN2C(=O)[C@@H](NC(=O)CCCCCCCCCNCCCCONC(=O)c2ccc(F)c(F)c2Nc2ccc(I)cc2F)C(C)(C)C)cc1] |
| CPD-036 | 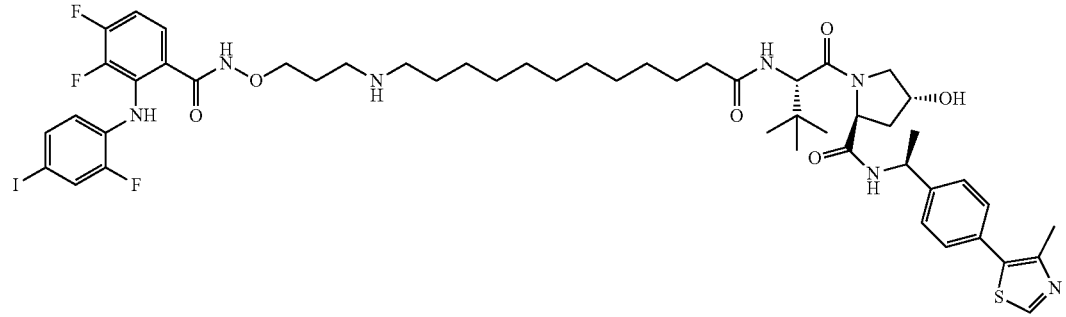 [SMILES: Cc1ncsc1-c1ccc([C@H](C)NC(=O)[C@@H]2C[C@@H](O)CN2C(=O)[C@@H](NC(=O)CCCCCCCCCCCNCCCONC(=O)c2ccc(F)c(F)c2Nc2ccc(I)cc2F)C(C)(C)C)cc1] |
| CPD-037 | 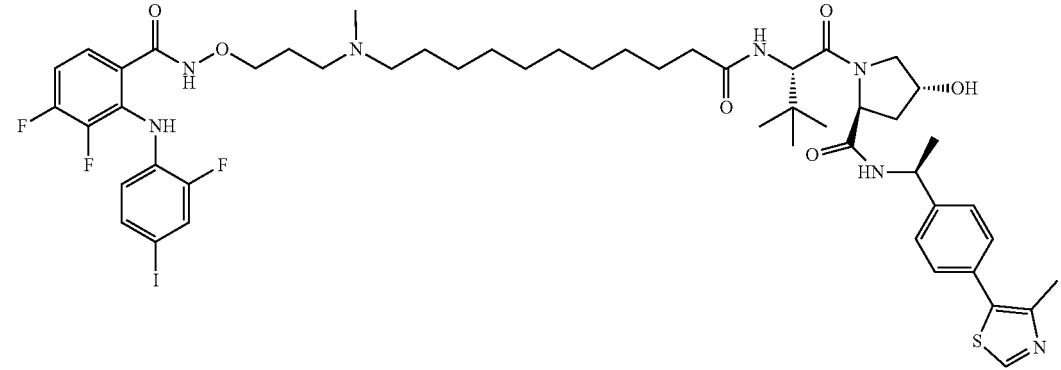 [SMILES: Cc1ncsc1-c1ccc([C@H](C)NC(=O)[C@@H]2C[C@@H](O)CN2C(=O)[C@@H](NC(=O)CCCCCCCCCCN(C)CCCONC(=O)c2ccc(F)c(F)c2Nc2ccc(I)cc2F)C(C)(C)C)cc1] |

TABLE 1-continued

| CPD | Structure |
|---|---|
| CPD-038 | 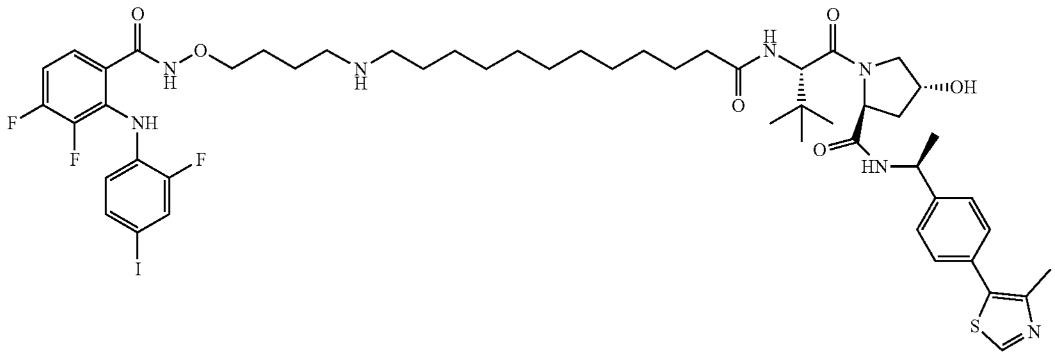 [SMILES: Cc1ncsc1-c1ccc([C@H](C)NC(=O)[C@@H]2C[C@@H](O)CN2C(=O)[C@@H](NC(=O)CCCCCCCCCCCNCCCCONC(=O)c2ccc(F)c(F)c2Nc2ccc(I)cc2F)C(C)(C)C)cc1] |
| CPD-039 | 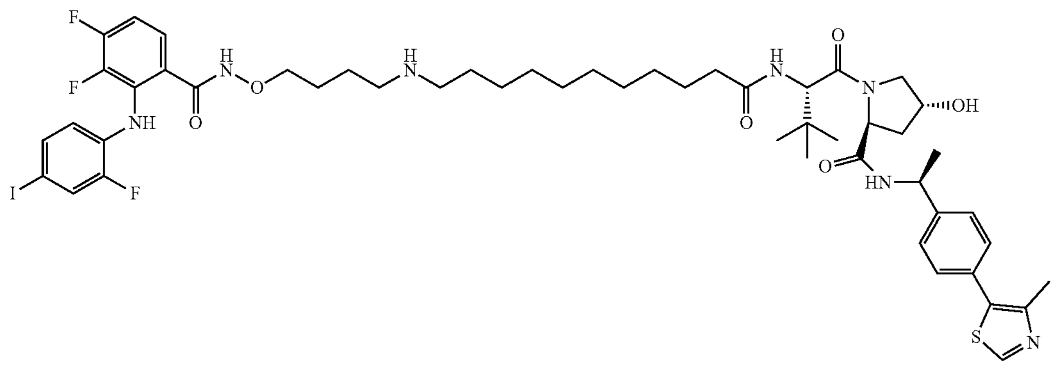 [SMILES: Cc1ncsc1-c1ccc([C@H](C)NC(=O)[C@@H]2C[C@@H](O)CN2C(=O)[C@@H](NC(=O)CCCCCCCCCCNCCCCONC(=O)c2ccc(F)c(F)c2Nc2ccc(I)cc2F)C(C)(C)C)cc1] |
| CPD-040 | 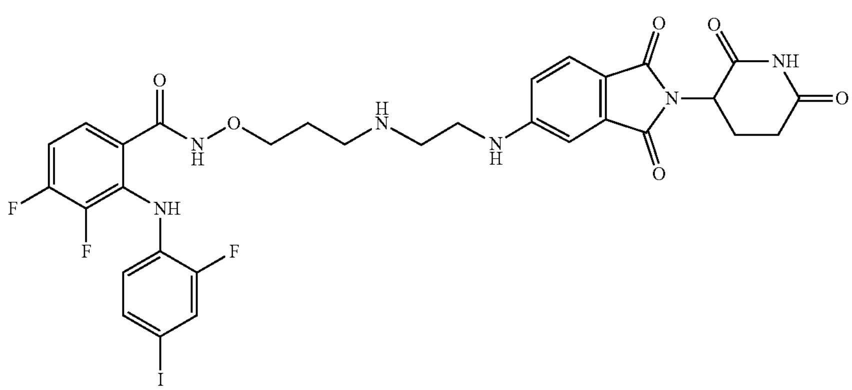 [SMILES: O=C1CCC(N2C(=O)c3ccc(NCCNCCCONC(=O)c4ccc(F)c(F)c4Nc4ccc(I)cc4F)cc3C2=O)C(=O)N1] |
| CPD-041 | 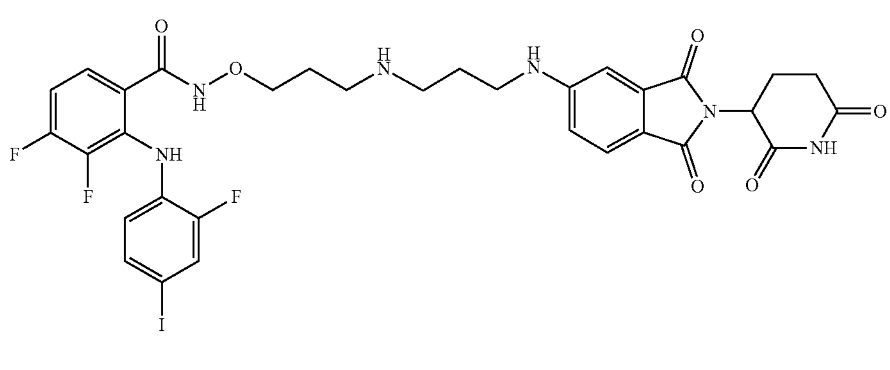 [SMILES: O=C1CCC(N2C(=O)c3ccc(NCCCNCCCONC(=O)c4ccc(F)c(F)c4Nc4ccc(I)cc4F)cc3C2=O)C(=O)N1] |

TABLE 1-continued

| CPD | Structure |
|---|---|
| CPD-042 | 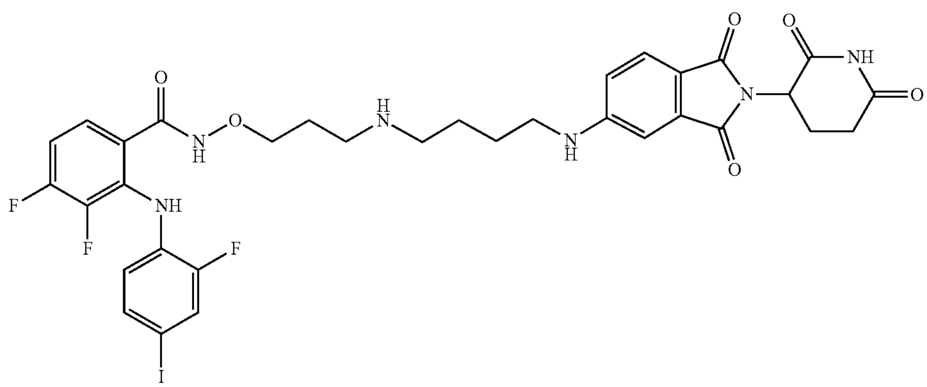 [SMILES: O=C1CCC(N2C(=O)c3ccc(NCCCCNCCCONC(=O)c4ccc(F)c(F)c4Nc4ccc(I)cc4F)cc3C2=O)C(=O)N1] |
| CPD-043 | 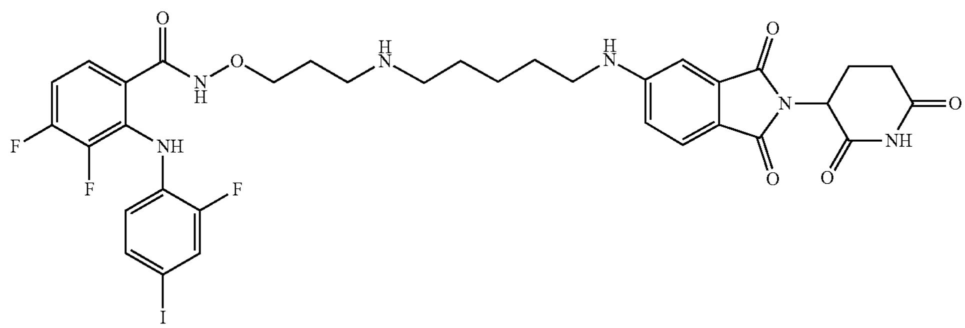 [SMILES: O=C1CCC(N2C(=O)c3ccc(NCCCCCNCCCONC(=O)c4ccc(F)c(F)c4Nc4ccc(I)cc4F)cc3C2=O)C(=O)N1] |
| CPD-044 | 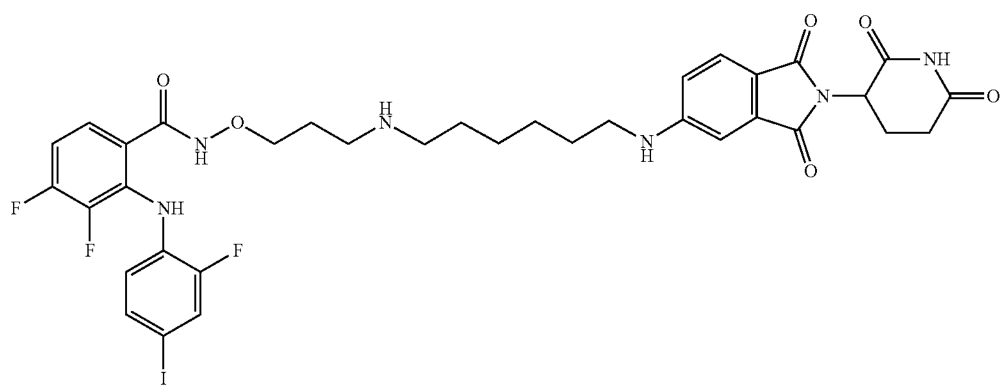 [SMILES: O=C1CCC(N2C(=O)c3ccc(NCCCCCCNCCCONC(=O)c4ccc(F)c(F)c4Nc4ccc(I)cc4F)cc3C2=O)C(=O)N1] |
| CPD-045 | 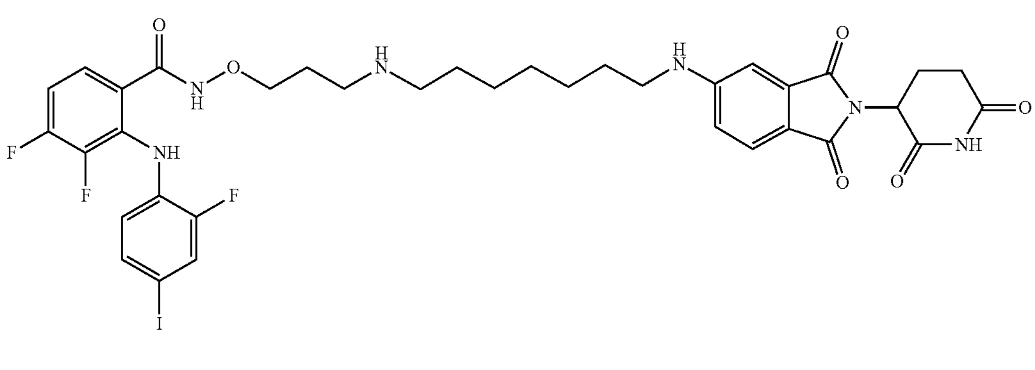 [SMILES: O=C1CCC(N2C(=O)c3ccc(NCCCCCCCNCCCONC(=O)c4ccc(F)c(F)c4Nc4ccc(I)cc4F)cc3C2=O)C(=O)N1] |

TABLE 1-continued

| CPD | Structure |
|---|---|
| CPD-046 | (structure) |
| CPD-047 | (structure) |
| CPD-048 | (structure) |
| CPD-049 | (structure) |

TABLE 1-continued

| CPD | Structure |
|---|---|
| CPD-050 | 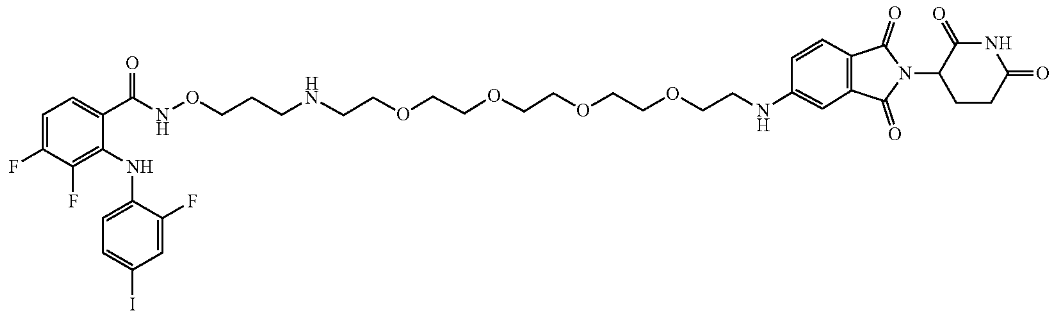 [SMILES: O=C1CCC(N2C(=O)c3ccc(NCCOCCOCCOCCOCCNCCCONC(=O)c4ccc(F)c(F)c4Nc4ccc(I)cc4F)cc3C2=O)C(=O)N1] |
| CPD-051 | 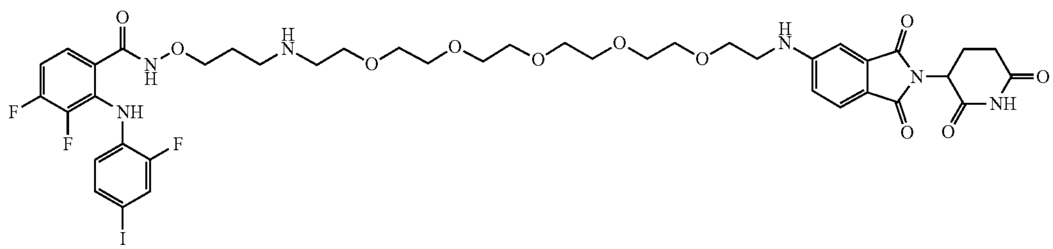 [SMILES: O=C1CCC(N2C(=O)c3ccc(NCCOCCOCCOCCOCCOCCNCCCONC(=O)c4ccc(F)c(F)c4Nc4ccc(I)cc4F)cc3C2=O)C(=O)N1] |
| CPD-052 | 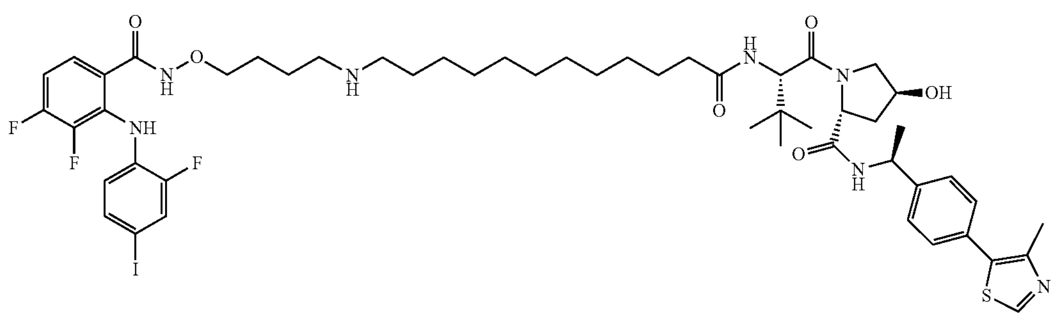 [SMILES: Cc1ncsc1-c1ccc([C@H](C)NC(=O)[C@H]2C[C@H](O)CN2C(=O)[C@@H](NC(=O)CCCCCCCCCCCNCCCCONC(=O)c2ccc(F)c(F)c2Nc2ccc(I)cc2F)C(C)(C)C)cc1] |
| CPD-053 | 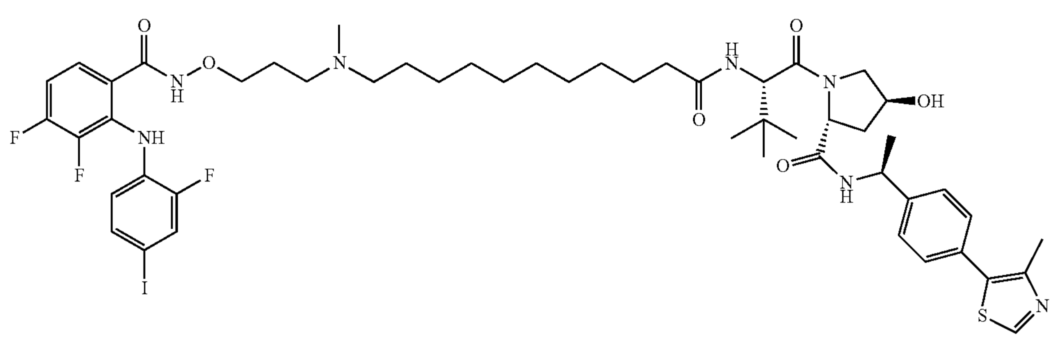 [SMILES: Cc1ncsc1-c1ccc([C@H](C)NC(=O)[C@H]2C[C@H](O)CN2C(=O)[C@@H](NC(=O)CCCCCCCCCCN(C)CCCONC(=O)c2ccc(F)c(F)c2Nc2ccc(I)cc2F)C(C)(C)C)cc1] |

TABLE 1-continued

| CPD | Structure |
|---|---|
| CPD-054 | 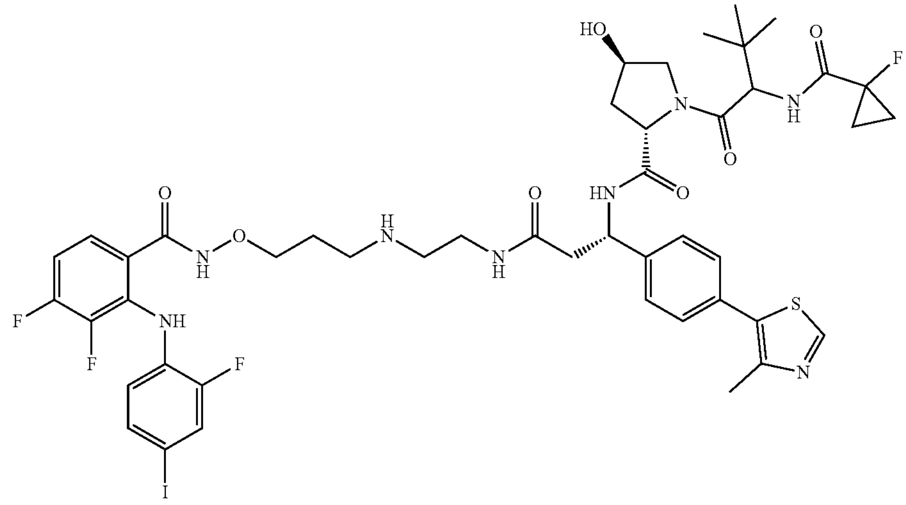 [SMILES: Cc1ncsc1-c1ccc([C@H](CC(=O)NCCNCCCONC(=O)c2ccc(F)c(F)c2Nc2ccc(I)cc2F)NC(=O)[C@@H]2C[C@@H](O)CN2C(=O)C(NC(=O)C2(F)CC2)C(C)(C)C)cc1] |
| CPD-055 | 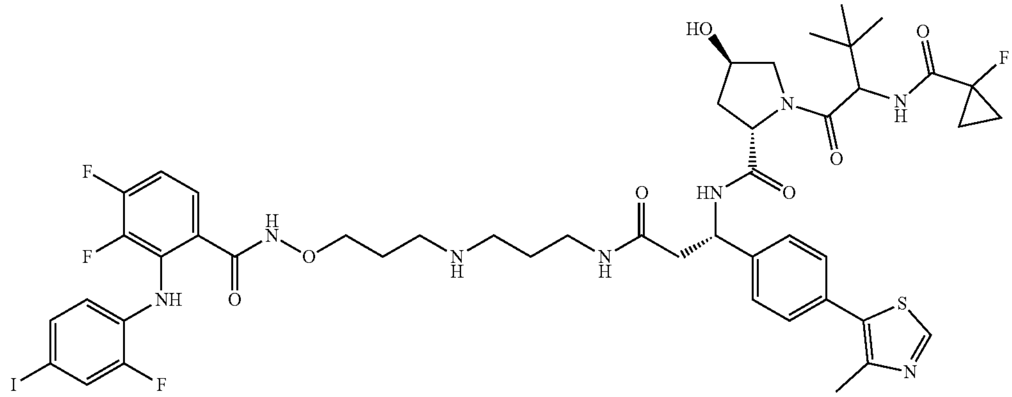 [SMILES: Cc1ncsc1-c1ccc([C@H](CC(=O)NCCCNCCCONC(=O)c2ccc(F)c(F)c2Nc2ccc(I)cc2F)NC(=O)[C@@H]2C[C@@H](O)CN2C(=O)C(NC(=O)C2(F)CC2)C(C)(C)C)cc1] |
| CPD-056 | 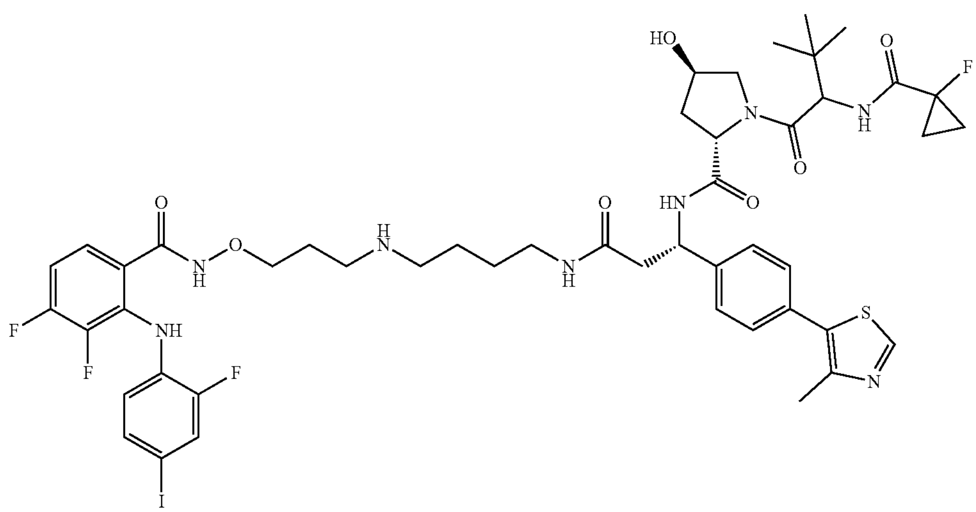 [SMILES: Cc1ncsc1-c1ccc([C@H](CC(=O)NCCCCNCCCONC(=O)c2ccc(F)c(F)c2Nc2ccc(I)cc2F)NC(=O)[C@@H]2C[C@@H](O)CN2C(=O)C(NC(=O)C2(F)CC2)C(C)(C)C)cc1] |

TABLE 1-continued
| CPD | Structure |
|---|---|
| CPD-057 | 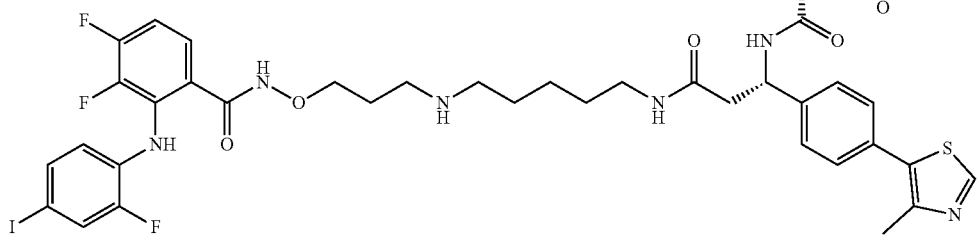 |
| CPD-058 | 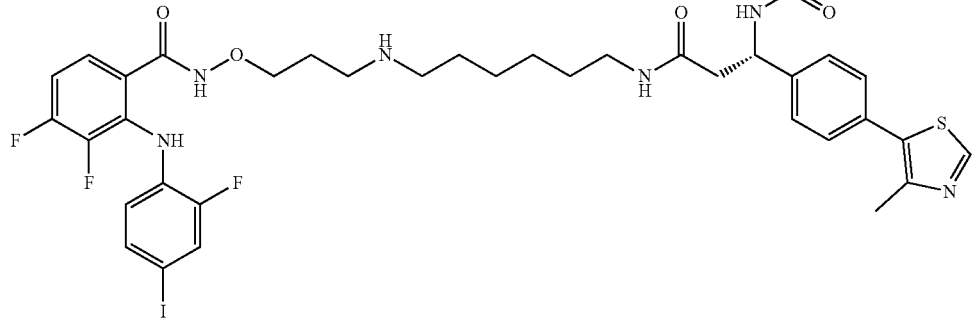 |
| CPD-059 | 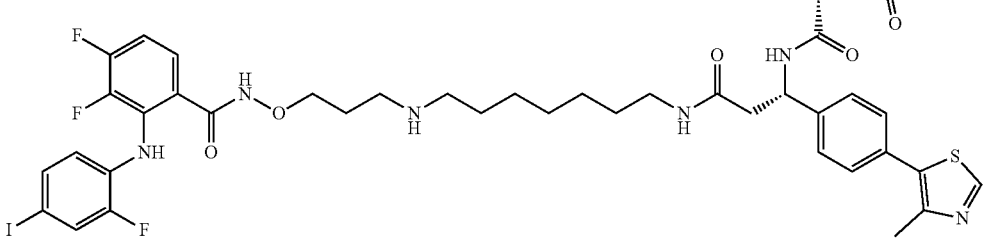 |

TABLE 1-continued

| CPD | Structure |
|---|---|
| CPD-060 | 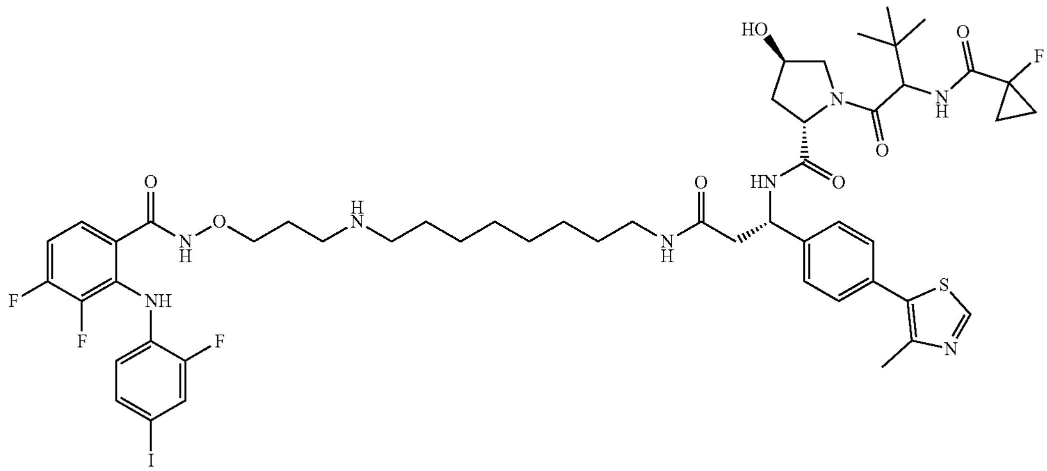 [SMILES: Cc1ncsc1-c1ccc([C@H](CC(=O)NCCCCCCCCNCCCONC(=O)c2ccc(F)c(F)c2Nc2ccc(I)cc2F)NC(=O)[C@@H]2C[C@@H](O)CN2C(=O)C(NC(=O)C2(F)CC2)C(C)(C)C)cc1] |
| CPD-061 | 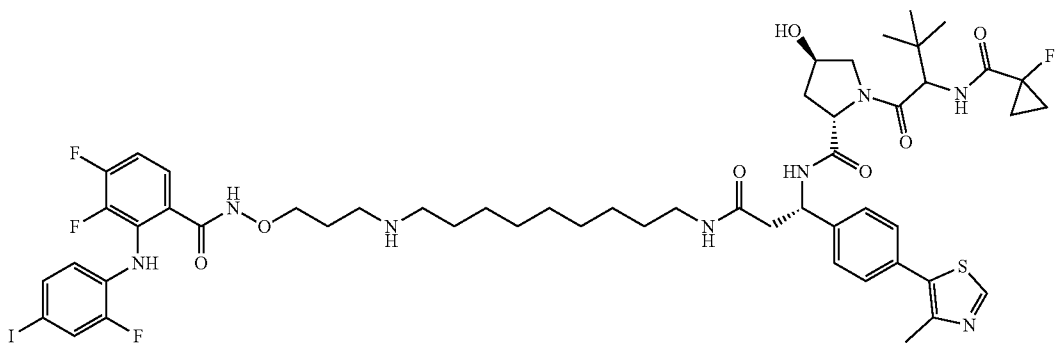 [SMILES: Cc1ncsc1-c1ccc([C@H](CC(=O)NCCCCCCCCCNCCCONC(=O)c2ccc(F)c(F)c2Nc2ccc(I)cc2F)NC(=O)[C@@H]2C[C@@H](O)CN2C(=O)C(NC(=O)C2(F)CC2)C(C)(C)C)cc1] |
| CPD-062 | 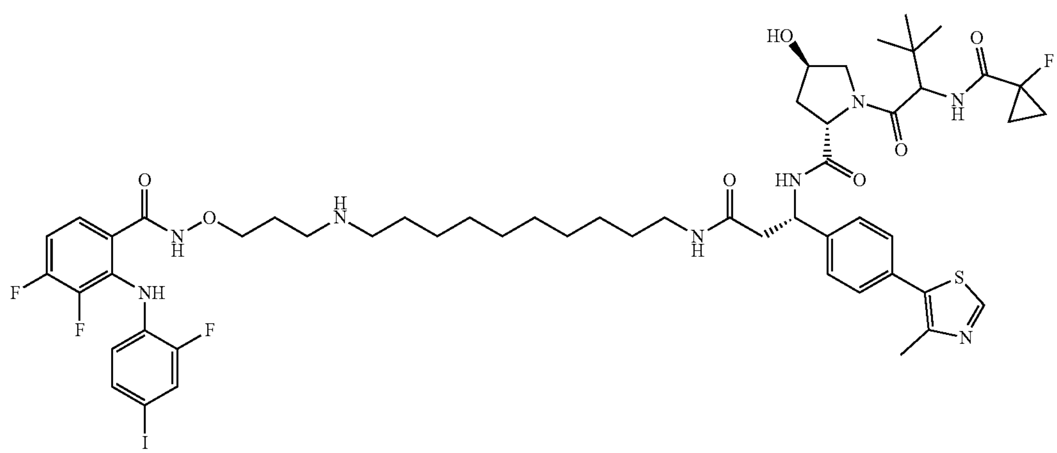 [SMILES: Cc1ncsc1-c1ccc([C@H](CC(=O)NCCCCCCCCCCNCCCONC(=O)c2ccc(F)c(F)c2Nc2ccc(I)cc2F)NC(=O)[C@@H]2C[C@@H](O)CN2C(=O)C(NC(=O)C2(F)CC2)C(C)(C)C)cc1] |
| CPD-063 | 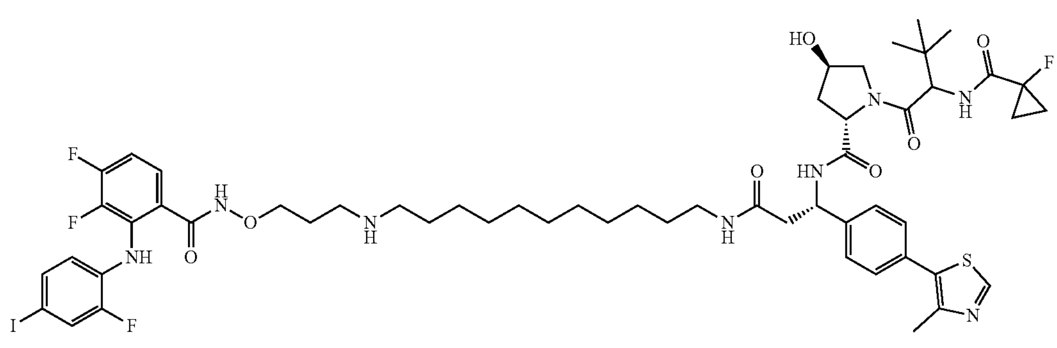 [SMILES: Cc1ncsc1-c1ccc([C@H](CC(=O)NCCCCCCCCCCCNCCCONC(=O)c2ccc(F)c(F)c2Nc2ccc(I)cc2F)NC(=O)[C@@H]2C[C@@H](O)CN2C(=O)C(NC(=O)C2(F)CC2)C(C)(C)C)cc1] |

TABLE 1-continued
| CPD | Structure |
|---|---|
| CPD-064 | 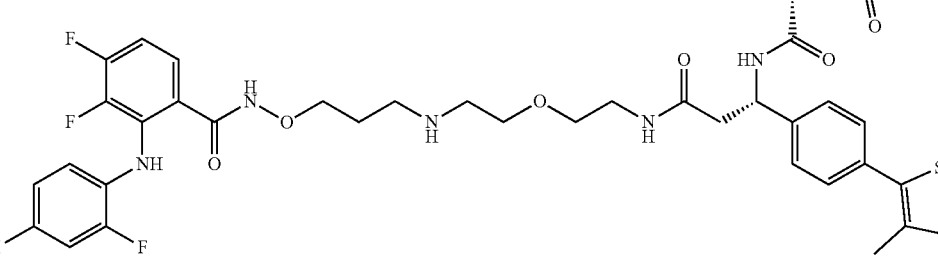 |
| CPD-065 | 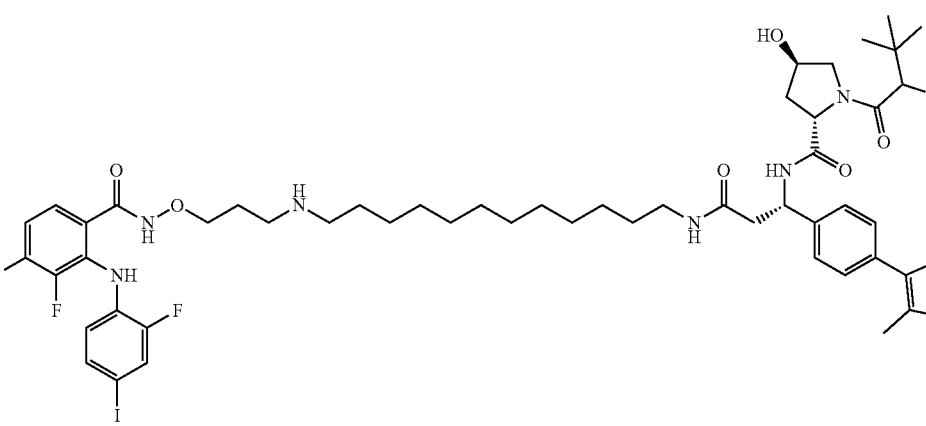 |
| CPD-066 | 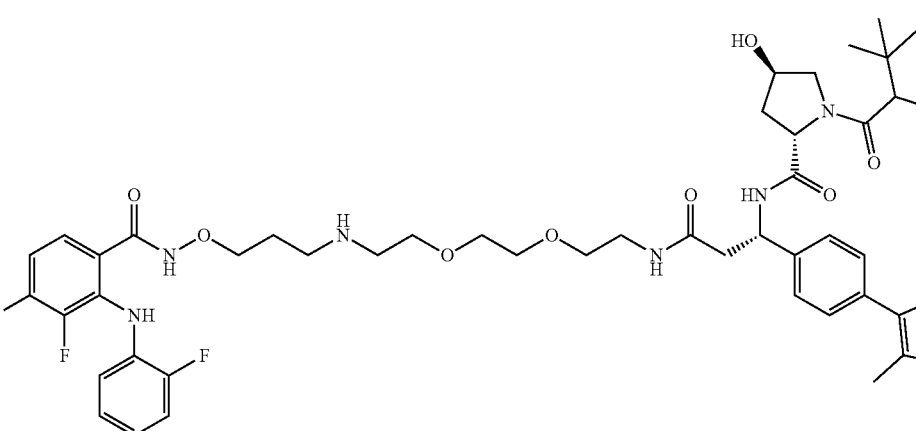 |
| CPD-067 | 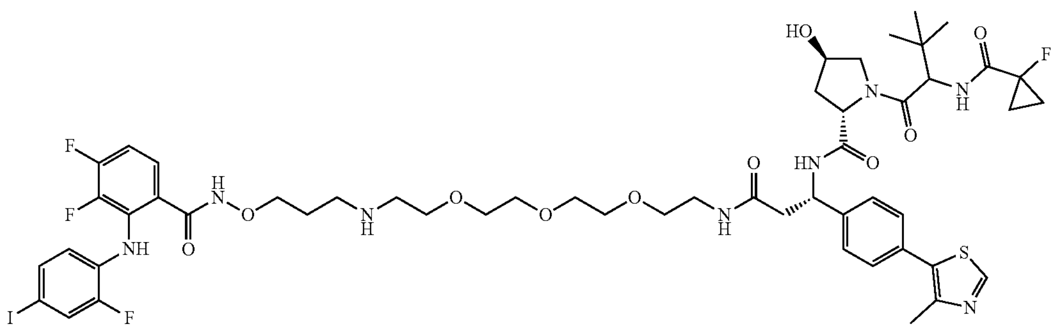 [SMILES: Cc1ncsc1-c1ccc([C@H](CC(=O)NCCOCCOCCOCCNCCCONC(=O)c2ccc(F)c(F)c2Nc2ccc(I)cc2F)NC(=O)[C@@H]2C[C@@H](O)CN2C(=O)C(NC(=O)C2(F)CC2)C(C)(C)C)cc1] |

TABLE 1-continued
| CPD | Structure |
|---|---|
| CPD-068 | 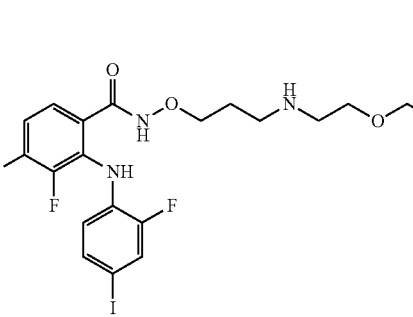 |
| CPD-069 | 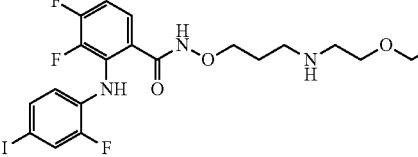 |
| CPD-070 | 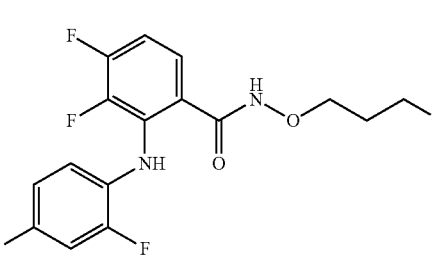 |
| CPD-071 | 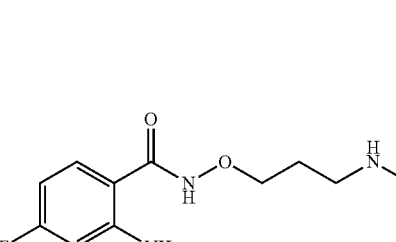 |

TABLE 1-continued
| CPD | Structure |
|---|---|
| CPD-072 | 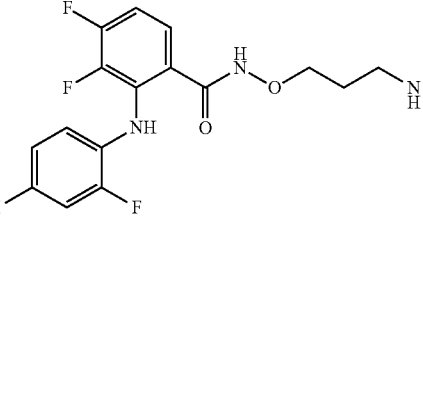 |
| CPD-073 | 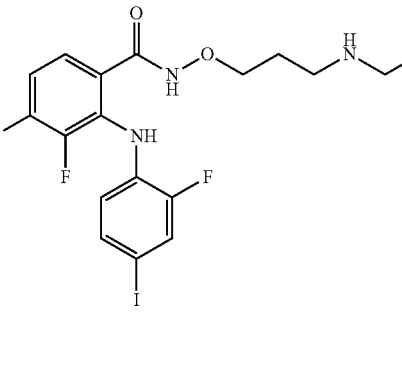 |
| CPD-074 | 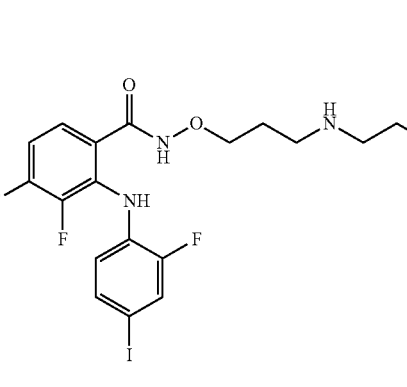 |
| CPD-075 | 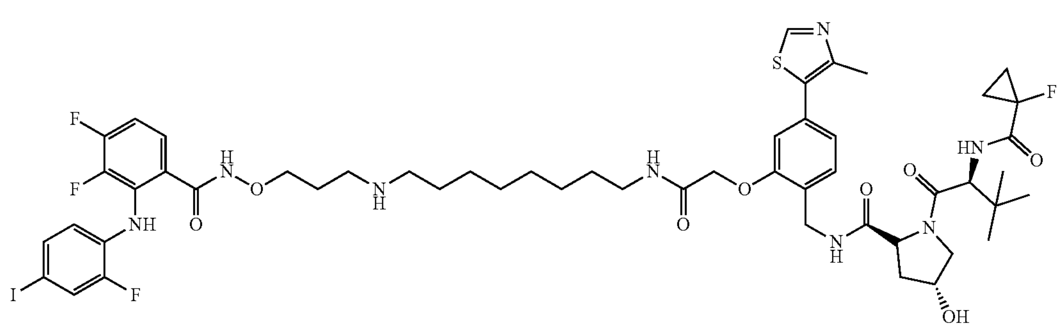 |

TABLE 1-continued

| CPD | Structure |
|---|---|
| CPD-076 | 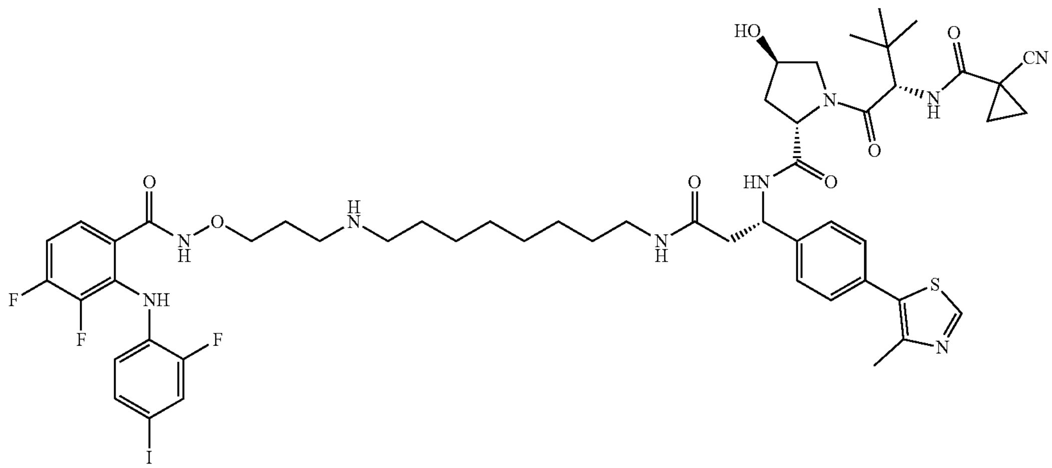 [SMILES: Cc1ncsc1-c1ccc([C@H](CC(=O)NCCCCCCCCNCCCONC(=O)c2ccc(F)c(F)c2Nc2ccc(I)cc2F)NC(=O)[C@@H]2C[C@@H](O)CN2C(=O)[C@@H](NC(=O)C2(C#N)CC2)C(C)(C)C)cc1] |
| CPD-077 | 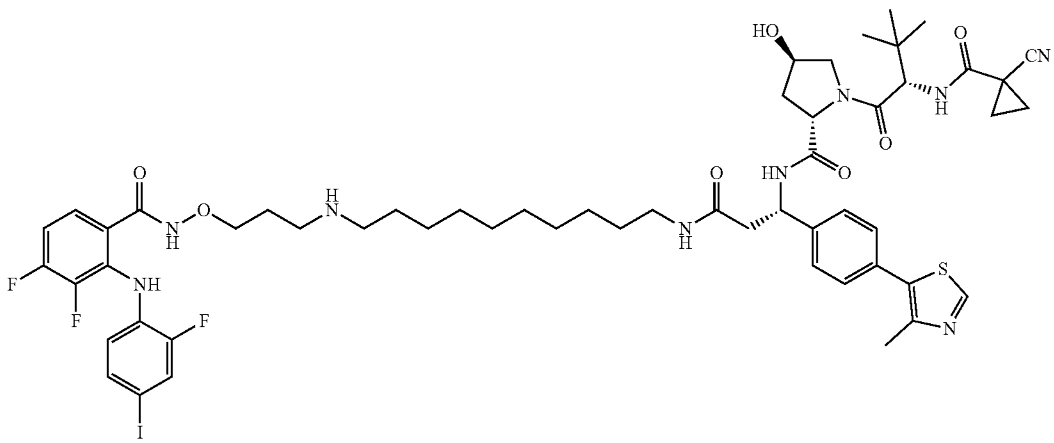 [SMILES: Cc1ncsc1-c1ccc([C@H](CC(=O)NCCCCCCCCCCNCCCONC(=O)c2ccc(F)c(F)c2Nc2ccc(I)cc2F)NC(=O)[C@@H]2C[C@@H](O)CN2C(=O)[C@@H](NC(=O)C2(C#N)CC2)C(C)(C)C)cc1] |
| CPD-078 | 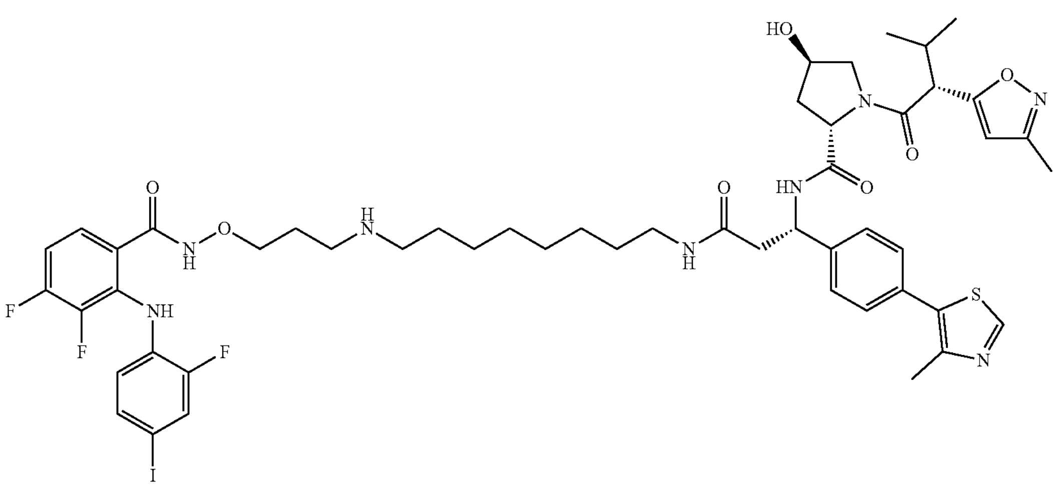 [SMILES: Cc1cc([C@H](C(=O)N2C[C@H](O)C[C@H]2C(=O)N[C@@H](CC(=O)NCCCCCCCCNCCCONC(=O)c2ccc(F)c(F)c2Nc2ccc(I)cc2F)c2ccc(-c3scnc3C)cc2)C(C)C)on1] |

TABLE 1-continued
| CPD | Structure |
|---|---|
| CPD-079 | 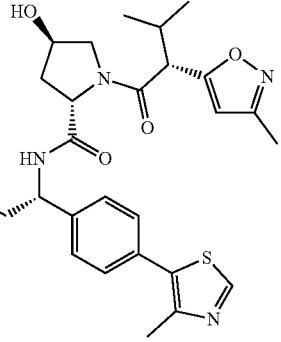 |
| CPD-080 | 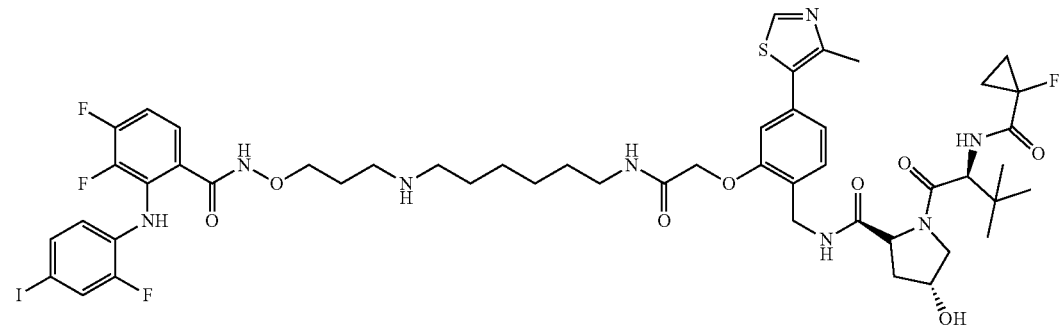 |
| CPD-081 | 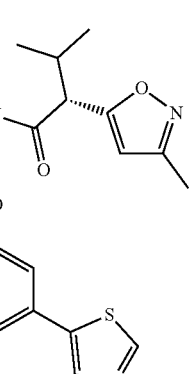 |

TABLE 1-continued
| CPD | Structure |
|---|---|
| CPD-082 | 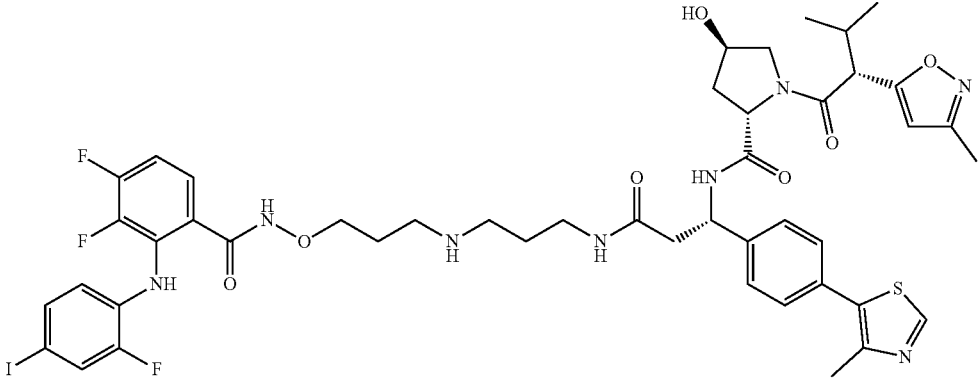 [SMILES: Cc1cc([C@H](C(=O)N2C[C@H](O)C[C@H]2C(=O)N[C@@H](CC(=O)NCCCNCCCONC(=O)c2ccc(F)c(F)c2Nc2ccc(I)cc2F)c2ccc(-c3scnc3C)cc2)C(C)C)on1] |
| CPD-083 | 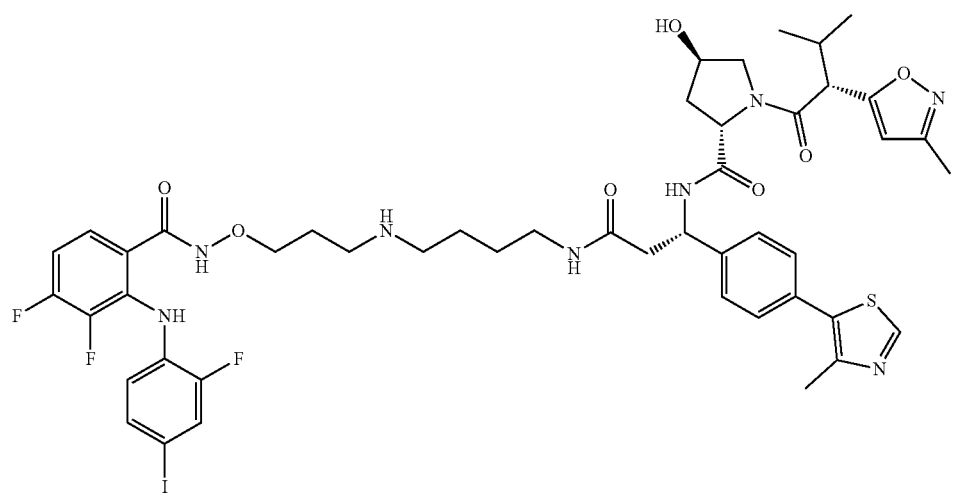 [SMILES: Cc1cc([C@H](C(=O)N2C[C@H](O)C[C@H]2C(=O)N[C@@H](CC(=O)NCCCCNCCCONC(=O)c2ccc(F)c(F)c2Nc2ccc(I)cc2F)c2ccc(-c3scnc3C)cc2)C(C)C)on1] |
| CPD-084 | 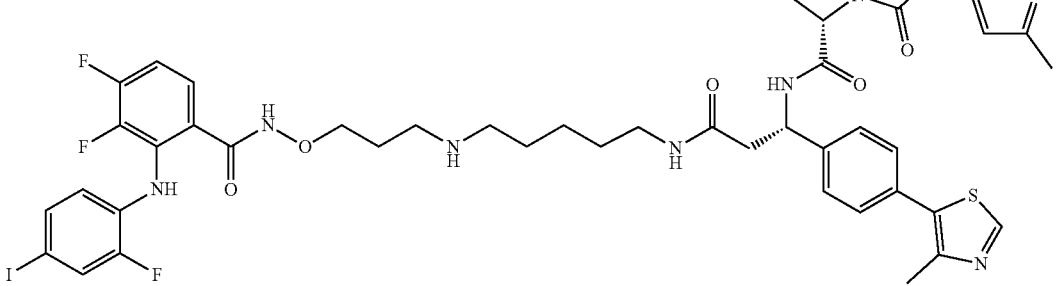 |

TABLE 1-continued

| CPD | Structure |
|---|---|
| CPD-085 | 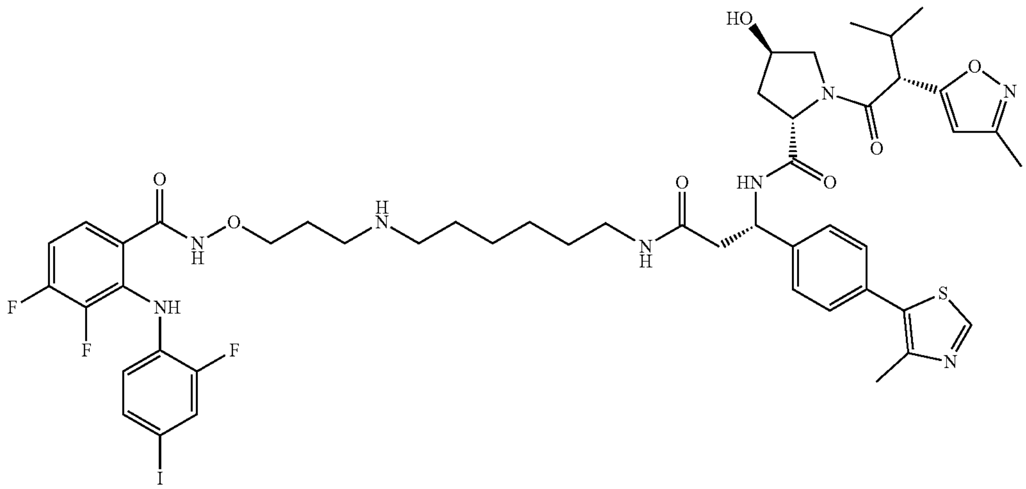 [SMILES: Cc1cc([C@H](C(=O)N2C[C@H](O)C[C@H]2C(=O)N[C@@H](CC(=O)NCCCCCCNCCCONC(=O)c2ccc(F)c(F)c2Nc2ccc(I)cc2F)c2ccc(-c3scnc3C)cc2)C(C)C)on1] |
| CPD-086 | 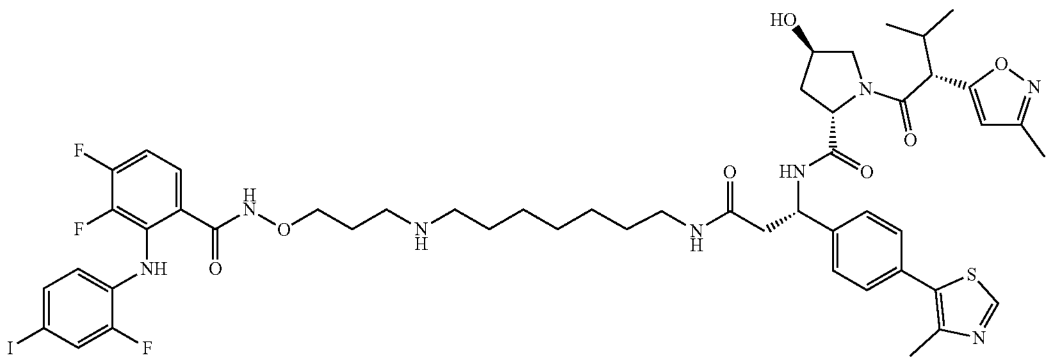 [SMILES: Cc1cc([C@H](C(=O)N2C[C@H](O)C[C@H]2C(=O)N[C@@H](CC(=O)NCCCCCCCNCCCONC(=O)c2ccc(F)c(F)c2Nc2ccc(I)cc2F)c2ccc(-c3scnc3C)cc2)C(C)C)on1] |
| CPD-087 | 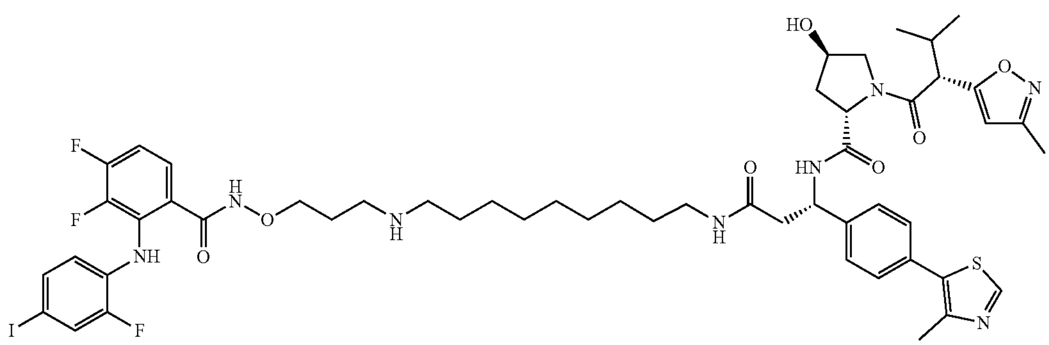 [SMILES: Cc1cc([C@H](C(=O)N2C[C@H](O)C[C@H]2C(=O)N[C@@H](CC(=O)NCCCCCCCCCNCCCONC(=O)c2ccc(F)c(F)c2Nc2ccc(I)cc2F)c2ccc(-c3scnc3C)cc2)C(C)C)on1] |
| CPD-088 | 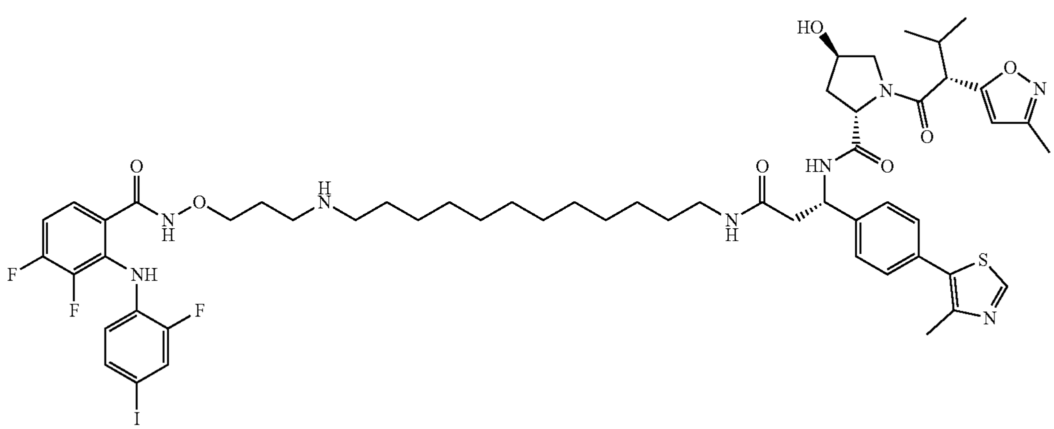 [SMILES: Cc1cc([C@H](C(=O)N2C[C@H](O)C[C@H]2C(=O)N[C@@H](CC(=O)NCCCCCCCCCCCCNCCCONC(=O)c2ccc(F)c(F)c2Nc2ccc(I)cc2F)c2ccc(-c3scnc3C)cc2)C(C)C)on1] |

US 12,103,924 B2
371                                                             372
TABLE 1-continued
| CPD | Structure |
|---|---|
| CPD-089 | 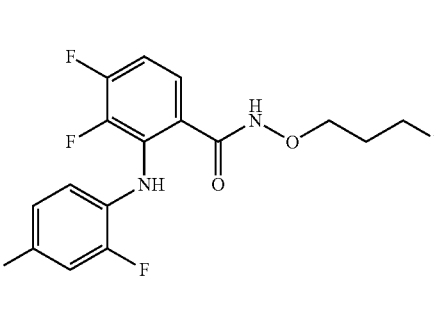 |
| CPD-090 | 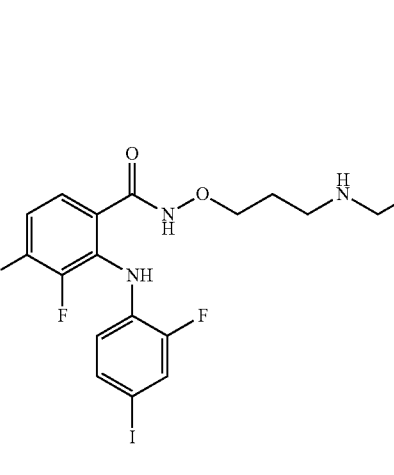 |
| CPD-091 | 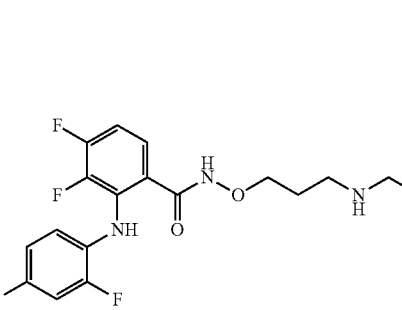 |
| CPD-092 | 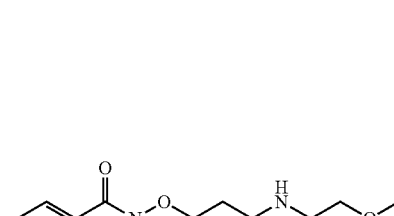 |

TABLE 1-continued

| CPD | Structure |
|---|---|
| CPD-093 | 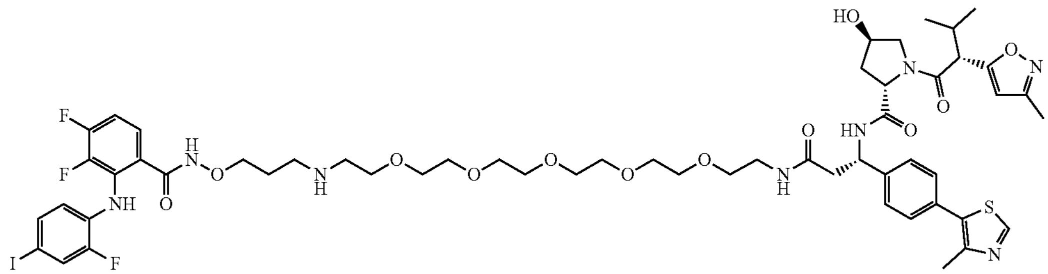 [SMILES: Cc1cc([C@H](C(=O)N2C[C@H](O)C[C@H]2C(=O)N[C@@H](CC(=O)NCCOCCOCCOCCOCCOCCNCCCONC(=O)c2ccc(F)c(F)c2Nc2ccc(I)cc2F)c2ccc(-c3scnc3C)cc2)C(C)C)on1] |
| CPD-094 | 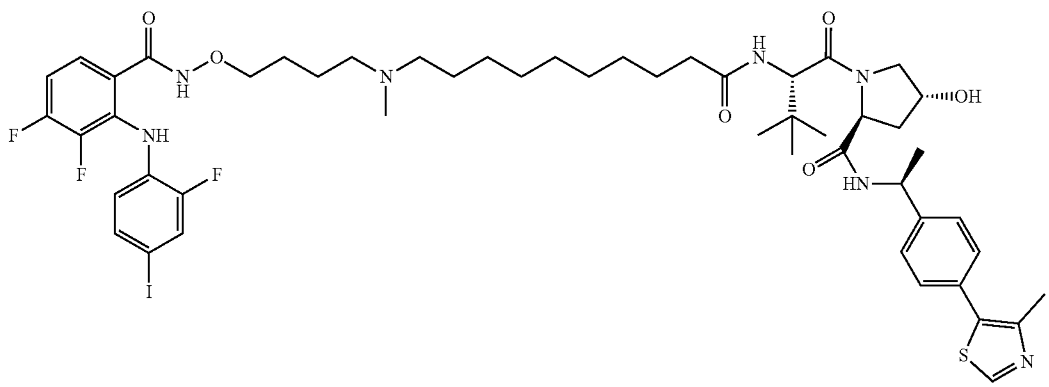 [SMILES: Cc1ncsc1-c1ccc([C@H](C)NC(=O)[C@@H]2C[C@@H](O)CN2C(=O)[C@@H](NC(=O)CCCCCCCCCN(C)CCCCONC(=O)c2ccc(F)c(F)c2Nc2ccc(I)cc2F)C(C)(C)C)cc1] |
| CPD-095 | 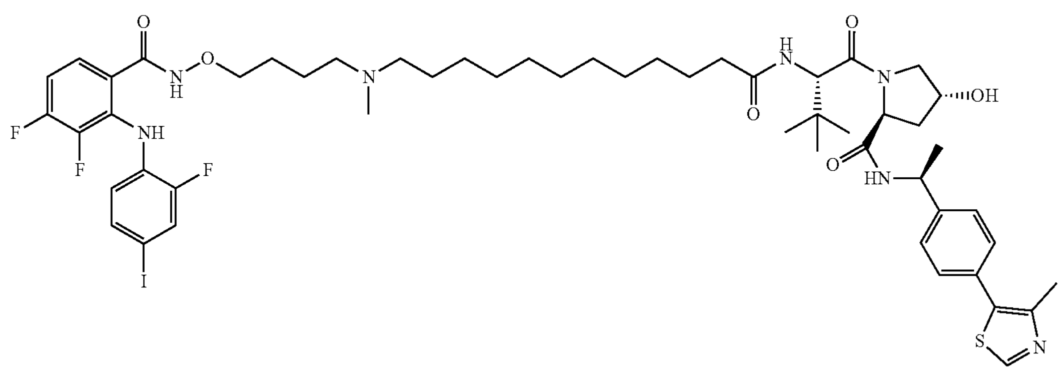 [SMILES: Cc1ncsc1-c1ccc([C@H](C)NC(=O)[C@@H]2C[C@@H](O)CN2C(=O)[C@@H](NC(=O)CCCCCCCCCCCN(C)CCCCONC(=O)c2ccc(F)c(F)c2Nc2ccc(I)cc2F)C(C)(C)C)cc1] |
| CPD-096 | 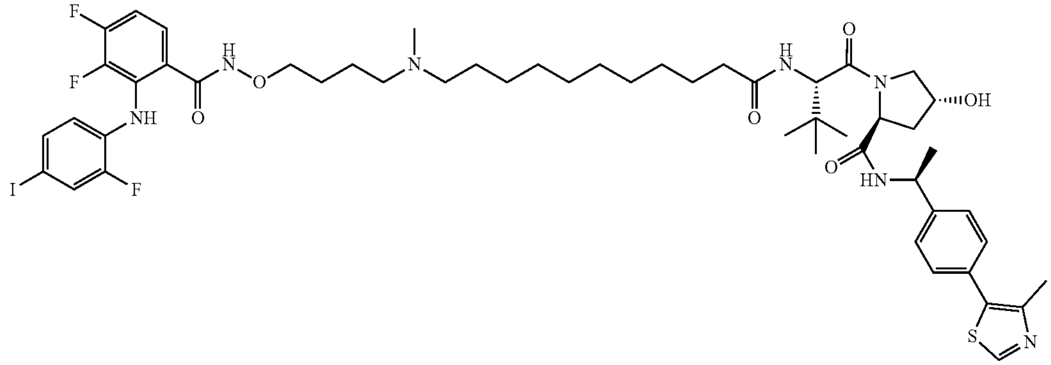 [SMILES: Cc1ncsc1-c1ccc([C@H](C)NC(=O)[C@@H]2C[C@@H](O)CN2C(=O)[C@@H](NC(=O)CCCCCCCCCCN(C)CCCCONC(=O)c2ccc(F)c(F)c2Nc2ccc(I)cc2F)C(C)(C)C)cc1] |

TABLE 1-continued

| CPD | Structure |
|---|---|
| CPD-097 | (structure image) |

| CPD | Chemical Name |
|---|---|
| CPD-001 | (2S,4R)-1-((S)-16-(tert-butyl)-1-(3,4-difluoro-2-((2-fluoro-4-iodophenyl)amino)phenyl)-1,14-dioxo-3-oxa-2,7,15-triazaheptadecan-17-oyl)-4-hydroxy-N-(4-(4-methylthiazol-5-yl)benzyl)pyrrolidine-2-carboxamide |
| CPD-002 | (2S,4R)-1-((S)-14-(tert-butyl)-1-(3,4-difluoro-2-((2-fluoro-4-iodophenyl)amino)phenyl)-1,12-dioxo-3,10-dioxa-2,7,13-triazapentadecan-15-oyl)-4-hydroxy-N-(4-(4-methylthiazol-5-yl)benzyl)pyrrolidine-2-carboxamide |
| CPD-003 | (2S,4R)-1-((S)-15-(tert-butyl)-1-(3,4-difluoro-2-((2-fluoro-4-iodophenyl)amino)phenyl)-1,13-dioxo-3,10-dioxa-2,7,14-triazahexadecan-16-oyl)-4-hydroxy-N-(4-(4-methylthiazol-5-yl)benzyl)pyrrolidine-2-carboxamide |
| CPD-004 | (2S,4R)-1-((S)-18-(tert-butyl)-1-(3,4-difluoro-2-((2-fluoro-4-iodophenyl)amino)phenyl)-1,16-dioxo-3,10,13-trioxa-2,7,17-triazanonadecan-19-oyl)-4-hydroxy-N-(4-(4-methylthiazol-5-yl)benzyl)pyrrolidine-2-carboxamide |
| CPD-005 | (2S,4R)-1-((S)-11-(tert-butyl)-1-(3,4-difluoro-2-((2-fluoro-4-iodophenyl)amino)phenyl)-1,9-dioxo-3-oxa-2,7,10-triazadodecan-12-oyl)-4-hydroxy-N-(4-(4-methylthiazol-5-yl)benzyl)pyrrolidine-2-carboxamide |
| CPD-006 | (2S,4R)-1-((S)-12-(tert-butyl)-1-(3,4-difluoro-2-((2-fluoro-4-iodophenyl)amino)phenyl)-1,10-dioxo-3-oxa-2,7,11-triazatridecan-13-oyl)-4-hydroxy-N-(4-(4-methylthiazol-5-yl)benzyl)pyrrolidine-2-carboxamide |
| CPD-007 | (2S,4R)-1-((S)-14-(tert-butyl)-1-(3,4-difluoro-2-((2-fluoro-4-iodophenyl)amino)phenyl)-1,12-dioxo-3-oxa-2,7,13-triazapentadecan-15-oyl)-4-hydroxy-N-(4-(4-methylthiazol-5-yl)benzyl)pyrrolidine-2-carboxamide |
| CPD-008 | (2S,4R)-1-((S)-13-(tert-butyl)-1-(3,4-difluoro-2-((2-fluoro-4-iodophenyl)amino)phenyl)-1,11-dioxo-3-oxa-2,7,12-triazatetradecan-14-oyl)-4-hydroxy-N-(4-(4-methylthiazol-5-yl)benzyl)pyrrolidine-2-carboxamide |
| CPD-009 | (2S,4R)-1-((S)-15-(tert-butyl)-1-(3,4-difluoro-2-((2-fluoro-4-iodophenyl)amino)phenyl)-1,13-dioxo-3-oxa-2,7,14-triazahexadecan-16-oyl)-4-hydroxy-N-(4-(4-methylthiazol-5-yl)benzyl)pyrrolidine-2-carboxamide |
| CPD-010 | (2S,4R)-1-((S)-18-(tert-butyl)-1-(3,4-difluoro-2-((2-fluoro-4-iodophenyl)amino)phenyl)-1,16-dioxo-3-oxa-2,7,17-triazanonadecan-19-oyl)-4-hydroxy-N-(4-(4-methylthiazol-5-yl)benzyl)pyrrolidine-2-carboxamide |
| CPD-011 | (2S,4R)-1-((S)-17-(tert-butyl)-1-(3,4-difluoro-2-((2-fluoro-4- |

TABLE 1-continued

| CPD | Structure |
|---|---|
| CPD-012 | iodophenyl)amino)phenyl)-1,15-dioxo-3-oxa-2,7,16-triazaoctadecan-18-oyl)-4-hydroxy-N-(4-(4-methylthiazol-5-yl)benzyl)pyrrolidine-2-carboxamide |
| CPD-013 | (2S,4R)-1-((S)-17-(tert-butyl)-1-(3,4-difluoro-2-((2-fluoro-4-iodophenyl)amino)phenyl)-1,5-dioxo-3,10,13-trioxa-2,7,16-triazaoctadecan-18-oyl)-4-hydroxy-N-(4-(4-methylthiazol-5-yl)benzyl)pyrrolidine-2-carboxamide |
| CPD-014 | (2S,4R)-1-((S)-19-(tert-butyl)-1-(3,4-difluoro-2-((2-fluoro-4-iodophenyl)amino)phenyl)-1,17-dioxo-3-oxa-2,7,18-triazaicosan-20-oyl)-4-hydroxy-N-(4-(4-methylthiazol-5-yl)benzyl)pyrrolidine-2-carboxamide |
| CPD-015 | (2S,4R)-1-((S)-20-(tert-butyl)-1-(3,4-difluoro-2-((2-fluoro-4-iodophenyl)amino)phenyl)-1,18-dioxo-3-oxa-2,7,19-triazahenicosan-21-oyl)-4-hydroxy-N-(4-(4-methylthiazol-5-yl)benzyl)pyrrolidine-2-carboxamide |
| CPD-016 | (2S,4R)-1-((S)-20-(tert-butyl)-1-(3,4-difluoro-2-((2-fluoro-4-iodophenyl)amino)phenyl)-1,18-dioxo-3,10,13,16-tetraoxa-2,7,19-triazahenicosan-21-oyl)-4-hydroxy-N-(4-(4-methylthiazol-5-yl)benzyl)pyrrolidine-2-carboxamide |
| CPD-017 | (2S,4R)-1-((S)-21-(tert-butyl)-1-(3,4-difluoro-2-((2-fluoro-4-iodophenyl)amino)phenyl)-1,19-dioxo-3,10,13,16-tetraoxa-2,7,20-triazadocosan-22-oyl)-4-hydroxy-N-(4-(4-methylthiazol-5-yl)benzyl)pyrrolidine-2-carboxamide |
| CPD-018 | (2S,4R)-1-((S)-24-(tert-butyl)-1-(3,4-difluoro-2-((2-fluoro-4-iodophenyl)amino)phenyl)-1,22-dioxo-3,10,13,16,19-pentaoxa-2,7,23-triazapentacosan-25-oyl)-4-hydroxy-N-(4-(4-methylthiazol-5-yl)benzyl)pyrrolidine-2-carboxamide |
| CPD-019 | (2S,4R)-1-((S)-27-(tert-butyl)-1-(3,4-difluoro-2-((2-fluoro-4-iodophenyl)amino)phenyl)-1,25-dioxo-3,10,13,16,19,22-hexaoxa-2,7,26-triazaoctacosan-28-oyl)-4-hydroxy-N-(4-(4-methylthiazol-5-yl)benzyl)pyrrolidine-2-carboxamide |
| CPD-020 | N-(3-((2-(2-((2-(2,6-dioxopiperidin-3-yl)-1,3-dioxoisoindolin-4-yl)amino)ethoxy)ethyl)amino)propoxy)-3,4-difluoro-2-((2-fluoro-4-iodophenyl)amino)benzamide |
| CPD-021 | N-(3-((2-(2-(2-((2-(2,6-dioxopiperidin-3-yl)-1,3-dioxoisoindolin-4-yl)amino)ethoxy)ethoxy)ethyl)amino)propoxy)-3,4-difluoro-2-((2-fluoro-4-iodophenyl)amino)benzamide |
| CPD-022 | N-((1-((2-(2,6-dioxopiperidin-3-yl)-1,3-dioxoisoindolin-4-yl)amino)-3,6,9-trioxa-12-azapentadecan-15-yl)oxy)-3,4-difluoro-2-((2-fluoro-4-iodophenyl)amino)benzamide |
| CPD-023 | N-((1-((2-(2,6-dioxopiperidin-3-yl)-1,3-dioxoisoindolin-4-yl)amino)-3,6,9,12-tetraoxa-15-azaoctadecan-18-yl)oxy)-3,4-difluoro-2-((2-fluoro-4-iodophenyl)amino)benzamide |
| CPD-024 | N-((1-((2-(2,6-dioxopiperidin-3-yl)-1,3-dioxoisoindolin-4-yl)amino)-3,6,9,12,15-pentaoxa-18-azahenicosan-21-yl)oxy)-3,4-difluoro-2-((2-fluoro-4-iodophenyl)amino)benzamide |
| CPD-024 | N-(3-((2-((2-(2,6-dioxopiperidin-3-yl)-1,3-dioxoisoindolin-4- |

TABLE 1-continued

| CPD | Structure |
|---|---|
| | yl)amino)ethyl)amino)propoxy)-3,4-difluoro-2-((2-fluoro-4-iodophenyl)amino)benzamide |
| CPD-025 | N-(3-((3-((2-(2,6-dioxopiperidin-3-yl)-1,3-dioxoisoindolin-4-yl)amino)propyl)amino)propoxy)-3,4-difluoro-2-((2-fluoro-4-iodophenyl)amino)benzamide |
| CPD-026 | N-(3-((4-((2-(2,6-dioxopiperidin-3-yl)-1,3-dioxoisoindolin-4-yl)amino)butyl)amino)propoxy)-3,4-difluoro-2-((2-fluoro-4-iodophenyl)amino)benzamide |
| CPD-027 | N-(3-((5-((2-(2,6-dioxopiperidin-3-yl)-1,3-dioxoisoindolin-4-yl)amino)pentyl)amino)propoxy)-3,4-difluoro-2-((2-fluoro-4-iodophenyl)amino)benzamide |
| CPD-028 | N-(3-((6-((2-(2,6-dioxopiperidin-3-yl)-1,3-dioxoisoindolin-4-yl)amino)hexyl)amino)propoxy)-3,4-difluoro-2-((2-fluoro-4-iodophenyl)amino)benzamide |
| CPD-029 | N-(3-((7-((2-(2,6-dioxopiperidin-3-yl)-1,3-dioxoisoindolin-4-yl)amino)heptyl)amino)propoxy)-3,4-difluoro-2-((2-fluoro-4-iodophenyl)amino)benzamide |
| CPD-030 | N-(3-((8-((2-(2,6-dioxopiperidin-3-yl)-1,3-dioxoisoindolin-4-yl)amino)octyl)amino)propoxy)-3,4-difluoro-2-((2-fluoro-4-iodophenyl)amino)benzamide |
| CPD-031 | (2S,4R)-1-((S)-20-(tert-butyl)-1-(3,4-difluoro-2-((2-fluoro-4-iodophenyl)amino)phenyl)-1,18-dioxo-3-oxa-2,7,19-triazahenicosan-21-oyl)-4-hydroxy-N-((S)-1-(4-(4-methylthiazol-5-yl)phenyl)ethyl)pyrrolidine-2-carboxamide |
| CPD-032 | (2S,4R)-1-((S)-21-(tert-butyl)-1-(3,4-difluoro-2-((2-fluoro-4-iodophenyl)amino)phenyl)-1,19-dioxo-3-oxa-2,7,20-triazadocosan-22-oyl)-4-hydroxy-N-(4-(4-methylthiazol-5-yl)benzyl)pyrrolidine-2-carboxamide |
| CPD-033 | (2S,4R)-1-((S)-21-(tert-butyl)-1-(3,4-difluoro-2-((2-fluoro-4-iodophenyl)amino)phenyl)-1,19-dioxo-3-oxa-2,7,20-triazadocosan-22-oyl)-4-hydroxy-N-((S)-1-(4-(4-methylthiazol-5-yl)phenyl)ethyl)pyrrolidine-2-carboxamide |
| CPD-034 | (2R,4S)-1-((S)-20-(tert-butyl)-1-(3,4-difluoro-2-((2-fluoro-4-iodophenyl)amino)phenyl)-1,18-dioxo-3-oxa-2,7,19-triazahenicosan-21-oyl)-4-hydroxy-N-((S)-1-(4-(4-methylthiazol-5-yl)phenyl)ethyl)pyrrolidine-2-carboxamide |
| CPD-035 | (2S,4R)-1-((S)-20-(tert-butyl)-1-(3,4-difluoro-2-((2-fluoro-4-iodophenyl)amino)phenyl)-1,18-dioxo-3-oxa-2,8,19-triazahenicosan-21-oyl)-4-hydroxy-N-((S)-1-(4-(4-methylthiazol-5-yl)phenyl)ethyl)pyrrolidine-2-carboxamide |
| CPD-036 | (2S,4R)-1-((S)-19-(tert-butyl)-1-(3,4-difluoro-2-((2-fluoro-4-iodophenyl)amino)phenyl)-1,17-dioxo-3-oxa-2,7,18-triazaicosan-20-oyl)-4-hydroxy-N-((S)-1-(4-(4-methylthiazol-5-yl)phenyl)ethyl)pyrrolidine-2-carboxamide |

TABLE 1-continued

| CPD | Structure |
|---|---|
| CPD-037 | (2S,4R)-1-((S)-20-(tert-butyl)-1-(3,4-difluoro-2-((2-fluoro-4-iodophenyl)amino)phenyl)-7-methyl-1,18-dioxo-3-oxa-2,7,19-triazahenicosan-21-oyl)-4-hydroxy-N-((S)-1-(4-(4-methylthiazol-5-yl)phenyl)ethyl)pyrrolidine-2-carboxamide |
| CPD-038 | (2S,4R)-1-((S)-22-(tert-butyl)-1-(3,4-difluoro-2-((2-fluoro-4-iodophenyl)amino)phenyl)-1,20-dioxo-3-oxa-2,8,21-triazatricosan-23-oyl)-4-hydroxy-N-((S)-1-(4-(4-methylthiazol-5-yl)phenyl)ethyl)pyrrolidine-2-carboxamide |
| CPD-039 | (2S,4R)-1-((2S)-21-(tert-butyl)-1-(3,4-difluoro-2-((2-fluoro-4-iodophenyl)amino)phenyl)-1,19-dioxo-3-oxa-2,8,20-triazadocosan-22-oyl)-4-hydroxy-N-((S)-1-(4-(4-methylthiazol-5-yl)phenyl)ethyl)pyrrolidine-2-carboxamide |
| CPD-040 | N-(3-((2-((2-(2,6-dioxopiperidin-3-yl)-1,3-dioxoisoindolin-5-yl)amino)ethyl)amino)propoxy)-3,4-difluoro-2-((2-fluoro-4-iodophenyl)amino)benzamide |
| CPD-041 | N-(3-((3-((2-(2,6-dioxopiperidin-3-yl)-1,3-dioxoisoindolin-5-yl)amino)propyl)amino)propoxy)-3,4-difluoro-2-((2-fluoro-4-iodophenyl)amino)benzamide |
| CPD-042 | N-(3-((4-((2-(2,6-dioxopiperidin-3-yl)-1,3-dioxoisoindolin-5-yl)amino)butyl)amino)propoxy)-3,4-difluoro-2-((2-fluoro-4-iodophenyl)amino)benzamide |
| CPD-043 | N-(3-((5-((2-(2,6-dioxopiperidin-3-yl)-1,3-dioxoisoindolin-5-yl)amino)pentyl)amino)propoxy)-3,4-difluoro-2-((2-fluoro-4-iodophenyl)amino)benzamide |
| CPD-044 | N-(3-((6-((2-(2,6-dioxopiperidin-3-yl)-1,3-dioxoisoindolin-5-yl)amino)hexyl)amino)propoxy)-3,4-difluoro-2-((2-fluoro-4-iodophenyl)amino)benzamide |
| CPD-045 | N-(3-((7-((2-(2,6-dioxopiperidin-3-yl)-1,3-dioxoisoindolin-5-yl)amino)heptyl)amino)propoxy)-3,4-difluoro-2-((2-fluoro-4-iodophenyl)amino)benzamide |
| CPD-046 | N-(3-((8-((2-(2,6-dioxopiperidin-3-yl)-1,3-dioxoisoindolin-5-yl)amino)octyl)amino)propoxy)-3,4-difluoro-2-((2-fluoro-4-iodophenyl)amino)benzamide |
| CPD-047 | N-(3-((2-(2-((2-(2,6-dioxopiperidin-3-yl)-1,3-dioxoisoindolin-5-yl)amino)ethoxy)ethyl)amino)propoxy)-3,4-difluoro-2-((2-fluoro-4-iodophenyl)amino)benzamide |
| CPD-048 | N-(3-((2-(2-(2-((2-(2,6-dioxopiperidin-3-yl)-1,3-dioxoisoindolin-5-yl)amino)ethoxy)ethoxy)ethyl)amino)propoxy)-3,4-difluoro-2-((2-fluoro-4-iodophenyl)amino)benzamide |
| CPD-049 | N-((1-((2-(2,6-dioxopiperidin-3-yl)-1,3-dioxoisoindolin-5-yl)amino)-3,6,9-trioxa-12-azapentadecan-15-yl)oxy)-3,4-difluoro-2-((2-fluoro-4-iodophenyl)amino)benzamide |
| CPD-050 | N-((1-((2-(2,6-dioxopiperidin-3-yl)-1,3-dioxoisoindolin-5-yl)amino)-3,6,9,12-tetraoxa-15-azaoctadecan-18-yl)oxy)-3,4-difluoro-2-((2-fluoro-4-iodophenyl)amino)benzamide |

TABLE 1-continued

| CPD | Structure |
|---|---|
| CPD-051 | N-((1-((2-(2,6-dioxopiperidin-3-yl)-1,3-dioxoisoindolin-5-yl)amino)-3,6,9,12,15-pentaoxa-18-azahenicosan-21-yl)oxy)-3,4-difluoro-2-((2-fluoro-4-iodophenyl)amino)benzamide |
| CPD-052 | (2R,4S)-1-((S)-22-(tert-butyl)-1-(3,4-difluoro-2-((2-fluoro-4-iodophenyl)amino)phenyl)-1,20-dioxo-3-oxa-2,8,21-triazatricosan-23-oyl)-4-hydroxy-N-((S)-1-(4-(4-methylthiazol-5-yl)phenyl)ethyl)pyrrolidine-2-carboxamide |
| CPD-053 | (2R,4S)-1-((S)-20-(tert-butyl)-1-(3,4-difluoro-2-((2-fluoro-4-iodophenyl)amino)phenyl)-7-methyl-1,18-dioxo-3-oxa-2,7,19-triazahenicosan-21-oyl)-4-hydroxy-N-((S)-1-(4-(4-methylthiazol-5-yl)phenyl)ethyl)pyrrolidine-2-carboxamide |
| CPD-054 | (2S,4R)-N-((S)-1-(3,4-difluoro-2-((2-fluoro-4-iodophenyl)amino)phenyl)-13-(4-(4-methylthiazol-5-yl)phenyl)-1,11-dioxo-3-oxa-2,7,10-triazatridecan-13-yl)-1-(2-(1-fluorocyclopropane-1-carboxamido)-3,3-dimethylbutanoyl)-4-hydroxypyrrolidine-2-carboxamide |
| CPD-055 | (2S,4R)-N-((S)-1-(3,4-difluoro-2-((2-fluoro-4-iodophenyl)amino)phenyl)-14-(4-(4-methylthiazol-5-yl)phenyl)-1,12-dioxo-3-oxa-2,7,11-triazatetradecan-14-yl)-1-(2-(1-fluorocyclopropane-1-carboxamido)-3,3-dimethylbutanoyl)-4-hydroxypyrrolidine-2-carboxamide |
| CPD-056 | (2S,4R)-N-((S)-1-(3,4-difluoro-2-((2-fluoro-4-iodophenyl)amino)phenyl)-15-(4-(4-methylthiazol-5-yl)phenyl)-1,13-dioxo-3-oxa-2,7,12-triazapentadecan-15-yl)-1-(2-(1-fluorocyclopropane-1-carboxamido)-3,3-dimethylbutanoyl)-4-hydroxypyrrolidine-2-carboxamide |
| CPD-057 | (2S,4R)-N-((S)-1-(3,4-difluoro-2-((2-fluoro-4-iodophenyl)amino)phenyl)-16-(4-(4-methylthiazol-5-yl)phenyl)-1,14-dioxo-3-oxa-2,7,13-triazahexadecan-16-yl)-1-(2-(1-fluorocyclopropane-1-carboxamido)-3,3-dimethylbutanoyl)-4-hydroxypyrrolidine-2-carboxamide |
| CPD-058 | (2S,4R)-N-((S)-1-(3,4-difluoro-2-((2-fluoro-4-iodophenyl)amino)phenyl)-17-(4-(4-methylthiazol-5-yl)phenyl)-1,15-dioxo-3-oxa-2,7,14-triazaheptadecan-17-yl)-1-(2-(1-fluorocyclopropane-1-carboxamido)-3,3-dimethylbutanoyl)-4-hydroxypyrrolidine-2-carboxamide |
| CPD-059 | (2S,4R)-N-((S)-1-(3,4-difluoro-2-((2-fluoro-4-iodophenyl)amino)phenyl)-18-(4-(4-methylthiazol-5-yl)phenyl)-1,16-dioxo-3-oxa-2,7,15-triazaoctadecan-18-yl)-1-(2-(1-fluorocyclopropane-1-carboxamido)-3,3-dimethylbutanoyl)-4-hydroxypyrrolidine-2-carboxamide |
| CPD-060 | (2S,4R)-N-((S)-1-(3,4-difluoro-2-((2-fluoro-4-iodophenyl)amino)phenyl)-19-(4-(4-methylthiazol-5-yl)phenyl)-1,17-dioxo-3-oxa-2,7,16-triazanonadecan-19-yl)-1-((S)-2-(1-fluorocyclopropane-1-carboxamido)-3,3-dimethylbutanoyl)-4-hydroxypyrrolidine-2-carboxamide |
| CPD-061 | (2S,4R)-N-((S)-1-(3,4-difluoro-2-((2-fluoro-4-iodophenyl)amino)phenyl)- |

| CPD | Structure |
|---|---|
| CPD-062 | 20-(4-(4-methylthiazol-5-yl)phenyl)-1,18-dioxo-3-oxa-2,7,17-triazaicosan-20-yl)-1-(2-(1-fluorocyclopropane-1-carboxamido)-3,3-dimethylbutanoyl)-4-hydroxypyrrolidine-2-carboxamide |
| CPD-063 | (2S,4R)-N-((S)-1-(3,4-difluoro-2-((2-fluoro-4-iodophenyl)amino)phenyl)-21-(4-(4-methylthiazol-5-yl)phenyl)-1,19-dioxo-3-oxa-2,7,18-triazahenicosan-21-yl)-1-((S)-2-(1-fluorocyclopropane-1-carboxamido)-3,3-dimethylbutanoyl)-4-hydroxypyrrolidine-2-carboxamide |
| CPD-064 | (2S,4R)-N-((S)-1-(3,4-difluoro-2-((2-fluoro-4-iodophenyl)amino)phenyl)-22-(4-(4-methylthiazol-5-yl)phenyl)-1,20-dioxo-3-oxa-2,7,19-triazadocosan-22-yl)-1-(2-(1-fluorocyclopropane-1-carboxamido)-3,3-dimethylbutanoyl)-4-hydroxypyrrolidine-2-carboxamide |
| CPD-065 | (2S,4R)-N-((S)-1-(3,4-difluoro-2-((2-fluoro-4-iodophenyl)amino)phenyl)-16-(4-(4-methylthiazol-5-yl)phenyl)-1,14-dioxo-3,10-dioxa-2,7,13-triazahexadecan-16-yl)-1-(2-(1-fluorocyclopropane-1-carboxamido)-3,3-dimethylbutanoyl)-4-hydroxypyrrolidine-2-carboxamide |
| CPD-066 | (2S,4R)-N-((S)-1-(3,4-difluoro-2-((2-fluoro-4-iodophenyl)amino)phenyl)-23-(4-(4-methylthiazol-5-yl)phenyl)-1,21-dioxo-3-oxa-2,7,20-triazatricosan-23-yl)-1-(2-(1-fluorocyclopropane-1-carboxamido)-3,3-dimethylbutanoyl)-4-hydroxypyrrolidine-2-carboxamide |
| CPD-067 | (2S,4R)-N-((S)-1-(3,4-difluoro-2-((2-fluoro-4-iodophenyl)amino)phenyl)-19-(4-(4-methylthiazol-5-yl)phenyl)-1,17-dioxo-3,10,13-trioxa-2,7,16-triazanonadecan-19-yl)-1-(2-(1-fluorocyclopropane-1-carboxamido)-3,3-dimethylbutanoyl)-4-hydroxypyrrolidine-2-carboxamide |
| CPD-068 | (2S,4R)-N-((S)-1-(3,4-difluoro-2-((2-fluoro-4-iodophenyl)amino)phenyl)-22-(4-(4-methylthiazol-5-yl)phenyl)-1,20-dioxo-3,10,13,16-tetraoxa-2,7,19-triazadocosan-22-yl)-1-(2-(1-fluorocyclopropane-1-carboxamido)-3,3-dimethylbutanoyl)-4-hydroxypyrrolidine-2-carboxamide |
| CPD-069 | (2S,4R)-N-((S)-1-(3,4-difluoro-2-((2-fluoro-4-iodophenyl)amino)phenyl)-25-(4-(4-methylthiazol-5-yl)phenyl)-1,23-dioxo-3,10,13,16,19-pentaoxa-2,7,22-triazapentacosan-25-yl)-1-(2-(1-fluorocyclopropane-1-carboxamido)-3,3-dimethylbutanoyl)-4-hydroxypyrrolidine-2-carboxamide |
| CPD-070 | (2S,4R)-N-((S)-1-(3,4-difluoro-2-((2-fluoro-4-iodophenyl)amino)phenyl)-28-(4-(4-methylthiazol-5-yl)phenyl)-1,26-dioxo-3,10,13,16,19,22-hexaoxa-2,7,25-triazaoctacosan-28-yl)-1-(2-(1-fluorocyclopropane-1-carboxamido)-3,3-dimethylbutanoyl)-4-hydroxypyrrolidine-2-carboxamide |
| | (2R,4R)-N-(2-((1-(3,4-difluoro-2-((2-fluoro-4-iodophenyl)amino)phenyl)-1,11-dioxo-3-oxa-2,7,10-triazadodecan-12-yl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |

TABLE 1-continued

| CPD | Structure |
|---|---|
| CPD-071 | (2R,4R)-N-(2-((1-(3,4-difluoro-2-((2-fluoro-4-iodophenyl)amino)phenyl)-1,12-dioxo-3-oxa-2,7,11-triazatridecan-13-yl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |
| CPD-072 | (2R,4R)-N-(2-((1-(3,4-difluoro-2-((2-fluoro-4-iodophenyl)amino)phenyl)-1,13-dioxo-3-oxa-2,7,12-triazatetradecan-14-yl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |
| CPD-073 | (2R,4R)-N-(2-((1-(3,4-difluoro-2-((2-fluoro-4-iodophenyl)amino)phenyl)-1,14-dioxo-3-oxa-2,7,13-triazapentadecan-15-yl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |
| CPD-074 | (2R,4R)-N-(2-((1-(3,4-difluoro-2-((2-fluoro-4-iodophenyl)amino)phenyl)-1,16-dioxo-3-oxa-2,7,15-triazaheptadecan-17-yl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |
| CPD-075 | (2R,4R)-N-(2-((1-(3,4-difluoro-2-((2-fluoro-4-iodophenyl)amino)phenyl)-1,17-dioxo-3-oxa-2,7,16-triazaoctadecan-18-yl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide |
| CPD-076 | (2S,4R)-1-((S)-2-(1-cyanocyclopropane-1-carboxamido)-3,3-dimethylbutanoyl)-N-((S)-1-(3,4-difluoro-2-((2-fluoro-4-iodophenyl)amino)phenyl)-19-(4-(4-methylthiazol-5-yl)phenyl)-1,17-dioxo-3-oxa-2,7,16-triazanonadecan-19-yl)-4-hydroxypyrrolidine-2-carboxamide |
| CPD-077 | (2S,4R)-1-((S)-2-(1-cyanocyclopropane-1-carboxamido)-3,3-dimethylbutanoyl)-N-((S)-1-(3,4-difluoro-2-((2-fluoro-4-iodophenyl)amino)phenyl)-21-(4-(4-methylthiazol-5-yl)phenyl)-1,19-dioxo-3-oxa-2,7,18-triazahenicosan-21-yl)-4-hydroxypyrrolidine-2-carboxamide |
| CPD-078 | (2S,4R)-N-((S)-1-(3,4-difluoro-2-((2-fluoro-4-iodophenyl)amino)phenyl)-19-(4-(4-methylthiazol-5-yl)phenyl)-1,17-dioxo-3-oxa-2,7,16-triazanonadecan-19-yl)-4-hydroxy-1-((R)-3-methyl-2-(3-methylisoxazol-5-yl)butanoyl)pyrrolidine-2-carboxamide |
| CPD-079 | (2S,4R)-N-((S)-1-(3,4-difluoro-2-((2-fluoro-4-iodophenyl)amino)phenyl)-21-(4-(4-methylthiazol-5-yl)phenyl)-1,19-dioxo-3-oxa-2,7,18-triazahenicosan-21-yl)-4-hydroxy-1-((R)-3-methyl-2-(3-methylisoxazol-5-yl)butanoyl)pyrrolidine-2-carboxamide |
| CPD-080 | (2R,4R)-N-(2-((1-(3,4-difluoro-2-((2-fluoro-4-iodophenyl)amino)phenyl)-1,15-dioxo-3-oxa-2,7,14-triazahexadecan-16-yl)oxy)-4-(4-methylthiazol-5-yl)benzyl)-1-((S)-2-(1-fluorocyclopropane-1-carboxamido)- |

TABLE 1-continued

| CPD | Structure |
|---|---|
| CPD-081 | 3,3-dimethylbutanoyl)-4-hydroxypyrrolidine-2-carboxamide |
| CPD-082 | (2S,4R)-N-((S)-1-(3,4-difluoro-2-((2-fluoro-4-iodophenyl)amino)phenyl)-13-(4-(4-methylthiazol-5-yl)phenyl)-1,11-dioxo-3-oxa-2,7,10-triazatridecan-13-yl)-4-hydroxy-1-((R)-3-methyl-2-(3-methylisoxazol-5-yl)butanoyl)pyrrolidine-2-carboxamide |
| CPD-083 | (2S,4R)-N-((S)-1-(3,4-difluoro-2-((2-fluoro-4-iodophenyl)amino)phenyl)-14-(4-(4-methylthiazol-5-yl)phenyl)-1,12-dioxo-3-oxa-2,7,11-triazatetradecan-14-yl)-4-hydroxy-1-((R)-3-methyl-2-(3-methylisoxazol-5-yl)butanoyl)pyrrolidine-2-carboxamide |
| CPD-084 | (2S,4R)-N-((S)-1-(3,4-difluoro-2-((2-fluoro-4-iodophenyl)amino)phenyl)-15-(4-(4-methylthiazol-5-yl)phenyl)-1,13-dioxo-3-oxa-2,7,12-triazapentadecan-15-yl)-4-hydroxy-1-((R)-3-methyl-2-(3-methylisoxazol-5-yl)butanoyl)pyrrolidine-2-carboxamide |
| CPD-085 | (2S,4R)-N-((S)-1-(3,4-difluoro-2-((2-fluoro-4-iodophenyl)amino)phenyl)-16-(4-(4-methylthiazol-5-yl)phenyl)-1,14-dioxo-3-oxa-2,7,13-triazahexadecan-16-yl)-4-hydroxy-1-((R)-3-methyl-2-(3-methylisoxazol-5-yl)butanoyl)pyrrolidine-2-carboxamide |
| CPD-086 | (2S,4R)-N-((S)-1-(3,4-difluoro-2-((2-fluoro-4-iodophenyl)amino)phenyl)-17-(4-(4-methylthiazol-5-yl)phenyl)-1,15-dioxo-3-oxa-2,7,14-triazaheptadecan-17-yl)-4-hydroxy-1-((R)-3-methyl-2-(3-methylisoxazol-5-yl)butanoyl)pyrrolidine-2-carboxamide |
| CPD-087 | (2S,4R)-N-((S)-1-(3,4-difluoro-2-((2-fluoro-4-iodophenyl)amino)phenyl)-18-(4-(4-methylthiazol-5-yl)phenyl)-1,16-dioxo-3-oxa-2,7,15-triazaoctadecan-18-yl)-4-hydroxy-1-((R)-3-methyl-2-(3-methylisoxazol-5-yl)butanoyl)pyrrolidine-2-carboxamide |
| CPD-088 | (2S,4R)-N-((S)-1-(3,4-difluoro-2-((2-fluoro-4-iodophenyl)amino)phenyl)-20-(4-(4-methylthiazol-5-yl)phenyl)-1,18-dioxo-3-oxa-2,7,17-triazaicosan-20-yl)-4-hydroxy-1-((R)-3-methyl-2-(3-methylisoxazol-5-yl)butanoyl)pyrrolidine-2-carboxamide |
| CPD-089 | (2S,4R)-N-((S)-1-(3,4-difluoro-2-((2-fluoro-4-iodophenyl)amino)phenyl)-23-(4-(4-methylthiazol-5-yl)phenyl)-1,21-dioxo-3-oxa-2,7,20-triazatricosan-23-yl)-4-hydroxy-1-((R)-3-methyl-2-(3-methylisoxazol-5-yl)butanoyl)pyrrolidine-2-carboxamide |
| CPD-090 | (2S,4R)-N-((S)-1-(3,4-difluoro-2-((2-fluoro-4-iodophenyl)amino)phenyl)-16-(4-(4-methylthiazol-5-yl)phenyl)-1,14-dioxo-3,10-dioxa-2,7,13-triazahexadecan-16-yl)-4-hydroxy-1-((R)-3-methyl-2-(3-methylisoxazol-5-yl)butanoyl)pyrrolidine-2-carboxamide |
| CPD-091 | (2S,4R)-N-((S)-1-(3,4-difluoro-2-((2-fluoro-4-iodophenyl)amino)phenyl)-19-(4-(4-methylthiazol-5-yl)phenyl)-1,17-dioxo-3,10,13-trioxa-2,7,16-triazanonadecan-19-yl)-4-hydroxy-1-((R)-3-methyl-2-(3-methylisoxazol-5-yl)butanoyl)pyrrolidine-2-carboxamide |
| | (2S,4R)-N-((S)-1-(3,4-difluoro-2-((2-fluoro-4-iodophenyl)amino)phenyl)-22-(4-(4-methylthiazol-5-yl)phenyl)-1,20-dioxo-3,10,13,16-tetraoxa-2,7,19-triazadocosan-22-yl)-4-hydroxy-1- |

TABLE 1-continued

| CPD | Structure |
|---|---|
| CPD-092 | ((R)-3-methyl-2-(3-methylisoxazol-5-yl)butanoyl)pyrrolidine-2-carboxamide (2S,4R)-N-((S)-1-(3,4-difluoro-2-((2-fluoro-4-iodophenyl)amino)phenyl)-25-(4-(4-methylthiazol-5-yl)phenyl)-1,23-dioxo-3,10,13,16,19-pentaoxa-2,7,22-triazapentacosan-25-yl)-4-hydroxy-1-((R)-3-methyl-2-(3-methylisoxazol-5-yl)butanoyl)pyrrolidine-2-carboxamide |
| CPD-093 | (2S,4R)-N-((S)-1-(3,4-difluoro-2-((2-fluoro-4-iodophenyl)amino)phenyl)-28-(4-(4-methylthiazol-5-yl)phenyl)-1,26-dioxo-3,10,13,16,19,22-hexaoxa-2,7,25-triazaoctacosan-28-yl)-4-hydroxy-1-((R)-3-methyl-2-(3-methylisoxazol-5-yl)butanoyl)pyrrolidine-2-carboxamide |
| CPD-094 | (2S,4R)-1-((S)-20-(tert-butyl)-1-(3,4-difluoro-2-((2-fluoro-4-iodophenyl)amino)phenyl)-8-methyl-1,18-dioxo-3-oxa-2,8,19-triazahenicosan-21-oyl)-4-hydroxy-N-((S)-1-(4-(4-methylthiazol-5-yl)phenyl)ethyl)pyrrolidine-2-carboxamide |
| CPD-095 | (2S,4R)-1-((S)-22-(tert-butyl)-1-(3,4-difluoro-2-((2-fluoro-4-iodophenyl)amino)phenyl)-8-methyl-1,20-dioxo-3-oxa-2,8,21-triazatricosan-23-oyl)-4-hydroxy-N-((S)-1-(4-(4-methylthiazol-5-yl)phenyl)ethyl)pyrrolidine-2-carboxamide |
| CPD-096 | (2S,4R)-1-((S)-21-(tert-butyl)-1-(3,4-difluoro-2-((2-fluoro-4-iodophenyl)amino)phenyl)-8-methyl-1,19-dioxo-3-oxa-2,8,20-triazadocosan-22-oyl)-4-hydroxy-N-((S)-1-(4-(4-methylthiazol-5-yl)phenyl)ethyl)pyrrolidine-2-carboxamide |
| CPD-097 | 3,4-difluoro-2-((2-fluoro-4-iodophenyl)amino)-N-((1-((2-(1-methyl-2,6-dioxopiperidin-3-yl)-1,3-dioxoisoindolin-5-yl)amino)-3,6,9,12,15-pentaoxa-18-azahenicosan-21-yl)oxy)benzamide |

As used herein, in case of discrepancy between the structure and chemical name provided for a particular compound, the structure shall control.

Example 100. Selected MEK Degraders Suppressed the Growth of HT-29 Cells (Table 2)

MTT assay was conducted for HT-29 cells after 3 d treatment with indicated compounds with serial dilutions.

Example 101. Selected MEK Degraders Reduced MEK Protein Levels in HT-29 Cells (FIG. 1)

Cells were treated with DMSO or serial dilution of indicated compounds for 24 h. Compound concentrations are 0.3 µM, 1 µM and 3 µM. MEK1/2 protein levels were determined by western blots and normalized with α-tubulin.

Example 102. Selected Compounds Inhibited the Kinase Activity of MEK1 and MEK2 (FIG. 2)

Inhibition value for each concentration point was determined by measuring MEK1/2 kinase activity on ERK phosphorylation and normalized with DMSO control point.

Example 103. CPD-031 Reduces MEK1/2 Protein Levels and Inhibits the Downstream ERK Signaling in a Concentration-Dependent Manner (FIG. 3A-D)

HT-29 (A and C) and SK-MEL-28 (B and D) cells were treated with DMSO or serial dilution of CPD-031 for 24 h. The indicated protein levels were determined by western blots and normalized with α-tubulin.

Figure 3E:
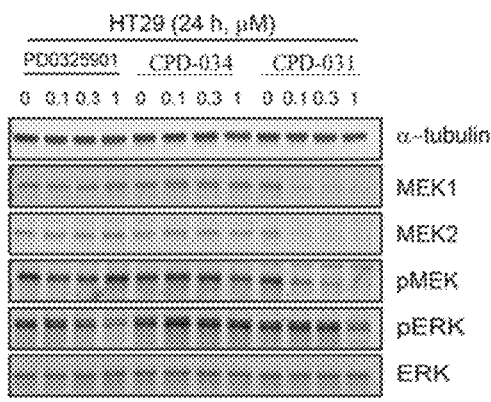
FIG. 3E-F. CPD-031, but not PD0325901 and CPD-034, reduced MEK1 and MEK2 protein levels in HT-29 and SK-MEL-28 cells. Compared with CPD-034, CPD-031 is more potent at the inhibition of MEK and ERK phosphorylation.
Figure 3F:
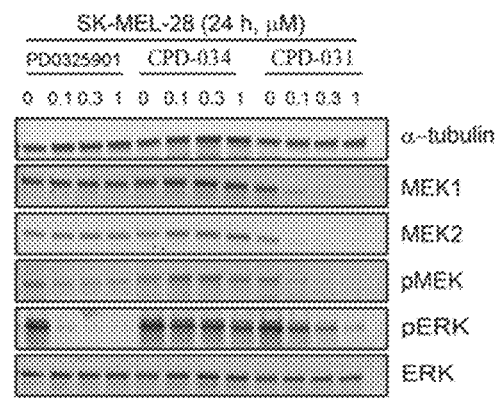

Example 104. The Effects of PD0325901, CPD-031 and CPD-034 on Reducing MEK1/2 Protein Levels and Inhibiting the Downstream ERK Signaling (FIG. 3E-F)

HT-29 (E) and SK-MEL-28 (F) cells were treated with DMSO or 0.1, 0.3, or 1 µM of PD0325901, CPD-031 and CPD-034 for 24 h.

Figure 4A:
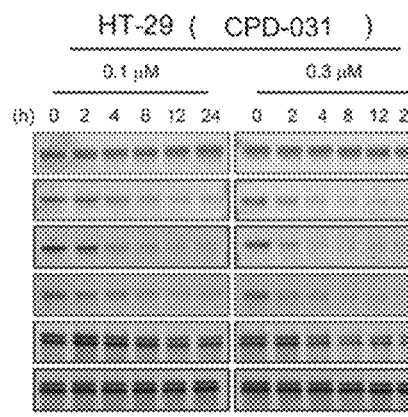
FIG. 4A-B. CPD-031 reduced MEK1 and MEK2 protein levels, and inhibited phosphorylation of MEK and ERK proteins in a time-dependent manner in HT-29 and SK-MEL-28 cells.
Figure 4B:
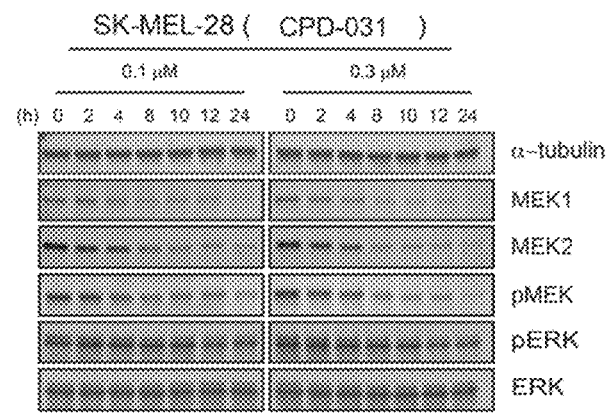

Example 105. CPD-031 Induced Degradation of MEK1 and MEK2 and Suppresses the Downstream ERK Signaling in a Time-Dependent Manner (FIG. 4A-B)

HT-29 (A) and SK-MEL-28 (B) cells were treated with 0.1 µM or 0.3 µM compound 23 for 24 h. Cells were harvested at indicated time points within 24 h and the indicated protein levels were determined by western blots.

Figure 5:
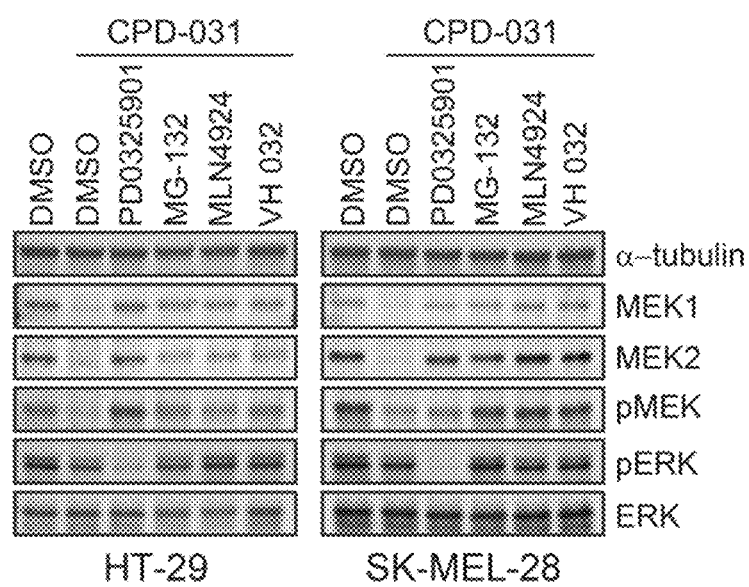
FIG. 5. Pretreatment HT-29 and SK-MEL-28 cells with PD0325901, MG-132, MLN4924 or VH 032 significantly impaired the potency of CPD-031 at the degradation of MEK1 and MEK2 proteins, and the inhibition of MEK phosphorylation.

Example 106. CPD-031 Induced MEK1/2 Protein Degradation Through Recruiting the VHL E3 Ubiquitin Ligase and Proteasome-Dependent Proteolysis (FIG. 5)

HT-29 and SK-MEL-28 cells were pretreated with DMSO, PD0325901 (1 µM), MG-132 (3 µM), MLN4924 (1 µM) or VH 032 (10 µM) for 2 h, followed by 10 h treatment with 0.3 µM CPD-031 for rescue experiments. The indicated protein levels were determined by western blots.

Figure 6A:
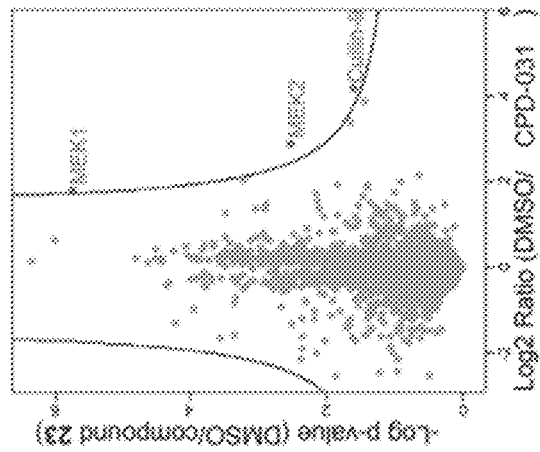
FIG. 6A-C. CPD-031 selectively degraded MEK1 and MEK2 proteins levels in HT-29 cells in the global proteomic study. And CPD-034 did not significantly modulate protein levels in HT-29 cells.
Figure 6B:
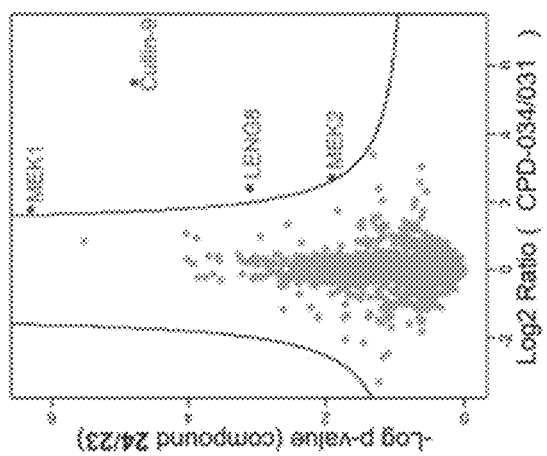
Figure 6C:
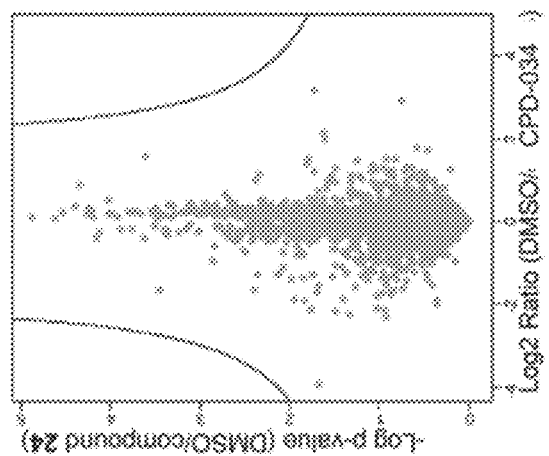

Example 107. Global Proteome Analyses of HT-29 Cells Treated with CPD-031, CPD-034 or DMSO Control (FIG. 6A-C)

Cells were harvested for proteome analysis after 10 h treatment with 0.1% DMSO, 0.1 µM CPD-031 or 0.1 µM CPD-034. Volcano plots of the −log 10 (P value) versus the log 2 ratio are displayed, with proteins outside the significance lines colored in pink or purple (FDR<0.05). P values were calculated from the data of two technical replicates. (A) DMSO compared to CPD-031 treated samples; (B) CPD-034 compared to CPD-031 treated samples; (C) DMSO compared to CPD-034 treated samples.

Example 108. CPD-31 Inhibited Cell Proliferation of HT-29 and SK-MEL-28 Cells (FIG. 7A-D)

MTT assay was conducted for HT-29 (A) and SK-MEL-28 (B) cells after 3 d treatment with DMSO or indicated compounds with serial dilutions. Clonogenic assay was performed in HT-29 (C) and SK-MEL-28 (D) cells for 14 d treatment with DMSO or indicated compounds with 10, 30 and 100 nM, in duplicate, respectively. Cells were then stained by crystal violet.

Figure 7A:
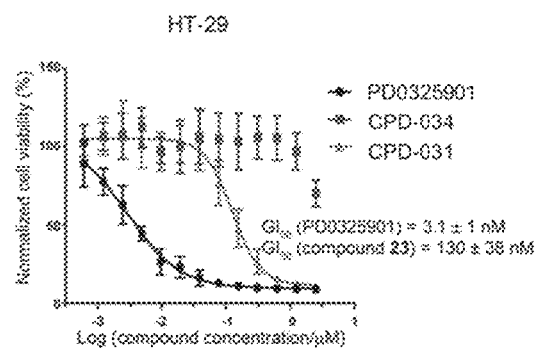
FIG. 7A-D. CPD-031 is more potent than CPD-034 at the inhibition of the growth of HT-29 and SK-MEL-28 cells.
Figure 7B:
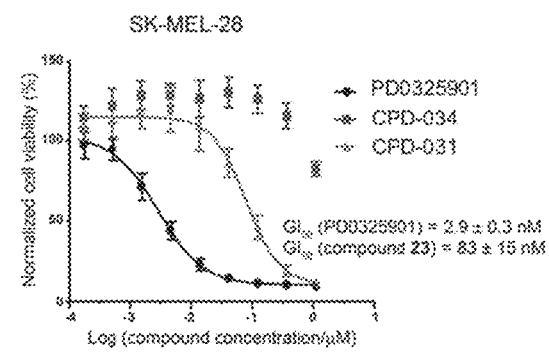
Figure 7C:
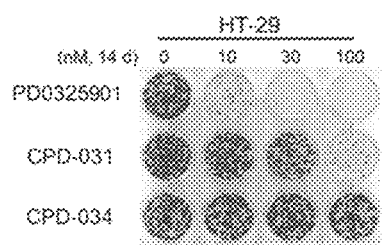
Figure 7D:
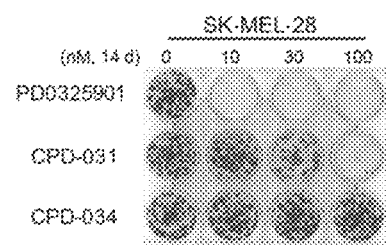
Figure 7E:
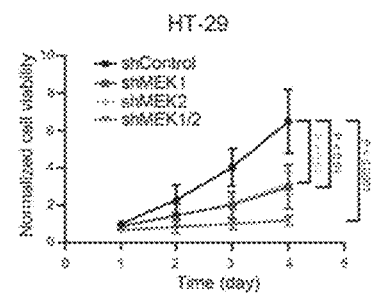
FIG. 7E-F. shRNA-mediated MEK1 and/or MEK2 knockdown significantly suppressed the growth of HT-29 and SK-MEL-28 cells.
Figure 7F:
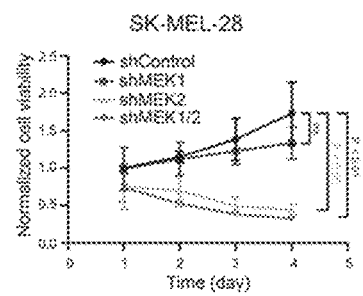

Example 109. shRNA-Mediated MEK1 and/or MEK2 Knockdown Suppressed Cell Growth (FIG. 7E-F)

shRNA-mediated MEK1/2 knockdown experiments were conducted in HT-29 (E) and SK-MEL-28 (F) cells. MTT assay was used to determine cell viability to assess the effect of MEK1/2 knockdown via shRNAs.

Figures 8A, 8B:
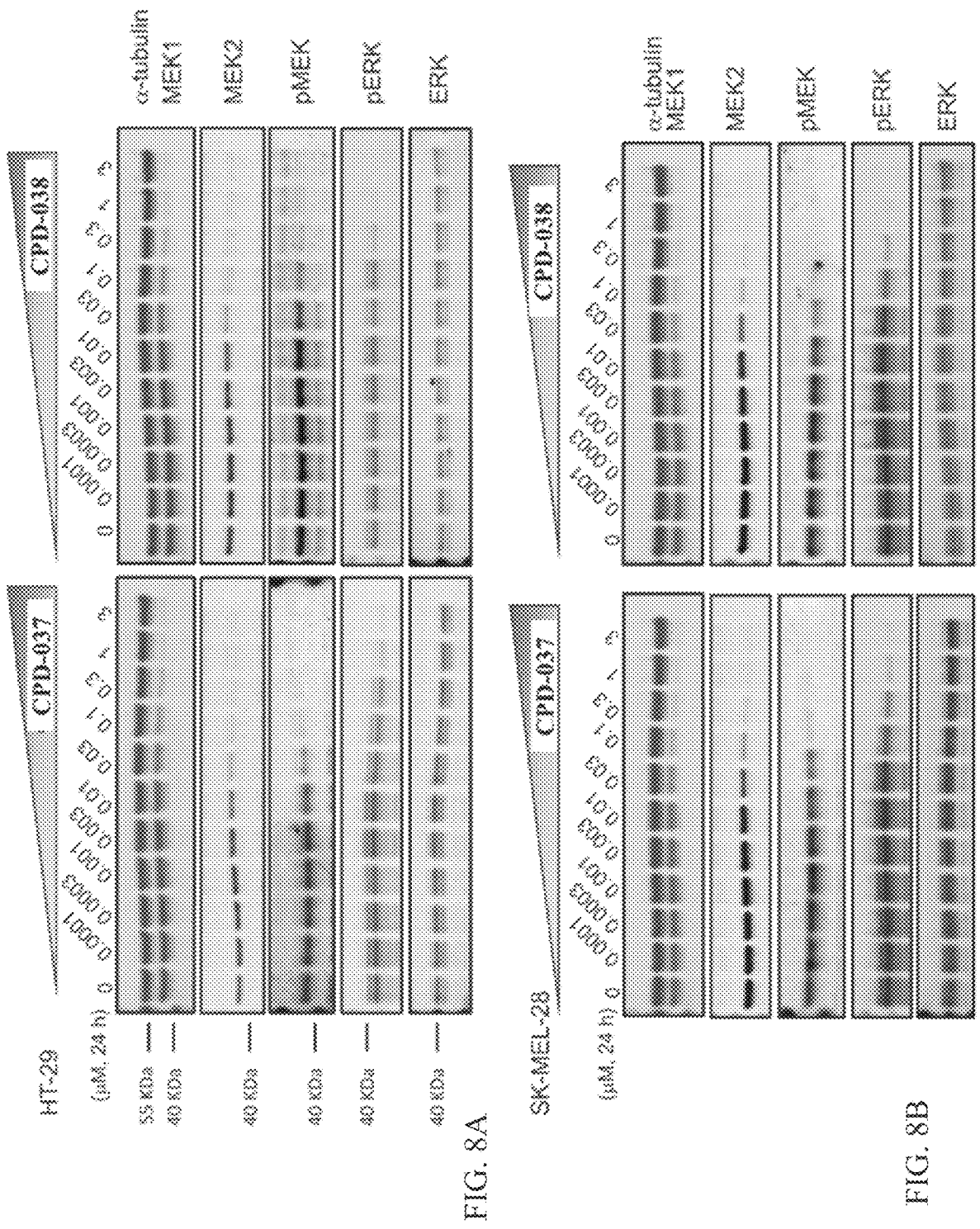
FIG. 8A-B. CPD-037 and CPD-038 degrade MEK1 and MEK2 and inhibit pMEK and pERK in a concentration-dependent manner in HT-29 and SK-MEL-28 cells.

Example 110. CPD-037 and CPD-038 Degraded MEK1 and MEK2 and Inhibited pMEK and pERK in a Concentration-Dependent Manner (FIG. 8A-B)

HT-29 (A) and SK-MEL-28 (B) cells were treated with DMSO or serial dilution of indicated compounds for 24 h. The indicated protein levels were determined by Western blots.

Figure 9A:
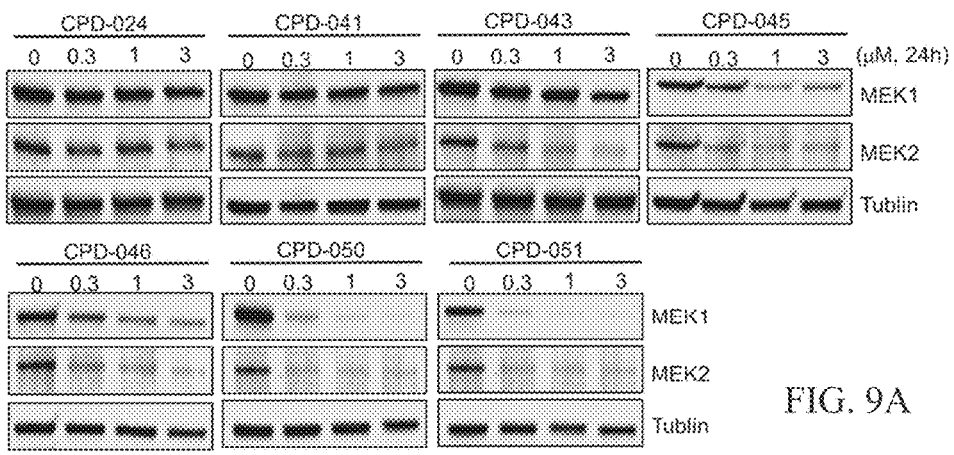
FIG. 9A. CPD-043, CPD-045, CPD-046, CPD-050, and CPD-051, but not CPD-024 and CPD-041, significantly degraded MEK1 and MEK2 protein levels in HT-29 cells.

Example 111. Selected MEK Degraders Reduced MEK Protein Levels in HT-29 Cells (FIG. 9A)

Cells were treated with DMSO or serial dilution of indicated compounds for 24 h. Compound concentrations are 0.3 µM, 1 µM and 3 µM. MEK1/2 protein levels were determined by western blots and normalized with α-tubulin.

Figure 9B:
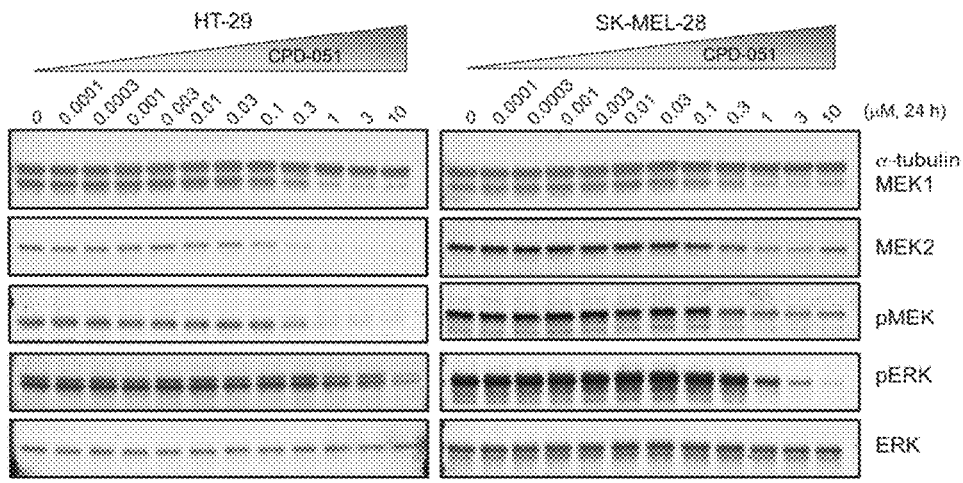
FIG. 9B. CPD-051 concentration-dependently reduced MEK1 and MEK2 protein levels, and inhibited phosphorylation of MEK and ERK proteins in HT-29 and SK-MEL-28 cells.

Example 112. CPD-051 Reduced MEK1/2 Protein Levels and Inhibits the Downstream ERK Signaling in a Concentration-Dependent Manner (FIG. 9B)

HT-29 and SK-MEL-28 cells were treated with DMSO or serial dilution of CPD-051 for 24 h. The indicated protein levels were determined by western blots and normalized with α-tubulin.

Figure 10:
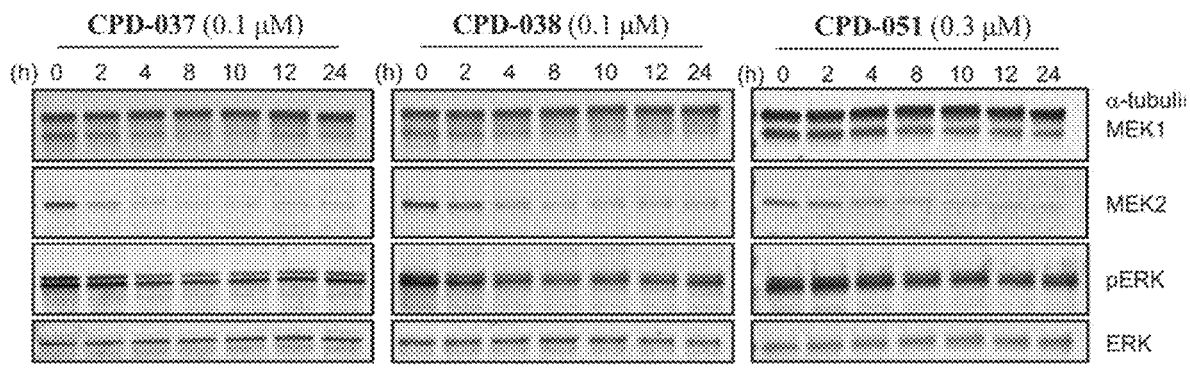
FIG. 10. CPD-037, CPD-038, and CPD-051 degrade MEK1 and MEK2 and inhibit pERK signaling in a time-dependent manner in HT-29 and SK-MEL-28 cells.

Example 113. CPD-037, CPD-038, and CPD-051 Degraded MEK1 and MEK2 and Inhibit pERK Signaling in a Time-Dependent Manner (FIG. 10)

HT-29 cells treated with 0.1 µM of CPD-037 or CPD-038, or 0.3 µM of CPD-051 were harvested at indicated time points. The indicated protein levels were determined by Western blots.

Figure 11:
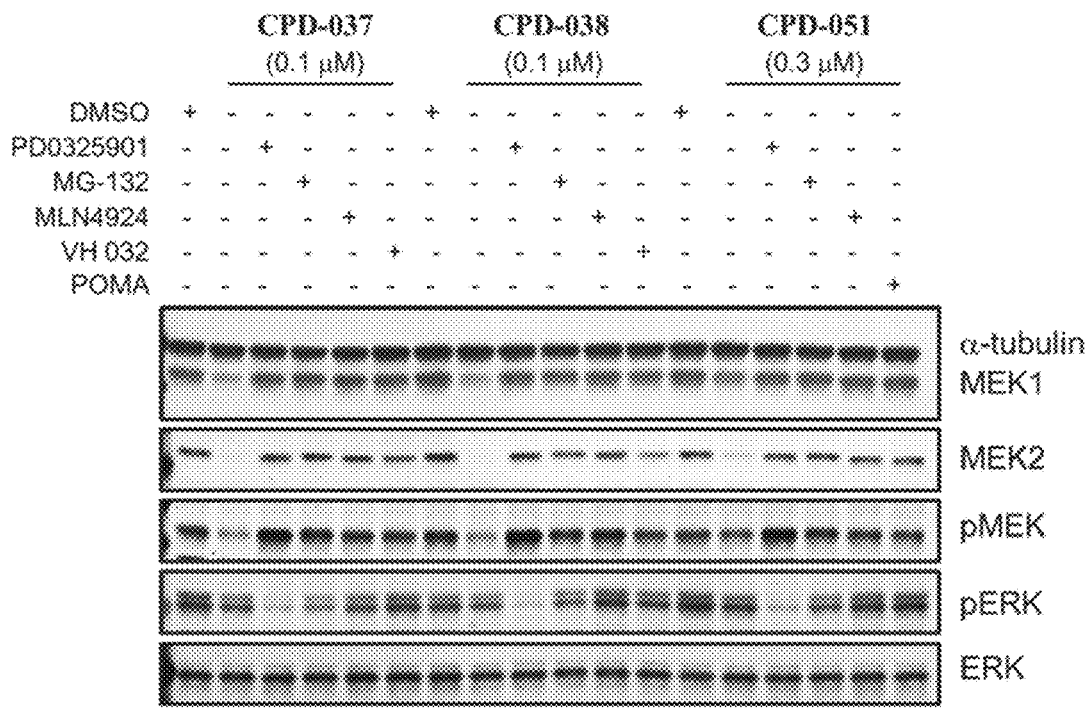
FIG. 11. Pretreatment HT-29 cells with PD0325901, MG-132, MLN4924, VH 032, or pomalidomide significantly impaired the potency of CPD-037, CPD-038, and CPD-051 at the degradation of MEK1 and MEK2 proteins, and the inhibition of MEK phosphorylation.
Figure 12A:
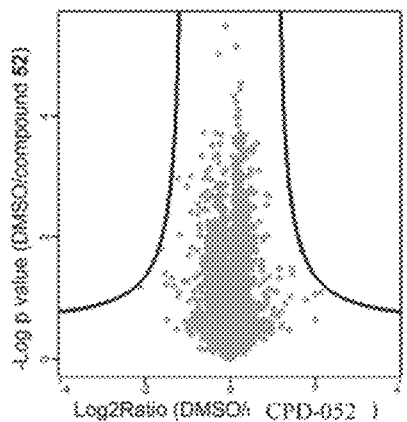
FIG. 12A-D. CPD-038 and CPD-051 selectively degraded MEK1 and MEK2 proteins levels in HT-29 cells in the global proteomic study. CPD-052 and CPD-097 did not significantly modulate protein levels in HT-29 cells.
Figure 12B:
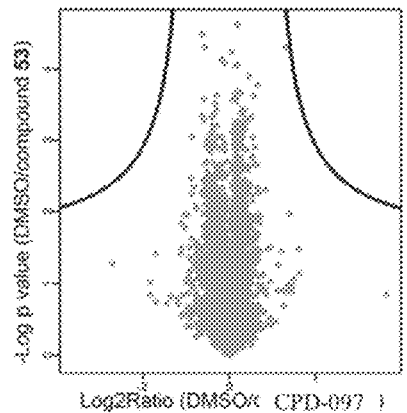
Figure 12C:
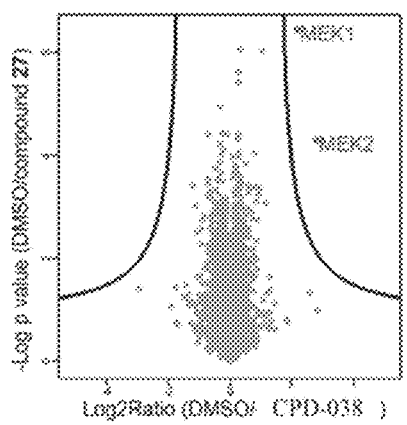
Figure 12D:
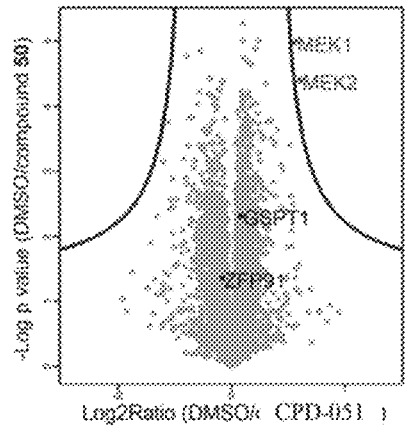

Example 114. Degradation of MEK1/2 Induced by CPD-037, CPD-038, and CPD-051 is Mediated by the Ubiquitin-Proteasome System (FIG. 11)

HT-29 cells were pretreated with DMSO, PD0325901 (1 µM), MG-132 (3 µM), MLN4924 (3 µM), VH 032 (10 µM) or pomalidomide (POMA, 5 µM) for 2 h, before 0.1 µM of CPD-037 or CPD-038, or 0.3 µM of CPD-051 was added. The cells were incubated for another 8 h. The indicated protein levels were determined by Western blots.

Example 115. CPD-038 and CPD-51 Selectively Degraded MEK1 and MEK2 in HT-29 Cells. (FIG. 12A-D)

HT-29 cells were treated with 0.1% DMSO, 0.1 µM of CPD-038, 0.3 µM of CPD-051, 0.1 µM of CPD-052 or 0.3 µM of CPD-097 for 8 h before they were harvested for mass spectrometry analysis. Volcano plots of the −log 10 (p value) vs the log 2 fold change are displayed. Proteins outside the significance lines were labeled with pink or purple color (FDR=0.05, S0=1). P values were calculated from the data of two technical replicates.

Example 116. CPD-037, CPD-038 and CPD-051 Significantly Suppress the Growth of HT-29 and SK-MEL-28 Cells (FIG. 13A-I)

HT-29 (A-C) and SK-MEL-28 (D-F) cells were treated with serial dilutions of indicated compounds for 3 d, followed by WST-8 assay to get live cell signal. (G-I) Clonogenic assay was conducted in HT-29 cells. HT-29 cells were treated with indicated compounds for 10 d. The Petri dish images are representative of two independent experiments. Cells were fixed and stained by crystal violet.

Example 117. Anti-Proliferation Effects of CPD-037 and CPD-038 Versus AZ Compound in Four Different Cancer Cell Lines (FIG. 14A-D)

HT-29 (A), SK-MEL-28 (B), H3122 (C) and SUDHL1 (D) cells were treated with serial dilutions of indicated compounds for 3 d, followed by WST-8 assay to get live cell signal.

Example 118. Concurrent Inhibition of BRAF or PI3K Potentiates Anti-Proliferation Potency of CPD-038 (FIG. 15A-B)

HT-29 (A) and SK-MEL-28 (B) cells were treated with indicated compounds for 3 d, followed by WST-8 assay to get live cell signal.

Example 119. Plasma Concentrations of CPD-031, CPD-037 and CPD-038 Following a Single Intraperitoneal Administration (FIG. 16)

Male Swiss Albino mice were dosed with 50 mg/kg of indicated degraders through intraperitoneal administration. Plasma concentrations of indicated degraders at 0.5, 2 and 8 h are plotted.

Materials and Methods

General Chemistry Methods

An Agilent 1200 series system with DAD detector and a 2.1 mm×150 mm Zorbax 300SB-C18 5 µm column with water containing 0.1% formic acid as solvent A and acetonitrile containing 0.1% formic acid as solvent B at a flow rate of 0.4 mL/min for chromatography were used to obtain high-performance liquid chromatography (HPLC) spectra for all compounds. The gradient program was as follows: 1% B (0-1 min), 1-99% B (1-4 min), and 99% B (4-8 min). A Waters Acquity I-Class Ultra-performance liquid chromatography (UPLC) system with a PDA detector was used to generate UPLC spectra for all compounds. Chromatography was performed using a 2.1×30 mm ACQUITY UPLC BEH C18 1.7 µm column with water containing 3% acetonitrile and 0.1% formic acid as solvent A and acetonitrile containing 0.1% formic acid as solvent B at a flow rate of 0.8 mL/min. The gradient program was as follows: 1-99% B (1-1.5 min), and 99-1% B (1.5-2.5 min). High-resolution mass spectra (HRMS) data were obtained in positive ion mode using an Agilent G1969A API-TOF with an electrospray ionization (ESI) source. Nuclear Magnetic Resonance (NMR) spectra were obtained on a Bruker DRX-600 spectrometer with 600 MHz for proton ($^1$H NMR) or a Bruker DXI 800 MHz spectrometer with 800 MHz for proton ($^1$H NMR) or 200 MHz for carbon ($^{13}$C NMR); chemical shifts are reported in ppm (δ). Preparative HPLC was performed using an Agilent Prep 1200 series with UV detector set to 220 nm. Samples were injected into a Phenomenex Luna 75×30 mm, 5 µm, C18 column at room temperature. The flow rate was 40 mL/min. A linear gradient was used with 10% (or 50%) of MeOH (A) in $H_2O$ (with 0.1% TFA) (B) to 100% of MeOH (A). HPLC and UPLC were used to establish the purity of target compounds. All final compounds had >95% purity using the HPLC and UPLC methods described above.

Kinase Inhibition Assay

The inhibition potencies of compounds against MEK1 and MEK2 kinases were determined using the HotSpot kinase assay by Reaction Biology company. This assay measures MEK kinase activity on ERK phosphorylation. Briefly, after incubating the compounds with the kinase reaction mixture of MEK and ERK proteins for 20 min at RT, $^{33}$P-ATP (specific activity 10 µCi/µl) was delivered into the reaction mixture to initiate the reaction for incubation for 2 hours at RT. Radioactivity was then detected by filter-binding method. Kinase activity data was expressed as the percent remaining kinase activity in samples compared to DMSO reactions. Purified kinase proteins, MEK1 (PV3303, Thermo Fisher Scientific) at 100 nM, MEK2 (PV3615, Thermo Fisher Scientific) at 150 nM and ERK kinase-dead mutant K52R (Reaction Biology) at 5µ were used in the reactions. $IC_{50}$ was determined using 10-concentration 3-fold serial dilution (top concentrations for PD0325901, compounds 23 and 24 were 3 µM, 30 µM and 30 µM, respectively) with DMSO as control point in two independent experiments.

Cell Culture

Cells were cultivated in DMEM, RPMI-1640 or RPMI-1640 medium supplemented with 10% FBS, 100 units/mL of penicillin and 100 µg/mL of streptomycin. Mycoplasma elimination using LookOut Mycoplasma Elimination Kit (MP0030, Sigma-Aldrich) was conducted before the cells used for experiments.

Western Blot

Cells were lysed on ice for 30 min with the lysis buffer (50 mM Tris pH 7.4, 1% IGEPAL CA-630, 150 mM NaCl, 1 mM EDTA and 1 mM AESBF), supplemented with protease and phosphatase inhibitor cocktail (A32961, Thermo Fisher Scientific). The sample was centrifuged at 12,000 g for 10 min at 4° C. to get supernatant as cell lysate. Protein concentrations were quantified using Pierce rapid gold BCA protein assay kit. The primary antibodies used were MEK1 (2352, CST), MEK2 (9147, CST), pMEK (9121, CST), ERK (4696, CST), pERK (4370, CST), α-tubulin (T6074, Sigma-Aldrich), VHL (68547, CST), CRBN (HPA045910, Sigma-Aldrich), Cullin-9 (A300-098A, Bethyl Laboratories), LENG8 (A304-947A, Bethyl Laboratories). Fluorescence-labeled secondary antibodies (IRDye 680, 800, LI-COR) and OdysseyCLx imaging system (LI-COR) were used to get protein signals which were then analyzed by Image Studio Lite software (LI-COR). $DC_{50}$ values were obtained with GraphPad Prism 8 from the data of three independent experiments.

Binding affinity assays. For most assays, kinase-tagged T7 phage strains were prepared in an E. coli host derived from the BL21 strain. E. coli were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 min at rt to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 111× stocks in 100% DMSO. Kds were determined using an 11-point 3-fold compound dilution series with three DMSO control points. All compounds for Kd measurements are distributed by acoustic transfer (non-contact dispensing) in 100% DMSO. The compounds were then diluted directly into the assays such that the final concentration of DMSO was 0.9%. All reactions performed in polypropylene 384-well plate. Each was a final volume of 0.02 mL. The assay plates were incubated at room temperature with shaking for 1 h and the affinity beads were washed with wash buffer (1×PBS, 0.05% Tween 20). The beads were then re-suspended in elution buffer (1×PBS, 0.05% Tween 20, 0.5 µM non-biotinylated affinity ligand) and incubated at room temperature with shaking for 30 min. The kinase concentration in the eluates was measured by qPCR.

Proteomics Studies

Protein Extraction and Digestion. Cells with indicated treatments were harvested and lysed in lysis buffer (6 M guanidine hydrochloride, 100 mM Tris-HCl pH 8.0). Sonication (5 s on, 5 s off, 2×30 s) was performed to shear genome DNA. Lysate were centrifugated for 30 min at 3,500 g at 4° C. and the supernatant were transferred to a clean tube, diluted 50% with Milli-Q $H_2O$, then precipitated by addition of cold acetone (four times the original volume), and placed at −20° C. overnight. Precipitated proteins were brought down at 20,000 g at 4° C. for 10 min, and washed with cold acetone after discarding the supernatant. The pellet was air-dried at RT for 5 min and solubilized with 50 mM Tris-HCl (PH 8.0), 8 M urea. Protein concentration was determined (BCA assay) and protein was reduced with 5 mM DTT (dithiothreitol), alkylated with 15 mM IAA (iodoacetamide) in the dark, then diluted with buffer 25 mM Tris (pH 8.0) and 1 mM $CaCl_2$ (three times the original volume). The final urea concentration is 2 M. Trypsin was added into protein solution with 1:100 ratio (trypsin:protein), and digested 12-16 h or overnight at RT.

Mass Spectrometry Analysis. Peptides were cleaned up by C18 stage tips and the concentration was determined (Peptide assay, 23275, Thermo Fisher Scientific). The clean peptides were dissolved in 0.1% formic acid and analyzed on a Q-Exactive HF-X coupled with an Easy nanoLC 1200 (Thermo Fisher Scientific, San Jose, CA). 0.5 µg of peptides were loaded onto an Acclain PepMap RSLC C18 Column (250 mm×75 µm ID, C18, 2 µm, Thermo Fisher Scientific). Analytical separation of all peptides was achieved with 130 min gradient. A linear gradient of 5 to 30% buffer B over 110 min was executed at a 300 nl/min flow rate followed a ramp to 100% B in 5 min, and 15-min wash with 100% B, where buffer A was aqueous 0.1% formic acid, and buffer B was 80% acetonitrile and 0.1% formic acid.

LC-MS experiments were performed in a data-dependent mode with full MS (externally calibrated to a mass accuracy of <5 ppm and a resolution of 60,000 at m/z 200) followed by high energy collision-activated dissociation-MS/MS of the top 20 most intense ions with a resolution of 15,000 at m/z 200. High energy collision-activated dissociation-MS/MS was used to dissociate peptides at a normalized collision energy of 27 eV in the presence of nitrogen bath gas atoms. Dynamic exclusion was 30.0 seconds. Each sample was subjected to two technical LC-MS replicates.

MS Data Analysis. Mass spectra processing and peptide identification were performed on the Andromeda search engine in MaxQuant software (Version 1.6.0.16) against the human UniProt database (UP000005640). All searches were conducted with a defined modification of cysteine carbamidomethylation, with methionine oxidation and protein amino-terminal acetylation as dynamic modifications. Peptides were confidently identified using a target-decoy approach with a peptide false discovery rate (FDR) of 1% and a protein FDR of 1%. A minimum peptide length of 7 amino acids was required, maximally two missed cleavages were allowed, initial mass deviation for precursor ion was up to 7 ppm, and the maximum allowed mass deviation for fragment ions was 0.5 Da. Data processing and statistical analysis were performed on Perseus (Version 1.6.0.7). Protein quantitation was performed on duplicate runs, and a two-sample t-test statistics was used to report statistically significant expression fold-changes.

Cell Viability Assay

Cells (2000 cells per well) were seeded into 96-well microplates. After 20 h, cells were treated with 0.1% DMSO or indicated serial dilutions of compounds in duplicate or triplicate for 3 days. Cell viability was tested using MTT (M6494, Thermo Fisher Scientific) or WST-8 reagent (CK04, Dojindo). Briefly, 12 mM MTT was prepared in PBS or WST-8 reagent was warmed up to room temperature. 20 µL MTT or CCK-8 was then added to each well and the plates were kept in incubator at 37° C. for 3 h in the dark. For the WST-8 assay, signal was obtained after the incubation. For the MTT assay, cell medium was replaced with 200 µL of DMSO after the incubation, and then cell plates were kept at 37° C. for another 30 min. Absorbance signals for MTT and WST-8 were read at 540 nm and 450 nm respectively, with 690 nm as reference performed with Infinite F PLEX plate reader (TECAN, Morrisville, NC, USA). $GI_{50}$ values were analyzed using GraphPad Prism 8 from the data of at least three independent experiments.

Clonogenic Assay

HT-29 or SK-MEL-28 cells (300 cells per well) were seeded in 12-well plates. After 20 h, cells were treated with DMSO or indicated concentrations of compounds in duplicate for two weeks. Medium containing indicated compounds was changed every 3 days. Cells were then fixed and stained with the solution containing 6% (v/v) glutaraldehyde (G5882, Sigma-Aldrich) and 0.5% (w/v) crystal violet for 1 h. To remove the background color, the plates with stained cells were immersed in running water until clear colonies were observed. The plates were dried at RT. The staining images were obtained with Epson Perfection V600 Photo.

shRNA-Mediated MEK Knockdown

HEK293T cells were transfected with PMD (VSVG)/pCMVΔ8.2/pLKO.1 plasmids for lentivirus packaging. 48 h later, virus was harvested in the medium and filtered. 1.5 mL of virus with 10 µg/mL of polybrene (TR-1003, Sigma-Aldrich) was added into 6-cm dishes to infect HT-29 or SK-MEL-28 cells. After 24 h, medium was changed into fresh full medium with 2 µg/mL of puromycin (P8833, Sigma-Aldrich) for 48 h for selection, and then 2000 cells of shControl, shMEK1 (TRCN0000002329, Sigma-Aldrich), shMEK2 (TRCN0000195037, Sigma-Aldrich), or shMEK1/2 cells, in nonuplicate, were seeded into 96-well plates for 4 d growth. MTT assay was performed every day to get cell viability signals. Meanwhile, knockdown efficiency of each shRNA was examined by western blot.

Mouse PK Study

The in vivo PK studies were conducted for indicated compounds using three male Swiss Albino mice per compound. The mice were administered intraperitoneally with solution formulation (5% NMP, 5% Solutol HS-15, and 90% normal saline) of indicated compounds at a single dose of 50 mg/kg. Sixty microliters of blood samples were collected from each mouse at 0.5, 2, and 8 h. Plasma was harvested by centrifugation of blood and stored at −70±10° C. until analysis. Plasma samples were quantified by fit-for-purpose LC-MS/MS method (LLOQ: 5.02 ng/mL for plasma).

Statistic Methods

For all data, number of biologically independent experiments and technical replicates, error bars and P values are described in figure legends, respectively. At least two independent experiments were conducted for all biological studies. The proteomics study was conducted in duplicate. Two-tailed Student's t-tests and two-way ANOVA were used for indicated analysis respectively, P≥0.05, ns; 0.01<P<0.05, *; 0.001<P<0.01, ; P<0.001, *.

The anti-proliferation results of selected heterobifunctional compounds are set forth in Table 2 below.

TABLE 2

| CPD | GI$_{50}$ (μM) HT-29 |
| --- | --- |
| CPD-001 | 1.4 ± 0.2 |
| CPD-002 | 4.0 ± 0.2 |
| CPD-003 | 4.8 ± 0.7 |
| CPD-004 | 1.6 ± 0.3 |
| CPD-005 | 1.8 ± 0.4 |
| CPD-006 | 5.0 ± 1.1 |
| CPD-007 | 3.0 ± 0.5 |
| CPD-008 | 11 ± 0.9 |
| CPD-009 | 2.1 ± 0.1 |
| CPD-010 | 0.6 ± 0.1 |
| CPD-011 | 0.5 ± 0.2 |
| CPD-012 | 1.6 ± 0.3 |
| CPD-013 | 0.5 ± 0.03 |
| CPD-014 | 0.4 ± 0.2 |
| CPD-015 | 1.3 ± 0.1 |
| CPD-016 | 3.3 ± 0.6 |
| CPD-017 | 1.7 ± 0.1 |
| CPD-019 | 1.2 ± 0.2 |
| CPD-020 | 1.3 ± 0.5 |
| CPD-021 | 0.8 ± 0.2 |
| CPD-022 | 0.6 ± 0.09 |
| CPD-023 | 0.6 ± 0.1 |
| CPD-024 | 0.4 ± 0.01 |
| CPD-025 | 1.1 ± 0.07 |
| CPD-026 | 1.9 ± 0.4 |
| CPD-027 | 1.8 ± 0.5 |
| CPD-028 | 3.8 ± 1.7 |
| CPD-029 | 4.5 ± 1.9 |
| CPD-030 | 3.5 ± 0.9 |
| CPD-031 | 0.13 ± 0.04 |
| CPD-033 | 0.099 ± 0.008 |
| CPD-035 | 0.055 ± 0.005 |
| CPD-036 | 0.24 ± 0.055 |
| CPD-037 | 0.032 ± 0.008 |
| CPD-038 | 0.023 ± 0.005 |
| CPD-039 | 0.043 ± 0.001 |
| CPD-041 | 0.5 ± 0.2 |
| CPD-042 | 1.0 ± 0.4 |
| CPD-043 | 0.5 ± 0.1 |
| CPD-044 | 1.1 ± 0.5 |
| CPD-045 | 0.5 ± 0.2 |
| CPD-046 | 0.3 ± 0.1 |
| CPD-047 | 1.4 ± 0.7 |
| CPD-048 | 1.1 ± 0.3 |
| CPD-049 | 1.5 ± 0.5 |
| CPD-050 | 0.5 ± 0.06 |
| CPD-051 | 0.3 ± 0.06 |

TABLE 2-continued

| CPD | GI$_{50}$ (μM) HT-29 |
| --- | --- |
| CPD-052 | 0.83 ± 0.085 |
| CPD-053 | 1.3 ± 0.16 |

GI$_{50}$ (μM) values of selected compounds in HT-29 cells.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A heterobifunctional compound having the following structure:

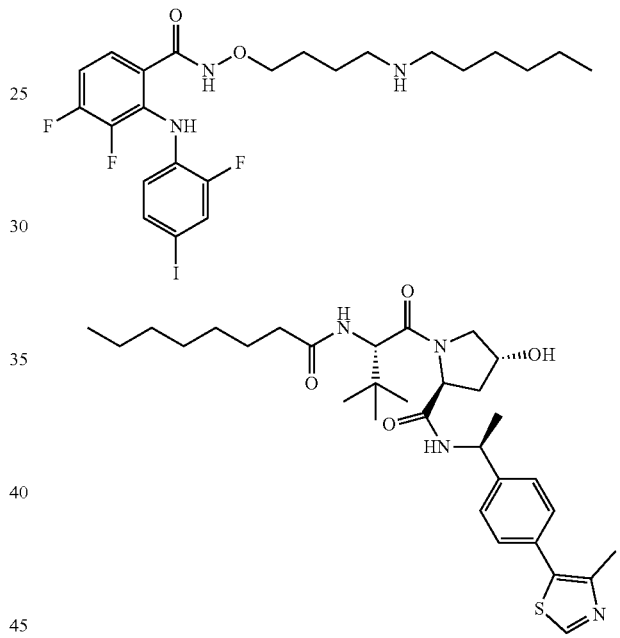

(CPD-038) or a pharmaceutically acceptable salt, hydrate, solvate, prodrug, stereoisomer, tautomer, or analog thereof.

2. A pharmaceutical composition, comprising the heterobifunctional compound of claim 1 and a pharmaceutically acceptable excipient, adjuvant or vehicle.

3. A method of treating an MEK-mediated disease, comprising administering to a subject in need thereof, a therapeutically effective amount of a heterobifunctional compound according to claim 1.

* * * * *